(12) United States Patent
Zhang et al.

(10) Patent No.: US 9,340,538 B2
(45) Date of Patent: May 17, 2016

(54) DIHYDROPYRIMIDINE COMPOUNDS AND THEIR APPLICATION IN PHARMACEUTICALS

(71) Applicant: SUNSHINE LAKE PHARMA CO., LTD., Dongguan, Guangdong (CN)

(72) Inventors: Yingjun Zhang, Dongguan (CN);
Qingyun Ren, Dongguan (CN);
Xinchang Liu, Dongguan (CN);
Siegfried Goldmann, Wuppertal (DE)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 57 days.

(21) Appl. No.: 14/416,061

(22) PCT Filed: Aug. 23, 2013

(86) PCT No.: PCT/CN2013/001001
§ 371 (c)(1),
(2) Date: Jan. 21, 2015

(87) PCT Pub. No.: WO2014/029193
PCT Pub. Date: Feb. 27, 2014

(65) Prior Publication Data
US 2015/0152096 A1  Jun. 4, 2015

(51) Int. Cl.
| | |
|---|---|
| *A01N 43/54* | (2006.01) |
| *A61K 31/535* | (2006.01) |
| *C07D 417/14* | (2006.01) |
| *C07D 413/14* | (2006.01) |
| *A61K 31/505* | (2006.01) |
| *A61K 31/506* | (2006.01) |
| *A61K 31/5377* | (2006.01) |
| *A61K 45/06* | (2006.01) |

(52) U.S. Cl.
CPC ............ *C07D 417/14* (2013.01); *A61K 31/505* (2013.01); *A61K 31/506* (2013.01); *A61K 31/5377* (2013.01); *A61K 45/06* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 5,250,531 A | 10/1993 | Cooper | |
| 6,057,332 A | 5/2000 | Michne et al. | |
| 6,218,538 B1 | 4/2001 | Downs et al. | |
| 6,436,943 B1 | 8/2002 | Stoltefuss et al. | |
| 6,503,913 B1 | 1/2003 | Goldmann et al. | |
| 6,696,451 B1 | 2/2004 | Stoltefuss et al. | |
| 7,074,784 B2 | 7/2006 | Goldmann et al. | |
| 7,157,461 B2 | 1/2007 | Murugesan et al. | |
| 8,106,196 B2 | 1/2012 | Li et al. | |
| 8,168,642 B2 | 5/2012 | Li et al. | |
| 8,329,902 B2 | 12/2012 | Li et al. | |
| RE44,987 E | 7/2014 | Goldmann et al. | |
| 8,802,669 B2 | 8/2014 | Li et al. | |
| 2003/0232842 A1* | 12/2003 | Goldmann et al. | ............ 514/256 |
| 2013/0267517 A1 | 10/2013 | Guo et al. | |

FOREIGN PATENT DOCUMENTS

| | | |
|---|---|---|
| CN | 101744823 B | 6/2013 |
| EP | 0202654 A2 | 11/1986 |
| WO | WO0058302 A1 | 10/2000 |
| WO | WO0168639 A1 | 9/2001 |
| WO | WO0168641 A1 | 9/2001 |
| WO | WO0168642 A1 | 9/2001 |

(Continued)

OTHER PUBLICATIONS

Gentile et al., Vertical transmission of hepatitis B virus: challenges and solutions, International Journal of Women's Health, 6: 605-611, 2014.*

(Continued)

*Primary Examiner* — Jeffrey S Lundgren
*Assistant Examiner* — Michael Schmitt
(74) *Attorney, Agent, or Firm* — Kam W. Law; Squire Patton Boggs

(57) ABSTRACT

Provided herein are dihydropyrimidine compounds and their pharmaceutical applications, especially for use in treating and preventing HBV diseases. Specifically, provided herein are compounds having Formula (I) or (Ia), or an enantiomer, a diastereoisomer, a tautomer, a hydrate, a solvate, or a pharmaceutically acceptable salt thereof, wherein the variables of the formulas are as defined in the specification. Also provided herein is the use of the compounds having Formula (I) or (Ia), or an enantiomer, a diastereoisomer, a tautomer, a hydrate, a solvate, or a pharmaceutically acceptable salt thereof for treating and preventing HBV diseases.

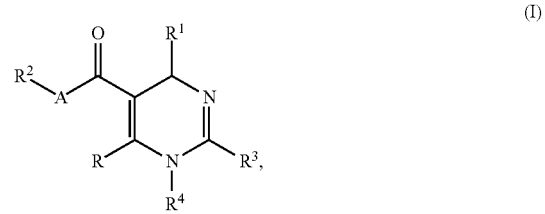

(I)

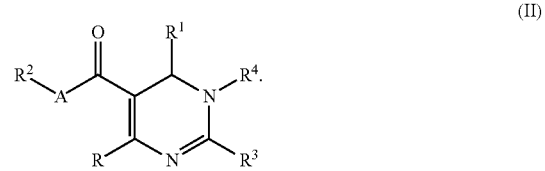

(II)

23 Claims, No Drawings

(56) References Cited

FOREIGN PATENT DOCUMENTS

| WO | WO0168647 A1 | | 9/2001 |
|----|---|---|---|
| WO | WO 01068641 A1 | * | 9/2001 |
| WO | WO2008154818 A1 | | 12/2008 |
| WO | WO2008154819 A1 | | 12/2008 |
| WO | WO2008154820 A1 | | 12/2008 |
| WO | WO2010069147 A1 | | 6/2010 |
| WO | WO2013019967 A1 | | 2/2013 |
| WO | WO2013102655 A1 | | 7/2013 |

OTHER PUBLICATIONS

Halegoua-De Marzio et al., Then and now: The progress in hepatitis B treatment over the past 20 years, World Journal of Gastroenterology, 20(2): 401-413, Jan. 2014.*
ISR.
Written Opinion.

* cited by examiner

DIHYDROPYRIMIDINE COMPOUNDS AND THEIR APPLICATION IN PHARMACEUTICALS

CROSS-REFERENCE TO RELATED APPLICATIONS

This is a U.S. national stage application of the International Patent Application No. PCT/CN2013/001001, filed Aug. 23, 2013, which claims priorities to Chinese Patent Application No. 201210303033.4, filed Aug. 24, 2012, and No. 201310116949.3, filed Apr. 3, 2013, all of which are incorporated herein by reference in their entirety.

FIELD OF THE INVENTION

The invention relates to dihydropyrimidine compounds and their application in pharmaceuticals, especially for use in treating and preventing Hepatitis B. The invention also relates to drugs comprising the dihydropyrimidine compounds, other antiviral agent, and the pharmaceutical compositions thereof, particularly for treating and preventing HBV infection.

BACKGROUND OF THE INVENTION

The hepatitis B virus belongs to the family of hepadnaviridae. It can cause acutely and/or persistently or progressively chronic diseases. Many other clinical manifestations in the pathological morphology are also caused by HBV—in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has good activity, its resistance develops rapidly during the treatment and relapse effects often appear after the treatment has stopped. The $IC_{50}$ value of lamivudine (3-TC) is 300 nM (*Science*, 2003, 299, 893-896).

Deres, et al, have reported heteroaryl-substituted dihydropyrimidine (HAP) compounds which were represented by Bay41-4109 and Bay39-5493, and these compounds play a role in blocking HBV replication by preventing the proper formation of viral core particles (nucleocapsids). Bay41-4109 has demonstrated better drug metabolic parameters in clinical study (*Science*, 2003, 299, 893-896). The study of these compounds' mechanism of action indicated that through reacting with 113-143 amino acid residues of a core protein, heteroaryl-substituted dihydropyrimidine compounds have changed the angle between dimers which can form nucleocapsids, and led to forming unstably expanded nucleocapsids, which accelerate the degradation of the core protein (*Biochem. Pharmacol.*, 2003, 66, 2273-2279).

New and effective antiviral compounds are urgently needed, especially for treating and/or preventing HBV infection.

SUMMARY OF THE INVENTION

The invention relates to novel dihydropyrimidine compounds and methods of treating and preventing HBV infection.

Specifically, these compounds and the pharmaceutically acceptable compositions thereof disclosed herein can inhibit HBV infection effectively.

In one aspect, provided herein are compounds having Formula (I) or (Ia) as shown below:

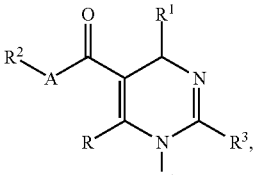

(I)

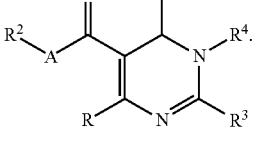

(II)

or an enantiomer, a diastereoisomer, a tautomer, a hydrate, a solvate, or a pharmaceutically acceptable salt thereof, wherein:
each A is a bond, —O—, —S—, or —$NR^5$—;
each R is —X—Z;
X is —$(CR^7R^{7a})_m$— or —C(=O)—;
Z has Formula (II) or (IIa):

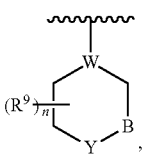

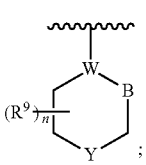

wherein each B is a bond, —$(CR^7R^{7a})_m$— or —C(=O)—;
each W is $CR^7$ or N;
each Y is —$(CR^7R^{7a})_m$—, —O—, —S—, —S(=O)$_q$— or —$NR^6$—;
each $R^1$ is aryl or heteroaryl;
each $R^2$ is H, alkyl, alkenyl, alkynyl, aryl, aralkyl, heteroaryl, heteroarylalkyl, cycloalkyl, cycloalkylalkyl, heterocyclyl, heterocyclylalkyl or alkoxycarbonyl;
each $R^3$ is aryl or heteroaryl;
each $R^4$ is H, or $C_{1-4}$ alkyl;
$R^5$ is H, alkyl, —$(CR^7R^{7a})_m$—C(=O)O—$R^8$, alkenyl or alkynyl;
each $R^6$ is alkyl, —$(CR^7R^{7a})_m$—C(=O)O—$R^8$, alkenyl or alkynyl;
each $R^{7a}$ and $R^7$ is independently H, F, Cl, Br, alkyl, haloalkyl, —$(CH_2)_m$—OH or —$(CH_2)_m$—C(=O)O—$R^8$;
each $R^8$ and $R^{8a}$ is independently H, alkyl, haloalkyl, aminoalkyl, Boc-NH-alkyl, alkoxy, —$(CH_2)_m$—OH, —$(CH_2)_m$—C(=O)O—$(CH_2)_m$—H or —$(CH_2)_m$—OC(=O)—$(CH_2)_m$—H;
Boc is tert-butyloxycarbonyl;
each $R^9$ is independently —$(CR^7R^{7a})_t$—OH, —$(CR^7R^{7a})_m$—S(=O)$_q$—$R^8$, —$(CR^7R^{7a})_m$—OS(=O)$_q$—$R^8$, —$(CR^7R^{7a})_m$—S(=O)$_q$—$R^8$, —$(CR^7R^{7a})_m$—C(=O)—$R^8$, —(CR⁷R⁷ᵃ)ₘ—C(=O)O—R⁸, —(CR⁷R⁷ᵃ)ₘ—C(=O)O—(CR⁷R⁷ᵃ)ₘ—OC(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₘ—C(=O)O—(CR⁷R⁷ᵃ)ₘ—C(=O)O—R⁸, —(CR⁷R⁷ᵃ)ₜ—OC(=O)—R⁸, triazolyl, tetrazolyl or —(CR⁷R⁷ᵃ)ₘ—C(=O)N(R⁸)₂, with the proviso that when R⁹ is —(CR⁷R⁷ᵃ)ₜ—OH, R³ is aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each n is independently 1, 2 or 3;
each t is independently 1, 2, 3 or 4;
each m is independently 0, 1, 2, 3 or 4;
each q is independently 0, 1 or 2; and
optionally each of aryl, heteroaryl, alkyl, haloalkyl, alkenyl, alkynyl, cycloalkyl, cycloalkylalkyl, alkoxycarbonyl, aralkyl, heteroarylalkyl, aminoalkyl, alkoxy, furanyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl, triazinyl, heterocyclyl and heterocyclylalkyl described above, is independently substituted with one or more substituents which are the same or different, wherein the substituent is H, F, Cl, Br, I, alkyl, alkoxy, cyano, hydroxy, nitro, alkylamino, amino, trifluoromethyl, trifluoromethoxy, —(CR⁷R⁷ᵃ)ₘ—C(=O)O—R⁸ᵃ, haloalkyl-substituted aryl, halogen-substituted aryl, —(CR⁷R⁷ᵃ)ₘ—C(=O)N(R⁸ᵃ)₂ or trifluoromethylsulfonyl.

In certain embodiments, Z has Formula (III) or (IIIa):

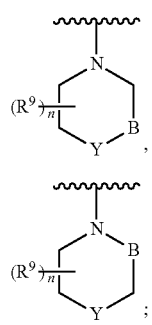

(III)

(IIIa)

wherein each B is a bond or —(CR⁷R⁷ᵃ)ₘ—;
each Y is —(CR⁷R⁷ᵃ)ₘ—, —O—, —S—, —S(=O)_q— or —NR⁶—;
each R⁶ is $C_{1-4}$ alkyl, —(CR⁷R⁷ᵃ)ₘ—C(=O)O—R⁸, $C_{2-4}$ alkenyl or $C_{2-4}$ alkynyl;
each R⁷ᵃ and R⁷ is independently H, F, Cl, Br, $C_{1-4}$ alkyl, —(CH₂)ₘ—OH, $C_{1-4}$ haloalkyl or —(CH₂)ₘ—C(=O)O—R⁸;
each R⁸ is independently H, $C_{1-6}$ alkyl, $C_{1-4}$ haloalkyl, amino-$C_{1-4}$-alkyl, Boc-NH—$C_{1-4}$-alkyl, $C_{1-4}$ alkoxy, —(CH₂)ₘ—OH, —(CH₂)ₘ—C(=O)O—(CH₂)ₘ—H or —(CH₂)ₘ—OC(=O)—(CH₂)ₘ—H;
each R⁹ is independently —(CR⁷R⁷ᵃ)ₜ—OH, —(CR⁷R⁷ᵃ)ₘ—C(=O)—R⁸, —(CR⁷R⁷ᵃ)ₘ—C(=O)O—R⁸, —(CR⁷R⁷ᵃ)ₘ—C(=O)O—(CR⁷R⁷ᵃ)ₘ—OC(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₘ—C(=O)O—(CR⁷R⁷ᵃ)ₘ—C(=O)O—R⁸, —(CR⁷R⁷ᵃ)ₜ—OC(=O)—R⁸, triazolyl, tetrazolyl or —(CR⁷R⁷ᵃ)ₘ—C(=O)N(R⁸)₂, with the proviso that when R⁹ is —(CR⁷R⁷ᵃ)ₜ—OH, R³ is $C_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each n is independently 1 or 2;
each t is independently 1, 2, 3 or 4; and
each m is independently 0, 1, 2, 3 or 4.

In other embodiments, Z is

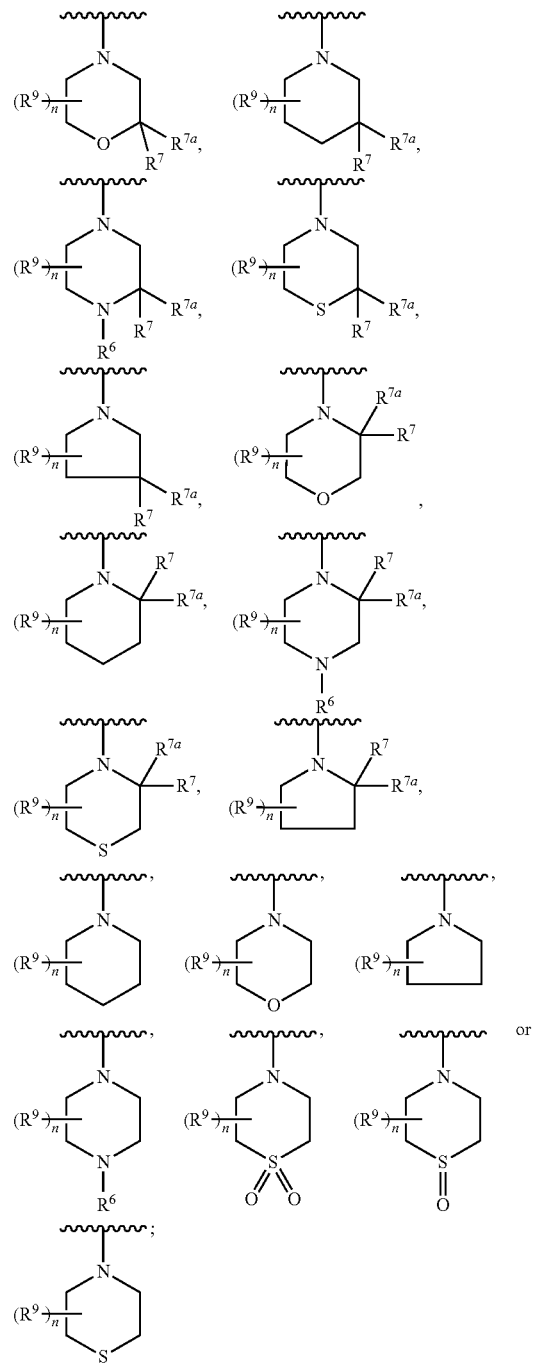

wherein each R⁶ is independently methyl, ethyl or propyl;
each R⁷ and R⁷ᵃ is independently H, methyl, ethyl, —(CH₂)ₘ—OH, —(CH₂)ₘ—C(=O)O—R⁸ or propyl;
each R⁸ is independently H, methyl, ethyl, propyl, isopropyl, butyl, 1-methylpropyl, 2-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —$(CH_2)_m$—OH, —$(CH_2)_m$—C(=O)O—$(CH_2)_m$—H, —$(CH_2)_m$—OC(=O)—$(CH_2)_m$—H or tert-butyl; and each $R^9$ is independently triazolyl, tetrazolyl, —$(CR^7R^{7a})_t$—OH, —$(CR^7R^{7a})_m$—C(=O)—$R^8$, —$(CR^7R^{7a})_m$—C(=O)O—$R^8$, —$(CR^7R^{7a})_m$—C(=O)O—$(CR^7R^{7a})_m$—OC(=O)O—$R^8$, —$(CR^7R^{7a})_m$—C(=O)O—$(CR^7R^{7a})_m$—OC(=O)—$R^8$, —$(CR^7R^{7a})_t$—OC(=O)—$R^8$ or —$(CR^7R^{7a})_m$—C(=O)N($R^8$)$_2$, with the proviso that when $R^9$ is —$(CR^7R^{7a})_t$—OH, $R^3$ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl.

In certain embodiments, $R^3$ is $C_{6\text{-}10}$ aryl or 5-6 membered heteroaryl, and optionally each of the heteroaryl and aryl is independently substituted with one or more substituents which are the same or different, wherein the substituent is H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;

each $R^{7a}$ and $R^7$ is independently H, F, Cl, Br, $C_{1\text{-}4}$ alkyl, $C_{1\text{-}4}$ haloalkyl, —$(CH_2)_m$—OH or —$(CH_2)_m$—C(=O)O—$R^8$; and each $R^{8a}$ and $R^8$ is independently H, $C_{1\text{-}4}$ alkyl, $C_{1\text{-}4}$ haloalkyl, amino-$C_{1\text{-}4}$-alkyl, Boc-NH—$C_{1\text{-}4}$-alkyl, $C_{1\text{-}4}$ alkoxy, —$(CH_2)_m$—OH, —$(CH_2)_m$—C(=O)O—$(CH_2)_m$—H or —$(CH_2)_m$—OC(=O)—$(CH_2)_m$—H.

In other embodiments, $R^3$ has one of the following formulae:

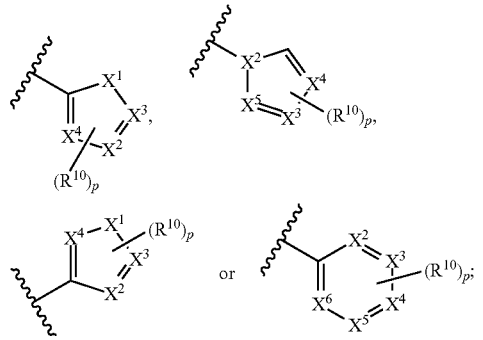

wherein each $X^1$ is independently O, S, $NR^{11}$ or $CR^{12}R^{12a}$;
each $X^2$, $X^3$, $X^4$, $X^5$ and $X^6$ is independently N or $CR^{12}$; wherein at most three or four of the $X^2$, $X^3$, $X^4$, $X^5$ and $X^6$ are N;
each $R^{10}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;
each $R^{11}$ is independently H, methyl, ethyl, propyl, isopropyl, butyl, trifluoromethyl, —$(CR^7R^{7a})_m$—C(=O)N($R^{8a}$)$_2$ or —$(CR^7R^{7a})_m$—C(=O)O—$R^{8a}$;
each $R^{12}$ and $R^{12a}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;

each $R^{7a}$ and $R^7$ is independently H, F, Cl, Br, $C_{1\text{-}4}$ alkyl, —$(CH_2)_m$—OH, $C_{1\text{-}4}$ haloalkyl or —$(CH_2)_m$—C(=O)O—$R^8$;

each $R^{8a}$ and $R^8$ is independently H, $C_{1\text{-}4}$ alkyl, $C_{1\text{-}4}$ haloalkyl, amino-$C_{1\text{-}4}$-alkyl, Boc-NH—$C_{1\text{-}4}$-alkyl, $C_{1\text{-}4}$ alkoxy, —$(CH_2)_m$—OH, —$(CH_2)_m$—C(=O)O—$(CH_2)_m$—H or —$(CH_2)_m$—OC(=O)—$(CH_2)_m$—H;

each m is independently 0, 1, 2, 3 or 4; and each p is independently 0, 1, 2 or 3.

In other embodiments, $R^3$ has one of the following formulae:

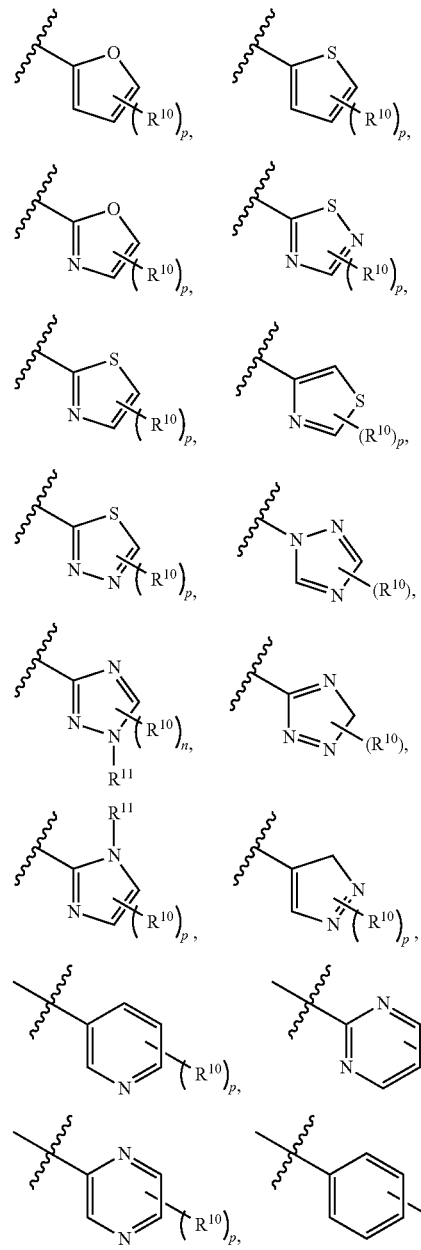

-continued

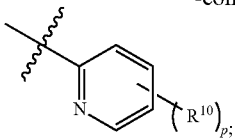

wherein each $R^{10}$ is independently H, F, Cl, methyl, ethyl, cyano, hydroxy, nitro, amino, methoxy, ethoxy, trifluoromethyl, trifluoromethoxy, —(CR$^7$R$^{7a}$)$_m$—C(=O)O—R$^{8a}$, —(CR$^7$R$^{7a}$)$_m$—C(=O)N(R$^{8a}$)$_2$ or trifluoromethylsulfonyl;

each $R^{11}$ is independently H, methyl, ethyl, propyl, isopropyl, butyl, trifluoromethyl or —(CR$^7$R$^{7a}$)$_m$—C(=O)O—R$^{8a}$;

each $R^{7a}$ and $R^7$ is independently H, methyl, ethyl, —(CH$_2$)$_m$—OH, —(CH$_2$)$_m$—C(=O)O—R$^8$ or propyl;

each $R^8$ and $R^{8a}$ is independently H, methyl, ethyl, propyl, isopropyl, butyl, 2-methylpropyl, 1-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —(CH$_2$)$_m$—OH, —(CH$_2$)$_m$—C(=O)O—(CH$_2$)$_m$—H, —(CH$_2$)$_m$—OC(=O)—(CH$_2$)$_m$—H or tert-butyl; and each p is independently 0, 1, 2 or 3.

In certain embodiments, $R^1$ is $C_{6-10}$ aryl, and the aryl is independently substituted with one or more substituents which are the same or different, wherein the substituent is H, F, Cl, Br, cyano, methyl, ethyl, methoxy, ethoxy, methylamino, ethylamino, nitro, 4-(trifluoromethyl)phenyl, 3,5-bis(trifluoromethyl)phenyl or trifluoromethyl;

$R^2$ is H, or $C_{1-4}$ alkyl; and
$R^5$ is H, or $C_{1-4}$ alkyl.

In other embodiments, $R^1$ is phenyl or a phenyl substituted with one or more substituents which are the same or different, wherein the substituent is H, F, Cl, Br, nitro, 4-(trifluoromethyl)phenyl, 3,5-bis(trifluoromethyl)phenyl or trifluoromethyl.

In certain embodiments, Formula (IV) or (IVa) is

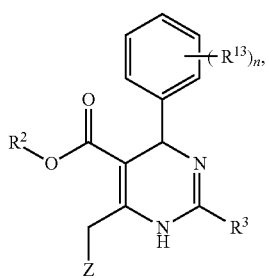

(IV)

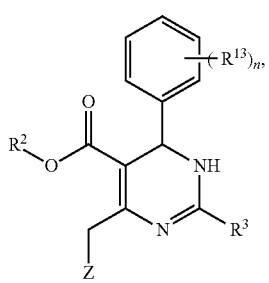

(IVa)

or an enantiomer, a diastereoisomer, a tautomer, a hydrate, a solvate, or a pharmaceutically acceptable salt thereof, wherein Z has Formula (II) or (IIa):

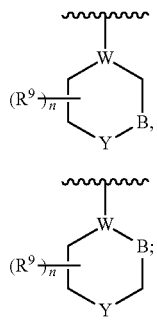

wherein each B is a bond or —(CR$^7$R$^{7a}$)$_m$—;
each W is CR$^7$ or N;
each Y is —(CR$^7$R$^{7a}$)$_m$, —O—, —S—, —S(=O)$_q$— or —NR$^6$—;
each $R^2$ is H, or $C_{1-4}$ alkyl;
each $R^3$ is $C_{6-10}$ aryl or 5-6 membered heteroaryl, and optionally each of the heteroaryl and aryl is independently substituted with one or more substituents which are the same or different, wherein the substituent is H, F, Cl, methyl, ethyl, propyl, cyano, trifluoromethyl, methoxy, —(CR$^7$R$^{7a}$)$_m$—C(=O)N(R$^{8a}$)$_2$ or —(CR$^7$R$^{7a}$)$_m$—C(=O)O—R$^{8a}$;
each $R^6$ is $C_{1-4}$ alkyl;
each $R^{7a}$ and $R^7$ is independently H, —(CH$_2$)$_m$—OH, —(CH$_2$)$_m$—C(=O)O—R$^8$ or $C_{1-4}$ alkyl;
each $R^8$ and $R^{8a}$ is independently H, amino-$C_{1-4}$-alkyl, Boc-NH—$C_{1-4}$-alkyl, $C_{1-4}$ alkoxy, —(CH$_2$)$_m$—OH, —(CH$_2$)$_m$—C(=O)O—(CH$_2$)$_m$—H, —(CH$_2$)$_m$—OC(=O)—(CH$_2$)$_m$—H or $C_{1-6}$ alkyl;
each $R^9$ is independently triazolyl, tetrazolyl, —(CR$^7$R$^{7a}$)$_t$—OH, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)—R$^8$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OC(=O)—R$^8$ or —(CR$^7$R$^{7a}$)$_m$—C(=O)N(R$^8$)$_2$, with the proviso that when $R^9$ is —(CR$^7$R$^{7a}$)$_t$—OH, $R^3$ is $C_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each $R^{13}$ is independently H, F, Cl, Br, cyano, nitro, 4-(trifluoromethyl)phenyl, 3,5-bis(trifluoromethyl)phenyl or trifluoromethyl;
each n is independently 1 or 2;
each t is independently 1, 2, 3 or 4;
each m is independently 0, 1, 2, 3 or 4; and
each q is independently 0, 1 or 2.

In certain embodiments, Z has Formula (II) or (IIa):

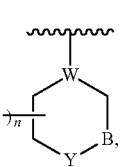

-continued

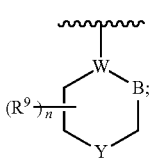
(IIa)

wherein each B is a bond or —(CR$^7$R$^{7a}$)$_m$—;
each W is CR$^7$ or N;
each Y is —(CR$^7$R$^{7a}$)$_m$—, —O—, —S—, —S(=O)$_q$— or —NR$^6$—;
each R$^6$ is methyl, ethyl or propyl;
each R$^{7a}$ and R$^7$ is independently H, methyl, —(CH$_2$)$_m$—OH, —(CH$_2$)$_m$—C(=O)O—R$^8$, ethyl or propyl;
each R$^8$ is independently H, methyl, ethyl, propyl, isopropyl, butyl, 1-methylpropyl, 2-methylpropyl, tert-butyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —(CH$_2$)$_m$—OH, —(CH$_2$)$_m$—C(=O)O—(CH$_2$)$_m$—H or —(CH$_2$)$_m$—OC(=O)—(CH$_2$)$_m$—H;
each R$^{8a}$ is independently H, methyl, ethyl, isopropyl or propyl;
each R$^9$ is independently —(CR$^7$R$^{7a}$)$_t$—OH, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OC(=O)—R$^8$, triazolyl, tetrazolyl or —(CR$^7$R$^{7a}$)$_m$—C(=O)N(R$^8$)$_2$, with the proviso that when R$^9$ is —(CR$^7$R$^{7a}$)$_t$—OH, R$^3$ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each m is independently 0, 1, 2, 3 or 4; and
each t is independently 1, 2, 3 or 4.

In other embodiments, Z is:

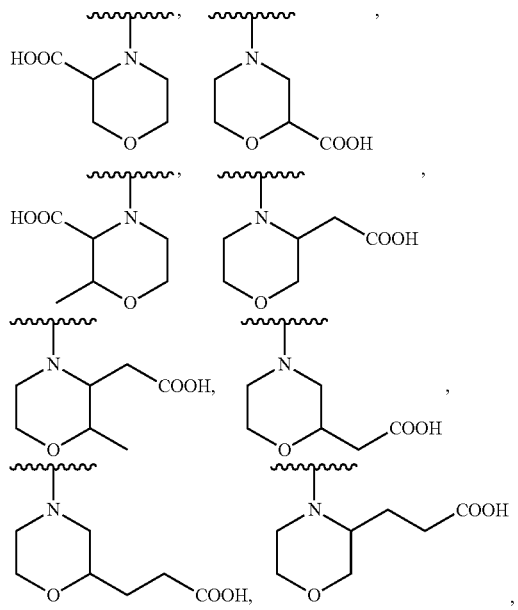

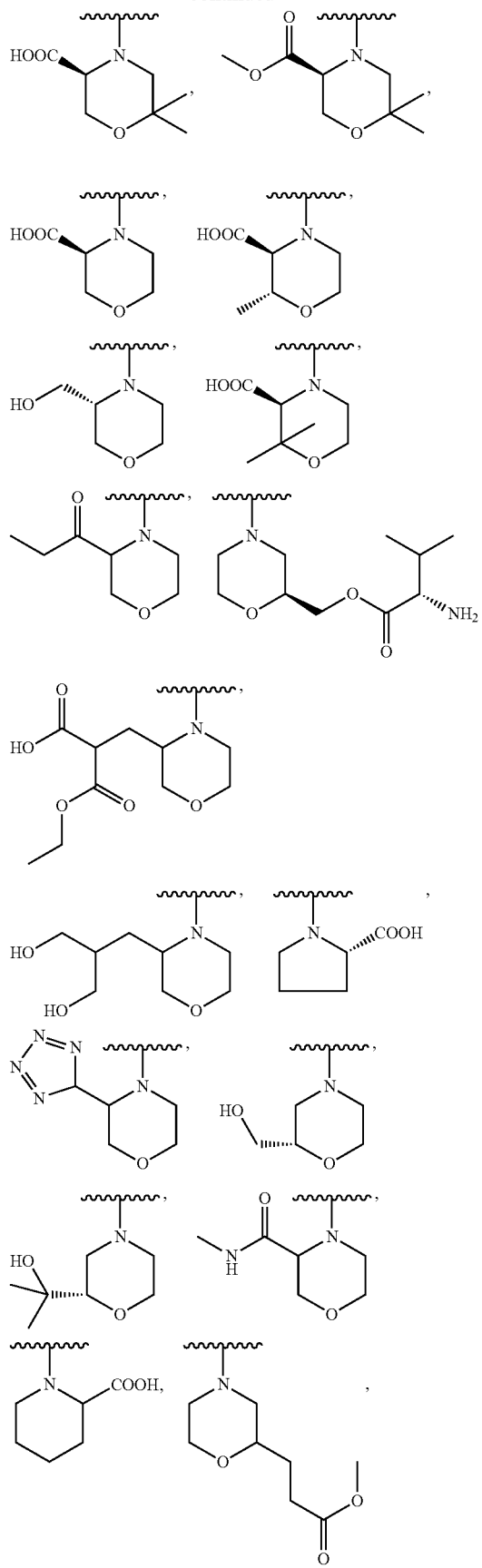

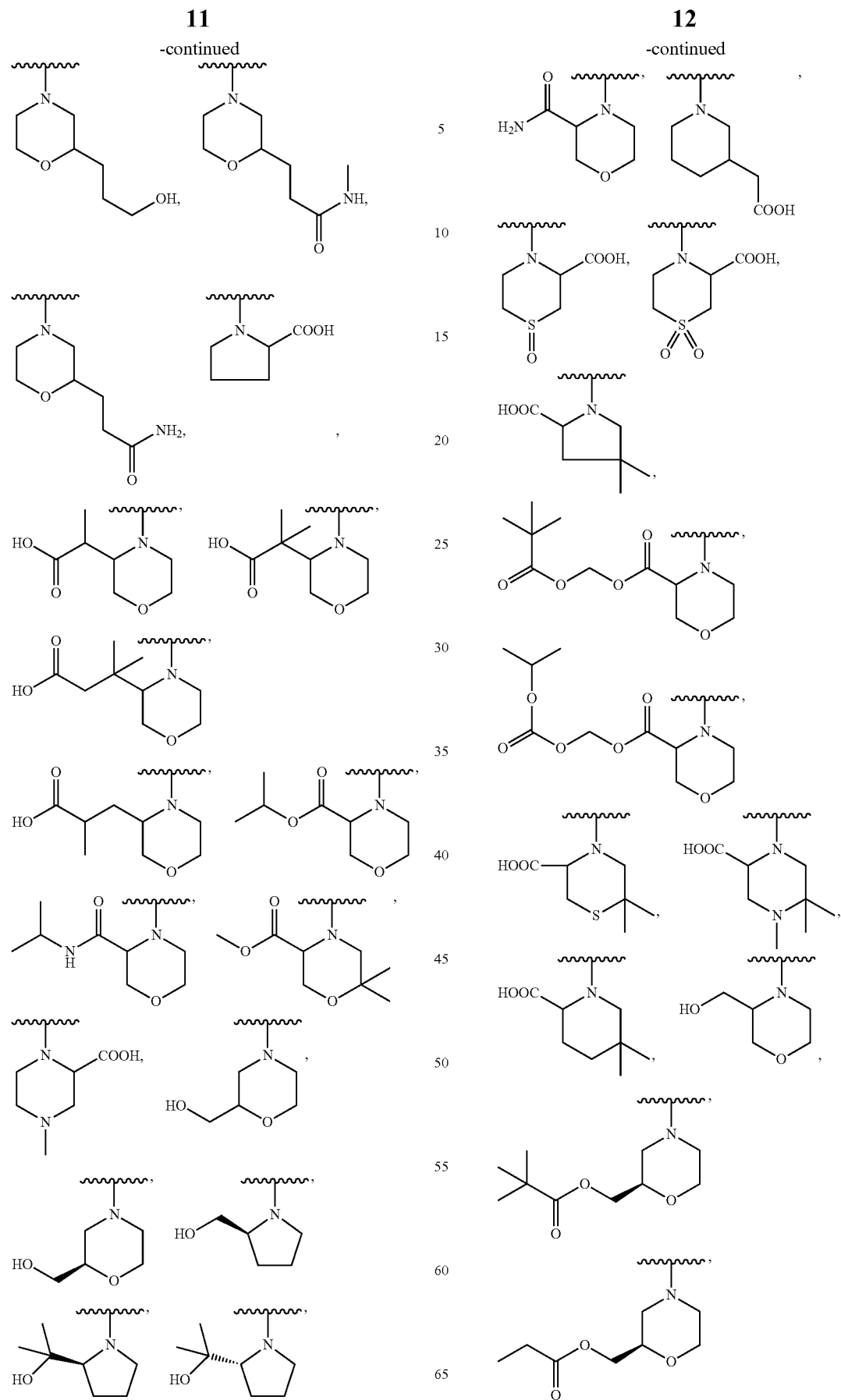

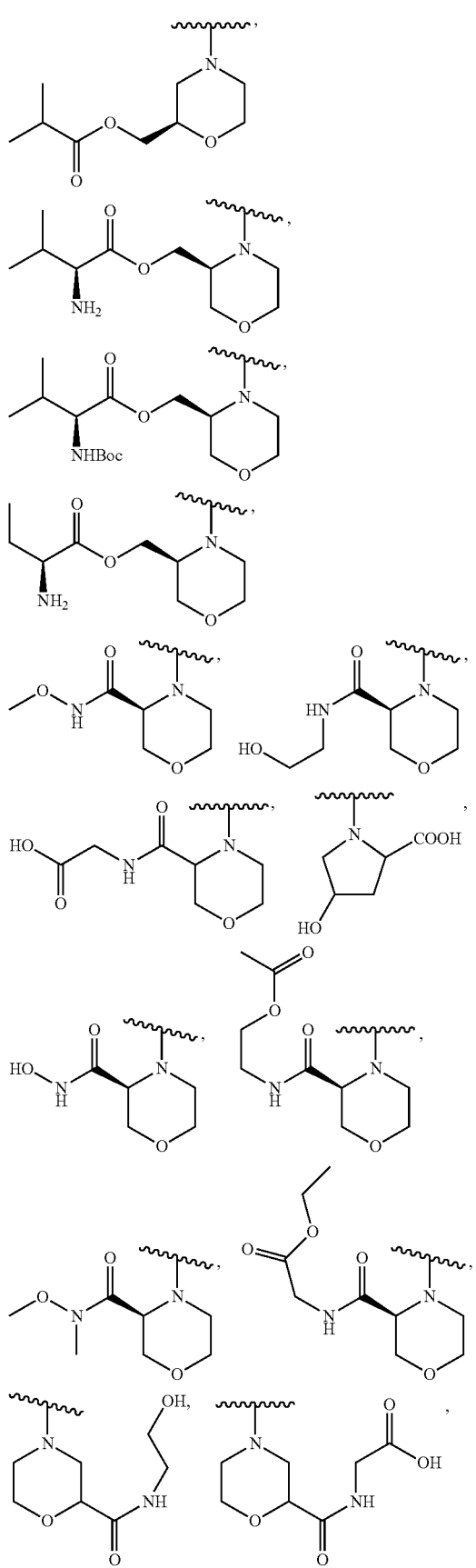
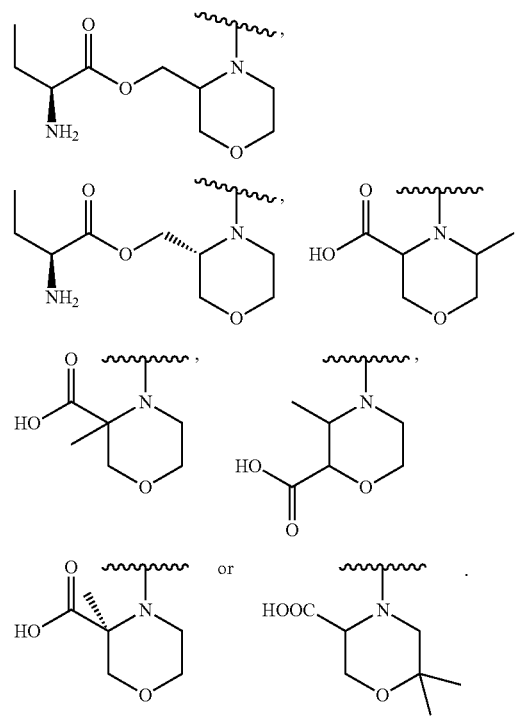
In certain embodiments, each R³ is independently:
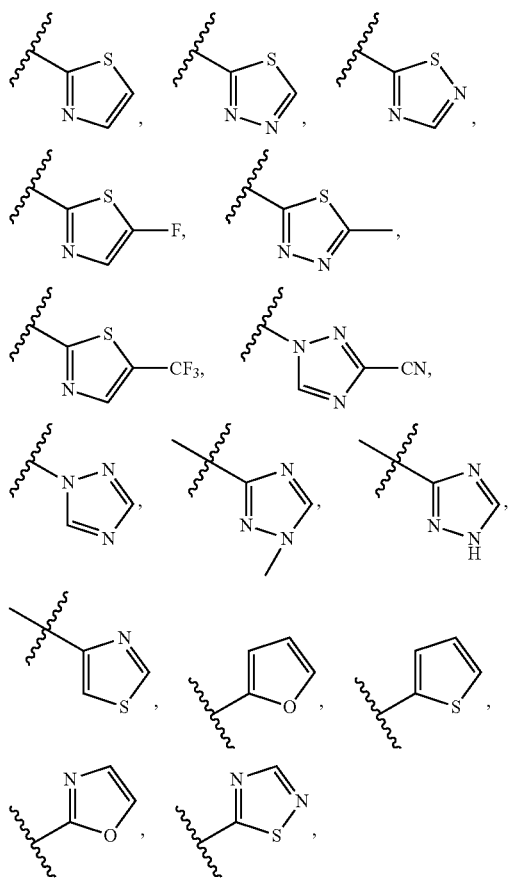

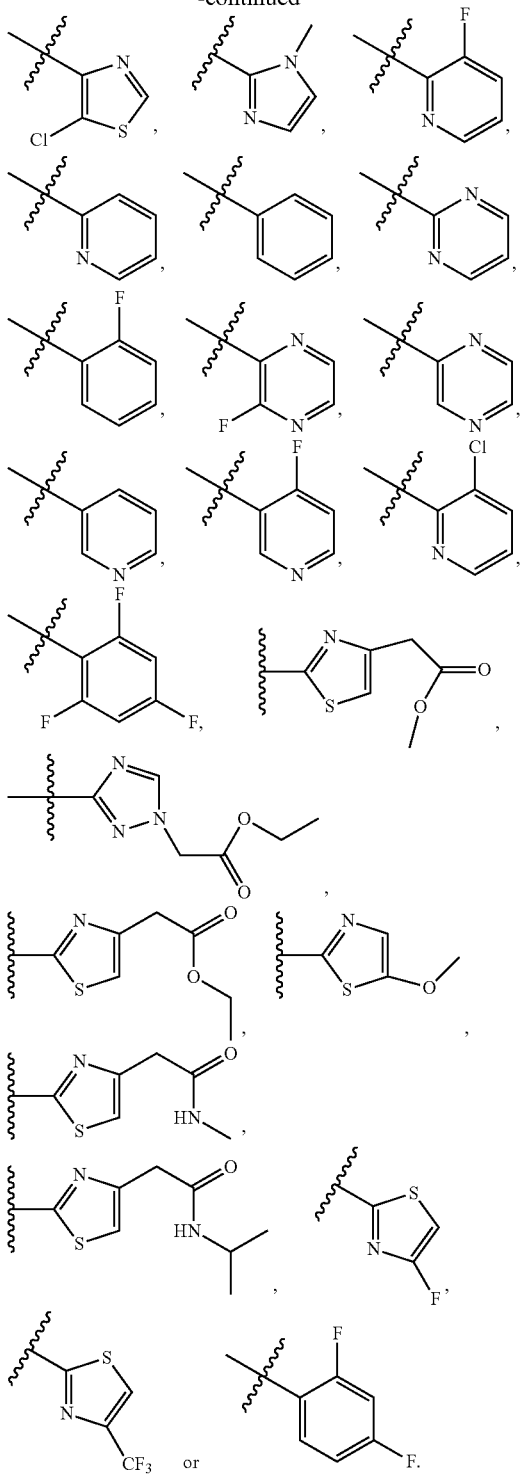

In one aspect, provided herein are compounds and a pharmaceutically acceptable carrier, excipient, diluent, adjuvant, vehicle or a combination thereof.

In certain embodiments, provided herein is the pharmaceutical composition further comprising an anti-HBV agent.

In certain embodiments, the pharmaceutical composition disclosed herein,
wherein the anti-HBV agent is a HBV polymerase inhibitor, immunomodulator or interferon.

In certain embodiments, the pharmaceutical composition disclosed herein, wherein the anti-HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxamide, peginterferon alfa-2a, ribavirin, roferon-A, sizofuran, euforavac, rintatolimod, phosphazid, heplisav, interferon α-2b, levamisole, or propagermanium.

In another aspect, provided herein is use of the compound or the pharmaceutical composition in the manufacture of a medicament for preventing, managing, treating or lessening a viral disease or a HBV disease in a patient.

In certain embodiments, the use is disclosed herein, wherein the viral disease or HBV disease is hepatitis B infection or a disease caused by hepatitis B infection.

In other embodiments, the use is disclosed herein, wherein the disease caused by hepatitis B infection is cirrhosis or hepatocellular carcinoma.

In another aspect, provided herein is use of the compound or the pharmaceutical composition in the manufacture of a medicament for preventing, managing, treating or lessening a viral disease or a HBV disease in a patient, comprising administering to the patient a therapeutically effective amount of the compound or the composition disclosed herein.

In another aspect, provided herein are methods for preventing, managing, treating or lessening a viral disease or a HBV disease in a patient, which comprises administering a pharmaceutically effective amount of the compound disclosed herein to the patient.

In another aspect, provided herein are methods for preventing, managing, treating or lessening a viral disease or a HBV disease in a patient, which comprises administering a pharmaceutically effective amount of the pharmaceutical composition disclosed herein to the patient.

In another aspect, provided herein is use of the compound disclosed herein in the manufacture of a medicament for preventing, managing or treating a viral disease or a HBV disease and lessening the severity of a viral disease or a HBV disease in a patient.

In another aspect, provided herein is use of the pharmaceutical composition comprising the compound disclosed herein in the manufacture of a medicament for preventing, managing or treating a viral disease or a HBV disease and lessening the severity of a viral disease or a HBV disease in a patient.

In some embodiments, the organism is a mammal; in other embodiments, the organism is a human. In still other embodiments, the method further comprises contacting the kinase with a HBV therapeutic agent.

In another aspect, provided herein is a method of inhibiting HBV infection, comprising contacting the cell with an effective HBV inhibiting amount of a compound disclosed herein or a composition thereof. In other embodiments, the method further comprises contacting the cell with a HBV therapeutic agent.

In another aspect, provided herein is a method of treating HBV disease in a patient, the method comprises administering to the patient in need of such treatment an effective therapeutic amount of a compound disclosed herein or a composition thereof. In other embodiments, the method further comprises administering a HBV therapeutic agent.

In another aspect, provided herein is a method of inhibiting HBV infection in a patient, the method comprises administering to the patient in need of an effective therapeutic amount of a compound disclosed herein or a composition thereof. In other embodiments, the method further comprises administering a HBV therapeutic agent.

In another aspect, provided herein include methods of preparing, methods of separating, and methods of purifying compounds of Formula (I) or (Ia).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the *Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

As described herein, compounds may optionally be substituted with one or more substituents, such as those illustrated above, or as exemplified by particular classes, subclasses, and species disclosed herein. In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents include, but are not limited to, hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, hydroxy-substituted alkyl, cycloalkyl, cycloalkylalkyl, alkoxycarbonyl, haloalkyl-substituted aryl, halogen-substituted aryl, —(CR$^7$R$^{7a}$)$_m$—C(=O)N(R$^{8a}$)$_2$, —(CR$^7$R$^{7a}$)$_m$—C(=O)O—R$^8$, —(CR$^7$R$^{7a}$)$_m$—C(=O)R$^8$, —(CR$^7$R$^{7a}$)$_m$—C(=O)—(CR$^7$R$^{7a}$)$_m$—OH, —(CR$^7$R$^{7a}$)$_t$—OC(=O)—R$^8$, —(CR$^7$R$^{7a}$)$_m$—C(=O)—(CR$^7$R$^{7a}$)$_m$—O—(CR$^7$R$^{7a}$)$_m$—O—R$^8$, —(CR$^7$R$^{7a}$)$_m$—C(=O)—(CR$^7$R$^{7a}$)$_m$—N(R$^7$R$^{7a}$), —(CR$^7$R$^{7a}$)$_m$—S(=O)$_q$—R$^8$, —(CR$^7$R$^{7a}$)$_m$—OS(=O)$_q$—R$^8$, —(CR$^7$R$^{7a}$)$_m$—S(=O)$_q$O—R$^8$, —(CR$^7$R$^{7a}$)$_m$—C(=O)O—R$^{8a}$, —(CH$_2$)$_m$—OH, —(CH$_2$)$_m$—C(=O)O—(CH$_2$)$_m$—H, —(CH$_2$)$_m$—OC(=O)—(CH$_2$)$_m$—H, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OH, —(CR$^7$R$^{7a}$)$_m$—C(=O)O—(CR$^7$R$^{7a}$)$_m$—C(=O)O—R$^8$ or —(CR$^7$R$^{7a}$)$_m$—C(=O)N(R$^8$)$_2$, and the like. Each R$^7$, R$^{7a}$, R$^8$, R$^{8a}$, m, q and t is as disclosed herein.

The term "alkyl" refers to a saturated linear or branched chain monovalent hydrocarbon radical of 1-20 carbon atoms, wherein the alkyl radical may be optionally substituted independently with one or more substituents described herein. In some embodiments, alkyl groups contain 1-10 carbon atoms. In other embodiments, alkyl groups contain 1-8 carbon atoms. In still other embodiments, alkyl groups contain 1-6 carbon atoms, and in yet other embodiments, alkyl groups contain 1-4 carbon atoms. In other embodiments, alkyl groups contain 1-3 carbon atoms. Further examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl or isobutyl (1-Bu, i-butyl, —CH$_2$CH(CH$_3$)$_2$), 1-methylpropyl or sec-butyl (s-Bu, s-butyl, —CH(CH$_3$)CH$_2$CH$_3$), 2-methyl-2-propyl or tert-butyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like. The terms "alkyl" and the prefix "alk-" are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "haloaliphatic" or "haloalkyl" refers to an aliphatic radical or alkyl radical substituted with one or more halogen atoms (i.e., F, Cl, Br or I), which may be either the same or different. Some non-limiting examples of such radicals include trifluoromethyl and trifluoroethyl.

The term "hydroxyaliphatic", "—(CR$^7$R$^{7a}$)$_t$—OH", "—(CR$^7$R$^{7a}$)$_m$—OH", "hydroxy-substituted alkyl" or "hydroxyalkyl" refers to an aliphatic radical or alkyl radical substituted with one or more hydroxy groups, wherein each t, m, aliphatic and alkyl is as defined above. Some non-limiting examples include hydroxyethyl, 2-hydroxypropyl, hydroxymethyl, and the like.

The term "alkenyl" refers to a linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Some non-limiting examples include ethenyl or vinyl (—CH=CH$_2$), allyl (—CH$_2$CH=CH$_2$), and the like.

The term "alkynyl" refers to a linear or branched-chain monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Specific examples include, but are not limited to, ethynyl (—C≡CH), propynyl (propargyl, —CH$_2$C≡CH), and the like.

The term "cycloaliphatic", "carbocycle", "carbocyclyl" or "cycloalkyl" refers to a monovalent or multivalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. And the term "cycloaliphatic", "carbocycle", "carbocyclyl" or "cycloalkyl" may be substituted or unsubstituted, wherein the substituent may be, but is not limited to, hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, cycloalkyl, cycloalkylalkyl, alkoxycarbonyl, hydroxy-substituted alkyl, haloalkyl-substituted aryl, halogen-substituted aryl, —(CR$^7$R$^{7a}$)$_m$—C(=O)N(R$^{8a}$)$_2$, —(CR$^7$R$^{7a}$)$_m$—C(=O)O—R$^8$, —(CR$^7$R$^{7a}$)$_m$—C(=O)R$^8$, —(CR$^7$R$^{7a}$)$_m$—C(=O)—(CR$^7$R$^{7a}$)$_m$—OH, —(CH$_2$)$_m$—OH, —(CH$_2$)$_m$—C(=O)O—(CH$_2$)$_m$—H, —(CH$_2$)$_m$—OC(=O)—(CH$_2$)$_m$—H, —(CR$^7$R$^{7a}$)$_t$—OC(=O)—R$^8$, —(CR$^7$R$^{7a}$)$_m$—C(=O)—(CR$^7$R$^{7a}$)$_m$—O—(CR$^7$R$^{7a}$)$_m$—O—R$^8$, —(CR$^7$R$^{7a}$)$_m$—C(=O)—(CR$^7$R$^{7a}$)$_m$—N(R$^7$R$^{7a}$), —(CR$^7$R$^{7a}$)$_m$—S(=O)$_q$—R$^8$, —(CR$^7$R$^{7a}$)$_m$—OS(=O)$_q$—R$^8$, —(CR$^7$R$^{7a}$)$_m$—S(=O)$_q$O—R$^8$, —(CR$^7$R$^{7a}$)$_m$—C(=O)O—R$^{8a}$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OH, —(CR$^7$R$^{7a}$)$_m$—C(=O)O—(CR$^7$R$^{7a}$)$_m$—C(=O)O—R$^8$ or —(CR$^7$R$^{7a}$)$_m$—C(=O)N(R$^8$)$_2$, and the like. Each R$^7$, R$^{7a}$, R$^8$, m, R$^{8a}$, q and t is as disclosed herein.

The term "heterocycle", "heterocyclyl", "heterocycloaliphatic" or "heterocyclic" as used interchangeably herein refers to a monocyclic, bicyclic or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described below. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "Heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidyl, morpholinyl, thiomorpholinyl, thioxanyl, piperazinyl, homopiperazinyl, azetidinyl, oxetanyl, thietanyl, homopiperidinyl, epoxypropyl, azepanyl, oxepanyl, thiepanyl, oxazepinyl, diazepinyl, thiazepinyl, 2-pyrrolinyl, 3-pyrrolinyl, dihydroindolinyl, 2H-pyranyl, 4H-pyranyl, dioxolanyl, 1,3-dioxopentyl, pyrazolinyl, dithianyl, dithiolanyl, dihydrothienyl, pyrazolidinylimidazolinyl, imidazolidinyl, 1,2,3,4-tetrahydroisoquinolinyl, 3-azabicyclo[3,1,0]hexyl, 3-azabicyclo[4,1,0]heptyl, azabicyclo[2,2,2]hexyl, 3H-indolylquinolizinyl and N-pyridyl urea. Further examples of heterocyclyl groups include 1,1-dioxothiomorpholinyl and heterocyclic group wherein 2 carbon atoms on the ring are substituted with oxo (=O) moieties are pyrimidindionyl. And the heterocyclyl disclosed herein, may be substituted or unsubstituted, wherein the substituents include, but are not limited to, hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, hydroxy-substituted alkyl, cycloalkyl, cycloalkylalkyl, alkoxycarbonyl, haloalkyl-substituted aryl, halogen-substituted aryl, —(CR$^7$R$^{7a}$)$_m$—C(=O)N(R$^{8a}$)$_2$, —(CR$^7$R$^{7a}$)$_m$—C(=O)O—R$^8$, —(CR$^7$R$^{7a}$)$_m$—C(=O)R$^8$, —(CR$^7$R$^{7a}$)$_m$—C(=O)—(CR$^7$R$^{7a}$)$_m$—OH, —(CR$^7$R$^{7a}$)$_t$—OC(=O)—R$^8$, —(CR$^7$R$^{7a}$)$_m$—C(=O)—(CR$^7$R$^{7a}$)$_m$—O—(CR$^7$R$^{7a}$)$_m$—O—R$^8$, —(CR$^7$R$^{7a}$)$_m$—C(=O)—(CR$^7$R$^{7a}$)$_m$—N(R$^7$R$^{7a}$), —(CR$^7$R$^{7a}$)$_m$—S(=O)$_q$—R$^8$, —(CR$^7$R$^{7a}$)$_m$—OS(=O)$_q$—R$^8$, —(CR$^7$R$^{7a}$)$_m$—S(=O)$_q$O—R$^8$, —(CR$^7$R$^{7a}$)$_m$—C(=O)O—R$^{8a}$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OH, —(CH$_2$)$_m$—OH, —(CH$_2$)$_m$—C(=O)O—(CH$_2$)$_m$—H, —(CH$_2$)$_m$—OC(=O)—(CH$_2$)$_m$—H, —(CR$^7$R$^{7a}$)$_m$—C(=O)O—(CR$^7$R$^{7a}$)$_m$—C(=O)O—R$^8$ or —(CR$^7$R$^{7a}$)$_m$—C(=O)N(R$^8$)$_2$, and the like, wherein each R$^7$, R$^{7a}$, R$^8$, R$^{8a}$, m, q and t is as disclosed herein.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. Wherein the heterocyclyl, alkyl, alkoxy and alkylamino group are as defined herein. Some non-limiting examples include pyrrol-2-ylmethyl, morpholin-4-ylmethyl, pyrrol-2-ylmethoxy, piperidin-2-ylethoxy, piperazin-2-ylethylamino, morpholin-4-ylpropoxy, morpholin-4-ylethylamino, and the like.

The term "heteroatom" refers to one or more of oxygen, sulfur, nitrogen, phosphorus or silicon, including any oxidized form of nitrogen, sulfur or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to that a moiety has one or more units of unsaturation.

The term "alkoxy" as used herein, refers to an alkyl group, as previously defined, attached to the principal carbon chain through an oxygen atom ("alkoxy").

The term "haloalkyl", "haloalkenyl" or "haloalkoxy" refers to alkyl, alkenyl or alkoxy, as the case may be, substituted with one or more halogen atoms. Some non-limiting examples of such radicals include trifluoromethyl, trifluoromethoxy, 2-fluoro-vinyl, and the like.

The term "aryl" used alone or as part of a larger moiety as in "aralkyl", "aralkoxy" or "aryloxyalkyl" refers to monocyclic, bicyclic and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl and anthryl. The aryl may be substituted or unsubstituted, wherein the substituents include, but are not limited to, hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, hydroxy-substituted alkyl, cycloalkyl, cycloalkylalkyl, alkoxycarbonyl, haloalkyl-substituted aryl, halogen-substituted aryl, $-(CR^7R^{7a})_m-C(=O)N(R^{8a})_2$, $-(CR^7R^{7a})_m-C(=O)O-R^8$, $-(CR^7R^{7a})_m-C(=O)R^8$, $-(CR^7R^{7a})_m-C(=O)-(CR^7R^{7a})_m-OH$, $-(CR^7R^{7a})_m-C(=O)-(CR^7R^{7a})_m-O-(CR^7R^{7a})_m-O-R^8$, $-(CR^7R^{7a})_m-C(=O)-(CR^7R^{7a})_m-N(R^7R^{7a})$, $-(CR^7R^{7a})_m-S(=O)_q-R^8$, $-(CR^7R^{7a})_m-OS(=O)_q-R^8$, $-(CR^7R^{7a})_m-S(=O)_qO-R^8$, $-(CR^7R^{7a})_m-C(=O)OR^{8a}$, $-(CR^7R^{7a})_m-C(=O)O-(CR^7R^{7a})_m-OC(=O)O-R^8$, $-(CR^7R^{7a})_t-OH$, $-(CR^7R^{7a})_m-C(=O)O-(CR^7R^{7a})_m-OC(=O)-R^8$, $-(CH_2)_m-OH$, $-(CH_2)_m-C(=O)O-(CH_2)_m-H$, $-(CH_2)_m-OC(=O)-(CH_2)_m-H$, $-(CR^7R^{7a})_t-OC(=O)-R^8$, $-(CR^7R^{7a})_m-C(=O)O-(CR^7R^{7a})_m-C(=O)O-R^8$ or $-(CR^7R^{7a})_m-C(=O)N(R^8)_2$, and the like, wherein each $R^7$, $R^{7a}$, $R^8$, $R^{8a}$, m, q and t is as disclosed herein.

The term "heteroaryl" used alone or as part of a larger moiety as in "heteroarylalkyl" or "heteroarylalkoxy" refers to monocyclic, bicyclic and tricyclic ring systems having a total of five to fourteen ring members, wherein at least one ring in the system is aromatic, and at least one ring in the system is inclusive of one or more heteroatoms as described herein, wherein each ring in the system contains 3 to 7 ring members and that has a single point of attachment to the rest of the molecule. The term "heteroaryl" may be used interchangeably with the term "heteroaryl ring" or "heteroaromatic compound". The heteroaryl defined herein may be substituted or unsubstituted, wherein the substituents include, but are not limited to, hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, hydroxy-substituted alkyl, cycloalkyl, cycloalkylalkyl, alkoxycarbonyl, haloalkyl-substituted aryl, halogen-substituted aryl, $-(CR^7R^{7a})_m-C(=O)N(R^{8a})_2$, $-(CR^7R^{7a})_m-C(=O)-(CR^7R^{7a})_m-OH$, $-(CR^7R^{7a})_t-OC(=O)-R^8$, $-(CR^7R^{7a})_m-C(=O)-(CR^7R^{7a})_m-O-(CR^7R^{7a})_m-O-R^8$, $-(CR^7R^{7a})_m-C(=O)-(CR^7R^{7a})_m-N(R^7R^{7a})$, $-(CR^7R^{7a})_m-S(=O)_q-R^8$, $-(CR^7R^{7a})_m-OS(=O)_q-R^8$, $-(CR^7R^{7a})_m-S(=O)_qO-R^8$, $-(CR^7R^{7a})_m-C(=O)-R^8$, $-(CR^7R^{7a})_m-C(=O)O-R^8$, $-(CR^7R^{7a})_m-C(=O)OR^{8a}$, $-(CR^7R^{7a})_m-C(=O)O-(CR^7R^{7a})_m-OC(=O)O-R^8$, $-(CH_2)_m-OH$, $-(CH_2)_m-C(=O)O-(CH_2)_m-H$, $-(CH_2)_m-OC(=O)-(CH_2)_m-H$, $-(CR^7R^{7a})_m-C(=O)O-(CR^7R^{7a})_m-OC(=O)-R^8$, $-(CR^7R^{7a})_t-OH$, $-(CR^7R^{7a})_m-C(=O)O-(CR^7R^{7a})_m-C(=O)O-R^8$ or $-(CR^7R^{7a})_m-C(=O)N(R^8)_2$, and the like, wherein each $R^7$, $R^{7a}$, $R^8$, $R^{8a}$, m, q and t is as disclosed herein.

In other embodiments, some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyranyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, diazolyl, thiadiazolyl, triazinyl; and the following bicycles: benzothiazolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl or 4-isoquinolinyl), and the like.

The term "heteroarylalkyl" refers to alkyl radicals substituted with one or more heteroaryl radicals, wherein the alkyl and heteroaryl groups are as defined herein. Some non-limiting examples of such radicals include pyridin-2-ylethyl, thiazol-2-ylmethyl, imidazol-2-ylethyl, pyrimidin-2-ylpropyl, and the like.

The term "sulfonyl", whether used alone or linked to other terms such as "alkylsulfonyl", refers to respectively divalent radicals $-SO_2-$. The term "alkylsulfonyl", refers to a sulfonyl radical substituted with an alkyl radical, forming an alkylsulfonyl ($-SO_2CH_3$).

The term "sulfamyl", "aminosulfonyl" or "sulfonamidyl" refers to a sulfonyl radical substituted with an amine radical, forming a sulfonamide ($-SO_2NH_2$).

The term "carboxy" or "carboxyl", whether used alone or with other terms, such as "carboxyalkyl", refers to $-CO_2H$. The term "carbonyl", whether used alone or with other terms, such as "aminocarbonyl" or "carbonyloxy", refers to $-(C=O)-$.

The term "alkylthio" refers to radicals containing a linear or branched-alkyl radical of one to ten carbon atoms, attached to a divalent sulfur atom. In other embodiments, alkylthio radicals are lower alkylthio radicals having one to three carbon atoms. Some non-limiting examples of "alkylthio" include methylthio ($CH_3S-$), ethylthio ($CH_3CH_2S-$), and the like.

The term "aralkyl" or "arylalkyl" refers to aryl-substituted alkyl radicals. In some embodiments, aralkyl radicals or arylalkyl radicals are "lower aralkyl" radicals having aryl radicals attached to alkyl radicals having one to six carbon atoms. In other embodiments, aralkyl radicals or arylalkyl radicals are "phenylalkylenyl" attached to alkyl portions having one to three carbon atoms. Some non-limiting examples of such radicals include benzyl, diphenylmethyl and phenylethyl. And the aryl in said aralkyl can be additionally substituted with hydroxy, amino, halo, cyano, trifluoromethoxy, aralkyl, heteroarylalkyl, haloalkyl, heterocyclylalkyl, alkylamino, trifluoromethylsulfonyl, aryl, heteroaryl, alkoxy, alkyl, alkenyl, alkynyl, heterocyclyl, mercapto, nitro, aryloxy, hydroxy-substituted alkyl, cycloalkyl, cycloalkylalkyl, alkoxycarbonyl, haloalkyl-substituted aryl, halogen-substituted aryl, $-(CR^7R^{7a})_m-C(=O)N(R^{8a})_2$, $-(CR^7R^{7a})_t-OC(=O)-R^8$, $-(CR^7R^{7a})_m-C(=O)-(CR^7R^{7a})_m-OH$, $-(CR^7R^{7a})_m-C(=O)-(CR^7R^{7a})_m-O-(CR^7R^{7a})_m-O-R^8$, $-(CH_2)_m-OH$, $-(CH_2)_m-C(=O)O-(CH_2)_m-H$, $-(CH_2)_m-OC(=O)-(CH_2)_m-H$, $-(CR^7R^{7a})_m-C(=O)-(CR^7R^{7a})_m-N(R^7R^{7a})$, $-(CR^7R^{7a})_m-S(=O)_q-R^8$, $-(CR^7R^{7a})_m-OS(=O)_q-R^8$, $-(CR^7R^{7a})_m-S(=O)_qO-R^8$, $-(CR^7R^{7a})_m-C(=O)-R^8$, $-(CR^7$ $R^{7a})_m$—C(=O)O—$R^{8a}$, —$(CR^7R^{7a})_m$—C(=O)O—$R^8$, —$(CR^7R^{7a})_m$—C(=O)O—$(CR^7R^{7a})_m$—OC(=O)O—$R^8$, —$(CR^7R^{7a})_t$—OH, —$(CR^7R^{7a})_m$—C(=O)O—$(CR^7R^{7a})_m$—OC(=O)—$R^8$, —$(CR^7R^{7a})_m$—C(=O)O—$(CR^7R^{7a})_m$—C(=O)O—$R^8$ or —$(CR^7R^{7a})_m$—C(=O)N$(R^8)_2$, and the like, wherein each $R^7$, $R^{7a}$, $R^8$, $R^{8a}$, m, q and t is as disclosed herein.

The term "alkylamino" refers to "N-alkylamino" and "N,N-dialkylamino" wherein amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "aminoalkyl" refers to a linear or branched-alkyl radical having one to ten carbon atoms, substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl or aminohexyl.

The term "alkoxycarbonyl" refers to alkyl-O—C(=O)—, wherein the alkyl is as defined herein. In some embodiments, alkyl radicals in alkoxycarbonyl are "lower alkyl" radicals having one to six carbon atoms. Some non-limiting examples of such radicals include methoxycarbonyl, ethoxycarbonyl and propoxycarbonyl.

The term "carboxyalkyl" refers to a linear or branched-alkyl radical having one to ten carbon atoms, substituted with one or more carboxy radicals. Some non-limiting examples of such radicals include carboxymethyl, carboxypropyl, and the like.

The term "haloalkyl-substituted aryl" refers to aryl radicals substituted with one or more haloalkyl radicals. Some non-limiting examples of such radicals include 2-trifluoromethylphenyl, 3,5-bis(trifluoromethyl)phenyl, 3-trifluoromethylphenyl, 4-trifluoromethylphenyl, 2,6-bis(trifluoromethyl)phenyl, and the like.

The term "halogen-substituted aryl" refers to an aryl substituted with one or more halogen atoms. Some non-limiting examples of such radicals include fluorophenyl, difluorophenyl, trifluorophenyl, chlorophenyl, dichlorophenyl, trichlorophenyl, bromophenyl, tribromophenyl, dibromophenyl, fluorochlorophenyl, fluorobromophenyl, chorobromophenyl, and the like.

The term "cycloalkylalkyl" refers to alkyl radicals substituted with one or more cycloalkyl radicals, wherein cycloalkyl and alkyl are as defined herein. Some non-limiting examples of such radicals include cyclohexylmethyl and cyclopropylethyl. The cycloalkyl in the radicals may be additionally substituted with halo, alkyl, alkoxy or hydroxy.

As described herein, a bond drawn from a substituent to the center of one ring within a ring system (as shown below) represents substitution of the substituent at any substitutable position on the rings. For example, Figure a represents possible substitution in any of the positions on the A ring and B ring, as shown in Figure b; or Figure c represents possible substitution in any of the positions on the ring, as shown in Figure d.

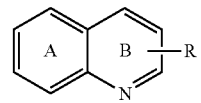
FIG. a

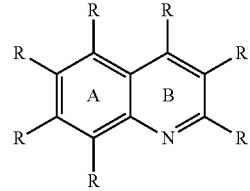
FIG. b

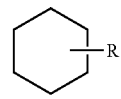
FIG. c

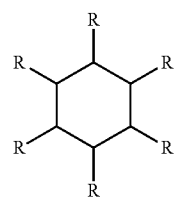
FIG. d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14 of the A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Review Drug Discovery*, 2008, 7, 255-270, and Hecker et al., Prodrugs of Phosphates and Phosphonates, *J Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker, et al., McGraw-Hill Dictionary of Chemical Terms (1984) McGraw-Hill Book Company, New York and Eliel, et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci,* 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid salt, 2-hydracrylic acid salt, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

DESCRIPTION OF COMPOUNDS OF THE INVENTION

Provided herein are compounds and pharmaceutically acceptable compositions thereof, which are useful in inhibiting viral disease, particularly in inhibiting HBV infections.

In one aspect, provided herein are compounds having Formula (I) or (Ia) as shown below:

(I)

[Structure: R²—A—C(=O)— attached to a 6-membered ring containing N—R⁴, N—R³, with R¹ and R substituents]

(Ia)

[Structure: similar to (I) with R⁴ and R³ on nitrogens]

or an enantiomer, a diastereoisomer, a tautomer, a hydrate, a solvate, or a pharmaceutically acceptable salt thereof, wherein:

each A is a bond, —O—, —S—, or —NR⁵—;
each R is —X—Z;
X is —(CR⁷R⁷ᵃ)$_m$— or —C(=O)—;
Z has Formula (II) or (IIa):

(II)

[Ring structure with W, Y, B and (R⁹)$_n$ substituent]

(IIa)

[Ring structure with W, Y, B and (R⁹)$_n$ substituent]

wherein each B is a bond, —(CR⁷R⁷ᵃ)$_m$— or —C(=O)—;
each W is CR⁷ or N;
each Y is —(CR⁷R⁷ᵃ)$_m$—, —O—, —S—, —S(=O)$_q$— or —NR⁶—;
each R¹ is aryl or heteroaryl;
each R² is H, alkyl, alkenyl, alkynyl, aryl, aralkyl, heteroaryl, heteroarylalkyl, cycloalkyl, cycloalkylalkyl, heterocyclyl, heterocyclylalkyl or alkoxycarbonyl;
each R³ is aryl or heteroaryl;
each R⁴ is H, or C$_{1-4}$ alkyl;
R⁵ is H, alkyl, —(CR⁷R⁷ᵃ)$_m$—C(=O)O—R⁸, alkenyl or alkynyl;
each R⁶ is alkyl, —(CR⁷R⁷ᵃ)$_m$—C(=O)O—R⁸, alkenyl or alkynyl;
each R⁷ᵃ and R⁷ is independently H, F, Cl, Br, alkyl, haloalkyl, —(CH₂)$_m$—OH or —(CH₂)$_m$—C(=O)O—R⁸;
each R⁸ and R⁸ᵃ is independently H, alkyl, haloalkyl, aminoalkyl, Boc-NH-alkyl, alkoxy, —(CH₂)$_m$—OH, —(CH₂)$_m$—C(=O)O—(CH₂)$_m$—H or —(CH₂)$_m$—OC(=O)—(CH₂)$_m$—H;
Boc is tert-butyloxycarbonyl;
each R⁹ is independently —(CR⁷R⁷ᵃ)$_t$—OH, —(CR⁷R⁷ᵃ)$_m$—S(=O)$_q$—R⁸, —(CR⁷R⁷ᵃ)$_m$—OS(=O)$_q$—R⁸, —(CR⁷R⁷ᵃ)$_m$—S(=O)$_q$O—R⁸, —(CR⁷R⁷ᵃ)$_m$—C(=O)—R⁸, —(CR⁷R⁷ᵃ)$_m$—C(=O)O—R⁸, —(CR⁷R⁷ᵃ)$_m$—C(=O)O—(CR⁷R⁷ᵃ)$_m$—OC(=O)O—R⁸, —(CR⁷R⁷ᵃ)$_m$—C(=O)O—(CR⁷R⁷ᵃ)$_m$—C(=O)O—(CR⁷R⁷ᵃ)$_m$—C(=O)O—R⁸, —(CR⁷R⁷ᵃ)$_t$—OC(=O)—R⁸, triazolyl, tetrazolyl or —(CR⁷R⁷ᵃ)$_m$—C(=O)N(R⁸)₂, with the proviso that when R⁹ is —(CR⁷R⁷ᵃ)$_t$—OH, R³ is aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each n is independently 1, 2 or 3;
each t is independently 1, 2, 3 or 4;
each m is independently 0, 1, 2, 3 or 4;
each q is independently 0, 1 or 2; and
optionally each of aryl, heteroaryl, alkyl, haloalkyl, alkenyl, alkynyl, cycloalkyl, cycloalkylalkyl, alkoxycarbonyl, aralkyl, heteroarylalkyl, aminoalkyl, alkoxy, furanyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl, triazinyl, heterocyclyl and heterocyclylalkyl described above, is independently substituted with one or more substituents which are the same or different, wherein the substituent is H, F, Cl, Br, I, alkyl, alkoxy, cyano, hydroxy, nitro, alkylamino, amino, trifluoromethyl, trifluoromethoxy, —(CR⁷R⁷ᵃ)$_m$—C(=O)O—R⁸ᵃ, haloalkyl-substituted aryl, halogen-substituted aryl, —(CR⁷R⁷ᵃ)$_m$—C(=O)N(R⁸ᵃ)₂ or trifluoromethylsulfonyl.

In certain embodiments, Z has Formula (III) or (IIIa):

(III)

[Ring structure with N, Y, B and (R⁹)$_n$ substituent]

(IIIa)

[Ring structure with N, Y, B and (R⁹)$_n$ substituent]

wherein each B is a bond or —(CR⁷R⁷ᵃ)$_m$—;
each Y is —(CR⁷R⁷ᵃ)$_m$—, —O—, —S—, —S(=O)$_q$— or —NR⁶—;
each R⁶ is C$_{1-4}$ alkyl, —(CR⁷R⁷ᵃ)$_m$—C(=O)O—R⁸, C$_{2-4}$ alkenyl or C$_{2-4}$ alkynyl;
each R⁷ᵃ and R⁷ is independently H, F, Cl, Br, C$_{1-4}$ alkyl, —(CH₂)$_m$—OH, C$_{1-4}$ haloalkyl or —(CH₂)$_m$—C(=O)O—R⁸;
each R⁸ is independently H, C$_{1-6}$ alkyl, C$_{1-4}$ haloalkyl, amino-C$_{1-4}$-alkyl, Boc-NH—C$_{1-4}$-alkyl, C$_{1-4}$ alkoxy, —(CH₂)$_m$—OH, —(CH₂)$_m$—C(=O)O—(CH₂)$_m$—H or —(CH₂)$_m$—OC(=O)—(CH₂)$_m$—H;
each R⁹ is independently —(CR⁷R⁷ᵃ)$_t$—OH, —(CR⁷R⁷ᵃ)$_m$—C(=O)—R⁸, —(CR⁷R⁷ᵃ)$_m$—C(=O)O—R⁸, —(CR⁷R⁷ᵃ)$_m$—C(=O)O—(CR⁷R⁷ᵃ)$_m$—OC(=O)O—R⁸, —(CR⁷R⁷ᵃ)$_m$—C(=O)O—(CR⁷R⁷ᵃ)$_m$—OC(=O)—R⁸, —(CR⁷R⁷ᵃ)$_m$—C(=O)O—(CR⁷R⁷ᵃ)$_m$—C(=O)O—R⁸, —(CR⁷R⁷ᵃ)$_t$—OC(=O)—R⁸, triazolyl, tetrazolyl or —(CR⁷R⁷ᵃ)$_m$—C(=O)N(R⁸)₂, with the proviso that when R⁹ is —(CR⁷R⁷ᵃ)$_t$—OH, R³ is C$_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each n is independently 1 or 2;
each t is independently 1, 2, 3 or 4; and
each m is independently 0, 1, 2, 3 or 4.
In other embodiments, Z is

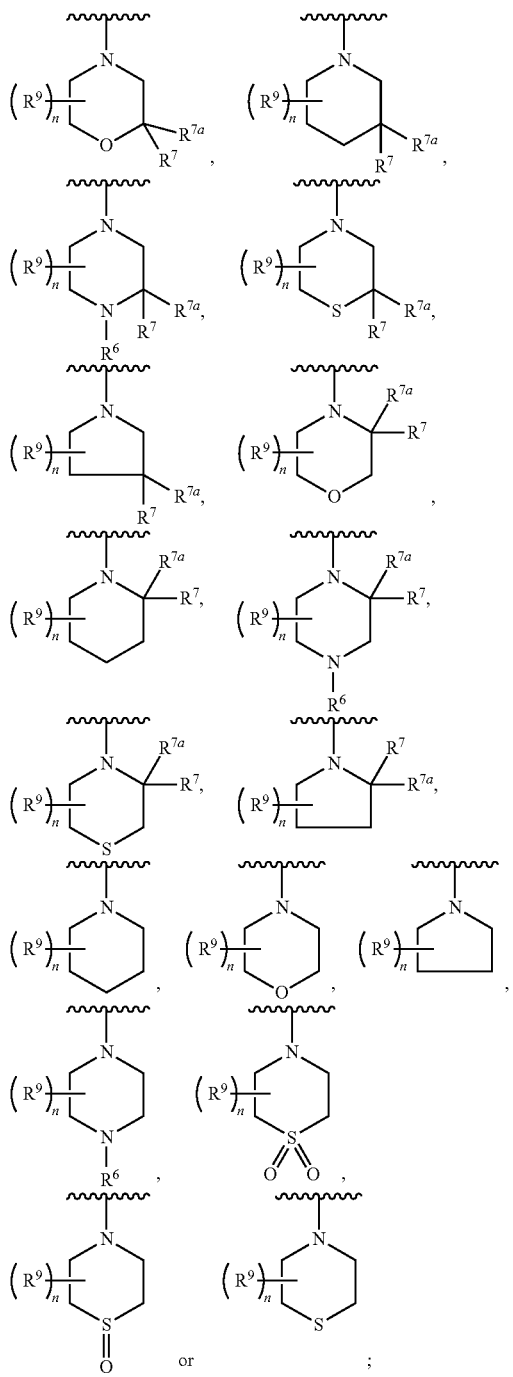

wherein each $R^6$ is independently methyl, ethyl or propyl;
each $R^7$ and $R^{7a}$ is independently H, methyl, ethyl, —$(CH_2)_m$—OH, —$(CH_2)_m$—C(=O)O—$R^8$ or propyl;
each $R^8$ is independently H, methyl, ethyl, propyl, isopropyl, butyl, 1-methylpropyl, 2-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —$(CH_2)_m$—OH, —$(CH_2)_m$—C(=O)O—$(CH_2)_m$—H, —$(CH_2)_m$—OC(=O)—$(CH_2)_m$—H or tert-butyl; and each $R^9$ is independently triazolyl, tetrazolyl, —$(CR^7R^{7a})_t$—OH, —$(CR^7R^{7a})_m$—C(=O)—$R^8$, —$(CR^7R^{7a})_m$—C(=O)O—$R^8$, —$(CR^7R^{7a})_m$—C(=O)O—$(CR^7R^{7a})_m$—OC(=O)—$R^8$, —$(CR^7R^{7a})_m$—C(=O)O—$(CR^7R^{7a})_m$—OC(=O)—$R^8$, —$(CR^7R^{7a})_t$—OC(=O)—$R^8$ or —$(CR^7R^{7a})_m$—C(=O)N($R^8$)$_2$, with the proviso that when $R^9$ is —$(CR^7R^{7a})_t$—OH, $R^3$ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl.

In certain embodiments, $R^3$ is $C_{6-10}$ aryl or 5-6 membered heteroaryl, and optionally each of the heteroaryl and aryl is independently substituted with one or more substituents which are the same or different, wherein the substituent is H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;

each $R^{7a}$ and $R^7$ is independently H, F, Cl, Br, $C_{1-4}$ alkyl, $C_{1-4}$ haloalkyl, —$(CH_2)_m$—OH or —$(CH_2)_m$—C(=O)O—$R^8$; and each $R^{8a}$ and $R^8$ is independently H, $C_{1-4}$ alkyl, $C_{1-4}$ haloalkyl, amino-$C_{1-4}$-alkyl, Boc-NH—$C_{1-4}$-alkyl, $C_{1-4}$ alkoxy, —$(CH_2)_m$—OH, —$(CH_2)_m$—C(=O)O—$(CH_2)_m$—H or —$(CH_2)_m$—OC(=O)—$(CH_2)_m$—H.

In other embodiments, $R^3$ has one of the following formulae:

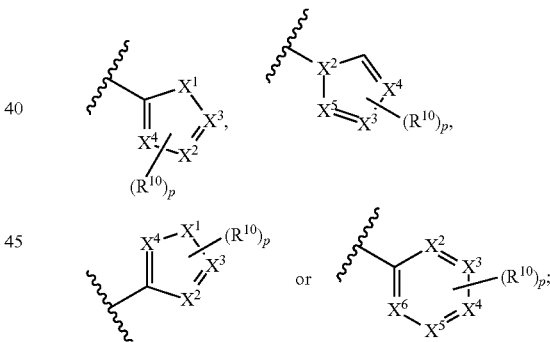

wherein each $X^1$ is independently O, S, $NR^{11}$ or $CR^{12}R^{12a}$;
each $X^2$, $X^3$, $X^4$, $X^5$ and $X^6$ is independently N or $CR^{12}$;
wherein at most three or four of the $X^2$, $X^3$, $X^4$, $X^5$ and $X^6$ are N;

each $R^{10}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;

each $R^{11}$ is independently H, methyl, ethyl, propyl, isopropyl, butyl, trifluoromethyl, —$(CR^7R^{7a})_m$—C(=O)N($R^{8a}$)$_2$ or —$(CR^7R^{7a})_m$—C(=O)O—$R^{8a}$;

each $R^{12}$ and $R^{12a}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, —$(CR^7R^{7a})_m$—C(=O)O—$R^{8a}$, —$(CR^7R^{7a})_m$—C(=O)N($R^{8a}$)$_2$ or trifluoromethylsulfonyl;

each $R^{7a}$ and $R^7$ is independently H, F, Cl, Br, $C_{1-4}$ alkyl, $-(CH_2)_m-OH$, $C_{1-4}$ haloalkyl or $-(CH_2)_m-C(=O)O-R^8$;

each $R^{8a}$ and $R^8$ is independently H, $C_{1-4}$ alkyl, $C_{1-4}$ haloalkyl, amino-$C_{1-4}$-alkyl, Boc-NH—$C_{1-4}$-alkyl, $C_{1-4}$ alkoxy, $-(CH_2)_m-OH$, $-(CH_2)_m-C(=O)O-(CH_2)_m-H$ or $-(CH_2)_m-OC(=O)-(CH_2)_m-H$;

each m is independently 0, 1, 2, 3 or 4; and each p is independently 0, 1, 2 or 3.

In other embodiments, $R^3$ has one of the following formulae:

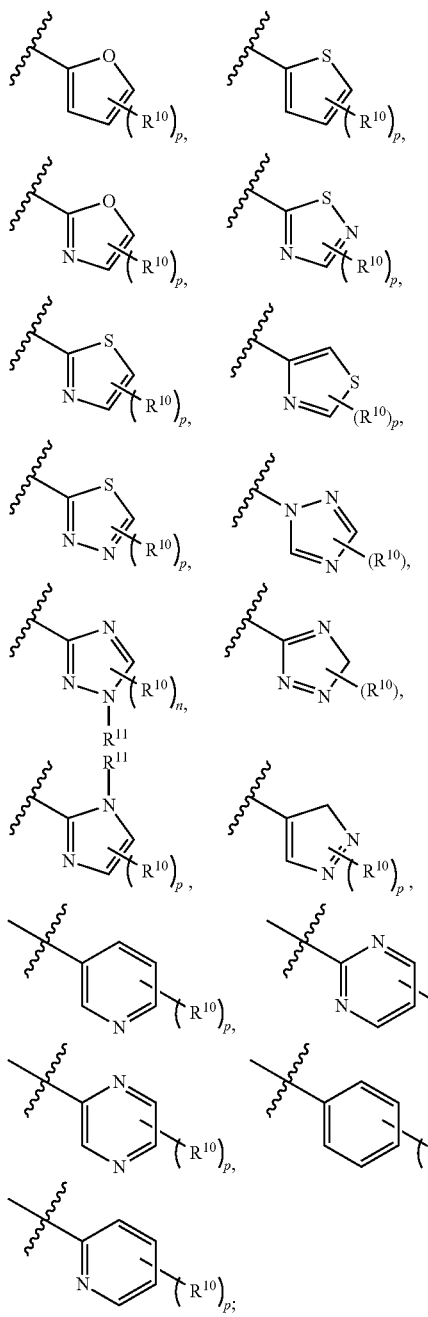

wherein each $R^{10}$ is independently H, F, Cl, methyl, ethyl, cyano, hydroxy, nitro, amino, methoxy, ethoxy, trifluoromethyl, trifluoromethoxy, $-(CR^7R^{7a})_m-C(=O)O-R^{8a}$, $-(CR^7R^{7a})_m-C(=O)N(R^{8a})_2$ or trifluoromethylsulfonyl;

each $R^{11}$ is independently H, methyl, ethyl, propyl, isopropyl, butyl, trifluoromethyl or $-(CR^7R^{7a})_m-C(=O)O-R^{8a}$;

each $R^{7a}$ and $R^7$ is independently H, methyl, ethyl, $-(CH_2)_m-OH$, $-(CH_2)_m-C(=O)O-R^8$ or propyl;

each $R^8$ and $R^{8a}$ is independently H, methyl, ethyl, propyl, isopropyl, butyl, 2-methylpropyl, 1-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, $-(CH_2)_m-OH$, $-(CH_2)_m-C(=O)O-(CH_2)_m-H$, $-(CH_2)_m-OC(=O)-(CH_2)_m-H$ or tert-butyl; and each p is independently 0, 1, 2 or 3.

In certain embodiments, $R^1$ is $C_{6-10}$ aryl, and the aryl is independently substituted with one or more substituents which are the same or different, wherein the substituent is H, F, Cl, Br, cyano, methyl, ethyl, methoxy, ethoxy, methylamino, ethylamino, nitro, 4-(trifluoromethyl)phenyl, 3,5-bis(trifluoromethyl)phenyl or trifluoromethyl;

$R^2$ is H, or $C_{1-4}$ alkyl; and $R^5$ is H, or $C_{1-4}$ alkyl.

In other embodiments, $R^1$ is phenyl or a phenyl substituted with one or more substituents which are the same or different, wherein the substituent is H, F, Cl, Br, nitro, 4-(trifluoromethyl)phenyl, 3,5-bis(trifluoromethyl)phenyl or trifluoromethyl.

In certain embodiments, Formula (IV) or (IVa) is

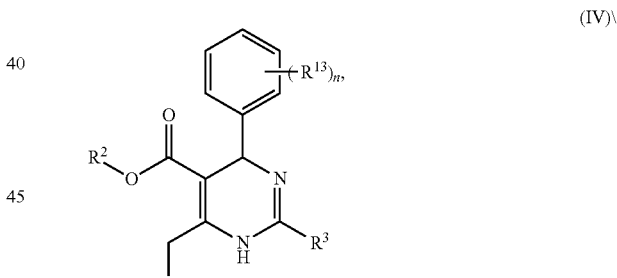

(IV)

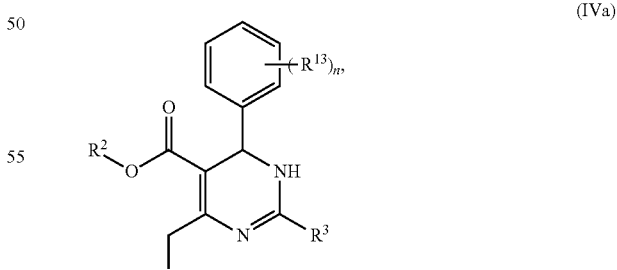

(IVa)

or an enantiomer, a diastereoisomer, a tautomer, a hydrate, a solvate, or a pharmaceutically acceptable salt thereof, wherein Z has Formula (II) or (IIa):

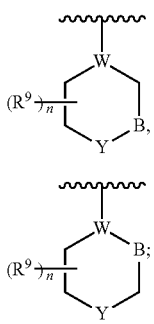

(II)

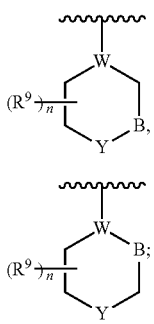

(IIa)

wherein each B is a bond or —(CR$^7$R$^{7a}$)$_m$—;
each W is CR$^7$ or N;
each Y is —(CR$^7$R$^{7a}$)$_m$—, —O—, —S—, —S(=O)$_q$— or —NR$^6$—;
each R$^2$ is H, or C$_{1-4}$ alkyl;
each R$^3$ is C$_{6-10}$ aryl or 5-6 membered heteroaryl, and optionally each of the heteroaryl and aryl is independently substituted with one or more substituents which are the same or different, wherein the substituent is H, F, Cl, methyl, ethyl, propyl, cyano, trifluoromethyl, methoxy, —(CR$^7$R$^{7a}$)$_m$—C(=O)N(R$^{8a}$)$_2$ or —(CR$^7$R$^{7a}$)$_m$—C(=O)O—R$^{8a}$;
each R$^6$ is C$_{1-4}$ alkyl;
each R$^{7a}$ and R$^7$ is independently H, —(CH$_2$)$_m$—OH, —(CH$_2$)$_m$—C(=O)O—R$^8$ or C$_{1-4}$ alkyl;
each R$^8$ and R$^{8a}$ is independently H, amino-C$_{1-4}$-alkyl, Boc-NH—C$_{1-4}$-alkyl, C$_{1-4}$ alkoxy, —(CH$_2$)$_m$—OH, —(CH$_2$)$_m$—C(=O)O—(CH$_2$)$_m$—H, —(CH$_2$)$_m$—OC(=O)—(CH$_2$)$_m$—H or C$_{1-6}$ alkyl;
each R$^9$ is independently triazolyl, tetrazolyl, —(CR$^7$R$^{7a}$)$_t$—OH, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)—R$^8$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OC(=O)—R$^8$ or —(CR$^7$R$^{7a}$)$_m$—C(=O)N(R$^8$)$_2$, with the proviso that when R$^9$ is —(CR$^7$R$^{7a}$)$_t$—OH, R$^3$ is C$_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each R$^{13}$ is independently H, F, Cl, Br, cyano, nitro, 4-(trifluoromethyl)phenyl, 3,5-bis(trifluoromethyl)phenyl or trifluoromethyl;
each n is independently 1 or 2;
each t is independently 1, 2, 3 or 4;
each m is independently 0, 1, 2, 3 or 4; and
each q is independently 0, 1 or 2.

In certain embodiments, Z has Formula (II) or (IIa):

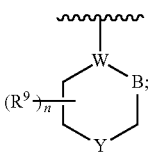

(II)

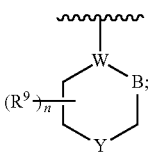

(IIa)

wherein each B is a bond or —(CR$^7$R$^{7a}$)$_m$—;
each W is CR$^7$ or N;
each Y is —(CR$^7$R$^{7a}$)$_m$—, —O—, —S—, —S(=O)$_q$— or —NR$^6$—;
each R$^6$ is methyl, ethyl or propyl;
each R$^{7a}$ and R$^7$ is independently H, methyl, —(CH$_2$)$_m$—OH, —(CH$_2$)$_m$—C(=O)O—R$^8$, ethyl or propyl;
each R$^8$ is independently H, methyl, ethyl, propyl, isopropyl, butyl, 1-methylpropyl, 2-methylpropyl, tert-butyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —(CH$_2$)$_m$—OH, —(CH$_2$)$_m$—C(=O)O—(CH$_2$)$_m$—H or —(CH$_2$)$_m$—OC(=O)—(CH$_2$)$_m$—H;
each R$^{8a}$ is independently H, methyl, ethyl, isopropyl or propyl;
each R$^9$ is independently —(CR$^7$R$^{7a}$)$_t$—OH, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_t$—OC(=O)—R$^8$, triazolyl, tetrazolyl or —(CR$^7$R$^{7a}$)$_m$—C(=O)N(R$^8$)$_2$, with the proviso that when R$^9$ is —(CR$^7$R$^{7a}$)$_t$—OH, R$^3$ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each m is independently 0, 1, 2, 3 or 4; and
each t is independently 1, 2, 3 or 4.

In other embodiments, Z is:

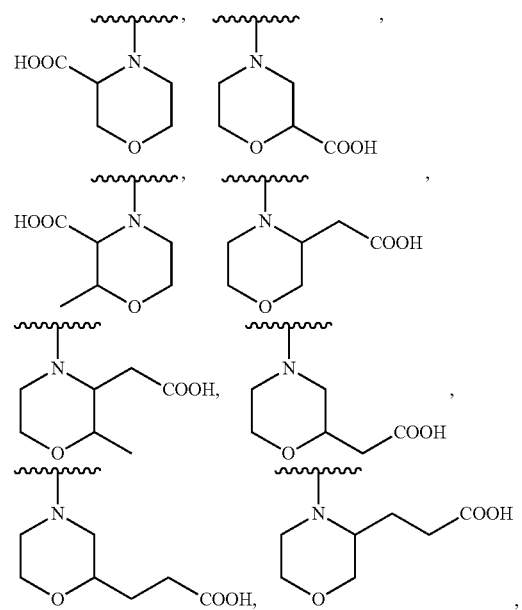

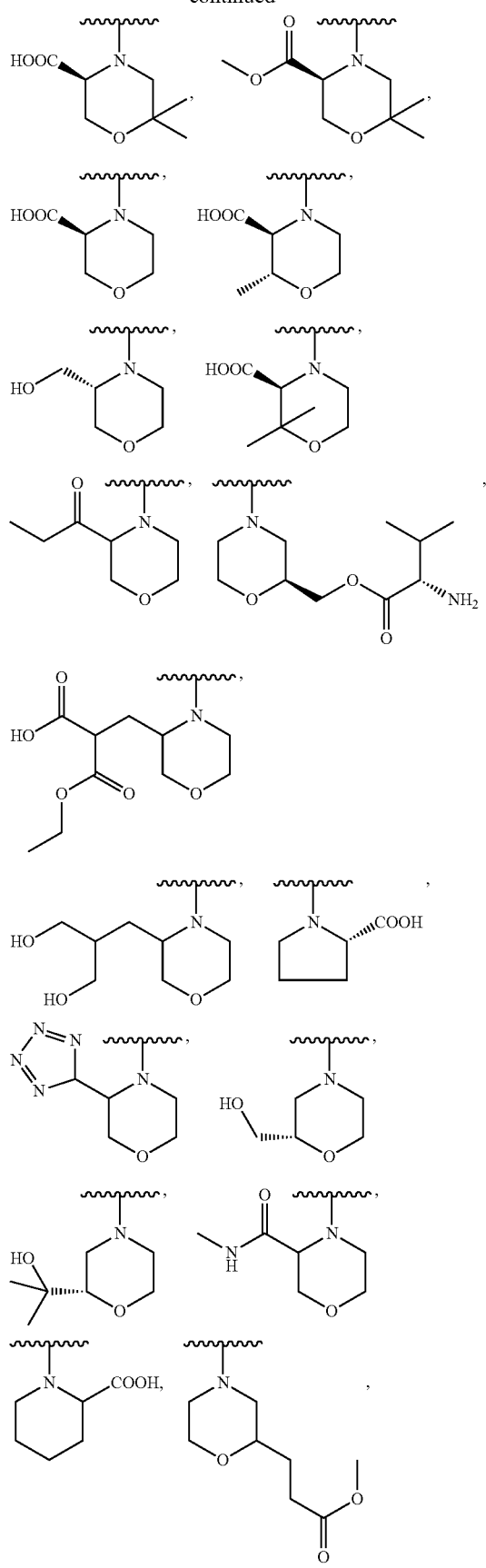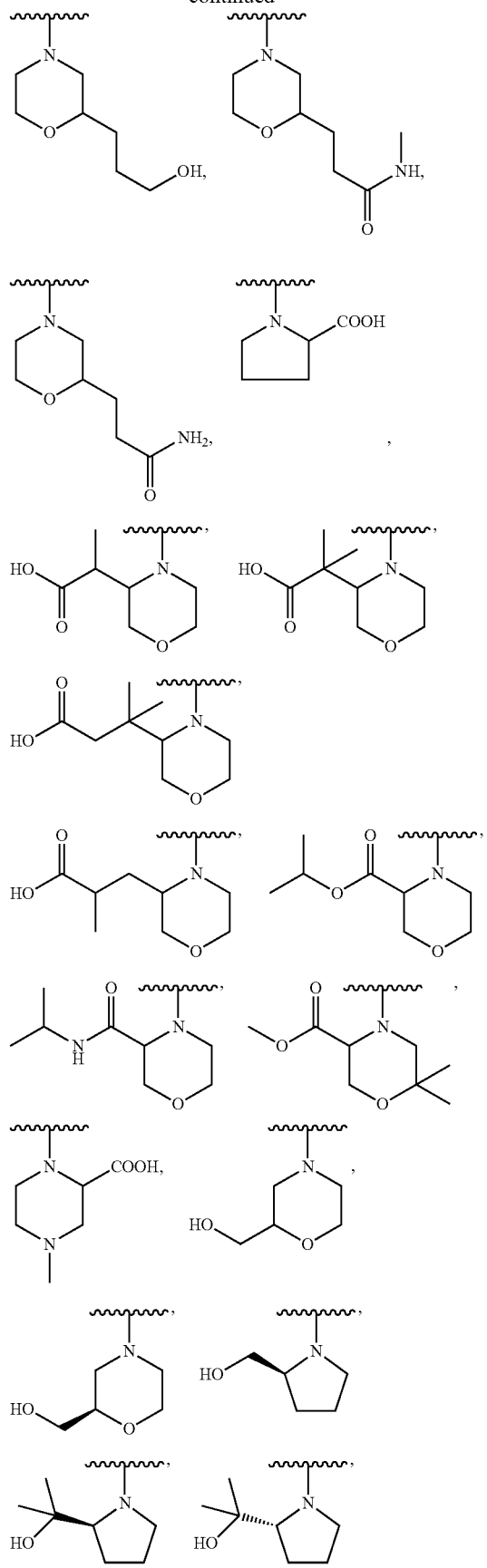

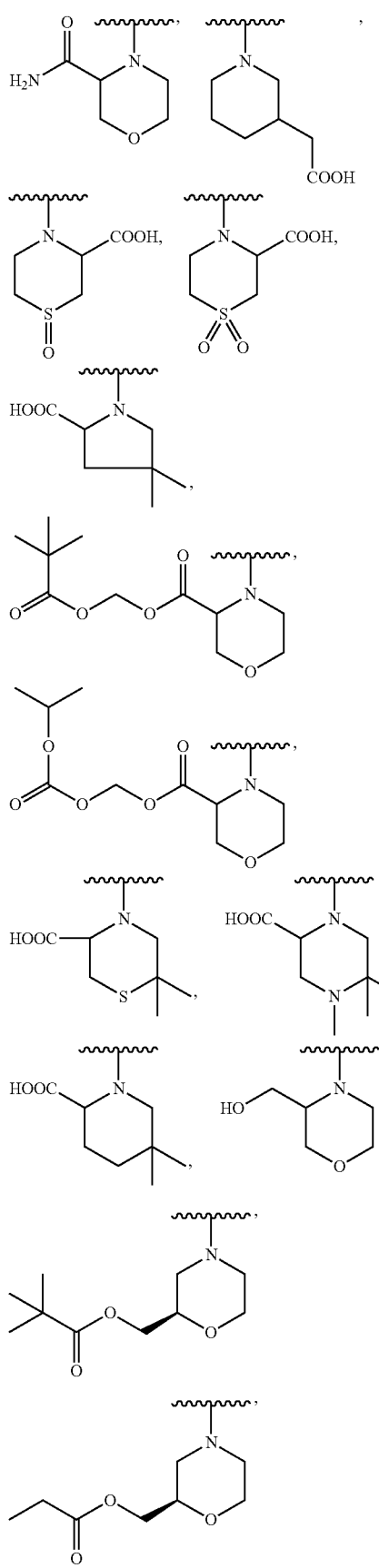
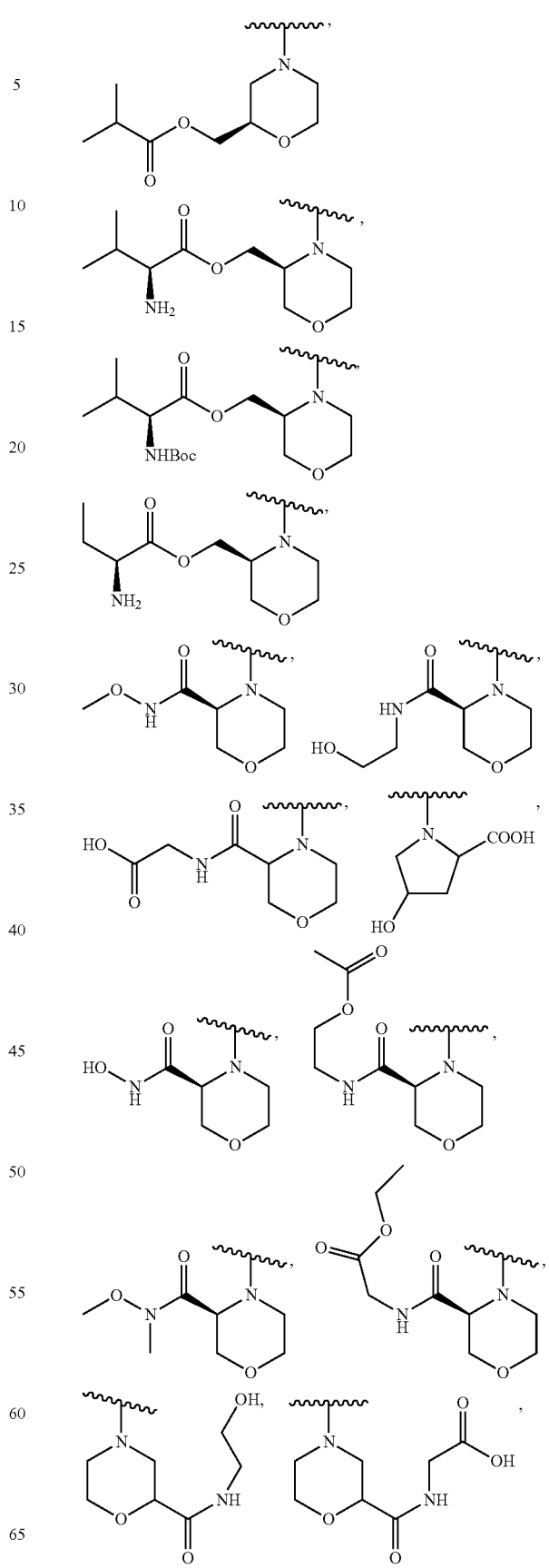

-continued
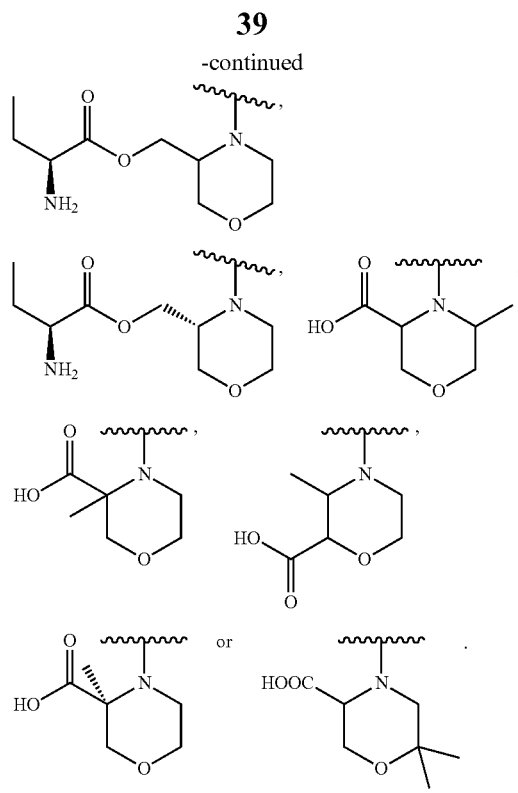
In certain embodiments, each R³ is independently:
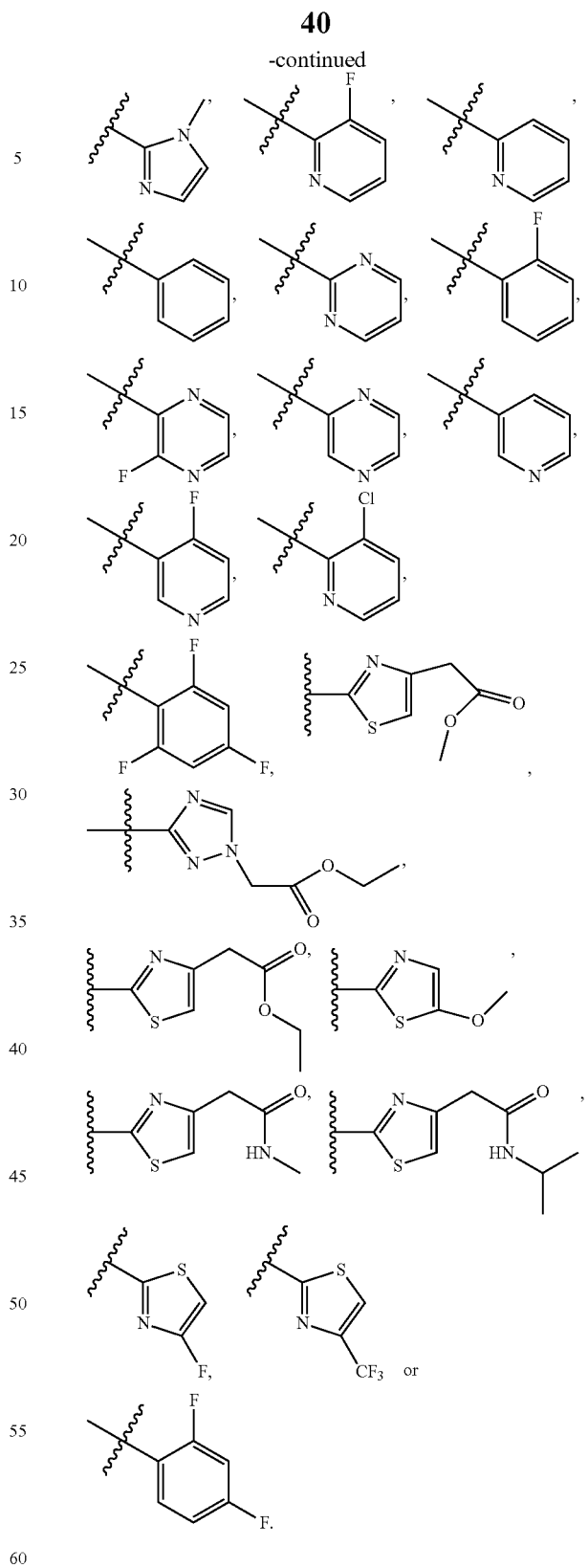
In another aspect, provided herein are one of the compounds as follows, or an enantiomer, a diastereoisomer, a tautomer, a hydrate, a solvate, or a pharmaceutically acceptable salt thereof, and not limited to:

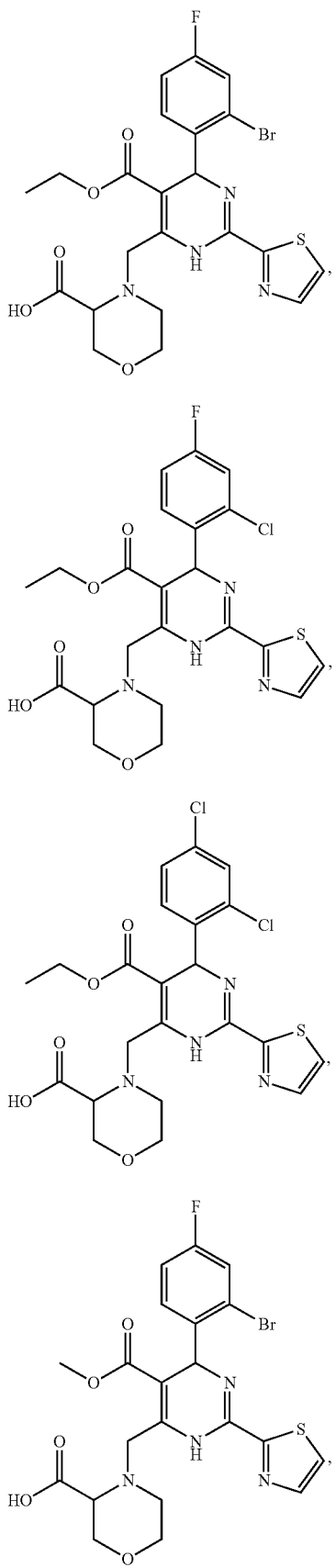
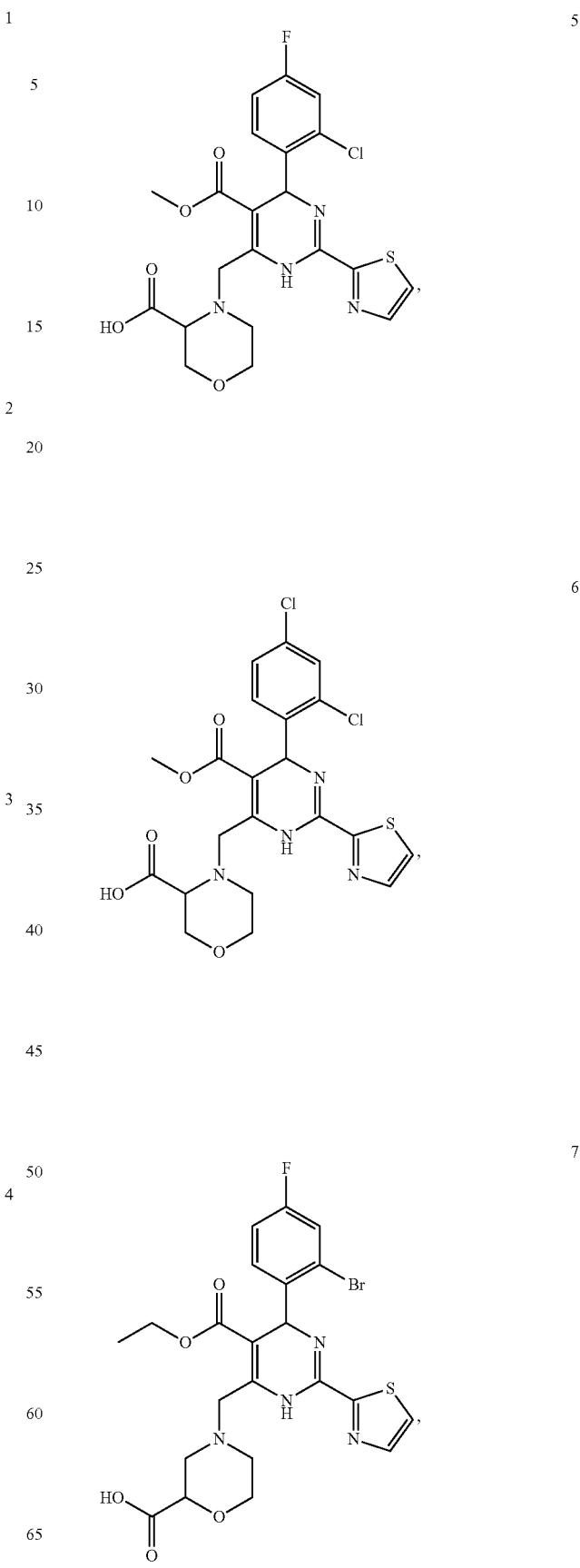

43
-continued
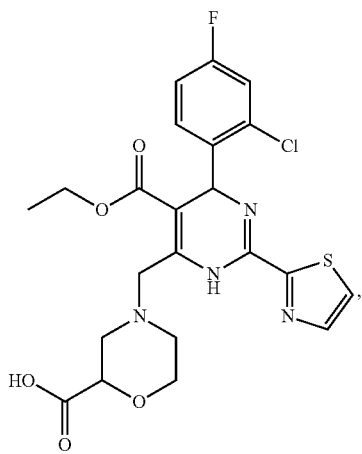
8
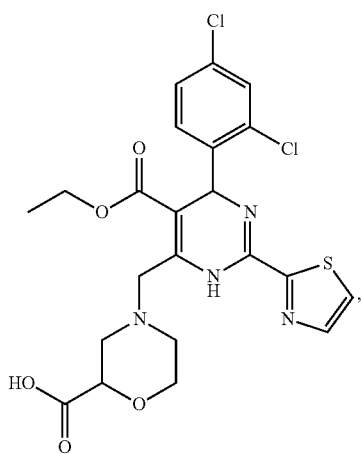
9
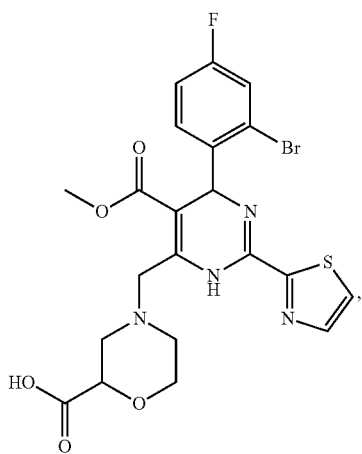
10
44
-continued
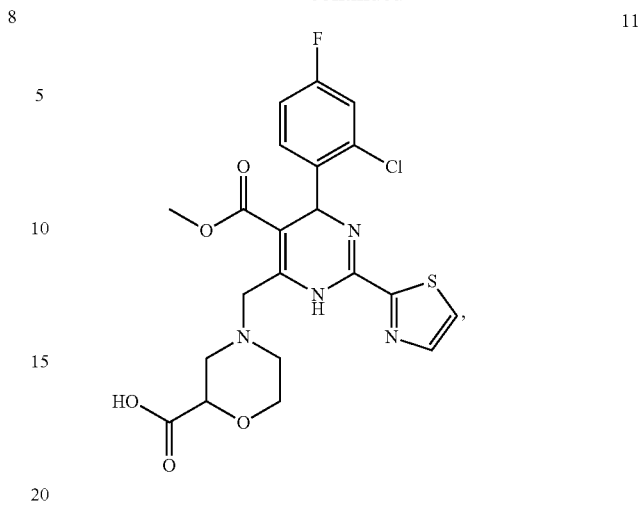
11
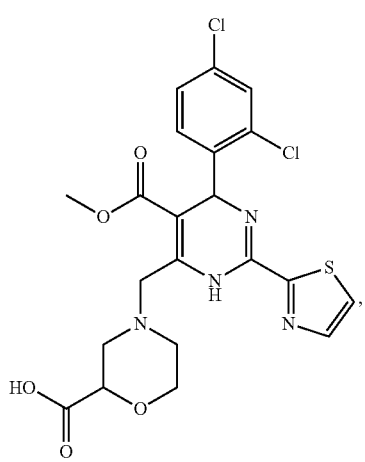
12
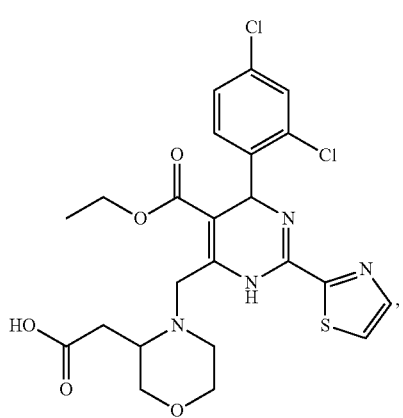
13

14
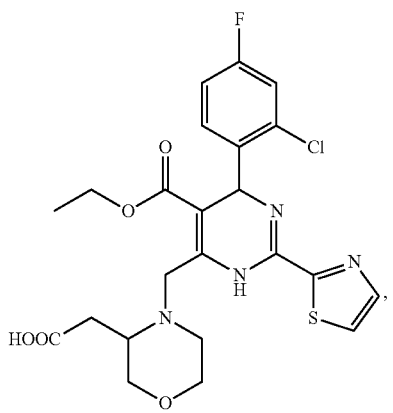
15
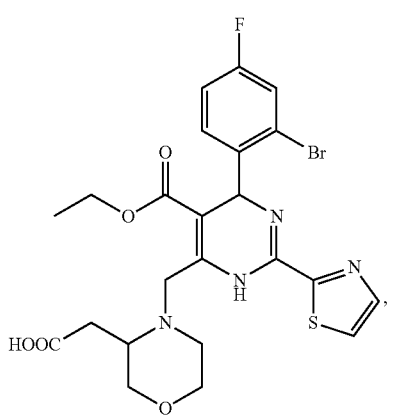
16
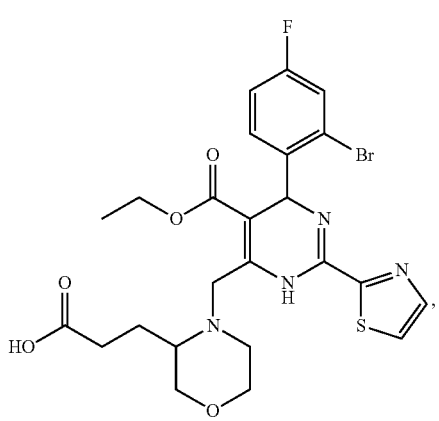
17
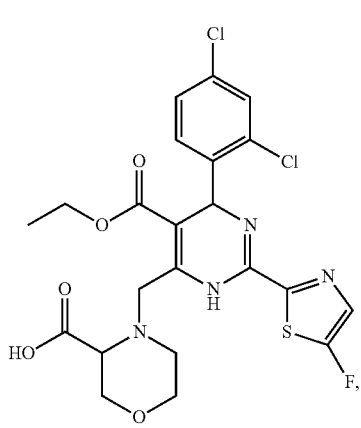
18
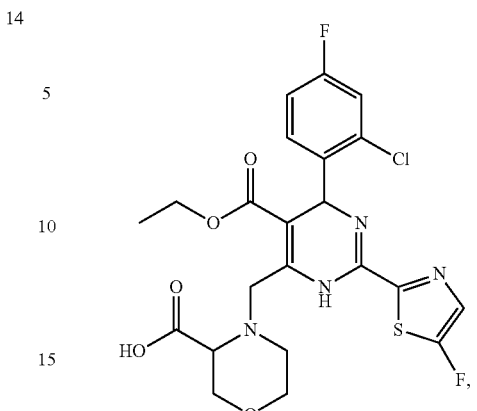
19
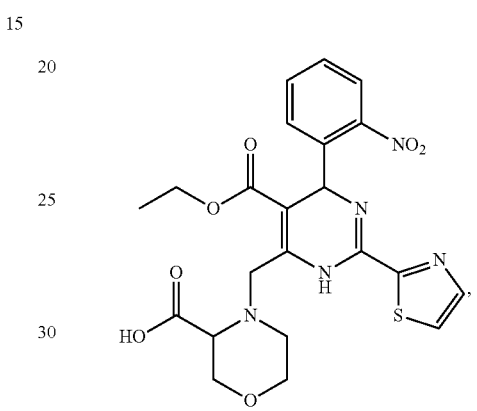
20
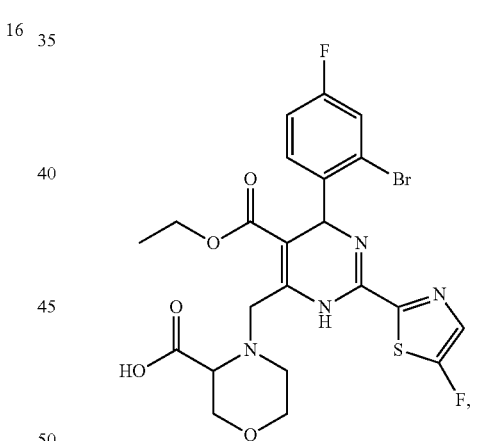
21
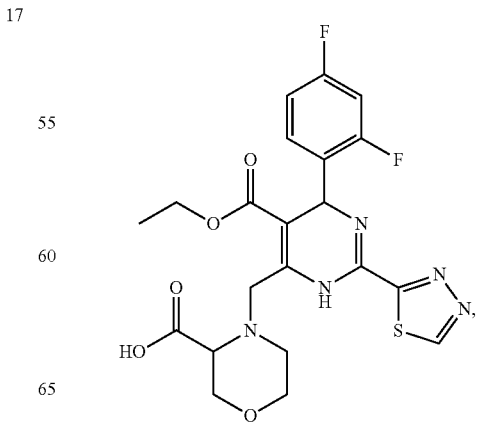

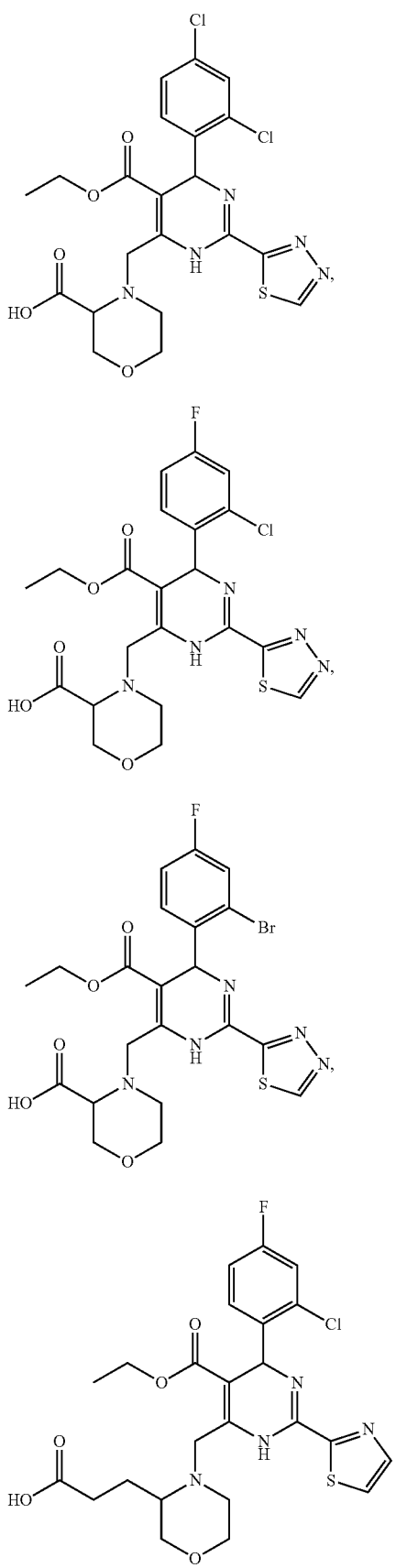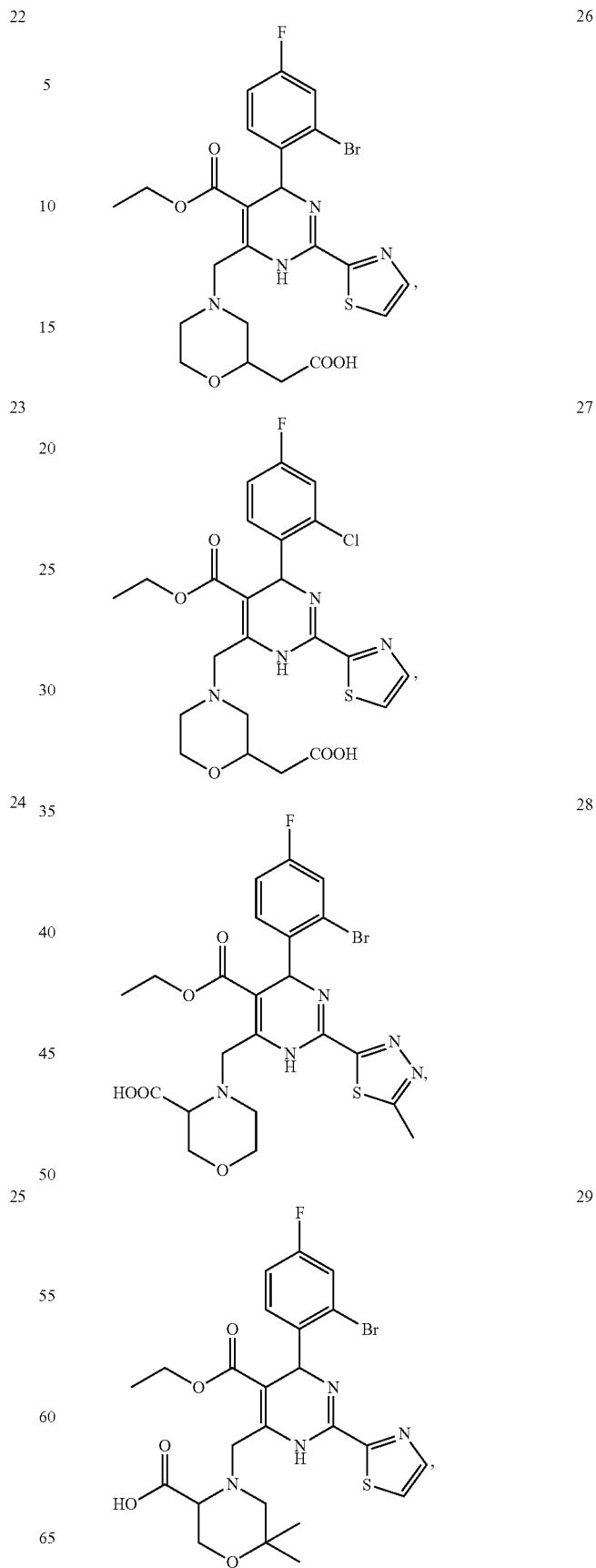

49
-continued
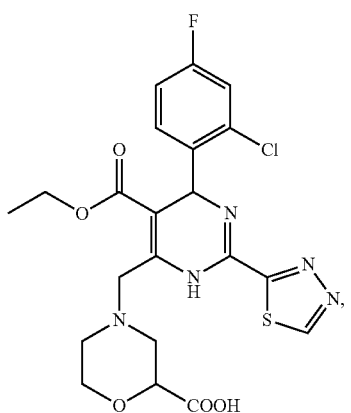
30
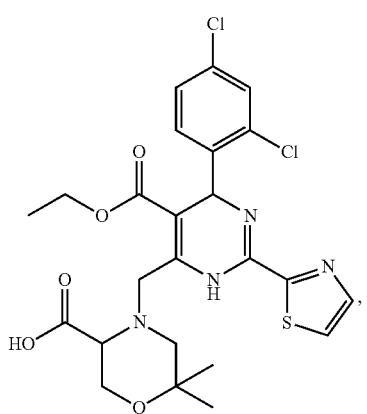
31
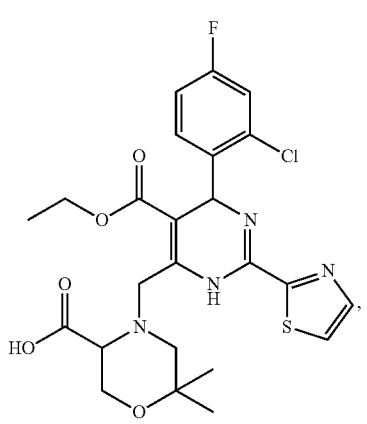
32
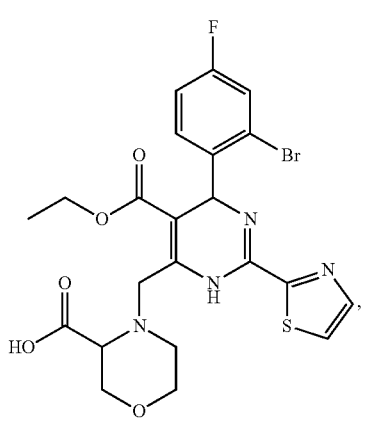
33
50
-continued
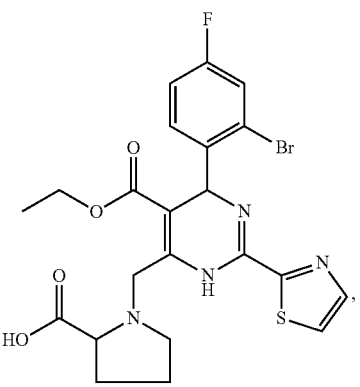
34
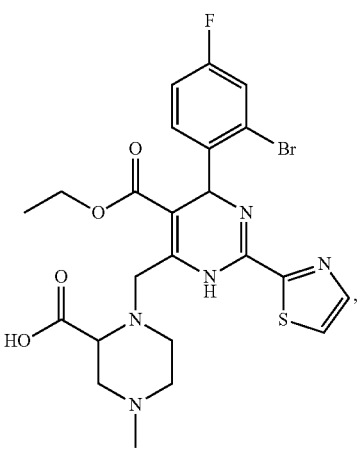
35
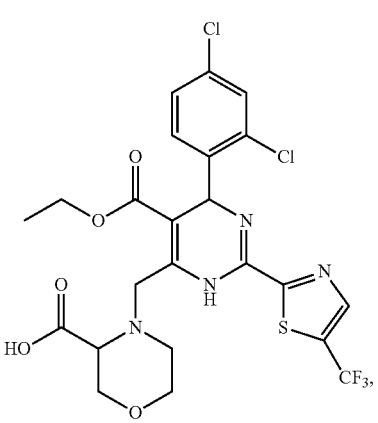
36
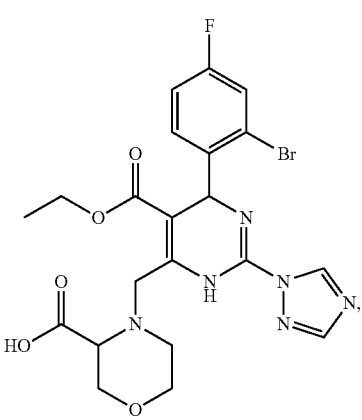
37

-continued
38
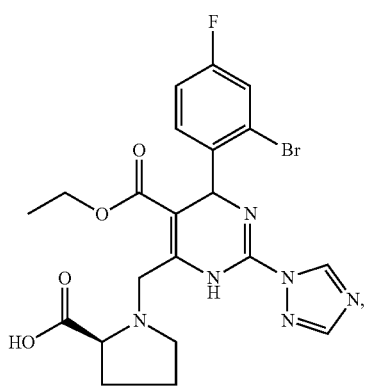
39
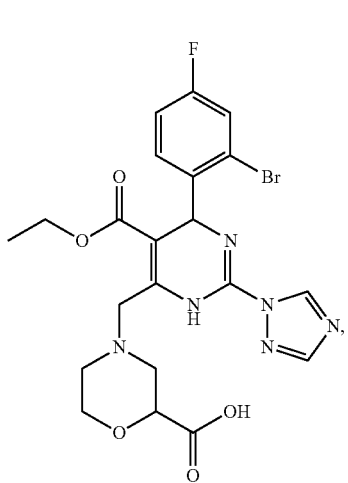
40
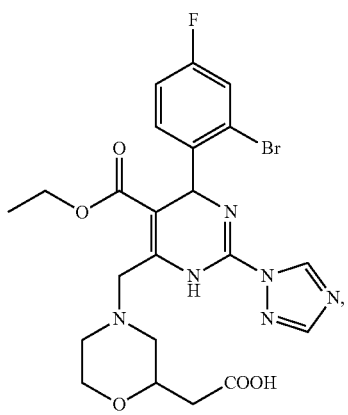
-continued
41
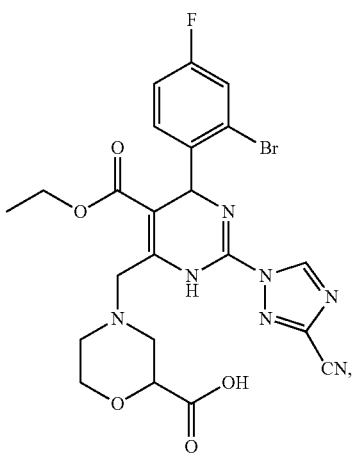
42
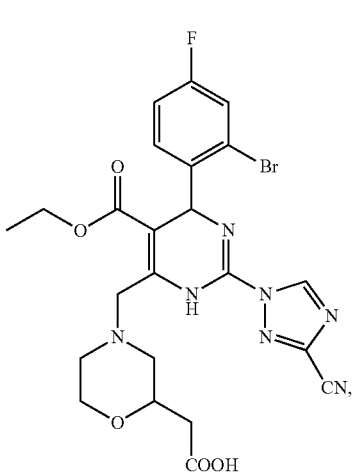
43
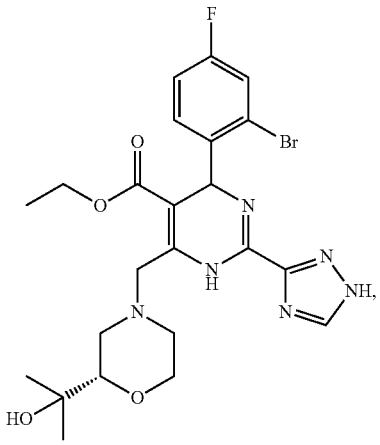

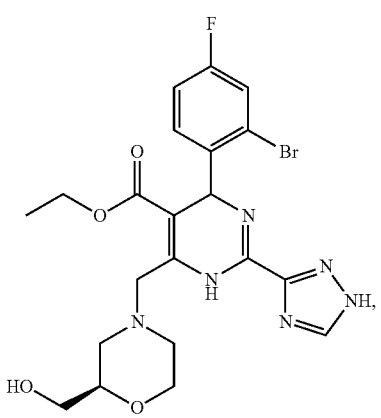
44
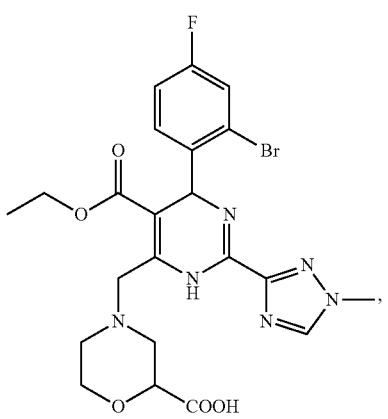
45
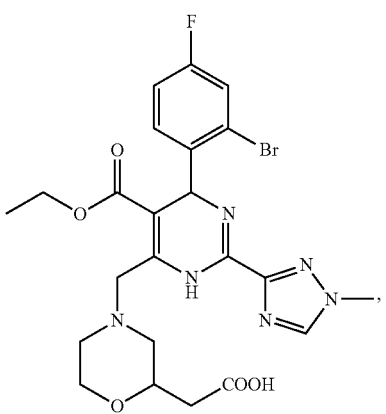
46
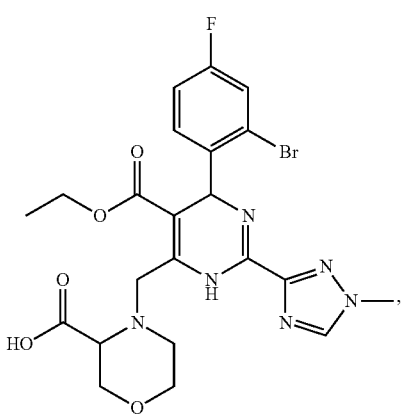
47
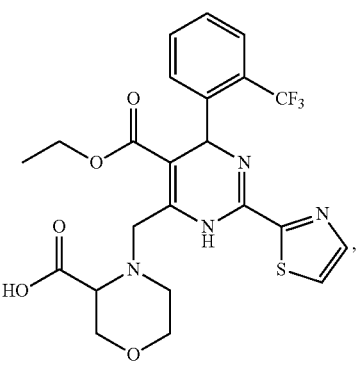
48
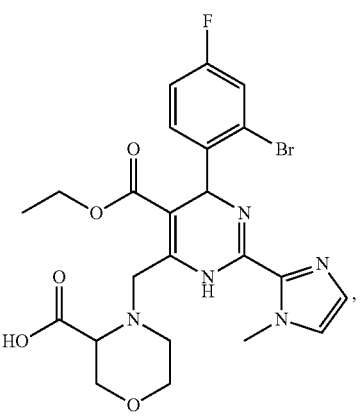
49
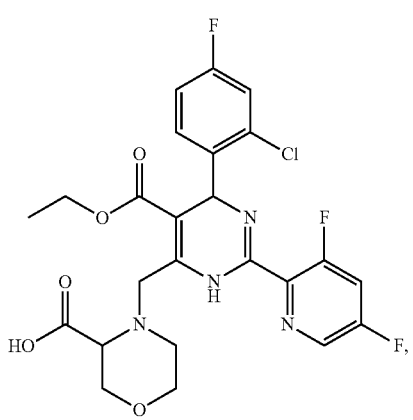
50
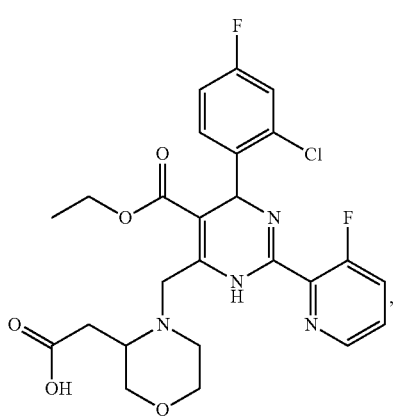
51

-continued
52
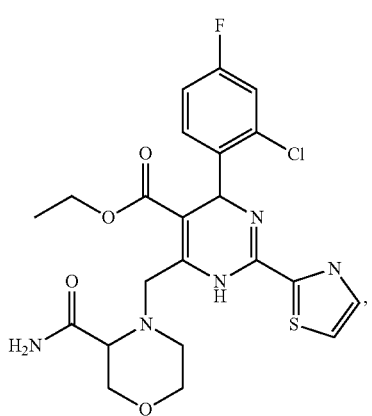
53
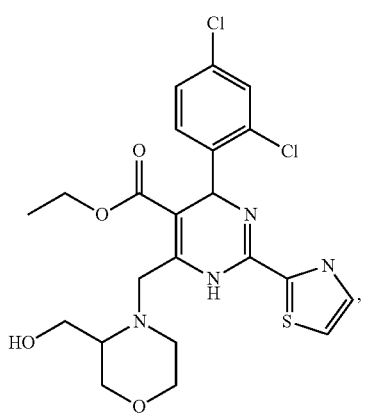
54
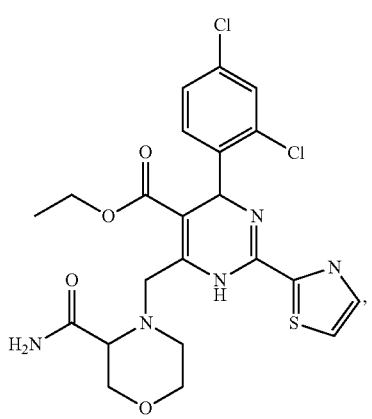
55
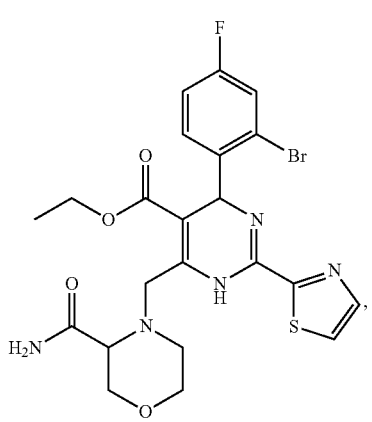
-continued
56
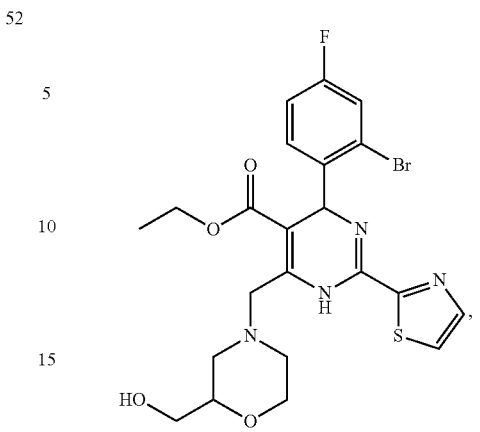
57
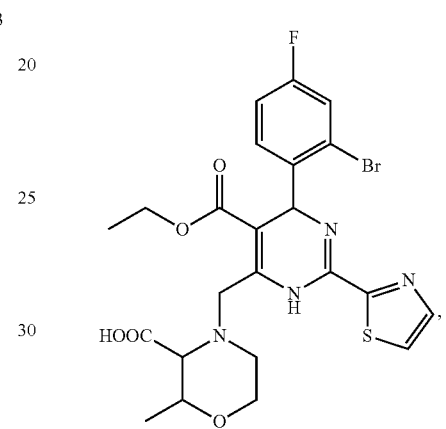
58
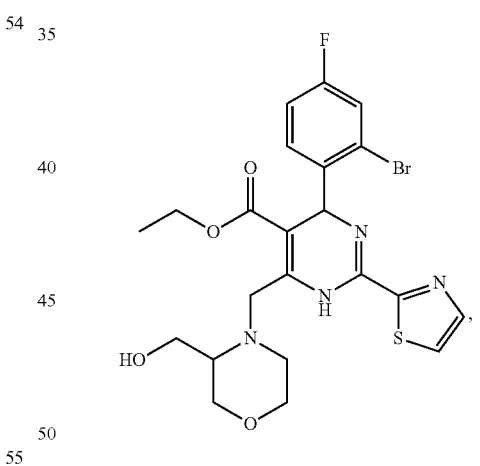
59
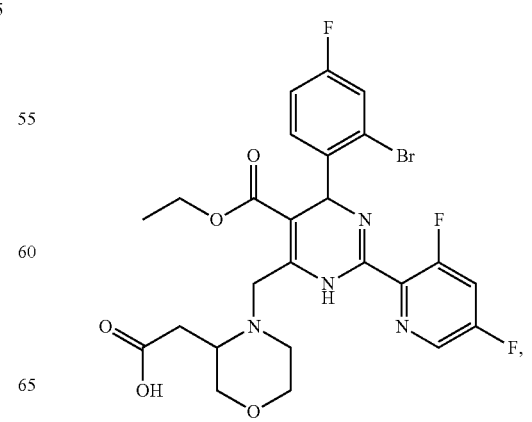

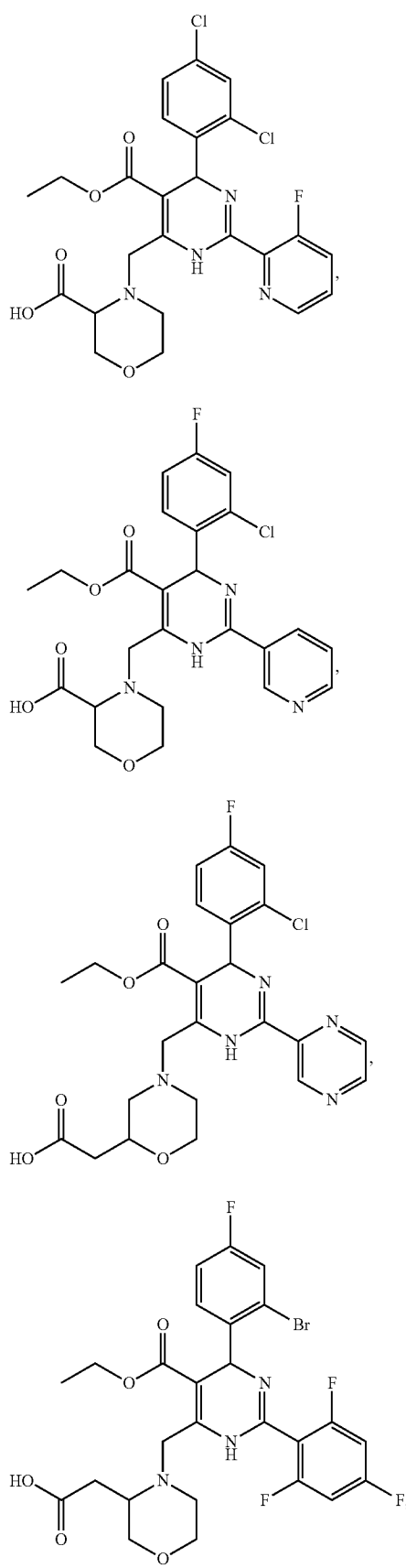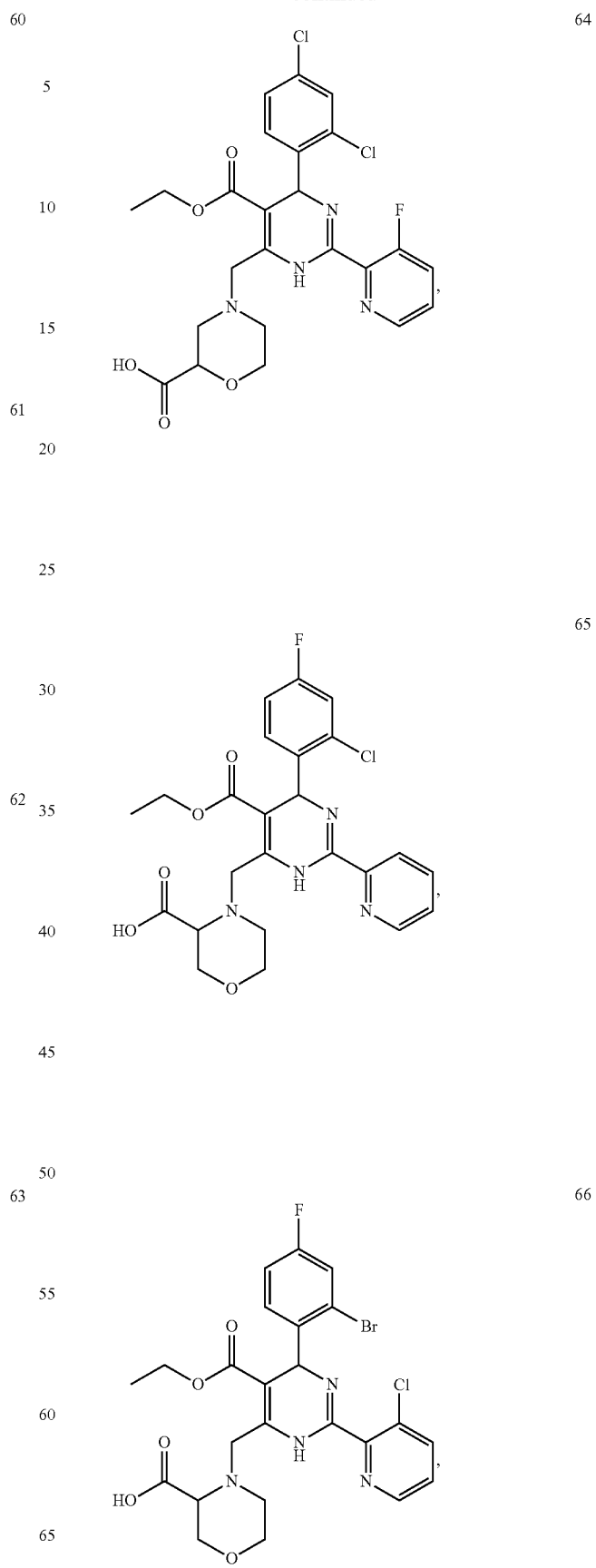

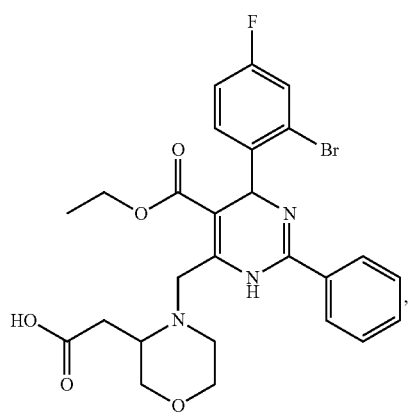
67
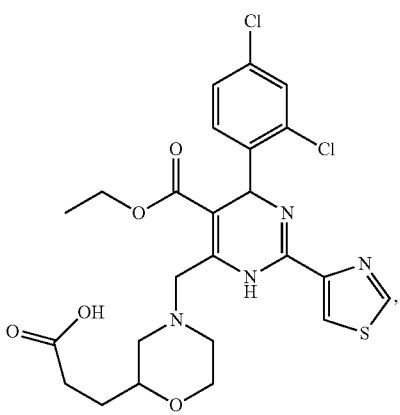
70
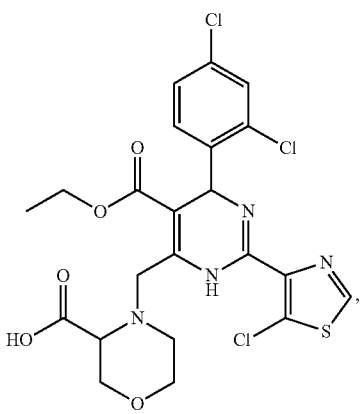
71
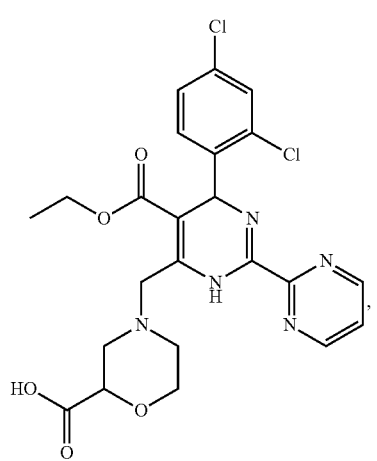
68
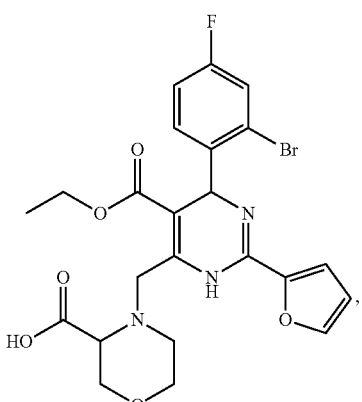
72
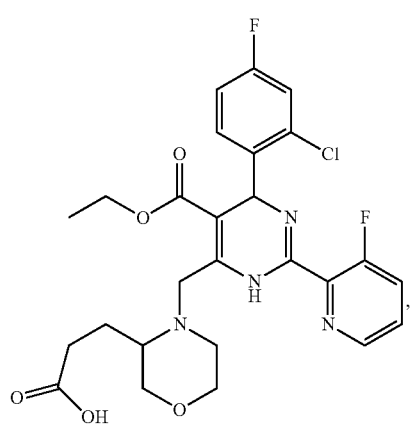
69
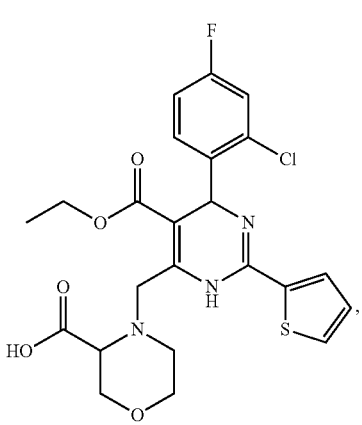
73

-continued
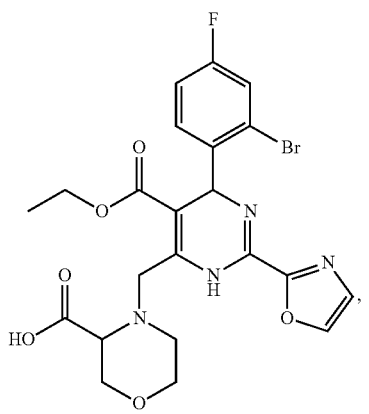
74
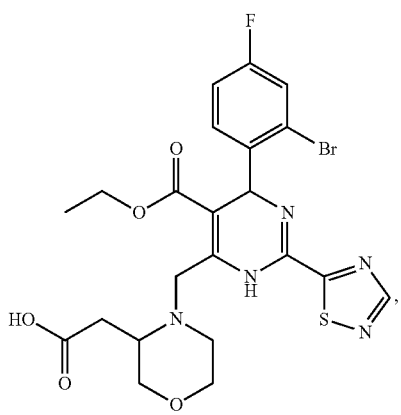
75
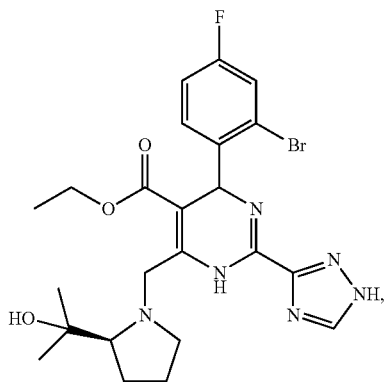
76
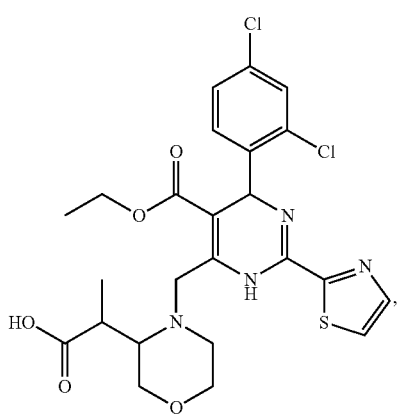
77
-continued
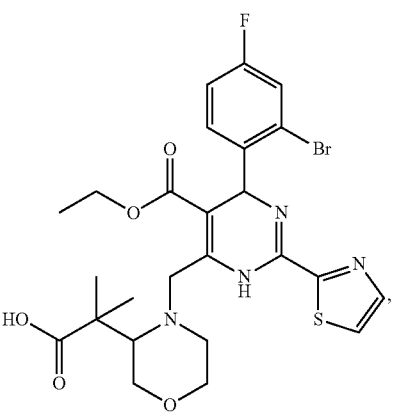
78
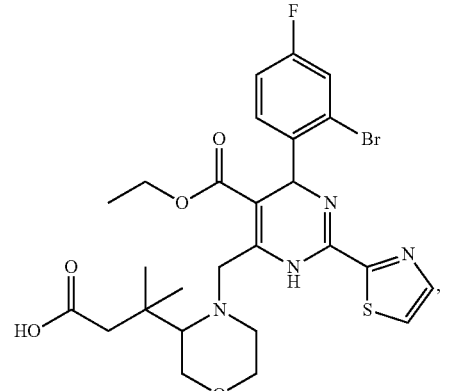
79
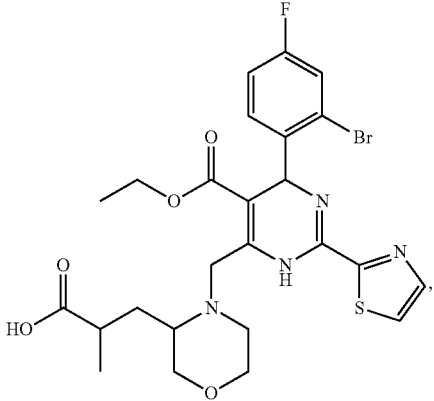
80
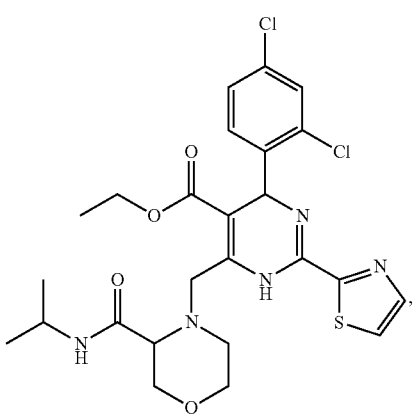
81

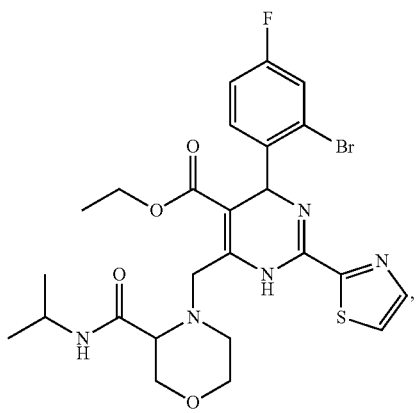
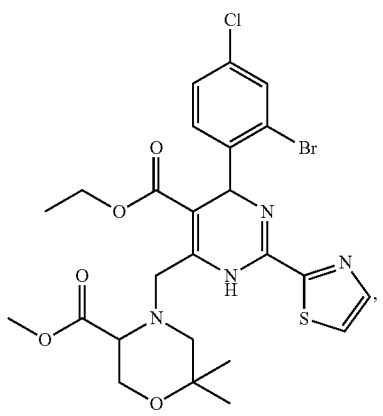
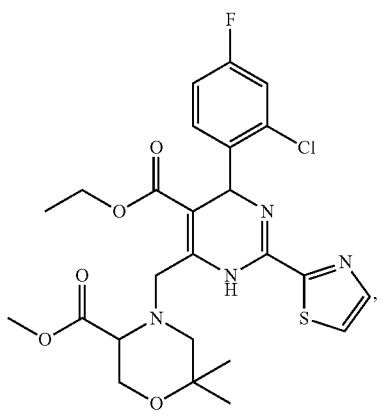
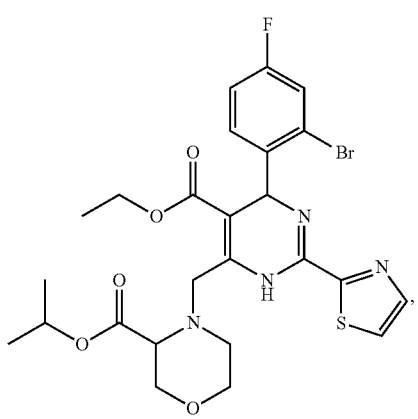
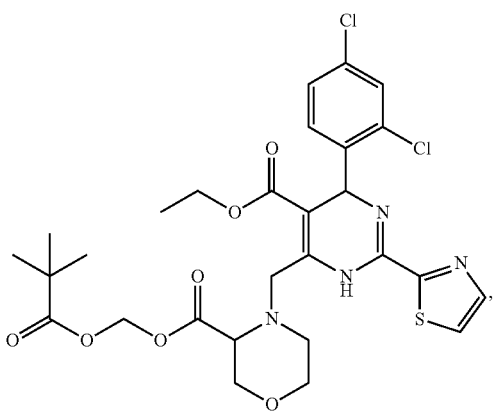
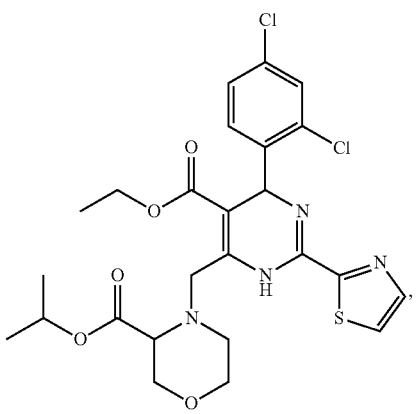

65
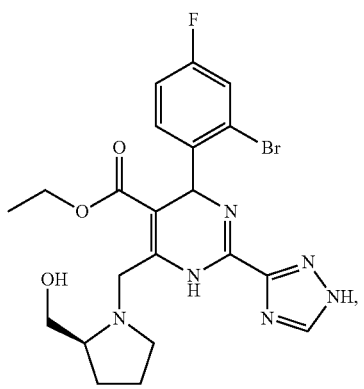
90
91
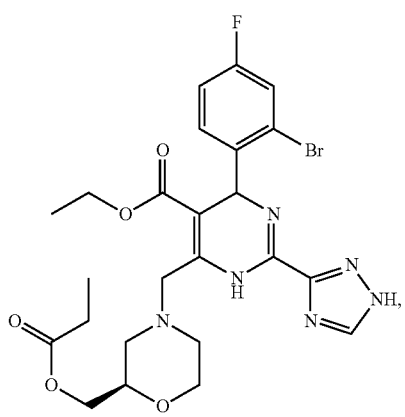
92
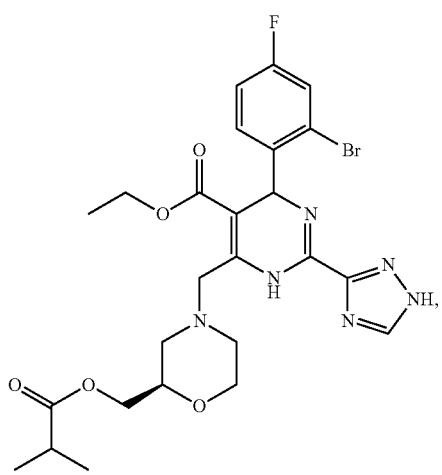
66
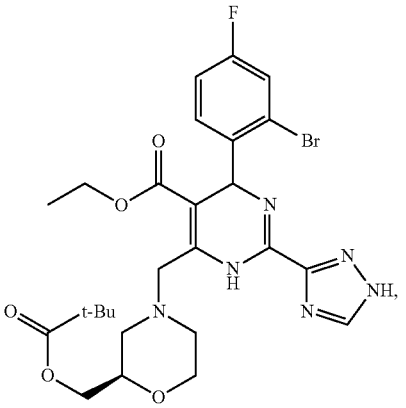
93
94
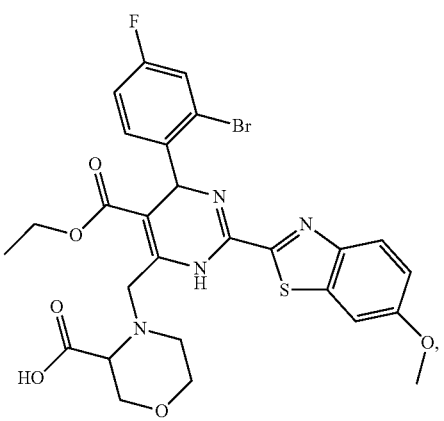
95
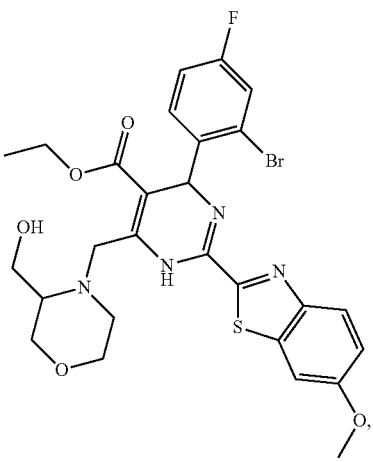

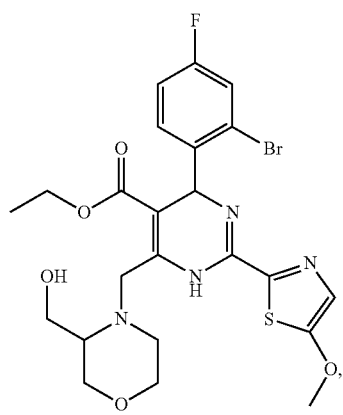
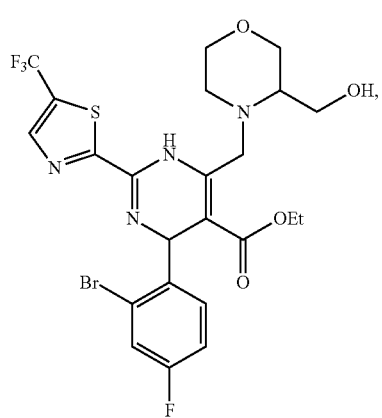
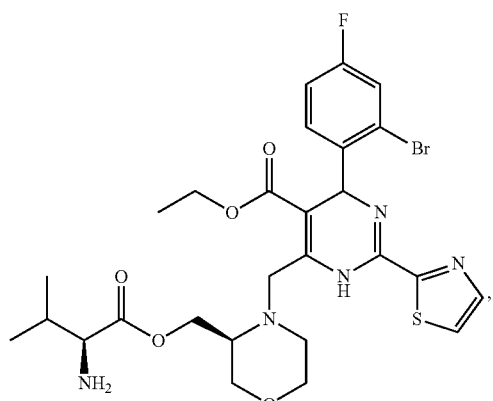
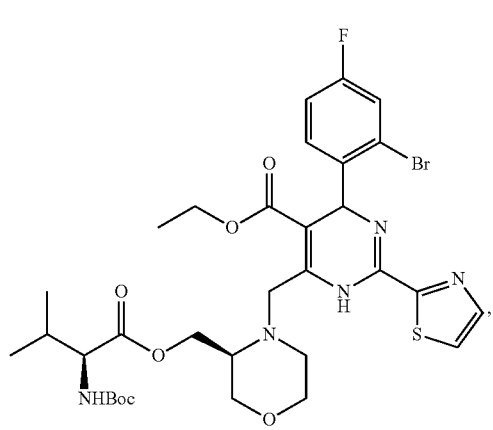
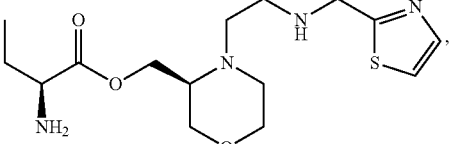
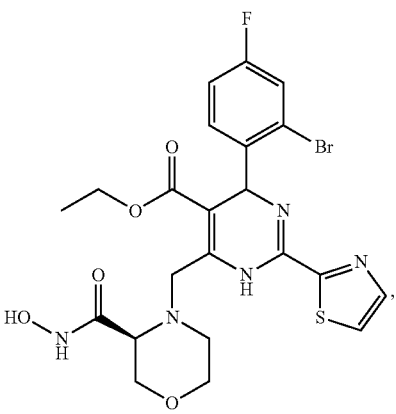
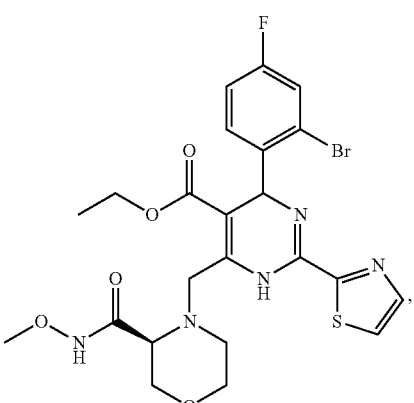
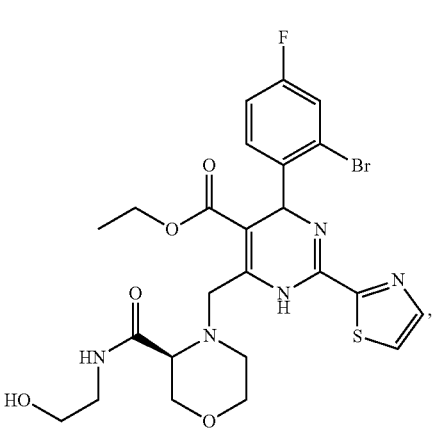

104
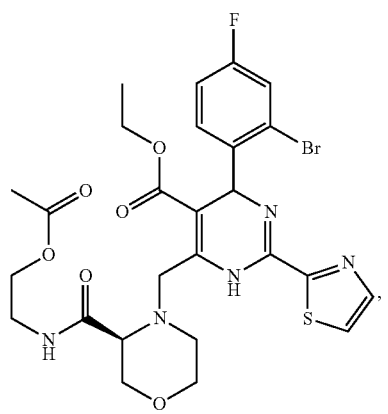
105
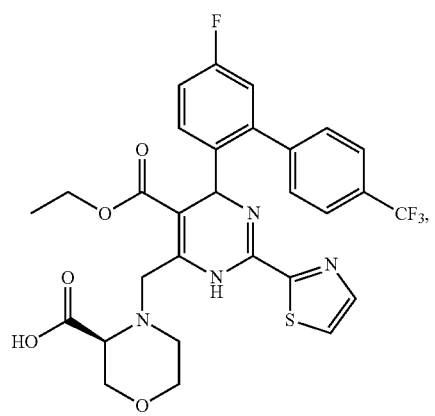
106
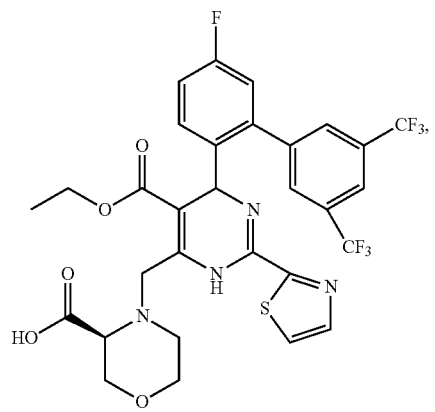
107
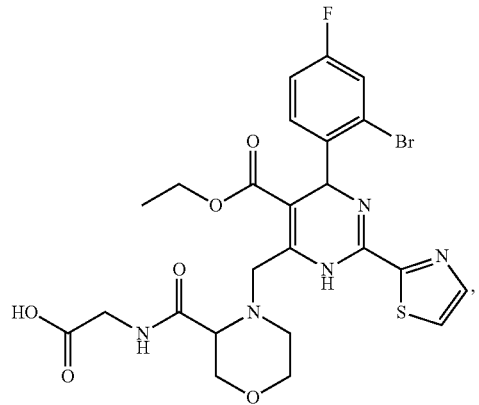
108
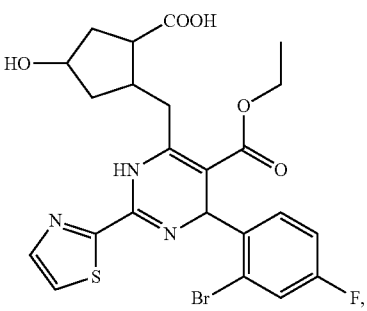
109
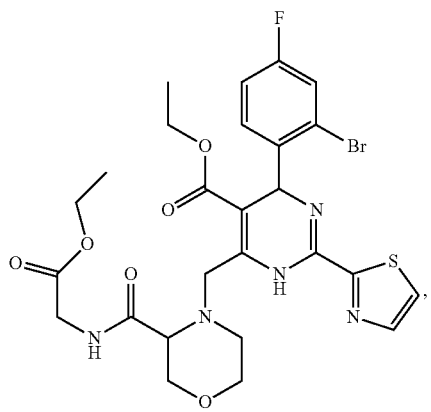
110
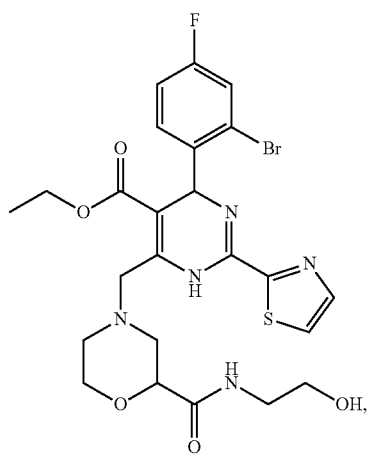
111
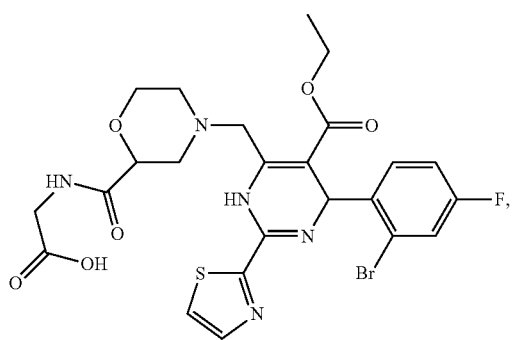

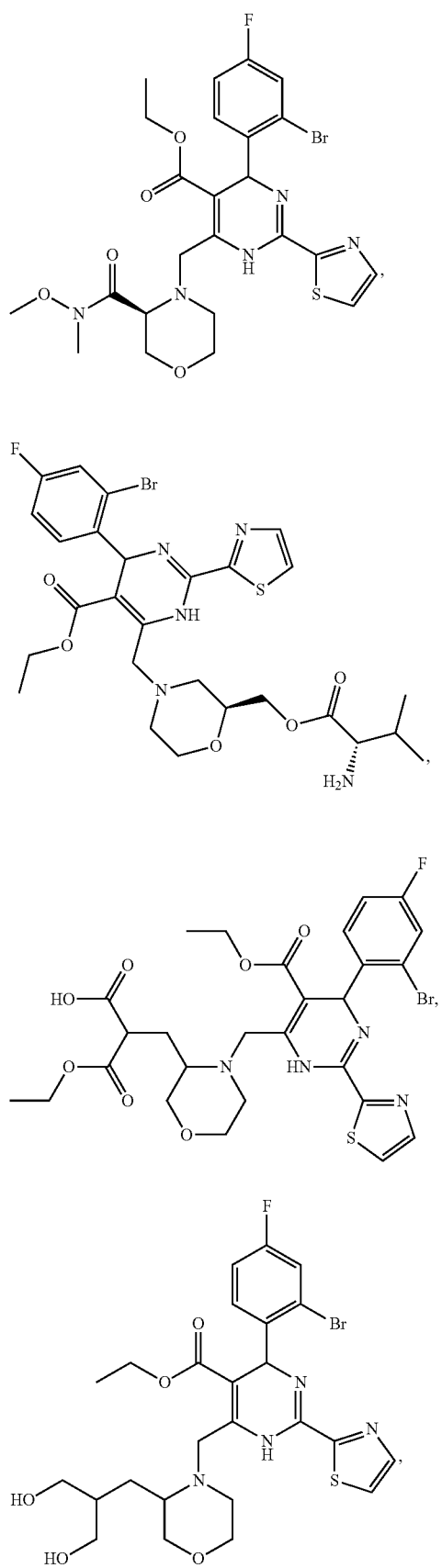

119
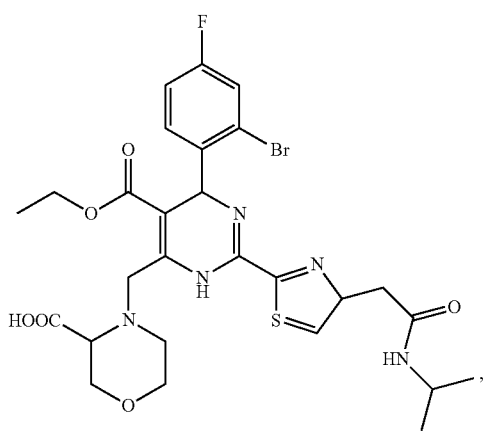
120
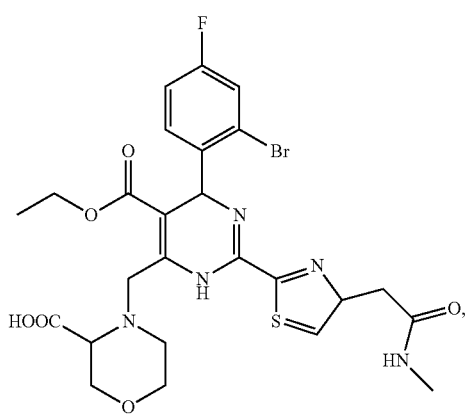
121
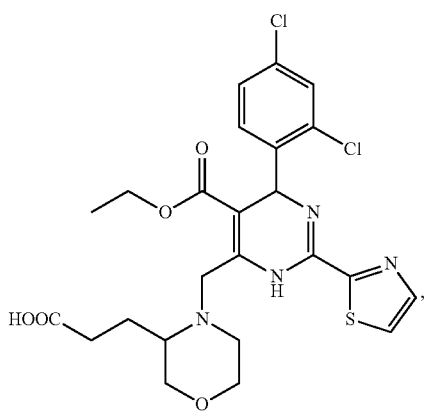
122
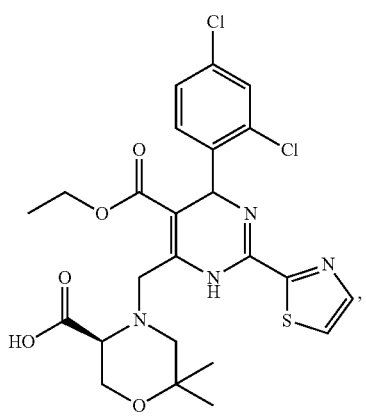
123
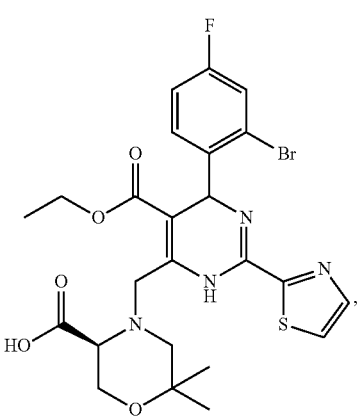
124
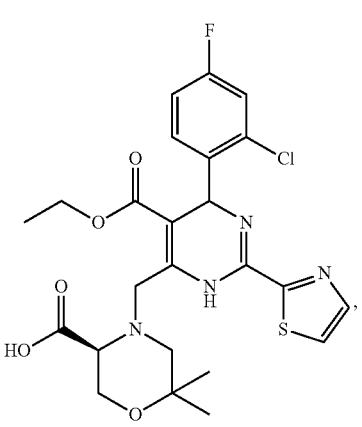
125
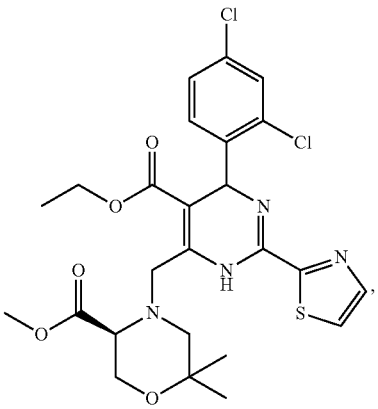
126
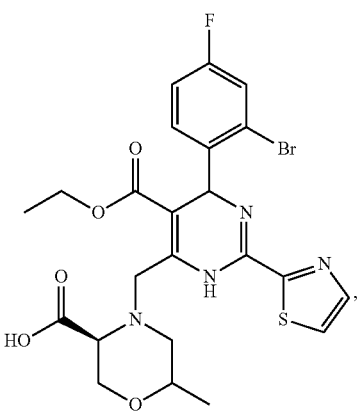

-continued
127
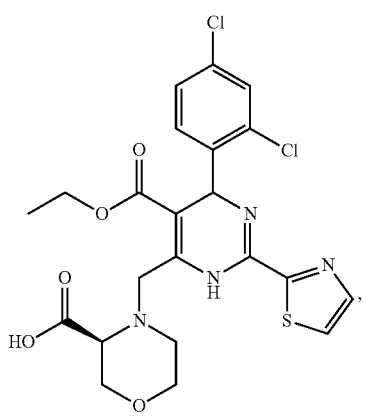
128
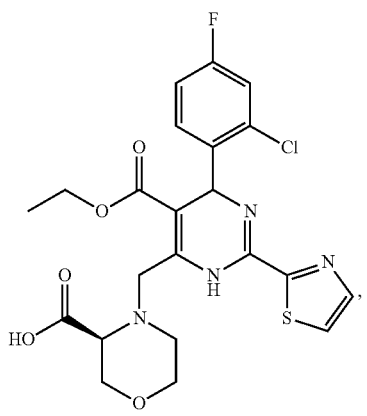
129
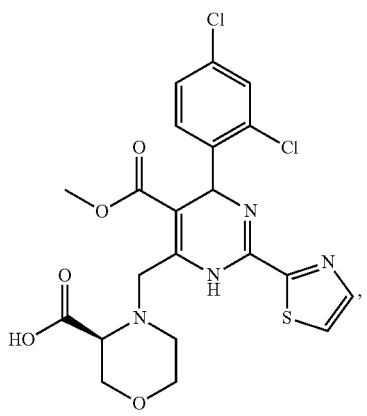
130
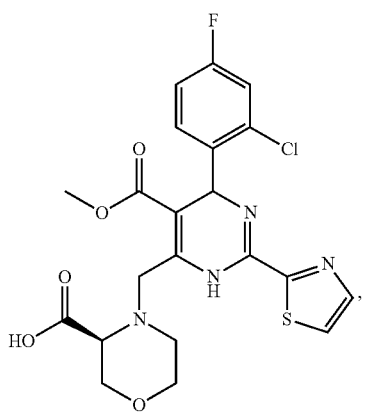
-continued
131
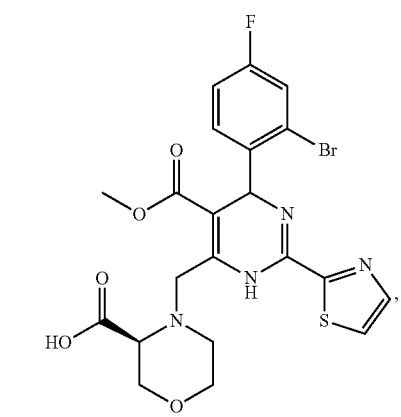
132
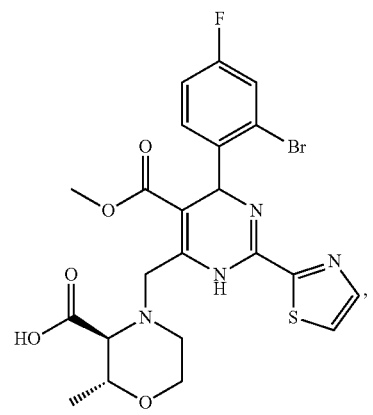
133
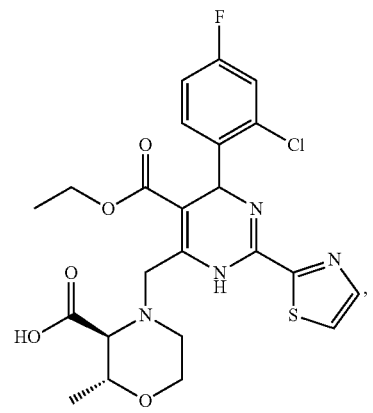
134
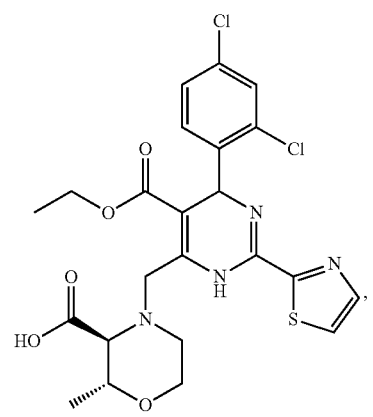

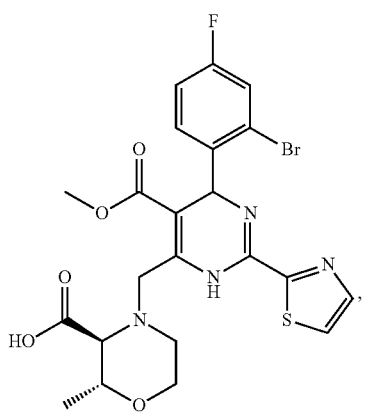
135
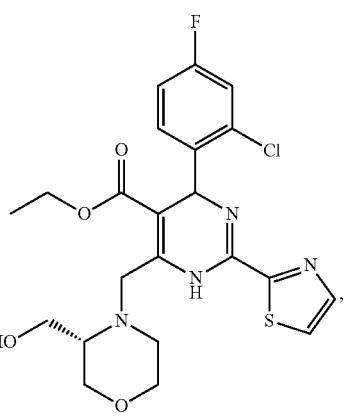
139
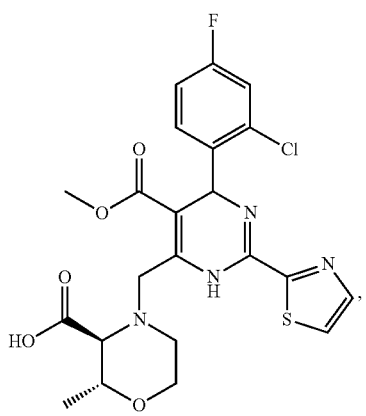
136
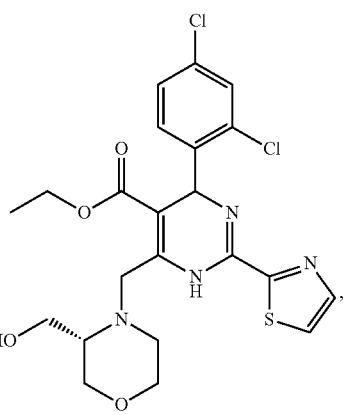
140
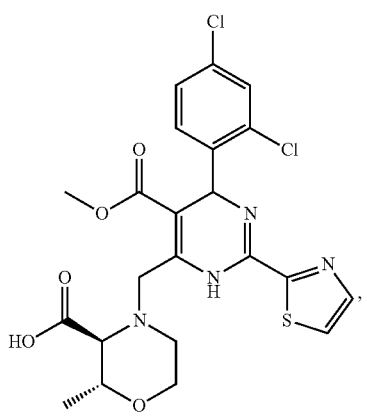
137
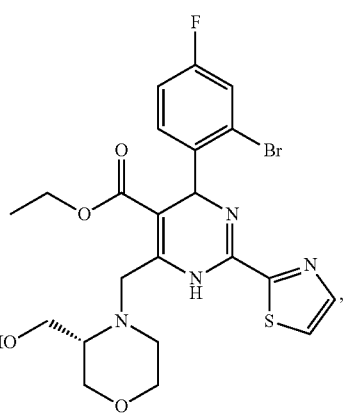
141
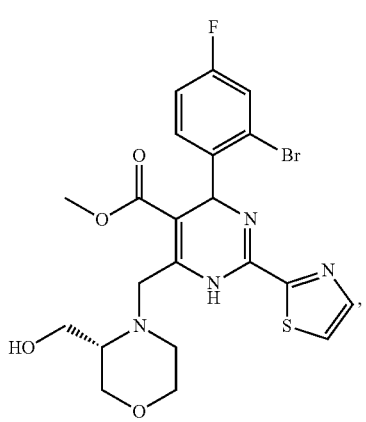
138
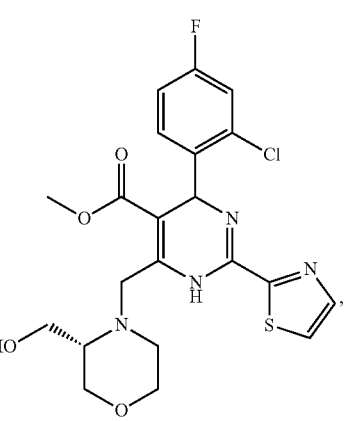
142

-continued
143
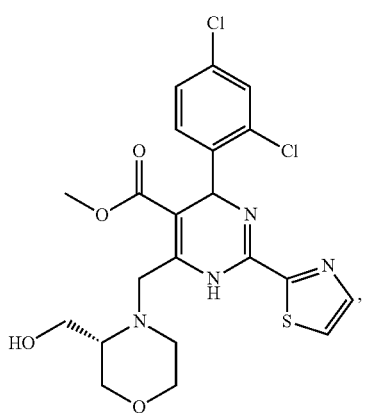
144
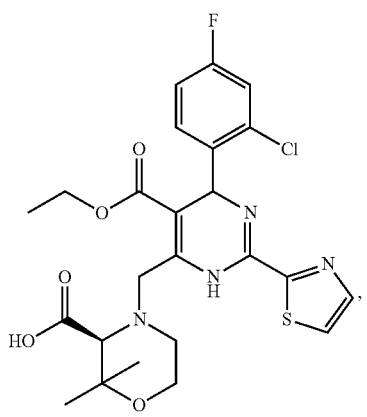
145
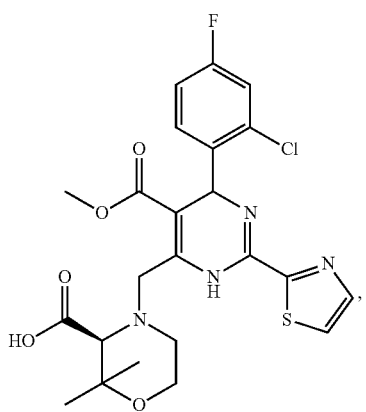
146
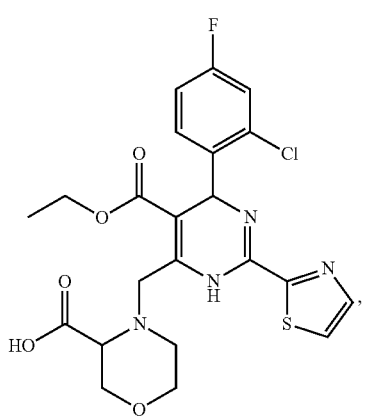
-continued
147
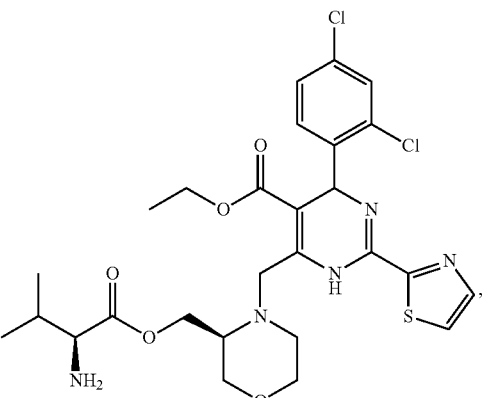
148
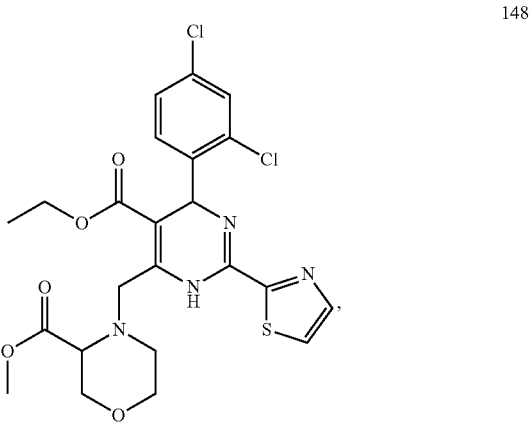
149
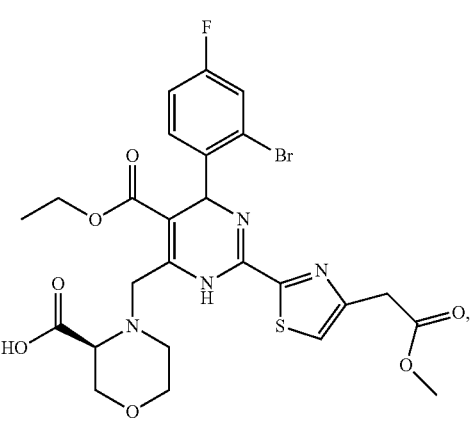
150
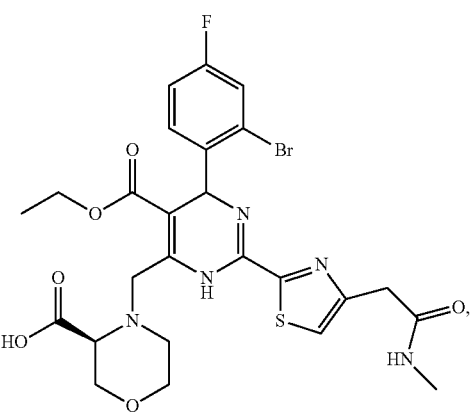

151 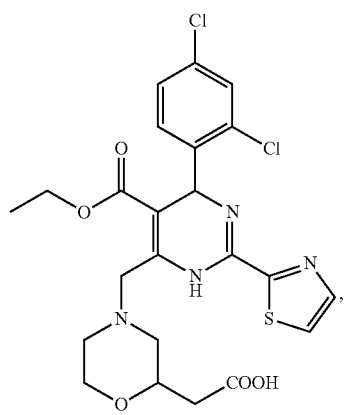
152 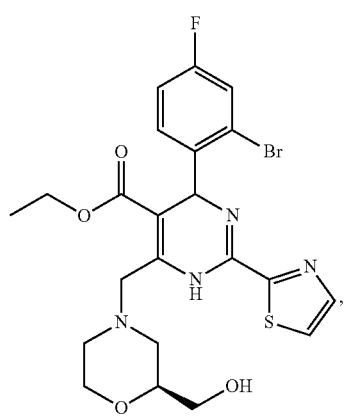
153 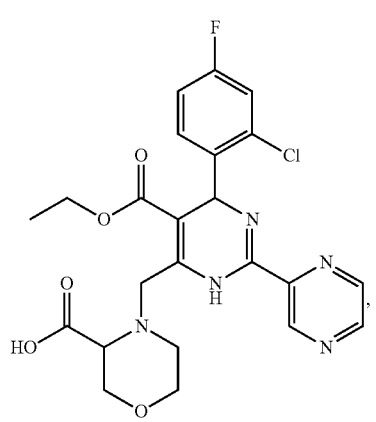
154 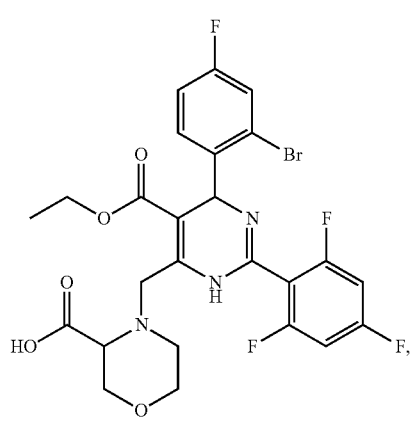
155 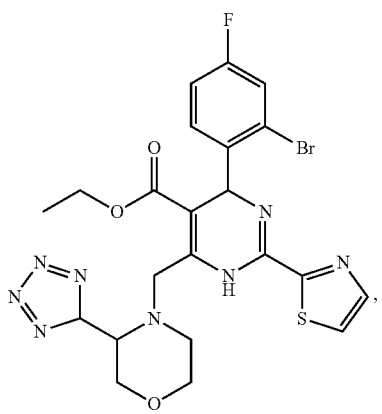
156 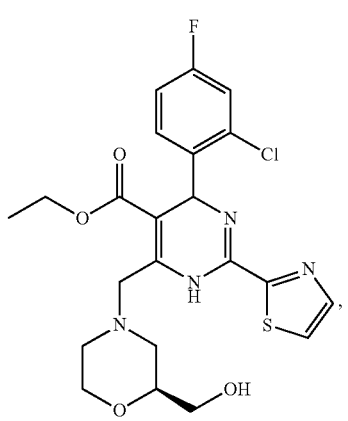
157 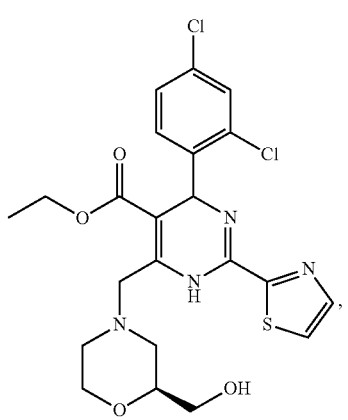
158 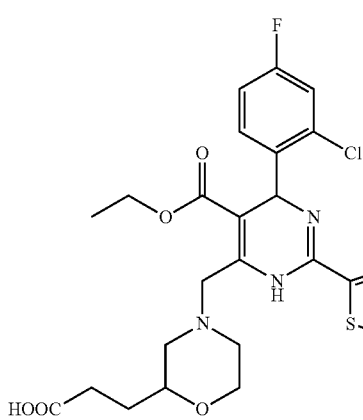

-continued
159
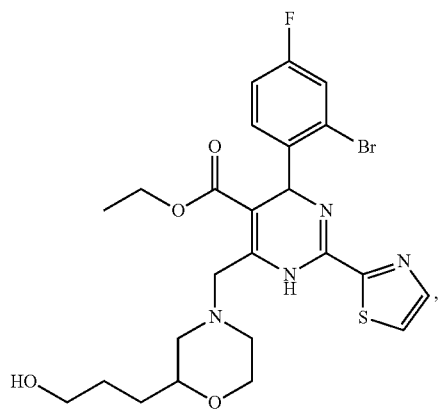
160
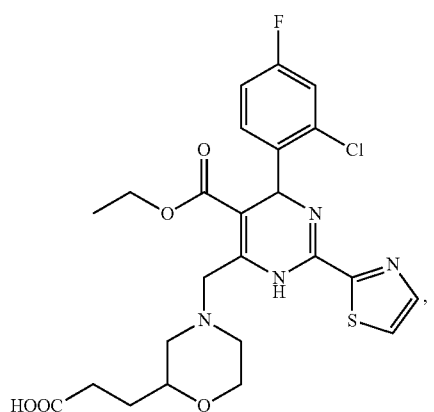
161
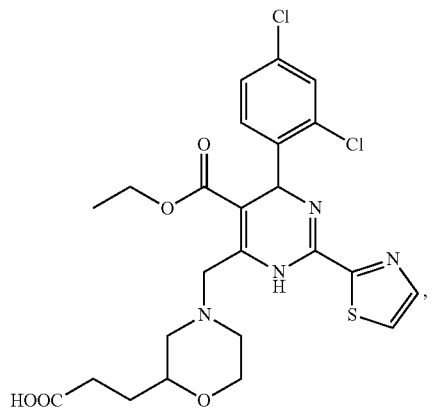
162
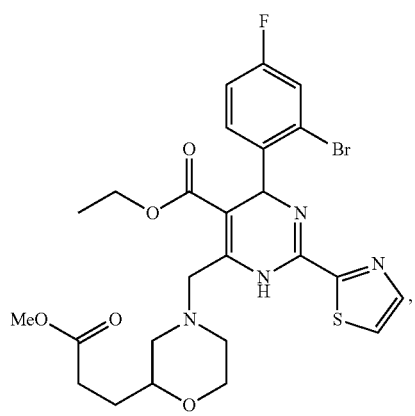
-continued
163
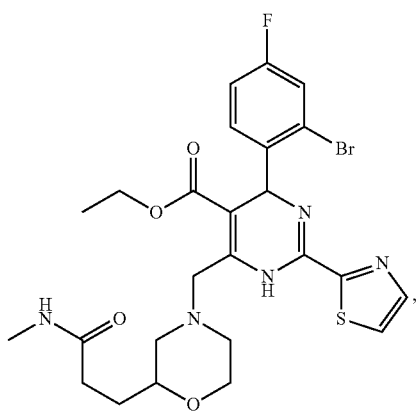
164
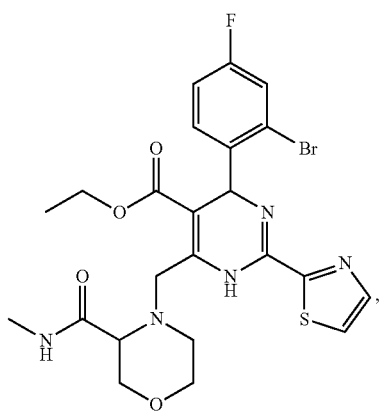
165
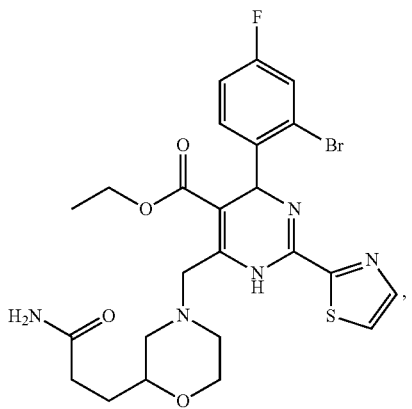
166
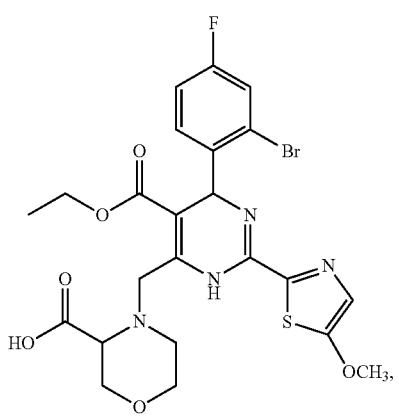

167 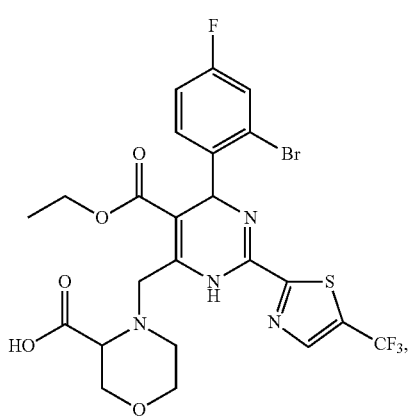

168 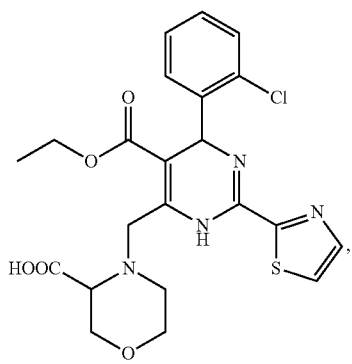

169 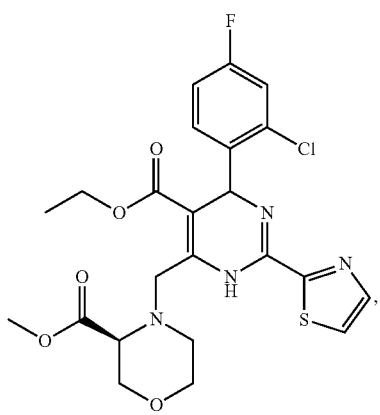

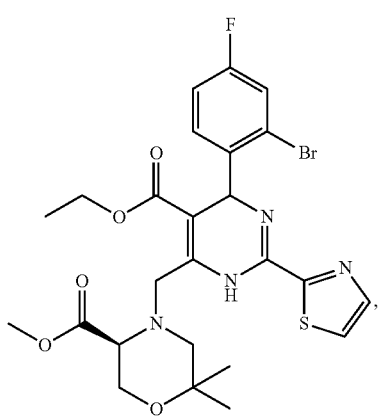

171 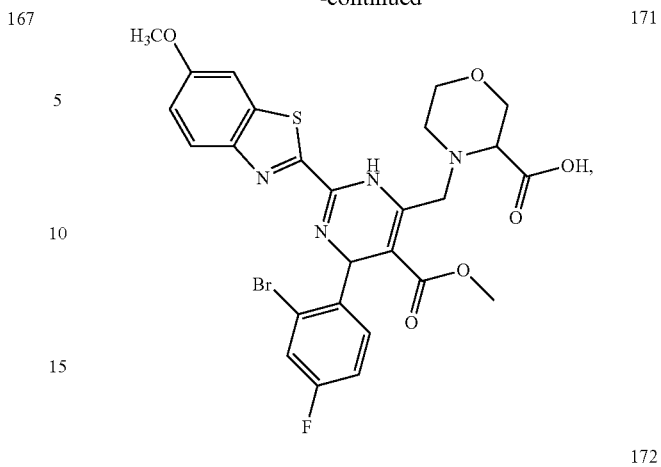

172 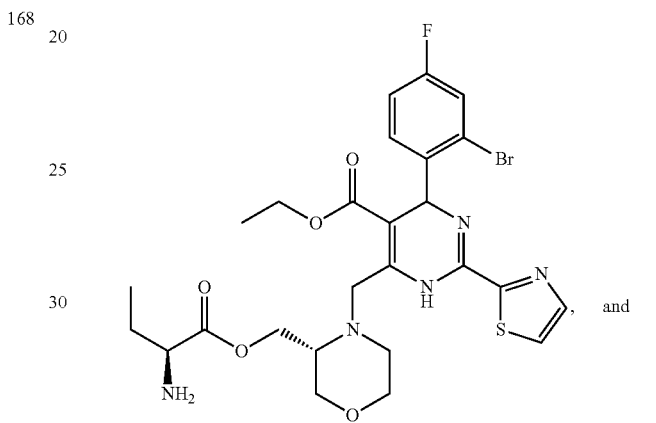

172 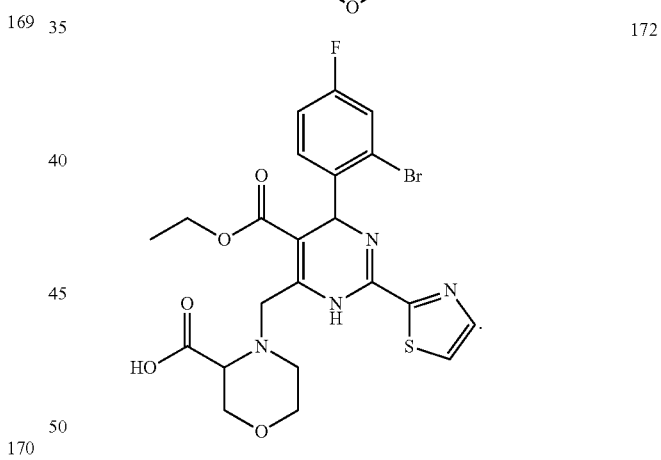, and

In one aspect, provided herein are compounds and a pharmaceutically acceptable carrier, excipient, diluent, adjuvant, vehicle or a combination thereof.

In certain embodiments, provided herein is the pharmaceutical composition further comprising an anti-HBV agent.

In certain embodiments, the pharmaceutical composition is disclosed herein, wherein the anti-HBV agent is a HBV polymerase inhibitor, immunomodulator or interferon.

In certain embodiments, the pharmaceutical composition is disclosed herein, wherein the anti-HBV agent is lamivudine, telbivudine, tenofovir, entecavir, adefovir dipivoxil, alfaferone, alloferon, celmoleukin, clevudine, emtricitabine, famciclovir, feron, fepatect CP, intefen, interferon α-1b, interferon α, interferon α-2, interferon α-2a, interferon α-2b, interferon β-1a, interleukin-2, mivotilate, nitazoxanide, peginterferon alfa-2a, ribavirin, roferon-A, sizofuran, euforavac, rintatolimod, phosphazid, heplisav, levamisole, or propagermanium.

In another aspect, provided herein is use of the compound disclosed herein or the pharmaceutical composition disclosed herein in the manufacture of a medicament for preventing, managing, or treating a viral disease or a HBV disease or lessening the severity of a viral disease or a HBV disease in a patient.

In another aspect, provided herein are methods for preventing, managing, treating or lessening a viral disease or a HBV disease in a patient, which comprises administering a pharmaceutically effective amount of the compound disclosed herein to the patient.

In another aspect, provided herein are methods for preventing, managing, treating or lessening a viral disease or a HBV disease in a patient, which comprises administering a pharmaceutically effective amount of the pharmaceutical composition disclosed herein to the patient.

In another aspect, provided herein are the compounds disclosed herein or the pharmaceutical compositions disclosed herein for use in preventing, managing or treating a viral disease or a HBV disease or lessening the severity of a viral disease or a HBV disease in a patient.

In certain embodiments, the viral disease or HBV disease is hepatitis B infection or a disease caused by hepatitis B infection.

In other embodiments, the disease caused by hepatitis B infection is cirrhosis or hepatocellular carcinoma.

In some embodiments, the organism or patient is a mammal; in other embodiments, the organism or patient is a human. In still other embodiments, the method further comprises contacting the kinase or organism with a HBV therapeutic agent.

In another aspect, provided herein is a method of inhibiting HBV infection, comprising contacting a cell or a plurality of cells with an effective HBV inhibiting amount of a compound disclosed herein or a composition thereof. In other embodiments, the method further comprises contacting the cells with a HBV therapeutic agent.

In another aspect, provided herein is a method of treating HBV disease in a patient, the method comprises administering to the patient in need of such treatment an effective therapeutic amount of a compound disclosed herein or a composition thereof. In other embodiments, the method further comprises administering to the patient a HBV therapeutic agent.

In another aspect, provided herein is a method of inhibiting a HBV infection in a patient, the method comprises administering to the patient in need of an effective therapeutic amount of a compound disclosed herein or a composition disclosed herein. In other embodiments, the method further comprises administering to the patient a HBV therapeutic agent.

In another aspect, provided herein include methods of preparing, methods of separating, and methods of purifying the compounds of Formula (I) or (Ia).

Provided herein includes the use of a compound disclosed herein, or a pharmaceutically acceptable salt thereof, in the manufacture of a medicament for inhibiting HBV infection effectively, including those described herein. The compounds disclosed herein are useful in the manufacture of a medicament for inhibiting HBV infection. The compounds disclosed herein are also useful in the manufacture of a medicament to attenuate, prevent, manage or treat disorders through inhibition of HBV. Also provided herein is a pharmaceutical composition comprising a therapeutically effective amount of a compound of Formula (I) or (Ia) in association with at least one pharmaceutically acceptable carrier, adjuvant or diluent.

Also provided herein is a method of inhibiting HBV disorders in a subject having or susceptible to such disorder, the method comprising treating the subject with a therapeutically effective amount of a compound of Formula (I) or (Ia).

Unless otherwise stated, all stereoisomers, geometric isomers, tautomers, N-oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula (I) or (Ia) and/or for separating enantiomers of compounds of Formula (I) or (Ia).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, malic acid, 2-hydroxy acrylic acid, lactic acid, citric acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, benzenesulfonic acid, methanesulfonic acid, ethanesulfonic acid or trifluoromethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium, a salt of $N^+(R^{14})_4$ or an alkaline earth metal hydroxide, and the like. Some non-limiting examples of suitable salts include organic salts derived from amino acids, such as glycine and arginine, ammonia (primary, secondary, and tertiary amines), salts of $N^+(R^{14})_4$, such as $R^{14}$ is H, $C_{1-4}$ alkyl, $C_{6-10}$ aryl or $C_{6-10}$ aryl-$C_{1-4}$-alkyl, and cyclic amines, such as piperidine, morpholine and piperazine, and inorganic salts derived from sodium, calcium, potassium, magnesium, manganese, iron, copper, zinc, aluminum, lithium, and the like. Further salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

COMPOSITION, FORMULATIONS, USES AND ADMINISTRATION OF COMPOUNDS AND COMPOSITIONS OF THE INVENTION

According to another aspect, the invention features pharmaceutical compositions that include a compound of Formula (I) or (Ia), a compound listed herein, or a compound named in Examples 1 to 157, and a pharmaceutically acceptable carrier, adjuvant, or vehicle. The compound disclosed herein can inhibit HBV effectively, and is suitable for use in treating the disease induced by viruses, especially acute and chronic persistent HBV infections. Chronic viral diseases induced by HBV can worsen the morbidity and the chronic HBV infection can cause liver cirrhosis and/or henatocellular carcinoma in many cases.

Areas of indication which may be mentioned for the compounds disclosed herein are, for example: the treatment of acute and chronic viral infections which may lead to infectious hepatitis, for example, infections with hepatitis B viruses. The compounds disclosed herein are particularly suitable for the treatment of chronic hepatitis B infections and the treatment of chronic hepatitis B infections and the treatment of acute and chronic hepatitis B viral infections.

The present invention includes pharmaceutical preparations which, besides nontoxic, inert pharmaceutically suitable carriers, comprise one or more compounds (I) or (Ia) disclosed herein or a combination thereof or which consist of one or more active ingredients (I) or (Ia) disclosed herein or a combination thereof.

The pharmaceutical preparations mentioned above may also comprise other active pharmaceutical ingredients apart from the compounds (I) or (Ia).

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, all of each of which are herein incorporated by reference in their entireties, are disclosed various carriers used in formulating pharmaceutically acceptable compositions and known techniques for the preparation thereof. Except in so far as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, aluminium, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants. As a matter of convenience, local anesthetics, preservatives, buffering agents and so on, can be dissolved in carriers directly.

The pharmaceutical composition comprising the compound disclosed herein may be administered in any of the following routes: orally, inhaled by spray, rectally, nasally, vaginally, topically, parenterally such as subcutaneous, intravenous, intramuscular, intraperitoneal, intrathecal, intraventricular, intrasternal, or intracranial injection or infusion, or administered with the aid of an explanted reservoir, wherein the administration routes by orally, intramuscular, intraperitoneal or intravenous injection are preferred.

The compound disclosed herein or the pharmaceutical composition comprising the compound may be administered in a unit dosage form. The dosage form may be in a liquid form, or a solid form. The liquid form includes true solution, colloids, particulates, emulsions, suspensions. Other dosage forms include tablets, capsules, dropping pills, aerosols, pills, powder, solutions, suspensions, emulsions, granules, suppositories, lyophilized powder for injection, clathrates, implants, patches, liniments, and the like.

Oral tablets and capsules may comprise excipients, e.g., binders such as syrup, Arabic gum, sorbitol, tragacanth, or polyvinylpyrrolidone, fillers such as lactose, sucrose, corn starch, calcium phosphate, sorbitol, aminoacetic acid, lubricants such as magnesium stearate, saponite, polyethylene glycol, silica, disintegrating agents such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other medium is added before use. This liquid preparation may comprise conventional additives, e.g., suspending agents such sorbitol, cellulose methyl ether, glucose syrup, gelatin, hydroxyethyl cellulose, carboxymethyl cellulose, aluminum stearate gel, hydrogenated edible grease; emulsifying agents such as lecithin, sorbitan monooleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppository may comprise a conventional suppository substrate, such as cocoa butter or other glyceride.

For non-gastric administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an enclosed bottle or ampoule.

For topical application on skin, the compound disclosed herein may be made into a suitable form of ointment, lotion or cream, wherein the active ingredient is suspended or dissolved in one or more carrier(s). Some non-limiting examples of the carriers used for an ointment include mineral oil, liquid vaseline, albolene, propylene glycol, polyoxyethylene, polyoxypropylene, emulsified wax, water, and the like; Some non-limiting examples of the carriers used for a lotion and a cream include mineral oil, sorbitan monostearic ester, tween 60, cetyl esters wax, hexadecylene aromatic alcohol, 2-octyl dodecanol, benzyl alcohol, water, and the like.

In general, it has been proved that, advantageously, whether in human medicine or in veterinary medicine, the total dose of the active compound disclosed herein is about 0.5 to 500 mg every 24 hours, preferably 1 to 100 mg per kg body weight. If appropriate, the drug is administrated by single dose for multiple times, to thereby achieve the desired effect. The amount of the active compound in a single dose is preferably about 1 to 80 mg, more preferably 1 to 50 mg per kg weight body. Nevertheless, the dose may also be varied according to the type and body weight of the object to be treated, the kind and extent of severity of diseases, the type of the preparation and the administration manner of the drug, and the administration period or the time interval.

In one aspect, provided herein is the pharmaceutical composition further comprising an anti-HBV agent. And the anti-HBV agent is a HBV polymerase inhibitor, immunomodulator or interferon.

The anti-HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofuran, euforavac, veldona, rintatolimod, phosphazid, heplisav, interferon α-2b, levamisole or propagermanium.

In another aspect, provided herein is use of a compound and the pharmaceutical composition in the manufacture of a medicament for preventing, managing, treating or lessening the HBV disease in a patient, comprising administering a pharmaceutically effective amount to a patient. The HBV disease is a hepatic disease caused by hepatitis B virus infection or hepatitis B infection, including acute hepatitis, chronic hepatitis, cirrhosis or hepatocellular carcinoma. The symptoms of acute hepatitis B virus infection may be asymptomatic or may be the same as acute hepatitis. A patient with chronic virus infection may develop active disease, which can progress to cirrhosis and liver cancer.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiment, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

The compound disclosed herein exhibits a relatively strong antiviral effect. This kind of compound has unexpected antiviral activity to HBV, and thus is adapted to be used for treating various virus-caused diseases, in particular acute and chronic vural diseases caused by HBV may lead to various syndromes having different extents of severity. As well known, chronic HBV infection may lead to hepatic cirrhosis and/or liver cell carcinoma.

Examples of indications capable of being treated by the compound disclosed herein include: acute and chronic viral infections capable of leading to infectious hepatitis, such as HBV infection, and particularly preferred chronic HBV infection and acute HBV infection.

The invention further relates to the use of the compounds and compositions defined above for producing a medicament for the treatment and prophylaxis of the diseases described above, preferably of viral diseases, in particular of hepatitis B.

GENERAL SYNTHETIC PROCEDURES

Generally, the compounds disclosed herein may be prepared by methods described herein, wherein the substituents are as defined for Formulas (I) or (Ia), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Column chromatography was conducted using a silica gel column. Silica gel (200-300 mesh) was purchased from Qingdao Ocean Chemical Factory. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets), br.s (broadened singlet). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pumps and a G1316A TCC (Temperature Control of Column, maintained at 30 t). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 micron). Injection volume was decided by the sample concentration. The flow rate is 0.6 mL/min. The mobile phase was (0.1% formic acid in $CH_3CN$ as mobile phase A) in (0.1% formic acid in $H_2O$ as mobile phase B) with UV detection at 210/254 nm. The conditions of gradient elution is described in Table 1:

TABLE 1

| t (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron), 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
MeCN, $CH_3CN$ acetonitrile
DCM, $CH_2Cl_2$ methylene chloride
$CHCl_3$ chloroform
$CDCl_3$ chloroform-d
$CCl_4$ carbon tetrachloride
Boc tert-butyloxycarbonyl
PE petroleum ether (60-90° C.)
EtOAc, EA ethyl acetate
HCl hydrochloric acid
$K_2CO_3$ potassium carbonate
$NaHCO_3$ sodium bicarbonate
NaOH sodium hydroxide
NaCl sodium chloride
$Na_2SO_4$ sodium sulfate
$Et_3N$, TEA triethylamine
NBS N-bromosuccinimide
$D_2O$ oxide
$H_2O$ water
mL milliliter
RT, rt room temperature
Rt retention time
$H_2$ hydrogen
EDC.HCl 1-(3-dimethylaminopropyl)-3-ethylcarbodiimide hydrochloride
HOAT 1-hydroxy-7-azabenzotriazole
DIPEA N,N-diisopropylethylamine
DCC N,N'-dicyclohexylcarbodiimide
DMF N,N-dimethylformamide
$LiAlH_4$ lithium aluminum hydride
THF tetrahydrofuran
DMSO dimethylsulfoxide
Pd/C, Pd—C palladium on carbon
CuCN copper (I) cyanide
$CH_3OH$ methanol
$N_2$ nitrogen
$NH_4Cl$ ammonium chloride
$Ac_2O$ Acetic anhydride
$t_{1/2}$ half-life period
AUC area under the curve
Vss apparent volume of distribution
CL clearance
F absolute bioavailability
$T_{max}$ time to peak
$C_{max}$ peak concentration
hr*ng/mL blood concentration*time

SYNTHESIS OF INTERMEDIATES

Synthesis of Intermediate 3A

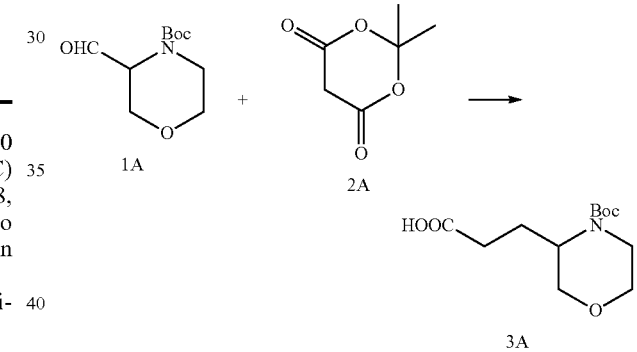

Intermediate 3A can be prepared by the process disclosed herein. Compound 1A reacts with compound 2A in an acidic condition to give intermediate 3A.

Synthesis of Intermediate 5A

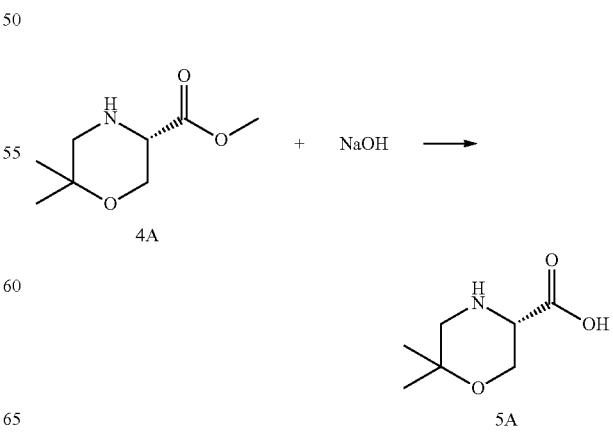

Intermediate 5A can be prepared by the process disclosed herein. Compound 4A is hydrolyzed in an alkaline condition to give intermediate 5A.

Synthesis of Intermediate 8A

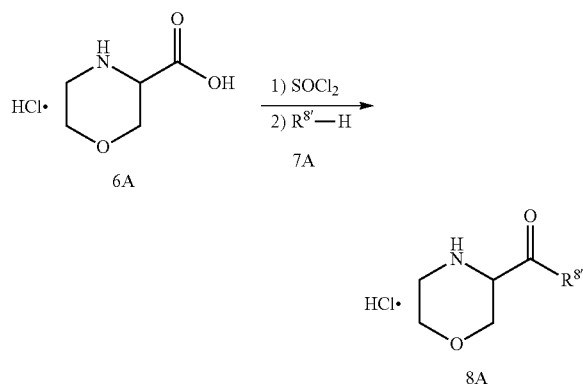

Intermediate 8A, wherein $R^{8'}$ is alkylamino, alkoxy or amino, can be prepared by the process disclosed herein. Compound 6A is transformed to an acyl chloride intermediate through acylation. The acyl chloride intermediate reacts with compound 7A to give intermediate 8A.

Synthesis of Intermediate 12A

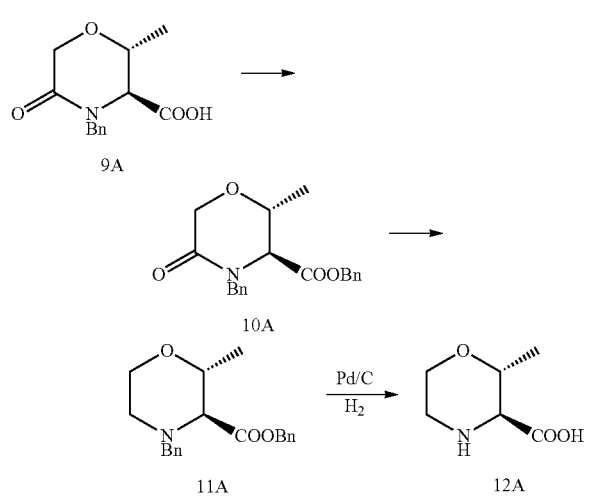

Intermediate 12A can be prepared by the process disclosed herein. Compound 9A reacts with benzyl bromide to afford compound 10A, which can be transformed to compound 11A under the action of borane tetrahydrofuran. Compound 11A is then reduced through catalytic hydrogenation to give intermediate 12A.

Synthesis of Intermediate 18A

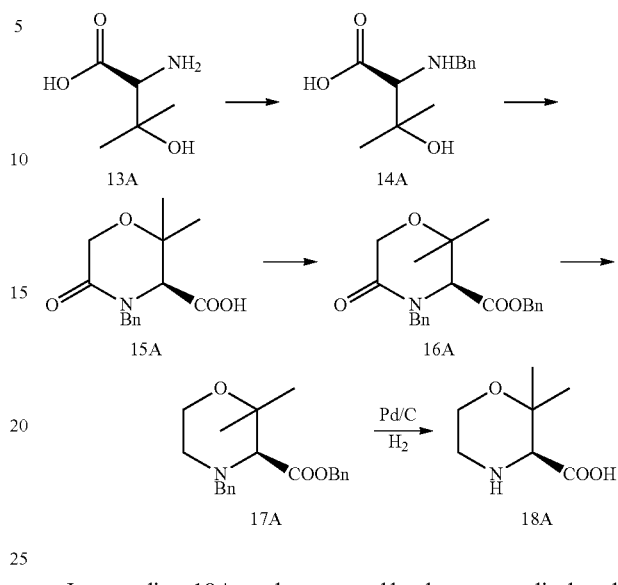

Intermediate 18A can be prepared by the process disclosed herein. Compound 13A reacts with benzaldehyde and sodium borohydride to give compound 14A. Compound 14A then reacts with chloroacetyl chloride in an alkaline condition to afford compound 15A followed by reacting with benzyl bromide to afford compound 16A, which can be transformed to compound 17A under the action of borane tetrahydrofuran. Compound 17A is then reduced through catalytic hydrogenation to give intermediate 18A.

Synthesis of Intermediate 22A

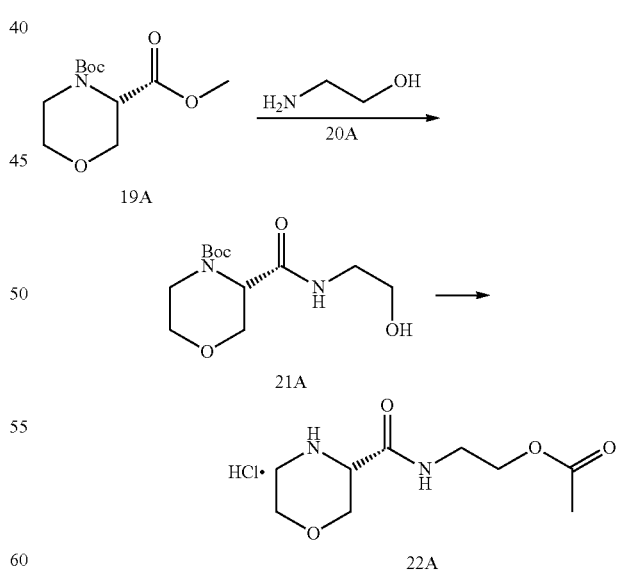

Intermediate 22A can be prepared by the process disclosed herein. Compound 19A reacts with 2-aminoethanol to afford compound 21A followed by reacting with hydrochloric acid in ethyl acetate under the action of acetic acid to give intermediate 22A.

Synthesis of Intermediate 25A

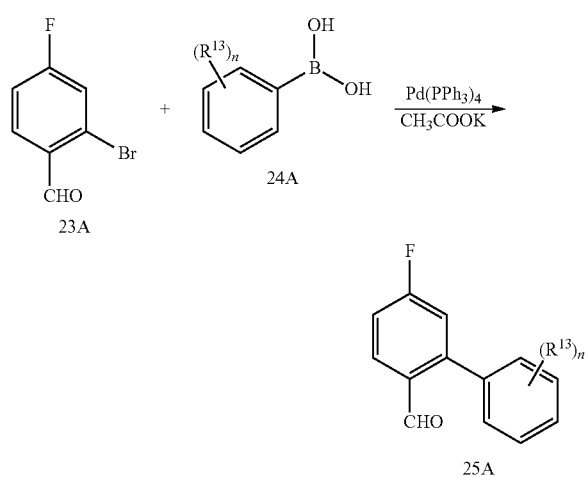

Intermediate 25A, wherein each $R^{13}$ and n is as defined above, can be prepared by the process disclosed herein. Compound 23A reacts with compound 24A under the action of tetrakis(triphenylphosphine)palladium in an alkaline condition to give intermediate 25A.

Synthesis of Intermediate 28A

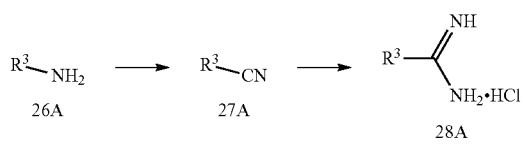

Intermediate 28A can be prepared by the process disclosed herein, wherein $R^3$ is as defined herein. Compound 26A can be transformed to compound 27A through the action of copper (I) cyanide. Compound 27A then reacts with hydroxylamine hydrochloride in the presence of Pd/C to give intermediate 28A.

Synthesis of Intermediate 34A

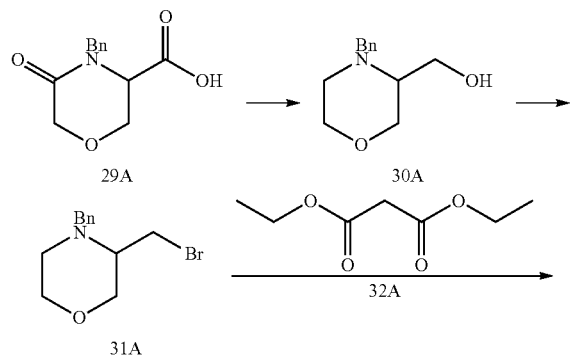

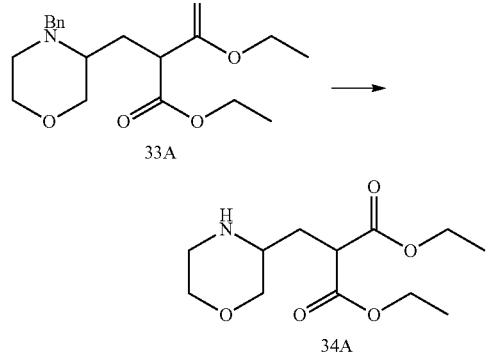

Intermediate 34A can be prepared by the process disclosed herein. Compound 31A can be prepared by the reduction and bromination of compound 29A. Compound 31A then reacts with compound 32A to afford compound 33A followed by reduction to give intermediate 34A.

Synthesis of Intermediate 36A

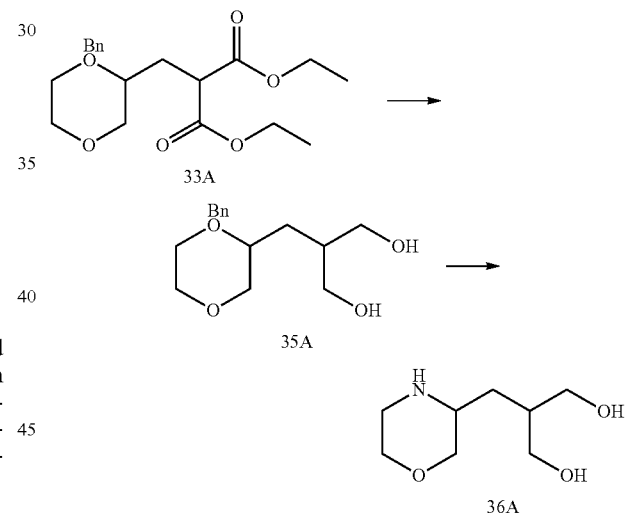

Intermediate 36A can be prepared by the process disclosed herein. Compound 33A is reduced twice by any reduction reaction that can reduce esters into alcohols or amides into amines to give intermediate 36A.

Synthesis of Intermediate 44A

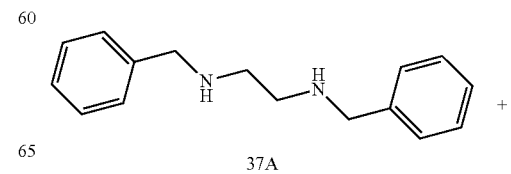

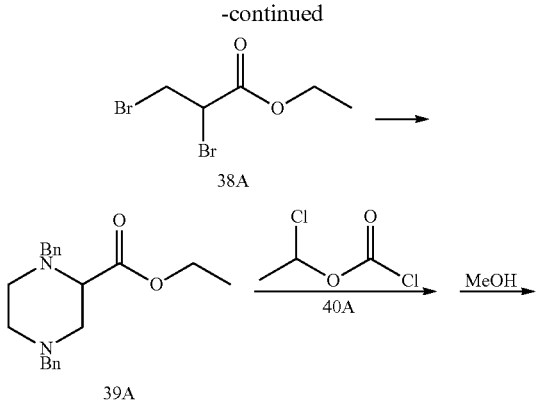

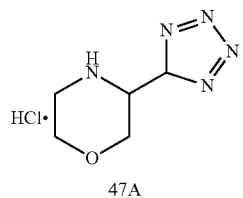

Intermediate 47A can be prepared by the process disclosed herein. Compound 45A is reacted with sodium azide and ammonium chloride to afford compound 46A followed by reduction through deprotection to give intermediate 47A.

Synthesis of Intermediate 53A

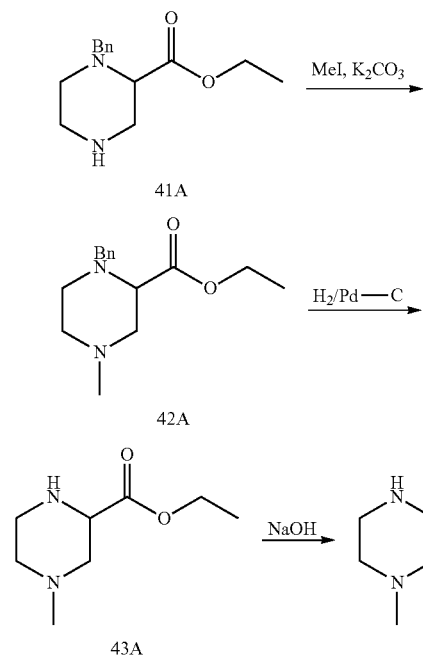

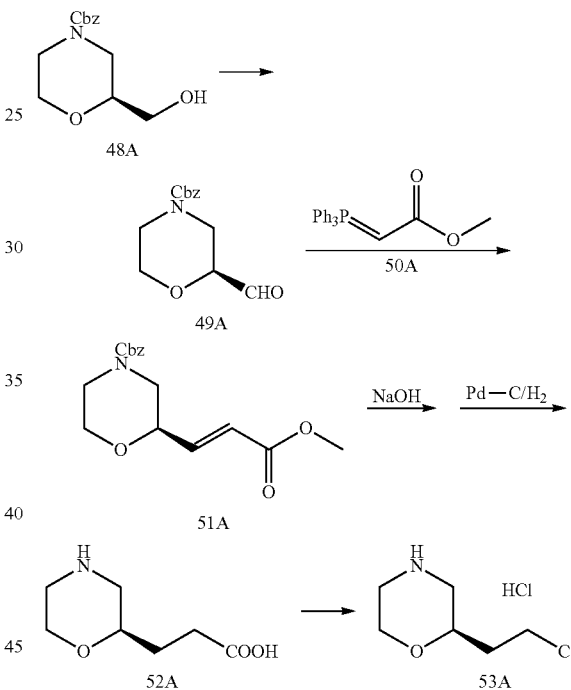

Intermediate 44A can be prepared by the process disclosed herein. Compound 37A reacts with compound 38A to afford compound 39A. A mixture of compound 39A and compound 40A in methanol is refluxed to afford compound 41A, followed by methylation, reduction through catalytic hydrogenation and hydrolyzation in an alkaline condition to give intermediate 44A.

Intermediate 53A can be prepared by the process disclosed herein. Compound 49A can be prepared through oxidation of compound 48A. Compound 49A then reacts with compound 50A to afford compound MA followed by basic hydrolysis, reduction and salt forming reaction to give intermediate 53A.

Synthesis of Intermediate 47A

Synthesis of Intermediate 60A

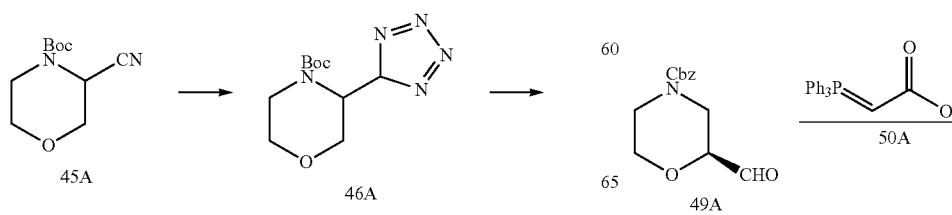

101

-continued

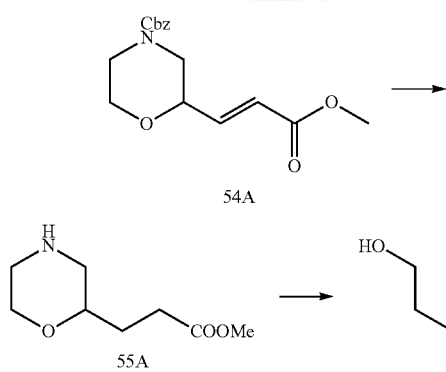

Intermediate 60A can be prepared by the process disclosed herein. Compound 49A reacts with compound 50A to afford compound MA, followed by reduction of the alkenyl and ester groups to give intermediate 60A.

Synthesis of Intermediate 61A

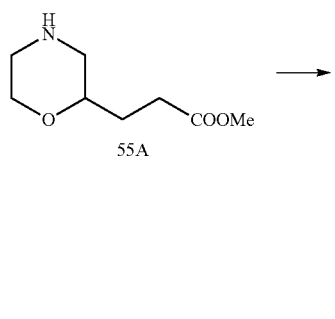

Intermediate 61A can be prepared by the process disclosed herein. Compound 55A is ammonolyzed to give intermediate 61A.

Synthesis of Intermediate 69A

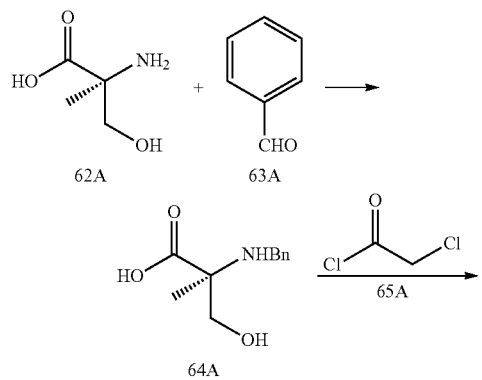

102

-continued

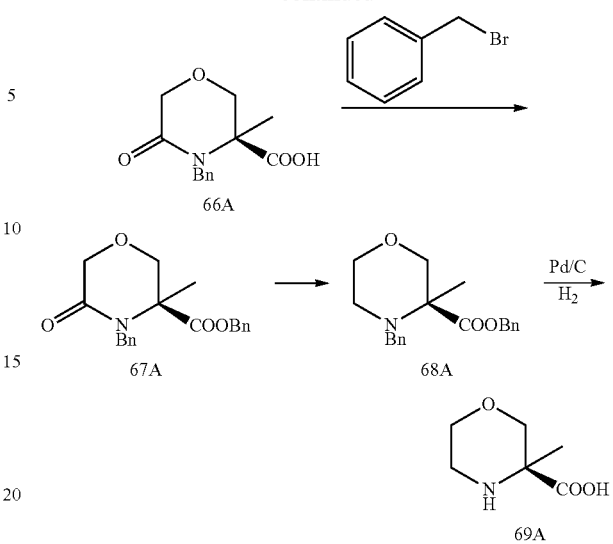

Intermediate 69A can be prepared by the process disclosed herein. Compound 62A reacts with compound 63A to afford compound 64A. Compound 64A reacts with compound 65A to afford compound 66A. Compound 66A reacts with (bromomethyl)benzene to afford compound 67A, which is reduced twice to give intermediate 69A.

SYNTHESIS OF COMPOUNDS

Compounds having Formula (I) or (Ia) may be prepared by methods described herein.

Scheme 1

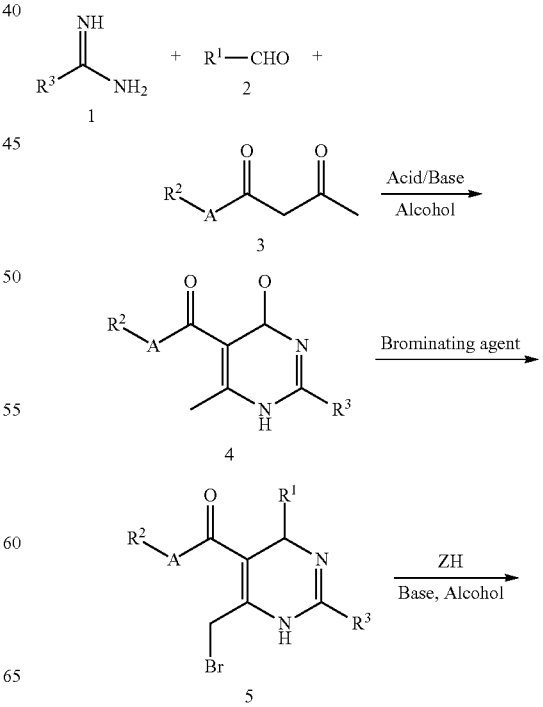

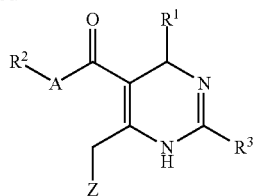
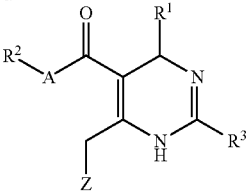

Pyrimidine 6, wherein each R¹, R², R³, A and Z is as defined herein, can be prepared by the process illustrated in Scheme 1. Amidines 1 or hydrochloride thereof, aldehydes 2 and compound 3 are cyclized in suitable inert solvent(s) (such as alcohol reagents) to give compound 4.

Compound 4 reacts with brominating agent in inert solvent(s) to give compound 5. Subsequently, compound 5 reacts with ZH in appropriate inert solvent(s) under an alkaline condition to yield pyrimidine 6.

Alternatively, pyrimidine 6, wherein each R¹, R², R³, A and Z is as defined herein, can be prepared by the process illustrated in Scheme 2. Amidines 7 or hydrochloride thereof, aldehydes 2 and compound 3 can be cyclized in suitable inert solvent(s) (such as alcohol reagents) to give compound 8.

Compound 8 can be reacted with chlorinating agent to give compound 9. Compound 9 reacts with R³H in suitable inert solvent(s) to yield compound 4. Compound 4 reacts with brominating agent in inert solvent(s) to give compound 5. Subsequently, compound 5 reacts with ZH in appropriate inert solvent(s) under an alkaline condition to yield pyrimidine 6.

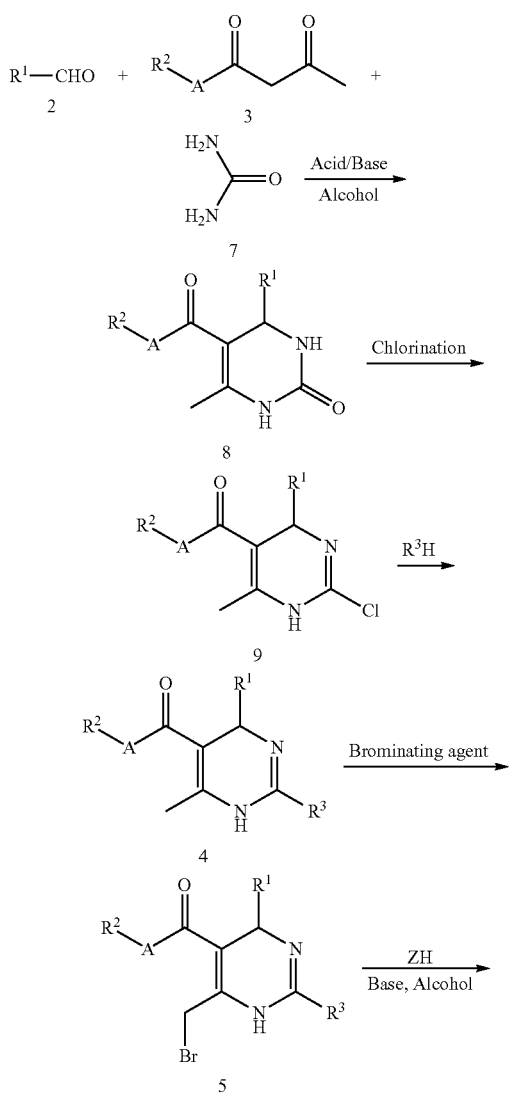
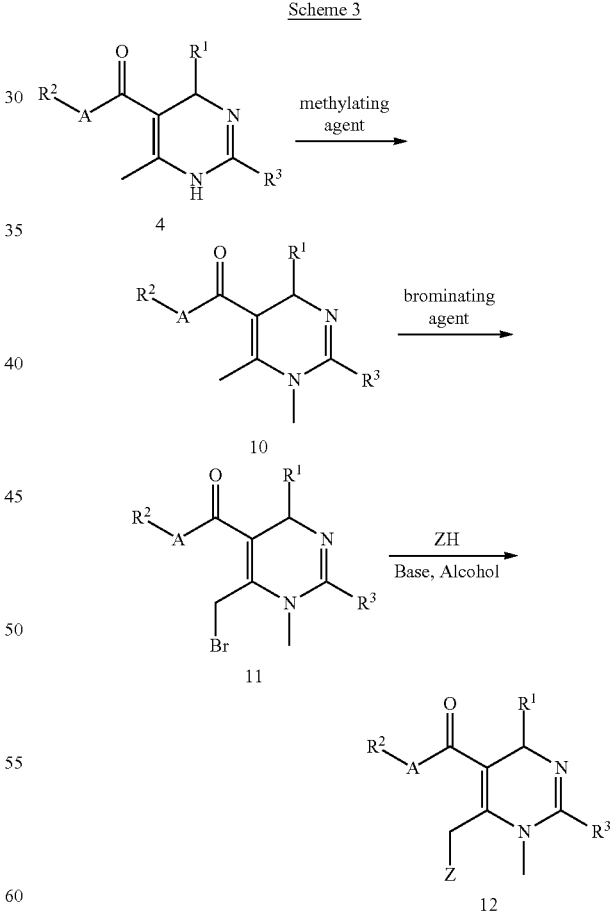

Pyrimidine 12, wherein each R¹, R², R³, A and Z is as defined above, can be prepared by the process illustrated in Scheme 3. Compound 4 reacts with methylating agent to afford compound 10 followed by reacting with brominating agent in inert solvent(s) to give compound 11. Subsequently, compound 11 reacts with ZH in appropriate inert solvent(s) under an alkaline condition to yield pyrimidine 12.

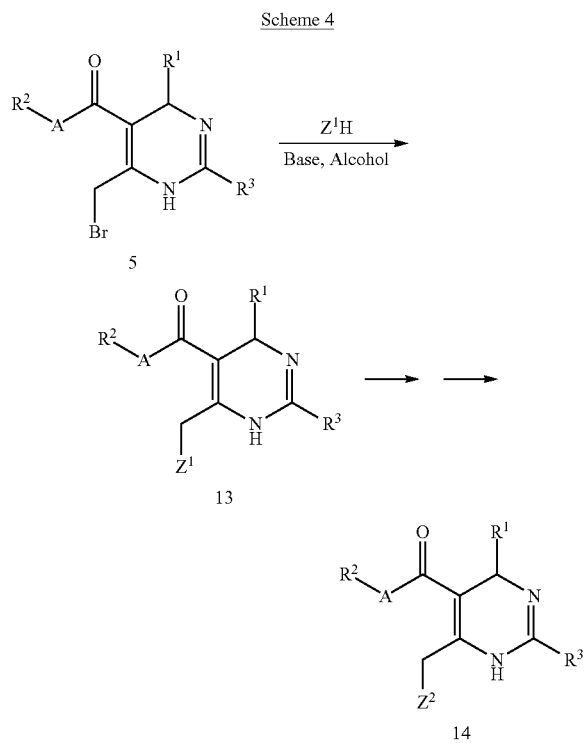

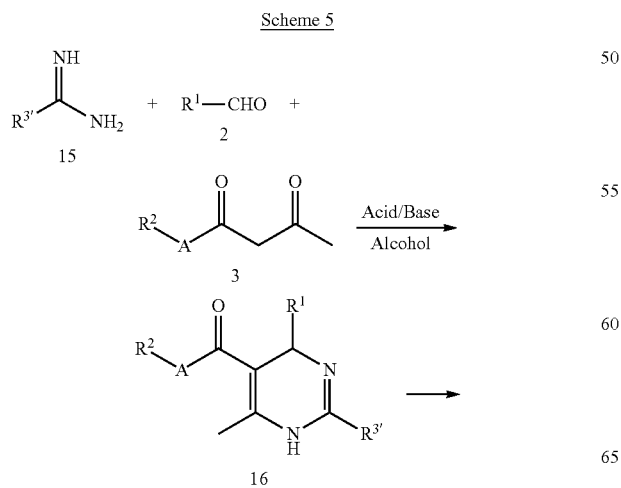

Pyrimidine 14 can be prepared by the process illustrated in Scheme 4, wherein when $Z^1$ is $—(CR^7R^{7a})_t—OH$, $Z^2$ is $—(CR^7R^{7a})_t—OC(=O)—R^8$; when $Z^1$ is $—(CR^7R^{7a})_m—C(=O)O—R^8$, $Z^2$ is $—(CR^7R^{7a})_m—C(=O)N(R^8)_2$, each $R^1$, $R^2$, $R^3$, $R^7$, $R^{7a}$, $R^8$, m and A is as defined herein. Compound 5 reacts with $Z^1H$ to afford compound 13 followed by esterification or amidation, and hydrolyzation to give pyrimidine 14.

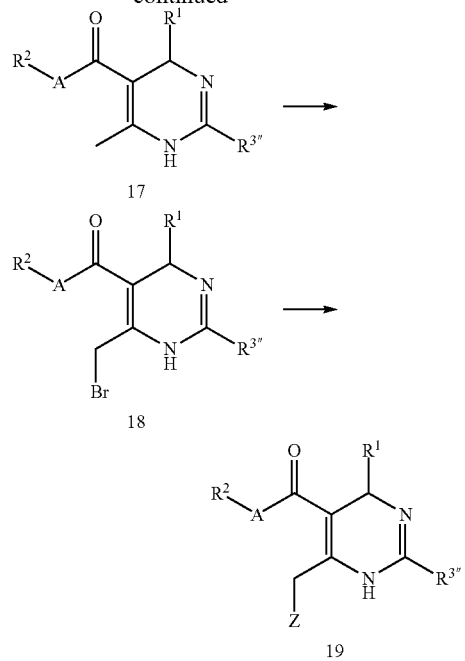

Pyrimidine 19 can be prepared by the process illustrated in Scheme 5, wherein $R^{3'}$ is heteroaryl substituted with $—(CR^7R^{7a})_m—C(=O)O—R^{8a}$, $R^{3''}$ is heteroaryl substituted with $—(CR^7R^{7a})_x—C(=O)N(R^{8a})_2$, each $R^1$, $R^2$, A, $R^7$, $R^{7a}$, $R^{8a}$, m and Z is as defined above. Amidines 15 or hydrochloride thereof, aldehydes 2 and compound 3 are cyclized in suitable inert solvent(s) (such as alcohol reagents) to afford compound 16. Compound 17 can be prepared through amidation of compound 16. Compound 17 then reacts with brominating agent in inert solvent(s) to give compound 18 followed by reacting with ZH under an alkaline condition in appropriate inert solvent(s) to yield pyrimidine 19.

EXAMPLES

The invention is illustrated further by the following examples, which are not be construed as limiting the invention in scope.

Example 1

4-((5-(ethoxycarbonyl)-2-(thiazol-2-yl)-6-(2-(trifluoromethyl)phenyl)-3,6-dihydropyrimidin-4-yl)methyl)morpholine-3-carboxylic acid

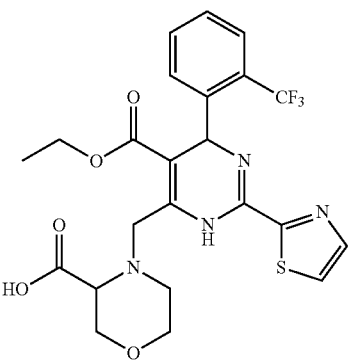 [SMILES: CCOC(=O)C1=C(CN2CCOCC2C(=O)O)NC(c2nccs2)=NC1c1ccccc1C(F)(F)F]

Step A: Ethyl 6-methyl-2-(thiazol-2-yl)-4-(2-(trifluoromethyl)phenyl)-1,4-dihydropyrimidine-5-carboxylate A mixture of 2-(trifluoromethyl)benzaldehyde (8.7 g, 50 mmol), thiazole-2-carboximidamide hydrochloride (8.2 g, 50 mmol), ethyl 3-oxobutanoate (7.8 g, 60 mmol) and sodium acetate (5.33 g, 65 mmol) in ethanol (90 mL) was refluxed at 80° C. for 12 hours under $N_2$. The resulting mixture was filtered and the filtrate was concentrated in vacuo. The residue was purified by a silica gel column chromatography (PETROLEUM ETHER/EtOAc (V/V)=3/1) to give the title compound as a yellow solid (12.62 g, 64%). The compound was characterized by the following spectroscopic data:

MS-ESI: (ESI, pos. ion) m/z: 396.1 [M+1]$^+$;

1H NMR (400 MHz, CDCl$_3$): δ 7.79 (d, 1H), 7.77 (d, 1H), 7.67-7.30 (m, 4H), 6.19 (s, 1H), 5.13 (br.s, 1H), 3.99 (q, 2H), 2.6 (s, 3H), 1.01 (t, 3H).

Step B: Ethyl 6-(bromomethyl)-2-(thiazol-2-yl)-4-(2-(trifluoromethyl)phenyl)-1,4-dihydropyrimidine-5-carboxylate To a solution of ethyl 6-methyl-2-(thiazol-2-yl)-4-(2-(trifluoromethyl)phenyl)-1,4-dihydropyrimidine-5-carboxylate (7.9 g, 20 mmol) in carbon tetrachloride (100 mL) was added NBS (3.74 g, 21 mmol) under $N_2$ at 60° C. The reaction mixture was stirred at 60° C. for 10 minutes, and cooled to 25° C. The resulting mixture was filtered and the filtrate was concentrated in vacuo. The residue was purified by a silica gel column chromatography (PETROLEUM ETHER/EtOAc (V/V)=3/1) to give the title compound as a yellow solid (6.64 g, 70%). The compound was characterized by the following spectroscopic data:

MS-ESI: (ESI, pos. ion) m/z: 474.1 [M+1]$^+$;

$^1$H NMR (400 MHz, CDCl$_3$): δ 7.81 (d, 1H), 7.72 (d, 1H), 7.68-7.31 (m, 4H), 6.18 (s, 1H), 5.13 (br.s, 1H), 4.53 (dd, 2H), 3.99 (q, 2H), 1.01 (t, 3H).

Step C: 4-((5-(ethoxycarbonyl)-2-(thiazol-2-yl)-6-(2-(trifluoromethyl)phenyl)-3,6-dihydropyrimidin-4-yl)methyl)morpholine-3-carboxylic acid A mixture of ethyl 6-(bromomethyl)-2-(thiazol-2-yl)-4-(2-(trifluoromethyl)phenyl)-1,4-dihydropyrimidine-5-carboxylate (3.8 g, 8 mmol), morpholine-3-carboxylic acid hydrochloride (2.62 g, 16 mmol) and potassium carbonate (4.2 g, 30 mmol) in ethanol (130 mL) was stirred at 25° C. for 12 hours. The resulting mixture was filtered and the filtrate was concentrated in vacuo. The residue was purified by a silica gel column chromatography (DCM/MeOH (V/V)=30/1) to give the title compound as a yellow solid (2.1 g, 50%). The compound was characterized by the following spectroscopic data:

MS-ESI: (ESI, pos. ion) m/z: 525.2 [M+1]$^+$;

$^1$H NMR (400 MHz, CDCl$_3$): δ 7.80 (d, 1H), 7.69 (d, 1H), 7.50-7.41 (m, 3H), 7.35-7.29 (m, 1H), 6.16 (s, 1H), 4.50-4.35 (m, 1H), 4.25-4.02 (m, 3H), 3.99-3.77 (m, 4H), 3.67-3.59 (m, 1H), 3.45-3.20 (m, 1H), 3.79-3.69 (m, 1H), 1.01 (t, 3H).

Example 2

4-((5-(ethoxycarbonyl)-6-(2-nitrophenyl)-2-(thiazol-2-yl)-3,6-dihydropyrimidin-4-yl)methyl)morpholine-3-carboxylic acid

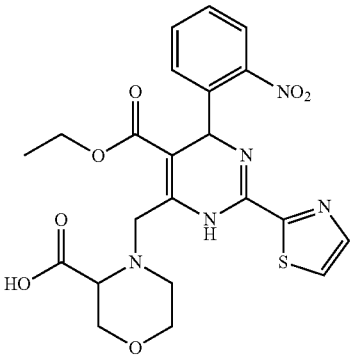 [SMILES: CCOC(=O)C1=C(CN2CCOCC2C(=O)O)NC(c2nccs2)=NC1c1ccccc1[N+](=O)[O-]]

Step A: Ethyl 6-methyl-4-(2-nitrophenyl)-2-(thiazol-2-yl)-1,4-dihydropyrimidine-5-carboxylate A mixture of 2-nitrobenzaldehyde (10 g, 66 mmol), thiazole-2-carboximidamide hydrochloride (10.8 g, 66 mmol), ethyl 3-oxobutanoate (8.6 g, 66 mmol) and sodium acetate (5.5 g, 66 mmol) in ethanol (250 mL) was stirred at 88° C. for 16 hours, then cooled to 25° C. The resulting mixture was filtered and the filtrate was concentrated in vacuo. The residue was purified by a silica gel column chromatography (PETROLEUM ETHER/EtOAc (V/V)=3/1) to give the title compound as a light yellow solid (12 g, 48%). The compound was characterized by the following spectroscopic data:

MS-ESI: (ESI, pos. ion) m/z: 373.1 [M+1]$^+$;

$^1$H NMR (400 MHz, CDCl$_3$): δ 7.80 (d, 1H), 7.62 (d, 1H), 7.52-7.48 (m, 2H), 7.45-7.40 (m, 1H), 7.37-7.32 (m, 1H), 6.06 (s, 1H), 4.01-3.85 (m, 2H), 2.51 (s, 3H), 1.13 (t, 3H).

Step B: Ethyl 6-(bromomethyl)-4-(2-nitrophenyl)-2-(thiazol-2-yl)-1,4-dihydropyrimidine-5-carboxylate To a solution of ethyl 6-methyl-4-(2-nitrophenyl)-2-(thiazol-2-yl)-1,4-dihydropyrimidine-5-carboxylate (7.45 g, 20 mmol) in carbon tetrachloride (100 mL) was added NBS (3.74 g, 21 mmol) under $N_2$ at 60° C. The mixture was stirred at 60° C. for 10 minutes, and cooled to 25° C. The resulting mixture was filtered and the filtrate was concentrated in vacuo. The residue was purified by a silica gel column chromatography (PETROLEUM ETHER/EtOAc (V/V)=3/1) to give the title compound as a yellow solid (6.32 g, 70%). The compound was characterized by the following spectroscopic data:

MS-ESI: (ESI, pos. ion) m/z: 451.1 [M+1]$^+$;

$^1$H NMR (400 MHz, CDCl$_3$): δ 7.73 (d, 1H), 7.63 (d, 1H), 7.52-7.49 (m, 2H), 7.45-7.39 (m, 1H), 7.37-7.33 (m, 1H), 6.07 (s, 1H), 4.66 (dd, 2H), 4.01-3.85 (m, 2H), 1.13 (t, 3H).

Step C: 4-((5-(ethoxycarbonyl)-6-(2-nitrophenyl)-2-(thiazol-2-yl)-3,6-dihydropyrimidin-4-yl)methyl)morpholine-3-carboxylic acid A mixture of ethyl 6-(bromomethyl)-4-(2-nitrophenyl)-2-(thiazol-2-yl)-1,4-dihydropyrimidine-5-carboxylate (2.4 g, 5.3 mmol), morpholine-3-carboxylic acid hydrochloride (0.9 g, 5.37 mmol) and potassium carbonate (1.48 g, 10.74 mmol) in ethanol (60 mL) was stirred at 25° C. for 12 hours. The mixture was filtered and the filtrate was concentrated in vacuo. The residue was purified by a silica gel column chromatography (DCM/MeOH (V/V)=25/1) to give the title compound as a light yellow solid (1.1 g, 41%). The compound was characterized by the following spectroscopic data:

MS-ESI: (ESI, pos. ion) m/z: 502.2 [M+1]$^+$;

$^1$H NMR (400 MHz, DMSO-d$_6$): δ 9.88 (s, 1H), 8.01 (d, 1H), 7.93 (d, 1H), 7.82-7.80 (m, 1H), 7.65-7.61 (m, 1H), 7.50-7.45 (m, 2H), 6.23 (s, 1H), 4.11 (br.s, 1H), 3.97-3.89 (m, 2H), 3.81-3.79 (m, 2H), 3.70-3.56 (m, 4H), 3.05-2.99 (m, 1H), 2.49-2.31 (m, 1H), 1.04 (t, 3H).

Example 3

4-((6-(2-bromo-4-fluorophenyl)-5-(ethoxycarbonyl)-2-(thiazol-2-yl)-3,6-dihydropyrimidin-4-yl)methyl) morpholine-3-carboxylic acid

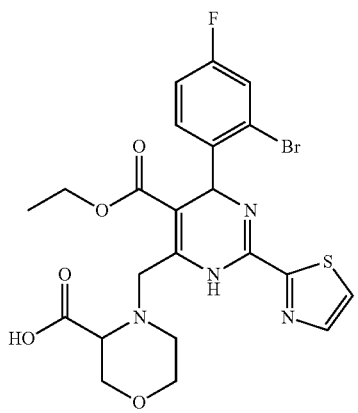

A mixture of ethyl 4-(2-bromo-4-fluorophenyl)-6-(bromomethyl)-2-(thiazol-2-yl)-1,4-dihydropyrimidine-5-carboxylate (3.02 g, 6 mmol) (The compound was synthesized according to the procedure as described in WO2010069147A), morpholine-3-carboxylic acid hydrochloride (1 g, 6 mmol) and triethylamine (1.21 g, 12 mmol) in ethanol (40 mL) was stirred at 25° C. for 12 hours under N$_2$. The mixture was concentrated in vacuo. The residue was purified by a silica gel column chromatography (DCM/MeOH (V/V)=25/1) to give the title compound as a yellow solid (1.5 g, 45%). The compound was characterized by the following spectroscopic data:

MS-ESI: (ESI, pos. ion) m/z: 553.1 [M+1]$^+$;

$^1$H NMR (400 MHz, DMSO-d$_6$): δ 12.69 (br.s, 1H), 9.84 (s, 1H), 8.04 (d, 1H), 7.95 (d, 1H), 7.58-7.55 (m, 1H), 7.40-7.36 (m, 1H), 7.24-7.19 (m, 1H), 6.02 (s, 1H), 4.13 (br.s, 2H), 3.97-3.94 (m, 2H), 3.92-3.81 (m, 2H), 3.74-3.66 (m, 2H), 3.53-3.51 (m, 1H), 3.08-3.06 (m, 1H), 2.54-2.52 (m, 1H), 1.06 (t, 3H).

Example 4

4-((6-(2-chloro-4-fluorophenyl)-5-(ethoxycarbonyl)-2-(thiazol-2-yl)-3,6-dihydropyrimidin-4-yl)methyl) morpholine-3-carboxylic acid

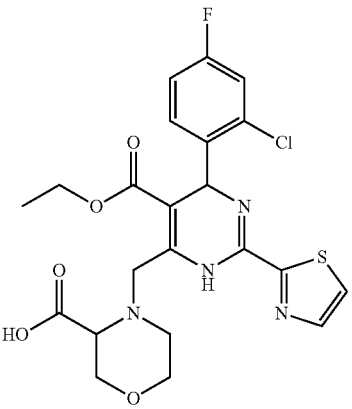 [SMILES: CCOC(=O)C1=C(CN2CCOCC2C(=O)O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (2.92 g, 6.36 mmol) (The compound was synthesized according to the procedure as described in WO2010069147A) was reacted with morpholine-3-carboxylic acid hydrochloride (1.07 g, 6.36 mmol) according to the procedure as described in Example 3 to give the title compound as a yellow solid (1.2 g, 37%). The compound was characterized by the following spectroscopic data:

MS-ESI: (ESI, pos. ion) m/z: 509.2 [M+1]$^+$;

$^1$H NMR (400 MHz, DMSO-d$_6$): δ 9.84 (s, 1H), 8.04 (d, 1H), 7.94 (d, 1H), 7.43-7.38 (m, 2H), 7.19-7.16 (m, 1H), 6.05 (s, 1H), 4.12 (br.s, 2H), 3.97-3.95 (m, 2H), 3.93-3.84 (m, 2H), 3.71-3.61 (m, 2H), 3.53-3.51 (m, 1H), 3.12-3.05 (m, 1H), 2.55-2.53 (m, 1H), 1.07 (t, 3H).

Example 5

4-((6-(2,4-dichlorophenyl)-5-(ethoxycarbonyl)-2-(thiazol-2-yl)-3,6-dihydropyrimidin-4-yl)methyl) morpholine-3-carboxylic acid

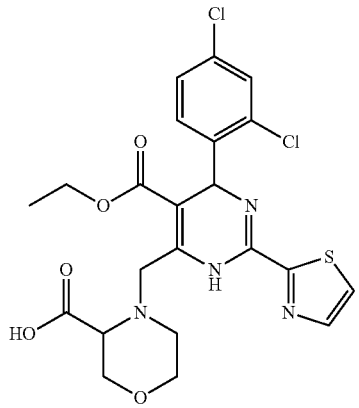 [SMILES: CCOC(=O)C1=C(CN2CCOCC2C(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (3.56 g, 7.5 mmol) (The compound was synthesized according to the procedure as described in WO2010069147A) was reacted with morpholine-3-carboxylic acid hydrochloride (1.26 g, 7.5 mmol) according to the procedure as described in Example 3 to give the title compound as a yellow solid (1.7 g, 43%). The compound was characterized by the following spectroscopic data:

MS-ESI: (ESI, pos. ion) m/z: 525.1 [M+1]⁺;
¹H NMR (400 MHz, DMSO-d₆): δ 9.86 (s, 1H), 8.03 (d, 1H), 7.94 (d, 1H), 7.60-7.59 (m, 1H), 7.41-7.38 (m, 2H), 6.05 (s, 1H), 4.22-4.00 (m, 2H), 3.98-3.95 (m, 2H), 3.94-3.80 (m, 2H), 3.71-3.61 (m, 2H), 3.60-3.59 (m, 1H), 3.10-3.02 (m, 1H), 2.43-2.38 (m, 1H), 1.07 (t, 3H).

Example 6

4-((6-(2-bromo-4-fluorophenyl)-5-(methoxycarbonyl)-2-(thiazol-2-yl)-3,6-dihydropyrimidin-4-yl)methyl)morpholine-3-carboxylic acid

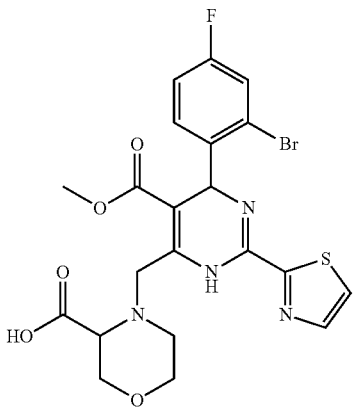

Methyl 4-(2-bromo-4-fluorophenyl)-6-(bromomethyl)-2-(thiazol-2-yl)-1,4-dihydropyrimidine-5-carboxylate (4.11 g, 8.4 mmol) (The compound was synthesized according to the procedure as described in WO2010069147A) was reacted with morpholine-3-carboxylic acid hydrochloride (1.4 g, 8.4 mmol) according to the procedure as described in Example 3 to give the title compound as a yellow solid (2.1 g, 46%). The compound was characterized by the following spectroscopic data:

MS-ESI: (ESI, pos. ion) m/z: 539.1 [M+1]⁺;
¹H NMR (400 MHz, DMSO-d₆): δ 9.89 (s, 1H), 8.03-8.02 (m, 1H), 7.94 (d, 1H), 7.57-7.54 (m, 1H), 7.39-7.35 (m, 1H), 7.22-7.17 (m, 1H), 6.01 (s, 1H), 4.19-4.05 (m, 2H), 3.93-3.82 (m, 2H), 3.75 (s, 3H), 3.70-3.60 (m, 3H), 3.09-3.07 (m, 1H), 2.55-2.35 (m, 1H).

Example 7

4-((6-(2-chloro-4-fluorophenyl)-5-(methoxycarbonyl)-2-(thiazol-2-yl)-3,6-dihydropyrimidin-4-yl)methyl)morpholine-3-carboxylic acid

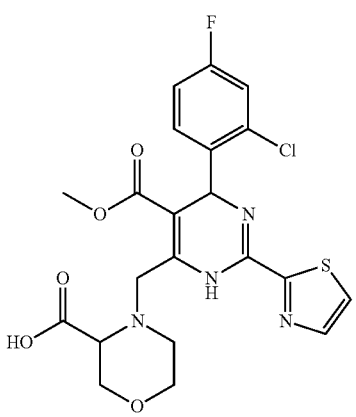 [SMILES: COC(=O)C1=C(CN2CCOCC2C(=O)O)NC(c2nccs2)=NC1c1ccc(F)cc1Cl]

Methyl 6-(bromomethyl)-4-(2-chloro-4-fluorophenyl)-2-(thiazol-2-yl)-1,4-dihydropyrimidine-5-carboxylate (2.94 g, 6.6 mmol) (The compound was synthesized according to the procedure as described in WO2010069147A) was reacted with morpholine-3-carboxylic acid hydrochloride (1.1 g, 6.6 mmol) according to the procedure as described in Example 3 to give the title compound as a yellow solid (1.5 g, 46%). The compound was characterized by the following spectroscopic data:

MS-ESI: (ESI, pos. ion) m/z: 495.1 [M+1]⁺;
¹H NMR (400 MHz, DMSO-d₆): δ 9.89 (s, 1H), 8.03 (d, 1H), 7.92 (d, 1H), 7.43-7.36 (m, 2H), 7.18-7.13 (m, 1H), 6.03 (s, 1H), 4.11-4.05 (m, 2H), 3.89-3.81 (m, 2H), 3.71-3.65 (m, 2H), 3.52 (s, 3H), 3.07-3.06 (m, 1H), 2.61-2.35 (m, 2H).

Example 8

4-((6-(2,4-dichlorophenyl)-5-(methoxycarbonyl)-2-(thiazol-2-yl)-3,6-dihydropyrimidin-4-yl)methyl)morpholine-3-carboxylic acid

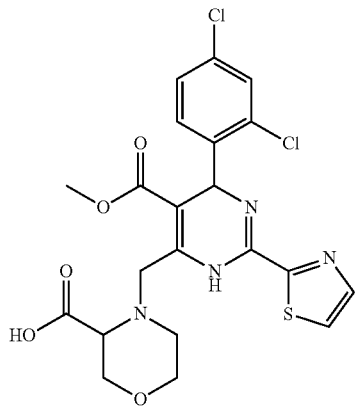 [SMILES: COC(=O)C1=C(CN2CCOCC2C(=O)O)NC(c2nccs2)=NC1c1ccc(Cl)cc1Cl]

Methyl 6-(bromomethyl)-4-(2,4-dichlorophenyl)-2-(thiazol-2-yl)-1,4-dihydropyrimidine-5-carboxylate (3.02 g, 6.54 mmol) (The compound was synthesized according to the procedure as described in WO2010069147A) was reacted with morpholine-3-carboxylic acid hydrochloride (1.1 g, 6.54 mmol) according to the procedure as described in Example 3 to give the title compound as a yellow solid (1.5 g, 45%). The compound was characterized by the following spectroscopic data:

MS-ESI: (ESI, pos. ion) m/z: 511.1 [M+1]⁺;
¹H NMR (400 MHz, DMSO-d₆): δ 9.80 (br.s, 1H), 7.85 (br.s, 1H), 7.47 (br.s, 1H), 7.40-7.39 (m, 1H), 7.23-7.21 (m, 1H), 7.19-7.16 (m, 1H), 6.17 (s, 1H), 4.42-4.31 (m, 1H), 4.19-3.95 (m, 3H), 3.86-3.79 (m, 2H), 3.59 (s, 3H), 3.57-3.56 (m, 1H), 3.25-3.11 (m, 1H), 2.65-2.59 (m, 1H).

Example 9

4-((6-(2-bromo-4-fluorophenyl)-5-(ethoxycarbonyl)-2-(thiazol-2-yl)-3,6-dihydropyrimidin-4-yl)methyl)morpholine-2-carboxylic acid

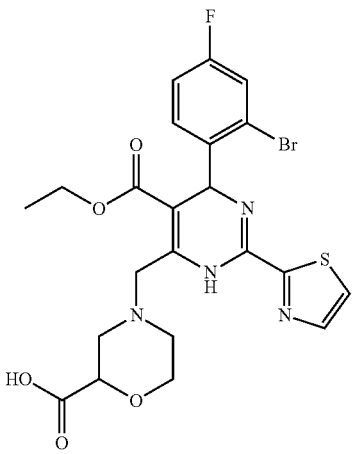

Ethyl 4-(2-bromo-4-fluorophenyl)-6-(bromomethyl)-2-(thiazol-2-yl)-1,4-dihydropyrimidine-5-carboxylate (0.6 g, 1.2 mmol) was reacted with morpholine-2-carboxylic acid hydrochloride (0.3 g, 1.8 mmol) according to the procedure as described in Example 3 to give the title compound as a yellow solid (0.2 g, 30%). The compound was characterized by the following spectroscopic data:

MS-ESI: (ESI, pos. ion) m/z: 553.1 [M+1]$^+$;
$^1$H NMR (400 MHz, DMSO-d$_6$): δ 9.56 (s, 1H), 8.00-7.98 (m, 1H), 7.92 (d, 1H), 7.56-7.53 (m, 1H), 7.42-7.35 (m, 1H), 7.25-7.17 (m, 1H), 6.02 (s, 1H), 4.17-4.15 (m, 1H), 4.04-3.87 (m, 4H), 3.64-3.56 (m, 2H), 3.06-2.85 (m, 2H), 2.69-2.39 (m, 2H), 1.06-1.02 (m, 3H).

Example 10

4-((6-(2-chloro-4-fluorophenyl)-5-(ethoxycarbonyl)-2-(thiazol-2-yl)-3,6-dihydropyrimidin-4-yl)methyl)morpholine-2-carboxylic acid

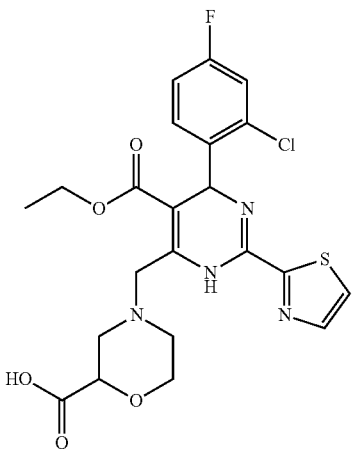 [SMILES: CCOC(=O)C1=C(CN2CCOC(C(=O)O)C2)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.69 g, 1.5 mmol) was reacted with morpholine-2-carboxylic acid hydrochloride (0.3 g, 1.8 mmol) according to the procedure as described in Example 3 to give the title compound as a yellow solid (0.32 g, 42%). The compound was characterized by the following spectroscopic data:

MS-ESI: (ESI, pos. ion) m/z: 509.1 [M+1]$^+$;
$^1$H NMR (400 MHz, DMSO-d$_6$): δ 9.57 (s, 1H), 8.01-8.00 (m, 1H), 7.94 (d, 1H), 7.44-7.41 (m, 2H), 7.19-7.15 (m, 1H), 6.06 (s, 1H), 4.17-4.16 (m, 1H), 4.15-3.93 (m, 4H), 3.65-3.57 (m, 2H), 3.06-2.86 (m, 2H), 2.69-2.45 (m, 2H), 1.07-1.03 (m, 3H).

Example 11

4-((6-(2,4-dichlorophenyl)-5-(ethoxycarbonyl)-2-(thiazol-2-yl)-3,6-dihydropyrimidin-4-yl)methyl)morpholine-2-carboxylic acid

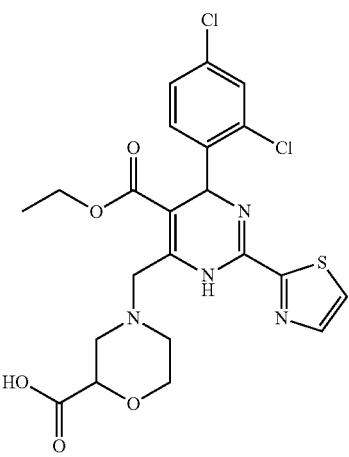 [SMILES: CCOC(=O)C1=C(CN2CCOC(C(=O)O)C2)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (1.43 g, 3 mmol) was reacted with morpholine-2-carboxylic acid hydrochloride (0.5 g, 3 mmol) according to the procedure as described in Example 3 to give the title compound as a yellow solid (0.49 g, 31%). The compound was characterized by the following spectroscopic data:

MS-ESI: (ESI, pos. ion) m/z: 525.1 [M+1]$^+$;
$^1$H NMR (400 MHz, DMSO-d$_6$): δ 9.56 (s, 1H), 7.99-7.97 (m, 1H), 7.92 (d, 1H), 7.59-7.58 (m, 1H), 7.36-7.35 (m, 2H), 6.02 (s, 1H), 4.14-4.11 (m, 1H), 3.96-3.88 (m, 4H), 3.63-3.51 (m, 2H), 3.05-2.85 (m, 2H), 2.67-2.35 (m, 2H), 1.05 (t, 3H).

Example 12

4-((6-(2-bromo-4-fluorophenyl)-5-(methoxycarbonyl)-2-(thiazol-2-yl)-3,6-dihydropyrimidin-4-yl)methyl)morpholine-2-carboxylic acid

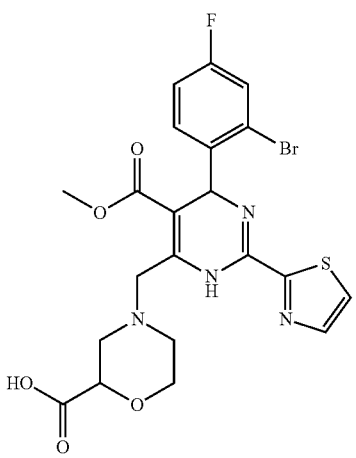

Methyl 4-(2-bromo-4-fluorophenyl)-6-(bromomethyl)-2-(thiazol-2-yl)-1,4-dihydropyrimidine-5-carboxylate (1.22 g, 2.5 mmol) was reacted with morpholine-2-carboxylic acid hydrochloride (0.5 g, 3 mmol) according to the procedure as described in Example 3 to give the title compound as a yellow solid (0.54 g, 40%). The compound was characterized by the following spectroscopic data:

MS-ESI: (ESI, pos. ion) m/z: 539.1 [M+1]$^+$;

$^1$H NMR (400 MHz, DMSO-d$_6$): δ 9.60 (s, 1H), 8.01-7.99 (m, 1H), 7.94 (d, 1H), 7.58-7.55 (m, 1H), 7.40-7.37 (m, 1H), 7.23-7.18 (m, 1H), 6.02 (s, 1H), 4.20-4.15 (m, 1H), 4.01-3.88 (m, 4H), 3.65-3.61 (m, 2H), 3.52 (s, 3H), 2.70-2.39 (m, 2H).

Example 13

4-((6-(2-chloro-4-fluorophenyl)-5-(methoxycarbonyl)-2-(thiazol-2-yl)-3,6-dihydropyrimidin-4-yl)methyl)morpholine-2-carboxylic acid

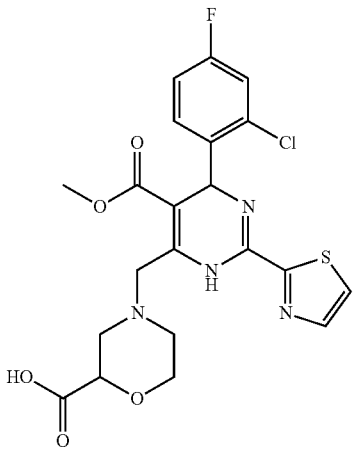 [SMILES: COC(=O)C1=C(CN2CCOC(C(=O)O)C2)NC(c2nccs2)=NC1c1ccc(F)cc1Cl]

Methyl 6-(bromomethyl)-4-(2-chloro-4-fluorophenyl)-2-(thiazol-2-yl)-1,4-dihydropyrimidine-5-carboxylate (1.11 g, 2.5 mmol) was reacted with morpholine-2-carboxylic acid hydrochloride (0.5 g, 3 mmol) according to the procedure as described in Example 3 to give the title compound as a yellow solid (0.5 g, 40%). The compound was characterized by the following spectroscopic data:

MS-ESI: (ESI, pos. ion) m/z: 495.1 [M+1]$^+$;

$^1$H NMR (400 MHz, DMSO-d$_6$): δ 9.64 (s, 1H), 8.02-8.01 (m, 1H), 7.94 (d, 1H), 7.45-7.39 (m, 2H), 7.20-7.17 (m, 1H), 6.05 (s, 1H), 4.17-4.16 (m, 1H), 4.03-3.88 (m, 4H), 3.55 (s, 3H), 3.08-2.86 (m, 2H), 2.72-2.40 (m, 2H).

Example 14

4-((6-(2,4-dichlorophenyl)-5-(methoxycarbonyl)-2-(thiazol-2-yl)-3,6-dihydropyrimidin-4-yl)methyl)morpholine-2-carboxylic acid

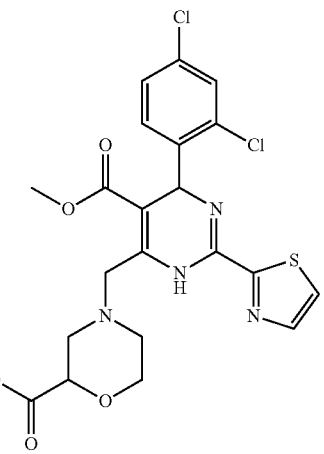

Methyl 6-(bromomethyl)-4-(2,4-dichlorophenyl)-2-(thiazol-2-yl)-1,4-dihydropyrimidine-5-carboxylate (1.15 g, 2.5 mmol) was reacted with morpholine-2-carboxylic acid hydrochloride (0.5 g, 3 mmol) according to the procedure as described in Example 3 to give the title compound as a yellow solid (0.47 g, 37%). The compound was characterized by the following spectroscopic data:

MS-ESI: (ESI, pos. ion) m/z: 511.1 [M+1]$^+$;

$^1$H NMR (400 MHz, DMSO-d$_6$): δ 9.60 (br.s, 1H), 7.85-7.83 (m, 1H), 7.45-7.43 (m, 1H), 7.40-7.39 (m, 1H), 7.25-7.24 (m, 1H), 7.20-7.16 (m, 1H), 6.19 (s, 1H), 4.43-4.38 (m, 1H), 4.22-3.95 (m, 2H), 3.93-3.85 (m, 2H), 3.59 (s, 3H), 3.18-3.05 (m, 2H), 2.81-2.61 (m, 2H).

Example 15

2-(4-((6-(2,4-dichlorophenyl)-5-(ethoxycarbonyl)-2-(thiazol-2-yl)-3,6-dihydropyrimidin-4-yl)methyl)morpholin-3-yl)acetic acid

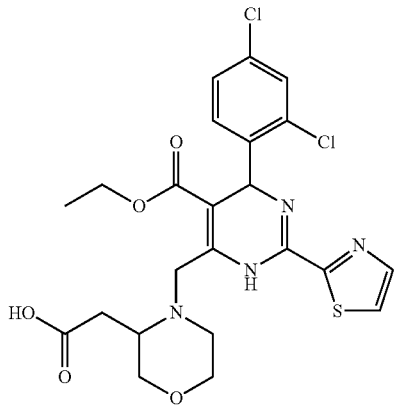 [SMILES: CCOC(=O)C1=C(CN2CCOCC2CC(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.29 g, 0.61 mmol) was reacted with 2-(morpholin-3-yl)acetic acid hydrochloride (0.11 g, 0.61 mmol) according to the procedure as described in Example 1, Step C to give the title compound as a light yellow solid (0.2 g, 60%). The compound was characterized by the following spectroscopic data:

MS-ESI: (ESI, pos. ion) m/z: 539.1 [M+1]+;

$^1$H NMR (400 MHz, DMSO-d$_6$): δ 12.12 (br.s, 1H), 9.71 (br.s, 1H), 8.03 (d, 1H), 7.94 (d, 1H), 7.59 (br.s, 1H), 7.41-7.34 (m, 2H), 6.04 (s, 1H), 4.20-3.90 (m, 4H), 3.75-3.45 (m, 4H), 3.10-2.65 (m, 3H), 2.45 (br.s, 2H), 1.05 (t, 3H).

Example 16

2-(4-((6-(2-chloro-4-fluorophenyl)-5-(ethoxycarbonyl)-2-(thiazol-2-yl)-3,6-dihydropyrimidin-4-yl)methyl)morpholin-3-yl)acetic acid

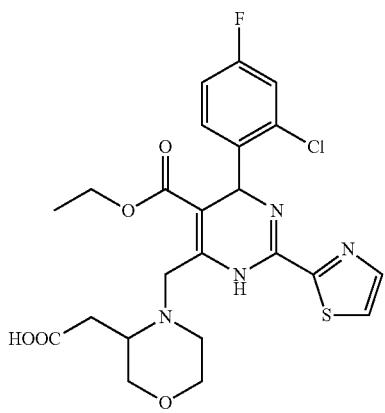 [SMILES: CCOC(=O)C1=C(CN2CCOCC2CC(=O)O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.18 g, 0.39 mmol) was reacted with 2-(morpholin-3-yl)acetic acid hydrochloride (0.07 g, 0.39 mmol) according to the procedure as described in Example 1, Step C to give the title compound as a light yellow solid (0.14 g, 67%). The compound was characterized by the following spectroscopic data:

MS-ESI: (ESI, pos. ion) m/z: 523.2 [M+1]+;

$^1$H NMR (400 MHz, DMSO-d$_6$): δ 12.10 (br.s, 1H), 9.71 (br.s, 1H), 8.03 (d, 1H), 7.94 (d, 1H), 7.43-7.40 (m, 2H), 7.16-7.12 (m, 1H), 6.04 (s, 1H), 4.15-3.89 (m, 4H), 3.74-3.50 (m, 4H), 3.08-2.65 (m, 3H), 2.40 (br.s, 2H), 1.05 (t, 3H).

Example 17

2-(4-((6-(2-bromo-4-fluorophenyl)-5-(ethoxycarbonyl)-2-(thiazol-2-yl)-3,6-dihydropyrimidin-4-yl)methyl)morpholin-3-yl)acetic acid

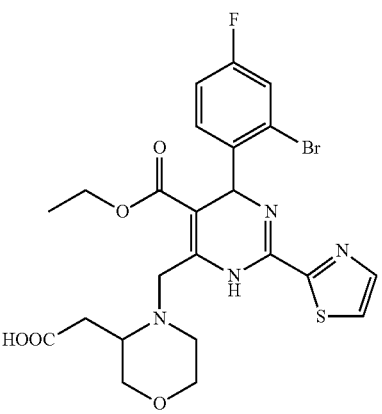 [SMILES: CCOC(=O)C1=C(CN2CCOCC2CC(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (0.7 g, 1.4 mmol) was reacted with 2-(morpholin-3-yl)acetic acid hydrochloride (0.25 g, 1.4 mmol) according to the procedure as described in Example 1, Step C to give the title compound as a pale yellow solid (0.57 g, 72%). The compound was characterized by the following spectroscopic data:

MS-ESI: (ESI, pos. ion) m/z: 567.1 [M+1]+;

$^1$H NMR (400 MHz, DMSO-d$_6$): δ 12.13 (br.s, 1H), 9.74 (br.s, 1H), 8.03 (d, 1H), 7.94 (d, 1H), 7.58-7.55 (m, 1H), 7.40-7.36 (m, 1H), 7.24-7.19 (m, 1H), 6.01 (s, 1H), 4.18-3.91 (m, 4H), 3.76-3.52 (m, 4H), 3.09-2.66 (m, 3H), 2.41 (br.s, 2H), 1.07 (t, 3H).

Example 18

3-(4-((6-(2-bromo-4-fluorophenyl)-5-(ethoxycarbonyl)-2-(thiazol-2-yl)-3,6-dihydropyrimidin-4-yl)methyl)morpholin-3-yl)propanoic acid

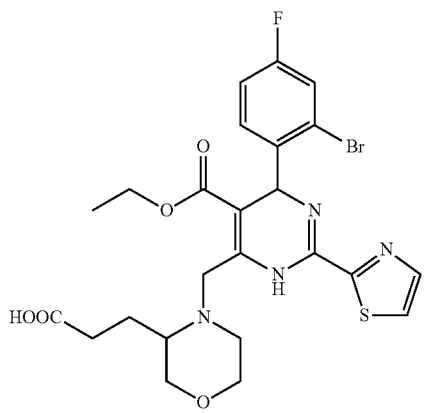

Step A: 3-(4-(tert-butoxycarbonyl)morpholin-3-yl)propanoic acid

A mixture of formic acid (2.26 mL, 58.9 mmol) and triethylamine (3.36 mL, 24.11 mmol) was stirred for 5 minutes in an ice bath. To the mixture were added tert-butyl 3-formylmorpholine-4-carboxylate (0.47 g, 2.2 mmol) and Meldrum's acid (0.32 g, 2.2 mmol) in turn at 0° C. The reaction mixture was heated at 100° C. for 5 hours, and cooled down in an ice bath. To the resulting mixture was added aqueous NaOH solution (2 mol/L, 40 mL). The aqueous layer was extracted with EtOAc (50 mL×3) and the organic layer was discarded. To the aqueous layer was added EtOAc (80 mL), and the mixture was adjusted to pH 4-5 with HCl (1 mol/L) under stirring. The aqueous layer was extracted with EtOAc (80 mL). The organic layer was dried over anhydrous $Na_2SO_4$, then filtered and the filtrate was concentrated in vacuo to give the title compound as a white solid (0.23 g, 40%). The compound was characterized by the following spectroscopic data:

MS-ESI: (ESI, pos. ion) m/z: 204.1 [M+1-56]$^+$;

$^1$H NMR (400 MHz, CDCl$_3$): δ 4.13-4.10 (m, 1H), 3.84-3.81 (m, 2H), 3.80-3.74 (m, 1H), 3.71-3.41 (m, 2H), 3.12-3.10 (m, 1H), 2.38-2.35 (m, 2H), 2.25-2.21 (m, 1H), 1.90-1.85 (m, 1H), 1.46 (s, 9H).

Step B: 3-(morpholin-3-yl)propanoic acid hydrochloride

To a solution of 3-(4-(tert-butoxycarbonyl)morpholin-3-yl)propanoic acid (0.3 g, 1.2 mmol) in EtOAc (2 mL) was added the solution of HCl in EtOAc (6 mol/L, 6 mL). The mixture was stirred closedly at 25° C. for 2 hours and filtered. The residue was washed with EtOAc (4 mL) to give the title compound as a white solid (0.21 g, 90%). The compound was characterized by the following spectroscopic data:

MS-ESI: (ESI, pos. ion) m/z: 160.3 [M+1]$^+$;

$^1$H NMR (400 MHz, CDCl$_3$): δ 4.06-3.91 (m, 2H), 3.76-3.70 (m, 1H), 3.54-3.51 (m, 1H), 3.48-3.36 (m, 2H), 3.30-3.18 (m, 1H), 2.53-2.48 (m, 2H), 1.90-1.80 (m, 2H).

Step C: 3-(4-((6-(2-bromo-4-fluorophenyl)-5-(ethoxycarbonyl)-2-(thiazol-2-yl)-3,6-dihydropyrimidin-4-yl)methyl)morpholin-3-yl)propanoic acid Ethyl 4-(2-bromo-4-fluorophenyl)-6-(bromomethyl)-2-(thiazol-2-yl)-1,4-dihydropyrimidine-5-carboxylate (1 g, 2 mmol) was reacted with 3-(morpholin-3-yl)propanoic acid hydrochloride (0.39 g, 2 mmol) according to the procedure as described in Example 1, Step C to give the title compound as a yellow solid (0.55 g, 47%). The compound was characterized by the following spectroscopic data:

MS-ESI: (ESI, pos. ion) m/z: 581.1 [M+1]$^+$;

$^1$H NMR (400 MHz, CDCl$_3$): δ 9.68 (s, 1H), 7.85 (s, 1H), 7.45 (s, 1H), 7.32-7.29 (m, 2H), 6.99-6.96 (m, 1H), 6.18 (s, 1H), 4.26-4.07 (m, 1H), 4.04-4.00 (m, 3H), 3.92-3.88 (m, 1H), 3.85-3.81 (m, 1H), 3.73-3.68 (m, 1H), 3.58-3.53 (m, 1H), 2.89-2.86 (m, 1H), 2.64 (br.s, 1H), 2.52-2.46 (m, 2H), 2.38-2.34 (m, 1H), 1.92-1.89 (m, 1H), 1.28-1.24 (m, 2H), 1.13 (t, 3H).

Example 19

3-(4-((6-(2-chloro-4-fluorophenyl)-5-(ethoxycarbonyl)-2-(thiazol-2-yl)-3,6-dihydropyrimidin-4-yl)methyl)morpholin-3-yl)propanoic acid

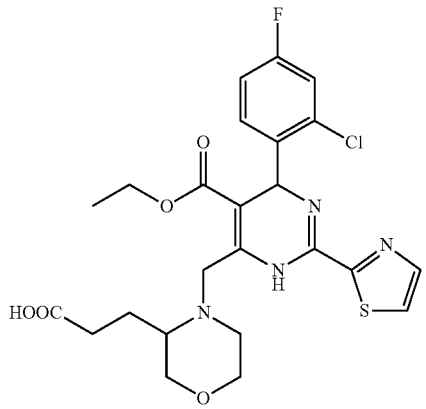 [SMILES: CCOC(=O)C1=C(CN2CCOCC2CCC(=O)O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.92 g, 2 mmol) was reacted with 3-(morpholin-3-yl)propanoic acid hydrochloride (0.39 g, 2 mmol) according to the procedure as described in Example 1, Step C to give the title compound as a yellow solid (0.45 g, 42%). The compound was characterized by the following spectroscopic data:

MS-ESI: (ESI, pos. ion) m/z: 537.2 [M+1]$^+$;

$^1$H NMR (400 MHz, CDCl$_3$): δ 12.88 (br.s, 1H), 9.71 (s, 1H), 7.95 (br.s, 1H), 7.55 (br.s, 1H), 7.39-7.29 (m, 2H), 7.12-7.01 (m, 1H), 6.12 (s, 1H), 4.26-4.11 (m, 1H), 4.09-4.01 (m, 3H), 3.95-3.87 (m, 1H), 3.84-3.80 (m, 1H), 3.75-3.69 (m, 1H), 3.59-3.52 (m, 1H), 2.89-2.83 (m, 1H), 2.63 (br.s, 1H), 2.53-2.46 (m, 2H), 2.38-2.32 (m, 1H), 1.92-1.88 (m, 1H), 1.28-1.23 (m, 2H), 1.13 (t, 3H).

Example 20

3-(4-((6-(2,4-dichlorophenyl)-5-(ethoxycarbonyl)-2-(thiazol-2-yl)-3,6-dihydropyrimidin-4-yl)methyl)morpholin-3-yl)propanoic acid

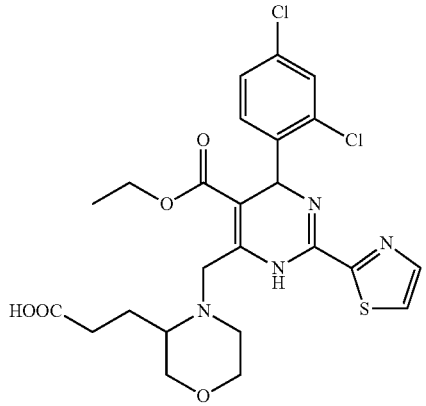 [SMILES: CCOC(=O)C1=C(CN2CCOCC2CCC(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.95 g, 2 mmol) was reacted with 3-(morpholin-3-yl)propanoic acid hydrochloride (0.39 g, 2 mmol) according to the procedure as described in Example 1, Step C to give the title compound as a yellow solid (0.61 g, 55%). The compound was characterized by the following spectroscopic data:

MS-ESI: (ESI, pos. ion) m/z: 553.2 [M+1]$^+$;

$^1$H NMR (400 MHz, CDCl$_3$): δ 12.75 (br.s, 1H), 9.64 (s, 1H), 7.93 (d, 1H), 7.55 (d, 1H), 7.41-7.28 (m, 2H), 7.09-7.01 (m, 1H), 6.13 (s, 1H), 4.20-4.07 (m, 1H), 4.05-3.94 (m, 3H), 3.92-3.86 (m, 1H), 3.84-3.80 (m, 1H), 3.75-3.67 (m, 1H), 3.58-3.52 (m, 1H), 2.89-2.83 (m, 1H), 2.63 (br.s, 1H), 2.52-2.45 (m, 2H), 2.38-2.33 (m, 1H), 1.92-1.86 (m, 1H), 1.28-1.23 (m, 2H), 1.13 (t, 3H).

Example 21

(3S)-4-((6-(2,4-dichlorophenyl)-5-(ethoxycarbonyl)-2-(thiazol-2-yl)-3,6-dihydropyrimidin-4-yl)methyl)-6,6-dimethylmorpholine-3-carboxylic acid

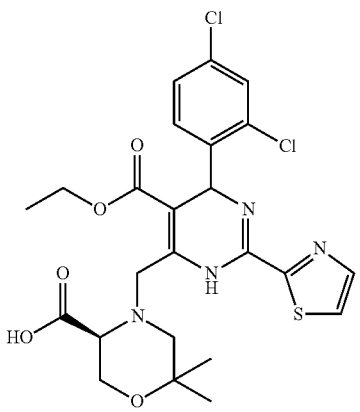 [SMILES: CCOC(=O)C1=C(CN2CC(C)(C)OC[C@H]2C(=O)O)NC(c2nccs2)=NC1c1ccc(Cl)cc1Cl]

Step A: (S)-6,6-dimethylmorpholine-3-carboxylic acid hydrochloride

To a solution of (S)-methyl 6,6-dimethylmorpholine-3-carboxylate (0.2 g, 1.2 mmol) (The compound was synthesized according to the procedure as described in WO2008024692) in anhydrous methanol (4 mL) was added a solution of sodium hydroxide (0.1 g, 2.4 mmol) in water (1 mL). The reaction mixture was stirred at 25° C. for 2 hours, and cooled to 0° C. The reaction mixture was adjusted to pH 1-2 with con. HCl. The mixture was concentrated in vacuo to give the title compound as a white solid (0.19 g, 100%). The compound was characterized by the following spectroscopic data:

MS-ESI: (ESI, pos. ion) m/z: 160.3 [M+1]$^+$;

$^1$H NMR (400 MHz, DMSO-d$_6$): δ 3.76-3.72 (m, 1H), 3.68-3.62 (m, 1H), 3.41-3.36 (m, 1H), 2.66 (d, 1H), 2.45 (d, 1H), 1.11 (s, 3H), 1.08 (s, 3H).

Step B: (3S)-4-((6-(2,4-dichlorophenyl)-5-(ethoxycarbonyl)-2-(thiazol-2-yl)-3,6-dihydropyrimidin-4-yl)methyl)-6,6-dimethylmorpholine-3-carboxylic acid Ethyl 6-(bromomethyl)-4-(2,4-dichlorophenyl)-2-(thiazol-2-yl)-1,4-dihydropyrimidine-5-carboxylate (0.24 g, 0.51 mmol) was reacted with (S)-6,6-dimethyl morpholine-3-carboxylic acid hydrochloride (0.1 g, 0.51 mmol) according to the procedure as described in Example 1, Step C to give the title compound as a yellow solid (0.19 g, 68%). The compound was characterized by the following spectroscopic data:

MS-ESI: (ESI, pos. ion) m/z: 553.1 [M+1]$^+$;

$^1$H NMR (400 MHz, CDCl$_3$): δ 7.81 (br.s, 1H), 7.44 (br.s, 1H), 7.40-7.38 (m, 1H), 7.30-7.26 (m, 1H), 7.18-7.16 (m, 1H), 6.19 (s, 1H), 4.38-4.21 (m, 2H), 4.12-3.85 (m, 4H), 3.45-3.43 (m, 1H), 2.90-2.79 (m, 1H), 2.37-2.32 (m, 1H), 1.25 (s, 3H), 1.24 (s, 3H), 1.11 (t, 3H).

Example 22

(3S)-4-((6-(2-bromo-4-fluorophenyl)-5-(ethoxycarbonyl)-2-(thiazol-2-yl)-3,6-dihydropyrimidin-4-yl)methyl)-6,6-dimethylmorpholine-3-carboxylic acid

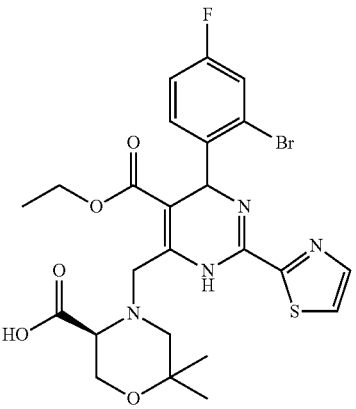 [SMILES: CCOC(=O)C1=C(CN2CC(C)(C)OC[C@H]2C(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (0.26 g, 0.51 mmol) was reacted with (S)-6,6-dimethylmorpholine-3-carboxylic acid hydrochloride (0.1 g, 0.51 mmol) according to the procedure as described in Example 1, Step C to give the title compound as a yellow solid (0.18 g, 63%). The compound was characterized by the following spectroscopic data:

MS-ESI: (ESI, pos. ion) m/z: 581.1 [M+1]$^+$;

$^1$H NMR (400 MHz, CDCl$_3$): δ 9.72 (s, 1H), 7.82 (d, 1H), 7.45 (d, 1H), 7.34-7.30 (m, 2H), 7.01-6.93 (m, 1H), 6.16 (s, 1H), 4.39-4.21 (m, 2H), 4.13-3.85 (m, 4H), 3.46-3.43 (m, 1H), 2.91-2.79 (m, 1H), 2.38-2.32 (m, 1H), 1.26 (s, 3H), 1.23 (s, 3H), 1.10 (t, 3H).

Example 23

(3S)-4-((6-(2-chloro-4-fluorophenyl)-5-(ethoxycarbonyl)-2-(thiazol-2-yl)-3,6-dihydropyrimidin-4-yl)methyl)-6,6-dimethylmorpholine-3-carboxylic acid

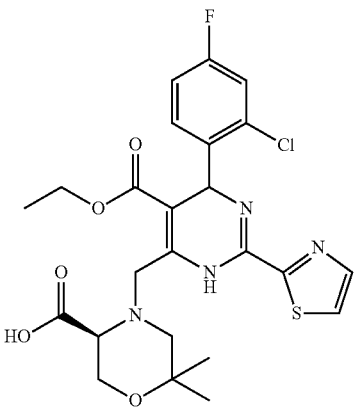

Ethyl 6-(bromomethyl)-4-(2-chloro-4-fluorophenyl)-2-(thiazol-2-yl)-1,4-dihydropyrimidine-5-carboxylate (0.26 g, 0.51 mmol) was reacted with (S)-6,6-dimethylmorpholine-3-carboxylic acid hydrochloride (0.1 g, 0.51 mmol) according to the procedure described in Example 1, Step C to give the title compound as a yellow solid (0.16 g, 59%). The compound was characterized by the following spectroscopic data:

MS-ESI: (ESI, pos. ion) m/z: 537.2 [M+1]$^+$;

$^1$H NMR (400 MHz, CDCl$_3$): δ 12.65 (br.s, 1H), 9.69 (s, 1H), 7.93 (br.s, 1H), 7.58 (br.s, 1H), 7.38-7.28 (m, 2H), 7.15-7.01 (m, 1H), 6.15 (s, 1H), 4.37-4.20 (m, 2H), 4.14-3.84 (m, 4H), 3.45-3.42 (m, 1H), 2.92-2.80 (m, 1H), 2.39-2.33 (m, 1H), 1.27 (s, 3H), 1.22 (s, 3H), 1.11 (t, 3H).

Example 24

Methyl (3S)-4-((6-(2,4-dichlorophenyl)-5-(ethoxycarbonyl)-2-(thiazol-2-yl)-3,6-dihydropyrimidin-4-yl)methyl)-6,6-dimethylmorpholine-3-carboxylate

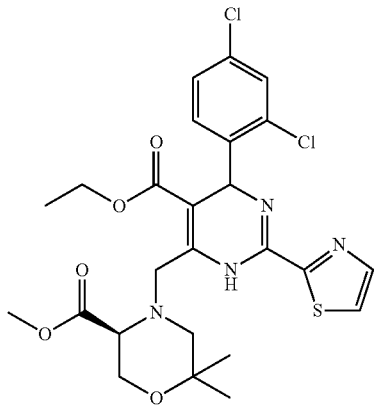 [SMILES: CCOC(=O)C1=C(CN2CC(C)(C)OC[C@H]2C(=O)OC)NC(c2nccs2)=NC1c1ccc(Cl)cc1Cl]

A mixture of ethyl 6-(bromomethyl)-4-(2,4-dichlorophenyl)-2-(thiazol-2-yl)-1,4-dihydropyrimidine-5-carboxylate (0.72 g, 1.52 mmol), (S)-methyl 6,6-dimethyl morpholine-3-carboxylate (0.26 g, 1.52 mmol) and potassium carbonate (0.42 g, 3.04 mmol) in acetonitrile (40 mL) was stirred at 25° C. for 3 hours. The reaction mixture was filtered and the filtrate was concentrated in vacuo. The residue was purified by a silica gel column chromatography (PETROLEUM ETHER/EtOAc (V/V)=3/1) to give the title compound as yellow oil (0.55 g, 64%). The compound was characterized by the following spectroscopic data:

MS-ESI: (ESI, pos. ion) m/z: 567.2 [M+1]$^+$;

$^1$H NMR (400 MHz, DMSO-d$_6$): δ 9.44 (br.s, 1H), 8.02 (d, 1H), 7.99 (d, 1H), 7.62-7.60 (m, 1H), 7.50-7.48 (m, 1H), 7.38-7.36 (m, 1H), 6.05 (s, 1H), 4.38-4.20 (m, 2H), 4.13-3.85 (m, 4H), 3.70 (s, 3H), 3.46-3.43 (m, 1H), 2.91-2.79 (m, 1H), 2.37-2.31 (m, 1H), 1.26 (s, 3H), 1.23 (s, 3H), 1.09 (t, 3H).

Example 25

Ethyl 4-(2-bromo-4-fluorophenyl)-6-((3-carbamoylmorpholino)methyl)-2-(thiazol-2-yl)-1,4-dihydropyrimidine-5-carboxylate

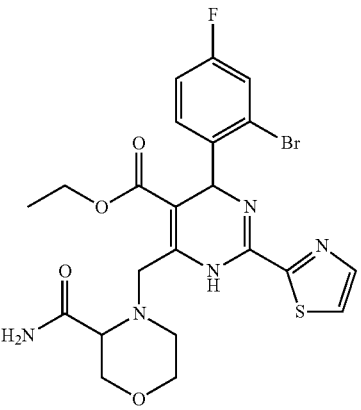 [SMILES: CCOC(=O)C1=C(CN2CCOCC2C(N)=O)NC(c2nccs2)=NC1c1ccc(F)cc1Br]

Step A: Morpholine-3-carboxamide

A mixture of methyl morpholine-3-carboxylate hydrochloride (0.55 g, 3.0 mmol) and a solution of NH$_3$ in methanol (7 mol/L, 20 mL) was stirred at 50° C. for 24 hours in a sealed tube. The mixture was concentrated in vacuo to give the title compound as glutinous semisolid (0.39 g, 99%). The compound was characterized by the following spectroscopic data:

MS-ESI: (ESI, pos. ion) m/z: 131.1 [M+1]$^+$;

$^1$H NMR (400 MHz, D$_2$O): δ 4.16-4.13 (m, 1H), 3.94-3.91 (m, 1H), 3.83-3.80 (m, 1H), 3.78-3.68 (m, 2H), 3.35-3.31 (m, 1H), 3.20-3.15 (m, 1H).

Step B: Ethyl 4-(2-bromo-4-fluorophenyl)-6-((3-carbamoylmorpholino)methyl)-2-(thiazol-2-yl)-1,4-dihydropyrimidine-5-carboxylate A mixture of ethyl 4-(2-bromo-4-fluorophenyl)-6-(bromomethyl)-2-(thiazol-2-yl)-1,4-dihydropyrimidine-5-carboxylate (3.02 g, 6 mmol), morpholine-3-carboxamide (0.78 g, 6 mmol) and potassium carbonate (1.66 g, 12 mmol) in anhydrous ethanol (70 mL) was stirred at 25° C. for 12 hours under N$_2$. The reaction mixture was filtered and the filtrate was concentrated in vacuo. The residue was purified by a silica gel column chromatography (DCM/MeOH (V/V)= 100/1) to give the title compound as a yellow solid (1.66 g, 50%). The compound was characterized by the following spectroscopic data:

MS-ESI: (ESI, pos. ion) m/z: 552.1 [M+1]$^+$;

$^1$H NMR (400 MHz, DMSO-d$_6$): δ 10.05 (s, 1H), 8.01 (d, 1H), 7.92 (d, 1H), 7.57-7.53 (m, 1H), 7.38-7.35 (m, 1H), 7.24-7.21 (m, 1H), 6.01 (s, 1H), 4.13-4.00 (m, 1H), 3.95-3.93 (m, 2H), 3.87-3.67 (m, 3H), 3.63-3.53 (m, 2H), 3.01-2.87 (m, 1H), 2.79-2.69 (m, 1H), 2.60-2.56 (m, 1H), 1.06 (t, 3H).

Example 26

Ethyl 6-((3-carbamoylmorpholino)methyl)-4-(2-chloro-4-fluorophenyl)-2-(thiazol-2-yl)-1,4-dihydropyrimidine-5-carboxylate

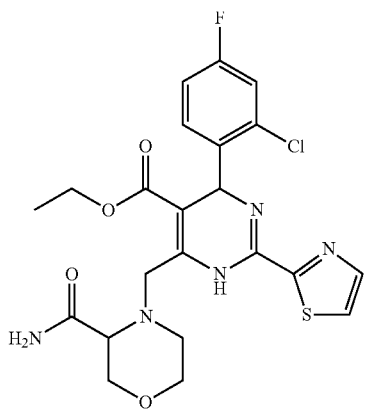 [SMILES: CCOC(=O)C1=C(CN2CCOCC2C(N)=O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (2.75 g, 6 mmol) was reacted with morpholine-3-carboxamide (0.78 g, 6 mmol) according to the procedure as described in Example 25, Step B to give the title compound as a yellow solid (1.37 g, 45%). The compound was characterized by the following spectroscopic data:

MS-ESI: (ESI, pos. ion) m/z: 508.1 [M+1]$^+$;

$^1$H NMR (400 MHz, DMSO-d$_6$): δ 10.04 (s, 1H), 8.02 (d, 1H), 7.91 (d, 1H), 7.43-7.40 (m, 1H), 7.39-7.36 (m, 1H), 7.24-7.17 (m, 1H), 6.04 (s, 1H), 4.13-4.05 (m, 1H), 3.96-3.93 (m, 2H), 3.89-3.86 (m, 1H), 3.67-3.41 (m, 4H), 3.00-2.86 (m, 1H), 2.79-2.67 (m, 1H), 2.58-2.54 (m, 1H), 1.03 (t, 3H).

Example 27

Ethyl 6-((3-carbamoylmorpholino)methyl)-4-(2,4-dichlorophenyl)-2-(thiazol-2-yl)-1,4-dihydropyrimidine-5-carboxylate

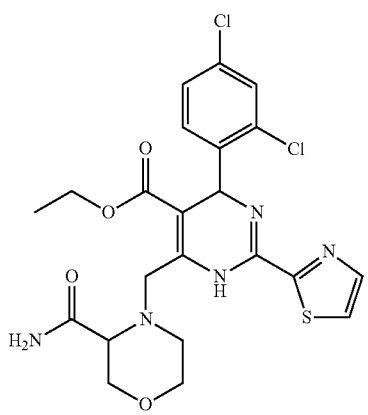 [SMILES: CCOC(=O)C1=C(CN2CCOCC2C(N)=O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (2.85 g, 6 mmol) was reacted with morpholine-3-carboxamide (0.78 g, 6 mmol) according to the procedure as described in Example 25, Step B to give the title compound as a yellow solid (1.54 g, 49%). The compound was characterized by the following spectroscopic data:

MS-ESI: (ESI, pos. ion) m/z: 524.0 [M+1]$^+$;

$^1$H NMR (400 MHz, DMSO-d$_6$): δ 10.06 (s, 1H), 8.02 (d, 1H), 7.91 (d, 1H), 7.68-7.62 (m, 1H), 7.58-7.38 (m, 1H), 7.24-7.20 (m, 1H), 6.03 (s, 1H), 4.12-4.05 (m, 1H), 3.95-3.85 (m, 3H), 3.75-3.66 (m, 1H), 3.62-3.57 (m, 1H), 3.55-3.35 (m, 2H), 3.00-2.87 (m, 1H), 2.79-2.65 (m, 1H), 2.57-2.54 (m, 1H), 1.03 (t, 3H).

Example 28

(3S)-4-((6-(2-bromo-4-fluorophenyl)-5-(ethoxycarbonyl)-2-(thiazol-2-yl)-3,6-dihydropyrimidin-4-yl)methyl)morpholine-3-carboxylic acid

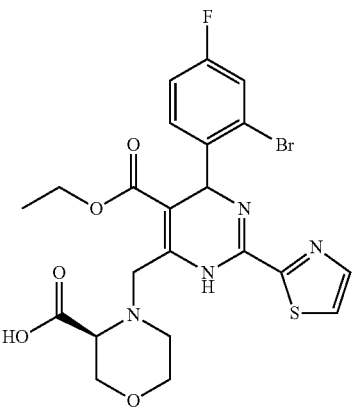 [SMILES: CCOC(=O)C1=C(CN2CCOC[C@H]2C(=O)O)NC(c2nccs2)=NC1c1ccc(F)cc1Br]

A mixture of ethyl 4-(2-bromo-4-fluorophenyl)-6-(bromomethyl)-2-(thiazol-2-yl)-1,4-dihydropyrimidine-5-carboxylate (7.7 g, 15.3 mmol), (S)-morpholine-3-carboxylic acid (2 g, 15.3 mmol) and potassium carbonate (4.23 g, 30.6 mmol) in anhydrous ethanol (154 mL) was stirred at 25° C. for 16 hours. The reaction mixture was filtered and the filtrate was concentrated in vacuo. The residue was purified by a silica gel column chromatography (DCM/MeOH (V/V)=25/1) to give the title compound as a yellow solid (7.26 g, 86%). The compound was characterized by the following spectroscopic data:

MS-ESI: (ESI, pos. ion) m/z: 553.2 [M+1]$^+$;

$^1$H NMR (400 MHz, DMSO-d$_6$): δ 12.90 (s, 1H), 9.84 (s, 1H), 8.04 (d, 1H), 7.95 (d, 1H), 7.57-7.55 (m, 1H), 7.43-7.37 (m, 1H), 7.23-7.19 (m, 1H), 6.03 (s, 1H), 4.30-3.92 (m, 5H), 3.84-3.82 (m, 1H), 3.74-3.52 (m, 3H), 3.11-3.07 (m, 1H), 2.55-2.39 (m, 1H), 1.06 (t, 3H).

Example 29

(3S)-4-((6-(2,4-dichlorophenyl)-5-(ethoxycarbonyl)-2-(thiazol-2-yl)-3,6-dihydropyrimidin-4-yl)methyl)morpholine-3-carboxylic acid

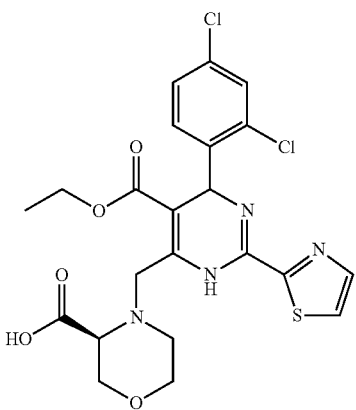 [SMILES: CCOC(=O)C1=C(CN2CCOC[C@H]2C(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (1.6 g, 3.37 mmol) was reacted with (S)-morpholine-3-carboxylic acid (0.44 g, 3.37 mmol) according to the procedure as described in Example 28 to give the title compound as a yellow solid (1.42 g, 80%). The compound was characterized by the following spectroscopic data:

MS-ESI: (ESI, pos. ion) m/z: 525.1 [M+1]$^+$;

$^1$H NMR (600 MHz, DMSO-d$_6$): δ 12.90 (br.s, 1H), 9.84 (s, 1H), 8.04 (d, 1H), 7.95 (d, 1H), 7.60 (br.s, 1H), 7.41-7.37 (m, 2H), 6.06 (s, 1H), 4.28-4.02 (m, 2H), 4.01-3.92 (m, 3H), 3.84-3.82 (m, 1H), 3.73-3.71 (m, 1H), 3.67-3.64 (m, 1H), 3.62-3.52 (m, 1H), 3.10-3.07 (m, 1H), 2.54-2.40 (m, 1H), 1.06 (t, 3H).

Example 30

(3S)-4-((6-(2-chloro-4-fluorophenyl)-5-(ethoxycarbonyl)-2-(thiazol-2-yl)-3,6-dihydropyrimidin-4-yl)methyl)morpholine-3-carboxylic acid

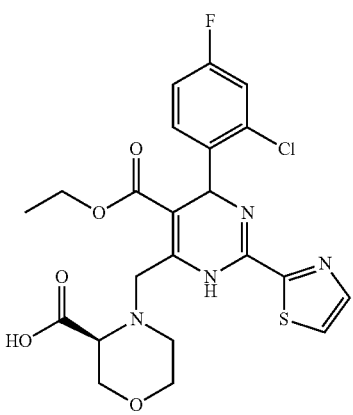 [SMILES: CCOC(=O)C1=C(CN2CCOC[C@H]2C(=O)O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (1.55 g, 3.37 mmol) was reacted with (S)-morpholine-3-carboxylic acid (0.44 g, 3.37 mmol) according to the procedure as described in Example 28 to give the title compound as a yellow solid (1.48 g, 86%). The compound was characterized by the following spectroscopic data:

MS-ESI: (ESI, pos. ion) m/z: 509.1 [M+1]$^+$;

$^1$H NMR (600 MHz, DMSO-d$_6$): δ 12.91 (br.s, 1H), 9.85 (s, 1H), 8.03 (br.s, 1H), 7.94 (br.s, 1H), 7.44-7.39 (m, 2H), 7.18-7.15 (m, 1H), 6.05 (s, 1H), 4.27-4.05 (m, 2H), 4.00-3.92 (m, 3H), 3.84-3.83 (m, 1H), 3.75-3.71 (m, 1H), 3.66-3.64 (m, 1H), 3.61-3.52 (m, 1H), 3.09-3.07 (m, 1H), 2.54-2.39 (m, 1H), 1.06 (t, 3H).

Example 31

(3S)-4-((6-(2,4-dichlorophenyl)-5-(methoxycarbonyl)-2-(thiazol-2-yl)-3,6-dihydropyrimidin-4-yl)methyl)morpholine-3-carboxylic acid

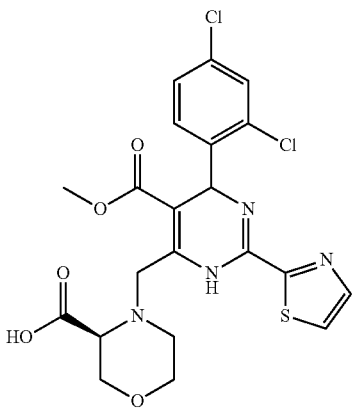 [SMILES: COC(=O)C1=C(CN2CCOC[C@H]2C(=O)O)NC(c2nccs2)=NC1c1ccc(Cl)cc1Cl]

Methyl 6-(bromomethyl)-4-(2,4-dichlorophenyl)-2-(thiazol-2-yl)-1,4-dihydropyrimidine-5-carboxylate (1.55 g, 3.37 mmol) was reacted with (S)-morpholine-3-carboxylic acid (0.44 g, 3.37 mmol) according to the procedure as described in Example 28 to give the title compound as a yellow solid (1.41 g, 82%). The compound was characterized by the following spectroscopic data:

MS-ESI: (ESI, pos. ion) m/z: 511.1 [M+1]$^+$;

$^1$H NMR (600 MHz, DMSO-d$_6$): δ 12.89 (br.s, 1H), 10.05 (br.s, 1H), 8.02 (br.s, 1H), 7.94 (br.s, 1H), 7.60-7.58 (m, 1H), 7.43-7.36 (m, 2H), 6.03 (s, 1H), 4.19-4.02 (m, 2H), 3.91-3.86 (m, 2H), 3.68 (br.s, 2H), 3.51 (s, 3H), 3.43 (br.s, 1H), 3.08-3.02 (m, 1H), 2.52-2.44 (m, 1H).

Example 32

(3S)-4-((6-(2-chloro-4-fluorophenyl)-5-(methoxycarbonyl)-2-(thiazol-2-yl)-3,6-dihydropyrimidin-4-yl)methyl)morpholine-3-carboxylic acid

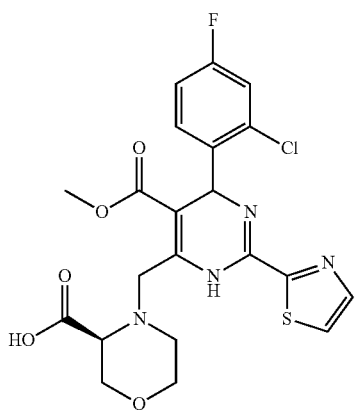 [SMILES: COC(=O)C1=C(CN2CCOC[C@H]2C(=O)O)NC(c2nccs2)=NC1c1ccc(F)cc1Cl]

Methyl 6-(bromomethyl)-4-(2-chloro-4-fluorophenyl)-2-(thiazol-2-yl)-1,4-dihydropyrimidine-5-carboxylate (1.5 g, 3.37 mmol) was reacted with (S)-morpholine-3-carboxylic acid (0.44 g, 3.37 mmol) according to the procedure as described in Example 28 to give the title compound as a yellow solid (1.33 g, 80%). The compound was characterized by the following spectroscopic data:

MS-ESI: (ESI, pos. ion) m/z: 495.1 [M+1]$^+$;

$^1$H NMR (600 MHz, DMSO-d$_6$): δ 12.90 (br.s, 1H), 9.89 (br.s, 1H), 8.03 (br.s, 1H), 7.94 (br.s, 1H), 7.43-7.37 (m, 2H), 7.18-7.15 (m, 1H), 6.04 (s, 1H), 4.25-4.01 (m, 2H), 3.99-3.90 (m, 1H), 3.85-3.83 (m, 1H), 3.71-3.61 (m, 2H), 3.51 (s, 3H), 3.44-3.41 (m, 1H), 3.09-3.07 (m, 1H), 2.51-2.44 (m, 1H).

Example 33

(3S)-4-((6-(2-bromo-4-fluorophenyl)-5-(methoxycarbonyl)-2-(thiazol-2-yl)-3,6-dihydropyrimidin-4-yl)methyl)morpholine-3-carboxylic acid

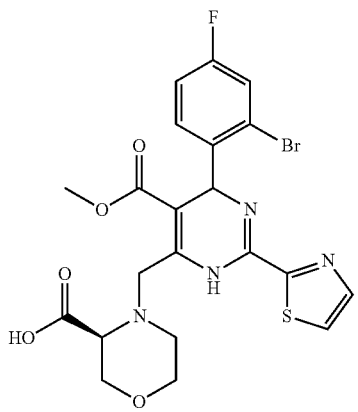

Methyl 4-(2-bromo-4-fluorophenyl)-6-(bromomethyl)-2-(thiazol-2-yl)-1,4-dihydropyrimidine-5-carboxylate (1.65 g, 3.37 mmol) was reacted with (S)-morpholine-3-carboxylic acid (0.44 g, 3.37 mmol) according to the procedure as described in Example 28 to give the title compound as a yellow solid (1.51 g, 83%). The compound was characterized by the following spectroscopic data:

MS-ESI: (ESI, pos. ion) m/z: 539.0 [M+1]$^+$;

$^1$H NMR (600 MHz, DMSO-d$_6$): δ 12.88 (br.s, 1H), 10.07 (br.s, 1H), 8.02 (br.s, 1H), 7.93 (br.s, 1H), 7.56-7.54 (m, 1H), 7.40-7.37 (m, 1H), 7.22-7.19 (m, 1H), 6.01 (s, 1H), 4.19-4.03 (m, 2H), 3.88-3.82 (m, 2H), 3.68-3.66 (m, 2H), 3.51 (s, 3H), 3.44-3.40 (m, 1H), 3.07-2.99 (m, 1H), 2.42-2.40 (m, 1H).

Example 34

(2R,3S)-4-((6-(2-bromo-4-fluorophenyl)-5-(ethoxycarbonyl)-2-(thiazol-2-yl)-3,6-dihydropyrimidin-4-yl)methyl)-2-methylmorpholine-3-carboxylic acid

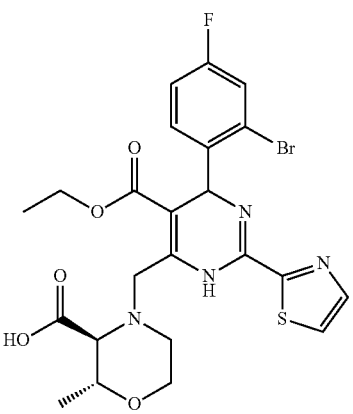

Step A: (2R,3S)-benzyl 4-benzyl-2-methyl-5-oxomorpholine-3-carboxylate

A mixture of (2R,3S)-4-benzyl-2-methyl-5-oxomorpholine-3-carboxylic acid (1.07 g, 4.25 mmol) (The compound was synthesized according to the procedure as described in Helvetica Chimica Acta, 87, 2004), (bromomethyl)benzene (0.87 g, 5.1 mmol) and potassium carbonate (1.16 g, 8.5 mmol) in acetonitrile (20 mL) was stirred at 65° C. for 6 hours. The reaction mixture was filtered and the filtrate was concentrated in vacuo. The residue was purified by a silica gel column chromatography (PETROLEUM ETHER/EtOAc (V/V)=4/1) to give the title compound as colorless oil (1.23 g, 85%). The compound was characterized by the following spectroscopic data:

MS-ESI: (ESI, pos. ion) m/z: 340.3 [M+1]$^+$;

$^1$H NMR (600 MHz, CDCl$_3$): δ 7.42-7.18 (m, 10H), 5.52 (d, 1H), 5.22 (q, 2H), 4.33 (q, 2H), 4.23-4.21 (m, 1H), 3.76-3.74 (m, 2H), 1.23 (d, 3H).

Step B: (2R,3S)-benzyl 4-benzyl-2-methylmorpholine-3-carboxylate

To a solution of (2R,3S)-benzyl 4-benzyl-2-methyl-5-oxomorpholine-3-carboxylate (15.7 g, 46.1 mmol) in THF (60 mL) was added a solution of borane in THF (1 mol/L, 69.2 mL) dropwise over a period of 1 hour at −10° C. under N₂. After the end of addition, the mixture was warmed to 25° C. and stirred for 16 hours, then cooled to −10° C. And to the mixture was added methanol slowly until gas evolution was ceased, then added water (10 mL). The mixture was concentrated in vacuo and the residue was dissolved in EtOAc (150 mL). The organic layer was washed with aqueous NaOH solution (2 mol/L, 50 mL×2) and brine (50 mL×2). The organic phase was concentrated in vacuo to give the title compound as colorless oil (13 g, 86.7%). The compound was characterized by the following spectroscopic data:

MS-ESI: (ESI, pos. ion) m/z: 326.3 [M+1]⁺;

¹H NMR (600 MHz, CDCl₃): δ 7.33-7.27 (m, 10H), 5.22 (s, 2H), 3.80-3.70 (m, 4H), 3.27 (d, 1H), 2.90 (d, 1H), 2.71 (d, 1H), 2.22-2.18 (m, 1H), 1.15 (d, 3H).

Step C: (2R,3S)-2-methylmorpholine-3-carboxylic acid

A mixture of (2R,3S)-benzyl 4-benzyl-2-methylmorpholine-3-carboxylate (10 g, 30.76 mmol) and Pd/C (10%, 1 g) in anhydrous methanol (100 mL) was stirred at 25° C. for 12 hours under H₂. The mixture was filtered and the filtrate was concentrated in vacuo to give the title compound as a white solid (3.8 g, 85%). The compound was characterized by the following spectroscopic data:

MS-ESI: (ESI, pos. ion) m/z: 146.2 [M+1]⁺;

¹H NMR (600 MHz, D₂O): δ 4.01-3.98 (m, 1H), 3.82-3.77 (m, 1H), 3.76-3.72 (m, 1H), 3.37 (d, 1H), 3.27-3.24 (m, 1H), 3.19-3.14 (m, 1H), 1.26 (d, 3H).

Step D: (2R,3S)-4-((6-(2-bromo-4-fluorophenyl)-5-(ethoxycarbonyl)-2-(thiazol-2-yl)-3,6-dihydropyrimidin-4-yl)methyl)-2-methylmorpholine-3-carboxylic acid A mixture of ethyl 4-(2-bromo-4-fluorophenyl)-6-(bromomethyl)-2-(thiazol-2-yl)-1,4-dihydropyrimidine-5-carboxylate (0.96 g, 1.9 mmol), (2R,3S)-2-methylmorpholine-3-carboxylic acid (0.28 g, 1.9 mmol) and potassium carbonate (0.53 g, 3.8 mmol) in anhydrous ethanol (35 mL) was stirred at 25° C. for 12 hours under N₂. The reaction mixture was filtered and the filtrate was concentrated in vacuo. The residue was purified by a silica gel column chromatography (DCM/MeOH (V/V)=15/1) to give the title compound as a yellow solid (0.48 g, 45%). The compound was characterized by the following spectroscopic data:

MS-ESI: (ESI, pos. ion) m/z: 567.1 [M+1]⁺;

¹H NMR (400 MHz, DMSO-d₆): δ 13.1 (br.s, 1H), 9.88 (s, 1H), 8.03-8.01 (m, 1H), 7.94-7.92 (m, 1H), 7.58-7.54 (m, 1H), 7.41-7.33 (m, 1H), 7.24-7.18 (m, 1H), 6.03 (s, 1H), 4.18-4.08 (m, 1H), 4.02-3.93 (m, 2H), 3.91-3.70 (m, 2H), 3.68-3.51 (m, 3H), 2.98-2.89 (m, 1H), 2.72-2.47 (m, 1H), 1.26 (br.s, 3H), 1.04 (t, 3H).

Example 35

(2R,3S)-4-((6-(2-chloro-4-fluorophenyl)-5-(ethoxycarbonyl)-2-(thiazol-2-yl)-3,6-dihydropyrimidin-4-yl)methyl)-2-methylmorpholine-3-carboxylic acid

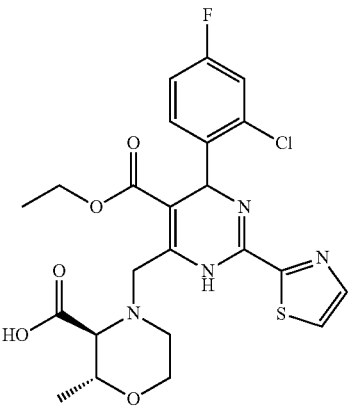 [SMILES: CCOC(=O)C1=C(CN2CCO[C@H](C)[C@H]2C(=O)O)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.87 g, 1.9 mmol) was reacted with (2R,3S)-2-methyl morpholine-3-carboxylic acid (0.28 g, 1.9 mmol) according to the procedure as described in Example 34, Step D to give the title compound as a yellow solid (0.6 g, 60%). The compound was characterized by the following spectroscopic data:

MS-ESI: (ESI, pos. ion) m/z: 523.2 [M+1]⁺;

¹H NMR (400 MHz, DMSO-d₆): δ 12.93 (br.s, 1H), 9.86 (s, 1H), 8.03 (d, 1H), 7.94 (d, 1H), 7.45-7.38 (m, 2H), 7.20-7.16 (m, 1H), 6.05 (s, 1H), 4.19-4.09 (m, 1H), 4.03-3.93 (m, 2H), 3.90-3.71 (m, 2H), 3.69-3.50 (m, 3H), 2.99-2.88 (m, 1H), 2.73-2.47 (m, 1H), 1.25 (br.s, 3H), 1.06 (t, 3H).

Example 36

(2R,3S)-4-((6-(2,4-dichlorophenyl)-5-(ethoxycarbonyl)-2-(thiazol-2-yl)-3,6-dihydropyrimidin-4-yl)methyl)-2-methylmorpholine-3-carboxylic acid

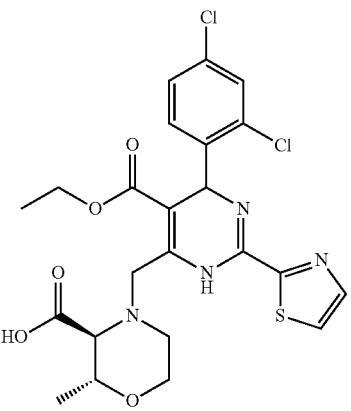 [SMILES: CCOC(=O)C1=C(CN2CCO[C@H](C)[C@H]2C(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.9 g, 1.9 mmol) was reacted with (2R,3S)-2-methyl morpholine-3-carboxylic acid (0.28 g, 1.9 mmol) according to the procedure as described in Example 34, Step D to give the title compound as a yellow solid (0.43 g, 42%). The compound was characterized by the following spectroscopic data:

MS-ESI: (ESI, pos. ion) m/z: 539.1 [M+1]+;
1H NMR (600 MHz, DMSO-d6): δ 12.91 (br.s, 1H), 9.85 (s, 1H), 8.04 (d, 1H), 7.96 (d, 1H), 7.58-7.55 (m, 1H), 7.42-7.37 (m, 2H), 6.06 (s, 1H), 4.17-4.08 (m, 1H), 4.02-3.92 (m, 2H), 3.92-3.71 (m, 2H), 3.69-3.52 (m, 3H), 2.99-2.89 (m, 1H), 2.71-2.47 (m, 1H), 1.25 (br.s, 3H), 1.06 (t, 3H).

Example 37

(2R,3S)-4-((6-(2-bromo-4-fluorophenyl)-5-(methoxycarbonyl)-2-(thiazol-2-yl)-3,6-dihydropyrimidin-4-yl)methyl)-2-methylmorpholine-3-carboxylic acid

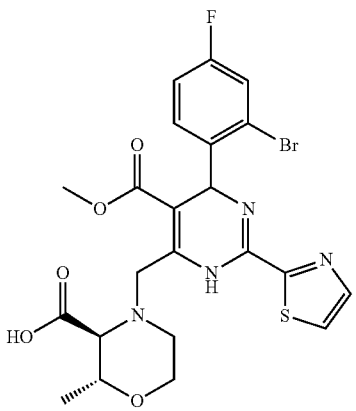

Methyl 4-(2-bromo-4-fluorophenyl)-6-(bromomethyl)-2-(thiazol-2-yl)-1,4-dihydropyrimidine-5-carboxylate (0.93 g, 1.9 mmol) was reacted with (2R,3S)-2-methyl morpholine-3-carboxylic acid (0.28 g, 1.9 mmol) according to the procedure as described in Example 34 to give the title compound as a yellow solid (0.52 g, 49%). The compound was characterized by the following spectroscopic data:

MS-ESI: (ESI, pos. ion) m/z: 553.1 [M+1]+;
1H NMR (400 MHz, DMSO-d6): δ 13.0 (br.s, 1H), 9.87 (s, 1H), 8.03 (d, 1H), 7.93 (d, 1H), 7.57-7.53 (m, 1H), 7.40-7.32 (m, 1H), 7.25-7.17 (m, 1H), 6.04 (s, 1H), 4.18-4.07 (m, 1H), 4.02-3.92 (m, 1H), 3.91-3.85 (m, 1H), 3.72 (s, 3H), 3.68-3.50 (m, 3H), 2.98-2.87 (m, 1H), 2.73-2.47 (m, 1H), 1.27 (br.s, 3H).

Example 38

(2R,3S)-4-((6-(2-chloro-4-fluorophenyl)-5-(methoxycarbonyl)-2-(thiazol-2-yl)-3,6-dihydropyrimidin-4-yl)methyl)-2-methylmorpholine-3-carboxylic acid

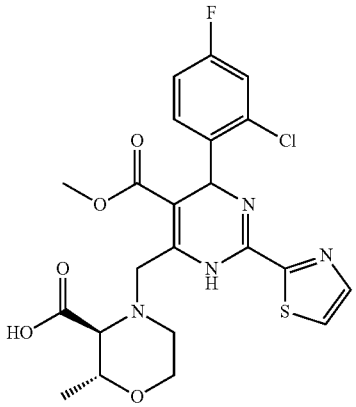 [SMILES: COC(=O)C1=C(CN2CCO[C@H](C)[C@H]2C(=O)O)NC(c2nccs2)=NC1c1ccc(F)cc1Cl]

Methyl 6-(bromomethyl)-4-(2-chloro-4-fluorophenyl)-2-(thiazol-2-yl)-1,4-dihydropyrimidine-5-carboxylate (0.85 g, 1.9 mmol) was reacted with (2R,3S)-2-methylmorpholine-3-carboxylic acid (0.28 g, 1.9 mmol) according to the procedure as described in Example 34 to give the title compound as a yellow solid (0.5 g, 52%). The compound was characterized by the following spectroscopic data:

MS-ESI: (ESI, pos. ion) m/z: 509.2 [M+1]+;
1H NMR (400 MHz, DMSO-d6): δ 12.94 (br.s, 1H), 9.87 (s, 1H), 8.04 (d, 1H), 7.92 (d, 1H), 7.46-7.39 (m, 2H), 7.21-7.15 (m, 1H), 6.04 (s, 1H), 4.19-4.08 (m, 1H), 4.03-3.94 (m, 1H), 3.89-3.79 (m, 1H), 3.71 (s, 3H), 3.69-3.51 (m, 3H), 2.99-2.87 (m, 1H), 2.74-2.48 (m, 1H), 1.25 (br.s, 3H).

Example 39

(2R,3S)-4-((6-(2,4-dichlorophenyl)-5-(methoxycarbonyl)-2-(thiazol-2-yl)-3,6-dihydropyrimidin-4-yl)methyl)-2-methylmorpholine-3-carboxylic acid

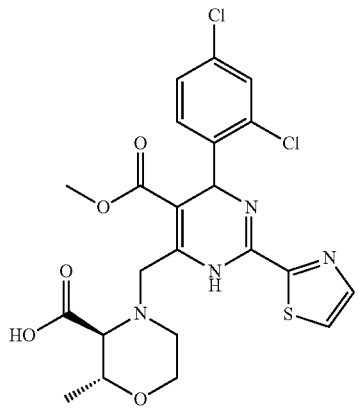 [SMILES: COC(=O)C1=C(CN2CCO[C@H](C)[C@H]2C(=O)O)NC(c2nccs2)=NC1c1ccc(Cl)cc1Cl]

Methyl 6-(bromomethyl)-4-(2,4-dichlorophenyl)-2-(thiazol-2-yl)-1,4-dihydropyrimidine-5-carboxylate (0.88 g, 1.9 mmol) was reacted with (2R,3S)-2-methylmorpholine-3-carboxylic acid (0.28 g, 1.9 mmol) according to the procedure as described in Example 34 to give the title compound as a yellow solid (0.51 g, 51%). The compound was characterized by the following spectroscopic data:

MS-ESI: (ESI, pos. ion) m/z: 525.1 [M+1]+;
1H NMR (400 MHz, DMSO-d6): δ 12.93 (br.s, 1H), 9.84 (s, 1H), 8.04 (d, 1H), 7.96 (d, 1H), 7.59-7.56 (m, 1H), 7.43-7.38 (m, 2H), 6.05 (s, 1H), 4.18-4.09 (m, 1H), 4.03-3.93 (m, 1H), 3.91-3.80 (m, 1H), 3.72 (s, 3H), 3.68-3.51 (m, 3H), 2.99-2.89 (m, 1H), 2.69-2.47 (m, 1H), 1.27 (br.s, 3H).

Example 40

Ethyl 4-(2-bromo-4-fluorophenyl)-6-(((S)-3-(hydroxymethyl)morpholino)methyl)-2-(thiazol-2-yl)-1,4-dihydropyrimidine-5-carboxylate

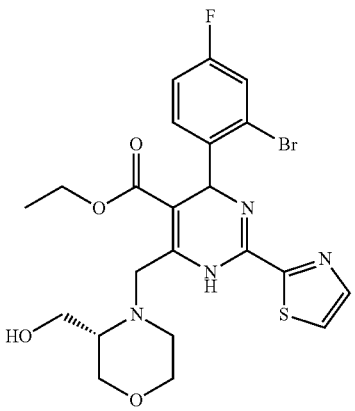

Ethyl 4-(2-bromo-4-fluorophenyl)-6-(bromomethyl)-2-(thiazol-2-yl)-1,4-dihydropyrimidine-5-carboxylate (1 g, 2 mmol) was reacted with (S)-morpholin-3-ylmethanol (0.24 g, 2 mmol) according to the procedure as described in Example 25, Step B to give the title compound as a pale yellow solid (0.6 g, 55%). The compound was characterized by the following spectroscopic data:

MS-ESI: (ESI, pos. ion) m/z: 539.2 [M+1]$^+$;
$^1$H NMR (400 MHz, DMSO-d$_6$): δ 9.86 (br.s, 1H), 8.04 (d, 1H), 7.95 (d, 1H), 7.58-7.56 (m, 1H), 7.43-7.38 (m, 1H), 7.25-7.19 (m, 1H), 6.03 (s, 1H), 4.83-4.74 (m, 1H), 4.37-4.24 (m, 1H), 4.01-3.89 (m, 3H), 3.82-3.69 (m, 2H), 3.59-3.38 (m, 4H), 2.86-2.69 (m, 1H), 2.57-2.43 (m, 1H), 1.06 (t, 3H).

Example 41

Ethyl 4-(2-chloro-4-fluorophenyl)-6-(((S)-3-(hydroxymethyl)morpholino)methyl)-2-(thiazol-2-yl)-1,4-dihydropyrimidine-5-carboxylate

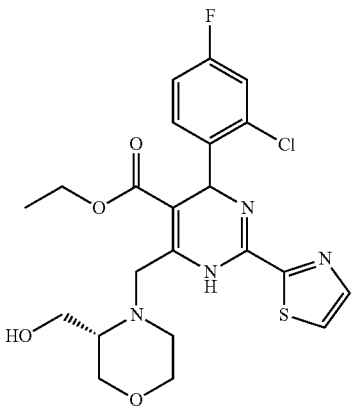 [SMILES: CCOC(=O)C1=C(CN2CCOC[C@@H]2CO)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.92 g, 2 mmol) was reacted with (S)-morpholin-3-ylmethanol (0.24 g, 2 mmol) according to the procedure as described in Example 25, Step B to give the title compound as a pale yellow solid (0.6 g, 61%). The compound was characterized by the following spectroscopic data:

MS-ESI: (ESI, pos. ion) m/z: 495.2 [M+1]$^+$;
$^1$H NMR (400 MHz, DMSO-d$_6$): δ 9.86 (br.s, 1H), 8.04 (d, 1H), 7.94 (d, 1H), 7.46-7.38 (m, 2H), 7.20-7.16 (m, 1H), 6.04 (s, 1H), 4.83-4.74 (m, 1H), 4.38-4.25 (m, 1H), 4.03-3.88 (m, 3H), 3.83-3.68 (m, 2H), 3.61-3.38 (m, 4H), 2.87-2.68 (m, 1H), 2.58-2.43 (m, 1H), 1.06 (t, 3H).

Example 42

Ethyl 4-(2,4-dichlorophenyl)-6-(((S)-3-(hydroxymethyl)morpholino)methyl)-2-(thiazol-2-yl)-1,4-dihydropyrimidine-5-carboxylate

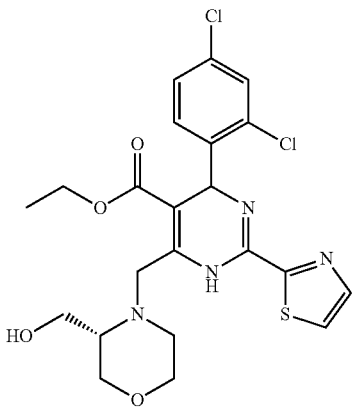 [SMILES: CCOC(=O)C1=C(CN2CCOC[C@@H]2CO)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.95 g, 2 mmol) was reacted with (S)-morpholin-3-ylmethanol (0.24 g, 2 mmol) according to the procedure as described in Example 25, Step B to give the title compound as a pale yellow solid (0.42 g, 41%). The compound was characterized by the following spectroscopic data:

MS-ESI: (ESI, pos. ion) m/z: 511.2 [M+1]$^+$;
$^1$H NMR (400 MHz, DMSO-d$_6$): δ 9.85 (br.s, 1H), 8.03 (d, 1H), 7.94 (d, 1H), 7.60-7.58 (m, 1H), 7.39-7.37 (m, 2H), 6.05 (s, 1H), 4.81 (br.s, 1H), 4.35-4.22 (m, 1H), 3.99-3.92 (m, 3H), 3.87-3.77 (m, 2H), 3.59-3.40 (m, 4H), 2.84-2.66 (m, 1H), 2.60-2.56 (m, 1H), 2.48-2.40 (m, 1H), 1.05 (t, 3H).

Example 43

Methyl 4-(2-bromo-4-fluorophenyl)-6-(((S)-3-(hydroxymethyl)morpholino)methyl)-2-(thiazol-2-yl)-1,4-dihydropyrimidine-5-carboxylate

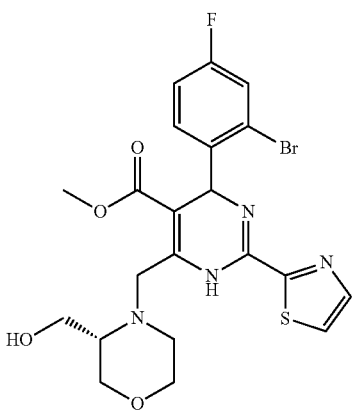 [SMILES: COC(=O)C1=C(CN2CCOC[C@@H]2CO)NC(c2nccs2)=NC1c1ccc(F)cc1Cl]

Methyl 4-(2-bromo-4-fluorophenyl)-6-(bromomethyl)-2-(thiazol-2-yl)-1,4-dihydropyrimidine-5-carboxylate (0.98 g, 2 mmol) was reacted with (S)-morpholin-3-ylmethanol (0.24 g, 2 mmol) according to the procedure as described in Example 25, Step B to give the title compound as a pale yellow solid (0.56 g, 53%). The compound was characterized by the following spectroscopic data:

MS-ESI: (ESI, pos. ion) m/z: 525.1 [M+1]$^+$;

$^1$H NMR (400 MHz, DMSO-d$_6$): δ 9.87 (br.s, 1H), 8.04 (d, 1H), 7.94 (d, 1H), 7.59-7.56 (m, 1H), 7.44-7.38 (m, 1H), 7.25-7.18 (m, 1H), 6.04 (s, 1H), 4.83-4.73 (m, 1H), 4.37-4.25 (m, 1H), 4.03-3.89 (m, 1H), 3.83-3.76 (m, 1H), 3.69 (s, 3H), 3.59-3.37 (m, 4H), 2.87-2.69 (m, 1H), 2.57-2.42 (m, 1H).

Example 44

Methyl 4-(2-chloro-4-fluorophenyl)-6-(((S)-3-(hydroxymethyl)morpholino)methyl)-2-(thiazol-2-yl)-1,4-dihydropyrimidine-5-carboxylate

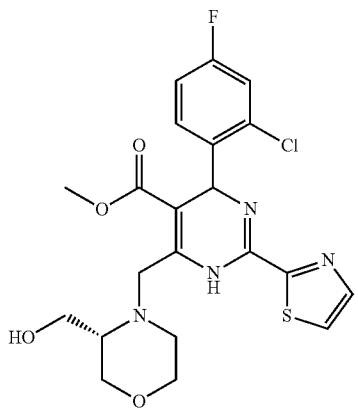

Methyl 6-(bromomethyl)-4-(2-chloro-4-fluorophenyl)-2-(thiazol-2-yl)-1,4-dihydropyrimidine-5-carboxylate (0.89 g, 2 mmol) was reacted with (S)-morpholin-3-ylmethanol (0.24 g, 2 mmol) according to the procedure as described in Example 25, Step B to give the title compound as a pale yellow solid (0.38 g, 39%). The compound was characterized by the following spectroscopic data:

MS-ESI: (ESI, pos. ion) m/z: 481.2 [M+1]$^+$;

$^1$H NMR (400 MHz, DMSO-d$_6$): δ 9.83 (br.s, 1H), 8.02 (d, 1H), 7.92 (d, 1H), 7.48-7.36 (m, 2H), 7.21-7.16 (m, 1H), 6.03 (s, 1H), 4.82-4.74 (m, 1H), 4.38-4.26 (m, 1H), 4.05-3.88 (m, 2H), 3.83-3.75 (m, 1H), 3.71 (s, 3H), 3.62-3.35 (m, 4H), 2.88-2.67 (m, 1H), 2.58-2.44 (m, 1H).

Example 45

Methyl 4-(2,4-dichlorophenyl)-6-(((S)-3-(hydroxymethyl)morpholino)methyl)-2-(thiazol-2-yl)-1,4-dihydropyrimidine-5-carboxylate Methyl 6-(bromomethyl)-4-(2,4-dichlorophenyl)-2-(thiazol-2-yl)-1,4-dihydropyrimidine-5-carboxylate (0.92 g, 2 mmol) was reacted with (S)-morpholin-3-ylmethanol (0.24 g, 2 mmol) according to the procedure as described in Example 25, Step B to give the title compound as a pale yellow solid (0.44 g, 44%). The compound was characterized by the following spectroscopic data:

MS-ESI: (ESI, pos. ion) m/z: 497.1 [M+1]$^+$;

$^1$H NMR (400 MHz, DMSO-d$_6$): δ 9.84 (br.s, 1H), 8.04 (d, 1H), 7.92 (d, 1H), 7.61-7.59 (m, 1H), 7.38-7.36 (m, 2H), 6.03 (s, 1H), 4.81 (br.s, 1H), 4.35-4.24 (m, 1H), 3.99-3.91 (m, 2H), 3.87-3.78 (m, 1H), 3.71 (s, 3H), 3.58-3.39 (m, 4H), 2.85-2.66 (m, 1H), 2.61-2.56 (m, 1H), 2.49-2.41 (m, 1H).

Example 46

(3S)-4-((6-(2-bromo-4-fluorophenyl)-5-(ethoxycarbonyl)-2-(thiazol-2-yl)-3,6-dihydropyrimidin-4-yl)methyl)-2,2-dimethylmorpholine-3-carboxylic acid

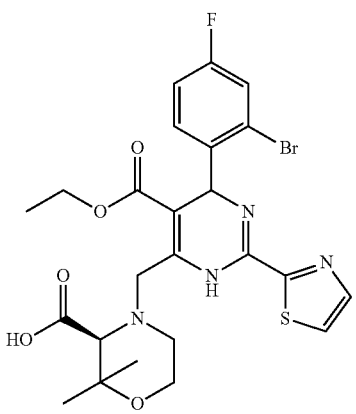

Step A:
(S)-2-(benzylamino)-3-hydroxy-3-methylbutanoic acid

A mixture of (S)-2-amino-3-hydroxy-3-methylbutanoic acid (18.6 g, 140 mmol), aqueous NaOH solution (2 mol/L, 70 mL) and benzaldehyde (14.56 g, 137 mmol) was stirred at 25° C. for 1 hour and cooled to 0° C. Then to the mixture was added sodium borohydride (3 g, 80 mmol) portion wise with the temperature maintained below 10° C. Then the mixture was warmed to 25° C. and stirred for another 12 hours. The aqueous layer was washed with DCM (30 mL×3) and the organic layer was discarded. The aqueous layer was cooled to 5° C., and adjusted to pH 1-2 with con. HCl. The mixture was stirred at 5° C. for 4 hours, and filtered to give the title compound as a white solid (18.8 g, 60%). The compound was characterized by the following spectroscopic data:
MS-ESI: (ESI, pos. ion) m/z: 224.1 [M+1]$^+$;
$^1$H NMR (400 MHz, D$_2$O): δ 7.35 (s, 5H), 4.24 (q, 2H), 3.63-3.61 (m, 1H), 1.25-1.23 (m, 6H).

Step B: (S)-4-benzyl-2,2-dimethyl-5-oxomorpholine-3-carboxylic acid

To a mixture of (S)-2-(benzylamino)-3-hydroxy-3-methylbutanoic acid (22.86 g, 102.4 mmol), tetrahydrofuran (110 mL), potassium carbonate (42.5 g, 307.2 mmol) and water (70 mL) was added chloroacetyl chloride slowly (17.8 g, 157.7 mmol) at 0° C. over a period of 1 hour, then the mixture was stirred at 0° C. for 3 hours. To the reaction mixture was added a solution of sodium hydroxide (16.4 g, 409.6 mmol) in water (40 mL) over a period of 1 hour. At the end of addition, the mixture was cooled to 3° C.-5° C., and the mixture was stirred at the temperature for 4 hours. Then the reaction mixture was warmed to room temperature, and washed with Petroleum ether (50 mL×2). The aqueous layer was cooled to 3° C. below and adjusted to pH 2 with con. HCl. The mixture was stirred at 6° C. below for 12 hours, then filtered. The filter cake was washed with water to give the title compound as a white solid (18.6 g, 69%). The compound was characterized by the following spectroscopic data:
MS-ESI: (ESI, pos. ion) m/z: 264.1 [M+1]$^+$;
$^1$H NMR (600 MHz, DMSO-d$_6$): δ 12.83 (br.s, 1H), 7.36-7.26 (m, 5H), 5.29 (d, 1H), 4.32-4.10 (m, 3H), 3.73 (d, 1H), 1.21-1.17 (m, 6H).

Step C: (S)-benzyl 4-benzyl-2,2-dimethyl-5-oxomorpholine-3-carboxylate (S)-4-benzyl-2,2-dimethyl-5-oxomorpholine-3-carboxylic acid (11.2 g, 42.5 mmol) was reacted with benzyl bromide (8.72 g, 51 mmol) according to the procedure as described in Example 34, Step A to give the title compound as a white solid (8.11 g, 54%). The compound was characterized by the following spectroscopic data:
MS-ESI: (ESI, pos. ion) m/z: 354.2 [M+1]$^+$;
$^1$H NMR (400 MHz, CDCl$_3$): δ 7.36-7.31 (m, 5H), 7.30-7.20 (m, 5H), 5.60 (d, 1H), 1H), 5.26 (q, 2H), 4.40-4.37 (m, 1H), 4.33-4.08 (m, 3H), 1.24-1.19 (m, 6H).

Step D: (S)-benzyl 4-benzyl-2,2-dimethylmorpholine-3-carboxylate (S)-benzyl 4-benzyl-2,2-dimethyl-5-oxomorpholine-3-carboxylate (163 g, 461 mmol) was reacted with a solution of borane in THF (1 mol/L, 692 mL) according to the procedure as described in Example 34, Step B to give the title compound as colorless oil (133 g, 85%). The compound was characterized by the following spectroscopic data:
MS-ESI: (ESI, pos. ion) m/z: 340.2 [M+1]$^+$;
$^1$H NMR (600 MHz, CDCl$_3$): δ 7.33-7.27 (m, 10H), 5.25 (s, 2H), 3.89-3.70 (m, 4H), 3.24 (d, 1H), 2.72 (d, 1H), 2.25-2.18 (m, 1H), 1.25-1.17 (m, 6H).

Step E: (S)-2,2-dimethylmorpholine-3-carboxylic acid (S)-benzyl 4-benzyl-2,2-dimethylmorpholine-3-carboxylate (10.4 g, 30.8 mmol) was reacted with H$_2$ by Pd/C catalysis (10%, 1 g) according to the procedure as described in Example 34, Step C to give the title compound as a white solid (3.4 g, 70%). The compound was characterized by the following spectroscopic data:
MS-ESI: (ESI, pos. ion) m/z: 160.1 [M+1]$^+$;
$^1$H NMR (600 MHz, D$_2$O): δ 4.06-3.98 (m, 1H), 3.85-3.77 (m, 1H), 3.76-3.75 (m, 1H), 3.27-3.26 (m, 1H), 3.19-3.13 (m, 1H), 1.26-1.19 (m, 6H).

Step F: (3S)-4-((6-(2-bromo-4-fluorophenyl)-5-(ethoxycarbonyl)-2-(thiazol-2-yl)-3,6-dihydropyrimidin-4-yl)methyl)-2,2-dimethylmorpholine-3-carboxylic acid A mixture of ethyl 4-(2-bromo-4-fluorophenyl)-6-(bromomethyl)-2-(thiazol-2-yl)-1,4-dihydropyrimidine-5-carboxylate (7.7 g, 15.3 mmol), (S)-2,2-dimethylmorpholine-3-carboxylic acid (2.44 g, 15.3 mmol) and potassium carbonate (4.23 g, 30.6 mmol) in anhydrous ethanol (154 mL) was stirred at 25° C. for 16 hours. The reaction mixture was filtered and the filtrate was concentrated in vacuo. The residue was purified by a silica gel column chromatography (DCM/MeOH (V/V)=25/1) to give the title compound as a yellow solid (5.8 g, 65%). The compound was characterized by the following spectroscopic data:
MS-ESI: (ESI, pos. ion) m/z: 581.1 [M+1]$^+$;
$^1$H NMR (400 MHz, DMSO-d$_6$): δ 12.90 (s, 1H), 9.87 (s, 1H), 8.06 (d, 1H), 7.92 (d, 1H), 7.58-7.55 (m, 1H), 7.43-7.37 (m, 1H), 7.25-7.19 (m, 1H), 6.06 (s, 1H), 4.20-4.07 (m, 1H), 4.02-3.93 (m, 2H), 3.90-3.70 (m, 2H), 3.68-3.49 (m, 3H), 2.69-2.47 (m, 1H), 1.27-1.21 (m, 6H).

Example 47

(3S)-4-((6-(2-chloro-4-fluorophenyl)-5-(methoxycarbonyl)-2-(thiazol-2-yl)-3,6-dihydropyrimidin-4-yl)methyl)-2,2-dimethylmorpholine-3-carboxylic acid

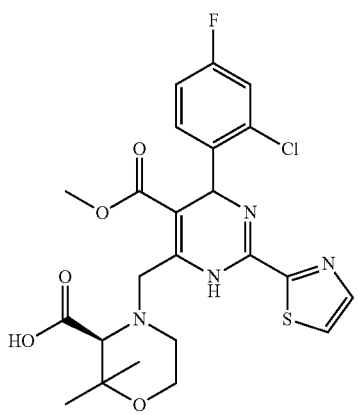

Methyl 6-(bromomethyl)-4-(2-chloro-4-fluorophenyl)-2-(thiazol-2-yl)-1,4-dihydropyrimidine-5-carboxylate (6.8 g, 15.3 mmol) was reacted with (S)-2,2-dimethylmorpholine-3-carboxylic acid (2.44 g, 15.3 mmol) according to the procedure as described in Example 46, Step F to give the title compound as a yellow solid (4.4 g, 55%). The compound was characterized by the following spectroscopic data:

MS-ESI: (ESI, pos. ion) m/z: 523.1 [M+1]$^+$;
$^1$H NMR (400 MHz, DMSO-d$_6$): δ 12.93 (s, 1H), 9.83 (s, 1H), 8.04 (d, 1H), 7.94 (d, 1H), 7.59-7.55 (m, 1H), 7.44-7.37 (m, 1H), 7.26-7.19 (m, 1H), 6.05 (s, 1H), 4.20-4.09 (m, 1H), 3.95-3.70 (m, 2H), 3.71 (s, 3H), 3.68-3.48 (m, 3H), 2.69-2.49 (m, 1H), 1.27-1.22 (m, 6H).

Example 48

4-((6-(2-chloro-4-fluorophenyl)-5-(ethoxycarbonyl)-3-methyl-2-(thiazol-2-yl)-3,6-dihydropyrimidin-4-yl)methyl)morpholine-3-carboxylic acid

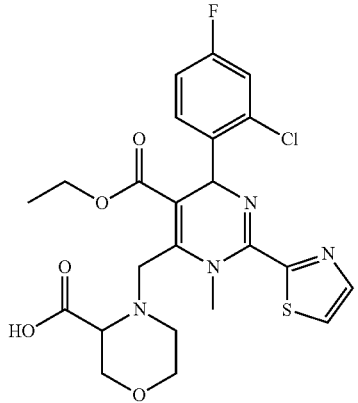 [SMILES: CCOC(=O)C1=C(CN2CCOCC2C(=O)O)N(C)C(c2nccs2)=NC1c1ccc(F)cc1Cl]

Step A: Ethyl 4-(2-chloro-4-fluorophenyl)-1,6-dimethyl-2-(thiazol-2-yl)-1,4-dihydropyrimidine-5-carboxylate A mixture of ethyl 4-(2-chloro-4-fluorophenyl)-6-methyl-2-(thiazol-2-yl)-1,4-dihydropyrimidine-5-carboxylate (2 g, 5.3 mmol), iodomethane (0.97 g, 6.84 mmol) and potassium carbonate (1.47 g, 10.6 mmol) in acetonitrile (50 mL) was stirred at 70° C. for 12 hours, and cooled to 25° C. The reaction mixture was filtered and the filtrate was concentrated in vacuo. The residue was purified by a silica gel column chromatography (PETROLEUM ETHER/EtOAc (V/V)=3/1) to give the title compound as a tawny solid (1.0 g, 48%). The compound was characterized by the following spectroscopic data:

MS-ESI: (ESI, pos. ion) m/z: 394.0 [M+1]$^+$;
$^1$H NMR (400 MHz, CDCl$_3$): δ 7.86 (d, 1H), 7.54-7.50 (m, 1H), 7.48 (d, 1H), 7.09-7.07 (m, 1H), 6.95-6.90 (m, 1H), 5.92 (s, 1H), 4.09 (q, 2H), 3.54 (s, 3H), 2.49 (s, 3H), 1.19 (t, 3H).

Step B: Ethyl 6-(bromomethyl)-4-(2-chloro-4-fluorophenyl)-1-methyl-2-(thiazol-2-yl)-1,4-dihydropyrimidine-5-carboxylate Ethyl 4-(2-chloro-4-fluorophenyl)-1,6-dimethyl-2-(thiazol-2-yl)-1,4-dihydropyrimidine-5-carboxylate (0.4 g, 1.02 mmol) was reacted with NBS (0.2 g, 1.12 mmol) according to the procedure as described in Example 1, Step B to give the title compound as yellow oil (0.19 g, 40%). The compound was characterized by the following spectroscopic data:

MS-ESI: (ESI, pos. ion) m/z: 472.10 [M+1]$^+$;
$^1$H NMR (400 MHz, CDCl$_3$): δ 7.86 (d, 1H), 7.54-7.50 (m, 1H), 7.48 (d, 1H), 7.09-7.07 (m, 1H), 6.95-6.90 (m, 1H), 5.92 (s, 1H), 4.84 (d, 1H), 4.60 (d, 1H), 4.09 (q, 2H), 3.54 (s, 3H), 1.19 (t, 3H).

Step C: 4-((6-(2-chloro-4-fluorophenyl)-5-(ethoxycarbonyl)-3-methyl-2-(thiazol-2-yl)-3,6-dihydropyrimidin-4-yl)methyl)morpholine-3-carboxylic acid Ethyl 6-(bromomethyl)-4-(2-chloro-4-fluorophenyl)-1-methyl-2-(thiazol-2-yl)-1,4-dihydropyrimidine-5-carboxylate (0.48 g, 1.02 mmol) was reacted with morpholine-3-carboxylic acid (0.4 g, 3.06 mmol) according to the procedure as described in Example 1, Step C to give the title compound as a yellow solid (0.1 g, 20%). The compound was characterized by the following spectroscopic data:

MS-ESI: (ESI, pos. ion) m/z: 523.2 [M+1]$^+$;
$^1$H NMR (400 MHz, D$_2$O): δ 8.08 (d, 2H), 7.60-7.56 (m, 1H), 7.33-7.31 (m, 1H), 7.12-7.10 (m, 1H), 6.23 (s, 1H), 4.38 (d, 1H), 4.21 (d, 1H), 4.08-3.80 (m, 6H), 3.69-3.57 (m, 2H), 3.41 (s, 3H), 3.26-3.22 (m, 1H), 1.10 (t, 3H).

Example 49

Ethyl 6-(((S)-3-((((S)-2-amino-3-methylbutanoyl)oxy)methyl)morpholino)methyl)-4-(2-bromo-4-fluorophenyl)-2-(thiazol-2-yl)-1,4-dihydropyrimidine-5-carboxylate

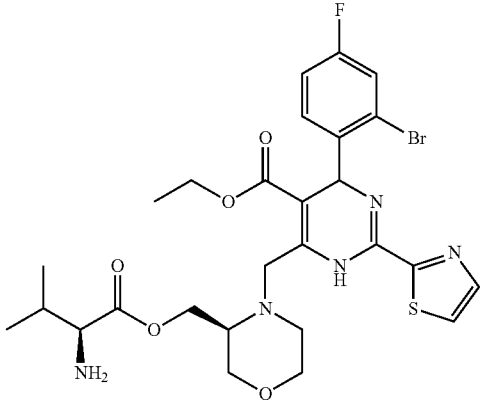 [SMILES: CCOC(=O)C1=C(CN2CCOC[C@H]2COC(=O)[C@@H](N)C(C)C)NC(c2nccs2)=NC1c1ccc(F)cc1Br]

To a solution of ethyl 4-(2-bromo-4-fluorophenyl)-6-(S)-3-(hydroxymethyl)morpholino)methyl)-2-(thiazol-2-yl)-1,4-dihydropyrimidine-5-carboxylate (1 g, 1.9 mmol), (S)-2-((tert-butoxycarbonyl)amino)-3-methylbutanoic acid (0.83 g, 3.8 mmol) and 4-dimethylaminopyridine (23 mg, 0.19 mmol) in DCM (30 mL) was added a solution of DCC (0.59 g, 2.85 mmol) in DCM (10 mL) dropwise over a period of 15 minutes at rt, then the mixture was stirred at rt for 12 hours. The reaction mixture was filtered and the filtrate was concentrated in vacuo. The residue was dissolved in a solution of HCl in EtOAc (6 mol/L, 40 mL), and the mixture was stirred at 25° C. for 12 hours. The reaction mixture was diluted with EtOAc (200 mL) and water (100 mL), and the mixture was adjusted to pH 8-9 with aqueous ammonia. The organic layer was dried over Na$_2$SO$_4$, and the mixture was filtered and concentrated in vacuo. The residue was purified by a silica gel column chromatography (DCM/MeOH (V/V)=30/1) to give the title compound as a yellow solid (0.65 g, 54%). The compound was characterized by the following spectroscopic data:

MS-ESI: (ESI, pos. ion) m/z: 638.1 [M+1]$^+$;
$^1$H NMR (400 MHz, DMSO-d$_6$): δ 11.22 (br.s, 1H), 8.82 (br.s, 2H), 8.12-8.08 (m, 1H), 7.62-7.55 (m, 1H), 7.30-7.26 (m, 1H), 6.03 (s, 1H), 4.30-4.21 (m, 3H), 4.06-3.94 (m, 3H), 3.88-3.72 (m, 4H), 3.68-3.52 (m, 2H), 2.89-2.74 (m, 2H), 2.06-1.98 (m, 1H), 1.08-1.04 (m, 3H), 0.82-0.74 (m, 6H).

Example 50

Ethyl 6-(((S)-3-((((S)-2-amino-3-methylbutanoyl)oxy)methyl)morpholino)methyl)-4-(2,4-dichlorophenyl)-2-(thiazol-2-yl)-1,4-dihydropyrimidine-5-carboxylate

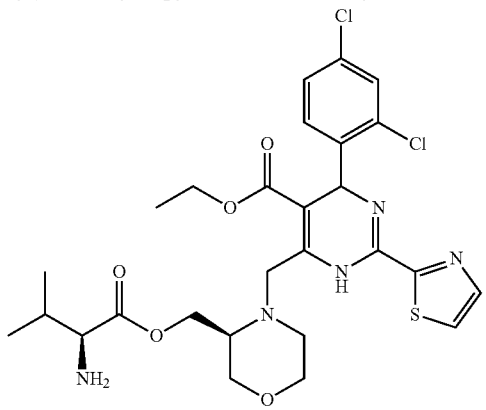 [SMILES: CCOC(=O)C1=C(CN2CCOC[C@H]2COC(=O)[C@@H](N)C(C)C)NC(c2nccs2)=NC1c1ccc(Cl)cc1Cl]

Ethyl 4-(2,4-dichlorophenyl)-6-(((S)-3-(hydroxymethyl)morpholino)methyl)-2-(thiazol-2-yl)-1,4-dihydropyrimidine-5-carboxylate (1 g, 1.96 mmol) was reacted with (S)-2-((tert-butoxycarbonyl)amino)-3-methylbutanoic acid (0.83 g, 3.8 mmol) according to the procedure as described in Example 49 to give the title compound as a yellow solid (0.43 g, 36%). The compound was characterized by the following spectroscopic data:

MS-ESI: (ESI, pos. ion) m/z: 610.1 [M+1]$^+$;
$^1$H NMR (400 MHz, DMSO-d$_6$): δ 9.85 (br.s, 1H), 8.74 (br.s, 2H), 8.05 (br.s, 2H), 7.61 (s, 1H), 7.48-7.41 (m, 2H), 6.04 (s, 1H), 4.29-4.20 (m, 3H), 4.07-3.94 (m, 3H), 3.89-3.72 (m, 4H), 3.68-3.52 (m, 2H), 2.89-2.75 (m, 2H), 2.06-1.96 (m, 1H), 1.08-1.04 (m, 3H), 0.82-0.74 (m, 6H).

Example 51

Methyl 4-((6-(2-bromo-4-fluorophenyl)-5-(ethoxycarbonyl)-2-(thiazol-2-yl)-3,6-dihydropyrimidin-4-yl)methyl)morpholine-3-carboxylate

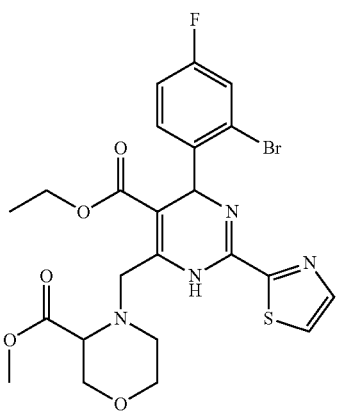 [SMILES: CCOC(=O)C1=C(CN2CCOCC2C(=O)OC)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (1.1 g, 2.2 mmol) was reacted with methyl morpholine-3-carboxylate (0.4 g, 2.2 mmol) according to the procedure as described in Example 24 to give the title compound as a yellow solid (0.62 g, 50%). The compound was characterized by the following spectroscopic data:

MS-ESI: (ESI, pos. ion) m/z: 567.1 [M+1]$^+$;
$^1$H NMR (400 MHz, DMSO-d$_6$): δ 9.74 (s, 1H), 8.03 (d, 1H), 7.94 (d, 1H), 7.57-7.54 (m, 1H), 7.41-7.37 (m, 1H), 7.24-7.18 (m, 1H), 6.02 (s, 1H), 4.32-4.09 (m, 2H), 4.05-4.00 (m, 1H), 3.99-3.92 (m, 2H), 3.83-3.73 (m, 3H), 3.70 (s, 3H), 3.65-3.52 (m, 1H), 3.10-3.04 (m, 1H), 2.58-2.42 (m, 1H), 1.06 (t, 3H).

Example 52

Ethyl 4-(2-bromo-4-fluorophenyl)-6-(((S)-3-(hydroxycarbamoyl)morpholino)methyl)-2-(thiazol-2-yl)-1,4-dihydropyrimidine-5-carboxylate

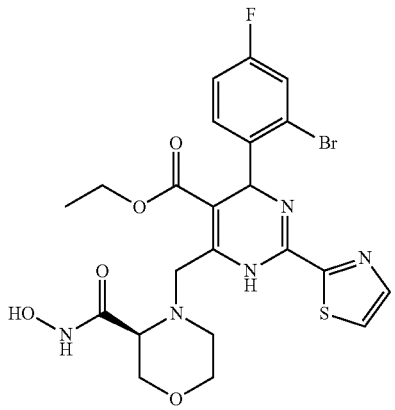 [SMILES: CCOC(=O)C1=C(CN2CCOC[C@H]2C(=O)NO)NC(c2nccs2)=NC1c1ccc(F)cc1Br]

A solution of (3S)-4-(((6-(2-bromo-4-fluorophenyl)-5-(ethoxycarbonyl)-2-(thiazol-2-yl)-3,6-dihydropyrimidin-4-yl)methyl)morpholine-3-carboxylic acid (0.74 g, 1.36 mmol), EDC.HCl (0.31 g, 1.62 mmol), HOAt (185 mg, 1.36 mmol) and DIPEA (210 mg, 1.62 mmol) in DCM (20 mL) was stirred at –10° C. for 30 minutes. Then to the mixture was added a solution of O-(tert-butyldimethylsilyl)hydroxylamine (0.2 g, 1.36 mmol) in DCM (2.0 mL) slowly at –10° C. Then the mixture was warmed to 25° C. and stirred for 12 hours. The mixture was concentrated in vacuo and the residue was dissolved in a solution of HCl in EtOAc (6 mol/L, 10 mL), then the mixture was stirred at 25° C. for 2 hours. The reaction mixture was diluted with EtOAc (200 mL) and water (100 mL), and the mixture was adjusted to pH 7 with aqueous ammonia. The organic layer was dried over Na$_2$SO$_4$, and concentrated in vacuo. The residue was purified by a silica gel column chromatography (DCM/MeOH (V/V)=30/1) to give the title compound as a yellow solid (0.05 g, 6.5%). The compound was characterized by the following spectroscopic data:

MS-ESI: (ESI, pos. ion) m/z: 568.2 [M+1]$^+$;
$^1$H NMR (400 MHz, DMSO-d$_6$): δ 11.30 (br.s, 1H), 9.86 (br.s, 1H), 8.04 (d, 1H), 7.95 (d, 1H), 7.57-7.55 (m, 1H), 7.43-7.37 (m, 1H), 7.23-7.19 (m, 1H), 6.02 (s, 1H), 4.32-4.15 (m, 3H), 4.10-3.91 (m, 2H), 3.84-3.82 (m, 1H), 3.74-3.52 (m, 3H), 3.11-3.07 (m, 1H), 2.55-2.39 (m, 1H), 1.05 (t, 3H).

Example 53

Ethyl 4-(2-bromo-4-fluorophenyl)-6-(((S)-3-(methoxycarbamoyl)morpholino)methyl)-2-(thiazol-2-yl)-1,4-dihydropyrimidine-5-carboxylate

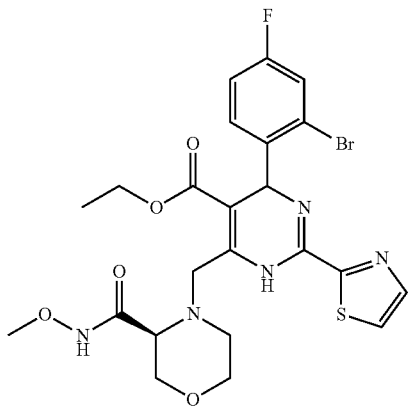 [SMILES: CCOC(=O)C1=C(CN2CCOC[C@H]2C(=O)NOC)NC(c2nccs2)=NC1c1ccc(F)cc1Br]

A mixture of (3S)-4-(((6-(2-bromo-4-fluorophenyl)-5-(ethoxycarbonyl)-2-(thiazol-2-yl)-3,6-dihydropyrimidin-4-yl)methyl)morpholine-3-carboxylic acid (0.5 g, 0.9 mmol), O-methylhydroxylamine hydrochloride (0.2 g, 2.25 mmol), EDC.HCl (1 g, 5.2 mmol), HOAt (1 g, 7.3 mmol) and TEA (1.45 g, 14.3 mmol) in DCM (30 mL) was stirred at 0 t for 1 hour. Then the mixture was warmed to 25° C. and stirred for another 10 hours. The mixture was concentrated in vacuo and the residue was purified by a silica gel column chromatography (DCM/MeOH (V/V)=30/1) to give the title compound as a yellow solid (0.4 g, 76%). The compound was characterized by the following spectroscopic data:

MS-ESI: (ESI, pos. ion) m/z: 582.0 [M+1]$^+$;

$^1$H NMR (400 MHz, CDCl$_3$): δ 7.98 (d, 1H), 7.71 (d, 1H), 7.40-7.33 (m, 2H), 7.09-7.05 (m, 1H), 6.18 (s, 1H), 4.72-4.65 (m, 1H), 4.55-4.44 (m, 1H), 4.31-4.21 (m, 2H), 4.11-4.00 (m, 3H), 3.94-3.84 (m, 2H), 3.80 (s, 3H), 3.56-3.40 (m, 2H), 3.35-3.27 (m, 1H), 1.12 (t, 3H).

Example 54

Ethyl 4-(2-bromo-4-fluorophenyl)-6-(((S)-3-((2-hydroxyethyl)carbamoyl)morpholino)methyl)-2-(thiazol-2-yl)-1,4-dihydropyrimidine-5-carboxylate

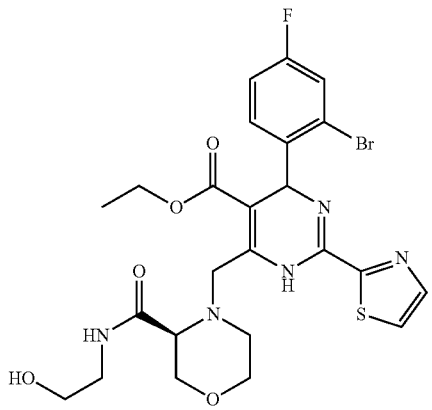 [SMILES: CCOC(=O)C1=C(CN2CCOC[C@H]2C(=O)NCCO)NC(c2nccs2)=NC1c1ccc(F)cc1Br]

(3S)-4-((6-(2-bromo-4-fluorophenyl)-5-(ethoxycarbonyl)-2-(thiazol-2-yl)-3,6-dihydropyrimidin-4-yl)methyl) morpholine-3-carboxylic acid (0.5 g, 0.9 mmol) was reacted with 2-aminoethanol (72 mg, 1.2 mmol) according to the procedure as described in Example 53 to give the title compound as a yellow solid (0.3 g, 56%). The compound was characterized by the following spectroscopic data:

MS-ESI: (ESI, pos. ion) m/z: 596.0 [M+1]$^+$;

$^1$H NMR (400 MHz, DMSO-d$_6$): δ 9.93 (s, 1H), 8.27 (br.s, 1H), 8.04 (d, 1H), 7.92 (d, 1H), 7.57-7.54 (m, 1H), 7.41-7.37 (m, 1H), 7.24-7.19 (m, 1H), 6.02 (s, 1H), 4.73-4.68 (m, 1H), 4.14-4.00 (m, 2H), 3.95-3.88 (m, 2H), 3.86-3.71 (m, 2H), 3.68-3.50 (m, 2H), 3.45-3.38 (m, 1H), 3.33-3.27 (m, 1H), 3.22-3.14 (m, 2H), 3.00-2.81 (m, 1H), 2.48-2.41 (m, 1H), 1.06 (t, 3H).

Example 55

Ethyl 6-(((S)-3-((2-acetoxyethyl)carbamoyl)morpholino)methyl)-4-(2-bromo-4-fluorophenyl)-2-(thiazol-2-yl)-1,4-dihydropyrimidine-5-carboxylate

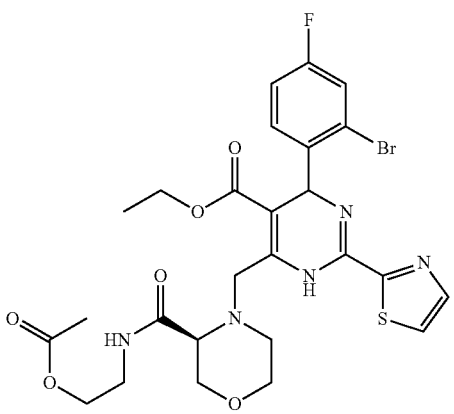 [SMILES: CCOC(=O)C1=C(CN2CCOC[C@H]2C(=O)NCCOC(C)=O)NC(c2nccs2)=NC1c1ccc(F)cc1Br]

Step A: (S)-tert-butyl 3-((2-hydroxyethyl)carbamoyl) morpholine-4-carboxylate A mixture of (S)-4-tert-butyl 3-methyl morpholine-3,4-dicarboxylate (0.93 g, 3.8 mmol) and 2-aminoethanol (5 g, 81.9 mmol) in methanol (2 mL) was stirred at 80° C. for 7 hours under N$_2$. The mixture was concentrated in vacuo, diluted with EtOAc (100 mL) and acetic acid (5 mL). The organic layer was washed with brine (80 mL×6), dried over Na$_2$SO$_4$, and filtered. The filtrate was concentrated in vacuo to give the title compound as a white solid (0.8 g, 77%). The compound was characterized by the following spectroscopic data:

MS-ESI: (ESI, pos. ion) m/z: 175.1 [M+1-100]$^+$;

$^1$H NMR (400 MHz, DMSO-d$_6$): δ 12.01 (br.s, 1H), 7.89 (s, 1H), 4.69 (br.s, 1H), 4.28-4.12 (m, 2H), 3.77-3.69 (m, 1H), 3.57-3.51 (m, 2H), 3.40-3.30 (m, 3H), 3.25-3.14 (m, 2H), 1.37 (s, 9H).

Step B: (S)-2-(morpholine-3-carboxamido)ethyl acetate hydrochloride

To a solution of (S)-tert-butyl 3-((2-hydroxyethyl)carbamoyl)morpholine-4-carboxylate (0.33 g, 1.2 mmol) in glacial acetic acid (0.5 mL) was added a solution of HCl in EtOAc (6 mol/L, 15 mL), then the mixture was stirred closedly at 25° C. for 12 hours. The mixture was concentrated in vacuo to give the title compound as glutinous semisolid (0.21 g, 70%). The compound was characterized by the following spectroscopic data:

MS-ESI: (ESI, pos. ion) m/z: 217.1 [M+1]+;

$^1$H NMR (400 MHz, D$_2$O): δ 4.65 (br.s, 1H), 4.31-4.18 (m, 2H), 3.82-3.71 (m, 1H), 3.60-3.50 (m, 2H), 3.46-3.35 (m, 3H), 3.23-3.11 (m, 2H), 1.98 (s, 3H).

Step C: Ethyl 6-(((S)-3-((2-acetoxyethyl)carbamoyl) morpholino)methyl)-4-(2-bromo-4-fluorophenyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (0.6 g, 1.2 mmol) was reacted with (S)-2-(morpholine-3-carboxamido)ethyl acetate hydrochloride (0.3 g, 1.2 mmol) according to the procedure as described in Example 24 to give the title compound as a yellow solid (0.2 g, 26%). The compound was characterized by the following spectroscopic data:

MS-ESI: (ESI, pos. ion) m/z: 638.1 [M+1]+;

$^1$H NMR (400 MHz, DMSO-d$_6$): δ 9.96 (s, 1H), 8.41 (d, 1H), 8.33 (d, 1H), 7.57-7.54 (m, 1H), 7.39-7.36 (m, 1H), 7.25-7.18 (m, 1H), 6.03 (s, 1H), 4.13-4.03 (m, 2H), 4.02-3.90 (m, 2H), 3.86-3.77 (m, 2H), 3.74-3.56 (m, 2H), 3.55-3.50 (m, 1H), 3.40-3.36 (m, 1H), 3.31-3.25 (m, 2H), 3.00-2.80 (m, 1H), 2.48-2.31 (m, 2H), 1.96 (s, 3H), 1.03 (t, 3H).

Example 56

(3S)-4-((5-(ethoxycarbonyl)-6-(5-fluoro-4'-(trifluoromethyl)-[1,1'-biphenyl]-2-yl)-2-(thiazol-2-yl)-3,6-dihydropyrimidin-4-yl)methyl)morpholine-3-carboxylic acid

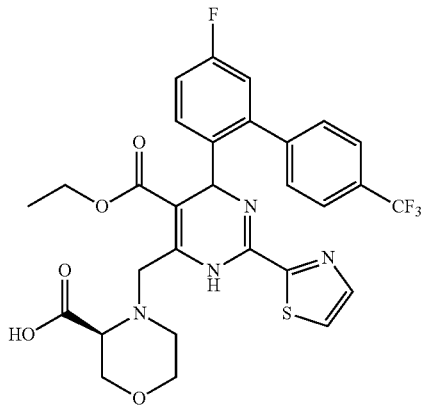 [SMILES: CCOC(=O)C1=C(CN2CCOC[C@H]2C(=O)O)NC(c2nccs2)=NC1c1ccc(F)cc1-c1ccc(C(F)(F)F)cc1]

Step A: 5-fluoro-4'-(trifluoromethyl)-[1,1'-biphenyl]-2-carbaldehyde

A mixture of 2-bromo-4-fluorobenzaldehyde (2 g, 9.85 mmol), (4-(trifluoromethyl)phenyl)boronic acid (2.25 g, 11.82 mmol), potassium acetate (2.42 g, 24.63 mmol) and Pd(PPh$_3$)$_4$ (1.14 g, 0.98 mmol) in DMF (40 mL) and water (13 mL) was stirred at 100° C. for 3 hours under N$_2$, then cooled to 25° C. To the mixture was added EtOAc (250 mL). The organic layer was washed with brine (200 mL×3), dried over Na$_2$SO$_4$ and filtered. The filtrate was concentrated in vacuo. The residue was purified by a silica gel column chromatography (PETROLEUM ETHER/EtOAc (V/V)=70/1) to give the title compound as colorless oil (2.11 g, 79%). The compound was characterized by the following spectroscopic data:

MS-ESI: (ESI, pos. ion) m/z: 269.1 [M+1]

$^1$H NMR (400 MHz, DMSO-d$_6$): δ 9.81 (s, 1H), 8.07-8.03 (m, 1H), 7.88 (dd, 4H), 7.52-7.47 (m, 1H), 7.45-7.42 (m, 1H).

Step B: Ethyl 4-(5-fluoro-4'-(trifluoromethyl)-[1,1'-biphenyl]-2-yl)-6-methyl-2-(thiazol-2-yl)-1,4-dihydropyrimidine-5-carboxylate 5-fluoro-4'-(trifluoromethyl)-[1,1'-biphenyl]-2-carbaldehyde (2.11 g, 7.87 mmol) was reacted with thiazole-2-carboximidamide hydrochloride (1.29 g, 7.87 mmol) and ethyl 3-oxobutanoate (1.23 g, 9.44 mmol) according to the procedure as described in Example 1, Step A to give the title compound as a yellow solid (1.22 g, 32%). The compound was characterized by the following spectroscopic data:

MS-ESI: (ESI, pos. ion) m/z: 490.1 [M+1]+;

$^1$H NMR (400 MHz, DMSO-d$_6$): δ 9.90 (s, 1H), 7.99 (d, 1H), 7.93 (d, 1H), 7.89 (s, 4H), 7.46-7.42 (m, 1H), 7.28-7.23 (m, 1H), 7.17-7.14 (m, 1H), 5.50 (s, 1H), 3.84 (q, 2H), 2.45 (s, 3H), 0.87 (t, 3H).

Step C: Ethyl 6-(bromomethyl)-4-(5-fluoro-4'-(trifluoromethyl)-[1,1'-biphenyl]-2-yl)-2-(thiazol-2-yl)-1,4-dihydropyrimidine-5-carboxylate Ethyl 4-(5-fluoro-4'-(trifluoromethyl)-[1,1'-biphenyl]-2-yl)-6-methyl-2-(thiazol-2-yl)-1,4-dihydropyrimidine-5-carboxylate (5 g, 10.2 mmol) was reacted with NBS (2.2 g, 12.2 mmol) according to the procedure as described in Example 1, Step B to give the title compound as a yellow solid (3.48 g, 60%). The compound was characterized by the following spectroscopic data:

MS-ESI: (ESI, pos. ion) m/z: 568.1 [M+1]+;

$^1$H NMR (400 MHz, DMSO-d$_6$): δ 9.98 (s, 1H), 7.96 (d, 1H), 7.90 (d, 1H), 7.80 (s, 4H), 7.47-7.41 (m, 1H), 7.28-7.21 (m, 1H), 7.16-7.11 (m, 1H), 5.58 (s, 1H), 4.66 (dd, 2H), 3.94 (q, 2H), 0.93 (t, 3H).

Step D: (3S)-4-((5-(ethoxycarbonyl)-6-(5-fluoro-4'-(trifluoromethyl)-[1,1'-biphenyl]-2-yl)-2-(thiazol-2-yl)-3,6-dihydropyrimidin-4-yl)methyl)morpholine-3-carboxylic acid Ethyl 6-(bromomethyl)-4-(5-fluoro-4'-(trifluoromethyl)-[1,1'-biphenyl]-2-yl)-2-(thiazol-2-yl)-1,4-dihydropyrimidine-5-carboxylate (3 g, 5.3 mmol) was reacted with (S)-morpholine-3-carboxylic acid (0.69 g, 5.3 mmol) according to the procedure as described in Example 1, Step C to give the title compound as a yellow solid (1.64 g, 50%). The compound was characterized by the following spectroscopic data:

MS-ESI: (ESI, pos. ion) m/z: 619.3 [M+1]+;

$^1$H NMR (400 MHz, DMSO-d$_6$): δ 12.96 (br.s, 1H), 9.87 (br.s, 1H), 8.04 (d, 1H), 7.96 (d, 1H), 7.89 (s, 4H), 7.51-7.46 (m, 1H), 7.25-7.22 (m, 1H), 7.18-7.15 (m, 1H), 5.56 (s, 1H), 4.23-4.10 (m, 1H), 4.08-4.04 (m, 1H), 4.02-3.96 (m, 1H), 3.88-3.83 (m, 3H), 3.75-3.63 (m, 2H), 3.57-3.45 (m, 1H), 3.07-3.04 (m, 1H), 2.38-2.36 (m, 1H), 0.90 (t, 3H).

Example 57

(3S)-4-((5-(ethoxycarbonyl)-6-(5-fluoro-3',5'-bis (trifluoromethyl)-[1,1'-biphenyl]-2-yl)-2-(thiazol-2-yl)-3,6-dihydropyrimidin-4-yl)methyl)morpholine-3-carboxylic acid

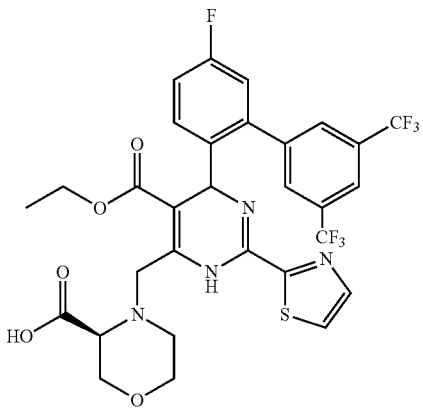 [SMILES: CCOC(=O)C1=C(CN2CCOC[C@H]2C(=O)O)NC(c2nccs2)=NC1c1ccc(F)cc1-c1cc(C(F)(F)F)cc(C(F)(F)F)c1]

Step A: 5-fluoro-3',5'-bis(trifluoromethyl)-[1,1'-biphenyl]-2-carbaldehyde 2-bromo-4-fluorobenzaldehyde (1.53 g, 7.5 mmol) was reacted with (3,5-bis(trifluoromethyl)phenyl)boronic acid (2.3 g, 9 mmol) according to the procedure as described in Example 56, Step A to give the title compound as a white solid (2.34 g, 92%). The compound was characterized by the following spectroscopic data:

MS-ESI: (ESI, pos. ion) m/z: 337.0 [M+1]$^+$;
$^1$H NMR (400 MHz, DMSO-d$_6$): δ 9.82 (s, 1H), 8.23 (s, 3H), 8.12-8.08 (m, 1H), 7.58-7.52 (m, 2H).

Step B: Ethyl 4-(5-fluoro-3',5'-bis(trifluoromethyl)-[1,1'-biphenyl]-2-yl)-6-methyl-2-(thiazol-2-yl)-1,4-dihydropyrimidine-5-carboxylate 5-fluoro-3',5'-bis(trifluoromethyl)-[1,1'-biphenyl]-2-carbaldehyde (2.34 g, 6.96 mmol) was reacted with thiazole-2-carboximidamide hydrochloride (1.14 g, 6.96 mmol) and ethyl 3-oxobutanoate (1.1 g, 8.35 mmol) according to the procedure as described in Example 1, Step A to give the title compound as a yellow solid (1 g, 26%). The compound was characterized by the following spectroscopic data:

MS-ESI: (ESI, pos. ion) m/z: 558.1 [M+1]$^+$;
$^1$H NMR (400 MHz, DMSO-d$_6$): δ 9.97 (s, 1H), 8.42 (s, 2H), 8.23 (s, 1H), 7.99 (d, 1H), 7.95 (d, 1H), 7.47-7.43 (m, 1H), 7.34-7.29 (m, 2H), 5.34 (s, 1H), 3.80 (q, 2H), 2.46 (s, 3H), 0.87 (t, 3H).

Step C: Ethyl 6-(bromomethyl)-4-(5-fluoro-3',5'-bis (trifluoromethyl)-[1,1'-biphenyl]-2-yl)-2-(thiazol-2-yl)-1,4-dihydropyrimidine-5-carboxylate Ethyl 4-(5-fluoro-3',5'-bis(trifluoromethyl)-[1,1'-biphenyl]-2-yl)-6-methyl-2-(thiazol-2-yl)-1,4-dihydropyrimidine-5-carboxylate (5.69 g, 10.2 mmol) was reacted with NBS (2.2 g, 12.2 mmol) according to the procedure as described in Example 1, Step B to give the title compound as a yellow solid (3.57 g, 55%). The compound was characterized by the following spectroscopic data:

MS-ESI: (ESI, pos. ion) m/z: 636.0 [M+1]$^+$;
$^1$H NMR (400 MHz, DMSO-d$_6$): δ 9.98 (s, 1H), 8.43 (s, 2H), 8.24 (s, 1H), 7.98 (d, 1H), 7.96 (d, 1H), 7.48-7.44 (m, 1H), 7.35-7.28 (m, 2H), 5.40 (s, 1H), 4.62 (dd, 2H), 3.88 (q, 2H), 0.89 (t, 3H).

Step D: (3S)-4-((5-(ethoxycarbonyl)-6-(5-fluoro-3',5'-bis(trifluoromethyl)-[1,1'-biphenyl]-2-yl)-2-(thiazol-2-yl)-3,6-dihydropyrimidin-4-yl)methyl)morpholine-3-carboxylic acid Ethyl 6-(bromomethyl)-4-(5-fluoro-3',5'-bis(trifluoromethyl)-[1,1'-biphenyl]-2-yl)-2-(thiazol-2-yl)-1,4-dihydropyrimidine-5-carboxylate (3.37 g, 5.3 mmol) was reacted with (S)-morpholine-3-carboxylic acid (0.69 g, 5.3 mmol) according to the procedure described in Example 1, Step C to give the title compound as a yellow solid (2.11 g, 58%). The compound was characterized by the following spectroscopic data:

MS-ESI: (ESI, pos. ion) m/z: 687.1 [M+1]$^+$;
$^1$H NMR (400 MHz, DMSO-d$_6$): δ 9.94 (br.s, 1H), 8.44 (s, 2H), 8.24 (s, 1H), 8.04 (d, 1H), 7.97 (d, 1H), 7.51-7.46 (m, 1H), 7.37-7.27 (m, 2H), 5.38 (s, 1H), 4.26-4.12 (m, 1H), 4.05-3.96 (m, 1H), 3.85-3.76 (m, 3H), 3.67-3.57 (m, 2H), 3.50-3.42 (m, 2H), 3.07-3.03 (m, 1H), 2.47-2.38 (m, 1H), 0.89 (t, 3H).

Example 58

2-(4-((6-(2-bromo-4-fluorophenyl)-5-(ethoxycarbonyl)-2-(thiazol-2-yl)-3,6-dihydropyrimidin-4-yl)methyl)morpholine-3-carboxamido)acetic acid

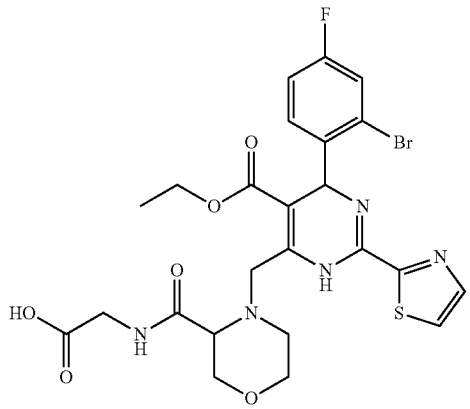 [SMILES: CCOC(=O)C1=C(CN2CCOCC2C(=O)NCC(=O)O)NC(c2nccs2)=NC1c1ccc(F)cc1Br]

Step A: Ethyl 4-(2-bromo-4-fluorophenyl)-6-((3-((2-ethoxy-2-oxoethyl)carbamoyl)morpholino)methyl)-2-(thiazol-2-yl)-1,4-dihydropyrimidine-5-carboxylate 4-((6-(2-bromo-4-fluorophenyl)-5-(ethoxycarbonyl)-2-(thiazol-2-yl)-3,6-dihydropyrimidin-4-yl)methyl)morpholine-3-carboxylic acid (0.5 g, 0.9 mmol) was reacted with ethyl 2-aminoacetate hydrochloride (0.15 g, 1.1 mmol) according to the procedure as described in Example 53 to give the title compound as a yellow solid (0.27 g, 47%). The compound was characterized by the following spectroscopic data:

MS-ESI: (ESI, pos. ion) m/z: 638.2 [M+1]⁺;
¹H NMR (400 MHz, CDCl₃): δ 7.89-7.84 (m, 1H), 7.54-7.46 (m, 1H), 7.39-7.30 (m, 2H), 7.07-6.92 (m, 1H), 6.22 (s, 1H), 4.45-4.18 (m, 2H), 4.16-4.03 (m, 6H), 4.01-3.81 (m, 3H), 3.78-3.50 (m, 1H), 3.42-3.36 (m, 1H), 3.08-2.85 (m, 1H), 2.75-2.51 (m, 1H), 1.31-1.23 (m, 3H), 1.17-1.13 (m, 3H).

Step B: 2-(4-((6-(2-bromo-4-fluorophenyl)-5-(ethoxycarbonyl)-2-(thiazol-2-yl)-3,6-dihydropyrimidin-4-yl)methyl)morpholine-3-carboxamido)acetic acid A mixture of ethyl 4-(2-bromo-4-fluorophenyl)-6-((3-((2-ethoxy-2-oxoethyl)carbamoyl)morpholino)methyl)-2-(thiazol-2-yl)-1,4-dihydropyrimidine-5-carboxylate (0.2 g, 0.31 mmol) and sodium hydroxide (0.13 g, 3.1 mmol) in ethanol (6 mL) and water (1 mL) was stirred at 25° C. for 20 minutes. The reaction solution was adjusted to pH 6-7 with con. HCl, and concentrated in vacuo. The residue was purified by a silica gel column chromatography (DCM/MeOH (V/V)=25/1) to give the title compound as a yellow solid (0.14 g, 74%). The compound was characterized by the following spectroscopic data:
MS-ESI: (ESI, pos. ion) m/z: 610.0 [M+1]⁺;
¹H NMR (400 MHz, DMSO-d₆): δ 12.41 (br.s, 1H), 9.94 (br.s, 1H), 8.60 (br.s, 1H), 8.04 (d, 1H), 7.93 (d, 1H), 7.57-7.54 (m, 1H), 7.38-7.33 (m, 1H), 7.25-7.21 (m, 1H), 5.99 (s, 1H), 4.16-3.96 (m, 2H), 3.94-3.84 (m, 2H), 3.82-3.71 (m, 3H), 3.60-3.51 (m, 2H), 3.39-3.35 (m, 2H), 2.99-2.77 (m, 1H), 2.46-2.40 (m, 1H), 1.07-1.02 (m, 3H).

Example 59

1-((6-(2-bromo-4-fluorophenyl)-5-(ethoxycarbonyl)-2-(thiazol-2-yl)-3,6-dihydropyrimidin-4-yl)methyl)-4-hydroxypyrrolidine-2-carboxylic acid

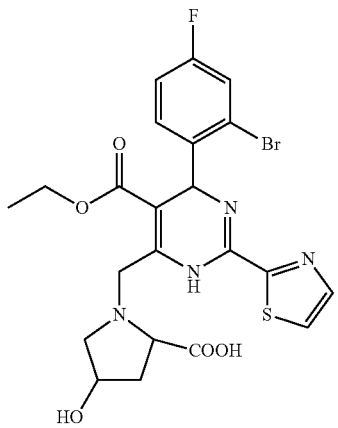 [SMILES: CCOC(=O)C1=C(CN2CC(O)CC2C(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (1.92 g, 3.81 mmol) was reacted with 4-hydroxypyrrolidine-2-carboxylic acid (0.5 g, 3.81 mmol) according to the procedure as described in Example 28 to give the title compound as a yellow solid (1.37 g, 65%). The compound was characterized by the following spectroscopic data:
MS-ESI: (ESI, pos. ion) m/z: 553.2 [M+1]⁺;
¹H NMR (400 MHz, DMSO-d₆): δ 12.41 (br.s, 1H), 9.86 (br.s, 1H), 7.99 (d, 1H), 7.92 (d, 1H), 7.59-7.54 (m, 1H), 7.45-7.35 (m, 1H), 7.28-7.20 (m, 1H), 6.02 (s, 1H), 5.09-5.01 (m, 1H), 4.40-4.30 (m, 3H), 3.99-3.94 (m, 3H), 3.76-3.66 (m, 1H), 2.07 (br.s, 2H), 1.06 (t, 3H).

Example 60

Ethyl 4-(2-bromo-4-fluorophenyl)-6-(((S)-3-(methoxy(methyl)carbamoyl)morpholino)methyl)-2-(thiazol-2-yl)-1,4-dihydropyrimidine-5-carboxylate

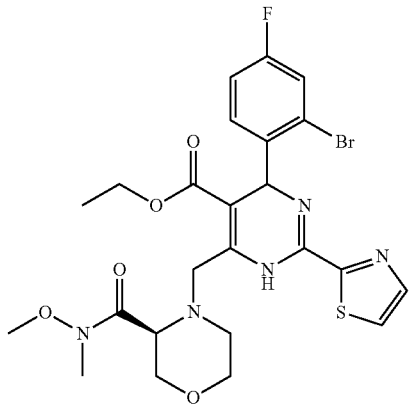 [SMILES: CCOC(=O)C1=C(CN2CCOC[C@H]2C(=O)N(C)OC)NC(c2nccs2)=NC1c1ccc(F)cc1Br]

(3S)-4-((6-(2-bromo-4-fluorophenyl)-5-(ethoxycarbonyl)-2-(thiazol-2-yl)-3,6-dihydropyrimidin-4-yl)methyl)morpholine-3-carboxylic acid (4 g, 7.2 mmol) was reacted with N,O-dimethylhydroxylamine hydrochloride (0.84 g, 8.64 mmol) according to the procedure as described in Example 53 to give the title compound as a yellow solid (1.5 g, 35%). The compound was characterized by the following spectroscopic data:
MS-ESI: (ESI, pos. ion) m/z: 596.0 [M+1]⁺;
¹H NMR (400 MHz, DMSO-d₆): δ 9.93 (br.s, 1H), 8.04 (d, 1H), 7.95 (d, 1H), 7.58-7.55 (m, 1H), 7.43-7.38 (m, 1H), 7.26-7.20 (m, 1H), 6.02 (s, 1H), 4.20-4.05 (m, 1H), 3.98-3.88 (m, 4H), 3.82-3.79 (m, 1H), 3.76 (s, 3H), 3.70-3.56 (m, 3H), 3.25-3.15 (m, 1H), 3.13 (s, 3H), 2.65-2.58 (m, 1H), 1.07 (t, 3H).

Example 61

(3S)-4-((6-(2-bromo-4-fluorophenyl)-5-(ethoxycarbonyl)-2-(4-(2-methoxy-2-oxoethyl)thiazol-2-yl)-3,6-dihydropyrimidin-4-yl)methyl)morpholine-3-carboxylic acid

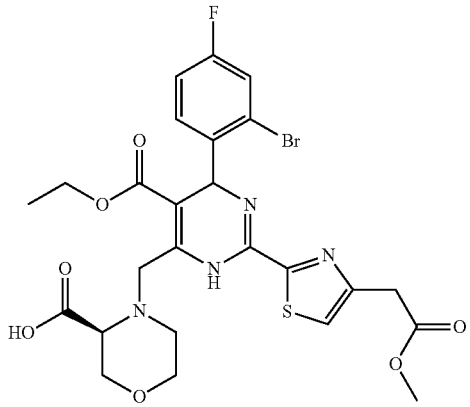 [SMILES: CCOC(=O)C1=C(CN2CCOC[C@H]2C(=O)O)NC(c2nc(CC(=O)OC)cs2)=NC1c1ccc(F)cc1Br]

Step A: Ethyl 2-(2-cyanothiazol-4-yl)acetate

To a mixture of tert-butyl nitrite (10 mL, 80 mmol) and CuCN (7.28 g, 80 mmol) in anhydrous acetonitrile (30 mL) was added a solution of ethyl 2-(2-aminothiazol-4-yl)acetate (7.5 g, 40 mmol) in anhydrous acetonitrile (20 mL) dropwise over a period of 1 hour at 50° C., then the mixture was stirred at the temperature for 2.5 hours. The mixture was concentrated in vacuo and the residue was purified by a silica gel column chromatography (PETROLEUM ETHER/EtOAc (V/V)=25/1) to give the title compound as yellowish liquid (2 g, 25%). The compound was characterized by the following spectroscopic data:

$^1$H NMR (400 MHz, DMSO-d$_6$): δ 4.01 (q, 2H), 3.72 (s, 2H), 1.16 (t, 3H).

Step B: Methyl 2-(2-carbamimidoylthiazol-4-yl)acetate hydrochloride

A mixture of ethyl 2-(2-cyanothiazol-4-yl)acetate (2.17 g, 11 mmol), sodium methylate (0.84 g, 15.5 mmol) and ammonium chloride (0.88 g, 16.5 mmol) in anhydrous methanol (50 mL) was stirred at 25° C. for 24 hours under N$_2$. The reaction mixture was filtered and the filtrate was concentrated in vacuo. Then to the residue was added acetone (12 mL). The mixture was stirred for 3 hours and filtered. The filter cake was washed with a little of acetone to give the title compound as a yellowish solid (1.63 g, 63%). The compound was characterized by the following spectroscopic data:

MS-ESI: (ESI, pos. ion) m/z: 200.1 [M+1]$^+$;

$^1$H NMR (400 MHz, D$_2$O): δ 6.76 (s, 1H), 3.77 (s, 3H), 3.68 (s, 2H).

Step C: Ethyl 4-(2-bromo-4-fluorophenyl)-2-(4-(2-methoxy-2-oxoethyl)thiazol-2-yl)-6-methyl-1,4-dihydropyrimidine-5-carboxylate Methyl 2-(2-carbamimidoylthiazol-4-yl)acetate hydrochloride (2.35 g, 10 mmol) was reacted with 2-bromo-4-fluorobenzaldehyde (2.03 g, 10 mmol) and ethyl 3-oxobutanoate (1.56 g, 12 mmol) according to the procedure as described in Example 1, Step A to give the title compound as a yellow solid (2.48 g, 50%). The compound was characterized by the following spectroscopic data:

MS-ESI: (ESI, pos. ion) m/z: 496.2 [M+1]$^+$;

$^1$H NMR (400 MHz, DMSO-d$_6$): δ 9.84 (br.s, 1H), 7.77 (s, 1H), 7.55-7.20 (m, 3H), 5.89 (s, 1H), 3.92 (q, 2H), 3.90 (s, 2H), 3.62 (s, 3H), 2.47 (s, 3H), 1.03 (t, 3H).

Step D: Ethyl 4-(2-bromo-4-fluorophenyl)-6-(bromomethyl)-2-(4-(2-methoxy-2-oxoethyl)thiazol-2-yl)-1,4-dihydropyrimidine-5-carboxylate Ethyl 4-(2-bromo-4-fluorophenyl)-2-(4-(2-methoxy-2-oxoethyl)thiazol-2-yl)-6-methyl-1,4-dihydropyrimidine-5-carboxylate (1 g, 2 mmol) was reacted with NBS (0.39 g, 2.2 mmol) according to the procedure as described in Example 1, Step B to give the title compound as a yellow solid (0.81 g, 70%). The compound was characterized by the following spectroscopic data:

MS-ESI: (ESI, pos. ion) m/z: 574.1 [M+1]$^+$;

$^1$H NMR (400 MHz, DMSO-d$_6$): δ 9.88 (br.s, 1H), 7.78 (s, 1H), 7.56-7.23 (m, 3H), 6.01 (s, 1H), 4.68 (dd, 2H), 3.98 (q, 2H), 3.91 (s, 2H), 3.62 (s, 3H), 1.06 (t, 3H).

Step E: (3S)-4-((6-(2-bromo-4-fluorophenyl)-5-(ethoxycarbonyl)-2-(4-(2-methoxy-2-oxoethyl)thiazol-2-yl)-3,6-dihydropyrimidin-4-yl)methyl)morpholine-3-carboxylic acid Ethyl 4-(2-bromo-4-fluorophenyl)-6-(bromomethyl)-2-(4-(2-methoxy-2-oxoethyl)thiazol-2-yl)-1,4-dihydropyrimidine-5-carboxylate (1.15 g, 2 mmol) was reacted with (S)-morpholine-3-carboxylic acid (0.39 g, 3 mmol) according to the procedure as described in Example 1, Step C to give the title compound as a yellow solid (0.75 g, 60%). The compound was characterized by the following spectroscopic data:

MS-ESI: (ESI, pos. ion) m/z: 625.0 [M+1]$^+$;

$^1$H NMR (400 MHz, DMSO-d$_6$): δ 9.93 (br.s, 1H), 7.72 (s, 1H), 7.56-7.54 (m, 1H), 7.43-7.37 (m, 1H), 7.21-7.17 (m, 1H), 6.02 (br.s, 1H), 4.37-4.09 (m, 2H), 4.06-3.94 (m, 3H), 3.91 (s, 2H), 3.83-3.74 (m, 2H), 3.65 (s, 3H), 3.55-3.49 (m, 2H), 3.11-3.08 (m, 1H), 2.50-2.34 (m, 1H), 1.06 (t, 3H).

Example 62

(3S)-4-((6-(2-bromo-4-fluorophenyl)-5-(ethoxycarbonyl)-2-(4-(2-(methylamino)-2-oxoethyl)thiazol-2-yl)-3,6-dihydropyrimidin-4-yl)methyl)morpholine-3-carboxylic acid

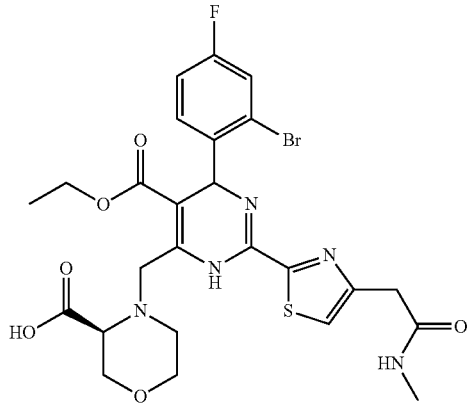 [SMILES: CCOC(=O)C1=C(CN2CCOC[C@H]2C(=O)O)NC(c2nc(CC(=O)NC)cs2)=NC1c1ccc(F)cc1Br]

Step A: 2-(2-(4-(2-bromo-4-fluorophenyl)-5-(ethoxycarbonyl)-6-methyl-1,4-dihydropyrimidin-2-yl)thiazol-4-yl)acetic acid Ethyl 4-(2-bromo-4-fluorophenyl)-2-(4-(2-methoxy-2-oxoethyl)thiazol-2-yl)-6-methyl-1,4-dihydropyrimidine-5-carboxylate (1 g, 2 mmol) was reacted with sodium hydroxide (0.24 g, 6 mmol) according to the procedure as described Example 58, Step B to give the title compound as a yellow solid (0.87 g, 90%). The compound was characterized by the following spectroscopic data:

MS-ESI: (ESI, pos. ion) m/z: 482.0 [M+1]$^+$;

$^1$H NMR (400 MHz, DMSO-d$_6$): δ 9.87 (br.s, 1H), 7.79 (s, 1H), 7.53-7.21 (m, 3H), 5.99 (s, 1H), 4.01 (q, 2H), 3.92 (s, 2H), 2.49 (s, 3H), 1.08 (t, 3H).

Step B: Ethyl 4-(2-bromo-4-fluorophenyl)-6-methyl-2-(4-(2-(methylamino)-2-oxoethyl)thiazol-2-yl)-1,4-dihydropyrimidine-5-carboxylate A solution of 2-(2-(4-(2-bromo-4-fluorophenyl)-5-(ethoxycarbonyl)-6-methyl-1,4-dihydropyrimidin-2-yl)thiazol-4-yl)acetic acid (3 g, 6.2 mmol), EDC.HCl (1.55 g, 8.06 mmol), HOAt (0.84 g, 6.2 mmol) and DIPEA (1.6 g, 12.4 mmol) in DMF (60 mL) was cooled to 10° C. and then stirred at −10° C. for 30 minutes. Then methanamine hydrochloride (0.63 g, 9.3 mmol) was added and the mixture was stirred for another 1 hour. The mixture was warmed to 50° C. and stirred for 4 hours. The reaction solution was diluted with EtOAc (150 mL), and washed with brine (100 mL×6). The organic layer was dried over $Na_2SO_4$, and concentrated in vacuo. The residue was purified by a silica gel column chromatography (PETROLEUM ETHER/EtOAc (V/V)=3/1) to give the title compound as a yellow solid (1.2 g, 39%). The compound was characterized by the following spectroscopic data:

MS-ESI: (ESI, pos. ion) m/z: 496.2 [M+1]$^+$;
$^1$H NMR (400 MHz, DMSO-$d_6$): δ 9.84 (br.s, 1H), 7.77 (s, 1H), 7.55-7.20 (m, 3H), 5.89 (s, 1H), 3.92 (q, 2H), 3.90 (s, 2H), 3.51 (s, 3H), 2.44 (s, 3H), 1.08 (t, 3H).

Step C: Ethyl 4-(2-bromo-4-fluorophenyl)-6-(bromomethyl)-2-(4-(2-(methylamino)-2-oxoethyl)thiazol-2-yl)-1,4-dihydropyrimidine-5-carboxylate Ethyl 4-(2-bromo-4-fluorophenyl)-6-methyl-2-(4-(2-(methylamino)-2-oxoethyl)thiazol-2-yl)-1,4-dihydropyrimidine-5-carboxylate (1 g, 2 mmol) was reacted with NBS (0.39 g, 2.2 mmol) according to the procedure as described in Example 1, Step B to give the title compound as a yellow solid (0.63 g, 55%). The compound was characterized by the following spectroscopic data:

MS-ESI: (ESI, pos. ion) m/z: 573.0 [M+1]$^+$;
$^1$H NMR (400 MHz, DMSO-$d_6$): δ 9.83 (br.s, 1H), 7.79 (s, 1H), 7.56-7.21 (m, 3H), 6.04 (s, 1H), 4.65 (dd, 2H), 3.99 (q, 2H), 3.90 (s, 2H), 3.52 (s, 3H), 1.07 (t, 3H).

Step D: (3S)-4-((6-(2-bromo-4-fluorophenyl)-5-(ethoxycarbonyl)-2-(4-(2-(methylamino)-2-oxoethyl)thiazol-2-yl)-3,6-dihydropyrimidin-4-yl)methyl)morpholine-3-carboxylic acid Ethyl 4-(2-bromo-4-fluorophenyl)-6-(bromomethyl)-2-(4-(2-(methylamino)-2-oxoethyl)thiazol-2-yl)-1,4-dihydropyrimidine-5-carboxylate (1.15 g, 2 mmol) was reacted with (S)-morpholine-3-carboxylic acid (0.39 g, 3 mmol) according to the procedure as described in Example 1, Step C to give the title compound as a yellow solid (0.66 g, 53%). The compound was characterized by the following spectroscopic data:

MS-ESI: (ESI, pos. ion) m/z: 624.1 [M+1]$^+$;
$^1$H NMR (400 MHz, DMSO-$d_6$): δ 12.86 (br.s, 1H), 9.93 (br.s, 1H), 7.76 (s, 1H), 7.56-7.47 (m, 1H), 7.43-7.35 (m, 1H), 7.21-7.15 (m, 1H), 6.02 (s, 1H), 4.37-4.11 (m, 2H), 4.06-3.96 (m, 3H), 3.91 (s, 2H), 3.85-3.74 (m, 2H), 3.56 (s, 3H), 3.54-3.45 (m, 2H), 3.11-3.08 (m, 1H), 2.50-2.38 (m, 1H), 1.06 (t, 3H).

Example 63

4-((6-(2-bromo-4-fluorophenyl)-5-(ethoxycarbonyl)-2-(4-(2-(isopropylamino)-2-oxoethyl)thiazol-2-yl)-3,6-dihydropyrimidin-4-yl)methyl)morpholine-3-carboxylic acid

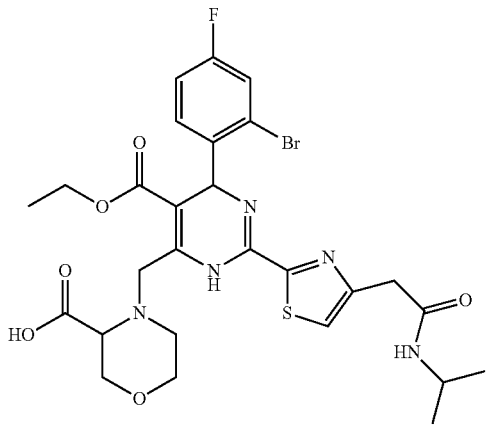 [SMILES: CCOC(=O)C1=C(CN2CCOCC2C(=O)O)NC(c2nc(CC(=O)NC(C)C)cs2)=NC1c1ccc(F)cc1Br]

Step A: Ethyl 4-(2-bromo-4-fluorophenyl)-2-(4-(2-(isopropylamino)-2-oxoethyl)thiazol-2-yl)-6-methyl-1,4-dihydropyrimidine-5-carboxylate 2-(2-(4-(2-bromo-4-fluorophenyl)-5-(ethoxycarbonyl)-6-methyl-1,4-dihydropyrimidin-2-yl)thiazol-4-yl)acetic acid (3 g, 6.2 mmol) was reacted with isopropylamine (0.55 g, 9.3 mmol) according to the procedure as described in Example 62, Step B to give the title compound as a yellow solid (1.46 g, 45%). The compound was characterized by the following spectroscopic data:

MS-ESI: (ESI, pos. ion) m/z: 523.1 [M+1]$^+$;
$^1$H NMR (400 MHz, DMSO-$d_6$): δ 9.88 (br.s, 1H), 7.75 (s, 1H), 7.51-7.20 (m, 3H), 5.92 (s, 1H), 4.01 (q, 2H), 3.90 (s, 2H), 3.86-3.82 (m, 1H), 2.49 (s, 3H), 1.08 (t, 3H), 0.97-0.89 (m, 6H).

Step B: Ethyl 4-(2-bromo-4-fluorophenyl)-6-(bromomethyl)-2-(4-(2-(isopropylamino)-2-oxoethyl)thiazol-2-yl)-1,4-dihydropyrimidine-5-carboxylate Ethyl 4-(2-bromo-4-fluorophenyl)-2-(4-(2-(isopropylamino)-2-oxoethyl)thiazol-2-yl)-6-methyl-1,4-dihydropyrimidine-5-carboxylate (1.05 g, 2 mmol) was reacted with NBS (0.39 g, 2.2 mmol) according to the procedure as described in Example 1, Step B to give the title compound as a yellow solid (0.6 g, 50%). The compound was characterized by the following spectroscopic data:

MS-ESI: (ESI, pos. ion) m/z: 601.0 [M+1]$^+$;
$^1$H NMR (400 MHz, DMSO-$d_6$): δ 9.88 (br.s, 1H), 7.76 (s, 1H), 7.51-7.24 (m, 3H), 6.01 (s, 1H), 4.68-4.57 (m, 2H), 4.06 (q, 2H), 3.94 (s, 2H), 3.85-3.80 (m, 1H), 1.05 (t, 3H), 0.97-0.84 (m, 6H).

Step C: 4-((6-(2-bromo-4-fluorophenyl)-5-(ethoxycarbonyl)-2-(4-(2-(isopropylamino)-2-oxoethyl)thiazol-2-yl)-3,6-dihydropyrimidin-4-yl)methyl)morpholine-3-carboxylic acid Ethyl 4-(2-bromo-4-fluorophenyl)-6-(bromomethyl)-2-(4-(2-(isopropylamino)-2-oxo ethyl)thiazol-2-yl)-1,4-dihydropyrimidine-5-carboxylate (1.2 g, 2 mmol) was reacted with morpholine-3-carboxylic acid (0.39 g, 3 mmol) according to the procedure as described in Example 1, Step C to give the title compound as a yellow solid (0.64 g, 49%). The compound was characterized by the following spectroscopic data:

MS-ESI: (ESI, pos. ion) m/z: 652.2 [M+1]$^+$;

$^1$H NMR (400 MHz, DMSO-d$_6$): δ 12.83 (br.s, 1H), 9.96 (br.s, 1H), 7.78 (s, 1H), 7.56-7.46 (m, 1H), 7.45-7.35 (m, 1H), 7.21-7.15 (m, 1H), 6.05 (s, 1H), 4.38-4.12 (m, 2H), 4.09-3.94 (m, 3H), 3.93 (s, 2H), 3.89-3.75 (m, 3H), 3.50-3.45 (m, 2H), 3.12-3.08 (m, 1H), 2.53-2.38 (m, 1H), 1.06 (t, 3H), 0.95-0.83 (m, 6H).

Example 64

Ethyl 4-(2-bromo-4-fluorophenyl)-6-((2-((2-hydroxyethyl)carbamoyl)morpholino)methyl)-2-(thiazol-2-yl)-1,4-dihydropyrimidine-5-carboxylate

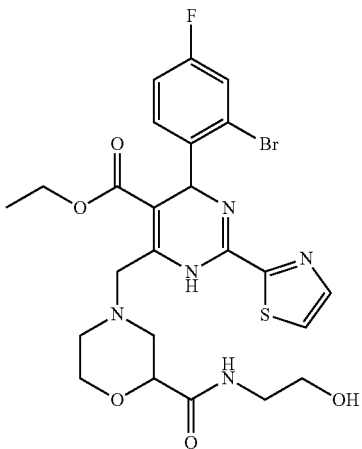 [SMILES: CCOC(=O)C1=C(CN2CCOC(C(=O)NCCO)C2)NC(c2nccs2)=NC1c1ccc(F)cc1Br]

4-((6-(2-bromo-4-fluorophenyl)-5-(ethoxycarbonyl)-2-(thiazol-2-yl)-3,6-dihydropyrimidin-4-yl)methyl)morpholine-2-carboxylic acid (0.5 g, 0.9 mmol) was reacted with 2-aminoethanol (72 mg, 1.2 mmol) according to the procedure as described in Example 53 to give the title compound as a yellow solid (0.32 g, 60%). The compound was characterized by the following spectroscopic data:

MS-ESI: (ESI, pos. ion) m/z: 596.1 [M+1]$^+$;

$^1$H NMR (400 MHz, DMSO-d$_6$): δ 9.63 (s, 1H), 8.01 (d, 1H), 7.95 (d, 1H), 7.59-7.56 (m, 1H), 7.42-7.38 (m, 1H), 7.25-7.19 (m, 1H), 6.03 (s, 1H), 4.72-4.68 (m, 1H), 4.03-3.92 (m, 5H), 3.71-3.61 (m, 1H), 3.43-3.39 (m, 2H), 3.17-3.14 (m, 2H), 2.99-2.81 (m, 1H), 2.67-2.39 (m, 1H), 2.34-2.21 (m, 2H), 1.05 (t, 3H).

Example 65

2-(4-((6-(2-bromo-4-fluorophenyl)-5-(ethoxycarbonyl)-2-(thiazol-2-yl)-3,6-dihydropyrimidin-4-yl)methyl)morpholine-2-carboxamido)acetic acid

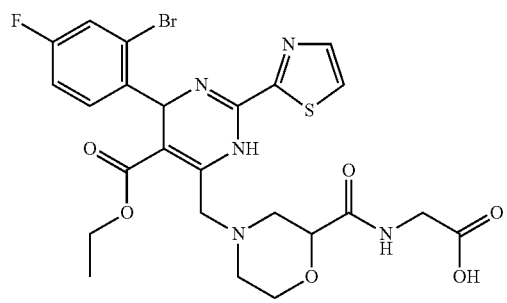 [SMILES: CCOC(=O)C1=C(CN2CCOC(C(=O)NCC(=O)O)C2)NC(c2nccs2)=NC1c1ccc(F)cc1Br]

Step A: Ethyl 4-(2-bromo-4-fluorophenyl)-6-((2-((2-ethoxy-2-oxoethyl)carbamoyl)morpholino)methyl)-2-(thiazol-2-yl)-1,4-dihydropyrimidine-5-carboxylate 4-((6-(2-bromo-4-fluorophenyl)-5-(ethoxycarbonyl)-2-(thiazol-2-yl)-3,6-dihydropyrimidin-4-yl)methyl)morpholine-2-carboxylic acid (0.8 g, 1.45 mmol) was reacted with ethyl 2-aminoacetate hydrochloride (0.31 g, 2.17 mmol) according to the procedure as described in Example 53 to give the title compound as a yellow solid (0.76 g, 82%). The compound was characterized by the following spectroscopic data:

MS-ESI: (ESI, pos. ion) m/z: 638.2 [M+1]$^+$;

$^1$H NMR (400 MHz, DMSO-d$_6$): δ 9.62 (br.s, 1H), 8.19 (br.s, 1H), 8.02 (d, 1H), 7.95 (d, 1H), 7.59 (dd, 1H), 7.42-7.39 (m, 1H), 7.25-7.19 (m, 1H), 6.04 (s, 1H), 4.12-4.07 (m, 2H), 4.06-4.03 (m, 1H), 4.02-3.99 (m, 2H), 3.98-3.89 (m, 3H), 3.83 (t, 2H), 3.73-3.64 (m, 1H), 3.17-2.97 (m, 1H), 2.86-2.69 (m, 1H), 2.46-2.22 (m, 2H), 1.21-1.16 (m, 3H), 1.06 (t, 3H).

Step B: 2-(4-((6-(2-bromo-4-fluorophenyl)-5-(ethoxycarbonyl)-2-(thiazol-2-yl)-3,6-dihydropyrimidin-4-yl)methyl)morpholine-2-carboxamido)acetic acid Ethyl 4-(2-bromo-4-fluorophenyl)-6-((2-((2-ethoxy-2-oxoethyl)carbamoyl)morpholino)methyl)-2-(thiazol-2-yl)-1,4-dihydropyrimidine-5-carboxylate (0.5 g, 0.8 mmol) was reacted with sodium hydroxide (0.32 g, 8 mmol) according to the procedure as described in Example 58, Step B to give the title compound as a yellow solid (0.43 g, 88%). The compound was characterized by the following spectroscopic data:

MS-ESI: (ESI, pos. ion) m/z: 610.2 [M+1]$^+$;

$^1$H NMR (400 MHz, DMSO-d$_6$): δ 12.27 (br.s, 1H), 9.63 (s, 1H), 8.01 (d, 1H), 7.95 (d, 1H), 7.58-7.56 (m, 1H), 7.42-7.39 (m, 1H), 7.25-7.20 (m, 1H), 6.04 (s, 1H), 4.06-3.89 (m, 6H), 3.77-3.64 (m, 3H), 3.17-2.98 (m, 1H), 2.86-2.69 (m, 1H), 2.46-2.22 (m, 2H), 1.06 (t, 3H).

Example 66

Ethyl 4-(2-bromo-4-fluorophenyl)-6-(((S)-2-(hydroxymethyl)morpholino)methyl)-2-(thiazol-2-yl)-1,4-dihydropyrimidine-5-carboxylate

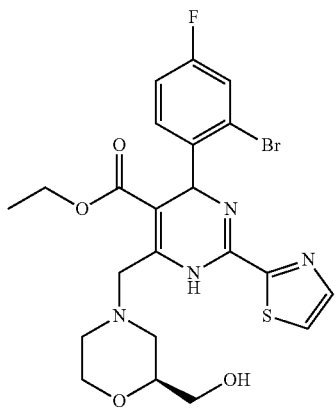

Ethyl 4-(2-bromo-4-fluorophenyl)-6-(bromomethyl)-2-(thiazol-2-yl)-1,4-dihydropyrimidine-5-carboxylate (1 g, 2 mmol) was reacted with (S)-morpholin-2-ylmethanol hydrochloride (0.34 g, 2.2 mmol) according to the procedure as described in Example 25, Step B to give the title compound as a yellow solid (0.25 g, 23%). The compound was characterized by the following spectroscopic data:

MS-ESI: (ESI, pos. ion) m/z: 539.1 [M+1]$^+$;

$^1$H NMR (400 MHz, CDCl$_3$): δ 9.66 (d, 1H), 8.01 (d, 1H), 7.94 (d, 1H), 7.56-7.48 (m, 1H), 7.40-7.32 (m, 1H), 7.20-7.13 (m, 1H), 6.02 (s, 1H), 3.98-3.34 (m, 7H), 2.95-2.62 (m, 4H), 2.45-2.00 (m, 2H), 1.05 (t, 3H).

Example 67

2-((4-((6-(2-bromo-4-fluorophenyl)-5-(ethoxycarbonyl)-2-(thiazol-2-yl)-3,6-dihydropyrimidin-4-yl)methyl)morpholin-3-yl)methyl)-3-ethoxy-3-oxopropanoic acid

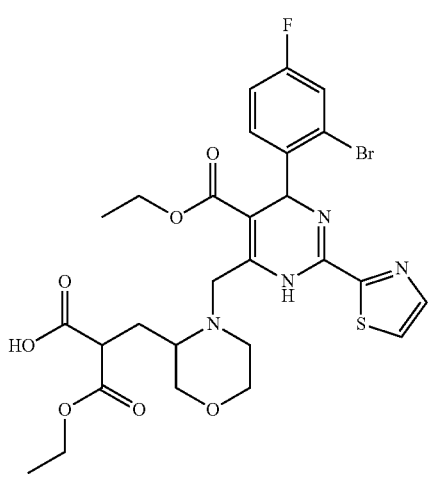 [SMILES: CCOC(=O)C1=C(CN2CCOCC2CC(C(=O)O)C(=O)OCC)NC(c2nccs2)=NC1c1ccc(F)cc1Br]

Step A: Diethyl 2-((4-benzylmorpholin-3-yl)methyl)malonate

Diethyl malonate (1.78 g, 11.1 mmol), DMF (25 mL), sodium hydroxide (0.22 g, 5.55 mmol) and 4-benzyl-3-(bromomethyl)morpholine (1 g, 3.7 mmol) (The compound was synthesized according to the procedure as described in Helvetica Chimica Acta, 87, 2004) were added to a dried flask in turn. The mixture was stirred at 80° C. for 4 hours under N$_2$, and cooled to 25° C. The reaction mixture was diluted with EtOAc (200 mL). The organic layer was washed with brine (100 mL×6), dried over unhydrous Na$_2$SO$_4$. The crude product was purified by a silica gel column chromatography (PETROLEUM ETHER/EtOAc (V/V)=15/1) to give the title compound as colorless oil (1.15 g, 89%). The compound was characterized by the following spectroscopic data:

MS-ESI: (ESI, pos. ion) m/z: 350.3 [M+1]$^+$;

$^1$H NMR (400 MHz, CDCl$_3$): δ 7.35-7.24 (m, 5H), 4.20-4.15 (m, 4H), 4.04 (d, 1H), 3.81-3.79 (m, 1H), 3.70-3.68 (m, 1H), 3.60-3.54 (m, 2H), 3.46-3.43 (m, 1H), 3.35 (d, 1H), 2.74-2.71 (m, 1H), 2.51 (br.s, 1H), 2.39-2.35 (m, 1H), 2.26 (m, 1H), 2.20-2.15 (m, 1H), 1.29-1.25 (m, 6H).

Step B: Diethyl 2-(morpholin-3-ylmethyl)malonate

Diethyl 2-((4-benzylmorpholin-3-yl)methyl)malonate (1 g, 2.86 mmol) was reacted with Pd/C (10%, 0.1 g) according to the procedure as described in Example 34, Step C to give the title compound as colorless oil (0.66 g, 89%). The compound was characterized by the following spectroscopic data:

MS-ESI: (ESI, pos. ion) m/z: 260.2 [M+1]$^+$;

$^1$H NMR (400 MHz, DMSO-d$_6$): δ 4.17-4.06 (m, 4H), 4.01-3.66 (m, 2H), 3.55-3.42 (m, 2H), 3.31-3.15 (m, 1H), 3.08-2.87 (m, 2H), 2.54-2.50 (m, 1H), 2.47-2.23 (m, 1H), 1.86-1.69 (m, 1H), 1.23-1.16 (m, 6H).

Step C: Diethyl 2-((4-((6-(2-bromo-4-fluorophenyl)-5-(ethoxycarbonyl)-2-(thiazol-2-yl)-3,6-dihydropyrimidin-4-yl)methyl)morpholin-3-yl)methyl)malonate Ethyl 4-(2-bromo-4-fluorophenyl)-6-(bromomethyl)-2-(thiazol-2-yl)-1,4-dihydropyrimidine-5-carboxylate (0.77 g, 1.53 mmol) was reacted with diethyl 2-(morpholin-3-ylmethyl)malonate (0.4 g, 1.53 mmol) according to the procedure as described in Example 24 to give the title compound as a pale yellow solid (0.32 g, 47%). The compound was characterized by the following spectroscopic data:

MS-ESI: (ESI, pos. ion) m/z: 681.1 [M+1]$^+$;

$^1$H NMR (400 MHz, DMSO-d$_6$): δ 9.67 (br.s, 1H), 8.01 (d, 1H), 7.95 (d, 1H), 7.58-7.56 (m, 1H), 7.42-7.37 (m, 1H), 7.24-7.18 (m, 1H), 6.04 (m, 1H), 4.25-4.04 (m, 5H), 4.02-3.89 (m, 4H), 3.72-3.60 (m, 4H), 2.96-2.62 (m, 5H), 1.17-1.04 (m, 9H).

Step D: 2-((4-((6-(2-bromo-4-fluorophenyl)-5-(ethoxycarbonyl)-2-(thiazol-2-yl)-3,6-dihydropyrimidin-4-yl)methyl)morpholin-3-yl)methyl)-3-ethoxy-3-oxopropanoic acid Diethyl 2-((4-(((6-(2-bromo-4-fluorophenyl)-5-(ethoxycarbonyl)-2-(thiazol-2-yl)-3,6-dihydropyrimidin-4-yl)methyl)morpholin-3-yl)methyl)malonate (0.3 g, 0.44 mmol), anhydrous ethanol (6 mL) and a solution of sodium hydroxide (17.6 mg, 0.44 mmol) in water (1 mL) were added to a dried flask in turn, then the mixture was stirred at 25° C. for 4 hours. The mixture was concentrated in vacuo and the residue was purified by a silica gel column chromatography (DCM/

MeOH (V/V)=25/1) to give the title compound as a yellow solid (0.22 g, 75%). The compound was characterized by the following spectroscopic data:

MS-ESI: (ESI, pos. ion) m/z: 653.1 [M+1]$^+$;

$^1$H NMR (400 MHz, DMSO-d$_6$): δ 13.03 (br.s, 1H), 9.72 (br.s, 1H), 8.07 (d, 1H), 7.94 (d, 1H), 7.58-7.55 (m, 1H), 7.41-7.38 (m, 1H), 7.25-7.21 (m, 1H), 6.02 (s, 1H), 4.23-4.10 (m, 2H), 4.04-3.87 (m, 5H), 3.75-3.59 (m, 3H), 2.97-2.90 (m, 1H), 2.81-2.66 (m, 3H), 2.60 (br.s, 1H), 1.18-1.04 (m, 6H).

Example 68

Ethyl 4-(2-bromo-4-fluorophenyl)-6-((3-(3-hydroxy-2-(hydroxymethyl)propyl)morpholino)methyl)-2-(thiazol-2-yl)-1,4-dihydropyrimidine-5-carboxylate

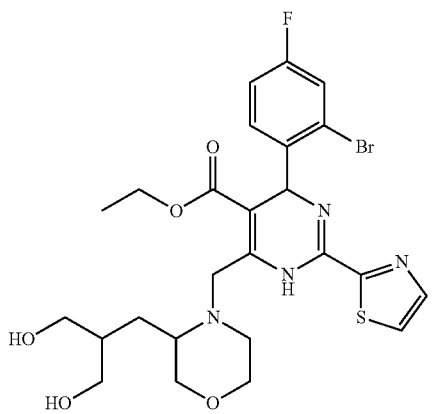 [SMILES: CCOC(=O)C1=C(CN2CCOCC2CC(CO)CO)NC(c2nccs2)=NC1c1ccc(F)cc1Br]

Step A:
2-((4-benzylmorpholin-3-yl)methyl)propane-1,3-diol

LiAlH$_4$ (0.35 g, 9.32 mmol) in a dried flask was cooled to 0° C., and then anhydrous THF (15 mL) was added. The mixture was stirred thoroughly and a solution of diethyl 2-((4-benzylmorpholin-3-yl)methyl)malonate (0.93 g, 2.66 mmol) in anhydrous THF (5 mL) was added, then the mixture was stirred at 70° C. for 6 hours and cooled to 30° C. To the reaction mixture were added water (0.5 mL), sodium hydroxide aqueous solution (10%, 0.5 mL) and water (3 mL) in turn, then the mixture was stirred at 25° C. for 10 minutes and filtered. The filtrate was concentrated in vacuo and the residue was purified by a silica gel column chromatography (PETROLEUM ETHER/EtOAc (V/V)=3/1) to give the title compound as colorless oil (0.38 g, 54%). The compound was characterized by the following spectroscopic data:

MS-ESI: (ESI, pos. ion) m/z: 266.3 [M+1]$^+$;

$^1$H NMR (400 MHz, CDCl$_3$): δ 7.33-7.29 (m, 5H), 4.25 (d, 1H), 3.85-3.83 (m, 1H), 3.76-3.59 (m, 7H), 3.33 (d, 1H), 2.77-2.74 (m, 1H), 2.66 (br.s, 1H), 2.31-2.27 (m, 1H), 1.93-1.89 (m, 1H), 1.84-1.80 (m, 1H), 1.74-1.69 (m, 2H).

Step B: 2-(morpholin-3-ylmethyl)propane-1,3-diol 2-((4-benzylmorpholin-3-yl)methyl)propane-1,3-diol (0.18 g, 0.68 mmol) was reacted with Pd/C (10%, 25 mg) according to the procedure as described in Example 34, Step C to give the title compound as colorless oil (0.1 g, 83%). The compound was characterized by the following spectroscopic data:

MS-ESI: (ESI, pos. ion) m/z: 176.3 [M+1]$^+$;

$^1$H NMR (400 MHz, CH$_3$OH-d$_4$): δ 4.38-4.18 (m, 1H), 4.14-3.91 (m, 2H), 3.74-3.57 (m, 5H), 3.55-3.50 (m, 1H), 3.45-3.36 (m, 2H), 3.25 (br.s, 1H), 3.13-3.07 (m, 1H), 2.99-2.83 (m, 1H), 2.17-2.14 (m, 1H), 1.77-1.61 (m, 2H).

Step C: Ethyl 4-(2-bromo-4-fluorophenyl)-6-((3-(3-hydroxy-2-(hydroxymethyl)propyl)morpholino)methyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (0.34 g, 0.68 mmol) was reacted with 2-(morpholin-3-ylmethyl)propane-1,3-diol (0.12 g, 0.68 mmol) according to the procedure as described in Example 25, Step B to give the title compound as a yellow solid (0.18 g, 44%). The compound was characterized by the following spectroscopic data:

MS-ESI: (ESI, pos. ion) m/z: 597.2 [M+1]$^+$;

$^1$H NMR (400 MHz, DMSO-d$_6$): δ 9.86 (br.s, 1H), 8.03 (d, 1H), 7.95 (d, 1H), 7.58-7.55 (m, 1H), 7.39-7.36 (m, 1H), 7.23-7.17 (m, 1H), 6.02 (s, 1H), 4.45-4.36 (m, 2H), 4.20-4.13 (m, 1H), 3.99 (q, 2H), 3.89-3.79 (m, 2H), 3.75-3.68 (m, 1H), 3.64-3.57 (m, 1H), 3.46-3.35 (m, 3H), 3.26-3.21 (m, 1H), 2.82-2.62 (m, 2H), 1.54-1.30 (m, 3H), 1.07 (t, 3H).

Example 69

4-((6-(2-bromo-4-fluorophenyl)-5-(ethoxycarbonyl)-2-(5-methyl-1,3,4-thiadiazol-2-yl)-3,6-dihydropyrimidin-4-yl)methyl)morpholine-3-carboxylic acid

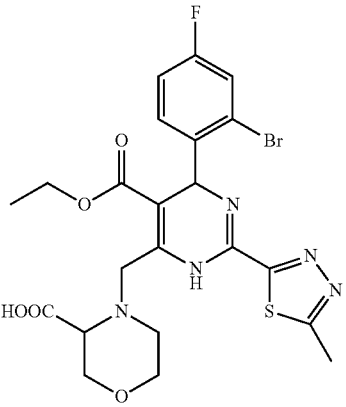 [SMILES: CCOC(=O)C1=C(CN2CCOCC2C(=O)O)NC(c2nnc(C)s2)=NC1c1ccc(F)cc1Br]

Step A: 5-methyl-1,3,4-thiadiazole-2-carbonitrile 5-methyl-1,3,4-thiadiazol-2-amine (11.5 g, 100 mmol) was reacted with CuCN (10.75 g, 120 mmol) according to the procedure as described in Example 61, Step A to give the title compound as a white solid (1.6 g, 13%). The compound was characterized by the following spectroscopic data:

MS-ESI: (ESI, pos. ion) m/z: 126.2 [M+1]$^+$;

$^1$H NMR (400 MHz, CDCl$_3$): δ 2.94 (s, 3H).

Step B:
5-methyl-1,3,4-thiadiazole-2-carboximidamide hydrochloride 5-methyl-1,3,4-thiadiazole-2-carbonitrile (1.25 g, 10 mmol) was reacted with sodium methoxide (0.54 g, 10 mmol)

and ammonium chloride (0.64 g, 12 mmol) according to the procedure as described in Example 61, Step B to give the title compound as a yellowish solid (1.25 g, 70%). The compound was characterized by the following spectroscopic data:

MS-ESI: (ESI, pos. ion) m/z: 143.1 [M+1]$^+$;
$^1$H NMR (400 MHz, D$_2$O): δ 2.99 (s, 3H).

Step C: Ethyl 4-(2-bromo-4-fluorophenyl)-6-methyl-2-(5-methyl-1,3,4-thiadiazol-2-yl)-1,4-dihydropyrimidine-5-carboxylate 5-methyl-1,3,4-thiadiazole-2-carboximidamide hydrochloride (1.8 g, 10 mmol) was reacted with 2-bromo-4-fluorobenzaldehyde (2.03 g, 10 mmol) and ethyl 3-oxobutanoate (1.56 g, 12 mmol) according to the procedure as described in Example 1, Step A to give the title compound as a yellow solid (1.0 g, 25%). The compound was characterized by the following spectroscopic data:

MS-ESI: (ESI, pos. ion) m/z: 440.9 [M+1]$^+$;
$^1$H NMR (400 MHz, DMSO-d$_6$): δ 10.24 (br.s, 1H), 7.56-7.21 (m, 3H), 5.98 (s, 1H), 3.93 (q, 2H), 2.72 (s, 3H), 2.46 (s, 3H), 1.10 (t, 3H).

Step D: Ethyl 4-(2-bromo-4-fluorophenyl)-6-(bromomethyl)-2-(5-methyl-1,3,4-thiadiazol-2-yl)-1,4-dihydropyrimidine-5-carboxylate Ethyl 4-(2-bromo-4-fluorophenyl)-6-methyl-2-(5-methyl-1,3,4-thiadiazol-2-yl)-1,4-dihydropyrimidine-5-carboxylate (0.88 g, 2 mmol) was reacted with NBS (0.36 g, 2 mmol) according to the procedure as described in Example 1, Step B to give the title compound as a yellow solid (0.73 g, 70%). The compound was characterized by the following spectroscopic data:

MS-ESI: (ESI, pos. ion) m/z: 517.2 [M+1]$^+$;
$^1$H NMR (400 MHz, DMSO-d$_6$): δ 10.25 (br.s, 1H), 7.57-7.20 (m, 3H), 6.01 (s, 1H), 4.65-4.43 (m, 2H), 3.92 (q, 2H), 2.78 (s, 3H), 1.08 (t, 3H).

Step E: 4-((6-(2-bromo-4-fluorophenyl)-5-(ethoxycarbonyl)-2-(5-methyl-1,3,4-thiadiazol-2-yl)-3,6-dihydropyrimidin-4-yl)methyl)morpholine-3-carboxylic acid Ethyl 4-(2-bromo-4-fluorophenyl)-6-(bromomethyl)-2-(5-methyl-1,3,4-thiadiazol-2-yl)-1,4-dihydropyrimidine-5-carboxylate (1.04 g, 2 mmol) was reacted with morpholine-3-carboxylic acid (0.26 g, 2 mmol) according to the procedure as described in Example 1, Step C to give the title compound as a yellow solid (0.63 g, 55%). The compound was characterized by the following spectroscopic data:

MS-ESI: (ESI, pos. ion) m/z: 568.1 [M+1]$^+$;
$^1$H NMR (400 MHz, CDCl$_3$): δ 9.85 (br.s, 1H), 7.33-6.98 (m, 3H), 6.18 (s, 1H), 4.11-4.09 (m, 2H), 4.06 (q, 2H), 4.02-4.01 (m, 1H), 3.95-3.88 (m, 1H), 3.83-3.65 (m, 3H), 3.58-3.45 (m, 1H), 3.23-3.13 (m, 1H), 2.74 (s, 3H), 2.63-2.57 (m, 1H), 1.13 (t, 3H).

Example 70

4-((6-(2,4-dichlorophenyl)-5-(ethoxycarbonyl)-2-(1,3,4-thiadiazol-2-yl)-3,6-dihydropyrimidin-4-yl)methyl)morpholine-3-carboxylic acid

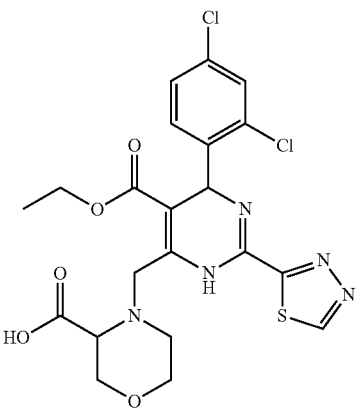 [SMILES: CCOC(=O)C1=C(CN2CCOCC2C(=O)O)NC(c2nncs2)=NC1c1ccc(Cl)cc1Cl]

Step A: 1,3,4-thiadiazole-2-carbonitrile 1,3,4-thiadiazol-2-amine (4.05 g, 40 mmol) was reacted with CuCN (7.2 g, 80 mmol) according to the procedure as described in Example 61, Step A to give the title compound as red liquid (1.78 g, 40%). The compound was characterized by the following spectroscopic data:

MS-ESI: (ESI, pos. ion) m/z: 112.0 [M+1]$^+$;
$^1$H NMR (400 MHz, DMSO-d$_6$): δ 9.56 (s, 1H).

Step B: 1,3,4-thiadiazole-2-carboximidamide hydrochloride 1,3,4-thiadiazole-2-carbonitrile (1.11 g, 10 mmol) was reacted with sodium methoxide (0.81 g, 15 mmol) and ammonium chloride (0.96 g, 18 mmol) according to the procedure as described in Example 61, Step B to give the title compound as an offwhite solid (1.15 g, 70%). The compound was characterized by the following spectroscopic data:

MS-ESI: (ESI, pos. ion) m/z: 129.0 [M+1]$^+$;
$^1$H NMR (400 MHz, D$_2$O): δ 9.52 (s, 1H).

Step C: Ethyl 4-(2,4-dichlorophenyl)-6-methyl-2-(1,3,4-thiadiazol-2-yl)-1,4-dihydro pyrimidine-5-carboxylate 1,3,4-thiadiazole-2-carboximidamide hydrochloride (1.43 g, 8.69 mmol) was reacted with 2,4-dichlorobenzaldehyde (1.52 g, 8.69 mmol) and ethyl 3-oxobutanoate (1.36 g, 10.5 mmol) according to the procedure as described in Example 1, Step A to give the title compound as a yellow solid (1.83 g, 53%). The compound was characterized by the following spectroscopic data:

MS-ESI: (ESI, pos. ion) m/z: 397.1 [M+1]$^+$;
$^1$H NMR (400 MHz, DMSO-d$_6$): δ 10.36 (br.s, 1H), 9.71 (s, 1H), 7.62-7.40 (m, 3H), 6.06 (s, 1H), 3.99 (q, 2H), 2.53 (s, 3H), 1.06 (t, 3H).

Step D: Ethyl 6-(bromomethyl)-4-(2,4-dichlorophenyl)-2-(1,3,4-thiadiazol-2-yl)-1,4-dihydropyrimidine-5-carboxylate Ethyl 4-(2,4-dichlorophenyl)-6-methyl-2-(1,3,4-thiadiazol-2-yl)-1,4-dihydropyrimidine-5-carboxylate (1 g, 2.5 mmol) was reacted with NBS (0.5 g, 2.8 mmol) according to the procedure as described in Example 1, Step B to give the title compound as a yellow solid (0.71 g, 60%). The compound was characterized by the following spectroscopic data:

MS-ESI: (ESI, pos. ion) m/z: 475.1 [M+1]$^+$;

$^1$H NMR (400 MHz, DMSO-d$_6$): δ 10.38 (br.s, 1H), 9.70 (s, 1H), 7.61-7.38 (m, 3H), 6.05 (s, 1H), 4.65-4.48 (m, 2H), 4.01 (q, 2H), 1.06 (t, 3H).

Step E: 4-((6-(2,4-dichlorophenyl)-5-(ethoxycarbonyl)-2-(1,3,4-thiadiazol-2-yl)-3,6-dihydropyrimidin-4-yl)methyl)morpholine-3-carboxylic acid Ethyl 6-(bromomethyl)-4-(2,4-dichlorophenyl)-2-(1,3,4-thiadiazol-2-yl)-1,4-dihydropyrimidine-5-carboxylate (0.7 g, 1.5 mmol) was reacted with morpholine-3-carboxylic acid (0.2 g, 1.5 mmol) according to the procedure as described in Example 1, Step C to give the title compound as a yellow solid (0.44 g, 56%). The compound was characterized by the following spectroscopic data:

MS-ESI: (ESI, pos. ion) m/z: 526.0 [M+1]$^+$;

$^1$H NMR (400 MHz, CDCl$_3$): δ 9.17 (s, 1H), 7.41-7.39 (m, 1H), 7.29-7.26 (m, 1H), 7.21-7.17 (m, 1H), 6.23 (s, 1H), 4.35-4.15 (m, 2H), 4.10-3.92 (m, 4H), 3.85-3.78 (m, 2H), 3.62-3.51 (m, 1H), 3.25-3.15 (m, 1H), 2.65-2.59 (m, 1H), 1.10 (t, 3H).

Example 71

4-((6-(2-bromo-4-fluorophenyl)-5-(ethoxycarbonyl)-2-(1,3,4-thiadiazol-2-yl)-3,6-dihydropyrimidin-4-yl)methyl)morpholine-3-carboxylic acid

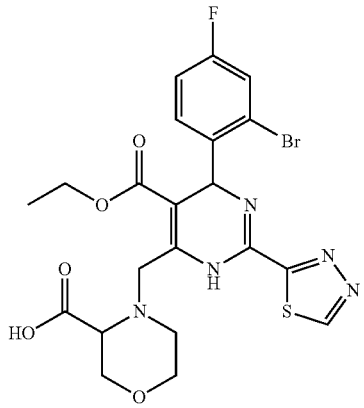 [SMILES: CCOC(=O)C1=C(CN2CCOCC2C(=O)O)NC(c2nncs2)=NC1c1ccc(F)cc1Br]

Step A: Ethyl 4-(2-bromo-4-fluorophenyl)-6-methyl-2-(1,3,4-thiadiazol-2-yl)-1,4-dihydropyrimidine-5-carboxylate 1,3,4-thiadiazole-2-carboximidamide hydrochloride (1.43 g, 8.69 mmol) was reacted with 2-bromo-4-fluorobenzaldehyde (1.76 g, 8.69 mmol) and ethyl 3-oxobutanoate (1.36 g, 10.5 mmol) according to the procedure as described in Example 1, Step A to give the title compound as a yellow solid (1.74 g, 47%). The compound was characterized by the following spectroscopic data:

MS-ESI: (ESI, pos. ion) m/z: 425.0 [M+1]$^+$;

$^1$H NMR (400 MHz, DMSO-d$_6$): δ 10.37 (br.s, 1H), 9.68 (s, 1H), 7.57-7.23 (m, 3H), 6.01 (s, 1H), 4.03 (q, 2H), 2.51 (s, 3H), 1.06 (t, 3H).

Step B: Ethyl 4-(2-bromo-4-fluorophenyl)-6-(bromomethyl)-2-(1,3,4-thiadiazol-2-yl)-1,4-dihydropyrimidine-5-carboxylate Ethyl 4-(2-bromo-4-fluorophenyl)-6-methyl-2-(1,3,4-thiadiazol-2-yl)-1,4-dihydropyrimidine-5-carboxylate (1.06 g, 2.5 mmol) was reacted with NBS (0.5 g, 2.8 mmol) according to the procedure as described in Example 1, Step B to give the title compound as a yellow solid (0.89 g, 71%). The compound was characterized by the following spectroscopic data:

MS-ESI: (ESI, pos. ion) m/z: 503.1 [M+1]$^+$;

$^1$H NMR (400 MHz, DMSO-d$_6$): δ 10.38 (br.s, 1H), 9.69 (s, 1H), 7.56-7.22 (m, 3H), 6.00 (s, 1H), 4.65-4.47 (m, 2H), 4.03 (q, 2H), 1.08 (t, 3H).

Step C: 4-((6-(2-bromo-4-fluorophenyl)-5-(ethoxycarbonyl)-2-(1,3,4-thiadiazol-2-yl)-3,6-dihydropyrimidin-4-yl)methyl)morpholine-3-carboxylic acid Ethyl 4-(2-bromo-4-fluorophenyl)-6-(bromomethyl)-2-(1,3,4-thiadiazol-2-yl)-1,4-dihydropyrimidine-5-carboxylate (0.76 g, 1.5 mmol) was reacted with morpholine-3-carboxylic acid (0.2 g, 1.5 mmol) according to the procedure as described in Example 1, Step C to give the title compound as a yellow solid (0.6 g, 72%). The compound was characterized by the following spectroscopic data:

MS-ESI: (ESI, pos. ion) m/z: 554.0 [M+1]$^+$;

$^1$H NMR (400 MHz, CDCl$_3$): δ 9.17 (s, 1H), 7.35-7.26 (m, 2H), 7.01-6.97 (m, 1H), 6.22 (s, 1H), 4.32-4.13 (m, 2H), 4.11-3.91 (m, 4H), 3.86-3.76 (m, 2H), 3.61-3.49 (m, 1H), 3.26-3.14 (m, 1H), 2.66-2.58 (m, 1H), 1.13 (t, 3H).

Example 72

4-((6-(2-chloro-4-fluorophenyl)-5-(ethoxycarbonyl)-2-(1,3,4-thiadiazol-2-yl)-3,6-dihydropyrimidin-4-yl)methyl)morpholine-3-carboxylic acid

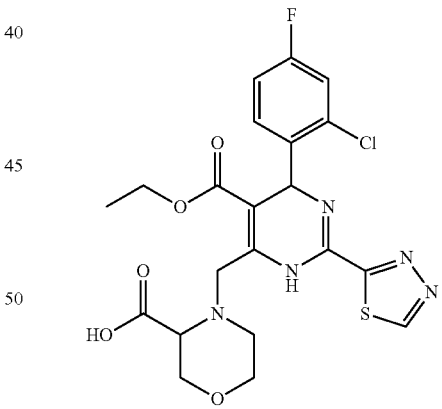

Step A: Ethyl 4-(2-chloro-4-fluorophenyl)-6-methyl-2-(1,3,4-thiadiazol-2-yl)-1,4-dihydropyrimidine-5-carboxylate 1,3,4-thiadiazole-2-carboximidamide hydrochloride (1.43 g, 8.69 mmol) was reacted with 2-chloro-4-fluorobenzaldehyde (1.38 g, 8.69 mmol) and ethyl 3-oxobutanoate (1.36 g, 10.5 mmol) according to the procedure as described in Example 1, Step A to give the title compound as a yellow solid (1.82 g, 55%). The compound was characterized by the following spectroscopic data:

MS-ESI: (ESI, pos. ion) m/z: 381.0 [M+1]⁺;
¹H NMR (400 MHz, DMSO-$d_6$): δ 10.36 (br.s, 1H), 9.71 (s, 1H), 7.62-7.40 (m, 3H), 6.03 (s, 1H), 3.99 (q, 2H), 2.52 (s, 3H), 1.10 (t, 3H).

Step B: Ethyl 6-(bromomethyl)-4-(2-chloro-4-fluorophenyl)-2-(1,3,4-thiadiazol-2-yl)-1,4-dihydropyrimidine-5-carboxylate Ethyl 4-(2-chloro-4-fluorophenyl)-6-methyl-2-(1,3,4-thiadiazol-2-yl)-1,4-dihydropyrimidine-5-carboxylate (0.76 g, 2 mmol) was reacted with NBS (0.36 g, 2 mmol) according to the procedure as described in Example 1, Step B to give the title compound as a yellow solid (0.46 g, 50%). The compound was characterized by the following spectroscopic data:
MS-ESI: (ESI, pos. ion) m/z: 459.0 [M+1]⁺;
¹H NMR (400 MHz, DMSO-$d_6$): δ 9.96 (br.s, 1H), 9.71 (s, 1H), 7.60-7.39 (m, 3H), 6.01 (s, 1H), 4.59-4.41 (m, 2H), 4.01 (q, 2H), 1.03 (t, 3H).

Step C: 4-((6-(2-chloro-4-fluorophenyl)-5-(ethoxycarbonyl)-2-(1,3,4-thiadiazol-2-yl)-3,6-dihydropyrimidin-4-yl)methyl)morpholine-3-carboxylic acid Ethyl 6-(bromomethyl)-4-(2-chloro-4-fluorophenyl)-2-(1,3,4-thiadiazol-2-yl)-1,4-dihydropyrimidine-5-carboxylate (0.69 g, 1.5 mmol) was reacted with morpholine-3-carboxylic acid (0.2 g, 1.5 mmol) according to the procedure as described in Example 1, Step C to give the title compound as a yellow solid (0.47 g, 61%). The compound was characterized by the following spectroscopic data:
MS-ESI: (ESI, pos. ion) m/z: 510.1 [M+1]⁺;
¹H NMR (400 MHz, CDCl₃): δ 9.18 (s, 1H), 7.34-7.26 (m, 1H), 7.15-7.11 (m, 1H), 6.96-6.92 (m, 1H), 6.23 (s, 1H), 4.35-4.11 (m, 2H), 4.09-3.98 (m, 4H), 3.90-3.79 (m, 2H), 3.61-3.50 (m, 1H), 3.26-3.13 (m, 1H), 2.61 (br.s, 1H), 1.12 (t, 3H).

Example 73

4-((6-(2,4-difluorophenyl)-5-(ethoxycarbonyl)-2-(1,3,4-thiadiazol-2-yl)-3,6-dihydropyrimidin-4-yl)methyl)morpholine-3-carboxylic acid

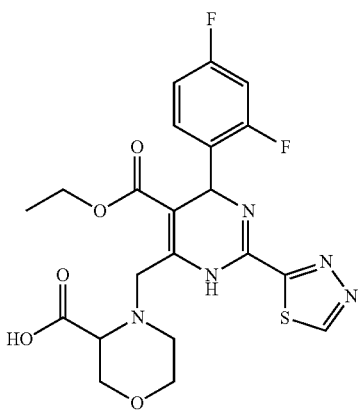

Step A: Ethyl 4-(2,4-difluorophenyl)-6-methyl-2-(1,3,4-thiadiazol-2-yl)-1,4-dihydropyrimidine-5-carboxylate 1,3,4-thiadiazole-2-carboximidamide hydrochloride (1.43 g, 8.69 mmol) was reacted with 2,4-difluorobenzaldehyde (1.23 g, 8.69 mmol) and ethyl 3-oxobutanoate (1.36 g, 10.5 mmol) according to the procedure as described in Example 1, Step A to give the title compound as a yellow solid (1.3 g, 41%). The compound was characterized by the following spectroscopic data:
MS-ESI: (ESI, pos. ion) m/z: 365.1 [M+1]⁺;
¹H NMR (400 MHz, CDCl₃): δ 9.15 (s, 1H), 7.85 (br.s, 1H), 7.30-7.27 (m, 1H), 6.83-6.78 (m, 2H), 6.06 (s, 1H), 4.08 (q, 2H), 2.48 (s, 3H), 1.17 (t, 3H).

Step B: Ethyl 6-(bromomethyl)-4-(2,4-difluorophenyl)-2-(1,3,4-thiadiazol-2-yl)-1,4-dihydropyrimidine-5-carboxylate Ethyl 4-(2,4-difluorophenyl)-6-methyl-2-(1,3,4-thiadiazol-2-yl)-1,4-dihydropyrimidine-5-carboxylate (0.73 g, 2 mmol) was reacted with NBS (0.36 g, 2 mmol) according to the procedure as described in Example 1, Step B to give the title compound as a yellow solid (0.53 g, 60%). The compound was characterized by the following spectroscopic data:
MS-ESI: (ESI, pos. ion) m/z: 443.0 [M+1]⁺;
¹H NMR (400 MHz, CDCl₃): δ 9.17 (s, 1H), 7.86 (br.s, 1H), 7.30-7.27 (m, 1H), 6.83-6.78 (m, 2H), 6.05 (s, 1H), 4.61-4.49 (m, 2H), 4.06 (q, 2H), 1.17 (t, 3H).

Step C: 4-((6-(2,4-difluorophenyl)-5-(ethoxycarbonyl)-2-(1,3,4-thiadiazol-2-yl)-3,6-dihydropyrimidin-4-yl)methyl)morpholine-3-carboxylic acid Ethyl 6-(bromomethyl)-4-(2,4-difluorophenyl)-2-(1,3,4-thiadiazol-2-yl)-1,4-dihydropyrimidine-5-carboxylate (0.66 g, 1.5 mmol) was reacted with morpholine-3-carboxylic acid (0.2 g, 1.5 mmol) according to the procedure as described in Example 1, Step C to give the title compound as a yellow solid (0.3 g, 41%). The compound was characterized by the following spectroscopic data:
MS-ESI: (ESI, pos. ion) m/z: 494.1 [M+1]⁺;
¹H NMR (400 MHz, CDCl₃): δ 9.17 (s, 1H), 7.31-7.28 (m, 1H), 6.82-6.79 (m, 2H), 6.05 (s, 1H), 4.21-4.11 (m, 1H), 4.09-3.92 (m, 5H), 3.85-3.78 (m, 2H), 3.56-3.45 (m, 1H), 3.19-3.09 (m, 1H), 2.62-2.56 (m, 1H), 1.12 (t, 3H).

Example 74

2-(4-((6-(2-bromo-4-fluorophenyl)-5-(ethoxycarbonyl)-2-(thiazol-2-yl)-3,6-dihydropyrimidin-4-yl)methyl)morpholin-2-yl)acetic acid

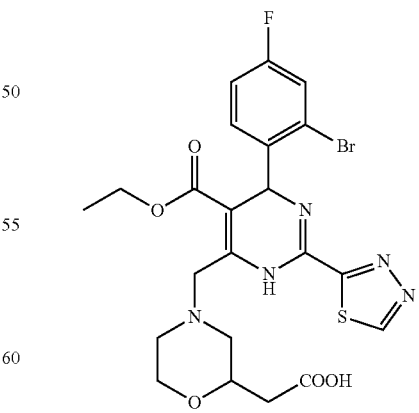

Ethyl 4-(2-bromo-4-fluorophenyl)-6-(bromomethyl)-2-(thiazol-2-yl)-1,4-dihydropyrimidine-5-carboxylate (0.69 g, 1.37 mmol) was reacted with 2-(morpholin-2-yl)acetic acid hydrochloride (0.3 g, 1.65 mmol) according to the procedure as described in Example 3 to give the title compound as a yellow solid (0.46 g, 60%). The compound was characterized by the following spectroscopic data:

MS-ESI: (ESI, pos. ion) m/z: 567.1 [M+1]$^+$;

$^1$H NMR (400 MHz, CDCl$_3$): δ 9.57 (br.s, 1H), 7.85 (d, 1H), 7.44 (d, 1H), 7.32-7.27 (m, 2H), 6.98-6.94 (m, 1H), 6.19 (s, 1H), 4.14-3.84 (m, 7H), 2.78-2.35 (m, 6H), 1.13 (t, 3H).

Example 75

2-(4-((6-(2-chloro-4-fluorophenyl)-5-(ethoxycarbonyl)-2-(thiazol-2-yl)-3,6-dihydropyrimidin-4-yl)methyl)morpholin-2-yl)acetic acid

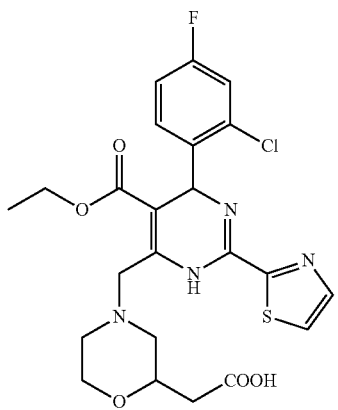 [SMILES: CCOC(=O)C1=C(CN2CCOC(CC(=O)O)C2)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.63 g, 1.37 mmol) was reacted with 2-(morpholin-2-yl)acetic acid hydrochloride (0.3 g, 1.65 mmol) according to the procedure as described in Example 3 to give the title compound as a yellow solid (0.38 g, 53%). The compound was characterized by the following spectroscopic data:

MS-ESI: (ESI, pos. ion) m/z: 523.2 [M+1]$^+$;

$^1$H NMR (400 MHz, CDCl$_3$): δ 9.57 (br.s, 1H), 7.85 (d, 1H), 7.44 (d, 1H), 7.31-7.27 (m, 1H), 7.13-7.11 (m, 1H), 6.93-6.89 (m, 1H), 6.21 (s, 1H), 4.08-3.82 (m, 7H), 2.90-2.24 (m, 6H), 1.13 (t, 3H).

Example 76

2-(4-((6-(2,4-dichlorophenyl)-5-(ethoxycarbonyl)-2-(thiazol-2-yl)-3,6-dihydropyrimidin-4-yl)methyl)morpholin-2-yl)acetic acid

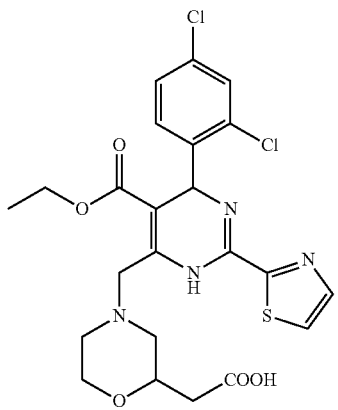 [SMILES: CCOC(=O)C1=C(CN2CCOC(CC(=O)O)C2)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.65 g, 1.37 mmol) was reacted with 2-(morpholin-2-yl)acetic acid hydrochloride (0.3 g, 1.65 mmol) according to the procedure as described in Example 3 to give the title compound as a yellow solid (0.36 g, 49%). The compound was characterized by the following spectroscopic data:

MS-ESI: (ESI, pos. ion) m/z: 539.2 [M+1]$^+$;

$^1$H NMR (400 MHz, CDCl$_3$): δ 9.60 (br.s, 1H), 7.83 (d, 1H), 7.59-7.54 (m, 1H), 7.42 (d, 1H), 7.41-7.35 (m, 2H), 6.19 (s, 1H), 4.08-3.93 (m, 3H), 3.91-3.85 (m, 2H), 3.84-3.79 (m, 2H), 2.90-2.75 (m, 2H), 2.73-2.56 (m, 2H), 2.43-2.24 (m, 2H), 1.08 (t, 3H).

Example 77

Isopropyl 4-((6-(2-bromo-4-fluorophenyl)-5-(ethoxycarbonyl)-2-(thiazol-2-yl)-3,6-dihydropyrimidin-4-yl)methyl)morpholine-3-carboxylate

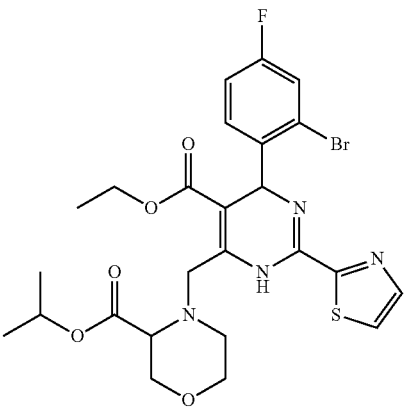 [SMILES: CCOC(=O)C1=C(CN2CCOCC2C(=O)OC(C)C)NC(c2nccs2)=NC1c1ccc(F)cc1Br]

Step A: Isopropyl morpholine-3-carboxylate hydrochloride

To a suspension of morpholine-3-carboxylic acid hydrochloride (2 g, 12 mmol) in isopropanol (30 mL) was added SOCl$_2$ (1.9 g, 15.6 mmol) at 5° C., then the mixture was stirred at 80° C. for 6 hours. The mixture was concentrated in vacuo to give the title compound as pale brown oil (2.39 g, 95%). The compound was characterized by the following spectroscopic data:

MS-ESI: (ESI, pos. ion) m/z: 174.1 [M+1]$^+$.

Step B: Isopropyl 4-((6-(2-bromo-4-fluorophenyl)-5-(ethoxycarbonyl)-2-(thiazol-2-yl)-3,6-dihydropyrimidin-4-yl)methyl)morpholine-3-carboxylate Ethyl 4-(2-bromo-4-fluorophenyl)-6-(bromomethyl)-2-(thiazol-2-yl)-1,4-dihydropyrimidine-5-carboxylate (2.52 g, 5 mmol) was reacted with isopropyl morpholine-3-carboxylate hydrochloride (1.05 g, 5 mmol) according to the procedure as described in Example 24 to give the title compound as a yellow solid (1.79 g, 60%). The compound was characterized by the following spectroscopic data:

MS-ESI: (ESI, pos. ion) m/z: 595.0 [M+1]$^+$;

$^1$H NMR (400 MHz, CDCl$_3$): δ 9.78 (br.s, 1H), 7.85 (d, 1H), 7.43 (d, 1H), 7.34-7.26 (m, 2H), 6.96-6.94 (m, 1H), 6.18 (s, 1H), 5.14-5.08 (m, 1H), 4.29-4.19 (m, 1H), 4.08-3.99 (m, 4H), 3.95-3.91 (m, 1H), 3.89-3.80 (m, 2H), 3.47-3.40 (m, 1H), 3.17-3.07 (m, 1H), 2.54-2.48 (m, 1H), 1.30-1.25 (m, 6H), 1.13 (t, 3H).

Example 78

Isopropyl 4-((6-(2,4-dichlorophenyl)-5-(ethoxycarbonyl)-2-(thiazol-2-yl)-3,6-dihydropyrimidin-4-yl)methyl)morpholine-3-carboxylate

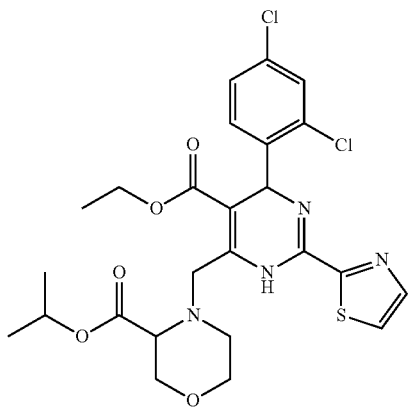 [SMILES: CCOC(=O)C1=C(CN2CCOCC2C(=O)OC(C)C)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (2.38 g, 5 mmol) was reacted with isopropyl morpholine-3-carboxylate hydrochloride (1.05 g, 5 mmol) according to the procedure as described in Example 24 to give the title compound as a yellow solid (1.79 g, 63%). The compound was characterized by the following spectroscopic data:

MS-ESI: (ESI, pos. ion) m/z: 567.1 [M+1]$^+$;

$^1$H NMR (400 MHz, CDCl$_3$): δ 9.79 (br.s, 1H), 7.86-7.84 (m, 1H), 7.43-7.41 (m, 1H), 7.40-7.38 (m, 1H), 7.30-7.24 (m, 1H), 7.17-7.14 (m, 1H), 6.21 (s, 1H), 5.15-5.07 (m, 1H), 4.28-4.18 (m, 1H), 4.10-3.99 (m, 4H), 3.94-3.91 (m, 1H), 3.89-3.80 (m, 2H), 3.46-3.41 (m, 1H), 3.19-3.08 (m, 1H), 2.53-2.49 (m, 1H), 1.29-1.23 (m, 6H), 1.15 (t, 3H).

Example 79

(Pivaloyloxy)methyl 4-((6-(2,4-dichlorophenyl)-5-(ethoxycarbonyl)-2-(thiazol-2-yl)-3,6-dihydropyrimidin-4-yl)methyl)morpholine-3-carboxylate

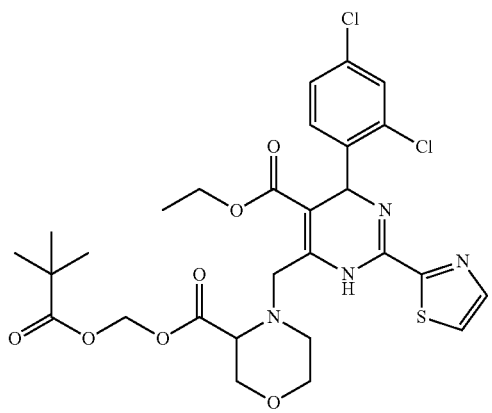 [SMILES: CCOC(=O)C1=C(CN2CCOCC2C(=O)OCOC(=O)C(C)(C)C)NC(c2nccs2)=NC1c1ccc(Cl)cc1Cl]

To a solution of 4-(((6-(2,4-dichlorophenyl)-5-(ethoxycarbonyl)-2-(thiazol-2-yl)-3,6-dihydropyrimidin-4-yl)methyl) morpholine-3-carboxylic acid (0.12 g, 0.23 mmol) and TEA (0.06 g, 0.6 mmol) in DMF (6 mL) was added chloromethyl pivalate (0.12 g, 0.8 mmol). And the mixture was stirred at 60° C. for 3 hours, and cooled to 25° C. To the reaction mixture was added DCM (100 mL). The organic layer was washed with brine (80 mL×6) and dried over unhydrous Na$_2$SO$_4$. The crude product was purified by a silica gel column chromatography (PETROLEUM ETHER/EtOAc (V/V)=8/1) to give the title compound as yellow oil (0.09 g, 62%). The compound was characterized by the following spectroscopic data:

MS-ESI: (ESI, pos. ion) m/z: 539.1 [M+1]$^+$;

$^1$H NMR (400 MHz, CDCl$_3$): δ 9.71 (br.s, 1H), 7.85-7.83 (m, 1H), 7.43 (d, 1H), 7.39 (d, 1H), 7.30-7.23 (m, 1H), 7.18-7.14 (m, 1H), 6.20 (s, 1H), 5.87-5.79 (m, 2H), 4.30-4.21 (m, 1H), 4.09-3.98 (m, 5H), 3.83-3.81 (m, 2H), 3.55-3.49 (m, 1H), 3.25-3.15 (m, 1H), 2.57-2.48 (m, 1H), 1.25 (s, 9H), 1.18 (t, 3H).

Example 80

((Isopropoxycarbonyl)oxy)methyl 4-((6-(2,4-dichlorophenyl)-5-(ethoxycarbonyl)-2-(thiazol-2-yl)-3,6-dihydropyrimidin-4-yl)methyl)morpholine-3-carboxylate

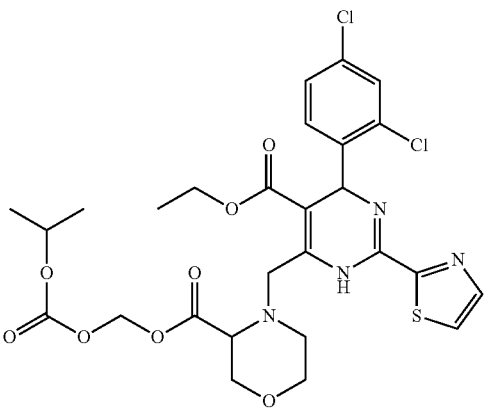 [SMILES: CCOC(=O)C1=C(CN2CCOCC2C(=O)OCOC(=O)OC(C)C)NC(c2nccs2)=NC1c1ccc(Cl)cc1Cl]

4-((6-(2,4-dichlorophenyl)-5-(ethoxycarbonyl)-2-(thiazol-2-yl)-3,6-dihydropyrimidin-4-yl)methyl)morpholine-3-carboxylic acid (0.22 g, 0.4 mmol) was reacted with chloromethyl isopropyl carbonate (0.25 g, 1.64 mmol) according to the procedure as described in Example 79 to give the title compound as yellow oil (0.12 g, 47%). The compound was characterized by the following spectroscopic data:

MS-ESI: (ESI, pos. ion) m/z: 641.1 [M+1]$^+$;

$^1$H NMR (400 MHz, CDCl$_3$): δ 9.67 (br.s, 1H), 7.84 (br.s, 1H), 7.43 (d, 1H), 7.38 (d, 1H), 7.31-7.23 (m, 1H), 7.18-7.14 (m, 1H), 6.20 (s, 1H), 5.82 (s, 2H), 4.92-4.88 (m, 1H), 4.33-4.18 (m, 2H), 4.15-4.03 (m, 3H), 3.82 (br.s, 2H), 3.56-3.52 (m, 1H), 3.23-3.15 (m, 1H), 2.56-2.46 (m, 1H), 1.42-1.25 (m, 6H), 1.13 (t, 3H).

Example 81

Ethyl 4-(2,4-dichlorophenyl)-6-((3-(isopropylcarbamoyl)morpholino)methyl)-2-(thiazol-2-yl)-1,4-dihydropyrimidine-5-carboxylate

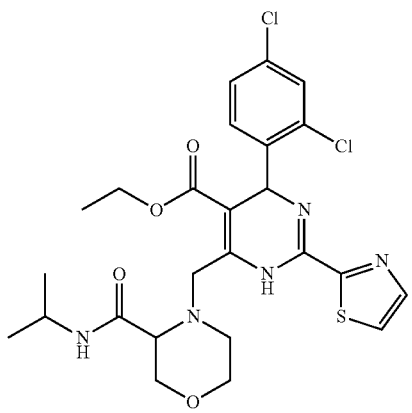 [SMILES: CCOC(=O)C1=C(CN2CCOCC2C(=O)NC(C)C)NC(c2nccs2)=NC1c1ccc(Cl)cc1Cl]

Step A: N-isopropylmorpholine-3-carboxamide

A mixture of methyl morpholine-3-carboxylate hydrochloride (0.22 g, 1.2 mmol) and propan-2-amine (2.78 g, 47 mmol) was stirred at 60° C. for 12 hours under $N_2$. The mixture was concentrated in vacuo to give the title compound as brownish sticky oil (0.2 g, 95%). The compound was characterized by the following spectroscopic data:

MS-ESI: (ESI, pos. ion) m/z: 173.2 [M+1]$^+$.

Step B: Ethyl 4-(2,4-dichlorophenyl)-6-((3-(isopropylcarbamoyl)morpholino)methyl)-2-(thiazol-2-yl)-1,4-dihydropyrimidine-5-carboxylate Ethyl 6-(bromomethyl)-4-(2,4-dichlorophenyl)-2-(thiazol-2-yl)-1,4-dihydropyrimidine-5-carboxylate (0.57 g, 1.2 mmol) was reacted with N-isopropylmorpholine-3-carboxamide (0.21 g, 1.2 mmol) according to the procedure as described in Example 24 to give the title compound as a yellow solid (0.2 g, 30%). The compound was characterized by the following spectroscopic data:

MS-ESI: (ESI, pos. ion) m/z: 566.1 [M+1]$^+$;

$^1$H NMR (400 MHz, CDCl$_3$): δ 9.59 (s, 1H), 7.89-7.86 (m, 1H), 7.49-7.39 (m, 2H), 7.27-7.18 (m, 2H), 6.22 (s, 1H), 4.31-4.18 (m, 1H), 4.15-3.99 (m, 4H), 3.95-3.83 (m, 2H), 3.76-3.66 (m, 2H), 3.30-3.27 (m, 1H), 2.95-2.89 (m, 1H), 2.65-2.49 (m, 1H), 1.26-1.11 (m, 6H), 1.07 (t, 3H).

Example 82

Ethyl 4-(2-bromo-4-fluorophenyl)-6-((3-(isopropylcarbamoyl)morpholino)methyl)-2-(thiazol-2-yl)-1,4-dihydropyrimidine-5-carboxylate

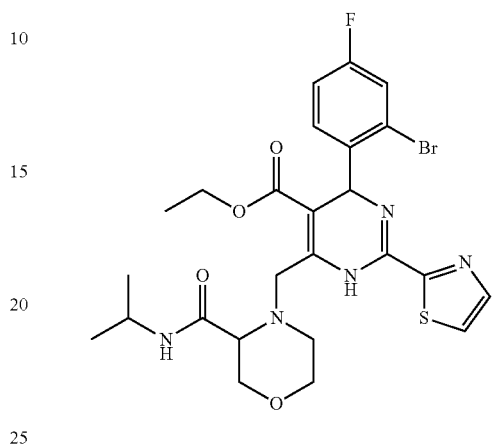

Ethyl 4-(2-bromo-4-fluorophenyl)-6-(bromomethyl)-2-(thiazol-2-yl)-1,4-dihydropyrimidine-5-carboxylate (0.6 g, 1.2 mmol) was reacted with N-isopropylmorpholine-3-carboxamide (0.21 g, 1.2 mmol) according to the procedure as described in Example 24 to give the title compound as a yellow solid (0.25 g, 35%). The compound was characterized by the following spectroscopic data:

MS-ESI: (ESI, pos. ion) m/z: 594.1 [M+1]$^+$;

$^1$H NMR (400 MHz, CDCl$_3$): δ 9.58 (s, 1H), 7.88-7.85 (m, 1H), 7.48 (d, 1H), 7.35 (d, 1H), 7.31-7.25 (m, 1H), 6.98-6.93 (m, 1H), 4.33-4.15 (m, 1H), 4.12-3.99 (m, 4H), 3.93-3.82 (m, 2H), 3.78-3.67 (m, 2H), 3.29-3.22 (m, 1H), 2.94-2.81 (m, 1H), 2.66-2.62 (m, 1H), 1.20-1.12 (m, 3H), 1.08 (d, 3H), 0.98 (d, 3H).

Example 83

4-((6-(2-bromo-4-fluorophenyl)-5-(ethoxycarbonyl)-2-(1-methyl-1H-1,2,4-triazol-3-yl)-3,6-dihydropyrimidin-4-yl)methyl)morpholine-2-carboxylic acid

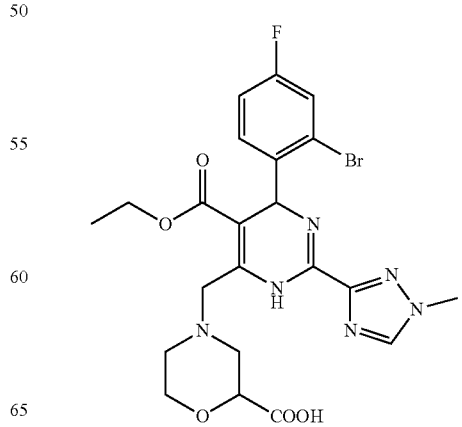

Step A: 1-methyl-1H-1,2,4-triazole-3-carbonitrile 1H-1,2,4-triazole-3-carbonitrile (2.35 g, 25 mmol) was reacted with iodomethane (3.53 g, 25 mmol) according to the procedure as described in Example 48, Step A to give the title compound as a white solid (2.3 g, 85%). The compound was characterized by the following spectroscopic data:
MS-ESI: (ESI, pos. ion) m/z: 109.0 [M+1]+.
$^1$H NMR (400 MHz, CDCl$_3$): δ 8.29 (s, 1H), 3.19 (s, 3H).

Step B: 1-methyl-1H-1,2,4-triazole-3-carboximidamide hydrochloride 1-methyl-1H-1,2,4-triazole-3-carbonitrile (20 g, 185 mmol) was reacted with sodium methoxide (14 g, 295 mmol) and ammonium chloride (14.8 g, 277.5 mmol) according to the procedure as described in Example 61, Step B to give the title compound as a white solid (23.44 g, 78.8%). The compound was characterized by the following spectroscopic data:
MS-ESI: (ESI, pos. ion) m/z: 126.1 [M+1]+;
$^1$H NMR (400 MHz, D$_2$O): δ 8.40 (s, 1H), 3.89 (s, 3H).

Step C: Ethyl 4-(2-bromo-4-fluorophenyl)-6-methyl-2-(1-methyl-1H-1,2,4-triazol-3-yl)-1,4-dihydropyrimidine-5-carboxylate 1-methyl-1H-1,2,4-triazole-3-carboximidamide hydrochloride (3.3 g, 20 mmol) was reacted with 2-bromo-4-fluorobenzaldehyde (4 g, 20 mmol) and ethyl 3-oxobutanoate (2.6 g, 20 mmol) according to the procedure as described in Example 1, Step A to give the title compound as a white solid (5.3 g, 63%). The compound was characterized by the following spectroscopic data:
MS-ESI: (ESI, pos. ion) m/z: 422.1 [M+1]+;
$^1$H NMR (400 MHz, CDCl$_3$): δ 8.03 (s, 1H), 7.39-6.93 (m, 3H), 6.15 (s, 1H), 4.07-4.02 (m, 2H), 3.96 (s, 3H), 2.53 (s, 3H), 1.14 (t, 3H).

Step D: Ethyl 4-(2-bromo-4-fluorophenyl)-6-(bromomethyl)-2-(1-methyl-1H-1,2,4-triazol-3-yl)-1,4-dihydropyrimidine-5-carboxylate Ethyl 4-(2-bromo-4-fluorophenyl)-6-methyl-2-(1-methyl-1H-1,2,4-triazol-3-yl)-1,4-dihydropyrimidine-5-carboxylate (5 g, 12 mmol) was reacted with NBS (2.1 g, 12 mmol) in chloroform (150 mL) according to the procedure as described in Example 1, Step B to give the title compound as a yellow solid (2.4 g, 40%). The compound was characterized by the following spectroscopic data:
MS-ESI: (ESI, pos. ion) m/z: 501.0 [M+1]+;
$^1$H NMR (400 MHz, DMSO-d$_6$): δ 9.81 (br.s, 1H), 8.06 (s, 1H), 7.35-6.90 (m, 3H), 6.11 (s, 1H), 4.23 (q, 2H), 4.01 (q, 2H), 3.92 (s, 3H), 1.15 (t, 3H).

Step E: 4-((6-(2-bromo-4-fluorophenyl)-5-(ethoxycarbonyl)-2-(1-methyl-1H-1,2,4-triazol-3-yl)-3,6-dihydropyrimidin-4-yl)methyl)morpholine-2-carboxylic acid Ethyl 4-(2-bromo-4-fluorophenyl)-6-(bromomethyl)-2-(1-methyl-1H-1,2,4-triazol-3-yl)-1,4-dihydropyrimidine-5-carboxylate (1 g, 2 mmol) was reacted with morpholine-2-carboxylic acid hydrochloride (0.34 g, 2 mmol) according to the procedure as described in Example 1, Step C to give the title compound as a yellow solid (0.42 g, 38%). The compound was characterized by the following spectroscopic data:
MS-ESI: (ESI, pos. ion) m/z: 551.1 [M+1]+;
$^1$H NMR (400 MHz, CDCl$_3$): δ 8.09 (s, 1H), 7.36-6.93 (m, 3H), 6.20 (s, 1H), 4.20-3.99 (m, 4H), 3.95 (s, 3H), 3.93-3.80 (m, 3H), 2.73-2.36 (m, 4H), 1.09 (t, 3H).

Example 84

2-(4-((6-(2-bromo-4-fluorophenyl)-5-(ethoxycarbonyl)-2-(1-methyl-1H-1,2,4-triazol-3-yl)-3,6-dihydropyrimidin-4-yl)methyl)morpholin-2-yl)acetic acid

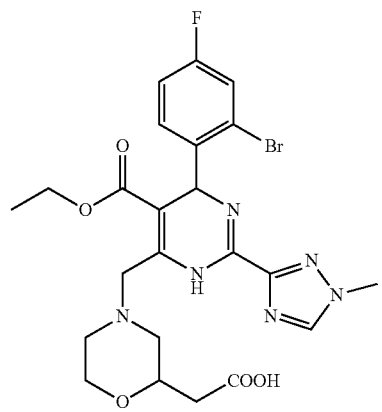 [SMILES: CCOC(=O)C1=C(CN2CCOC(CC(=O)O)C2)NC(c2ncn(C)n2)=NC1c1ccc(F)cc1Br]

Ethyl 4-(2-bromo-4-fluorophenyl)-6-(bromomethyl)-2-(1-methyl-1H-1,2,4-triazol-3-yl)-1,4-dihydropyrimidine-5-carboxylate (1 g, 2 mmol) was reacted with 2-(morpholin-2-yl)acetic acid hydrochloride (0.36 g, 2 mmol) according to the procedure as described in Example 1, Step C to give the title compound as a yellow solid (0.47 g, 42%). The compound was characterized by the following spectroscopic data:
MS-ESI: (ESI, pos. ion) m/z: 565.1 [M+1]+;
$^1$H NMR (400 MHz, CDCl$_3$): δ 8.09 (s, 1H), 7.34-6.94 (m, 3H), 6.22 (s, 1H), 4.13-3.84 (m, 7H), 3.95 (s, 3H), 2.94-2.18 (m, 6H), 1.14-1.11 (m, 3H).

Example 85

2-(4-((6-(2-bromo-4-fluorophenyl)-2-(3-cyano-1H-1,2,4-triazol-1-yl)-5-(ethoxycarbonyl)-3,6-dihydropyrimidin-4-yl)methyl)morpholin-2-yl)acetic acid

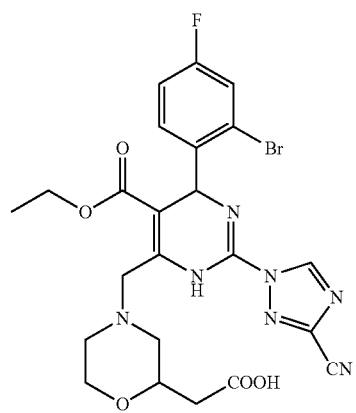 [SMILES: CCOC(=O)C1=C(CN2CCOC(CC(=O)O)C2)NC(n2cnc(C#N)n2)=NC1c1ccc(F)cc1Br]

Step A: Ethyl 4-(2-bromo-4-fluorophenyl)-6-methyl-2-oxo-1,2,3,4-tetrahydropyrimidine-5-carboxylate A mixture of urea (2.90 g, 48 mmol), ethyl 3-oxobutanoate (5.22 g, 40 mmol), 2-bromo-4-fluorobenzaldehyde (8.12 g, 40 mmol), chlorotrimethylsilane (3.75 g, 35 mmol) and sodium iodide (4.85 g, 35 mmol) in anhydrous acetonitrile (50 mL) was stirred at 25° C. for 12 hours in the dark. The mixture was filtered and the filter cake was washed with a little acetonitrile to give the title compound as a white solid (5.72 g, 40%). The compound was characterized by the following spectroscopic data:

MS-ESI: (ESI, pos. ion) m/z: 357.0 [M+1]$^+$;
$^1$H NMR (400 MHz, DMSO-d$_6$): δ 9.80 (br.s, 1H), 9.22 (br.s, 1H), 6.97-6.85 (m, 3H), 6.10 (s, 1H), 4.06 (q, 2H), 2.52 (s, 3H), 1.12 (t, 3H).

Step B: Ethyl 4-(2-bromo-4-fluorophenyl)-2-chloro-6-methyl-1,4-dihydropyrimidine-5-carboxylate A mixture of ethyl 4-(2-bromo-4-fluorophenyl)-6-methyl-2-oxo-1,2,3,4-tetrahydropyrimidine-5-carboxylate (3.56 g, 10 mmol) and POCl$_3$ (15 mL) was stirred at 110° C. for 4 hours under N$_2$, then cooled to 25° C. POCl$_3$ was removed in vacuo and the residue was dissolved in chloroform (100 mL). Then the mixture was adjusted to pH 6-8 with strong ammonia. The organic phase was washed with brine (80 mL×3), dried over Na$_2$SO$_4$ and filtered. The filtrate was concentrated in vacuo. The residue was purified by a silica gel column chromatography (PETROLEUM ETHER/EtOAc (V/V)=5/1) to give the title compound as a white solid (1.73 g, 46%). The compound was characterized by the following spectroscopic data:

MS-ESI: (ESI, pos. ion) m/z: 375.0 [M+1]$^+$;
$^1$H NMR (400 MHz, DMSO-d$_6$): δ 9.82 (br.s, 1H), 6.92-6.83 (m, 3H), 6.12 (s, 1H), 4.08 (q, 2H), 2.52 (s, 3H), 1.08 (t, 3H).

Step C: Ethyl 4-(2-bromo-4-fluorophenyl)-2-(3-cyano-1H-1,2,4-triazol-1-yl)-6-methyl-1,4-dihydropyrimidine-5-carboxylate Ethyl 4-(2-bromo-4-fluorophenyl)-2-chloro-6-methyl-1,4-dihydropyrimidine-5-carboxylate (3.77 g, 10 mmol) was reacted with 1H-1,2,4-triazole-3-carbonitrile (2.82 g, 30 mmol) according to the procedure as described in Example 48, Step A to give the title compound as a pale yellow solid (2.16 g, 50%). The compound was characterized by the following spectroscopic data:

MS-ESI: (ESI, pos. ion) m/z: 433.0 [M+1]$^+$;
$^1$H NMR (400 MHz, DMSO-d$_6$): δ 9.68 (br.s, 1H), 8.14 (s, 1H), 7.53-7.19 (m, 3H), 6.12 (s, 1H), 4.06 (q, 2H), 2.46 (s, 3H), 1.12 (t, 3H).

Step D: Ethyl 4-(2-bromo-4-fluorophenyl)-6-(bromomethyl)-2-(3-cyano-1H-1,2,4-triazol-1-yl)-1,4-dihydropyrimidine-5-carboxylate Ethyl 4-(2-bromo-4-fluorophenyl)-2-(3-cyano-1H-1,2,4-triazol-1-yl)-6-methyl-1,4-dihydropyrimidine-5-carboxylate (0.35 g, 0.8 mmol) was reacted with NBS (0.14 g, 0.81 mmol) in chloroform (15 mL) according to the procedure as described in Example 1, Step B to give the title compound as pale yellow oil (0.33 g, 80%). The compound was characterized by the following spectroscopic data:

MS-ESI: (ESI, pos. ion) m/z: 511.0 [M+1]$^+$;
$^1$H NMR (400 MHz, DMSO-d$_6$): δ 9.67 (br.s, 1H), 8.15 (s, 1H), 7.52-7.18 (m, 3H), 6.10 (s, 1H), 4.59-4.40 (m, 2H), 4.09 (q, 2H), 1.10 (t, 3H).

Step E: 2-(4-((6-(2-bromo-4-fluorophenyl)-2-(3-cyano-1H-1,2,4-triazol-1-yl)-5-(ethoxycarbonyl)-3,6-dihydropyrimidin-4-yl)methyl)morpholin-2-yl) acetic acid Ethyl 4-(2-bromo-4-fluorophenyl)-6-(bromomethyl)-2-(3-cyano-1H-1,2,4-triazol-1-yl)-1,4-dihydropyrimidine-5-carboxylate (0.32 g, 0.62 mmol) was reacted with 2-(morpholin-2-yl)acetic acid hydrochloride (0.2 g, 1.1 mmol) according to the procedure as described in Example 1, Step C to give the title compound as a pale yellow solid (0.14 g, 40%). The compound was characterized by the following spectroscopic data:

MS-ESI: (ESI, pos. ion) m/z: 576.1 [M+1]$^+$;
$^1$H NMR (400 MHz, DMSO-d$_6$): δ 12.3 (br.s, 1H), 9.46 (br.s, 1H), 7.75 (s, 1H), 7.59-7.57 (m, 1H), 7.50-7.39 (m, 1H), 7.28-7.24 (m, 1H), 6.08 (s, 1H), 4.14-4.02 (m, 1H), 4.07-3.88 (m, 4H), 3.83-3.52 (m, 2H), 2.92-2.62 (m, 2H), 2.48-2.35 (m, 2H), 2.32-2.05 (m, 2H), 1.04 (t, 3H).

Example 86

4-((6-(2-bromo-4-fluorophenyl)-2-(3-cyano-1H-1,2,4-triazol-1-yl)-5-(ethoxycarbonyl)-3,6-dihydropyrimidin-4-yl)methyl)morpholine-2-carboxylic acid

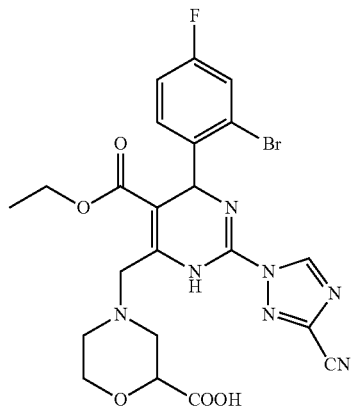 [SMILES: CCOC(=O)C1=C(CN2CCOC(C(=O)O)C2)NC(n2cnc(C#N)n2)=NC1c1ccc(F)cc1Br]

Ethyl 4-(2-bromo-4-fluorophenyl)-6-(bromomethyl)-2-(3-cyano-1H-1,2,4-triazol-1-yl)-1,4-dihydropyrimidine-5-carboxylate (0.32 g, 0.63 mmol) was reacted with morpholine-2-carboxylic acid hydrochloride (0.13 g, 0.75 mmol) according to the procedure as described in Example 3 to give the title compound as a pale yellow solid (0.15 g, 42%). The compound was characterized by the following spectroscopic data:

MS-ESI: (ESI, pos. ion) m/z: 562.1 [M+1]$^+$;
$^1$H NMR (400 MHz, CDCl$_3$): δ 9.17 (s, 1H), 8.03 (s, 1H), 7.85 (s, 1H), 7.58-7.22 (m, 3H), 6.07 (s, 1H), 4.11-3.97 (m, 2H), 3.86-3.71 (m, 2H), 3.67-3.41 (m, 4H), 3.25-2.91 (m, 3H), 1.05 (t, 3H).

Example 87

4-((6-(2-bromo-4-fluorophenyl)-5-(ethoxycarbonyl)-2-(1H-1,2,4-triazol-1-yl)-3,6-dihydropyrimidin-4-yl)methyl)morpholine-3-carboxylic acid

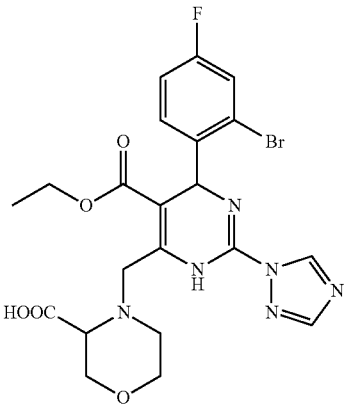 [SMILES: CCOC(=O)C1=C(CN2CCOCC2C(=O)O)NC(n2cncn2)=NC1c1ccc(F)cc1Br]

Step A: Ethyl 4-(2-bromo-4-fluorophenyl)-6-methyl-2-(1H-1,2,4-triazol-1-yl)-1,4-dihydropyrimidine-5-carboxylate Ethyl 4-(2-bromo-4-fluorophenyl)-2-chloro-6-methyl-1,4-dihydropyrimidine-5-carboxylate (15.04 g, 40 mmol) was reacted with 1H-1,2,4-triazole (8.28 g, 120 mmol) according to the procedure as described in Example 48, Step A to give the title compound as a yellow solid (9.8 g, 60%). The compound was characterized by the following spectroscopic data:

MS-ESI: (ESI, pos. ion) m/z: 408.1 [M+1]$^+$;

$^1$H NMR: (400 MHz, CDCl$_3$): δ 9.80 (s, 1H), 8.93 (s, 1H), 8.03 (s, 1H), 7.29-6.97 (m, 3H), 6.12 (s, 1H), 4.06 (q, 2H), 2.52 (s, 3H), 1.08 (t, 3H).

Step B: Ethyl 4-(2-bromo-4-fluorophenyl)-6-(bromomethyl)-2-(1H-1,2,4-triazol-1-yl)-1,4-dihydropyrimidine-5-carboxylate Ethyl 4-(2-bromo-4-fluorophenyl)-6-methyl-2-(1H-1,2,4-triazol-1-yl)-1,4-dihydropyrimidine-5-carboxylate (1.23 g, 3 mmol) was reacted with NBS (0.54 g, 3 mmol) according to the procedure as described in Example 1, Step B to give the title compound as a yellow solid (1.02 g, 70%). The compound was characterized by the following spectroscopic data:

MS-ESI: (ESI, pos. ion) m/z: 486.0 [M+1]$^+$;

$^1$H NMR: (400 MHz, CDCl$_3$): δ 9.82 (s, 1H), 8.90 (s, 1H), 8.01 (s, 1H), 7.27-6.95 (m, 3H), 6.10 (s, 1H), 4.56-4.41 (m, 2H), 4.05 (q, 2H), 1.07 (t, 3H).

Step C: 4-((6-(2-bromo-4-fluorophenyl)-5-(ethoxycarbonyl)-2-(1H-1,2,4-triazol-1-yl)-3,6-dihydropyrimidin-4-yl)methyl)morpholine-3-carboxylic acid Ethyl 4-(2-bromo-4-fluorophenyl)-6-(bromomethyl)-2-(1H-1,2,4-triazol-1-yl)-1,4-dihydropyrimidine-5-carboxylate (1.75 g, 3 mmol) was reacted with morpholine-3-carboxylic acid hydrochloride (0.6 g, 3.6 mmol) according to the procedure as described in Example 1, Step C to give the title compound as a pale yellow solid (0.6 g, 31%). The compound was characterized by the following spectroscopic data:

MS-ESI: (ESI, pos. ion) m/z: 537.1 [M+1]$^+$;

$^1$H NMR (400 MHz, CDCl$_3$): δ 9.80 (s, 1H), 8.93 (s, 1H), 8.03 (s, 1H), 7.36-6.97 (m, 3H), 6.17 (s, 1H), 4.20-4.00 (m, 4H), 3.85-3.62 (m, 4H), 3.58-3.45 (m, 1H), 3.22-3.11 (m, 1H), 2.62-2.56 (m, 1H), 1.12 (t, 3H).

Example 88

4-((6-(2-bromo-4-fluorophenyl)-5-(ethoxycarbonyl)-2-(1H-1,2,4-triazol-1-yl)-3,6-dihydropyrimidin-4-yl)methyl)morpholine-2-carboxylic acid

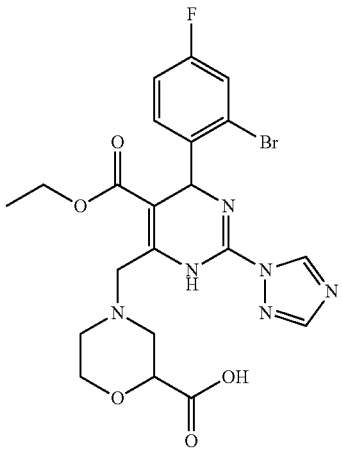 [SMILES: CCOC(=O)C1=C(CN2CCOC(C(=O)O)C2)NC(n2cncn2)=NC1c1ccc(F)cc1Br]

Ethyl 4-(2-bromo-4-fluorophenyl)-6-(bromomethyl)-2-(1H-1,2,4-triazol-1-yl)-1,4-dihydropyrimidine-5-carboxylate (0.5 g, 1.03 mmol) was reacted with morpholine-2-carboxylic acid hydrochloride (0.21 g, 1.23 mmol) according to the procedure as described in Example 1, Step C to give the title compound as a pale yellow solid (0.18 g, 33%). The compound was characterized by the following spectroscopic data:

MS-ESI: (ESI, pos. ion) m/z: 537.1 [M+1]$^+$;

$^1$H NMR (400 MHz, CDCl$_3$): δ 9.60 (s, 1H), 9.08 (s, 1H), 8.31 (s, 1H), 7.58-7.23 (m, 3H), 6.06 (s, 1H), 4.16-3.88 (m, 7H), 2.68-2.32 (m, 4H), 1.19 (t, 3H).

Example 89

2-(4-((6-(2-bromo-4-fluorophenyl)-5-(ethoxycarbonyl)-2-(1H-1,2,4-triazol-1-yl)-3,6-dihydropyrimidin-4-yl)methyl)morpholin-2-yl)acetic acid

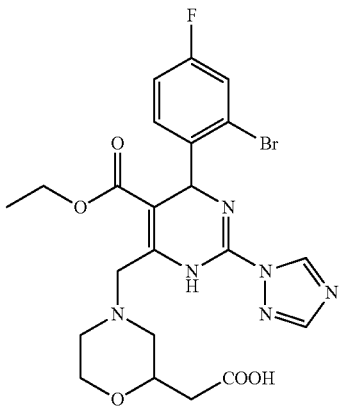 [SMILES: CCOC(=O)C1=C(CN2CCOC(CC(=O)O)C2)NC(n2cncn2)=NC1c1ccc(F)cc1Br]

Ethyl 4-(2-bromo-4-fluorophenyl)-6-(bromomethyl)-2-(1H-1,2,4-triazol-1-yl)-1,4-dihydropyrimidine-5-carboxylate (0.5 g, 1.03 mmol) was reacted with 2-(morpholin-2-yl) acetic acid hydrochloride (0.19 g, 1.03 mmol) according to the procedure as described in Example 1, Step C to give the title compound as a yellow solid (0.22 g, 39%). The compound was characterized by the following spectroscopic data:

MS-ESI: (ESI, pos. ion) m/z: 551.1 [M+1]$^+$;

$^1$H NMR (400 MHz, CDCl$_3$): δ 9.55 (s, 1H), 8.89 (s, 1H), 8.04 (s, 1H), 7.35-6.98 (m, 3H), 6.17 (s, 1H), 4.15-3.82 (m, 7H), 2.67-2.37 (m, 6H), 1.12 (t, 3H).

Example 90

2-(4-((6-(2-bromo-4-fluorophenyl)-2-(1-(2-ethoxy-2-oxoethyl)-1H-1,2,4-triazol-3-yl)-5-(ethoxycarbonyl)-3,6-dihydropyrimidin-4-yl)methyl)morpholin-2-yl) acetic acid

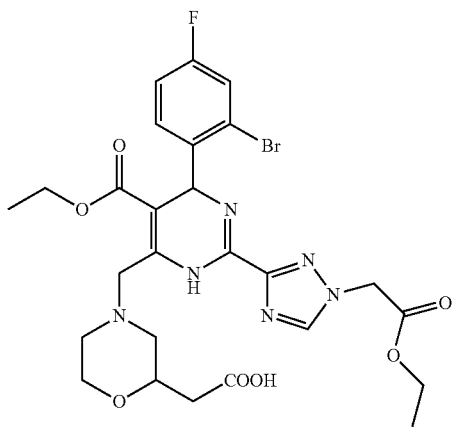 [SMILES: CCOC(=O)Cn1cnc(C2=NC(c3ccc(F)cc3Br)C(C(=O)OCC)=C(CN3CCOC(CC(=O)O)C3)N2)n1]

Step A: Ethyl 2-(3-cyano-1H-1,2,4-triazol-1-yl)acetate

Ethyl 2-bromoacetate (8.88 g, 53.15 mmol) was reacted with 1H-1,2,4-triazole-3-carbonitrile (5 g, 53.15 mmol) according to the procedure as described in Example 48, Step A to give the title compound as a white solid (8 g, 84%). The compound was characterized by the following spectroscopic data:

MS-ESI: (ESI, pos. ion) m/z: 181.2 [M+1]$^+$;

$^1$H NMR (400 MHz, CDCl$_3$): δ 8.34 (s, 1H), 5.06 (s, 2H), 4.31 (q, 2H), 1.32 (t, 3H).

Step B: Methyl 2-(3-carbamimidoyl-1H-1,2,4-triazol-1-yl)acetate hydrochloride

Ethyl 2-(3-cyano-1H-1,2,4-triazol-1-yl)acetate (2 g, 11.2 mmol) was reacted with sodium methoxide (0.85 g, 15.68 mmol) and ammonium chloride (0.89 g, 16.8 mmol) according to the procedure as described in Example 61, Step B to give the title compound as a white solid (1.35 g, 55%). The compound was characterized by the following spectroscopic data:

MS-ESI: (ESI, pos. ion) m/z: 184.2 [M+1]$^+$;

$^1$H NMR (400 MHz, D$_2$O): δ 8.60 (s, 1H), 8.34 (s, 1H), 5.26 (s, 2H), 3.73 (s, 3H).

Step C: Ethyl 4-(2-bromo-4-fluorophenyl)-2-(1-(2-ethoxy-2-oxoethyl)-1H-1,2,4-triazol-3-yl)-6-methyl-1,4-dihydropyrimidine-5-carboxylate Methyl 2-(3-carbamimidoyl-1H-1,2,4-triazol-1-yl)acetate hydrochloride (0.6 g, 2.73 mmol) was reacted with 2-bromo-4-fluorobenzaldehyde (0.55 g, 2.73 mmol) and ethyl 3-oxobutanoate (0.35 g, 2.73 mmol) according to the procedure as described in Example 1, Step A to give the title compound as a yellow solid (0.6 g, 45%). The compound was characterized by the following spectroscopic data:

MS-ESI: (ESI, pos. ion) m/z: 494.1 [M+1]$^+$;

$^1$H NMR (400 MHz, CDCl$_3$): δ 8.21 (s, 1H), 7.39-7.35 (m, 1H), 7.28-7.26 (m, 1H), 6.97-6.94 (m, 1H), 6.16 (s, 1H), 5.05 (s, 2H), 4.25 (q, 2H), 4.05 (q, 2H), 2.52 (br.s, 3H), 1.28 (t, 3H), 1.12 (t, 3H).

Step D: Ethyl 4-(2-bromo-4-fluorophenyl)-6-(bromomethyl)-2-(1-(2-ethoxy-2-oxoethyl)-1H-1,2,4-triazol-3-yl)-1,4-dihydropyrimidine-5-carboxylate Ethyl 4-(2-bromo-4-fluorophenyl)-2-(1-(2-ethoxy-2-oxoethyl)-1H-1,2,4-triazol-3-yl)-6-methyl-1,4-dihydropyrimidine-5-carboxylate (0.45 g, 0.91 mmol) was reacted with NBS (0.16 g, 0.91 mmol) according to the procedure as described in Example 1, Step B to give the title compound as a yellow solid (0.36 g, 69%). The compound was characterized by the following spectroscopic data:

MS-ESI: (ESI, pos. ion) m/z: 572.0 [M+1]$^+$;

$^1$H NMR (400 MHz, CDCl$_3$): δ 8.23 (s, 1H), 7.45-7.41 (m, 1H), 7.31-7.27 (m, 1H), 7.03-6.99 (m, 1H), 6.10 (s, 1H), 5.03 (s, 2H), 4.99 (d, 1H), 4.67 (d, 1H), 4.26 (q, 2H), 4.13 (q, 2H), 1.29 (t, 3H), 1.17 (t, 3H).

Step E: 2-(4-((6-(2-bromo-4-fluorophenyl)-2-(1-(2-ethoxy-2-oxoethyl)-1H-1,2,4-triazol-3-yl)-5-(ethoxycarbonyl)-3,6-dihydropyrimidin-4-yl)methyl)morpholin-2-yl)acetic acid Ethyl 4-(2-bromo-4-fluorophenyl)-6-(bromomethyl)-2-(1-(2-ethoxy-2-oxoethyl)-1H-1,2,4-triazol-3-yl)-1,4-dihydropyrimidine-5-carboxylate (0.57 g, 1 mmol) was reacted with 2-(morpholin-2-yl)acetic acid hydrochloride (0.3 g, 1.65 mmol) according to the procedure as described in Example 1, Step C to give the title compound as a yellow solid (0.34 g, 53%). The compound was characterized by the following spectroscopic data:

MS-ESI: (ESI, pos. ion) m/z: 637.2 [M+1]$^+$;

$^1$H NMR (400 MHz, CDCl$_3$): δ 8.23 (s, 1H), 7.34-7.30 (m, 1H), 7.28-7.26 (m, 1H), 6.96-6.92 (m, 1H), 6.24 (s, 1H), 5.3 (s, 2H), 4.24 (q, 2H), 4.13-3.82 (m, 7H), 2.80-2.15 (m, 6H), 1.28 (t, 3H), 1.14 (t, 3H).

Example 91

4-((6-(2-bromo-4-fluorophenyl)-2-(1-(2-ethoxy-2-oxoethyl)-1H-1,2,4-triazol-3-yl)-5-(ethoxycarbonyl)-3,6-dihydropyrimidin-4-yl)methyl)morpholine-2-carboxylic acid

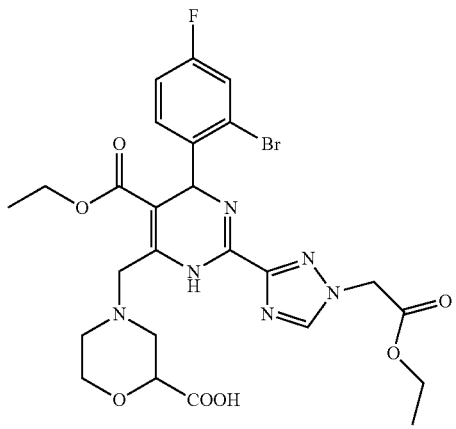 [SMILES: CCOC(=O)Cn1cnc(C2=NC(c3ccc(F)cc3Br)C(C(=O)OCC)=C(CN3CCOC(C(=O)O)C3)N2)n1]

Ethyl 4-(2-bromo-4-fluorophenyl)-6-(bromomethyl)-2-(1-(2-ethoxy-2-oxoethyl)-1H-1,2,4-triazol-3-yl)-1,4-dihydropyrimidine-5-carboxylate (0.57 g, 1 mmol) was reacted with morpholine-2-carboxylic acid hydrochloride (0.2 g, 1.2 mmol) according to the procedure as described in Example 1, Step C to give the title compound as a yellow solid (0.13 g, 20%). The compound was characterized by the following spectroscopic data:

MS-ESI: (ESI, pos. ion) m/z: 623.1 [M+1]$^+$;
$^1$H NMR (400 MHz, CDCl$_3$): δ 8.21 (s, 1H), 7.34-7.26 (m, 2H), 6.97-6.96 (m, 1H), 6.22 (s, 1H), 5.03 (s, 2H), 4.42-4.35 (m, 1H), 4.30-4.22 (m, 4H), 4.04-3.99 (m, 2H), 3.97-3.72 (m, 2H), 2.92-2.69 (m, 4H), 1.30 (t, 3H), 1.12 (t, 3H).

Example 92

1-((6-(2-bromo-4-fluorophenyl)-5-(ethoxycarbonyl)-2-(thiazol-2-yl)-3,6-dihydropyrimidin-4-yl)methyl)pyrrolidine-2-carboxylic acid

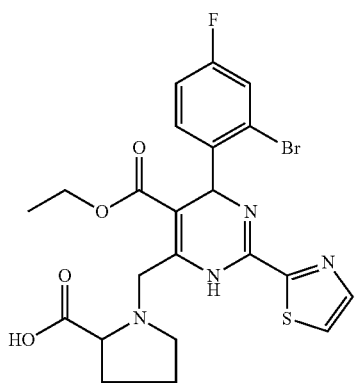 [SMILES: CCOC(=O)C1=C(CN2CCCC2C(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (1 g, 2 mmol) was reacted with pyrrolidine-2-carboxylic acid (0.23 g, 2 mmol) according to the procedure as described in Example 28 to give the title compound as a yellow solid (0.27 g, 25%). The compound was characterized by the following spectroscopic data:

MS-ESI: (ESI, pos. ion) m/z: 537.1 [M+1]$^+$;
$^1$H NMR (400 MHz, CDCl$_3$): δ 7.85 (br.s, 1H), 7.63-7.56 (m, 2H), 7.40-7.33 (m, 2H), 7.09-7.07 (m, 1H), 6.15 (s, 1H), 4.81-4.64 (m, 1H), 4.22-4.12 (m, 1H), 4.07 (q, 2H), 3.95-3.68 (m, 2H), 2.95-2.86 (m, 1H), 2.44-2.34 (m, 2H), 2.09-1.92 (m, 2H), 1.10 (t, 3H).

Example 93

1-((6-(2-bromo-4-fluorophenyl)-5-(ethoxycarbonyl)-2-(thiazol-2-yl)-3,6-dihydropyrimidin-4-yl)methyl)piperidine-2-carboxylic acid

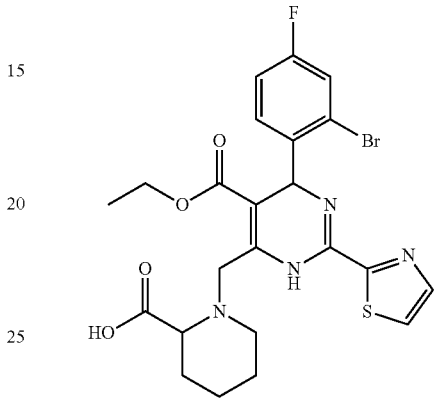

Ethyl 4-(2-bromo-4-fluorophenyl)-6-(bromomethyl)-2-(thiazol-2-yl)-1,4-dihydropyrimidine-5-carboxylate (1 g, 2 mmol) was reacted with piperidine-2-carboxylic acid (0.26 g, 2 mmol) according to the procedure as described in Example 28 to give the title compound as a yellow solid (0.3 g, 27%). The compound was characterized by the following spectroscopic data:

MS-ESI: (ESI, pos. ion) m/z: 551.0 [M+1]$^+$;
$^1$H NMR (400 MHz, CDCl$_3$): δ 7.84-7.80 (m, 2H), 7.50 (br.s, 1H), 7.33-7.26 (m, 2H), 7.05-6.95 (m, 1H), 6.14 (s, 1H), 4.45-4.35 (m, 1H), 4.05 (q, 2H), 3.75-3.45 (m, 4H), 2.15-1.95 (m, 2H), 1.78-1.45 (m, 4H), 1.10 (t, 3H).

Example 94

(2S)-1-((6-(2-bromo-4-fluorophenyl)-5-(ethoxycarbonyl)-2-(1H-1,2,4-triazol-1-yl)-3,6-dihydropyrimidin-4-yl)methyl)pyrrolidine-2-carboxylic acid

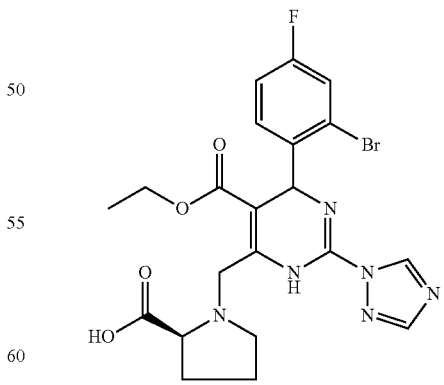

Ethyl 4-(2-bromo-4-fluorophenyl)-6-(bromomethyl)-2-(1H-1,2,4-triazol-1-yl)-1,4-dihydropyrimidine-5-carboxylate (0.5 g, 1.03 mmol) was reacted with (S)-pyrrolidine-2-carboxylic acid (0.12 g, 1.03 mmol) according to the procedure as described in Example 28 to give the title compound as a yellow solid (0.18 g, 33%). The compound was characterized by the following spectroscopic data:

MS-ESI: (ESI, pos. ion) m/z: 521.1 [M+1]$^+$;

$^1$H NMR (400 MHz, CDCl$_3$): δ 9.23 (s, 1H), 7.94 (s, 1H), 7.37-7.02 (m, 3H), 6.15 (d, 1H), 4.63-4.62 (m, 1H), 4.35-4.25 (m, 2H), 4.05 (q, 2H), 3.83-3.75 (m, 1H), 2.95-2.85 (m, 1H), 2.45-2.34 (m, 2H), 2.09-1.95 (m, 2H), 1.12 (t, 3H).

Example 95

4-((6-(2-chloro-4-fluorophenyl)-2-(3,5-difluoropyridin-2-yl)-5-(ethoxycarbonyl)-3,6-dihydropyrimidin-4-yl)methyl)morpholine-3-carboxylic acid

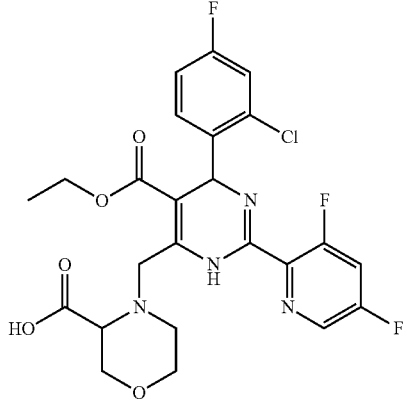 [SMILES: CCOC(=O)C1=C(CN2CCOCC2C(=O)O)NC(c2ncc(F)cc2F)=NC1c1ccc(F)cc1Cl]

Ethyl 6-(bromomethyl)-4-(2-chloro-4-fluorophenyl)-2-(3,5-difluoropyridin-2-yl)-1,4-dihydropyrimidine-5-carboxylate (0.75 g, 1.53 mmol) (The compound was synthesized according to the procedure as described in U.S. Pat. No. 7,074,784) was reacted with morpholine-3-carboxylic acid (0.2 g, 1.53 mmol) according to the procedure as described in Example 28 to give the title compound as a yellow solid (0.54 g, 65%). The compound was characterized by the following spectroscopic data:

MS-ESI: (ESI, pos. ion) m/z: 539.1 [M+1]$^+$;

$^1$H NMR (400 MHz, DMSO-d$_6$): δ 9.75 (s, 1H), 8.55 (d, 1H), 8.05-7.95 (m, 1H), 7.45-7.35 (m, 2H), 7.25-7.15 (m, 1H), 6.0 (s, 1H), 4.30-4.04 (m, 2H), 4.02-3.92 (m, 3H), 3.84-3.72 (m, 2H), 3.68-3.52 (m, 2H), 3.11-3.07 (m, 1H), 2.55-2.39 (m, 1H), 1.06 (t, 3H).

Example 96

2-(4-((6-(2-bromo-4-fluorophenyl)-2-(3,5-difluoropyridin-2-yl)-5-(ethoxycarbonyl)-3,6-dihydropyrimidin-4-yl)methyl)morpholin-3-yl)acetic acid

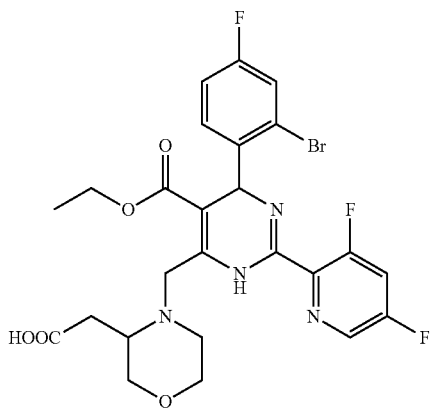 [SMILES: CCOC(=O)C1=C(CN2CCOCC2CC(=O)O)NC(c2ncc(F)cc2F)=NC1c1ccc(F)cc1Br]

Ethyl 6-(bromomethyl)-4-(2-chloro-4-fluorophenyl)-2-(3,5-difluoropyridin-2-yl)-1,4-dihydropyrimidine-5-carboxylate (0.82 g, 1.53 mmol) (The compound was synthesized according to the procedure as described in U.S. Pat. No. 7,074,784) was reacted with 2-(morpholin-3-yl)acetic acid hydrochloride (0.28 g, 1.53 mmol) according to the procedure as described in Example 28 to give the title compound as a yellow solid (0.38 g, 42%). The compound was characterized by the following spectroscopic data:

MS-ESI: (ESI, pos. ion) m/z: 597.1 [M+1]$^+$;

$^1$H NMR (400 MHz, DMSO-d$_6$): δ 9.75 (s, 1H), 8.55 (d, 1H), 8.05-7.95 (m, 1H), 7.58-7.55 (m, 1H), 7.44-7.38 (m, 1H), 7.24-7.18 (m, 1H), 4.19-3.90 (m, 4H), 3.77-3.53 (m, 4H), 3.11-2.69 (m, 3H), 2.51-2.41 (m, 2H), 1.07 (t, 3H).

Example 97

2-(4-((6-(2-chloro-4-fluorophenyl)-5-(ethoxycarbonyl)-2-(3-fluoropyridin-2-yl)-3,6-dihydropyrimidin-4-yl)methyl)morpholin-3-yl)acetic acid

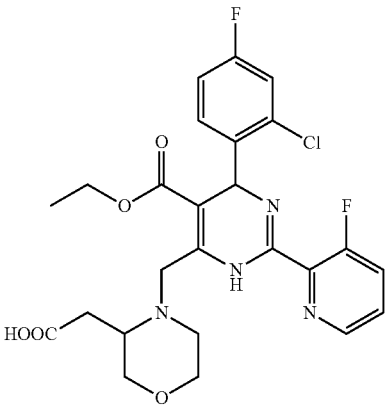 [SMILES: CCOC(=O)C1=C(CN2CCOCC2CC(=O)O)NC(c2ncccc2F)=NC1c1ccc(F)cc1Cl]

Step A: Ethyl 4-(2-chloro-4-fluorophenyl)-2-(3-fluoropyridin-2-yl)-6-methyl-1,4-dihydropyrimidine-5-carboxylate 3-fluoropicolinimidamide hydrochloride (5.53 g, 31.5 mmol) was reacted with 2-chloro-4-fluorobenzaldehyde (5 g, 31.5 mmol) and ethyl 3-oxobutanoate (4.1 g, 31.5 mmol) according to the procedure as described in Example 1, Step A to give the title compound as a yellow solid (5.56 g, 45%). The compound was characterized by the following spectroscopic data:

MS-ESI: (ESI, pos. ion) m/z: 392.1 [M+1]$^+$;

$^1$H NMR (400 MHz, DMSO-d$_6$): δ 10.03 (s, 1H), 8.80-8.16 (m, 1H), 7.78 (dd, 1H), 7.67-7.44 (m, 2H), 7.36 (dd, 1H), 7.04-6.92 (m, 1H), 6.27 (s, 1H), 4.08 (q, 2H), 2.51 (s, 3H), 1.10 (t, 3H).

Step B: Ethyl 6-(bromomethyl)-4-(2-chloro-4-fluorophenyl)-2-(3-fluoropyridin-2-yl)-1,4-dihydropyrimidine-5-carboxylate Ethyl 4-(2-chloro-4-fluorophenyl)-2-(3-fluoropyridin-2-yl)-6-methyl-1,4-dihydropyrimidine-5-carboxylate (3 g, 7.7 mmol) was reacted with NBS (1.51 g, 8.47 mmol) according to the procedure as described in Example 1, Step B to give the title compound as a yellow solid (2.2 g, 62%). The compound was characterized by the following spectroscopic data:

MS-ESI: (ESI, pos. ion) m/z: 470.0 [M+1]$^+$;

$^1$H NMR (400 MHz, DMSO-d$_6$): δ 10.75 (s, 1H), 8.50-8.32 (m, 1H), 7.78 (dd, 1H), 7.65-7.43 (m, 2H), 7.36-7.26 (m, 1H), 7.04-6.91 (m, 1H), 6.19 (s, 1H), 4.89-4.67 (m, 2H), 4.18 (q, 2H), 1.10 (t, 3H).

Step C: 2-(4-((6-(2-chloro-4-fluorophenyl)-5-(ethoxycarbonyl)-2-(3-fluoropyridin-2-yl)-3,6-dihydropyrimidin-4-yl)methyl)morpholin-3-yl)acetic acid Ethyl 6-(bromomethyl)-4-(2-chloro-4-fluorophenyl)-2-(3-fluoropyridin-2-yl)-1,4-dihydropyrimidine-5-carboxylate (0.72 g, 1.53 mmol) was reacted with 2-(morpholin-3-yl) acetic acid hydrochloride (0.28 g, 1.53 mmol) according to the procedure as described in Example 1, Step C to give the title compound as a yellow solid (0.39 g, 48%). The compound was characterized by the following spectroscopic data:

MS-ESI: (ESI, pos. ion) m/z: 535.2 [M+1]$^+$;

$^1$H NMR (400 MHz, DMSO-d$_6$): δ 9.80 (s, 1H), 8.59-8.51 (m, 1H), 7.62-7.51 (m, 2H), 7.42-7.35 (m, 2H), 7.17-7.12 (m, 1H), 6.15 (s, 1H), 4.20-3.91 (m, 4H), 3.81-3.52 (m, 4H), 3.11-2.65 (m, 3H), 2.56-2.45 (m, 2H), 1.05 (t, 3H).

Example 98

4-((6-(2,4-dichlorophenyl)-5-(ethoxycarbonyl)-2-(3-fluoropyridin-2-yl)-3,6-dihydropyrimidin-4-yl)methyl)morpholine-3-carboxylic acid

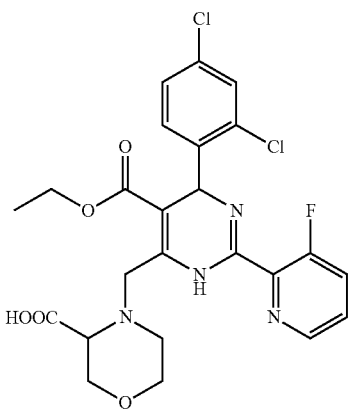 [SMILES: CCOC(=O)C1=C(CN2CCOCC2C(=O)O)NC(c2ncccc2F)=NC1c1ccc(Cl)cc1Cl]

Step A: Ethyl 4-(2,4-dichlorophenyl)-2-(3-fluoropyridin-2-yl)-6-methyl-1,4-dihydropyrimidine-5-carboxylate 3-fluoropicolinimidamide hydrochloride (5.53 g, 31.5 mmol) was reacted with 2,4-dichlorobenzaldehyde (5.51 g, 31.5 mmol) and ethyl 3-oxobutanoate (4.1 g, 31.5 mmol) according to the procedure as described in Example 1, Step A to give the title compound as a yellow solid (6.94 g, 54%). The compound was characterized by the following spectroscopic data:

MS-ESI: (ESI, pos. ion) m/z: 408.1 [M+1]$^+$;

$^1$H NMR (400 MHz, DMSO-d$_6$): δ 10.02 (s, 1H), 8.78-8.25 (m, 1H), 7.72 (d, 1H), 7.65-7.42 (m, 2H), 7.25-7.11 (m, 2H), 6.31 (s, 1H), 4.08 (q, 2H), 2.46 (s, 3H), 1.16 (t, 3H).

Step B: Ethyl 6-(bromomethyl)-4-(2,4-dichlorophenyl)-2-(3-fluoropyridin-2-yl)-1,4-dihydropyrimidine-5-carboxylate Ethyl 4-(2,4-dichlorophenyl)-2-(3-fluoropyridin-2-yl)-6-methyl-1,4-dihydropyrimidine-5-carboxylate (3.14 g, 7.7 mmol) was reacted with NBS (1.51 g, 8.47 mmol) according to the procedure as described in Example 1, Step B to give the title compound as a yellow solid (2.44 g, 65%). The compound was characterized by the following spectroscopic data:

MS-ESI: (ESI, pos. ion) m/z: 486.0 [M+1]$^+$;

$^1$H NMR (400 MHz, DMSO-d$_6$): δ 10.08 (s, 1H), 8.71-8.49 (m, 1H), 7.72 (d, 1H), 7.65-7.42 (m, 2H), 7.25-7.11 (m, 2H), 6.23 (s, 1H), 4.65-4.56 (m, 2H), 4.10 (q, 2H), 1.10 (t, 3H).

Step C: 4-((6-(2,4-dichlorophenyl)-5-(ethoxycarbonyl)-2-(3-fluoropyridin-2-yl)-3,6-dihydropyrimidin-4-yl)methyl)morpholine-3-carboxylic acid Ethyl 6-(bromomethyl)-4-(2,4-dichlorophenyl)-2-(3-fluoropyridin-2-yl)-1,4-dihydropyrimidine-5-carboxylate (0.75 g, 1.53 mmol) was reacted with morpholine-3-carboxylic acid (0.2 g, 1.53 mmol) according to the procedure as described in Example 1, Step C to give the title compound as a yellow solid (0.34 g, 41%). The compound was characterized by the following spectroscopic data:

MS-ESI: (ESI, pos. ion) m/z: 537.1 [M+1]

$^1$H NMR (400 MHz, DMSO-d$_6$): δ 9.83 (s, 1H), 8.59-8.50, 1H), 7.62-7.50 (m, 3H), 7.42-7.37 (m, 2H), 6.07 (s, 1H), 4.29-4.04 (m, 2H), 4.01-3.91 (m, 3H), 3.85-3.82 (m, 1H), 3.74-3.71 (m, 1H), 3.66-3.64 (m, 1H), 3.61-3.52 (m, 1H), 3.11-3.07 (m, 1H), 2.54-2.41 (m, 1H), 1.07 (t, 3H).

Example 99

4-((6-(2-chloro-4-fluorophenyl)-5-(ethoxycarbonyl)-2-(pyridin-3-yl)-3,6-dihydropyrimidin-4-yl)methyl)morpholine-3-carboxylic acid

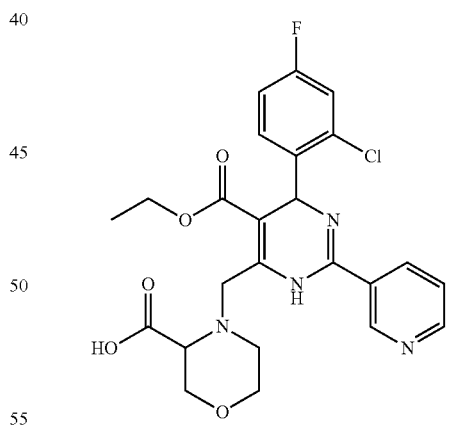

Step A: Ethyl 4-(2-chloro-4-fluorophenyl)-6-methyl-2-(pyridin-3-yl)-1,4-dihydropyrimidine-5-carboxylate Nicotinimidamide hydrochloride (4.97 g, 31.5 mmol) was reacted with 2-chloro-4-fluorobenzaldehyde (5 g, 31.5 mmol) and ethyl 3-oxobutanoate (4.1 g, 31.5 mmol) according to the procedure as described in Example 1, Step A to give the title compound as a yellow solid (5.89 g, 50%). The compound was characterized by the following spectroscopic data:

MS-ESI: (ESI, pos. ion) m/z: 374.1 [M+1]$^+$;

$^1$H NMR (400 MHz, DMSO-d$_6$): δ 9.88 (s, 1H), 9.08 (d, 1H), 8.75-8.65 (m, 1H), 8.30-8.20 (m, 1H), 7.78-7.68 (m, 1H), 7.58 (t, 1H), 7.36 (dd, 1H), 7.04-6.92 (m, 1H), 6.23 (s, 1H), 4.08 (q, 2H), 2.26 (s, 3H), 1.16 (t, 3H).

Step B: Ethyl 6-(bromomethyl)-4-(2-chloro-4-fluorophenyl)-2-(pyridin-3-yl)-1,4-dihydropyrimidine-5-carboxylate Ethyl 4-(2-chloro-4-fluorophenyl)-6-methyl-2-(pyridin-3-yl)-1,4-dihydropyrimidine-5-carboxylate (5 g, 13.4 mmol) was reacted with NBS (2.87 g, 16.1 mmol) according to the procedure as described in Example 1, Step B to give the title compound as a yellow solid (4.25 g, 70%). The compound was characterized by the following spectroscopic data:

MS-ESI: (ESI, pos. ion) m/z: 452.0 [M+1]$^+$;

$^1$H NMR (400 MHz, DMSO-d$_6$): δ 11.03 (s, 1H), 9.08 (d, 1H), 8.75-8.65 (m, 1H), 8.30-8.19 (m, 1H), 7.78-7.68 (m, 1H), 7.58-7.47 (m, 1H), 7.36-7.26 (m, 1H), 7.04-6.94 (m, 1H), 6.18 (s, 1H), 4.85-4.65 (m, 2H), 4.06 (q, 2H), 1.12 (t, 3H).

Step C: 4-((6-(2-chloro-4-fluorophenyl)-5-(ethoxycarbonyl)-2-(pyridin-3-yl)-3,6-dihydropyrimidin-4-yl)methyl)morpholine-3-carboxylic acid Ethyl 6-(bromomethyl)-4-(2-chloro-4-fluorophenyl)-2-(pyridin-3-yl)-1,4-dihydropyrimidine-5-carboxylate (1 g, 2.2 mmol) was reacted with morpholine-3-carboxylic acid (0.29 g, 2.2 mmol) according to the procedure as described in Example 1, Step C to give the title compound as a yellow solid (0.39 g, 35%). The compound was characterized by the following spectroscopic data:

MS-ESI: (ESI, pos. ion) m/z: 503.2 [M+1]$^+$;

$^1$H NMR (400 MHz, DMSO-d$_6$): δ 12.39 (s, 1H), 9.90 (s, 1H), 9.30-8.94 (m, 1H), 8.75 (dd, 1H), 8.30-8.21 (m, 1H), 7.78 (dd, 1H), 7.58-7.45 (m, 1H), 7.36-7.24 (m, 1H), 7.04-6.93 (m, 1H), 6.03 (s, 1H), 4.41-3.87 (m, 4H), 3.82-3.16 (m, 3H), 2.91-2.34 (m, 4H), 1.10 (t, 3H).

Example 100

4-((6-(2-chloro-4-fluorophenyl)-5-(ethoxycarbonyl)-2-(pyrazin-2-yl)-3,6-dihydropyrimidin-4-yl)methyl)morpholine-3-carboxylic acid

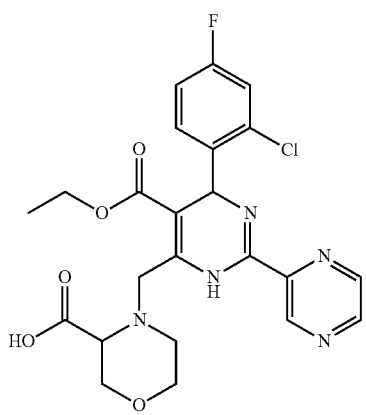 [SMILES: CCOC(=O)C1=C(CN2CCOCC2C(=O)O)NC(c2cnccn2)=NC1c1ccc(F)cc1Cl]

Step A: Ethyl 4-(2-chloro-4-fluorophenyl)-6-methyl-2-(pyrazin-2-yl)-1,4-dihydropyrimidine-5-carboxylate Pyrazine-2-carboximidamide hydrochloride (5 g, 31.5 mmol) was reacted with 2-chloro-4-fluorobenzaldehyde (5 g, 31.5 mmol) and ethyl 3-oxobutanoate (4.1 g, 31.5 mmol) according to the procedure as described in Example 1, Step A to give the title compound as a yellow solid (4.84 g, 41%). The compound was characterized by the following spectroscopic data:

MS-ESI: (ESI, pos. ion) m/z: 375.1 [M+1]$^+$;

$^1$H NMR (400 MHz, DMSO-d$_6$): δ 9.88 (s, 1H), 9.34 (s, 1H), 8.94-8.66 (m, 2H), 7.78 (dd, 1H), 7.36 (dd, 1H), 7.04-6.99 (m, 1H), 6.21 (s, 1H), 4.03 (q, 2H), 2.51 (s, 3H), 1.12 (t, 3H).

Step B: Ethyl 6-(bromomethyl)-4-(2-chloro-4-fluorophenyl)-2-(pyrazin-2-yl)-1,4-dihydropyrimidine-5-carboxylate Ethyl 4-(2-chloro-4-fluorophenyl)-6-methyl-2-(pyrazin-2-yl)-1,4-dihydropyrimidine-5-carboxylate (5.02 g, 13.4 mmol) was reacted with NBS (2.87 g, 16.1 mmol) according to the procedure as described in Example 1, Step B to give the title compound as a yellow solid (3.95 g, 65%). The compound was characterized by the following spectroscopic data:

MS-ESI: (ESI, pos. ion) m/z: 453.0 [M+1]$^+$;

$^1$H NMR (400 MHz, DMSO-d$_6$): δ 10.52 (s, 1H), 9.34 (s, 1H), 9.00-8.48 (m, 2H), 7.78-7.60 (m, 1H), 7.36-7.21 (m, 1H), 7.04-6.92 (m, 1H), 6.25 (s, 1H), 4.61-4.50 (m, 2H), 4.09 (q, 2H), 1.16 (t, 3H).

Step C: 4-((6-(2-chloro-4-fluorophenyl)-5-(ethoxycarbonyl)-2-(pyrazin-2-yl)-3,6-dihydropyrimidin-4-yl)methyl)morpholine-3-carboxylic acid Ethyl 6-(bromomethyl)-4-(2-chloro-4-fluorophenyl)-2-(pyrazin-2-yl)-1,4-dihydropyrimidine-5-carboxylate (1 g, 2.2 mmol) was reacted with morpholine-3-carboxylic acid (0.29 g, 2.2 mmol) according to the procedure as described in Example 1, Step C to give the title compound as a yellow solid (0.32 g, 29%). The compound was characterized by the following spectroscopic data:

MS-ESI: (ESI, pos. ion) m/z: 504.2 [M+1]$^+$;

$^1$H NMR (400 MHz, DMSO-d$_6$): δ 12.65 (br.s, 1H), 10.41 (s, 1H), 9.34 (s, 1H), 8.98-8.41 (m, 2H), 7.70-7.58 (m, 1H), 7.36-7.19 (m, 1H), 7.14-7.08 (m, 1H), 6.01 (s, 1H), 4.28-4.15 (m, 1H), 4.04 (q, 2H), 3.91-3.75 (m, 2H), 3.70-3.43 (m, 3H), 3.37 (s, 1H), 3.02-2.21 (m, 2H), 1.15 (t, 3H).

Example 101

4-((6-(2-bromo-4-fluorophenyl)-5-(ethoxycarbonyl)-2-(2,4,6-trifluorophenyl)-3,6-dihydropyrimidin-4-yl)methyl)morpholine-3-carboxylic acid

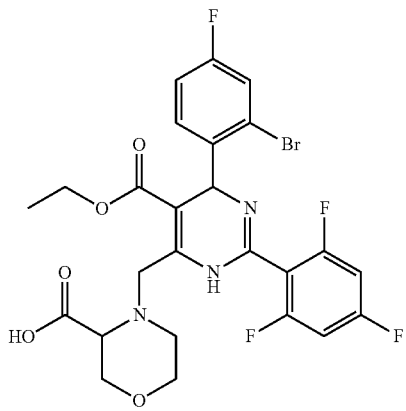 [SMILES: CCOC(=O)C1=C(CN2CCOCC2C(=O)O)NC(c2c(F)cc(F)cc2F)=NC1c1ccc(F)cc1Br]

Step A: Ethyl 4-(2-bromo-4-fluorophenyl)-6-(bromomethyl)-2-(2,4,6-trifluorophenyl)-1,4-dihydropyrimidine-5-carboxylate Ethyl 4-(2-bromo-4-fluorophenyl)-6-methyl-2-(2,4,6-trifluorophenyl)-1,4-dihydropyrimidine-5-carboxylate (6.31 g, 13.4 mmol) (The compound was synthesized according to the procedure as described in CN200610098646.3) was reacted with NBS (2.87 g, 16.1 mmol) according to the procedure as described in Example 1, Step B to give the title compound as a yellow solid (4.1 g, 55%). The compound was characterized by the following spectroscopic data:

MS-ESI: (ESI, pos. ion) m/z: 549.0 [M+1]$^+$;

$^1$H NMR (400 MHz, DMSO-d$_6$): δ 10.23 (s, 1H), 7.35-7.10 (m, 2H), 7.09-6.98 (m, 1H), 6.63-6.49 (m, 2H), 6.33 (s, 1H), 4.89-4.59 (m, 2H), 4.12 (q, 2H), 1.09 (t, 3H).

Step B: 4-((6-(2-bromo-4-fluorophenyl)-5-(ethoxycarbonyl)-2-(2,4,6-trifluorophenyl)-3,6-dihydropyrimidin-4-yl)methyl)morpholine-3-carboxylic acid Ethyl 4-(2-bromo-4-fluorophenyl)-6-(bromomethyl)-2-(2,4,6-trifluorophenyl)-1,4-dihydropyrimidine-5-carboxylate (1.21 g, 2.2 mmol) was reacted with morpholine-3-carboxylic acid (0.29 g, 2.2 mmol) according to the procedure as described in Example 1, Step C to give the title compound as a yellow solid (0.44 g, 33%). The compound was characterized by the following spectroscopic data:

MS-ESI: (ESI, pos. ion) m/z: 600.1 [M+1]$^+$;

$^1$H NMR (400 MHz, DMSO-d$_6$): δ 12.98 (br.s, 1H), 10.26 (s, 1H), 7.34-7.24 (m, 2H), 7.19-6.99 (m, 1H), 6.64-6.44 (m, 2H), 6.05 (s, 1H), 4.02-3.89 (m, 3H), 3.82-3.40 (m, 4H), 3.02-2.27 (m, 4H), 1.19 (t, 3H).

Example 102

4-((6-(2,4-dichlorophenyl)-5-(ethoxycarbonyl)-2-(3-fluoropyridin-2-yl)-3,6-dihydropyrimidin-4-yl)methyl)morpholine-2-carboxylic acid

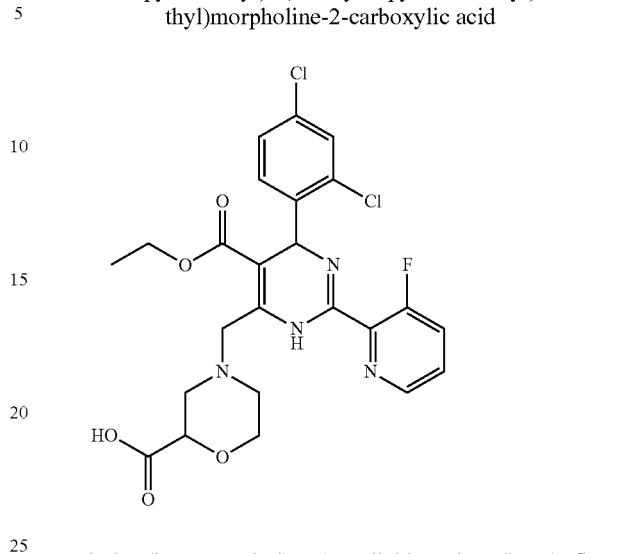

Ethyl 6-(bromomethyl)-4-(2,4-dichlorophenyl)-2-(3-fluoropyridin-2-yl)-1,4-dihydropyrimidine-5-carboxylate (0.75 g, 1.53 mmol) was reacted with morpholine-2-carboxylic acid (0.26 g, 1.53 mmol) according to the procedure as described in Example 1, Step C to give the title compound as a yellow solid (0.35 g, 43%). The compound was characterized by the following spectroscopic data:

MS-ESI: (ESI, pos. ion) m/z: 537.1 [M+1]$^+$;

$^1$H NMR (400 MHz, DMSO-d$_6$): δ 9.83 (s, 1H), 8.59-8.50 (m, 7.62-7.50 (m, 3H), 7.42-7.37 (m, 2H), 6.02 (s, 1H), 4.14-4.10 (m, 1H), 3.97-3.88 (m, 4H), 3.64-3.51 (m, 2H), 3.06-2.85 (m, 2H), 2.63-2.35 (m, 2H), 1.05 (t, 3H).

Example 103

4-((6-(2-chloro-4-fluorophenyl)-5-(ethoxycarbonyl)-2-(pyridin-2-yl)-3,6-dihydropyrimidin-4-yl)methyl)morpholine-3-carboxylic acid

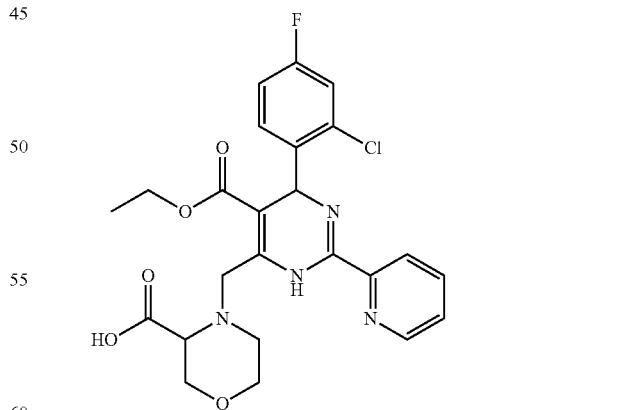

Ethyl 6-(bromomethyl)-4-(2-chloro-4-fluorophenyl)-2-(pyridin-2-yl)-1,4-dihydropyrimidine-5-carboxylate (0.69 g, 1.53 mmol) (The compound was synthesized according to the procedure as described in WO2010069147) was reacted with morpholine-3-carboxylic acid (0.2 g, 1.53 mmol) according to the procedure as described in Example 28 to give the title compound as a yellow solid (0.42 g, 55%). The compound was characterized by the following spectroscopic data:

MS-ESI: (ESI, pos. ion) m/z: 503.2 [M+1]+;

$^1$H NMR (400 MHz, DMSO-d$_6$): δ 12.69 (s, 1H), 10.12 (s, 1H), 8.72 (dd, 1H), 8.34 (dd, 1H), 8.13-7.99 (m, 1H), 7.78-7.67 (m, 1H), 7.57-7.28 (m, 2H), 7.04-6.89 (m, 1H), 5.98 (s, 1H), 4.41-3.87 (m, 4H), 3.77-3.32 (m, 3H), 2.98-2.25 (m, 4H), 1.10 (t, 3H).

Example 104

4-((6-(2-bromo-4-fluorophenyl)-2-(3-chloropyridin-2-yl)-5-(ethoxycarbonyl)-3,6-dihydropyrimidin-4-yl)methyl)morpholine-3-carboxylic acid

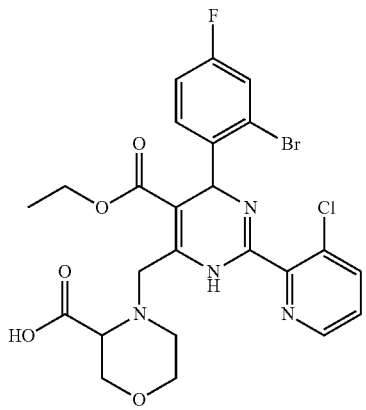 [SMILES: CCOC(=O)C1=C(CN2CCOCC2C(=O)O)NC(c2ncccc2Cl)=NC1c1ccc(F)cc1Br]

Step A: Ethyl 4-(2-bromo-4-fluorophenyl)-6-(bromomethyl)-2-(3-chloropyridin-2-yl)-1,4-dihydropyrimidine-5-carboxylate Ethyl 4-(2-bromo-4-fluorophenyl)-2-(3-chloropyridin-2-yl)-6-methyl-1,4-dihydropyrimidine-5-carboxylate (6.07 g, 13.4 mmol) (The compound was synthesized according to the procedure as described in WO0058302) was reacted with NBS (2.87 g, 16.1 mmol) according to the procedure as described in Example 1, Step B to give the title compound as a yellow solid (3.5 g, 49%). The compound was characterized by the following spectroscopic data:

MS-ESI: (ESI, pos. ion) m/z: 530.0 [M+1]+;

$^1$H NMR (400 MHz, DMSO-d$_6$): δ 11.04 (s, 1H), 8.80 (dd, 1H), 8.16 (dd, 1H), 7.78-7.65 (m, 1H), 7.35-7.23 (m, 2H), 7.19-6.97 (m, 1H), 6.60 (s, 1H), 4.97-4.79 (m, 2H), 4.02 (q, 2H), 1.12 (t, 3H).

Step B: 4-((6-(2-bromo-4-fluorophenyl)-2-(3-chloropyridin-2-yl)-5-(ethoxycarbonyl)-3,6-dihydropyrimidin-4-yl)methyl)morpholine-3-carboxylic acid Ethyl 4-(2-bromo-4-fluorophenyl)-6-(bromomethyl)-2-(3-chloropyridin-2-yl)-1,4-dihydropyrimidine-5-carboxylate (0.81 g, 1.53 mmol) was reacted with morpholine-3-carboxylic acid (0.2 g, 1.53 mmol) according to the procedure as described in Example 1, Step C to give the title compound as a yellow solid (0.36 g, 40%). The compound was characterized by the following spectroscopic data:

MS-ESI: (ESI, pos. ion) m/z: 581.1 [M+1]+;

$^1$H NMR (400 MHz, DMSO-d$_6$): δ 12.48 (s, 1H), 9.88 (s, 1H), 8.80 (dd, 1H), 8.43-7.98 (m, 1H), 7.68-7.57 (m, 1H), 7.32-7.27 (m, 2H), 7.19-6.97 (m, 1H), 5.94 (s, 1H), 4.66-3.87 (m, 4H), 3.85-3.23 (m, 3H), 2.91-2.21 (m, 4H), 1.13 (t, 3H).

Example 105

2-(4-((6-(2-bromo-4-fluorophenyl)-5-(ethoxycarbonyl)-2-phenyl-3,6-dihydropyrimidin-4-yl)methyl)morpholin-3-yl)acetic acid

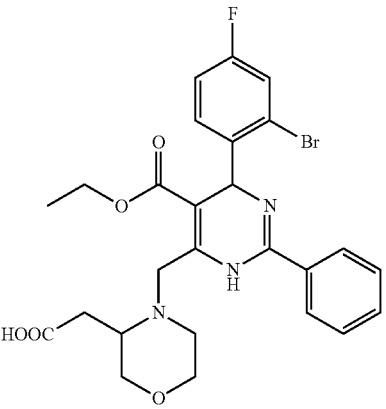 [SMILES: CCOC(=O)C1=C(CN2CCOCC2CC(=O)O)NC(c2ccccc2)=NC1c1ccc(F)cc1Br]

Ethyl 4-(2-bromo-4-fluorophenyl)-6-(bromomethyl)-2-phenyl-1,4-dihydropyrimidine-5-carboxylate (0.76 g, 1.53 mmol) (The compound was synthesized according to the procedure as described in WO2010069147) was reacted with 2-(morpholin-3-yl)acetic acid hydrochloride (0.28 g, 1.53 mmol) according to the procedure as described in Example 28 to give the title compound as a yellow solid (0.42 g, 49%). The compound was characterized by the following spectroscopic data:

MS-ESI: (ESI, pos. ion) m/z: 560.1 [M+1]+;

$^1$H NMR (400 MHz, DMSO-d$_6$): δ 12.31 (s, 1H), 10.17 (s, 1H), 7.85-7.67 (m, 2H), 7.56-7.44 (m, 3H), 7.38-7.28 (m, 1H), 7.31-7.26 (m, 1H), 7.10-6.99 (m, 1H), 6.25 (s, 1H), 4.21-3.94 (m, 3H), 3.76-3.43 (m, 2H), 3.27-3.06 (m, 1H), 3.00-2.95 (m, 2H), 2.72-2.65 (m, 1H), 2.62-2.58 (m, 2H), 2.52-2.47 (m, 1H), 2.33-2.11 (m, 1H), 1.08 (t, 3H).

Example 106

4-((6-(2,4-dichlorophenyl)-5-(ethoxycarbonyl)-3,6-dihydro-[2,2'-bipyrimidin]-4-yl)methyl)morpholine-2-carboxylic acid

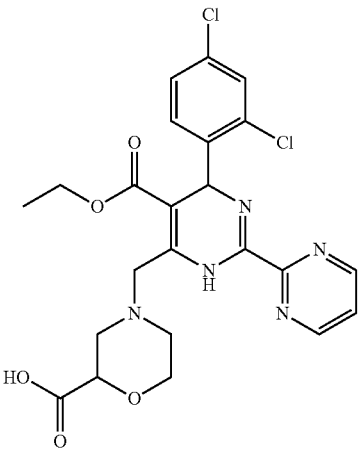

Ethyl 6-(bromomethyl)-4-(2,4-dichlorophenyl)-1,4-dihydro-[2,2'-bipyrimidine]-5-carboxylate (0.72 g, 1.53 mmol)

(The compound was synthesized according to the procedure as described in WO2010069147) was reacted with morpholine-2-carboxylic acid hydrochloride (0.26 g, 1.53 mmol) according to the procedure as described in Example 28 to give the title compound as a yellow solid (0.45 g, 56%). The compound was characterized by the following spectroscopic data:

MS-ESI: (ESI, pos. ion) m/z: 520.1 [M+1]

$^1$H NMR (400 MHz, DMSO-$d_6$): δ 12.86 (s, 1H), 9.84 (s, 1H), 9.09 (d, 2H), 7.87-7.80 (m, 1H), 7.72 (d, 1H), 7.25-7.09 (m, 2H), 6.23 (s, 1H), 4.01 (q, 2H), 3.81-3.76 (m, 1H), 3.72-3.39 (m, 3H), 3.05-2.88 (m, 1H), 2.79-2.57 (m, 3H), 2.50-2.45 (m, 1H), 1.06 (t, 3H).

Example 107

3-(4-((6-(2-chloro-4-fluorophenyl)-5-(ethoxycarbonyl)-2-(3-fluoropyridin-2-yl)-3,6-dihydropyrimidin-4-yl)methyl)morpholin-3-yl)propanoic acid

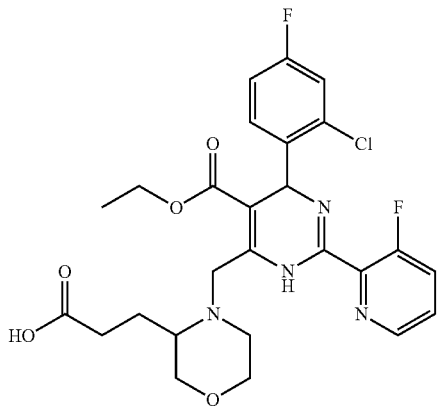 [SMILES: CCOC(=O)C1=C(CN2CCOCC2CCC(=O)O)NC(c2ncccc2F)=NC1c1ccc(F)cc1Cl]

Ethyl 6-(bromomethyl)-4-(2-chloro-4-fluorophenyl)-2-(3-fluoropyridin-2-yl)-1,4-dihydropyrimidine-5-carboxylate (0.72 g, 1.53 mmol) was reacted with 3-(morpholin-3-yl)propanoic acid hydrochloride (0.3 g, 1.53 mmol) according to the procedure as described in Example 28 to give the title compound as a yellow solid (0.3 g, 36%). The compound was characterized by the following spectroscopic data:

MS-ESI: (ESI, pos. ion) m/z: 549.3 [M+1]$^+$;

$^1$H NMR (400 MHz, DMSO-$d_6$): δ 9.80 (s, 1H), 8.59-8.51 (m, 1H), 7.62-7.51 (m, 2H), 7.42-7.35 (m, 2H), 7.17-7.12 (m, 1H), 6.13 (s, 1H), 4.26-4.10 (m, 1H), 4.09-4.02 (m, 3H), 3.95-3.88 (m, 1H), 3.84-3.81 (m, 1H), 3.76-3.69 (m, 1H), 3.59-3.53 (m, 1H), 2.89-2.82 (m, 1H), 2.63 (br.s, 1H), 2.54-2.45 (m, 2H), 2.38-2.33 (m, 1H), 1.93-1.88 (m, 1H), 1.29-1.23 (m, 2H), 1.13 (t, 3H).

Example 108

3-(4-((6-(2,4-dichlorophenyl)-5-(ethoxycarbonyl)-2-(thiazol-4-yl)-3,6-dihydropyrimidin-4-yl)methyl)morpholin-2-yl)propanoic acid

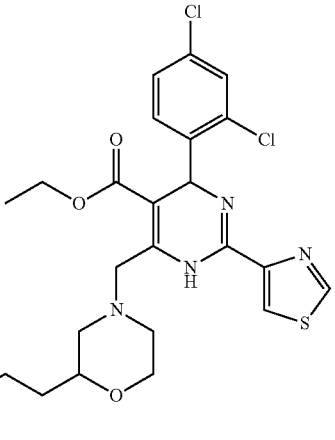

Step A: Ethyl 6-(bromomethyl)-4-(2,4-dichlorophenyl)-2-(thiazol-4-yl)-1,4-dihydropyrimidine-5-carboxylate Ethyl 4-(2,4-dichlorophenyl)-6-methyl-2-(thiazol-4-yl)-1,4-dihydropyrimidine-5-carboxylate (5.31 g, 13.4 mmol) (The compound was synthesized according to the procedure as described in CN200610098646.3) was reacted with NBS (2.87 g, 16.1 mmol) according to the procedure as described in Example 1, Step B to give the title compound as a yellow solid (3.63 g, 57%). The compound was characterized by the following spectroscopic data:

MS-ESI: (ESI, pos. ion) m/z: 474.0 [M+1]$^+$;

$^1$H NMR (400 MHz, DMSO-$d_6$): δ 10.06 (s, 1H), 9.11 (d, 1H), 8.44 (d, 1H), 7.96-7.60 (m, 1H), 7.25-7.15 (m, 2H), 6.27 (s, 1H), 4.56-4.43 (m, 2H), 4.08 (q, 2H), 1.11 (t, 3H).

Step B: 3-(4-((6-(2,4-dichlorophenyl)-5-(ethoxycarbonyl)-2-(thiazol-4-yl)-3,6-dihydropyrimidin-4-yl)methyl)morpholin-2-yl)propanoic acid Ethyl 6-(bromomethyl)-4-(2,4-dichlorophenyl)-2-(thiazol-4-yl)-1,4-dihydropyrimidine-5-carboxylate (0.73 g, 1.53 mmol) was reacted with 3-(morpholin-2-yl)propanoic acid hydrochloride (0.3 g, 1.53 mmol) according to the procedure as described in Example 28 to give the title compound as a yellow solid (0.38 g, 45%). The compound was characterized by the following spectroscopic data:

MS-ESI: (ESI, pos. ion) m/z: 553.1 [M+1]$^+$;

$^1$H NMR (400 MHz, DMSO-$d_6$): δ 12.71 (s, 1H), 10.04 (s, 1H), 9.11 (d, 1H), 8.44 (d, 1H), 7.94-7.48 (m, 1H), 7.35-7.27 (m, 2H), 6.35 (s, 1H), 3.98 (q, 2H), 3.78-3.44 (m, 3H), 3.37-3.22 (m, 2H), 2.83-2.54 (m, 3H), 2.33-2.13 (m, 2H), 2.12-2.09 (m, 1H), 1.67-1.57 (m, 2H), 1.06 (t, 3H).

Example 109

4-((2-(5-chlorothiazol-4-yl)-6-(2,4-dichlorophenyl)-5-(ethoxycarbonyl)-3,6-dihydropyrimidin-4-yl)methyl)morpholine-3-carboxylic acid

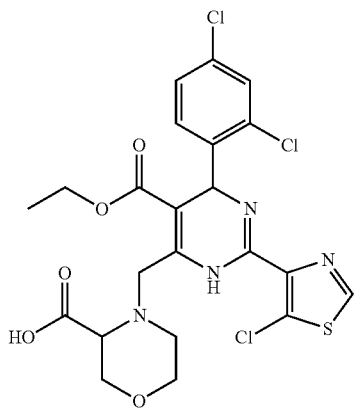 [SMILES: CCOC(=O)C1=C(CN2CCOCC2C(=O)O)NC(c2ncsc2Cl)=NC1c1ccc(Cl)cc1Cl]

Step A: Ethyl 6-(bromomethyl)-2-(5-chlorothiazol-4-yl)-4-(2,4-dichlorophenyl)-1,4-dihydropyrimidine-5-carboxylate Ethyl 2-(5-chlorothiazol-4-yl)-4-(2,4-dichlorophenyl)-6-methyl-1,4-dihydropyrimidine-5-carboxylate (5.77 g, 13.4 mmol) (The compound was synthesized according to the procedure as described in CN200610098646.3) was reacted with NBS (2.87 g, 16.1 mmol) according to the procedure as described in Example 1, Step B to give the title compound as a yellow solid (3.3 g, 48%). The compound was characterized by the following spectroscopic data:

MS-ESI: (ESI, pos. ion) m/z: 508.0 [M+1]$^+$;

$^1$H NMR (400 MHz, DMSO-d$_6$): δ 10.03 (s, 1H), 8.89 (s, 1H), 7.94-7.48 (m, 1H), 7.29-7.12 (m, 2H), 6.31 (s, 1H), 5.03-4.87 (m, 2H), 4.08 (q, 2H), 1.16 (t, 3H).

Step B: 4-((2-(5-chlorothiazol-4-yl)-6-(2,4-dichlorophenyl)-5-(ethoxycarbonyl)-3,6-dihydropyrimidin-4-yl)methyl)morpholine-3-carboxylic acid Ethyl 6-(bromomethyl)-2-(5-chlorothiazol-4-yl)-4-(2,4-dichlorophenyl)-1,4-dihydropyrimidine-5-carboxylate (0.78 g, 1.53 mmol) was reacted with morpholine-3-carboxylic acid (0.2 g, 1.53 mmol) according to the procedure as described in Example 28 to give the title compound as a yellow solid (0.29 g, 34%). The compound was characterized by the following spectroscopic data:

MS-ESI: (ESI, pos. ion) m/z: 559.1 [M+1]$^+$;

$^1$H NMR (400 MHz, DMSO-d$_6$): δ 12.69 (s, 1H), 11.30 (s, 1H), 8.89 (s, 1H), 8.00-7.50 (m, 1H), 7.20-7.10 (m, 2H), 6.31 (s, 1H), 4.39-3.96 (m, 4H), 3.91-3.30 (m, 3H), 3.02-2.32 (m, 4H), 1.03 (t, 3H).

Example 110

4-((6-(2-bromo-4-fluorophenyl)-5-(ethoxycarbonyl)-2-(furan-2-yl)-3,6-dihydropyrimidin-4-yl)methyl)morpholine-3-carboxylic acid

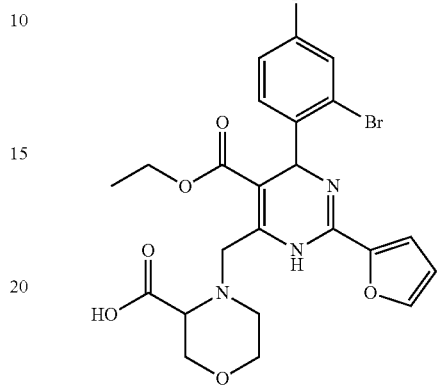

Ethyl 4-(2-bromo-4-fluorophenyl)-6-(bromomethyl)-2-(furan-2-yl)-1,4-dihydropyrimidine-5-carboxylate (0.74 g, 1.53 mmol) (The compound was synthesized according to the procedure as described in WO2010069147) was reacted with morpholine-3-carboxylic acid (0.2 g, 1.53 mmol) according to the procedure as described in Example 28 to give the title compound as a yellow solid (0.31 g, 38%). The compound was characterized by the following spectroscopic data:

MS-ESI: (ESI, pos. ion) m/z: 536.1 [M+1]$^+$;

$^1$H NMR (400 MHz, DMSO-d$_6$): δ 12.39 (s, 1H), 10.10 (s, 1H), 7.98 (dd, 1H), 7.48-7.19 (m, 3H), 7.17-7.00 (m, 1H), 6.75-6.63 (m, 1H), 6.25 (s, 1H), 4.09 (q, 2H), 3.96-3.91 (m, 1H), 3.90-3.41 (m, 4H), 2.85-2.35 (m, 4H), 1.06 (t, 3H).

Example 111

4-((6-(2-chloro-4-fluorophenyl)-5-(ethoxycarbonyl)-2-(thiophen-2-yl)-3,6-dihydropyrimidin-4-yl)methyl)morpholine-3-carboxylic acid

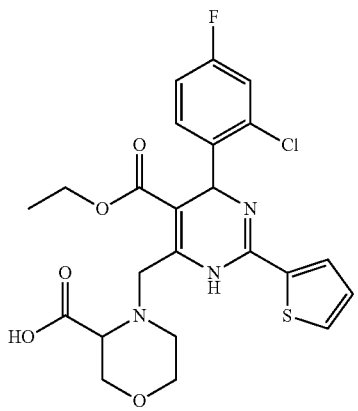 [SMILES: CCOC(=O)C1=C(CN2CCOCC2C(=O)O)NC(c2cccs2)=NC1c1ccc(F)cc1Cl]

Ethyl 6-(bromomethyl)-4-(2-chloro-4-fluorophenyl)-2-(thiophen-2-yl)-1,4-dihydropyrimidine-5-carboxylate (0.7 g, 1.53 mmol) (The compound was synthesized according to the procedure as described in WO2010069147) was reacted with morpholine-3-carboxylic acid (0.2 g, 1.53 mmol) according to the procedure as described in Example 28 to give the title compound as a yellow solid (0.33 g, 43%). The compound was characterized by the following spectroscopic data:

MS-ESI: (ESI, pos. ion) m/z: 508.1 [M+1]$^+$;

$^1$H NMR (400 MHz, DMSO-d$_6$): δ 12.59 (s, 1H), 10.11 (s, 1H), 7.78 (dd, 1H), 7.67 (dd, 1H), 7.45 (dd, 1H), 7.36 (dd, 1H), 7.21-6.95 (m, 2H), 5.89 (s, 1H), 4.19 (s, 1H), 4.09-3.83 (m, 3H), 3.75-3.40 (m, 3H), 2.88-2.44 (m, 4H), 1.18 (t, 3H).

Example 112

4-((6-(2-bromo-4-fluorophenyl)-5-(ethoxycarbonyl)-2-(oxazol-2-yl)-3,6-dihydropyrimidin-4-yl)methyl)morpholine-3-carboxylic acid

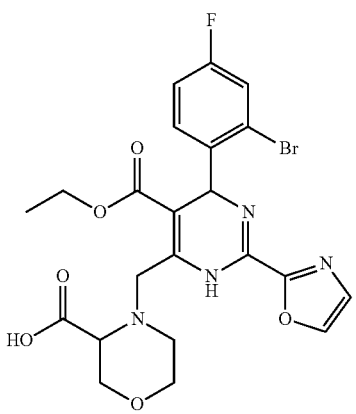

Step A: Oxazole-2-carboximidamide hydrochloride

Oxazole-2-carbonitrile (0.94 g, 10 mmol) was reacted with sodium methoxide (0.81 g, 15 mmol) and ammonium chloride (0.96 g, 18 mmol) according to the procedure as described in Example 61, Step B to give the title compound as an offwhite solid (1.25 g, 70%). The compound was characterized by the following spectroscopic data:

MS-ESI: (ESI, pos. ion) m/z: 112.0 [M+1]$^+$;

$^1$H NMR (400 MHz, DMSO-d$_6$): δ 10.67 (s, 1H), 7.59 (d, 1H), 7.14 (d, 1H), 6.89 (s, 2H).

Step B: Ethyl 4-(2-bromo-4-fluorophenyl)-6-methyl-2-(oxazol-2-yl)-1,4-dihydropyrimidine-5-carboxylate Oxazole-2-carboximidamide hydrochloride (1.28 g, 8.69 mmol) was reacted with 2-bromo-4-fluorobenzaldehyde (1.76 g, 8.69 mmol) and ethyl 3-oxobutanoate (1.36 g, 10.5 mmol) according to the procedure as described in Example 1, Step A to give the title compound as a yellow solid (1.35 g, 38%). The compound was characterized by the following spectroscopic data:

MS-ESI: (ESI, pos. ion) m/z: 408.0 [M+1]$^+$;

$^1$H NMR (400 MHz, DMSO-d$_6$): δ 9.82 (s, 1H), 7.58 (d, 1H), 7.33-7.25 (m, 2H), 7.19-7.00 (m, 2H), 6.13 (s, 1H), 4.07 (q, 2H), 2.45 (s, 3H), 1.19 (t, 3H).

Step C: Ethyl 4-(2-bromo-4-fluorophenyl)-6-(bromomethyl)-2-(oxazol-2-yl)-1,4-dihydropyrimidine-5-carboxylate Ethyl 4-(2-bromo-4-fluorophenyl)-6-methyl-2-(oxazol-2-yl)-1,4-dihydropyrimidine-5-carboxylate (5.47 g, 13.4 mmol) was reacted with NBS (2.87 g, 16.1 mmol) according to the procedure as described in Example 1, Step B to give the title compound as a yellow solid (3.3 g, 51%). The compound was characterized by the following spectroscopic data:

MS-ESI: (ESI, pos. ion) m/z: 486.0 [M+1]$^+$;

$^1$H NMR (400 MHz, DMSO-d$_6$): δ 10.10 (s, 1H), 7.60 (d, 1H), 7.33-7.25 (m, 2H), 7.20-7.03 (m, 2H), 6.03 (s, 1H), 4.95-4.69 (m, 2H), 4.02 (q, 2H), 1.04 (t, 3H).

Step D: 4-((6-(2-bromo-4-fluorophenyl)-5-(ethoxycarbonyl)-2-(oxazol-2-yl)-3,6-dihydropyrimidin-4-yl)methyl)morpholine-3-carboxylic acid Ethyl 4-(2-bromo-4-fluorophenyl)-6-(bromomethyl)-2-(oxazol-2-yl)-1,4-dihydropyrimidine-5-carboxylate (0.75 g, 1.53 mmol) was reacted with morpholine-3-carboxylic acid (0.2 g, 1.53 mmol) according to the procedure as described in Example 1, Step C to give the title compound as a yellow solid (0.29 g, 35%). The compound was characterized by the following spectroscopic data:

MS-ESI: (ESI, pos. ion) m/z: 537.1 [M+1]$^+$;

$^1$H NMR (400 MHz, DMSO-d$_6$): δ 12.79 (s, 1H), 9.95 (s, 1H), 7.58 (d, 1H), 7.32-7.23 (m, 2H), 7.21-7.07 (m, 2H), 6.09 (s, 1H), 4.24-4.13 (m, 1H), 4.08-3.85 (m, 3H), 3.79-3.39 (m, 3H), 2.96-2.41 (m, 4H), 1.06 (t, 3H).

Example 113

2-(4-((6-(2-bromo-4-fluorophenyl)-5-(ethoxycarbonyl)-2-(1,2,4-thiadiazol-5-yl)-3,6-dihydropyrimidin-4-yl)methyl)morpholin-3-yl)acetic acid

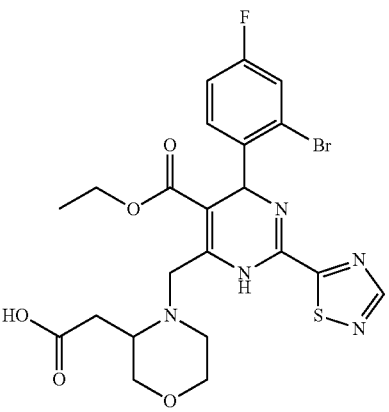 [SMILES: CCOC(=O)C1=C(CN2CCOCC2CC(=O)O)NC(c2ncns2)=NC1c1ccc(F)cc1Br]

Step A: 1,2,4-thiadiazole-5-carbonitrile 1,2,4-thiadiazol-5-amine (4.05 g, 40 mmol) was reacted with CuCN (7.2 g, 80 mmol) according to the procedure as described in Example 61, Step A to give the title compound as pink liquid (2.04 g, 46%). The compound was characterized by the following spectroscopic data:

MS-ESI: (ESI, pos. ion) m/z: 112.0 [M+1]$^+$;

$^1$H NMR (400 MHz, DMSO-d$_6$): δ 6.46 (s, 1H).

Step B: 1,2,4-thiadiazole-5-carboximidamide hydrochloride 1,2,4-thiadiazole-5-carbonitrile (1.11 g, 10 mmol) was reacted with sodium methoxide (0.81 g, 15 mmol) and ammonium chloride (0.96 g, 18 mmol) according to the procedure as described in Example 61, Step B to give the title compound as an offwhite solid (1.32 g, 80%). The compound was characterized by the following spectroscopic data:

MS-ESI: (ESI, pos. ion) m/z: 129.0 [M+1]$^+$;

$^1$H NMR (400 MHz, DMSO-d$_6$): δ 7.12 (s, 1H), 6.90 (s, 2H), 6.32 (s, 1H).

Step C: Ethyl 4-(2-bromo-4-fluorophenyl)-6-methyl-2-(1,2,4-thiadiazol-5-yl)-1,4-dihydropyrimidine-5-carboxylate 1,2,4-thiadiazole-5-carboximidamide hydrochloride (1.43 g, 8.69 mmol) was reacted with 2-bromo-4-fluorobenzaldehyde (1.76 g, 8.69 mmol) and ethyl 3-oxobutanoate (1.36 g, 10.5 mmol) according to the procedure as described in Example 1, Step A to give the title compound as a yellow solid (1.3 g, 35%). The compound was characterized by the following spectroscopic data:

MS-ESI: (ESI, pos. ion) m/z: 425.0 [M+1]$^+$;

$^1$H NMR (400 MHz, DMSO-d$_6$): δ 9.70 (s, 1H), 7.31-7.28 (m, 2H), 7.20-7.12 (m, 1H), 6.25 (s, 1H), 6.10 (s, 1H), 4.08 (q, 2H), 2.51 (s, 3H), 1.12 (t, 3H).

Step D: Ethyl 4-(2-bromo-4-fluorophenyl)-6-(bromomethyl)-2-(1,2,4-thiadiazol-5-yl)-1,4-dihydropyrimidine-5-carboxylate Ethyl 4-(2-bromo-4-fluorophenyl)-6-methyl-2-(1,2,4-thiadiazol-5-yl)-1,4-dihydropyrimidine-5-carboxylate (5.7 g, 13.4 mmol) was reacted with NBS (2.87 g, 16.1 mmol) according to the procedure as described in Example 1, Step B to give the title compound as a yellow solid (2.7 g, 40%). The compound was characterized by the following spectroscopic data:

MS-ESI: (ESI, pos. ion) m/z: 503.0 [M+1]$^+$;

$^1$H NMR (400 MHz, DMSO-d$_6$): δ 10.04 (s, 1H), 7.30-7.20 (m, 2H), 7.17-7.02 (m, 1H), 6.26 (s, 1H), 6.13 (s, 1H), 4.73 (s, 2H), 4.08 (q, 2H), 1.16 (t, 3H).

Step E: 2-(4-((6-(2-bromo-4-fluorophenyl)-5-(ethoxycarbonyl)-2-(1,2,4-thiadiazol-5-yl)-3,6-dihydropyrimidin-4-yl)methyl)morpholin-3-yl)acetic acid Ethyl 4-(2-bromo-4-fluorophenyl)-6-(bromomethyl)-2-(1,2,4-thiadiazol-5-yl)-1,4-dihydropyrimidine-5-carboxylate (0.77 g, 1.53 mmol) was reacted with 2-(morpholin-3-yl)acetic acid hydrochloride (0.28 g, 1.53 mmol) according to the procedure as described in Example 1, Step C to give the title compound as a yellow solid (0.29 g, 33%). The compound was characterized by the following spectroscopic data:

MS-ESI: (ESI, pos. ion) m/z: 568.1 [M+1]$^+$;

$^1$H NMR (400 MHz, DMSO-d$_6$): δ 12.41 (s, 1H), 9.68 (s, 1H), 7.38 (dd, 1H), 7.31 (dd, 1H), 7.10-6.99 (m, 1H), 6.18 (s, 1H), 5.91 (s, 1H), 4.04 (q, 2H), 3.76-3.48 (m, 2H), 3.43-3.26 (m, 2H), 3.21-3.03 (m, 1H), 2.99-2.89 (m, 1H), 2.82-2.53 (m, 4H), 2.29-2.04 (m, 1H), 1.16 (t, 3H).

Example 114

2-(4-((6-(2,4-dichlorophenyl)-5-(ethoxycarbonyl)-2-(thiazol-2-yl)-3,6-dihydropyrimidin-4-yl)methyl)morpholin-3-yl)propanoic acid

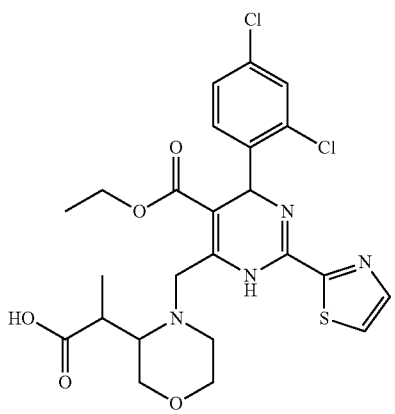 [SMILES: CCOC(=O)C1=C(CN2CCOCC2C(C)C(=O)O)NC(c2nccs2)=NC1c1ccc(Cl)cc1Cl]

Ethyl 6-(bromomethyl)-4-(2,4-dichlorophenyl)-2-(thiazol-2-yl)-1,4-dihydropyrimidine-5-carboxylate (0.73 g, 1.53 mmol) was reacted with 2-(morpholin-3-yl)propanoic acid hydrochloride (0.3 g, 1.53 mmol) according to the procedure as described in Example 28 to give the title compound as a yellow solid (0.34 g, 40%). The compound was characterized by the following spectroscopic data:

MS-ESI: (ESI, pos. ion) m/z: 553.1 [M+1]$^+$;

$^1$H NMR (400 MHz, DMSO-d$_6$): δ 10.63 (s, 1H), 9.88 (s, 1H), 8.10 (d, 1H), 7.93 (d, 1H), 7.72 (d, 1H), 7.25-7.09 (m, 2H), 6.09 (s, 1H), 4.19-3.98 (m, 3H), 3.73-3.47 (m, 2H), 3.40-3.25 (m, 1H), 3.15-3.08 (m, 1H), 3.00-2.92 (m, 1H), 2.84-2.48 (m, 3H), 2.37-2.28 (m, 1H), 1.46-0.82 (m, 6H).

Example 115

Ethyl 4-(2-bromo-4-fluorophenyl)-6-(((S)-2-(hydroxymethyl)pyrrolidin-1-yl)methyl)-2-(1H-1,2,4-triazol-3-yl)-1,4-dihydropyrimidine-5-carboxylate

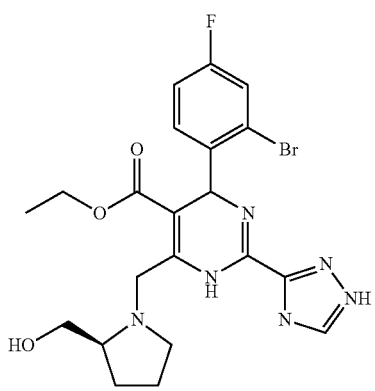 [SMILES: CCOC(=O)C1=C(CN2CCC[C@H]2CO)NC(c2nnc[nH]2)=NC1c1ccc(F)cc1Br]

Step A: 1H-1,2,4-triazole-3-carboximidamide hydrochloride 1H-1,2,4-triazole-3-carbonitrile (0.94 g, 10 mmol) was reacted with sodium methoxide (0.81 g, 15 mmol) and ammonium chloride (0.96 g, 18 mmol) according to the procedure as described in Example 61, Step B to give the title compound as an offwhite solid (0.59 g, 40%). The compound was characterized by the following spectroscopic data:

MS-ESI: (ESI, pos. ion) m/z: 112.0 [M+1]$^+$;

$^1$H NMR (400 MHz, D$_2$O): δ 8.52 (s, 1H), 2.65 (br.s, 2H).

Step B: Ethyl 4-(2-bromo-4-fluorophenyl)-6-methyl-2-(1H-1,2,4-triazol-3-yl)-1,4-dihydro pyrimidine-5-carboxylate 1H-1,2,4-triazole-3-carboximidamide hydrochloride (1.28 g, 8.69 mmol) was reacted with 2-bromo-4-fluorobenzaldehyde (1.76 g, 8.69 mmol) and ethyl 3-oxobutanoate (1.36 g, 10.5 mmol) according to the procedure as described in Example 1, Step A to give the title compound as a yellow solid (1.06 g, 30%). The compound was characterized by the following spectroscopic data:

MS-ESI: (ESI, pos. ion) m/z: 408.0 [M+1]$^+$;

$^1$H NMR (400 MHz, DMSO-d$_6$): δ 9.62 (s, 1H), 8.50 (s, 1H), 7.42-7.15 (m, 3H), 6.06 (s, 1H), 4.01 (q, 2H), 2.52 (s, 3H), 1.08 (t, 3H).

Step C: Ethyl 4-(2-bromo-4-fluorophenyl)-6-(bromomethyl)-2-(1H-1,2,4-triazol-3-yl)-1,4-dihydropyrimidine-5-carboxylate Ethyl 4-(2-bromo-4-fluorophenyl)-6-methyl-2-(1H-1,2,4-triazol-3-yl)-1,4-dihydropyrimidine-5-carboxylate (0.82 g, 2 mmol) was reacted with NBS (0.39 g, 2.2 mmol) in chloroform (40 mL) according to the procedure as described in Example 1, Step B to give the title compound as a yellow solid (0.44 g, 45%). The compound was characterized by the following spectroscopic data:

MS-ESI: (ESI, pos. ion) m/z: 486.0 [M+1]$^+$;

$^1$H NMR (400 MHz, DMSO-d$_6$): δ 9.63 (s, 1H), 8.51 (s, 1H), 7.40-7.16 (m, 3H), 6.03 (s, 1H), 4.65-4.49 (m, 2H), 4.03 (q, 2H), 1.06 (t, 3H).

Step D: Ethyl 4-(2-bromo-4-fluorophenyl)-6-(((S)-2-(hydroxymethyl)pyrrolidin-1-yl)methyl)-2-(1H-1,2,4-triazol-3-yl)-1,4-dihydropyrimidine-5-carboxylate Ethyl 4-(2-bromo-4-fluorophenyl)-6-(bromomethyl)-2-(1H-1,2,4-triazol-3-yl)-1,4-dihydropyrimidine-5-carboxylate (0.75 g, 1.53 mmol) was reacted with (S)-pyrrolidin-2-ylmethanol hydrochloride (0.21 g, 1.53 mmol) according to the procedure as described in Example 25, Step B to give the title compound as a yellow solid (0.25 g, 32%). The compound was characterized by the following spectroscopic data:

MS-ESI: (ESI, pos. ion) m/z: 507.1 [M+1]$^+$;

$^1$H NMR (400 MHz, DMSO-d$_6$): δ 10.77 (s, 1H), 8.27 (s, 1H), 7.32-7.23 (m, 2H), 7.17-6.98 (m, 1H), 5.97 (s, 1H), 4.48 (s, 1H), 4.32 (s, 1H), 4.07 (q, 2H), 3.67 (s, 1H), 3.46-3.00 (m, 2H), 3.00-2.73 (m, 1H), 2.63-2.26 (m, 2H), 1.88-1.25 (m, 4H), 1.16 (t, 3H).

Example 116

Ethyl 4-(2-bromo-4-fluorophenyl)-6-(((S)-2-(2-hydroxypropan-2-yl)pyrrolidin-1-yl)methyl)-2-(1H-1,2,4-triazol-3-yl)-1,4-dihydropyrimidine-5-carboxylate

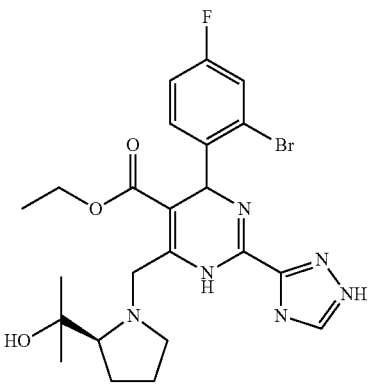 [SMILES: CCOC(=O)C1=C(CN2CCC[C@H]2C(C)(C)O)NC(c2nnc[nH]2)=NC1c1ccc(F)cc1Br]

Ethyl 4-(2-bromo-4-fluorophenyl)-6-(bromomethyl)-2-(1H-1,2,4-triazol-3-yl)-1,4-dihydropyrimidine-5-carboxylate (0.75 g, 1.53 mmol) was reacted with (S)-2-(pyrrolidin-2-yl)propan-2-ol hydrochloride (0.25 g, 1.53 mmol) according to the procedure as described in Example 25, Step B to give the title compound as a yellow solid (0.21 g, 26%). The compound was characterized by the following spectroscopic data:

MS-ESI: (ESI, pos. ion) m/z: 535.2 [M+1]$^+$;

$^1$H NMR (400 MHz, DMSO-d$_6$): δ 9.97 (s, 1H), 8.30 (s, 1H), 7.35-7.22 (m, 2H), 7.17-7.03 (m, 1H), 6.12 (s, 1H), 5.08-4.92 (m, 2H), 4.01 (q, 2H), 3.10-2.71 (m, 1H), 2.64-2.19 (m, 2H), 1.80-1.33 (m, 5H), 1.26-1.08 (m, 9H).

Example 117

Ethyl 4-(2-bromo-4-fluorophenyl)-6-(((R)-2-(hydroxymethyl)morpholino)methyl)-2-(1H-1,2,4-triazol-3-yl)-1,4-dihydropyrimidine-5-carboxylate

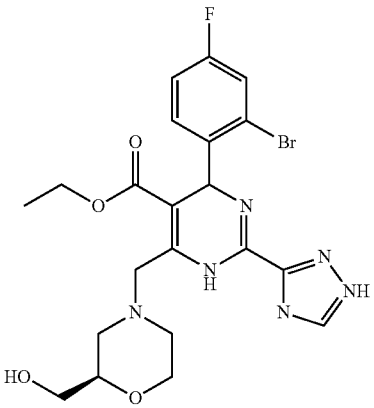 [SMILES: CCOC(=O)C1=C(CN2CCO[C@@H](CO)C2)NC(c2nnc[nH]2)=NC1c1ccc(F)cc1Br]

Ethyl 4-(2-bromo-4-fluorophenyl)-6-(bromomethyl)-2-(1H-1,2,4-triazol-3-yl)-1,4-dihydropyrimidine-5-carboxylate (0.75 g, 1.53 mmol) was reacted with (R)-morpholin-2-ylmethanol hydrochloride (0.24 g, 1.53 mmol) according to the procedure as described in Example 25, Step B to give the title compound as a yellow solid (0.41 g, 51%). The compound was characterized by the following spectroscopic data:

MS-ESI: (ESI, pos. ion) m/z: 523.1 [M+1]$^+$;

$^1$H NMR (400 MHz, DMSO-d$_6$): δ 9.64 (s, 1H), 8.50 (s, 1H), 7.41-7.17 (m, 3H), 6.06 (s, 1H), 4.23-4.03 (m, 3H), 3.98-3.34 (m, 6H), 2.95-2.62 (m, 2H), 2.45-2.23 (m, 2H), 1.05 (t, 3H).

Example 118

Ethyl 6-((3-(5H-tetrazol-5-yl)morpholino)methyl)-4-(2-bromo-4-fluorophenyl)-2-(thiazol-2-yl)-1,4-dihydropyrimidine-5-carboxylate

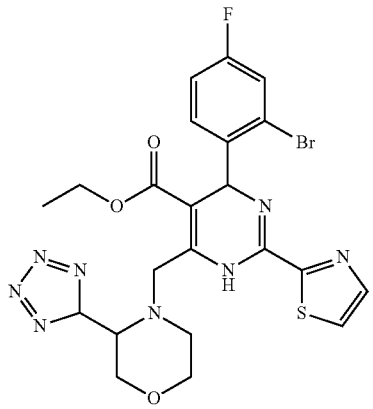 [SMILES: CCOC(=O)C1=C(CN2CCOCC2C2N=NN=N2)NC(c2nccs2)=NC1c1ccc(F)cc1Br]

Step A: Tert-butyl 3-(5H-tetrazol-5-yl)morpholine-4-carboxylate

A mixture of tert-butyl 3-cyanomorpholine-4-carboxylate (5 g, 23.6 mmol, the compound was synthesized according to the procedure as described in *J. Med. Chem.* 2007, 50(20), 4953-4975), sodium azide (1.53 g, 23.6 mmol) and ammonium chloride (0.63 g, 11.8 mmol) in anhydrous DMF (30 mL) was stirred at 100° C. for 72 hours and cooled to 25° C. The reaction mixture was diluted with EtOAc (300 mL), then washed with brine (150 mL×6). The organic phase was concentrated in vacuo and the residue was purified by a silica gel column chromatography (PETROLEUM ETHER/EtOAc (V/V)=1/1) to give the title compound as a brownish solid (2.5 g, 41%). The compound was characterized by the following spectroscopic data:

MS-ESI: (ESI, pos. ion) m/z: 200.1 [M+1-56]$^+$;

$^1$H NMR (400 MHz, DMSO-d$_6$): δ 3.93-3.86 (m, 1H), 3.83-3.73 (m, 1H), 3.70-3.60 (m, 2H), 3.58-3.46 (m, 2H), 3.45-3.34 (m, 1H), 1.41 (s, 9H).

Step B: 3-(5H-tetrazol-5-yl)morpholine hydrochloride

Tert-butyl 3-(5H-tetrazol-5-yl)morpholine-4-carboxylate (2 g, 7.8 mmol) was reacted with a solution of HCl in EtOAc (6 mol/L, 30 mL) according to the procedure as described in Example 18, Step B to give the title compound as a grey solid (1.05 g, 70%). The compound was characterized by the following spectroscopic data:

MS-ESI: (ESI, pos. ion) m/z: 156.1 [M+1]$^+$;

$^1$H NMR (400 MHz, DMSO-d$_6$): δ 3.68-3.50 (m, 2H), 3.28-3.15 (m, 1H), 3.14-2.99 (m, 2H), 2.96-2.90 (m, 1H), 2.87-2.78 (m, 1H), 1.92 (br.s, 1H).

Step C: Ethyl 6-((3-(5H-tetrazol-5-yl)morpholino)methyl)-4-(2-bromo-4-fluorophenyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (0.5 g, 1 mmol) was reacted with 3-(5H-tetrazol-5-yl)morpholine hydrochloride (0.19 g, 1 mmol) according to the procedure as described in Example 28 to give the title compound as a yellow solid (0.24 g, 42%). The compound was characterized by the following spectroscopic data:

MS-ESI: (ESI, pos. ion) m/z: 577.1 [M+1]$^+$;

$^1$H NMR (400 MHz, DMSO-d$_6$): δ 10.01 (s, 1H), 8.10 (d, 1H), 7.93 (d, 1H), 7.34-7.23 (m, 2H), 7.19-6.93 (m, 1H), 6.09 (s, 1H), 4.18-3.86 (m, 3H), 3.72-3.41 (m, 3H), 3.17-3.08 (m, 1H), 2.86-2.46 (m, 3H), 2.14-2.05 (m, 1H), 1.06 (t, 3H).

Example 119

4-((6-(2,4-dichlorophenyl)-5-(ethoxycarbonyl)-2-(4-(trifluoromethyl)thiazol-2-yl)-3,6-dihydropyrimidin-4-yl)methyl)morpholine-3-carboxylic acid

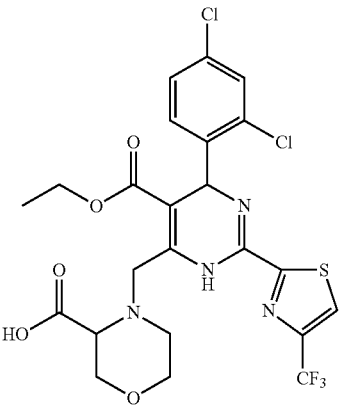 [SMILES: CCOC(=O)C1=C(CN2CCOCC2C(=O)O)NC(c2nc(C(F)(F)F)cs2)=NC1c1ccc(Cl)cc1Cl]

Step A: 4-(trifluoromethyl)thiazole-2-carbonitrile 4-(trifluoromethyl)thiazol-2-amine (2.52 g, 15 mmol) was reacted with CuCN (2.95 g, 33 mmol) according to the procedure as described in Example 61, Step A to give the title compound as brown oil (0.90 g, 34%). The compound was characterized by the following spectroscopic data:

MS-ESI: (ESI, pos. ion) m/z: 179.0 [M+1]$^+$;

$^1$H NMR (400 MHz, CDCl$_3$): δ 8.15 (s, 1H).

Step B: 4-(trifluoromethyl)thiazole-2-carboximidamide acetate

To a solution of 4-(trifluoromethyl)thiazole-2-carbonitrile (0.9 g, 5 mmol) and TEA (1.1 mL, 7.5 mmol) in DCM (20 mL) was added hydroxylamine hydrochloride (0.35 g, 5 mmol), then the mixture was stirred at 25° C. for 2 hours. The mixture was concentrated in vacuo and the residue was purified by a silica gel column chromatography (PETROLEUM ETHER/EtOAc (V/V)=10/1) to give the crude product as a white solid. To the white solid in acetic acid (25 mL) were added Ac$_2$O (0.32 mL, 3.33 mmol) and Pd—C (10%, 0.2 g), then the mixture was stirred at 25° C. for 12 hours under N$_2$. The reaction mixture was filtered and the filtrate was concentrated in vacuo. Then the residue was crystallized from EtOAc (2 mL) and ether (10 mL) to give the title compound as a white solid (0.74 g, 58%). The compound was characterized by the following spectroscopic data:

MS-ESI: (ESI, pos. ion) m/z: 196.0 [M+1]$^+$;

$^1$H NMR (400 MHz, DMSO-d$_6$): δ 7.44 (s, 1H), 3.12 (br.s, 2H), 1.99 (s, 3H).

Step C: Ethyl 4-(2,4-dichlorophenyl)-6-methyl-2-(4-(trifluoromethyl)thiazol-2-yl)-1,4-dihydropyrimidine-5-carboxylate 4-(trifluoromethyl)thiazole-2-carboximidamide acetate (0.38 g, 1.49 mmol) was reacted with 2,4-dichlorobenzaldehyde (0.26 g, 1.49 mmol) and ethyl 3-oxobutanoate (0.2 g, 1.49 mmol) according to the procedure as described in Example 1, Step A to give the title compound as a yellow solid (0.44 g, 64%). The compound was characterized by the following spectroscopic data:

MS-ESI: (ESI, pos. ion) m/z: 464.0 [M+1]$^+$;

$^1$H NMR (400 MHz, CDCl$_3$): δ 7.33 (d, 1H), 7.17 (d, 1H), 7.08-7.01 (m, 1H), 6.96 (s, 1H), 5.99 (br.s, 1H), 4.16 (q, 2H), 2.53 (s, 3H), 1.25 (t, 3H).

Step D: Ethyl 6-(bromomethyl)-4-(2,4-dichlorophenyl)-2-(4-(trifluoromethyl)thiazol-2-yl)-1,4-dihydropyrimidine-5-carboxylate Ethyl 4-(2,4-dichlorophenyl)-6-methyl-2-(4-(trifluoromethyl)thiazol-2-yl)-1,4-dihydropyrimidine-5-carboxylate (0.44 g, 0.94 mmol) was reacted with NBS (0.21 g, 0.94 mmol) according to the procedure as described in Example 1, Step B to give the title compound as a yellow solid (0.36 g, 70%). The compound was characterized by the following spectroscopic data:

MS-ESI: (ESI, pos. ion) m/z: 541.9 [M+1]$^+$;

$^1$H NMR (400 MHz, CDCl$_3$): δ 7.33 (s, 1H), 7.11-7.07 (m, 1H), 7.00 (s, 1H), 6.72 (s, 1H), 5.99 (d, 1H), 4.76 (dd, 2H), 4.21 (q, 2H), 1.07 (t, 3H).

Step E: 4-((6-(2,4-dichlorophenyl)-5-(ethoxycarbonyl)-2-(4-(trifluoromethyl)thiazol-2-yl)-3,6-dihydropyrimidin-4-yl)methyl)morpholine-3-carboxylic acid Ethyl 6-(bromomethyl)-4-(2,4-dichlorophenyl)-2-(4-(trifluoromethyl)thiazol-2-yl)-1,4-dihydropyrimidine-5-carboxylate (0.1 g, 0.18 mmol) was reacted with morpholine-3-carboxylic acid hydrochloride (0.03 g, 0.18 mmol) according to the procedure as described in Example 1, Step C to give the title compound as a yellow solid (0.09 g, 80%). The compound was characterized by the following spectroscopic data:

MS-ESI: (ESI, pos. ion) m/z: 593.1 [M+1]$^+$;

$^1$H NMR (400 MHz, DMSO-d$_6$): δ 12.67 (br.s, 1H), 7.32 (s, 1H), 7.69-7.59 (m, 1H), 7.23-7.07 (m, 2H), 6.17 (s, 1H), 4.30-3.92 (m, 5H), 3.84-3.82 (m, 1H), 3.74-3.52 (m, 3H), 3.11-3.07 (m, 1H), 2.55-2.39 (m, 1H), 1.06 (t, 3H).

Example 120

4-((6-(2-bromo-4-fluorophenyl)-5-(ethoxycarbonyl)-2-(5-fluorothiazol-2-yl)-3,6-dihydropyrimidin-4-yl)methyl)morpholine-3-carboxylic acid

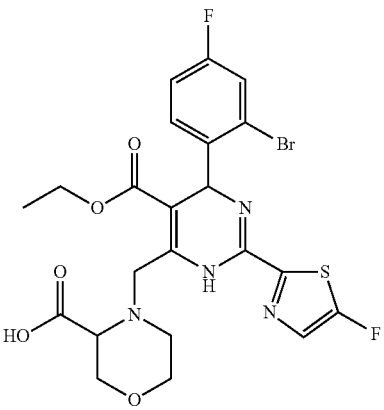 [SMILES: CCOC(=O)C1=C(CN2CCOCC2C(=O)O)NC(c2ncc(F)s2)=NC1c1ccc(F)cc1Br]

Step A: 5-fluorothiazole-2-carbonitrile 5-fluorothiazol-2-amine (2.36 g, 20 mmol) (The compound was synthesized according to the procedure as described in *Chinese Journal of Synthetic Chemistry*, 2011, 19(1), 139-141) was reacted with CuCN (3.94 g, 44 mmol) according to the procedure as described in Example 61, Step A to give the title compound as brownish liquid (0.51 g, 20%). The compound was characterized by the following spectroscopic data:

MS-ESI: (ESI, pos. ion) m/z: 129.0 [M+1]$^+$.

Step B: 5-fluorothiazole-2-carboximidamide acetate 5-fluorothiazole-2-carbonitrile (0.52 g, 4 mmol) was reacted with hydroxylamine hydrochloride (0.56 g, 8 mmol) according to the procedure as described in Example 119, Step B to give the title compound as a white solid (0.5 g, 63%). The compound was characterized by the following spectroscopic data:

MS-ESI: (ESI, pos. ion) m/z: 146.0 [M+1]$^+$;

$^1$H NMR (400 MHz, CDCl$_3$): δ 7.72 (d, 1H), 3.23 (br.s, 2H), 1.89 (s, 3H).

Step C: Ethyl 4-(2-bromo-4-fluorophenyl)-2-(5-fluorothiazol-2-yl)-6-methyl-1,4-dihydropyrimidine-5-carboxylate 5-fluorothiazole-2-carboximidamide acetate (0.22 g, 1.07 mmol) was reacted with 2-bromo-4-fluorobenzaldehyde (0.22 g, 1.07 mmol) and ethyl 3-oxobutanoate (0.14 g, 1.07 mmol) according to the procedure as described in Example 1, Step A to give the title compound as a yellow solid (0.21 g, 45%). The compound was characterized by the following spectroscopic data:

MS-ESI: (ESI, pos. ion) m/z: 442.0 [M+1]$^+$;

$^1$H NMR (400 MHz, CDCl$_3$): δ 7.86 (d, 1H), 7.60-7.51 (m, 1H), 7.40-7.29 (m, 1H), 7.19-7.10 (m, 1H), 5.98 (br.s, 1H), 4.16 (q, 2H), 2.53 (s, 3H), 1.25 (t, 3H).

Step D: Ethyl 4-(2-bromo-4-fluorophenyl)-6-(bromomethyl)-2-(5-fluorothiazol-2-yl)-1,4-dihydropyrimidine-5-carboxylate Ethyl 4-(2-bromo-4-fluorophenyl)-2-(5-fluorothiazol-2-yl)-6-methyl-1,4-dihydropyrimidine-5-carboxylate (0.51 g, 1.16 mmol) was reacted with NBS (0.21 g, 1.16 mmol) according to the procedure as described in Example 1, Step B to give the title compound as a yellow solid (0.52 g, 86%). The compound was characterized by the following spectroscopic data:
MS-ESI: (ESI, pos. ion) m/z: 519.9 [M+1]$^+$;
$^1$H NMR (400 MHz, CDCl$_3$): 7.86 (d, 1H), 7.60-7.52 (m, 1H), 7.40-7.25 (m, 1H), 7.19-7.08 (m, 1H), 5.98 (br.s, 1H), 5.74 (d, 1H), 4.64 (d, 1H), 4.21 (q, 2H), 1.27 (t, 3H).

Step E: 4-((6-(2-bromo-4-fluorophenyl)-5-(ethoxycarbonyl)-2-(5-fluorothiazol-2-yl)-3,6-dihydropyrimidin-4-yl)methyl)morpholine-3-carboxylic acid Ethyl 4-(2-bromo-4-fluorophenyl)-6-(bromomethyl)-2-(5-fluorothiazol-2-yl)-1,4-dihydropyrimidine-5-carboxylate (0.63 g, 1.2 mmol) was reacted with morpholine-3-carboxylic acid hydrochloride (0.23 g, 1.4 mmol) according to the procedure as described in Example 28 to give the title compound as a yellowish solid (0.41 g, 60%). The compound was characterized by the following spectroscopic data:
MS-ESI: (ESI, pos. ion) m/z: 571.0 [M+1]$^+$;
$^1$H NMR (400 MHz, CDCl$_3$): δ 9.82 (s, 1H), 7.86 (d, 1H), 7.59-7.50 (m, 1H), 7.41-7.22 (m, 1H), 7.19-7.07 (m, 1H), 5.98 (br.s, 1H), 4.33-3.91 (m, 5H), 3.86-3.82 (m, 1H), 3.75-3.51 (m, 3H), 3.14-3.08 (m, 1H), 2.58-2.37 (m, 1H), 1.06 (t, 3H).

Example 121

4-((6-(2-chloro-4-fluorophenyl)-5-(ethoxycarbonyl)-2-(5-fluorothiazol-2-yl)-3,6-dihydropyrimidin-4-yl)methyl)morpholine-3-carboxylic acid

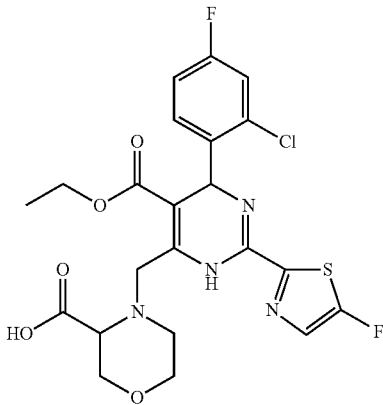 [SMILES: CCOC(=O)C1=C(CN2CCOCC2C(=O)O)NC(c2ncc(F)s2)=NC1c1ccc(F)cc1Cl]

Step A: Ethyl 4-(2-chloro-4-fluorophenyl)-2-(5-fluorothiazol-2-yl)-6-methyl-1,4-dihydropyrimidine-5-carboxylate 5-fluorothiazole-2-carboximidamide acetate (0.22 g, 1.07 mmol) was reacted with 2-chloro-4-fluorobenzaldehyde (0.17 g, 1.07 mmol) and ethyl 3-oxobutanoate (0.14 g, 1.07 mmol) according to the procedure as described in Example 1, Step A to give the title compound as a yellow solid (0.17 g, 39%). The compound was characterized by the following spectroscopic data:

MS-ESI: (ESI, pos. ion) m/z: 398.0 [M+1]$^+$;
$^1$H NMR (400 MHz, CDCl$_3$): δ 7.88 (d, 1H), 7.40-7.28 (m, 2H), 7.17-7.09 (m, 1H), 6.00 (d, 1H), 4.16 (q, 2H), 2.47 (s, 3H), 1.20 (t, 3H).

Step B: Ethyl 6-(bromomethyl)-4-(2-chloro-4-fluorophenyl)-2-(5-fluorothiazol-2-yl)-1,4-dihydropyrimidine-5-carboxylate Ethyl 4-(2-chloro-4-fluorophenyl)-2-(5-fluorothiazol-2-yl)-6-methyl-1,4-dihydropyrimidine-5-carboxylate (0.17 g, 0.41 mmol) was reacted with NBS (0.07 g, 0.41 mmol) according to the procedure as described in Example 1, Step B to give the title compound as a yellow solid (0.13 g, 65%). The compound was characterized by the following spectroscopic data:
MS-ESI: (ESI, pos. ion) m/z: 476.0 [M+1]$^+$;
$^1$H NMR (400 MHz, CDCl$_3$): δ 7.81 (d, 1H), 7.40-7.22 (m, 2H), 7.17-7.10 (m, 1H), 6.03 (d, 1H), 5.74 (d, 1H), 4.64 (d, 1H), 4.21 (q, 2H), 1.17 (t, 3H).

Step C: 4-((6-(2-chloro-4-fluorophenyl)-5-(ethoxycarbonyl)-2-(5-fluorothiazol-2-yl)-3,6-dihydropyrimidin-4-yl)methyl)morpholine-3-carboxylic acid Ethyl 6-(bromomethyl)-4-(2-chloro-4-fluorophenyl)-2-(5-fluorothiazol-2-yl)-1,4-dihydropyrimidine-5-carboxylate (0.2 g, 0.41 mmol) was reacted with morpholine-3-carboxylic acid hydrochloride (0.07 g, 0.41 mmol) according to the procedure as described in Example 1, Step C to give the title compound as a yellow solid (0.2 g, 90%). The compound was characterized by the following spectroscopic data:
MS-ESI: (ESI, pos. ion) m/z: 527.1 [M+1]$^+$;
$^1$H NMR (400 MHz, CDCl$_3$): δ 7.88 (d, 1H), 7.40-7.24 (m, 2H), 7.17-7.10 (m, 1H), 6.00 (s, 1H), 4.33-3.92 (m, 5H), 3.87-3.82 (m, 1H), 3.72-3.52 (m, 3H), 3.13-3.07 (m, 1H), 2.52-2.39 (m, 1H), 1.03 (t, 3H).

Example 122

4-((6-(2,4-dichlorophenyl)-5-(ethoxycarbonyl)-2-(5-fluorothiazol-2-yl)-3,6-dihydropyrimidin-4-yl)methyl)morpholine-3-carboxylic acid

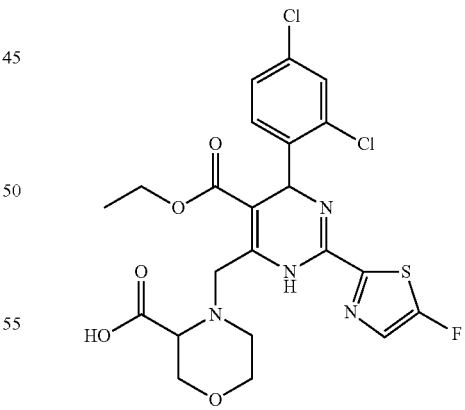

Step A: Ethyl 4-(2,4-dichlorophenyl)-2-(5-fluorothiazol-2-yl)-6-methyl-1,4-dihydropyrimidine-5-carboxylate 5-fluorothiazole-2-carboximidamide acetate (0.25 g, 1.22 mmol) was reacted with 2,4-dichlorobenzaldehyde (0.21 g, 1.22 mmol) and ethyl 3-oxobutanoate (0.16 g, 1.22 mmol)

according to the procedure as described in Example 1, Step A to give the title compound as a yellow solid (0.41 g, 80%). The compound was characterized by the following spectroscopic data:

MS-ESI: (ESI, pos. ion) m/z: 414.0 [M+1]$^+$;
$^1$H NMR (400 MHz, CDCl$_3$): δ 7.87 (s, 1H), 7.59 (s, 1H), 7.36 (s, 2H), 6.00 (s, 1H), 4.16 (q, 2H), 2.43 (s, 3H), 1.05 (t, 3H).

Step B: Ethyl 6-(bromomethyl)-4-(2,4-dichlorophenyl)-2-(5-fluorothiazol-2-yl)-1,4-dihydropyrimidine-5-carboxylate Ethyl 4-(2,4-dichlorophenyl)-2-(5-fluorothiazol-2-yl)-6-methyl-1,4-dihydropyrimidine-5-carboxylate (0.44 g, 1.06 mmol) was reacted with NBS (0.19 g, 1.06 mmol) according to the procedure as described in Example 1, Step B to give the title compound as a yellow solid (0.36 g, 70%). The compound was characterized by the following spectroscopic data:

MS-ESI: (ESI, pos. ion) m/z: 491.9 [M+1]$^+$;
$^1$H NMR (400 MHz, CDCl$_3$): δ 7.87 (s, 1H), 7.59 (s, 1H), 7.36 (s, 2H), 6.00 (s, 1H), 5.68 (d, 1H), 4.60 (d, 1H), 4.11 (q, 2H), 1.07 (t, 3H).

Step C: 4-((6-(2,4-dichlorophenyl)-5-(ethoxycarbonyl)-2-(5-fluorothiazol-2-yl)-3,6-dihydropyrimidin-4-yl)methyl)morpholine-3-carboxylic acid Ethyl 6-(bromomethyl)-4-(2,4-dichlorophenyl)-2-(5-fluorothiazol-2-yl)-1,4-dihydropyrimidine-5-carboxylate (0.52 g, 1.06 mmol) was reacted with morpholine-3-carboxylic acid hydrochloride (0.21 g, 1.28 mmol) according to the procedure as described in Example 1, Step C to give the title compound as a yellowish solid (0.35 g, 60%). The compound was characterized by the following spectroscopic data:

MS-ESI: (ESI, pos. ion) m/z: 543.1 [M+1]$^+$;
$^1$H NMR (400 MHz, DMSO-d$_6$): δ 9.89 (s, 1H), 7.87 (s, 1H), 7.59 (s, 1H), 7.36 (s, 2H), 6.00 (s, 1H), 4.28-3.92 (m, 5H), 3.85-3.82 (m, 1H), 3.71-3.52 (m, 3H), 3.09-3.07 (m, 1H), 2.52-2.37 (m, 1H), 1.09 (t, 3H).

Example 123

4-((6-(2-bromo-4-fluorophenyl)-5-(ethoxycarbonyl)-2-(1-methyl-1H-1,2,4-triazol-3-yl)-3,6-dihydropyrimidin-4-yl)methyl)morpholine-3-carboxylic acid

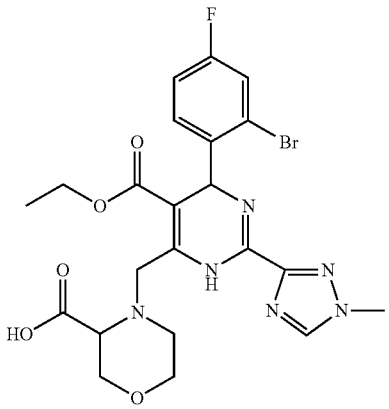 [SMILES: CCOC(=O)C1=C(CN2CCOCC2C(=O)O)NC(c2ncn(C)n2)=NC1c1ccc(F)cc1Br]

Ethyl 4-(2-bromo-4-fluorophenyl)-6-(bromomethyl)-2-(1-methyl-1H-1,2,4-triazol-3-yl)-1,4-dihydropyrimidine-5-carboxylate (0.5 g, 1 mmol) was reacted with morpholine-3-carboxylic acid hydrochloride (0.17 g, 1 mmol) according to the procedure as described in Example 1, Step C to give the title compound as a yellow solid (0.25 g, 45%). The compound was characterized by the following spectroscopic data:

MS-ESI: (ESI, pos. ion) m/z: 551.1 [M+1]$^+$;
$^1$H NMR (400 MHz, CDCl$_3$): δ 8.03 (s, 1H), 7.60 (s, 1H), 7.37-7.29 (m, 1H), 7.26-7.13 (m, 1H), 6.95-6.84 (m, 1H), 6.21 (s, 1H), 4.33-3.99 (m, 5H), 3.96 (s, 3H), 3.81-3.78 (m, 1H), 3.71-3.52 (m, 3H), 3.11-3.07 (m, 1H), 2.52-2.39 (m, 1H), 1.06 (t, 3H).

Example 124

1-((6-(2-bromo-4-fluorophenyl)-5-(ethoxycarbonyl)-2-(thiazol-2-yl)-3,6-dihydropyrimidin-4-yl)methyl)-4-methylpiperazine-2-carboxylic acid

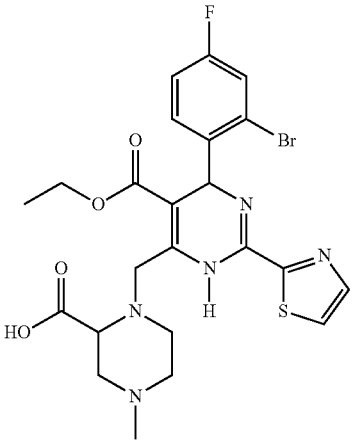 [SMILES: CCOC(=O)C1=C(CN2CCN(C)CC2C(=O)O)NC(c2nccs2)=NC1c1ccc(F)cc1Br]

Step A: Ethyl 1,4-dibenzylpiperazine-2-carboxylate

To a solution of N$^1$,N$^2$-dibenzylethane-1,2-diamine (24 g, 100 mmol) in toluene (100 mL) was added TEA (24.2 g, 240 mmol). The mixture was heated to 80° C., and a solution of ethyl 2,3-dibromopropanoate (27.3 g, 105 mmol) in toluene (100 mL) was added dropwise over a period of 0.5 hour at 80° C. Then the mixture was stirred at the temperature for 12 hours and cooled to 25° C. The reaction mixture was washed with saturated NaHCO$_3$ aqueous solution. The organic layer was dried over Na$_2$SO$_4$, and concentrated in vacuo. The residue was purified by a silica gel column chromatography (PETROLEUM ETHER/EtOAc (V/V)=5/1) to give the title compound as yellow oil (22.7 g, 67%). The compound was characterized by the following spectroscopic data:

MS-ESI: (ESI, pos. ion) m/z: 339.2 [M+1]$^+$;
$^1$H NMR (400 MHz, CDCl$_3$): δ 7.34-7.22 (m, 10H), 4.20-4.08 (m, 2H), 3.92 (d, 1H), 3.62-3.48 (m, 2H), 3.38 (d, 1H), 3.35-3.24 (m, 1H), 3.12-3.02 (m, 1H), 2.80-2.59 (m, 2H), 2.57-2.38 (m, 3H), 1.24 (t, 3H).

Step B: Ethyl 1-benzylpiperazine-2-carboxylate

To a solution of ethyl 1,4-dibenzylpiperazine-2-carboxylate (6.76 g, 20 mmol) in 1,2-dichloroethane (20 mL) was added 1-chloroethyl carbonochloridate (3.15 g, 22 mmol) dropwise over a period of 30 minutes at 0° C., and the mixture was stirred at the temperature for another 15 minutes. Then the mixture was stirred at 90° C. for 1 hour. The mixture was concentrated in vacuo, and to the residue was added methanol (15 mL). The mixture was stirred at 70° C. for 1 hour and concentrated in vacuo. The residue was diluted with water and washed with DCM. The aqueous layer was adjusted to pH 9 with NaHCO$_3$ aqueous solution and extracted with DCM.

The organic layer was dried over Na₂SO₄, and concentrated in vacuo to give the title compound as yellow oil (3.06 g, 60%). The compound was characterized by the following spectroscopic data:

MS-ESI: (ESI, pos. ion) m/z: 249.2 [M+1]⁺;
¹H NMR (400 MHz, CDCl₃): δ 7.26-7.15 (m, 5H), 4.15 (q, 2H), 3.60 (dd, 2H), 3.15-3.02 (m, 3H), 2.91-2.72 (m, 3H), 2.24-2.17 (m, 1H), 1.68 (br.s, 1H), 1.23 (t, 3H).

Step C: Ethyl 1-benzyl-4-methylpiperazine-2-carboxylate

Ethyl 1-benzylpiperazine-2-carboxylate (3.03 g, 12.2 mmol) was reacted with iodomethane (1.73 g, 12.2 mmol) according to the procedure as described in Example 48, Step A to give the title compound as yellow oil (2.33 g, 73%). The compound was characterized by the following spectroscopic data:

MS-ESI: (ESI, pos. ion) m/z: 263.2 [M+1]⁺;
¹H NMR (400 MHz, CDCl₃): δ 7.34-7.24 (m, 5H), 4.21 (q, 2H), 3.90 (d, 1H), 3.52-3.45 (m, 1H), 3.30 (t, 1H), 3.02 (br.s, 1H), 2.64 (br.s, 2H), 2.36-2.26 (m, 3H), 2.25 (s, 3H), 1.27 (t, 3H).

Step D: Ethyl 4-methylpiperazine-2-carboxylate

Ethyl 1-benzyl-4-methylpiperazine-2-carboxylate (11.54 g, 44 mmol) was reacted with Pd—C (10%, 1 g) according to the procedure as described in Example 34, Step C to give the title compound as colorless oil (6.2 g, 82%). The compound was characterized by the following spectroscopic data:

MS-ESI: (ESI, pos. ion) m/z: 173.1 [M+1]⁺;
¹H NMR (400 MHz, CDCl₃): δ 4.21 (q, 2H), 3.69 (d, 1H), 3.52-3.46 (m, 1H), 3.30 (t, 1H), 3.02 (br.s, 1H), 2.36-2.28 (m, 3H), 2.26 (s, 3H), 1.29 (t, 3H).

Step E: 4-methylpiperazine-2-carboxylic acid

Ethyl 4-methylpiperazine-2-carboxylate (1.03 g, 6 mmol) was reacted with NaOH (0.48 g, 12 mmol) according to the procedure as described in Example 21, Step A to give the title compound as colorless oil (0.86 g, 100%). The compound was characterized by the following spectroscopic data:

MS-ESI: (ESI, pos. ion) m/z: 145.1 [M+1]⁺;
¹H NMR (400 MHz, CDCl₃): δ 3.69 (d, 1H), 3.54-3.48 (m, 1H), 3.30 (t, 1H), 3.02 (br.s, 1H), 2.36-2.27 (m, 3H), 2.26 (s, 3H).

Step F: 1-((6-(2-bromo-4-fluorophenyl)-5-(ethoxycarbonyl)-2-(thiazol-2-yl)-3,6-dihydropyrimidin-4-yl)methyl)-4-methylpiperazine-2-carboxylic acid Ethyl 4-(2-bromo-4-fluorophenyl)-6-(bromomethyl)-2-(thiazol-2-yl)-1,4-dihydropyrimidine-5-carboxylate (1.5 g, 3 mmol) was reacted with 4-methylpiperazine-2-carboxylic acid (0.43 g, 3 mmol) according to the procedure as described in Example 1, Step C to give the title compound as a yellow solid (1.00 g, 59%). The compound was characterized by the following spectroscopic data:

MS-ESI: (ESI, pos. ion) m/z: 566.1 [M+1]⁺;
¹H NMR (400 MHz, DMSO-d₆): δ 10.90 (br.s, 1H), 8.00-7.96 (m, 1H), 7.87-7.82 (m, 1H), 7.52-7.48 (m, 1H), 7.39-7.31 (m, 1H), 7.24-7.18 (m, 1H), 6.01 (s, 1H), 4.30-3.92 (m, 2H), 3.69-3.56 (m, 2H), 3.52-3.39 (m, 2H), 3.30-3.15 (m, 1H), 3.02 (br.s, 1H), 2.36-2.29 (m, 3H), 2.26 (s, 3H), 1.06 (t, 3H).

Example 125

4-((6-(2-bromo-4-fluorophenyl)-5-(ethoxycarbonyl)-2-(1-methyl-1H-imidazol-2-yl)-3,6-dihydropyrimidin-4-yl)methyl)morpholine-3-carboxylic acid

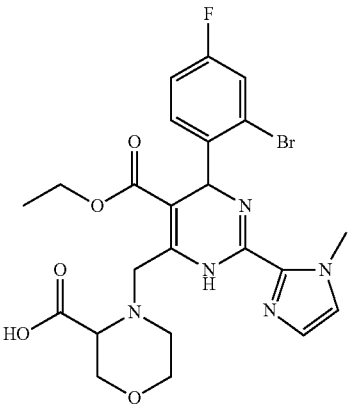 [SMILES: CCOC(=O)C1=C(CN2CCOCC2C(=O)O)NC(c2nccn2C)=NC1c1ccc(F)cc1Br]

Ethyl 4-(2-bromo-4-fluorophenyl)-6-(bromomethyl)-2-(1-methyl-1H-imidazol-2-yl)-1,4-dihydropyrimidine-5-carboxylate (1 g, 2 mmol) (The compound was synthesized according to the procedure as described in WO2010069147) was reacted with morpholine-3-carboxylic acid (0.26 g, 2 mmol) according to the procedure as described in Example 28 to give the title compound as a yellowish solid (0.49 g, 45%). The compound was characterized by the following spectroscopic data:

MS-ESI: (ESI, pos. ion) m/z: 550.1 [M+1]⁺;
¹H NMR (400 MHz, DMSO-d₆): δ 9.83 (s, 1H), 7.69-7.48 (m, 2H), 7.32-7.28 (m, 1H), 7.23-7.12 (m, 2H), 6.17 (s, 1H), 4.30-3.88 (m, 5H), 3.84-3.78 (m, 1H), 3.74-3.50 (m, 3H), 3.49 (s, 3H), 3.11-3.03 (m, 1H), 2.55-2.34 (m, 1H), 1.06 (t, 3H).

Example 126

Ethyl 6-(((S)-2-((((S)-2-amino-3-methylbutanoyl)oxy)methyl)morpholino)methyl)-4-(2-bromo-4-fluorophenyl)-2-(thiazol-2-yl)-1,4-dihydropyrimidine-5-carboxylate

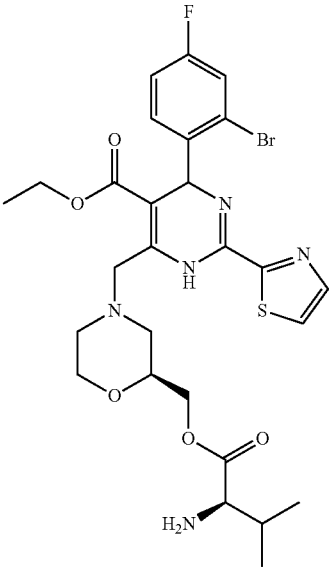 [SMILES: CCOC(=O)C1=C(CN2CCO[C@H](COC(=O)[C@H](N)C(C)C)C2)NC(c2nccs2)=NC1c1ccc(F)cc1Br]

Ethyl 4-(2-bromo-4-fluorophenyl)-6-(((S)-2-(hydroxymethyl)morpholino)methyl)-2-(thiazol-2-yl)-1,4-dihydropyrimidine-5-carboxylate (1 g, 1.9 mmol) was reacted with (S)-2-((tert-butoxycarbonyl)amino)-3-methylbutanoic acid (0.63 g, 2.9 mmol) according to the procedure as described in Example 49 to give the title compound as a yellow solid (0.57 g, 47%). The compound was characterized by the following spectroscopic data:

MS-ESI: (ESI, pos. ion) m/z: 638.1 [M+1]$^+$;
$^1$H NMR (400 MHz, D$_2$O): δ 7.92-7.87 (m, 2H), 7.49-7.41 (m, 2H), 7.13-7.09 (m, 1H), 6.15 (br.s, 1H), 4.51-4.35 (m, 4H), 4.34-4.19 (m, 2H), 4.11-3.98 (m, 4H), 3.79-3.66 (m, 2H), 3.44-3.28 (m, 2H), 2.31-2.25 (m, 1H), 1.07-1.03 (m, 3H), 0.98-0.91 (m, 6H).

Example 127

Ethyl 4-(2-chloro-4-fluorophenyl)-6-(((S)-2-(hydroxymethyl)morpholino)methyl)-2-(thiazol-2-yl)-1,4-dihydropyrimidine-5-carboxylate

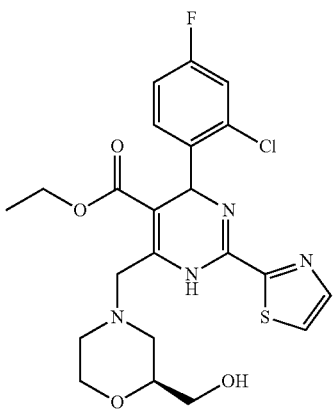 [SMILES: CCOC(=O)C1=C(CN2CCO[C@H](CO)C2)NC(c2nccs2)=NC1c1ccc(Cl)cc1Cl]

Ethyl 6-(bromomethyl)-4-(2-chloro-4-fluorophenyl)-2-(thiazol-2-yl)-1,4-dihydropyrimidine-5-carboxylate (0.92 g, 2 mmol) was reacted with (S)-morpholin-2-ylmethanol (0.34 g, 2.2 mmol) according to the procedure as described in Example 25, Step B to give the title compound as a yellow solid (0.30 g, 30%). The compound was characterized by the following spectroscopic data:

MS-ESI: (ESI, pos. ion) m/z: 495.1 [M+1]$^+$;
$^1$H NMR (400 MHz, CDCl$_3$): δ 9.68 (d, 1H), 7.96 (d, 1H), 7.80 (d, 1H), 7.56-7.50 (m, 1H), 7.40-7.35 (m, 1H), 7.20-7.16 (m, 1H), 6.00 (s, 1H), 3.98-3.30 (m, 7H), 2.97-2.61 (m, 4H), 2.45-2.05 (m, 2H), 1.05 (t, 3H).

Example 128

Ethyl 4-(2,4-dichlorophenyl)-6-(((S)-2-(hydroxymethyl)morpholino)methyl)-2-(thiazol-2-yl)-1,4-dihydropyrimidine-5-carboxylate

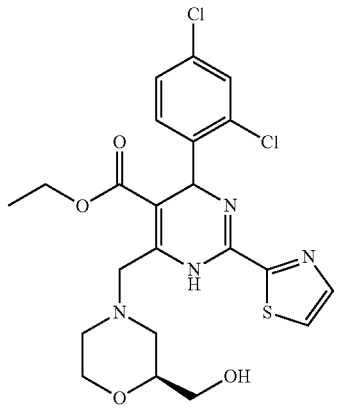

Ethyl 6-(bromomethyl)-4-(2,4-dichlorophenyl)-2-(thiazol-2-yl)-1,4-dihydropyrimidine-5-carboxylate (0.95 g, 2 mmol) was reacted with (S)-morpholin-2-ylmethanol (0.34 g, 2.2 mmol) according to the procedure as described in Example 25, Step B to give the title compound as a yellow solid (0.34 g, 33%). The compound was characterized by the following spectroscopic data:

MS-ESI: (ESI, pos. ion) m/z: 511.1 [M+1]$^+$;
$^1$H NMR (400 MHz, CDCl$_3$): δ 9.64 (d, 1H), 8.00 (d, 1H), 7.90 (d, 1H), 7.56-7.46 (m, 1H), 7.38-7.29 (m, 1H), 7.20-7.13 (m, 1H), 6.02 (s, 1H), 3.98-3.29 (m, 7H), 2.99-2.62 (m, 4H), 2.45-2.01 (m, 2H), 1.05 (t, 3H).

Example 129

3-(4-((6-(2-bromo-4-fluorophenyl)-5-(ethoxycarbonyl)-2-(thiazol-2-yl)-3,6-dihydropyrimidin-4-yl)methyl)morpholin-2-yl)propanoic acid

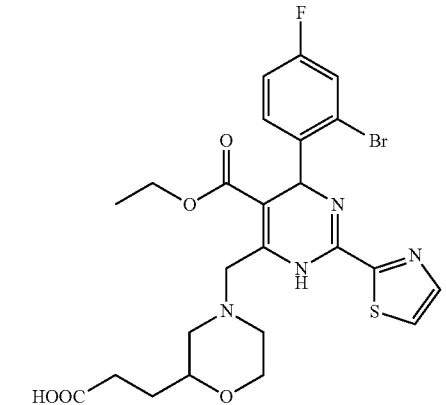 [SMILES: CCOC(=O)C1=C(CN2CCOC(CCC(=O)O)C2)NC(c2nccs2)=NC1c1ccc(F)cc1Br]

Step A: Benzyl 2-(3-methoxy-3-oxoprop-1-en-1-yl)morpholine-4-carboxylate

A mixture of benzyl 2-formylmorpholine-4-carboxylate (1.5 g, 6 mmol) and methyl 2-(triphenylphosphoranylidene)

acetate (2.01 g, 6 mmol) in DCM (30 mL) was stirred at 25° C. for 12 hours under $N_2$. The mixture was concentrated in vacuo, and the residue was purified by a silica gel column chromatography (PETROLEUM ETHER/EtOAc (V/V)=3/1) to give the title compound as colorless oil (0.88 g, 48%). The compound was characterized by the following spectroscopic data:

MS-ESI: (ESI, pos. ion) m/z: 306.1 [M+1]$^+$;
$^1$H NMR (400 MHz, CDCl$_3$): δ 7.35-7.29 (m, 5H), 6.82-6.78 (m, 1H), 6.09-6.01 (m, 1H), 5.15-5.10 (m, 2H), 4.20-4.11 (q, 2H), 3.94-3.88 (m, 2H), 3.77-3.65 (m, 3H), 3.60-3.58 (m, 1H), 3.02 (br.s, 1H), 2.74 (br.s, 1H).

Step B: 3-(4-((benzyloxy)carbonyl)morpholin-2-yl)acrylic acid

Benzyl 2-(3-methoxy-3-oxoprop-1-en-1-yl)morpholine-4-carboxylate (0.86 g, 2.82 mmol) was reacted with NaOH (1.12 g, 28.2 mmol) according to the procedure as described in Example 21, Step A to give the title compound as colorless oil (0.79 g, 96%). The compound was characterized by the following spectroscopic data:

MS-ESI: (ESI, pos. ion) m/z: 292.1 [M+1]$^+$;
$^1$H NMR (400 MHz, CDCl$_3$): δ 7.37-7.19 (m, 5H), 6.82-6.79 (m, 1H), 6.09-6.02 (m, 1H), 5.15-5.08 (m, 2H), 4.10-4.01 (m, 2H), 3.94-3.80 (m, 2H), 3.60-3.55 (m, 1H), 3.02 (br.s, 1H), 2.74 (br.s, 1H).

Step C: 3-(morpholin-2-yl)propanoic acid 3-(4-((benzyloxy)carbonyl)morpholin-2-yl)acrylic acid (0.52 g, 1.8 mmol) was reacted with Pd—C (10%, 0.05 g) according to the procedure as described in Example 34, Step C to give the title compound as a white solid (0.2 g, 70%). The compound was characterized by the following spectroscopic data:

MS-ESI: (ESI, pos. ion) m/z: 160.1 [M+1]$^+$;
$^1$H NMR (400 MHz, CDCl$_3$): δ 3.66-3.52 (m, 3H), 2.96-2.69 (m, 4H), 2.33-2.21 (m, 2H), 1.69-1.54 (m, 2H).

Step D: 3-(4-((6-(2-bromo-4-fluorophenyl)-5-(ethoxycarbonyl)-2-(thiazol-2-yl)-3,6-dihydropyrimidin-4-yl)methyl)morpholin-2-yl)propanoic acid Ethyl 4-(2-bromo-4-fluorophenyl)-6-(bromomethyl)-2-(thiazol-2-yl)-1,4-dihydropyrimidine-5-carboxylate (0.7 g, 1.4 mmol) was reacted with 3-(morpholin-2-yl)propanoic acid (0.22 g, 1.4 mmol) according to the procedure as described in Example 28 to give the title compound as a yellow solid (0.40 g, 50%). The compound was characterized by the following spectroscopic data:

MS-ESI: (ESI, pos. ion) m/z: 581.1 [M+1]$^+$;
$^1$H NMR (400 MHz, DMSO-d$_6$): δ 9.81 (s, 1H), 7.84 (d, 1H), 7.43-7.36 (m, 1H), 7.33 (d, 1H), 7.28 (d, 1H), 6.95-6.87 (m, 1H), 6.19 (s, 1H), 4.30-3.92 (m, 5H), 3.84-3.82 (m, 1H), 3.74-3.52 (m, 3H), 2.82-2.69 (m, 3H), 2.55-2.14 (m, 3H), 1.06 (t, 3H).

Example 130

3-(4-((6-(2-chloro-4-fluorophenyl)-5-(ethoxycarbonyl)-2-(thiazol-2-yl)-3,6-dihydropyrimidin-4-yl)methyl)morpholin-2-yl)propanoic acid

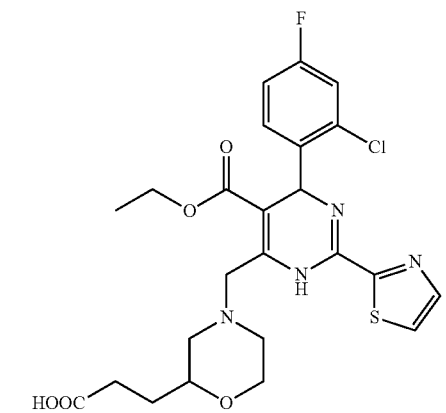 [SMILES: CCOC(=O)C1=C(CN2CCOC(CCC(=O)O)C2)NC(c2nccs2)=NC1c1ccc(F)cc1Cl]

Ethyl 6-(bromomethyl)-4-(2-chloro-4-fluorophenyl)-2-(thiazol-2-yl)-1,4-dihydropyrimidine-5-carboxylate (0.64 g, 1.4 mmol) was reacted with 3-(morpholin-2-yl)propanoic acid (0.22 g, 1.4 mmol) according to the procedure as described in Example 28 to give the title compound as a yellow solid (0.45 g, 60%). The compound was characterized by the following spectroscopic data:

MS-ESI: (ESI, pos. ion) m/z: 537.1 [M+1]$^+$;
$^1$H NMR (400 MHz, DMSO-d$_6$): δ 12.91 (br.s, 1H), 9.82 (s, 1H), 7.89 (d, 1H), 7.42-7.37 (m, 1H), 7.30 (d, 1H), 7.26 (d, 1H), 6.99-6.89 (m, 1H), 6.20 (s, 1H), 4.33-3.92 (m, 5H), 3.84-3.80 (m, 1H), 3.71-3.52 (m, 3H), 2.82-2.65 (m, 3H), 2.55-2.19 (m, 3H), 1.05 (t, 3H).

Example 131

3-(4-((6-(2,4-dichlorophenyl)-5-(ethoxycarbonyl)-2-(thiazol-2-yl)-3,6-dihydropyrimidin-4-yl)methyl)morpholin-2-yl)propanoic acid

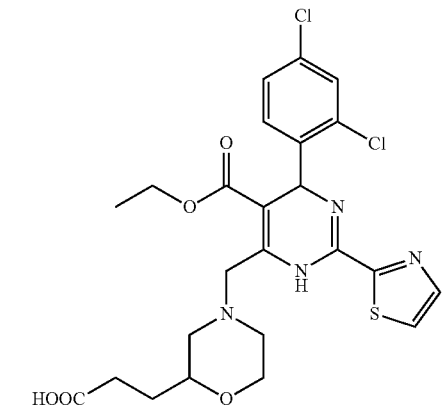

Ethyl 6-(bromomethyl)-4-(2,4-dichlorophenyl)-2-(thiazol-2-yl)-1,4-dihydropyrimidine-5-carboxylate (0.67 g, 1.4 mmol) was reacted with 3-(morpholin-2-yl)propanoic acid (0.22 g, 1.4 mmol) according to the procedure as described in Example 28 to give the title compound as a yellow solid (0.35 g, 45%). The compound was characterized by the following spectroscopic data:

MS-ESI: (ESI, pos. ion) m/z: 553.1 [M+1]$^+$;

$^1$H NMR (400 MHz, DMSO-d$_6$): δ 12.90 (br.s, 1H), 9.86 (br.s, 1H), 7.79 (d, 1H), 7.41-7.39 (m, 1H), 7.32 (d, 1H), 7.26 (d, 1H), 7.00-6.89 (m, 1H), 6.09 (s, 1H), 4.30-3.92 (m, 5H), 3.88-3.82 (m, 1H), 3.78-3.52 (m, 3H), 2.89-2.69 (m, 3H), 2.57-2.14 (m, 3H), 1.05 (t, 3H).

Example 132

Ethyl 4-(2-bromo-4-fluorophenyl)-6-((2-(3-methoxy-3-oxopropyl)morpholino)methyl)-2-(thiazol-2-yl)-1,4-dihydropyrimidine-5-carboxylate

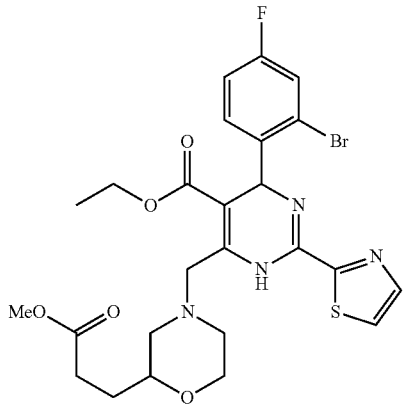 [SMILES: CCOC(=O)C1=C(CN2CCOC(CCC(=O)OC)C2)NC(c2nccs2)=NC1c1ccc(F)cc1Br]

Step A: Methyl 3-(morpholin-2-yl)propanoate

Benzyl 2-(3-methoxy-3-oxoprop-1-en-1-yl)morpholine-4-carboxylate (6.47 g, 21.2 mmol) was reacted with Pd—C (10%, 0.65 g) according to the procedure as described in Example 34, Step C to give the title compound as colorless oil (3.21 g, 87%). The compound was characterized by the following spectroscopic data:

MS-ESI: (ESI, pos. ion) m/z: 174.1 [M+1]$^+$;

$^1$H NMR (400 MHz, CDCl$_3$): δ 3.66-3.49 (m, 3H), 2.96-2.78 (m, 4H), 2.33-2.21 (m, 2H), 1.69-1.55 (m, 2H), 1.29-1.21 (m, 3H).

Step B: Ethyl 4-(2-bromo-4-fluorophenyl)-6-((2-(3-methoxy-3-oxopropyl)morpholino)methyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (1 g, 2 mmol) was reacted with methyl 3-(morpholin-2-yl)propanoate (0.38 g, 2.2 mmol) according to the procedure as described in Example 25, Step B to give the title compound as a yellow solid (0.53 g, 45%). The compound was characterized by the following spectroscopic data:

MS (ESI, pos. ion) m/z: 595.1 [M+1]$^+$;

$^1$H NMR (600 MHz, CDCl$_3$): 9.63 (s, 1H), 7.84 (t, 1H), 7.43 (d, 1H), 7.30-7.27 (m, 1H), 6.96-6.83 (m, 1H), 6.20 (s, 1H), 4.00-3.85 (m, 5H), 3.65 (s, 1H), 3.63-3.51 (m, 2H), 2.92-2.82 (m, 1H), 2.79-2.65 (m, 3H), 2.39-2.14 (m, 4H), 1.65-1.58 (m, 2H), 1.09 (t, 3H).

Example 133

Ethyl 4-(2-bromo-4-fluorophenyl)-6-((2-(3-hydroxypropyl)morpholino)methyl)-2-(thiazol-2-yl)-1,4-dihydropyrimidine-5-carboxylate

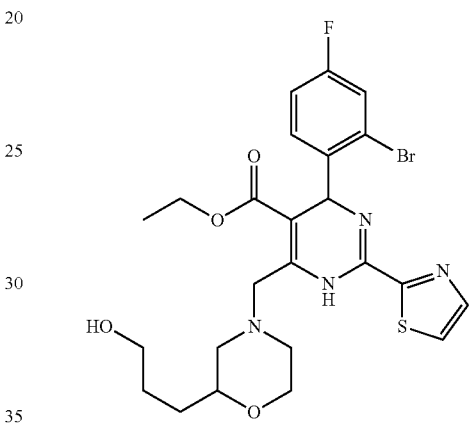

Step A: 3-(morpholin-2-yl)propan-1-ol

Methyl 3-(morpholin-2-yl)propanoate (0.69 g, 4 mmol) was reacted with LiAlH$_4$ (0.23 g, 6 mmol) according to the procedure as described in Example 68, Step A to give the title compound as colorless oil (0.43 g, 75%). The compound was characterized by the following spectroscopic data:

MS-ESI: (ESI, pos. ion) m/z: 146.1 [M+1]$^+$.

Step B: Ethyl 4-(2-bromo-4-fluorophenyl)-6-((2-(3-hydroxypropyl)morpholino)methyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (1.26 g, 2.5 mmol) was reacted with 3-(morpholin-2-yl)propan-1-ol (0.43 g, 3 mmol) according to the procedure as described in Example 25, Step B to give the title compound as a yellow solid (1.0 g, 70%). The compound was characterized by the following spectroscopic data:

MS (ESI, pos. ion) m/z: 567.1 [M+1]$^+$;

$^1$H NMR (600 MHz, CDCl$_3$): δ 9.68 (s, 1H), 8.01-7.99 (m, 1H), 7.92-7.89 (m, 1H), 7.53-7.49 (m, 1H), 7.41-7.38 (m, 1H), 7.20-7.16 (m, 1H), 6.04 (s, 1H), 4.03-3.73 (m, 5H), 3.62-3.59 (m, 4H), 2.78-2.65 (m, 2H), 2.46-2.33 (m, 3H), 2.23-2.07 (m, 1H), 1.82-1.70 (m, 2H), 1.23 (t, 3H).

Example 134

Ethyl 4-(2-bromo-4-fluorophenyl)-6-((2-(3-(methylamino)-3-oxopropyl)morpholino)methyl)-2-(thiazol-2-yl)-1,4-dihydropyrimidine-5-carboxylate

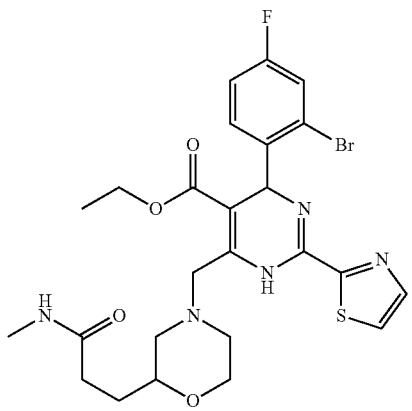 [SMILES: CCOC(=O)C1=C(CN2CCOC(CCC(=O)NC)C2)NC(c2nccs2)=NC1c1ccc(F)cc1Br]

3-(4-((6-(2-bromo-4-fluorophenyl)-5-(ethoxycarbonyl)-2-(thiazol-2-yl)-3,6-dihydropyrimidin-4-yl)methyl)morpholin-2-yl)propanoic acid (0.69 g, 1.19 mmol) was reacted with methanamine hydrochloride (0.12 g, 1.8 mmol) according to the procedure as described in Example 62, Step B to give the title compound as a yellow solid (0.27 g, 38%). The compound was characterized by the following spectroscopic data:

MS (ESI, pos. ion) m/z: 594.1 [M+1]$^+$;

$^1$H NMR (600 MHz, CDCl$_3$): δ 9.65 (s, 1H), 8.04 (d, 1H), 7.94 (d, 1H), 7.70-7.68 (m, 1H), 7.55-7.50 (m, 1H), 7.39-7.31 (m, 1H), 7.23-7.19 (m, 1H), 6.03 (s, 1H), 4.00-3.85 (m, 3H), 3.63-3.51 (m, 2H), 3.05 (s, 3H), 2.92-2.82 (m, 1H), 2.79-2.65 (m, 3H), 2.39-2.14 (m, 4H), 1.65-1.48 (m, 2H), 1.09 (t, 3H).

Example 135

Ethyl 6-((2-(3-amino-3-oxopropyl)morpholino)methyl)-4-(2-bromo-4-fluorophenyl)-2-(thiazol-2-yl)-1,4-dihydropyrimidine-5-carboxylate

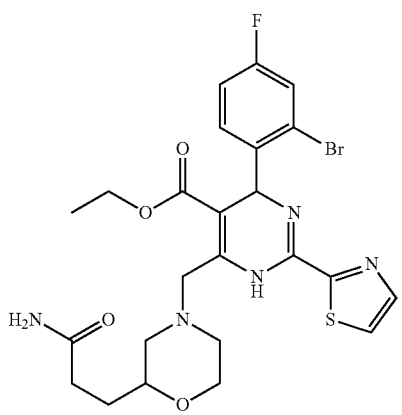 [SMILES: CCOC(=O)C1=C(CN2CCOC(CCC(N)=O)C2)NC(c2nccs2)=NC1c1ccc(F)cc1Br]

Step A: 3-(morpholin-2-yl)propanamide

Methyl 3-(morpholin-2-yl)propanoate (0.58 g, 3.35 mmol) was reacted with a solution of NH$_3$ in methanol (7 mol/L, 10 mL) according to the procedure as described in Example 25, Step A to give the title compound as brownish oil (0.41 g, 78%). The compound was characterized by the following spectroscopic data:

MS-ESI: (ESI, pos. ion) m/z: 159.1 [M+1]$^+$.

Step B: Ethyl 6-((2-(3-amino-3-oxopropyl)morpholino)methyl)-4-(2-bromo-4-fluorophenyl)-2-(thiazol-2-yl)-1,4-dihydropyrimidine-5-carboxylate Ethyl 4-(2-bromo-4-fluorophenyl)-6-(bromomethyl)-2-(thiazol-2-yl)-1,4-dihydropyrimidine-5-carboxylate (1.51 g, 3 mmol) was reacted with 3-(morpholin-2-yl)propanamide (0.47 g, 3 mmol) according to the procedure as described in Example 25, Step B to give the title compound as a yellow solid (1.5 g, 86%). The compound was characterized by the following spectroscopic data:

MS (ESI, pos. ion) m/z: 580.1 (M+1)$^+$;

$^1$H NMR (600 MHz, CDCl$_3$): δ 9.69 (d, 1H), 8.06-8.01 (m, 1H), 7.97-7.90 (m, 1H), 7.60-7.54 (m, 1H), 7.42-7.39 (m, 1H), 7.27-7.16 (m, 2H), 6.72 (d, 1H), 6.07 (d, 1H), 4.00-3.85 (m, 5H), 3.63-3.51 (m, 2H), 2.92-2.82 (m, 1H), 2.79-2.65 (m, 1H), 2.39-2.14 (m, 4H), 1.65-1.60 (m, 2H), 1.09 (t, 3H).

Example 136

Ethyl 4-(2-bromo-4-fluorophenyl)-6-((3-(methylcarbamoyl)morpholino)methyl)-2-(thiazol-2-yl)-1,4-dihydropyrimidine-5-carboxylate

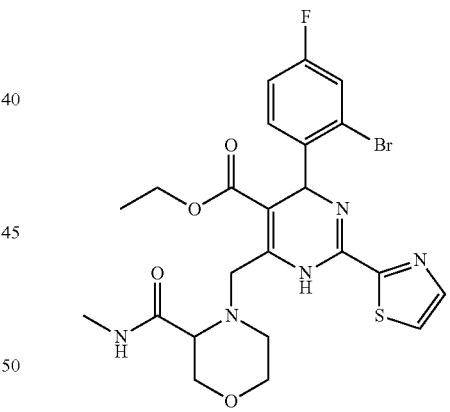

4-((6-(2-bromo-4-fluorophenyl)-5-(ethoxycarbonyl)-2-(thiazol-2-yl)-3,6-dihydropyrimidin-4-yl)methyl)morpholine-3-carboxylic acid (2 g, 3.6 mmol) was reacted with methanamine hydrochloride (0.49 g, 7.2 mmol) according to the procedure as described in Example 62, Step B to give the title compound as a yellow solid (0.69 g, 34%). The compound was characterized by the following spectroscopic data:

MS-ESI: (ESI, pos. ion) m/z: 566.1 [M+1]$^+$;

$^1$H NMR (400 MHz, DMSO-d$_6$): δ 9.95 (d, 1H), 8.15-8.08 (m, 1H), 8.02 (t, 1H), 7.91-7.87 (m, 1H), 7.54-7.51 (m, 1H), 7.38-7.31 (m, 1H), 7.21-7.18 (m, 1H), 6.00 (d, 1H), 4.28-3.92 (m, 5H), 3.86-3.82 (m, 1H), 3.74-3.50 (m, 3H), 3.11-3.07 (m, 1H), 3.07 (s, 3H), 2.55-2.39 (m, 1H), 1.06 (t, 3H).

Example 137

4-((6-(2-bromo-4-fluorophenyl)-2-(((6-methoxybenzo[d]thiazol-2-yl)-5-(methoxycarbonyl)-3,6-dihydropyrimidin-4-yl)methyl)morpholine-3-carboxylic acid

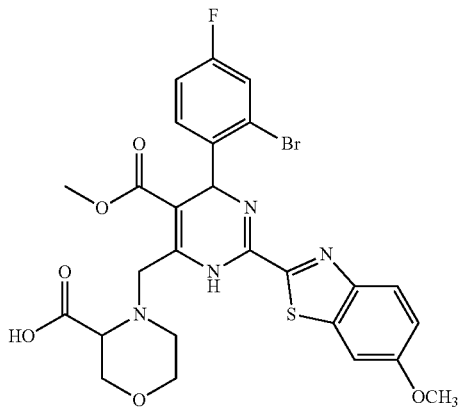 [SMILES: COC(=O)C1=C(CN2CCOCC2C(=O)O)NC(c2nc3ccc(OC)cc3s2)=NC1c1ccc(F)cc1Br]

Step A: 6-methoxybenzo[d]thiazole-2-carbonitrile 6-methoxybenzo[d]thiazol-2-amine (9 g, 50 mmol) was reacted with CuCN (8.96 g, 100 mmol) according to the procedure as described in Example 61, Step A to give the title compound as a white solid (2.1 g, 22%). The compound was characterized by the following spectroscopic data:

MS-ESI: (ESI, pos. ion) m/z: 191.0 [M+1]$^+$;
$^1$H NMR (400 MHz, CDCl$_3$): δ 8.08 (d, 1H), 7.36 (q, 1H), 7.24 (dd, 1H), 3.65 (s, 3H).

Step B: 6-methoxybenzo[d]thiazole-2-carboximidamide hydrochloride 6-methoxybenzo[d]thiazole-2-carbonitrile (1 g, 5.26 mmol) was reacted with sodium methoxide (0.28 g, 5.26 mmol) and ammonium chloride (0.6 g, 11 mmol) according to the procedure as described in Example 61, Step B to give the title compound as a white solid (0.96 g, 75%). The compound was characterized by the following spectroscopic data:

MS-ESI: (ESI, pos. ion) m/z: 208.0 [M+1]$^+$.

Step C: Methyl 4-(2-bromo-4-fluorophenyl)-2-(((6-methoxybenzo[d]thiazol-2-yl)-6-methyl-1,4-dihydropyrimidine-5-carboxylate 6-methoxybenzo[d]thiazole-2-carboximidamide hydrochloride (2.4 g, 10 mmol) was reacted with 2-bromo-4-fluorobenzaldehyde (2.03 g, 10 mmol) and methyl 3-oxobutanoate (1.16 g, 10 mmol) according to the procedure as described in Example 1, Step A to give the title compound as a yellow solid (2.7 g, 55%). The compound was characterized by the following spectroscopic data:

MS-ESI: (ESI, pos. ion) m/z: 490.0 [M+1]$^+$;
$^1$H NMR (400 MHz, CDCl$_3$): δ 8.06-7.85 (m, 2H), 7.59-7.29 (m, 2H), 7.17-6.93 (m, 2H), 6.19-6.05 (m, 1H), 3.88-3.87 (m, 3H), 3.63-3.60 (m, 3H), 2.59-2.55 (m, 3H).

Step D: Methyl 4-(2-bromo-4-fluorophenyl)-6-(bromomethyl)-2-(((6-methoxybenzo[d]thiazol-2-yl)-1,4-dihydropyrimidine-5-carboxylate Methyl 4-(2-bromo-4-fluorophenyl)-2-(((6-methoxybenzo[d]thiazol-2-yl)-6-methyl-1,4-dihydropyrimidine-5-carboxylate (1.29 g, 2.63 mmol) was reacted with NBS (0.47 g, 2.63 mmol) in DCM (50 mL) according to the procedure as described in Example 1, Step B to give the title compound as a yellow solid (0.82 g, 55%). The compound was characterized by the following spectroscopic data:

MS-ESI: (ESI, pos. ion) m/z: 567.9 [M+1]$^+$;
$^1$H NMR (400 MHz, DMSO-d$_6$): δ 7.97 (d, 1H), 7.69 (d, 1H), 7.58 (dd, 1H), 7.41 (m, 1H), 7.25 (m, 1H), 7.17 (dd, 1H), 5.99 (m, 1H), 4.86 (br.s, 2H), 3.85 (s, 3H), 3.57 (s, 3H).

Step E: 4-((6-(2-bromo-4-fluorophenyl)-2-(((6-methoxybenzo[d]thiazol-2-yl)-5-(methoxycarbonyl)-3,6-dihydropyrimidin-4-yl)methyl)morpholine-3-carboxylic acid Methyl 4-(2-bromo-4-fluorophenyl)-6-(bromomethyl)-2-(((6-methoxybenzo[d]thiazol-2-yl)-1,4-dihydropyrimidine-5-carboxylate (0.46 g, 0.8 mmol) was reacted with morpholine-3-carboxylic acid (0.21 g, 1.6 mmol) according to the procedure as described in Example 1, Step C to give the title compound as a yellowish solid (0.3 g, 60%). The compound was characterized by the following spectroscopic data:

MS-ESI: (ESI, pos. ion) m/z: 619.1 [M+1]$^+$;
$^1$H NMR (400 MHz, DMSO-d$_6$): δ 12.9 (br.s, 1H), 9.85 (s, 1H), 7.97 (d, 1H), 7.69 (d, 1H), 7.58 (dd, 1H), 7.41-7.38 (m, 1H), 7.25-7.21 (m, 1H), 7.17 (dd, 1H), 5.99 (s, 1H), 4.27-3.92 (m, 4H), 3.84-3.79 (m, 1H), 3.75 (s, 3H), 3.74-3.65 (m, 2H), 3.57 (s, 3H), 3.11-3.07 (m, 1H), 2.55-2.39 (m, 1H).

Example 138

Ethyl 4-(2-bromo-4-fluorophenyl)-6-((3-(hydroxymethyl)morpholino)methyl)-2-(((6-methoxybenzo[d]thiazol-2-yl)-1,4-dihydropyrimidine-5-carboxylate

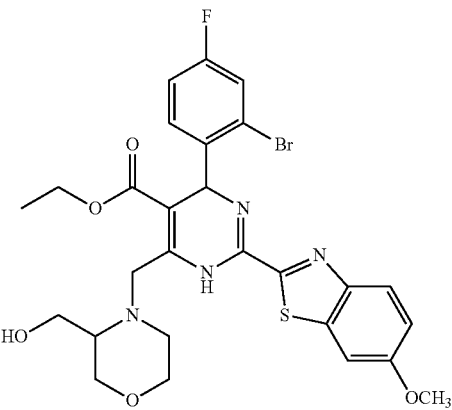 [SMILES: CCOC(=O)C1=C(CN2CCOCC2CO)NC(c2nc3ccc(OC)cc3s2)=NC1c1ccc(F)cc1Br]

Step A: Ethyl 4-(2-bromo-4-fluorophenyl)-2-(((6-methoxybenzo[d]thiazol-2-yl)-6-methyl-1,4-dihydropyrimidine-5-carboxylate 6-methoxybenzo[d]thiazole-2-carboximidamide hydrochloride (2.4 g, 10 mmol) was reacted with 2-bromo-4-fluorobenzaldehyde (2.03 g, 10 mmol) and ethyl 3-oxobutanoate (1.3 g, 10 mmol) according to the procedure as described in Example 1, Step A to give the title compound as a yellow solid (3.1 g, 62%). The compound was characterized by the following spectroscopic data:

MS-ESI: (ESI, pos. ion) m/z: 504.0 [M+1]$^+$;
$^1$H NMR (400 MHz, CDCl$_3$): δ 8.06-7.85 (m, 2H), 7.59-7.29 (m, 2H), 7.17-6.93 (m, 2H), 6.19-6.05 (m, 1H), 3.88-3.87 (m, 2H), 3.63-3.60 (m, 3H), 2.59-2.55 (m, 3H), 1.05 (t, 3H).

Step B: Ethyl 4-(2-bromo-4-fluorophenyl)-6-(bromomethyl)-2-(((6-methoxybenzo[d]thiazol-2-yl)-1,4-dihydropyrimidine-5-carboxylate Ethyl 4-(2-bromo-4-fluorophenyl)-2-(((6-methoxybenzo[d]thiazol-2-yl)-6-methyl-1,4-dihydropyrimidine-5-carboxylate (1.26 g, 2.5 mmol) was reacted with NBS (0.47 g, 2.63 mmol) in DCM (50 mL) according to the procedure as described in Example 1, Step B to give the title compound as a yellow solid (0.82 g, 55%). The compound was characterized by the following spectroscopic data:
MS-ESI: (ESI, pos. ion) m/z: 581.9 [M+1]$^+$;
$^1$H NMR (400 MHz, DMSO-d$_6$): δ 8.02-7.82 (m, 2H), 7.56-7.29 (m, 2H), 7.18-6.93 (m, 2H), 6.09-6.05 (m, 1H), 4.99 (dd, 2H), 3.88-3.83 (m, 2H), 3.65-3.60 (m, 3H), 2.59-2.55 (m, 3H), 1.05 (t, 3H).

Step C: 4-(2-bromo-4-fluorophenyl)-6-((3-(hydroxymethyl)morpholino)methyl)-2-(((6-methoxybenzo[d]thiazol-2-yl)-1,4-dihydropyrimidine-5-carboxylate Ethyl 4-(2-bromo-4-fluorophenyl)-6-(bromomethyl)-2-(((6-methoxybenzo[d]thiazol-2-yl)-1,4-dihydropyrimidine-5-carboxylate (0.58 g, 1 mmol) was reacted with morpholin-3-ylmethanol hydrochloride (0.18 g, 1.2 mmol) according to the procedure as described in Example 25, Step B to give the title compound as a yellowish solid (0.50 g, 80%). The compound was characterized by the following spectroscopic data:
MS-ESI: (ESI, pos. ion) m/z: 619.1 [M+1]$^+$;
$^1$H NMR (400 MHz, CDCl$_3$): δ 7.99 (d, 1H), 7.69-7.60 (m, 1H), 7.57-7.50 (m, 1H), 7.40-7.38 (m, 1H), 7.25-7.20 (m, 1H), 7.17-7.10 (m, 1H), 5.99 (s, 1H), 4.31-3.99 (m, 4H), 3.92 (s, 3H), 3.84-3.81 (m, 1H), 3.79-3.53 (m, 4H), 3.11-3.07 (m, 3H), 2.55-2.39 (m, 1H), 1.05 (t, 3H).

Example 139

4-((6-(2-bromo-4-fluorophenyl)-5-(ethoxycarbonyl)-2-(5-methoxythiazol-2-yl)-3,6-dihydropyrimidin-4-yl)methyl)morpholine-3-carboxylic acid

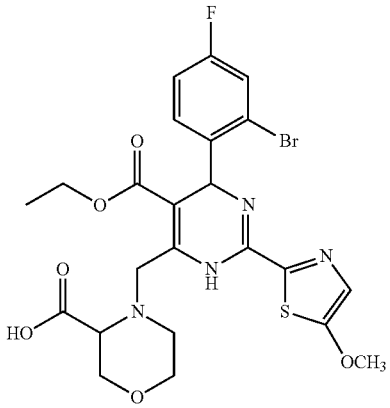 [SMILES: CCOC(=O)C1=C(CN2CCOCC2C(=O)O)NC(c2ncc(OC)s2)=NC1c1ccc(F)cc1Br]

Step A: 5-methoxythiazole-2-carbonitrile 5-methoxythiazol-2-amine (2.6 g, 20 mmol) was reacted with CuCN (4 g, 44 mmol) according to the procedure as described in Example 61, Step A to give the title compound as brownish oil (0.84 g, 30%). The compound was characterized by the following spectroscopic data:

MS-ESI: (ESI, pos. ion) m/z: 141.0 [M+1]$^+$;
$^1$H NMR (400 MHz, CDCl$_3$): δ 7.04 (s, 1H), 3.83 (s, 3H).

Step B: 5-methoxythiazole-2-carboximidamide hydrochloride 5-methoxythiazole-2-carbonitrile (0.74 g, 5.26 mmol) was reacted with sodium methoxide (0.28 g, 5.26 mmol) and ammonium chloride (0.6 g, 11 mmol) according to the procedure as described in Example 61, Step B to give the title compound as a white solid (0.51 g, 50%). The compound was characterized by the following spectroscopic data:
MS-ESI: (ESI, pos. ion) m/z: 158.2 [M+1]$^+$.

Step C: Ethyl 4-(2-bromo-4-fluorophenyl)-2-(5-methoxythiazol-2-yl)-6-methyl-1,4-dihydropyrimidine-5-carboxylate 5-methoxythiazole-2-carboximidamide hydrochloride (3.3 g, 17 mmol) was reacted with 2-bromo-4-fluorobenzaldehyde (3.46 g, 17 mmol) and ethyl 3-oxobutanoate (2.2 g, 17 mmol) according to the procedure as described in Example 1, Step A to give the title compound as a yellow solid (4.56 g, 59%). The compound was characterized by the following spectroscopic data:
MS-ESI: (ESI, pos. ion) m/z: 454.0 [M+1]$^+$;
$^1$H NMR (400 MHz, CDCl$_3$): δ 7.37-7.35 (m, 1H), 7.32-7.17 (m, 2H), 7.11 (s, 1H), 6.03 (s, 1H), 4.12 (q, 2H), 3.87 (s, 3H), 2.46 (s, 3H), 1.14 (t, 3H).

Step D: Ethyl 4-(2-bromo-4-fluorophenyl)-6-(bromomethyl)-2-(5-methoxythiazol-2-yl)-1,4-dihydropyrimidine-5-carboxylate Ethyl 4-(2-bromo-4-fluorophenyl)-2-(5-methoxythiazol-2-yl)-6-methyl-1,4-dihydropyrimidine-5-carboxylate (2 g, 4.4 mmol) was reacted with NBS (0.78 g, 4.4 mmol) in DCM (50 mL) according to the procedure as described in Example 1, Step B to give the title compound as a yellow solid (0.80 g, 34%). The compound was characterized by the following spectroscopic data:
MS-ESI: (ESI, pos. ion) m/z: 532.0 [M+1]$^+$;
$^1$H NMR (400 MHz, DMSO-d$_6$): δ 7.39-7.36 (m, 1H), 7.31-7.28 (m, 1H), 7.08 (s, 1H), 6.99-6.91 (m, 1H), 6.03 (s, 1H), 4.90-4.82 (m, 1H), 4.56-4.51 (m, 1H), 4.12 (q, 2H), 3.95 (s, 3H), 1.14 (t, 3H).

Step E: 4-((6-(2-bromo-4-fluorophenyl)-5-(ethoxycarbonyl)-2-(5-methoxythiazol-2-yl)-3,6-dihydropyrimidin-4-yl)methyl)morpholine-3-carboxylic acid Ethyl 4-(2-bromo-4-fluorophenyl)-6-(bromomethyl)-2-(5-methoxythiazol-2-yl)-1,4-dihydropyrimidine-5-carboxylate (0.53 g, 1 mmol) was reacted with morpholine-3-carboxylic acid hydrochloride (0.2 g, 1.2 mmol) according to the procedure as described in Example 1, Step C to give the title compound as a yellowish solid (0.30 g, 52%). The compound was characterized by the following spectroscopic data:
MS-ESI: (ESI, pos. ion) m/z: 583.1 [M+1]$^+$;
$^1$H NMR (400 MHz, DMSO-d$_6$): δ 12.23 (br.s, 1H), 9.79 (br.s, 1H), 7.53-7.50 (m, 1H), 7.40 (s, 1H), 7.35-7.31 (m, 1H), 7.19-7.15 (m, 1H), 5.95 (s, 1H), 4.24-3.92 (m, 4H), 3.90 (s, 3H), 3.86-3.81 (m, 4H), 3.72-3.52 (m, 2H), 3.11-3.07 (m, 1H), 1.14 (t, 3H).

Example 140

4-((6-(2-bromo-4-fluorophenyl)-5-(ethoxycarbonyl)-2-(5-(trifluoromethyl)thiazol-2-yl)-3,6-dihydropyrimidin-4-yl)methyl)morpholine-3-carboxylic acid

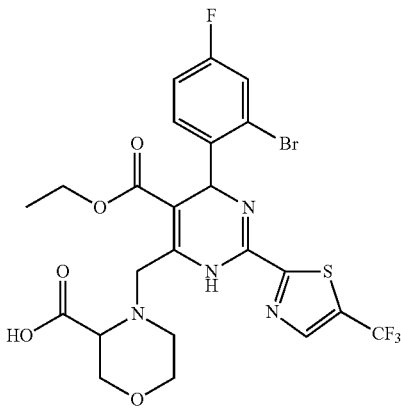 [SMILES: CCOC(=O)C1=C(CN2CCOCC2C(=O)O)NC(c2ncc(C(F)(F)F)s2)=NC1c1ccc(F)cc1Br]

Step A: 5-(trifluoromethyl)thiazole-2-carbonitrile 5-(trifluoromethyl)thiazol-2-amine (2.52 g, 15 mmol) was reacted with CuCN (2.7 g, 30.2 mmol) according to the procedure as described in Example 61, Step A to give the title compound as oil (1.25 g, 47%). The compound was characterized by the following spectroscopic data:
MS-ESI: (ESI, pos. ion) m/z: 179.0 [M+1]$^+$;
$^1$H NMR (600 MHz, CDCl$_3$): δ 7.19 (s, 1H).

Step B: 5-(trifluoromethyl)thiazole-2-carboximidamide hydrochloride 5-(trifluoromethyl)thiazole-2-carbonitrile (1.25 g, 7 mmol) was reacted with sodium methoxide (0.38 g, 7 mmol) and ammonium chloride (0.76 g, 14 mmol) according to the procedure as described in Example 61, Step B to give the title compound as an offwhite solid (1.3 g, 80%). The compound was characterized by the following spectroscopic data:
MS-ESI: (ESI, pos. ion) m/z: 196.0 [M+1]$^+$.

Step C: Ethyl 4-(2-bromo-4-fluorophenyl)-6-methyl-2-(5-(trifluoromethyl)thiazol-2-yl)-1,4-dihydropyrimidine-5-carboxylate 5-(trifluoromethyl)thiazole-2-carboximidamide hydrochloride (0.93 g, 4 mmol) was reacted with 2-bromo-4-fluorobenzaldehyde (0.81 g, 4 mmol) and ethyl 3-oxobutanoate (0.55 g, 4.2 mmol) according to the procedure as described in Example 1, Step A to give the title compound as a yellow solid (0.45 g, 23%). The compound was characterized by the following spectroscopic data:
MS-ESI: (ESI, pos. ion) m/z: 492.0 [M+1]$^+$;
$^1$H NMR (600 MHz, CDCl$_3$): δ 8.06 (s, 1H), 7.30-7.18 (m, 2H), 6.99-6.91 (m, 2H), 6.15 (s, 1H), 4.06 (q, 2H), 2.54 (s, 3H), 1.13 (t, 3H).

Step D: Ethyl 4-(2-bromo-4-fluorophenyl)-6-(bromomethyl)-2-(5-(trifluoromethyl)thiazol-2-yl)-1,4-dihydropyrimidine-5-carboxylate Ethyl 4-(2-bromo-4-fluorophenyl)-6-methyl-2-(5-(trifluoromethyl)thiazol-2-yl)-1,4-dihydropyrimidine-5-carboxylate (0.44 g, 0.89 mmol) was reacted with NBS (0.17 g, 0.94 mmol) in DCM (30 mL) according to the procedure as described in Example 1, Step B to give the title compound as a yellow solid (0.37 g, 72%). The compound was characterized by the following spectroscopic data:
MS-ESI: (ESI, pos. ion) m/z: 569.9 [M+1]$^+$;
$^1$H NMR (600 MHz, CDCl$_3$): δ 8.06 (s, 1H), 7.34-7.28 (m, 2H), 6.98-6.90 (m, 2H), 6.15 (s, 1H), 4.88 (dd, 2H), 3.97 (s, 2H), 1.12 (t, 3H).

Step E: 4-((6-(2-bromo-4-fluorophenyl)-5-(ethoxycarbonyl)-2-(5-(trifluoromethyl)thiazol-2-yl)-3,6-dihydropyrimidin-4-yl)methyl)morpholine-3-carboxylic acid Ethyl 4-(2-bromo-4-fluorophenyl)-6-(bromomethyl)-2-(5-(trifluoromethyl)thiazol-2-yl)-1,4-dihydropyrimidine-5-carboxylate (0.37 g, 0.65 mmol) was reacted with morpholine-3-carboxylic acid (0.1 g, 0.71 mmol) according to the procedure as described in Example 1, Step C to give the title compound as a yellow solid (0.26 g, 65%). The compound was characterized by the following spectroscopic data:
MS-ESI: (ESI, pos. ion) m/z: 621.0 [M+1]$^+$;
$^1$H NMR (400 MHz, DMSO-d$_6$): δ 12.31 (br.s, 1H), 9.82 (s, 1H), 8.66 (s, 1H), 7.58-7.51 (m, 1H), 7.39-7.31 (m, 1H), 7.22-7.17 (m, 1H), 6.05 (br.s, 1H), 4.28-3.90 (m, 5H), 3.88-3.82 (m, 1H), 3.77-3.52 (m, 3H), 3.16-3.07 (m, 1H), 2.59-2.39 (m, 1H), 1.06 (t, 3H).

Example 141

4-((6-(2-chlorophenyl)-5-(ethoxycarbonyl)-2-(thiazol-2-yl)-3,6-dihydropyrimidin-4-yl)methyl)morpholine-3-carboxylic acid

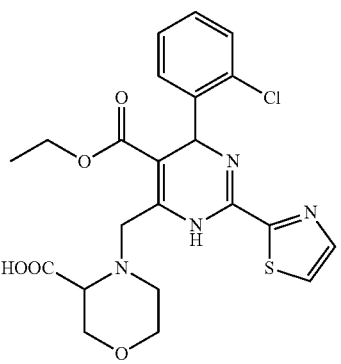 [SMILES: CCOC(=O)C1=C(CN2CCOCC2C(=O)O)NC(c2nccs2)=NC1c1ccccc1Cl]

Step A: Ethyl 4-(2-chlorophenyl)-6-methyl-2-(thiazol-2-yl)-1,4-dihydropyrimidine-5-carboxylate Thiazole-2-carboximidamide hydrochloride (11.63 g, 71.1 mmol) was reacted with 2-chlorobenzaldehyde (10 g, 71.1 mmol) and ethyl 3-oxobutanoate (11.1 g, 85.3 mmol) according to the procedure as described in Example 1, Step A to give the title compound as a yellow solid (14.2 g, 55%). The compound was characterized by the following spectroscopic data:
MS-ESI: (ESI, pos. ion) m/z: 362.1 [M+1]$^+$;
$^1$H NMR (400 MHz, DMSO-d$_6$): δ 9.67 (s, 1H), 8.14 (d, 1H), 7.83 (d, 1H), 7.35-7.07 (m, 4H), 6.24 (s, 1H), 3.98 (q, 2H), 2.53 (s, 3H), 1.10 (t, 3H).

Step B: Ethyl 6-(bromomethyl)-4-(2-chlorophenyl)-2-(thiazol-2-yl)-1,4-dihydropyrimidine-5-carboxylate Ethyl 4-(2-chlorophenyl)-6-methyl-2-(thiazol-2-yl)-1,4-dihydropyrimidine-5-carboxylate (10 g, 27.6 mmol) was reacted with NBS (5.41 g, 30.4 mmol) according to the procedure as described in Example 1, Step B to give the title compound as a yellow solid (7.3 g, 60%). The compound was characterized by the following spectroscopic data:
MS-ESI: (ESI, pos. ion) m/z: 440.0 [M+1]$^+$;
$^1$H NMR (400 MHz, DMSO-d$_6$): δ 9.73 (s, 1H), 8.04 (d, 1H), 7.89 (d, 1H), 7.39-7.07 (m, 4H), 6.14 (s, 1H), 4.92 (dd, 2H), 4.02 (q, 2H), 1.12 (t, 3H).

Step C: 4-((6-(2-chlorophenyl)-5-(ethoxycarbonyl)-2-(thiazol-2-yl)-3,6-dihydropyrimidin-4-yl)methyl)morpholine-3-carboxylic acid Ethyl 6-(bromomethyl)-4-(2-chlorophenyl)-2-(thiazol-2-yl)-1,4-dihydropyrimidine-5-carboxylate (2 g, 4.5 mmol) was reacted with morpholine-3-carboxylic acid hydrochloride (0.75 g, 4.5 mmol) according to the procedure as described in Example 1, Step C to give the title compound as a yellow solid (0.99 g, 45%). The compound was characterized by the following spectroscopic data:
MS-ESI: (ESI, pos. ion) m/z: 491.0 [M+1]$^+$;
$^1$H NMR (400 MHz, DMSO-d$_6$): δ 12.83 (s, 1H), 9.75 (s, 1H), 8.02 (d, 1H), 7.91 (d, 1H), 7.49-7.11 (m, 4H), 6.03 (s, 1H), 4.23-3.98 (m, 5H), 3.91-3.87 (m, 1H), 3.78-3.54 (m, 3H), 3.17-3.07 (m, 1H), 2.57-2.39 (m, 1H), 1.09 (t, 3H).

Example 142

4-((6-(2-chloro-4-fluorophenyl)-5-(ethoxycarbonyl)-2-(1,3,4-thiadiazol-2-yl)-3,6-dihydropyrimidin-4-yl)methyl)morpholine-2-carboxylic acid

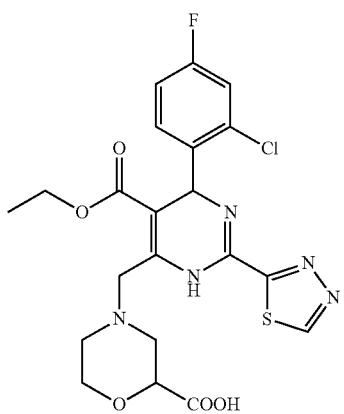 [SMILES: CCOC(=O)C1=C(CN2CCOC(C(=O)O)C2)NC(c2nncs2)=NC1c1ccc(F)cc1Cl]

Ethyl 6-(bromomethyl)-4-(2-chloro-4-fluorophenyl)-2-(1,3,4-thiadiazol-2-yl)-1,4-dihydropyrimidine-5-carboxylate (0.69 g, 1.5 mmol) was reacted with morpholine-2-carboxylic acid hydrochloride (0.25 g, 1.5 mmol) according to the procedure as described in Example 1, Step C to afford the title compound as a yellow solid (0.43 g, 56%). The compound was characterized by the following spectroscopic data:
MS-ESI: (ESI, pos. ion) m/z: 510.1 [M+1]$^+$;
$^1$H NMR (400 MHz, DMSO-d$_6$): δ 12.86 (br.s, 1H), 9.90 (s, 1H), 9.00 (s, 1H), 7.78 (dd, 1H), 7.36 (dd, 1H), 7.04-6.97 (m, 1H), 5.97 (s, 1H), 4.08 (q, 2H), 3.94 (s, 1H), 3.80 (t, 1H), 3.59-3.43 (m, 2H), 3.19-3.10 (m, 1H), 2.77-2.56 (m, 3H), 2.54 (s, 1H), 1.16 (t, 3H).

Example 143

Ethyl 4-(2-bromo-4-fluorophenyl)-6-(((S)-2-(2-hydroxypropan-2-yl)morpholino)methyl)-2-(1H-1,2,4-triazol-3-yl)-1,4-dihydropyrimidine-5-carboxylate

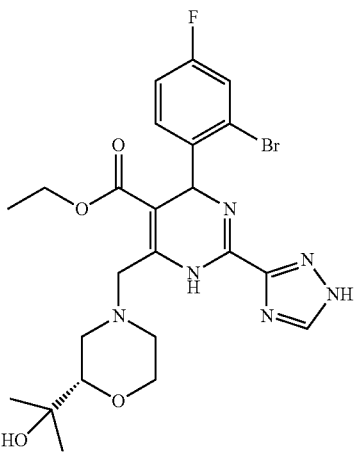 [SMILES: CCOC(=O)C1=C(CN2CCO[C@H](C(C)(C)O)C2)NC(c2nc[nH]n2)=NC1c1ccc(F)cc1Br]

Ethyl 4-(2-bromo-4-fluorophenyl)-6-(bromomethyl)-2-(1H-1,2,4-triazol-3-yl)-1,4-dihydropyrimidine-5-carboxylate (0.75 g, 1.53 mmol) was reacted with (S)-2-(morpholin-2-yl)propan-2-ol hydrochloride (0.28 g, 1.53 mmol) according to the procedure as described in Example 25, Step B to give the title compound as a yellow solid (0.19 g, 22%). The compound was characterized by the following spectroscopic data:
MS-ESI: (ESI, pos. ion) m/z: 551.1 [M+1]$^+$;
$^1$H NMR (400 MHz, DMSO-d$_6$): δ 10.44 (s, 1H), 8.30 (s, 1H), 7.63-6.71 (m, 3H), 6.22 (s, 1H), 4.47 (s, 1H), 4.08 (q, 2H), 3.83-3.78 (m, 1H), 3.59-3.41 (m, 2H), 3.37 (d, 2H), 2.82-2.79 (m, 1H), 2.67-2.56 (m, 2H), 2.23-2.17 (m, 1H), 1.42-0.92 (m, 9H).

Example 144

2-(4-((6-(2-chloro-4-fluorophenyl)-5-(ethoxycarbonyl)-2-(pyrazin-2-yl)-3,6-dihydropyrimidin-4-yl)methyl)morpholin-2-yl)acetic acid

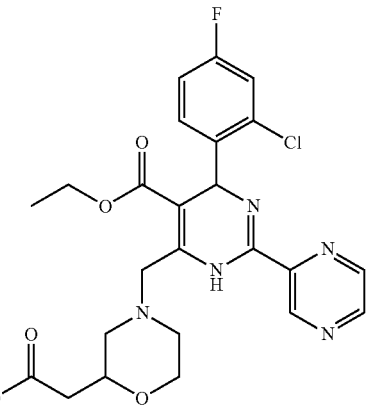

Ethyl 6-(bromomethyl)-4-(2-chloro-4-fluorophenyl)-2-(pyrazin-2-yl)-1,4-dihydropyrimidine-5-carboxylate (1 g, 2.2 mmol) was reacted with 2-(morpholin-2-yl)acetic acid hydrochloride (0.4 g, 2.2 mmol) according to the procedure as described in Example 1, Step C to give the title compound as a yellow solid (0.36 g, 32%). The compound was characterized by the following spectroscopic data:

MS-ESI: (ESI, pos. ion) m/z: 518.2 [M+1]+;
1H NMR (400 MHz, DMSO-d6): δ 12.90 (br.s, 1H), 9.99 (s, 1H), 9.55-9.17 (m, 1H), 9.01-8.41 (m, 2H), 7.78 (dd, 1H), 7.36 (dd, 1H), 7.04-6.97 (m, 1H), 6.32 (s, 1H), 4.23-3.84 (m, 3H), 3.75 (s, 1H), 3.59-3.46 (m, 2H), 2.77-2.56 (m, 4H), 2.50-2.45 (m, 1H), 2.22-2.10 (m, 2H), 1.16 (t, 3H).

Example 145

2-(4-((6-(2-bromo-4-fluorophenyl)-5-(ethoxycarbonyl)-2-(2,4,6-trifluorophenyl)-3,6-dihydropyrimidin-4-yl)methyl)morpholin-3-yl)acetic acid

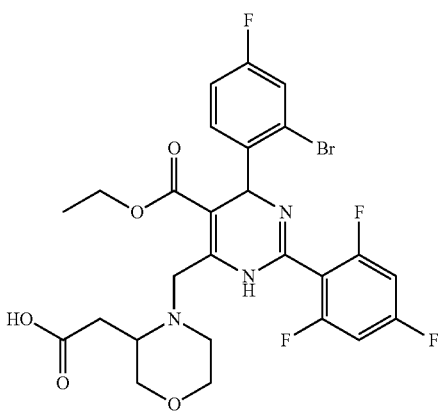 [SMILES: CCOC(=O)C1=C(CN2CCOCC2CC(=O)O)NC(c2c(F)cc(F)cc2F)=NC1c1ccc(F)cc1Br]

Ethyl 4-(2-bromo-4-fluorophenyl)-6-(bromomethyl)-2-(2,4,6-trifluorophenyl)-1,4-dihydropyrimidine-5-carboxylate (1.21 g, 2.2 mmol) was reacted with 2-(morpholin-3-yl)acetic acid hydrochloride (0.4 g, 2.2 mmol) according to the procedure as described in Example 1, Step C to give the title compound as a yellow solid (0.58 g, 43%). The compound was characterized by the following spectroscopic data:
MS-ESI: (ESI, pos. ion) m/z: 614.1 [M+1]+;
1H NMR (400 MHz, DMSO-d6): δ 12.01 (br.s, 1H), 11.06 (s, 1H), 7.35-7.24 (m, 2H), 7.17-7.02 (m, 1H), 6.80-6.37 (m, 2H), 5.89 (s, 1H), 4.08 (q, 2H), 3.73 (s, 1H), 3.70-3.43 (m, 3H), 3.41 (s, 1H), 3.29 (dd, 1H), 3.02-2.81 (m, 1H), 2.80-2.48 (m, 3H), 2.24-2.16 (m, 1H), 1.16 (t, 3H).

Example 146

2-(4-((6-(2-bromo-4-fluorophenyl)-5-(ethoxycarbonyl)-2-(thiazol-2-yl)-3,6-dihydropyrimidin-4-yl)methyl)morpholin-3-yl)-2-methylpropanoic acid

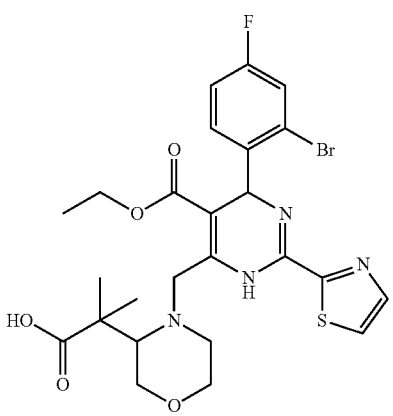 [SMILES: CCOC(=O)C1=C(CN2CCOCC2C(C)(C)C(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (3.02 g, 6 mmol) was reacted with 2-methyl-2-(morpholin-3-yl)propanoic acid hydrochloride (1.26 g, 6 mmol) according to the procedure as described in Example 1, Step C to give the title compound as a yellow solid (1.39 g, 39%). The compound was characterized by the following spectroscopic data:
MS-ESI: (ESI, pos. ion) m/z: 595.1 [M+1]+;
1H NMR (400 MHz, DMSO-d6): δ 12.38 (br.s, 1H), 10.02 (s, 1H), 8.10 (d, 1H), 7.93 (d, 1H), 7.34-7.26 (m, 2H), 7.18-7.05 (m, 1H), 6.04 (s, 1H), 4.08 (q, 2H), 3.91 (s, 1H), 3.72-3.50 (m, 2H), 3.40 (dd, 1H), 2.71-2.59 (m, 3H), 2.39-2.25 (m, 2H), 1.33-0.99 (m, 9H).

Example 147

3-(4-((6-(2-bromo-4-fluorophenyl)-5-(ethoxycarbonyl)-2-(thiazol-2-yl)-3,6-dihydropyrimidin-4-yl)methyl)morpholin-3-yl)-3-methylbutanoic acid

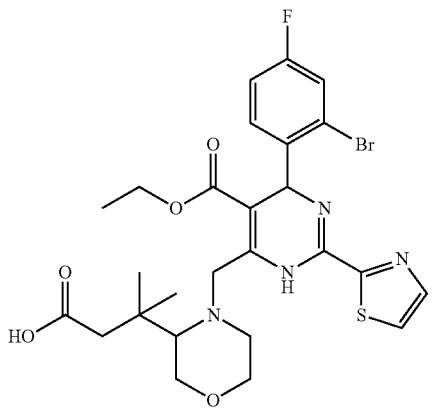 [SMILES: CCOC(=O)C1=C(CN2CCOCC2C(C)(C)CC(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (3.02 g, 6 mmol) was reacted with 3-methyl-3-(morpholin-3-yl)butanoic acid hydrochloride (1.34 g, 6 mmol) according to the procedure as described in Example 1, Step C to give the title compound as a yellow solid (1.5 g, 41%). The compound was characterized by the following spectroscopic data:
MS-ESI: (ESI, pos. ion) m/z: 609.1 [M+1]+;
1H NMR (400 MHz, DMSO-d6): δ 11.99 (br.s, 1H), 10.81 (s, 1H), 8.09 (d, 1H), 7.92 (d, 1H), 7.34-7.15 (m, 2H), 7.11-6.99 (m, 1H), 6.23 (s, 1H), 4.07 (q, 2H), 3.82 (s, 1H), 3.71-3.48 (m, 2H), 3.46-3.31 (m, 2H), 3.27-3.04 (m, 2H), 2.67-2.51 (m, 2H), 2.52 (s, 2H), 1.16 (t, 3H), 0.92 (s, 6H).

Example 148

3-(4-((6-(2-bromo-4-fluorophenyl)-5-(ethoxycarbonyl)-2-(thiazol-2-yl)-3,6-dihydropyrimidin-4-yl)methyl)morpholin-3-yl)-2-methylpropanoic acid

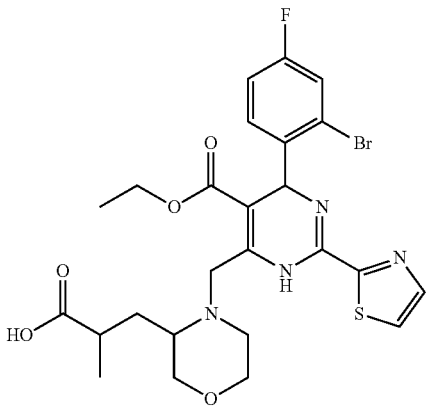 [SMILES: CCOC(=O)C1=C(CN2CCOCC2CC(C)C(=O)O)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (3.02 g, 6 mmol) was reacted with 2-methyl-3-(morpholin-3-yl)propanoic acid hydrochloride (1.26 g, 6 mmol) according to the procedure as described in Example 1, Step C to give the title compound as a yellow solid (0.89 g, 25%). The compound was characterized by the following spectroscopic data:

MS-ESI: (ESI, pos. ion) m/z: 595.1 [M+1]$^+$;

$^1$H NMR (400 MHz, DMSO-d$_6$): δ 11.86 (br.s, 1H), 10.63 (s, 1H), 8.10 (d, 1H), 7.93 (d, 1H), 7.35-7.19 (m, 2H), 7.15-7.02 (m, 1H), 6.37 (s, 1H), 4.08 (q, 2H), 3.81 (s, 1H), 3.72-3.46 (m, 2H), 3.43-3.02 (m, 3H), 2.86 (t, 1H), 2.67-2.56 (m, 2H), 2.50-2.19 (m, 2H), 1.59 (t, 1H), 1.16 (t, 3H), 1.07 (d, 3H).

Example 149

(3S)-methyl 4-((6-(2-chloro-4-fluorophenyl)-5-(ethoxycarbonyl)-2-(thiazol-2-yl)-3,6-dihydropyrimidin-4-yl)methyl)-6,6-dimethylmorpholine-3-carboxylate

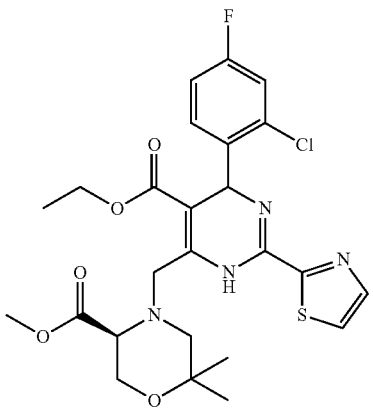

Ethyl 6-(bromomethyl)-4-(2-chloro-4-fluorophenyl)-2-(thiazol-2-yl)-1,4-dihydropyrimidine-5-carboxylate (0.7 g, 1.52 mmol) was reacted with (9-methyl 6,6-dimethylmorpholine-3-carboxylate (0.26 g, 1.52 mmol) according to the procedure as described in Example 24 to give the title compound as yellow oil (0.17 g, 20%). The compound was characterized by the following spectroscopic data:

MS-ESI: (ESI, pos. ion) m/z: 551.2 [M+1]$^+$;

$^1$H NMR (400 MHz, DMSO-d$_6$): δ 10.15 (s, 1H), 8.01 (dd, 2H), 7.78 (dd, 1H), 7.36 (dd, 1H), 7.04-7.01 (m, 1H), 5.99 (s, 1H), 4.32 (dd, 1H), 4.08 (dd, 3H), 3.66 (s, 3H), 3.60 (dd, 1H), 2.88-2.47 (m, 3H), 2.26 (d, 1H), 1.25 (s, 6H), 1.16 (t, 3H).

Example 150

(3S)-methyl 4-((6-(2-bromo-4-fluorophenyl)-5-(ethoxycarbonyl)-2-(thiazol-2-yl)-3,6-dihydropyrimidin-4-yl)methyl)-6,6-dimethylmorpholine-3-carboxylate

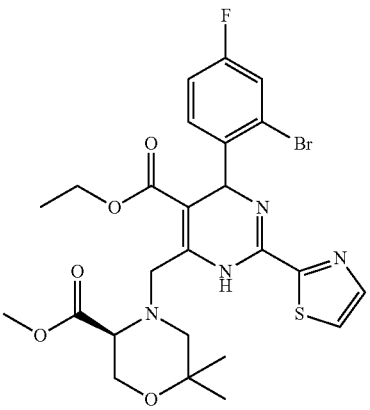 [SMILES: CCOC(=O)C1=C(CN2CC(C)(C)OC[C@H]2C(=O)OC)NC(c2nccs2)=NC1c1ccc(F)cc1Br]

Ethyl 4-(2-bromo-4-fluorophenyl)-6-(bromomethyl)-2-(thiazol-2-yl)-1,4-dihydropyrimidine-5-carboxylate (0.76 g, 1.52 mmol) was reacted with (S)-methyl 6,6-dimethylmorpholine-3-carboxylate (0.26 g, 1.52 mmol) according to the procedure as described in Example 24 to give the title compound as yellow oil (0.24 g, 27%). The compound was characterized by the following spectroscopic data:

MS-ESI: (ESI, pos. ion) m/z: 595.1 [M+1]$^+$;

$^1$H NMR (400 MHz, DMSO-d$_6$): δ 10.15 (s, 1H), 8.02 (dd, 2H), 7.35-7.21 (m, 2H), 7.19-6.98 (m, 1H), 5.95 (s, 1H), 4.33 (dd, 1H), 4.18-3.91 (m, 3H), 3.66 (s, 3H), 3.60 (dd, 1H), 2.91-2.43 (m, 3H), 2.27 (d, 1H), 1.27 (s, 6H), 1.13 (t, 3H).

Example 151

Ethyl 4-(2-bromo-4-fluorophenyl)-6-(((R)-2-((propionyloxy)methyl)morpholino)methyl)-2-(1H-1,2,4-triazol-3-yl)-1,4-dihydropyrimidine-5-carboxylate

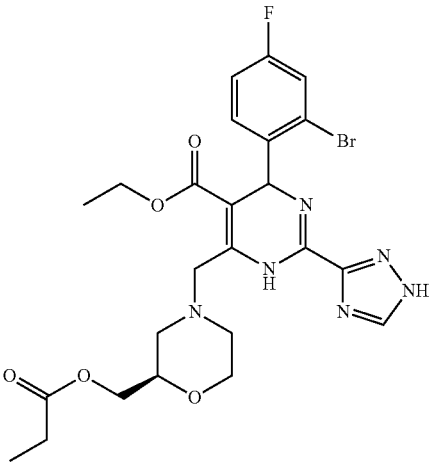 [SMILES: CCOC(=O)C1=C(CN2CCO[C@@H](COC(=O)CC)C2)NC(c2nc[nH]n2)=NC1c1ccc(F)cc1Br]

Ethyl 4-(2-bromo-4-fluorophenyl)-6-(((R)-2-(hydroxymethyl)morpholino)methyl)-2-(1H-1,2,4-triazol-3-yl)-1,4-dihydropyrimidine-5-carboxylate (2 g, 3.8 mmol) was reacted with propionic acid (0.37 g, 5 mmol) according to the procedure as described in Example 49 to give the title compound as yellow oil (0.84 g, 38%). The compound was characterized by the following spectroscopic data:

MS-ESI: (ESI, pos. ion) m/z: 579.1 [M+1]$^+$;

$^1$H NMR (400 MHz, DMSO-d$_6$): δ 10.78 (s, 1H), 8.30 (s, 1H), 7.34-7.23 (m, 2H), 7.19-6.97 (m, 1H), 5.89 (s, 1H), 4.52-4.18 (m, 2H), 4.17-3.95 (m, 3H), 3.79-3.41 (m, 3H), 3.21 (s, 1H), 2.94-2.54 (m, 3H), 2.41 (q, 2H), 2.29-2.02 (m, 1H), 1.18-1.16 (m, 6H).

Example 152

Ethyl 4-(2-bromo-4-fluorophenyl)-6-(((R)-2-((isobutyryloxy)methyl)morpholino)methyl)-2-(1H-1,2,4-triazol-3-yl)-1,4-dihydropyrimidine-5-carboxylate

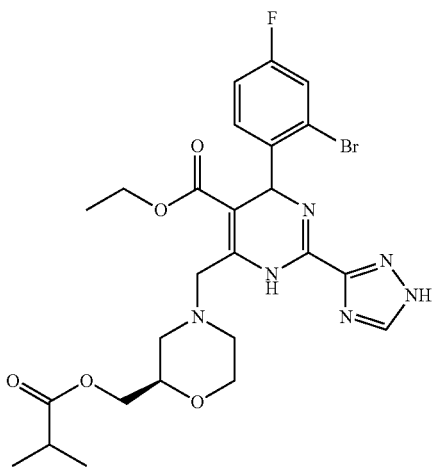 [SMILES: CCOC(=O)C1=C(CN2CCO[C@@H](COC(=O)C(C)C)C2)NC(c2nc[nH]n2)=NC1c1ccc(F)cc1Br]

Ethyl 4-(2-bromo-4-fluorophenyl)-6-(((R)-2-(hydroxymethyl)morpholino)methyl)-2-(1H-1,2,4-triazol-3-yl)-1,4-dihydropyrimidine-5-carboxylate (2 g, 3.8 mmol) was reacted with isobutyric acid (0.44 g, 5 mmol) according to the procedure as described in Example 49 to give the title compound as yellow oil (0.79 g, 35%). The compound was characterized by the following spectroscopic data:

MS-ESI: (ESI, pos. ion) m/z: 593.1 [M+1]$^+$;

$^1$H NMR (400 MHz, DMSO-d$_6$): δ 10.85 (s, 1H), 8.30 (s, 1H), 7.35-7.24 (m, 2H), 7.20-7.01 (m, 1H), 5.91 (s, 1H), 4.40-4.17 (m, 2H), 4.15-4.00 (m, 3H), 3.59-3.43 (m, 2H), 3.37 (d, 2H), 2.92-2.42 (m, 4H), 2.31-1.92 (m, 1H), 1.33-0.98 (m, 9H).

Example 153

Ethyl 4-(2-bromo-4-fluorophenyl)-6-(((R)-2-((pivaloyloxy)methyl)morpholino)methyl)-2-(1H-1,2,4-triazol-3-yl)-1,4-dihydropyrimidine-5-carboxylate

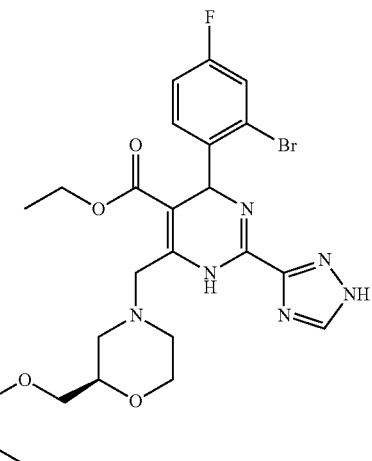

Ethyl 4-(2-bromo-4-fluorophenyl)-6-(((R)-2-(hydroxymethyl)morpholino)methyl)-2-(1H-1,2,4-triazol-3-yl)-1,4-dihydropyrimidine-5-carboxylate (2 g, 3.8 mmol) was reacted with pivalic acid (0.51 g, 5 mmol) according to the procedure as described in Example 49 to give the title compound as yellow oil (0.99 g, 43%). The compound was characterized by the following spectroscopic data:

MS-ESI: (ESI, pos. ion) m/z: 607.2 [M+1]$^+$;

$^1$H NMR (400 MHz, DMSO-d$_6$): δ 10.76 (s, 1H), 8.32 (s, 1H), 7.33-7.23 (m, 2H), 7.19-7.00 (m, 1H), 6.51 (s, 1H), 4.47-4.18 (m, 2H), 4.16-3.97 (m, 3H), 3.57-3.48 (m, 2H), 3.43 (d, 2H), 2.81-2.59 (m, 3H), 2.47 (dd, 1H), 1.26 (s, 9H), 1.16 (t, 3H).

Example 154

Ethyl 4-(2-bromo-4-fluorophenyl)-6-((3-(hydroxymethyl)morpholino)methyl)-2-(5-methoxythiazol-2-yl)-1,4-dihydropyrimidine-5-carboxylate

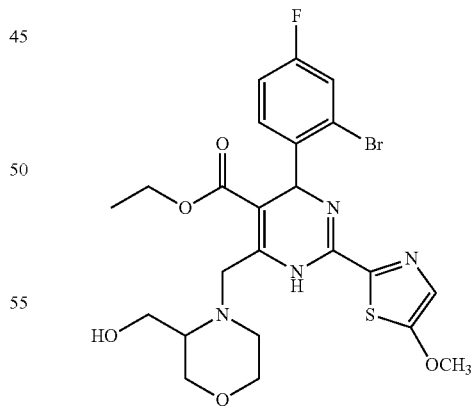

Ethyl 4-(2-bromo-4-fluorophenyl)-6-(bromomethyl)-2-(5-methoxythiazol-2-yl)-1,4-dihydropyrimidine-5-carboxylate (0.53 g, 1 mmol) was reacted with morpholin-3-ylmethanol hydrochloride (0.18 g, 1.2 mmol) according to the procedure as described in Example 25, Step B to give the title compound as a yellowish solid (0.27 g, 48%). The compound was characterized by the following spectroscopic data:

MS-ESI: (ESI, pos. ion) m/z: 569.1 [M+1]⁺;
¹H NMR (400 MHz, DMSO-d₆): δ 10.22 (s, 1H), 7.33-7.20 (m, 2H), 7.24 (s, 1H), 7.18-6.99 (m, 1H), 5.54 (s, 1H), 4.47 (d, 2H), 4.08 (q, 2H), 3.83 (s, 3H), 3.68-3.45 (m, 2H), 3.34 (dd, 1H), 3.24-2.95 (m, 3H), 2.64-2.58 (m, 2H), 2.51 (s, 1H), 1.90-1.88 (m, 1H), 1.16 (t, 3H).

Example 155

Ethyl 4-(2-bromo-4-fluorophenyl)-6-((3-(hydroxymethyl)morpholino)methyl)-2-(5-(trifluoromethyl)thiazol-2-yl)-1,4-dihydropyrimidine-5-carboxylate

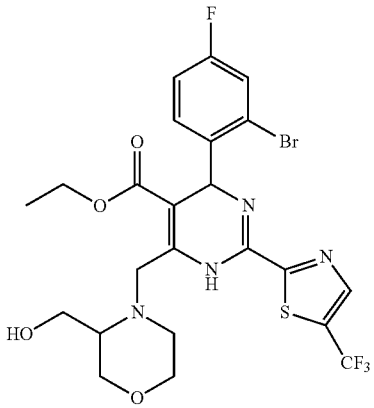 [SMILES: CCOC(=O)C1=C(CN2CCOCC2CO)NC(c2ncc(C(F)(F)F)s2)=NC1c1ccc(F)cc1Br]

Ethyl 4-(2-bromo-4-fluorophenyl)-6-(bromomethyl)-2-(5-(trifluoromethyl)thiazol-2-yl)-1,4-dihydropyrimidine-5-carboxylate (0.74 g, 1.3 mmol) was reacted with morpholin-3-ylmethanol hydrochloride (0.23 g, 1.5 mmol) according to the procedure as described in Example 25, Step B to give the title compound as a yellowish solid (0.34 g, 43%). The compound was characterized by the following spectroscopic data:
MS-ESI: (ESI, pos. ion) m/z: 607.1 [M+1]⁺;
¹H NMR (400 MHz, DMSO-d₆): δ 10.09 (s, 1H), 7.32-7.27 (m, 2H), 7.25 (s, 1H), 7.16-7.06 (m, 1H), 6.12 (s, 1H), 4.49 (s, 1H), 4.33 (s, 1H), 4.08 (q, 2H), 3.81-3.47 (m, 2H), 3.34 (dd, 1H), 3.25-2.97 (m, 3H), 2.61-2.56 (m, 2H), 2.45 (s, 1H), 1.88-1.79 (m, 1H), 1.16 (t, 3H).

Example 156

Ethyl 6-(((R)-3-((((S)-2-aminobutanoyl)oxy)methyl)morpholino)methyl)-4-(2-bromo-4-fluorophenyl)-2-(thiazol-2-yl)-1,4-dihydropyrimidine-5-carboxylate

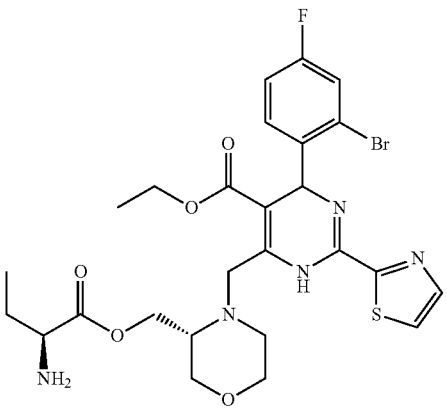 [SMILES: CCOC(=O)C1=C(CN2CCOC[C@@H]2COC(=O)[C@@H](N)CC)NC(c2nccs2)=NC1c1ccc(F)cc1Br]

Ethyl 4-(2-bromo-4-fluorophenyl)-6-(((S)-3-(hydroxymethyl)morpholino)methyl)-2-(thiazol-2-yl)-1,4-dihydropyrimidine-5-carboxylate (1 g, 1.9 mmol) was reacted with (S)-2-((tert-butoxycarbonyl)amino)butanoic acid (0.61 g, 3 mmol) according to the procedure as described in Example 49 to give the title compound as yellow oil (0.37 g, 31%). The compound was characterized by the following spectroscopic data:
MS-ESI: (ESI, pos. ion) m/z: 624.1 [M+1]⁺;
¹H NMR (400 MHz, DMSO-d₆): δ 10.17 (s, 1H), 8.90 (br.s, 2H), 8.10 (d, 1H), 7.93 (d, 1H), 7.37-7.28 (m, 2H), 7.19-7.01 (m, 1H), 6.28 (s, 1H), 4.35 (dd, 1H), 4.22-3.86 (m, 4H), 3.74-3.44 (m, 2H), 3.25 (dd, 1H), 3.16-2.96 (m, 2H), 2.71-2.63 (m, 2H), 2.48 (s, 1H), 2.36-2.23 (m, 1H), 2.06-1.68 (m, 2H), 1.16 (t, 3H), 0.86 (t, 3H).

Example 157

(3S)-4-((6-(2-bromo-4-fluorophenyl)-5-(ethoxycarbonyl)-2-(thiazol-2-yl)-3,6-dihydropyrimidin-4-yl)methyl)-3-methylmorpholine-3-carboxylic acid

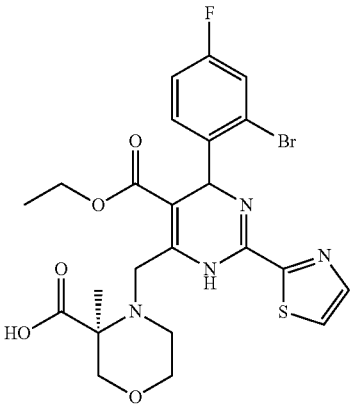 [SMILES: CCOC(=O)C1=C(CN2CCOC[C@@]2(C)C(=O)O)NC(c2nccs2)=NC1c1ccc(F)cc1Br]

Step A:
(S)-2-(benzylamino)-3-hydroxy-2-methylpropanoic acid (S)-2-amino-3-hydroxy-2-methylpropanoic acid (1.2 g, 10 mmol) was reacted with benzaldehyde (1.06 g, 10 mmol) according to the procedure as described in Example 46, Step A to give the title compound as a gray solid (1.05 g, 50%). The compound was characterized by the following spectroscopic data:
MS-ESI: (ESI, pos. ion) m/z: 210.1 [M+1]⁺;
¹H NMR (400 MHz, DMSO-d₆): δ 12.19 (s, 1H), 7.38-7.26 (m, 5H), 4.90 (s, 1H), 3.98-3.77 (m, 4H), 2.78 (br.s, 1H), 1.49 (s, 3H).

Step B:
(S)-4-benzyl-3-methyl-5-oxomorpholine-3-carboxylic acid (S)-2-(benzylamino)-3-hydroxy-2-methylpropanoic acid (2.09 g, 10 mmol) was reacted with chloroacetyl chloride (1.74 g, 15.4 mmol) according to the procedure as described in Example 46, Step B to give the title compound as a gray solid (1.62 g, 65%). The compound was characterized by the following spectroscopic data:

MS-ESI: (ESI, pos. ion) m/z: 250.1 [M+1]$^+$;

$^1$H NMR (400 MHz, DMSO-d$_6$): δ 12.03 (s, 1H), 7.41-7.21 (m, 5H), 4.86 (s, 1H), 4.54 (d, 1H), 4.31 (s, 2H), 4.15 (s, 1H), 4.00 (d, 1H), 1.69 (s, 3H).

Step C: (S)-benzyl 4-benzyl-3-methyl-5-oxomorpholine-3-carboxylate (S)-4-benzyl-3-methyl-5-oxomorpholine-3-carboxylic acid (2.49 g, 10 mmol) was reacted with benzyl bromide (2.05 g, 12 mmol) according to the procedure as described in Example 34, Step A to give the title compound as colorless oil (2.38 g, 70%). The compound was characterized by the following spectroscopic data:

MS-ESI: (ESI, pos. ion) m/z: 340.1 [M+1]$^+$;

$^1$H NMR (400 MHz, DMSO-d$_6$): δ 7.41-7.24 (m, 10H), 5.24 (s, 2H), 4.40 (d, 2H), 4.24 (s, 2H), 3.86 (dd, 2H), 1.74 (s, 3H).

Step D: (S)-benzyl 4-benzyl-3-methylmorpholine-3-carboxylate (S)-benzyl 4-benzyl-3-methyl-5-oxomorpholine-3-carboxylate (3.4 g, 10 mmol) was reacted with a solution of borane in THF (1 mol/L, 20 mL) according to the procedure as described in Example 34, Step B to give the title compound as colorless oil (2.3 g, 70%). The compound was characterized by the following spectroscopic data:

MS-ESI: (ESI, pos. ion) m/z: 326.1 [M+1]$^+$;

$^1$H NMR (400 MHz, DMSO-d$_6$): δ 7.30-7.16 (m, 10H), 5.26 (s, 2H), 3.68-3.51 (m, 5H), 3.23 (d, 1H), 2.77-2.55 (m, 2H), 1.54 (s, 3H).

Step E: (S)-3-methylmorpholine-3-carboxylic acid (S)-benzyl 4-benzyl-3-methylmorpholine-3-carboxylate (3.26 g, 10 mmol) was reacted with H$_2$ by Pd/C catalysis (10%, 0.33 g) according to the procedure as described in Example 34, Step C to give the title compound as a gray solid (0.97 g, 67%). The compound was characterized by the following spectroscopic data:

MS-ESI: (ESI, pos. ion) m/z: 146.1 [M+1]$^+$;

$^1$H NMR (400 MHz, DMSO-d$_6$): δ 12.11 (s, 1H), 3.72-3.52 (m, 3H), 3.17 (d, 1H), 3.01-2.78 (m, 2H), 2.06 (s, 1H), 1.49 (s, 3H).

Step F: (3S)-4-((6-(2-bromo-4-fluorophenyl)-5-(ethoxycarbonyl)-2-(thiazol-2-yl)-3,6-dihydropyrimidin-4-yl)methyl)-3-methylmorpholine-3-carboxylic acid Ethyl 4-(2-bromo-4-fluorophenyl)-6-(bromomethyl)-2-(thiazol-2-yl)-1,4-dihydropyrimidine-5-carboxylate (0.77 g, 1.53 mmol) was reacted with (S)-3-methylmorpholine-3-carboxylic acid (0.22 g, 1.53 mmol) according to the procedure as described in Example 46, Step F to give the title compound as a yellow solid (0.52 g, 60%). The compound was characterized by the following spectroscopic data:

MS-ESI: (ESI, pos. ion) m/z: 567.1 [M+1]$^+$;

$^1$H NMR (400 MHz, DMSO-d$_6$): δ 12.45 (s, 1H), 9.87 (s, 1H), 8.10 (d, 1H), 7.93 (d, 1H), 7.34-7.10 (m, 3H), 5.94 (s, 1H), 4.08 (q, 2H), 3.92-3.50 (m, 6H), 3.21-2.98 (m, 2H), 1.49 (s, 3H), 1.16 (s, 3H).

Example 158

In-Vitro Anti-HBV Activity of Compounds in Stable HBV-Producing Cell Line (HepG2.2.15)

I. Assay Method

HBV DNA contents in cell culture fluid were detected by the qPCR-based assay and percents of HBV inhibition by compounds (% Inh) were calculated. Specific procedures are as follows:

HepG2.2.15 cells were seeded into each well of 96-well plates, 40,000 cells per well. Cells were treated with cell culture medium containing compounds 24 hours after cell seeding. Each compound to detected percent inhibition was in duplicate and the final concentration of each compound was 500 nmol in each well. The compound-containing mediums were refreshed on day 4 post cell seeding. Culture media were collected from the HepG2.2.15 plates on day 7 post cell seeding followed by HBV DNA extraction.

HBV DNA extraction: using QIAamp 96 DNA Blood Kit (QIAGEN 51161).

PCR for quantification: PCR mix was prepared according to PCR system; PCR mix was dispensed to 384-well optical reaction plates (special for quantification); The standard diluted proportionally was added; The sample was added; The plates were sealed with optical adhesive film; PCR system was performed according to programs.

Percent of HBV inhibition of DNA replication by compound was calculated using the following equation:

% Inh.=[1-HBV DNA quantity of sample/HBV DNA quantity of DMSO control]*100.

II. Assay Results

Percents of HBV inhibition of DNA replication by compounds disclosed herein were detected with the methods above. The results are shown in Table 2:

TABLE 2

| Example | HBV (% Inh.) (500 nmol) |
|---|---|
| Example 1 | 75.85 |
| Example 2 | 31.3 |
| Example 3 | 84.5 |
| Example 4 | 90 |
| Example 5 | 95 |
| Example 6 | 99.9 |
| Example 9 | 93.1 |
| Example 10 | 89.7 |
| Example 11 | 95.6 |
| Example 12 | 53.8 |
| Example 13 | 54.5 |
| Example 21 | 51.2 |
| Example 23 | 45 |
| Example 24 | 56.1 |
| Example 25 | 91.9 |
| Example 26 | 96.0 |
| Example 27 | 91.9 |
| Example 34 | 94.35 |
| Example 40 | 95 |
| Example 42 | 91.9 |
| Example 49 | 96.2 |
| Example 51 | 91.3 |
| Example 52 | 89.51 |
| Example 53 | 92.62 |
| Example 54 | 91.05 |
| Example 55 | 92.96 |
| Example 60 | 93.96 |
| Example 61 | 91.08 |
| Example 66 | 88.79 |
| Example 69 | 36.5 |
| Example 70 | 63.6 |
| Example 71 | 43.4 |

TABLE 2-continued

| Example | HBV (% Inh.) (500 nmol) |
|---|---|
| Example 74 | 91.7 |
| Example 77 | 91.9 |
| Example 78 | 87.9 |
| Example 80 | 91.9 |
| Example 81 | 91.9 |
| Example 82 | 96.0 |
| Example 83 | 36.0 |
| Example 119 | 94 |
| Example 121 | 48.5 |
| Example 122 | 46.2 |
| Example 123 | 37.55 |
| Example 125 | 92.55 |
| Example 126 | 94.65 |
| Example 129 | 92 |
| Example 133 | 92.61 |
| Example 135 | 93.35 |
| Example 136 | 95.85 |

III. Conclusions

The compounds disclosed herein showed potent inhibitory effect on HBV. Such compounds have surprising antiviral activity and can be applied in the treatment of various kinds of disorders by HBV infection.

Example 159

Test Compounds' PK Assay in ICR Mice

I. Assay Method

The test compounds were poured into ICR mice stomach through mouth with 10 mg/kg or administered 2 mg/kg or 10 mg/kg to ICR mice by tail-intravenous injection. Blood sample of orbital vein was taken at 0.083, 0.25, 0.5, 1, 2, 4, 6, 8 and 24 hours after administration, and collected in anticoagulation tube added with EDTA-$K_2$. The test compounds were extracted from plasma samples and chromatographed on a tandem mass spectrometer. Quantitation was performed using multiple reaction monitoring (MRM). Pharmacokinetic parameters were calculated using WinNonlin 6.1 software with non compartment model.

II. Assay Results

Test compounds' PK were detected with the methods above. The results are shown in Table 3:

TABLE 3

| E. | A.R. | Dose mg/kg | $T_{max}$ h | $C_{max}$ ng/mL | $t_{1/2}$ h | $AUC_{last}$ hr*ng/ mL | $AUC_{INF}$ hr*ng/ mL | F % | CL L/h/ Kg | Vss L/Kg |
|---|---|---|---|---|---|---|---|---|---|---|
| R. | iv | 2 | 0.083 | 654.37 | 2.87 | 379.13 | 381.2 | N/A | 5.25 | 7.91 |
|    | po | 10 | 0.25 | 78.2 | 3.69 | 145.05 | 147.71 | 7.75 | N/A | N/A |
| 74 | iv | 10 | N/A | N/A | 1.02 | 10630 | 11160 | N/A | 0.93 | 0.82 |
|    | po | 10 | 0.25 | 7328 | 1.18 | 7892 | 8165 | 74.2 | N/A | N/A |
| 129 | iv | 2 | 0.08 | 3863.33 | 2.42 | 1633.7 | 1638.94 | N/A | 1.22 | 0.9 |
|    | po | 10 | 0.08 | 8606.67 | 6.62 | 5332.25 | 5346.58 | 65.24 | N/A | N/A |

E.—Examples;
R.—Reference;
A.R.—Administration Routes;
Reference—Ethyl 4-(2-bromo-4-fluorophenyl)-2-(thiazol-2-yl)-6-((4-morpholino)methyl)-1,4-dihydropyrimidine-5-carboxylate (The compound was synthesized according to the procedure as described in WO2008154817);
N/A—There is no detection;
$AUC_{last}$—AUC in 0-24 hours;
$AUC_{INF}$—AUC in 0 hour to infinite time.

III. Conclusions

After intragastric administration of drugs in ICR mice, Example 74 and Example 129 were rapidly absorbed and the peak time in plasma were 0.25 hour and 0.08 hour respectively. The $AUC_{last}$ of Example 74 was 7892 hr*ng/mL, and the $AUC_{last}$ of Example 129 was 5332.25 hr*ng/mL. Both compounds have better exposure, which are apparently higher than reference. It showed that compounds were absorbed well in ICR mice. After administration by intravenous injection, the CL of Example 74 and Example 129 were 0.93 L/h/Kg and 1.22 L/h/Kg respectively, and Vss of Example 74 and Example 129 were 0.82 L/Kg and 0.9 L/Kg. Calculated by the $AUC_{last}$ of Example 74 and Example 129, F were 74.2% and 65.24% respectively when the test compounds were poured into ICR mice stomach through mouth with 10 mg/kg. Both compounds have better bioavailability, which are much higher than reference (7.75%).

Activity data comparison showed that the activity of most compounds disclosed herein were higher than reference, and thus it will show a good prospect in anti-HBV.

Although the present invention has been described by a way of a detailed description in which general description, examples and assays have been described, it will be obvious to one skilled in the art that certain changes and modifications may be made without departing from the invention, and therefore, all such changes and modifications are within the scope of the invention.

The invention claimed is:

1. A compound of Formula (I) or (Ia)

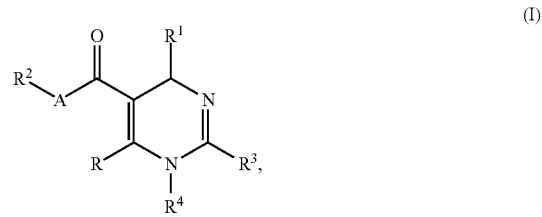

(I)

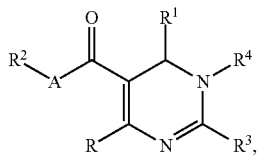

(Ia)

or an enantiomer, a diastereoisomer, a tautomer, a hydrate, a solvate, or a pharmaceutically acceptable salt thereof, wherein:

each A is a bond, —O—, —S—, or —NR$^5$—;
each R is —X—Z;
X is —(CR$^7$R$^{7a}$)$_m$— or —C(=O)—;
Z has Formula (II) or (IIa):

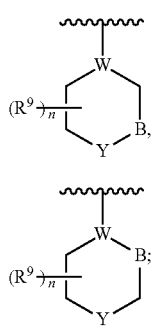

(II)

(IIa)

wherein each B is a bond, —(CR$^7$R$^{7a}$)$_m$— or —C(=O)—;
each W is CR$^7$ or N;
each Y is —(CR$^7$R$^{7a}$)$_m$— or —O—;
each R$^1$ is aryl or heteroaryl;
each R$^2$ is H, alkyl, alkenyl, alkynyl, aryl, aralkyl, heteroaryl, heteroarylalkyl, cycloalkyl, cycloalkylalkyl, heterocyclyl, heterocyclylalkyl or alkoxycarbonyl;
each R$^3$ is aryl or heteroaryl;
each R$^4$ is H, or C$_{1-4}$ alkyl;
R$^5$ is H, alkyl, —(CR$^7$R$^{7a}$)$_m$—C(=O)O—R$^8$, alkenyl or alkynyl;
each R$^{7a}$ and R$^7$ is independently H, F, Cl, Br, alkyl, haloalkyl, —(CH$_2$)$_m$—OH or —(CH$_2$)$_m$—C(=O)O—R$^8$;
each R$^8$ and R$^{8a}$ is independently H, alkyl, haloalkyl, aminoalkyl, Boc-NH-alkyl, alkoxy, —(CH$_2$)$_m$—OH, —(CH$_2$)$_m$—C(=O)O—(CH$_2$)$_m$—H or —(CH$_2$)$_m$—OC(=O)—(CH$_2$)$_m$—H;
Boc is tert-butyloxycarbonyl;
each R$^9$ is independently —(CR$^7$R$^{7a}$)$_t$—OH, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_t$—OC(=O)—R$^8$, or —(CR$^7$R$^{7a}$)$_m$—C(=O)N(R$^8$)$_2$, with the proviso that when R$^9$ is —(CR$^7$R$^{7a}$)$_t$—OH, R$^3$ is aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each n is independently 1, 2 or 3;
each t is independently 1, 2, 3 or 4;
each m is independently 0, 1, 2, 3 or 4; and optionally each of aryl, heteroaryl, alkyl, haloalkyl, alkenyl, alkynyl, cycloalkyl, cycloalkylalkyl, alkoxycarbonyl, aralkyl, heteroarylalkyl, aminoalkyl, alkoxy, furanyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl, triazinyl, heterocyclyl and heterocyclylalkyl described above, is independently substituted with one or more substituents which are the same or different, wherein the substituent is H, F, Cl, Br, I, alkyl, alkoxy, cyano, hydroxy, nitro, alkylamino, amino, trifluoromethyl, trifluoromethoxy, —(CR$^7$R$^{7a}$)$_m$—C(=O)O—R$^{8a}$, haloalkyl-substituted aryl, halogen-substituted aryl, —(CR$^7$R$^{7a}$)$_m$—C(=O)N(R$^{8a}$)$_2$ or trifluoromethylsulfonyl.

2. The compound according to claim 1, wherein Z has Formula (III) or (IIIa):

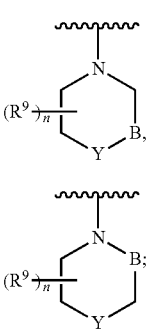

(III)

(IIIa)

wherein each B is a bond or —(CR$^7$R$^{7a}$)$_m$—;
each Y is —(CR$^7$R$^{7a}$)$_m$— or —O—;
each R$^{7a}$ and R$^7$ is independently H, F, Cl, Br, C$_{1-4}$ alkyl, —(CH$_2$)$_m$—OH, C$_{1-4}$ haloalkyl or —(CH$_2$)$_m$—C(=O)O—R$^8$;
each R$^8$ is independently H, C$_{1-6}$ alkyl, C$_{1-4}$ haloalkyl, amino-C$_{1-4}$-alkyl, Boc-NH—C$_{1-4}$-alkyl, C$_{1-4}$ alkoxy, —(CH$_2$)$_m$—OH, —(CH$_2$)$_m$—C(=O)O—(CH$_2$)$_m$—H or —(CH$_2$)$_m$—OC(=O)—(CH$_2$)$_m$—H;
each R$^9$ is independently —(CR$^7$R$^{7a}$)$_t$—OH, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_t$—OC(=O)—R$^8$, or —(CR$^7$R$^{7a}$)$_m$—C(=O)N(R$^8$)$_2$, with the proviso that when R$^9$ is —(CR$^7$R$^{7a}$)$_t$—OH, R$^3$ is C$_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;
each n is independently 1 or 2;
each t is independently 1, 2, 3 or 4; and
each m is independently 0, 1, 2, 3 or 4.

3. The compound according to claim 2, wherein Z is

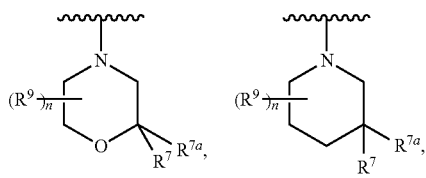

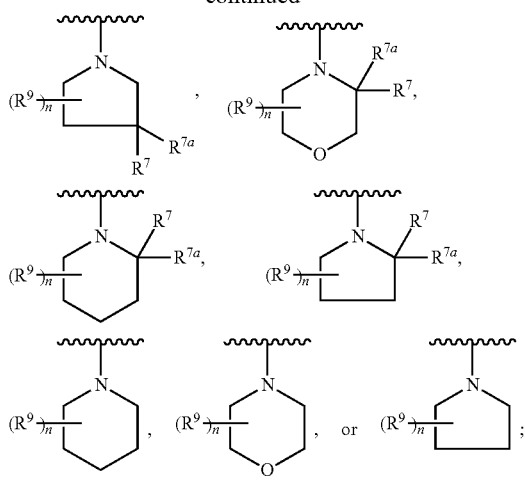

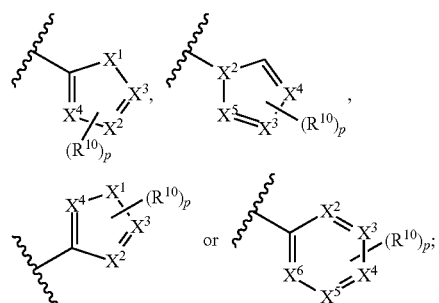

wherein each $X^1$ is independently O, S, $NR^{11}$ or $CR^{12}R^{12a}$;

each $X^2$, $X^3$, $X^4$, $X^5$ and $X^6$ is independently N or $CR^{12}$; wherein at most three or four of the $X^2$, $X^3$, $X^4$, $X^5$ and $X^6$ are N;

each $R^{16}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, $-(CR^7R^{7a})_m-C(=O)O-R^{8a}$, $-(CR^7R^{7a})_m-C(=O)N(R^{8a})_2$ or trifluoromethylsulfonyl;

each $R^{11}$ is independently H, methyl, ethyl, propyl, isopropyl, butyl, trifluoromethyl, $-(CR^7R^{7a})_m-C(=O)N(R^{8a})_2$ or $-(CR^7R^{7a})_m-C(=O)O-R^{8a}$;

each $R^{12}$ and $R^{12a}$ is independently H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, $-(CR^7R^{7a})_m-C(=O)O-R^{8a}$, $-(CR^7R^{7a})_m-C(=O)N(R^{8a})_2$ or trifluoromethylsulfonyl;

each $R^{7a}$ and $R^7$ is independently H, F, Cl, Br, $C_{1-4}$ alkyl, $-(CH_2)_m-OH$, $C_{1-4}$ haloalkyl or $-(CH_2)_m-C(=O)O-R^8$;

each $R^{8a}$ and $R^8$ is independently H, $C_{1-4}$ alkyl, $C_{1-4}$ haloalkyl, amino-$C_{1-4}$-alkyl, Boc-NH-$C_{1-4}$-alkyl, $C_{1-4}$ alkoxy, $-(CH_2)_m-OH$, $-(CH_2)_m-C(=O)O-(CH_2)_m-H$ or $-(CH_2)_m-OC(=O)-(CH_2)_m-H$;

each m is independently 0, 1, 2, 3 or 4; and each p is independently 0, 1, 2 or 3.

6. The compound according to claim 5, wherein $R^3$ has one of the following formulae:

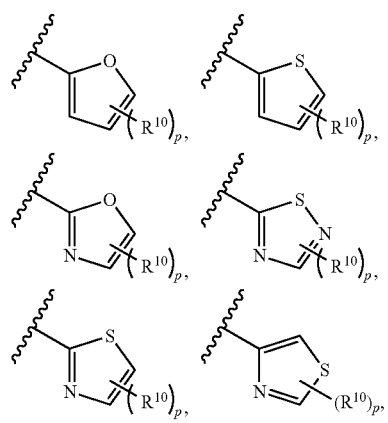

wherein each $R^7$ and $R^{7a}$ is independently H, methyl, ethyl, $-(CH_2)_m-OH$, $-(CH_2)_m-C(=O)O-R^8$ or propyl;

each $R^8$ is independently H, methyl, ethyl, propyl, isopropyl, butyl, 1-methylpropyl, 2-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, $-(CH_2)_m-OH$, $-(CH_2)_m-C(=O)O-(CH_2)_m-H$, $-(CH_2)_m-OC(=O)-(CH_2)_m-H$ or tert-butyl; and each $R^9$ is independently $-(CR^7R^{7a})_t-OH$, $-(CR^7R^{7a})_m-C(=O)O-R^8$, $-(CR^7R^{7a})_m-C(=O)O-(CR^7R^{7a})_m-OC(=O)O-R^8$, $-(CR^7R^{7a})_m-C(=O)O-(CR^7R^{7a})_m-OC(=O)-R^8$, $-(CR^7R^{7a})_t-OC(=O)-R^8$ or $-(CR^7R^{7a})_m-C(=O)N(R^8)_2$, with the proviso that when $R^9$ is $-(CR^7R^{7a})_t-OH$, $R^3$ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl.

4. The compound according to claim 1, wherein $R^3$ is $C_{6-10}$ aryl or 5-6 membered heteroaryl, and optionally each of the heteroaryl and aryl is independently substituted with one or more substituents which are the same or different, wherein the substituent is H, F, Cl, Br, I, methyl, ethyl, propyl, isopropyl, butyl, methoxy, ethoxy, methylamino, ethylamino, cyano, hydroxy, nitro, amino, trifluoromethyl, trifluoromethoxy, $-(CR^7R^{7a})_m-C(=O)O-R^{8a}$, $-(CR^7R^{7a})_m-C(=O)N(R^{8a})_2$ or trifluoromethylsulfonyl;

each $R^{7a}$ and $R^7$ is independently H, F, Cl, Br, $C_{1-4}$ alkyl, $C_{1-4}$ haloalkyl, $-(CH_2)_m-OH$ or $-(CH_2)_m-C(=O)O-R^8$; and each $R^{8a}$ and $R^8$ is independently H, $C_{1-4}$ alkyl, $C_{1-4}$ haloalkyl, amino-$C_{1-4}$-alkyl, Boc-NH-$C_{1-4}$-alkyl, $C_{1-4}$ alkoxy, $-(CH_2)_m-OH$, $-(CH_2)_m-C(=O)O-(CH_2)_m-H$ or $-(CH_2)_m-OC(=O)-(CH_2)_m-H$.

5. The compound according to claim 4, wherein $R^3$ has one of the following formulae:

-continued wherein each R[10] is independently H, F, Cl, methyl, ethyl, cyano, hydroxy, nitro, amino, methoxy, ethoxy, trifluoromethyl, trifluoromethoxy, —(CR[7]R[7a])$_m$—C(=O)O—R[8a], —(CR[7]R[7a])$_m$—C(=O)N(R[8a])$_2$ or trifluoromethylsulfonyl;

each R[11] is independently H, methyl, ethyl, propyl, isopropyl, butyl, trifluoromethyl or —(CR[7]R[7a])$_m$—C(=O)O—R[8a];

each R[7a] and R[7] is independently H, methyl, ethyl, —(CH$_2$)$_m$—OH, —(CH$_2$)$_m$—C(=O)O—R[8] or propyl;

each R[8] and R[8a] is independently H, methyl, ethyl, propyl, isopropyl, butyl, 2-methylpropyl, 1-methylpropyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —(CH$_2$)$_m$—OH, —(CH$_2$)$_m$—C(=O)O—(CH$_2$)$_m$—H, —(CH$_2$)$_m$—OC(=O)—(CH$_2$)$_m$—H or tert-butyl; and each p is independently 0, 1, 2 or 3.

7. The compound according to claim 1, wherein R[1] is C$_{6-10}$ aryl, and the aryl is independently substituted with one or more substituents which are the same or different, wherein the substituent is H, F, Cl, Br, cyano, methyl, ethyl, methoxy, ethoxy, methylamino, ethylamino, nitro, 4-(trifluoromethyl)phenyl, 3,5-bis(trifluoromethyl)phenyl or trifluoromethyl;

R[2] is H, or C$_{1-4}$ alkyl; and

R[5] is H, or C$_{1-4}$ alkyl.

8. The compound according to claim 7, wherein R[1] is phenyl or a phenyl substituted with one or more substituents which are the same or different, wherein the substituent is H, F, Cl, Br, nitro, 4-(trifluoromethyl)phenyl, 3,5-bis(trifluoromethyl)phenyl or trifluoromethyl.

9. The compound according to claim 1 having Formula (IV) or (IVa), (IV)

(IVa)

or an enantiomer, a diastereoisomer, a tautomer, a hydrate, a solvate, or a pharmaceutically acceptable salt thereof, wherein Z has Formula (II) or (IIa):

(II)

(IIa)

wherein each B is a bond or —(CR[7]R[7a])$_m$—;

each W is CR[7] or N;

each Y is —(CR[7]R[7a])$_m$— or —O—;

each R[2] is H, or C$_{1-4}$ alkyl;

each R[3] is C$_{6-10}$ aryl or 5-6 membered heteroaryl, and optionally each of the heteroaryl and aryl is independently substituted with one or more substituents which are the same or different, wherein the substituent is H, F, Cl, methyl, ethyl, propyl, cyano, trifluoromethyl, methoxy, —(CR[7]R[7a])$_m$—C(=O)N(R[8a])$_2$ or —(CR[7]R[7a])$_m$—C(=O)O—R[8a];

each R[7a] and R[7] is independently H, —(CH$_2$)$_m$—OH, —(CH$_2$)$_m$—C(=O)O—R[8] or C$_{1-4}$ alkyl;

each R[8] and R[8a] is independently H, amino-C$_{1-4}$-alkyl, Boc-NH—C$_{1-4}$-alkyl, C$_{1-4}$ alkoxy, —(CH$_2$)$_m$—OH, —(CH$_2$)$_m$—C(=O)O—(CH$_2$)$_m$—H, —(CH$_2$)$_m$—OC(=O)—(CH$_2$)$_m$—H or C$_{1-6}$ alkyl;

each R[9] is independently —(CR[7]R[7a])$_t$—OH, —(CR[7]R[7a])$_m$—C(=O)O—(CR[7]R[7a])$_m$—OC(=O)O—R[8], —(CR⁷R⁷ᵃ)ₘ—C(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₜ—OC(=O)—R⁸ or —(CR⁷R⁷ᵃ)ₘ—C(=O)N(R⁸)₂, with the proviso that when R⁹ is —(CR⁷R⁷ᵃ)ₜ—OH, R³ is $C_{6-10}$ aryl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each R¹³ is independently H, F, Cl, Br, cyano, nitro, 4-(trifluoromethyl)phenyl, 3,5-bis(trifluoromethyl)phenyl or trifluoromethyl;

each n is independently 1 or 2;

each t is independently 1, 2, 3 or 4; and each m is independently 0, 1, 2, 3 or 4.

10. The compound according to claim 9, wherein Z has Formula (II) or (IIa):

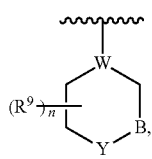
(II)

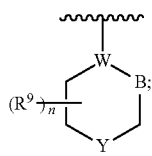
(IIa)

wherein each B is a bond or —(CR⁷R⁷ᵃ)ₘ—;

each W is CR⁷ or N;

each Y is —(CR⁷R⁷ᵃ)ₘ— or —O—;

each R⁷ᵃ and R⁷ is independently H, methyl, —(CH₂)ₘ—OH, —(CH₂)ₘ—C(=O)O—R⁸, ethyl or propyl;

each R⁸ is independently H, methyl, ethyl, propyl, isopropyl, butyl, 1-methylpropyl, 2-methylpropyl, tert-butyl, aminomethyl, 1-amino-2-methylpropyl, 1-aminoethyl, 2-aminoethyl, 1-aminobutyl, 1-aminopropyl, 2-aminopropyl, Boc-NH-methyl, 1-Boc-NH-2-methylpropyl, 1-Boc-NH-ethyl, 2-Boc-NH-ethyl, 1-Boc-NH-butyl, 1-Boc-NH-propyl, 2-Boc-NH-propyl, methoxy, ethoxy, —(CH₂)ₘ—OH, —(CH₂)ₘ—C(=O)O—(CH₂)ₘ—H or —(CH₂)ₘ—OC(=O)—(CH₂)ₘ—H;

each R⁸ᵃ is independently H, methyl, ethyl, isopropyl or propyl;

each R⁹ is independently —(CR⁷R⁷ᵃ)ₜ—OH, —(CR⁷R⁷ᵃ)ₘ—C(=O)O—R⁸, —(CR⁷R⁷ᵃ)ₘ—C(=O)O—(CR⁷R⁷ᵃ)ₘ—OC(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₜ—OC(=O)—R⁸, or —(CR⁷R⁷ᵃ)ₘ—C(=O)N(R⁸)₂, with the proviso that when R⁹ is —(CR⁷R⁷ᵃ)ₜ—OH, R³ is phenyl, furyl, imidazolyl, isoxazolyl, oxazolyl, pyrrolyl, pyrimidinyl, pyridazinyl, thiazolyl, diazolyl, triazolyl, tetrazolyl, thienyl, pyrazolyl, isothiazolyl, oxadiazolyl, thiadiazolyl, pyrazinyl, pyranyl or triazinyl;

each m is independently 0, 1, 2, 3 or 4; and each t is independently 1, 2, 3 or 4.

11. The compound according to claim 10, wherein Z is:

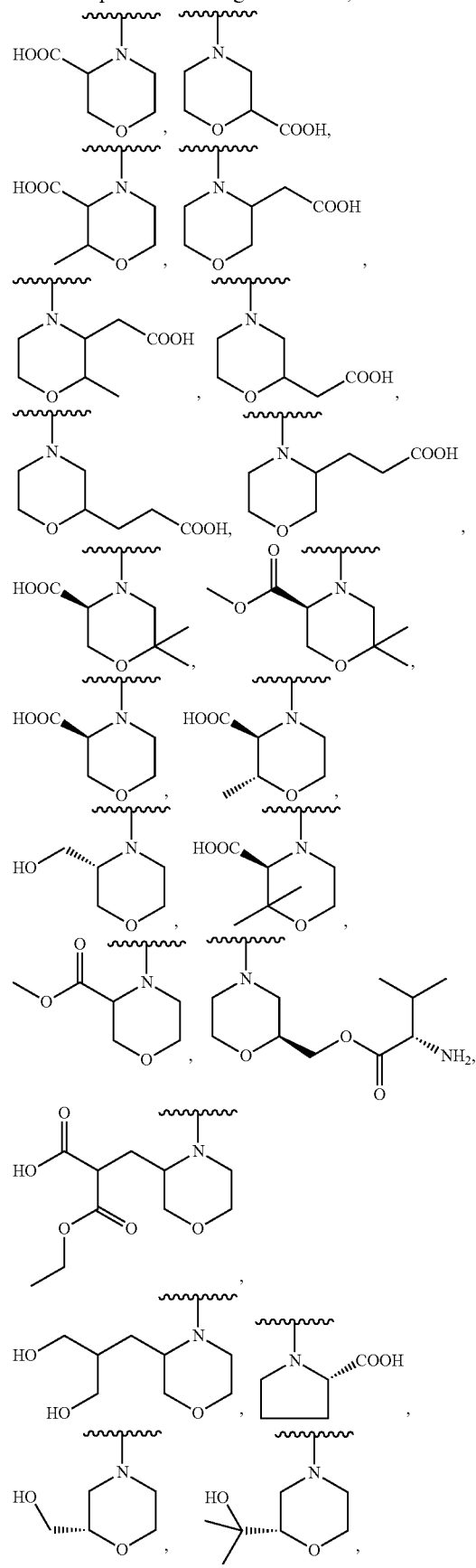

251
-continued
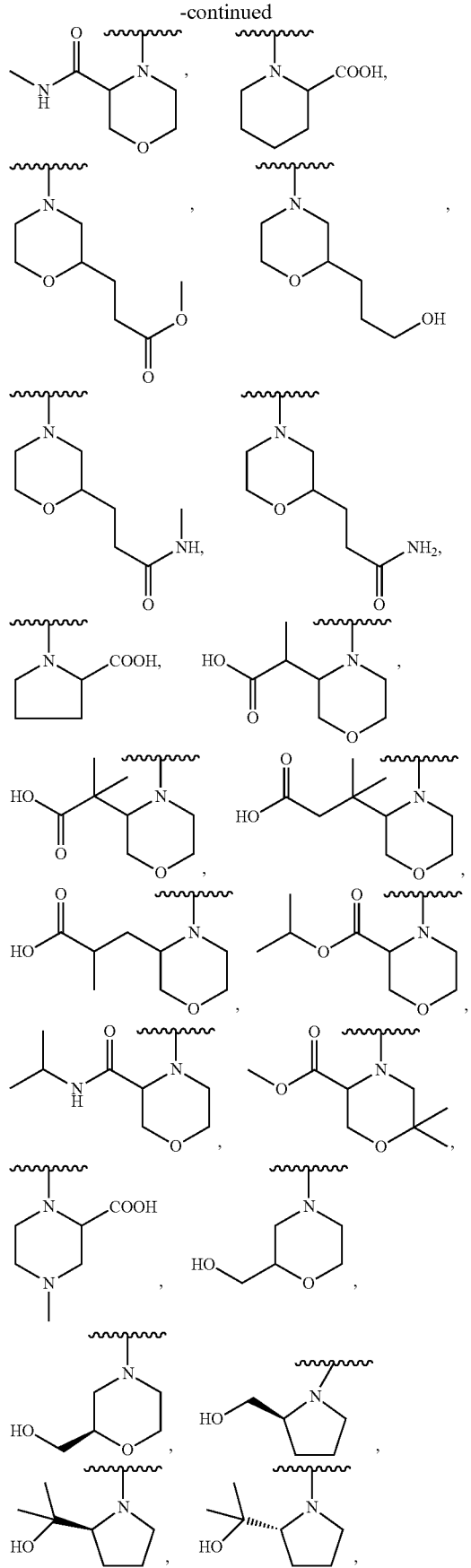
252
-continued
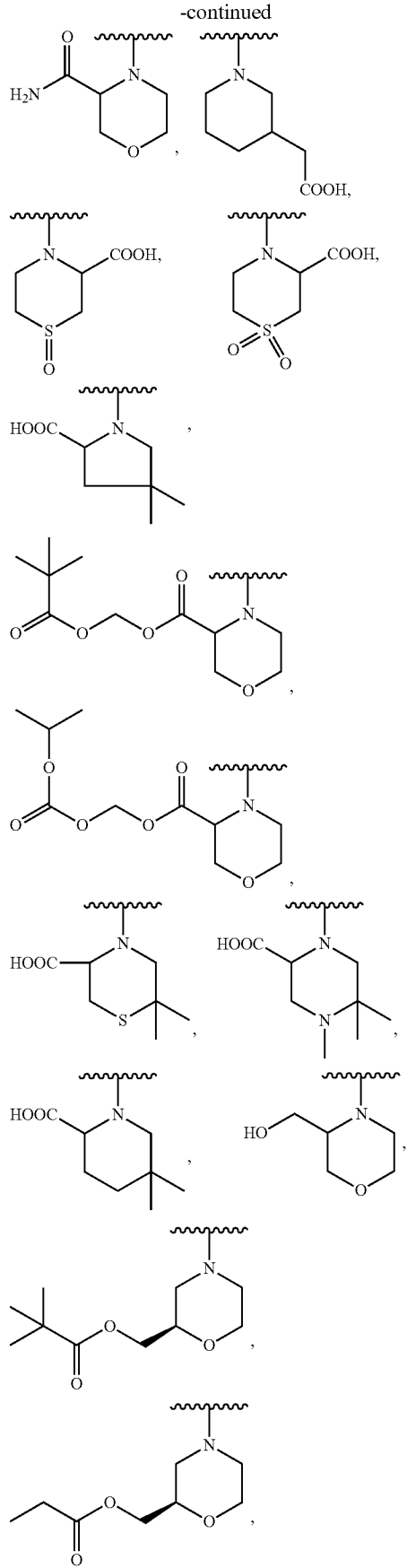

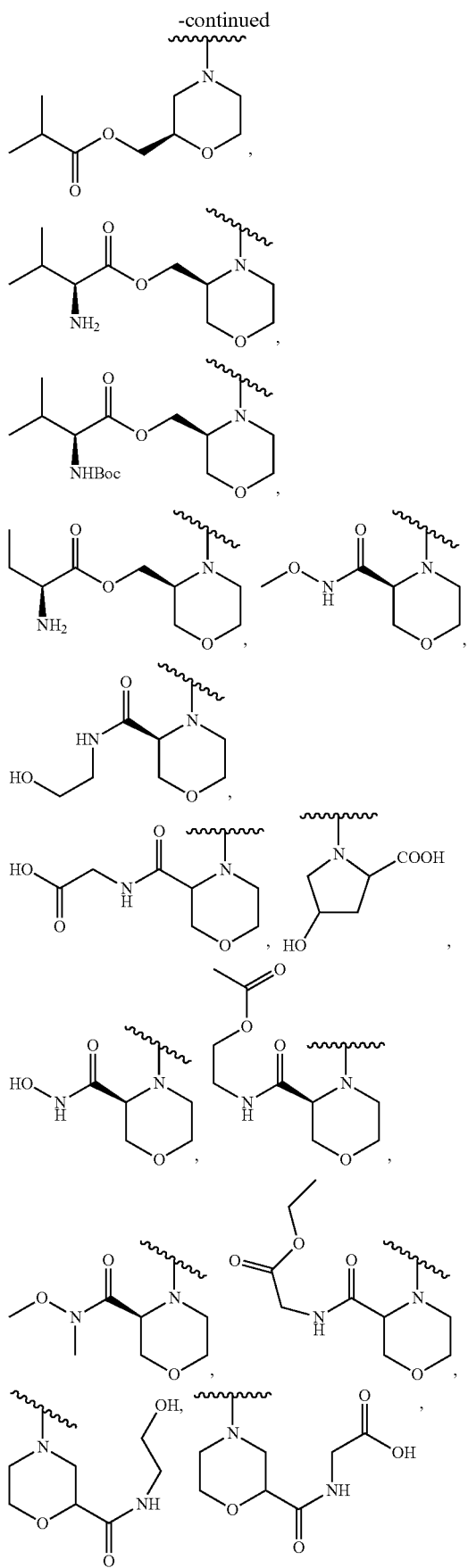
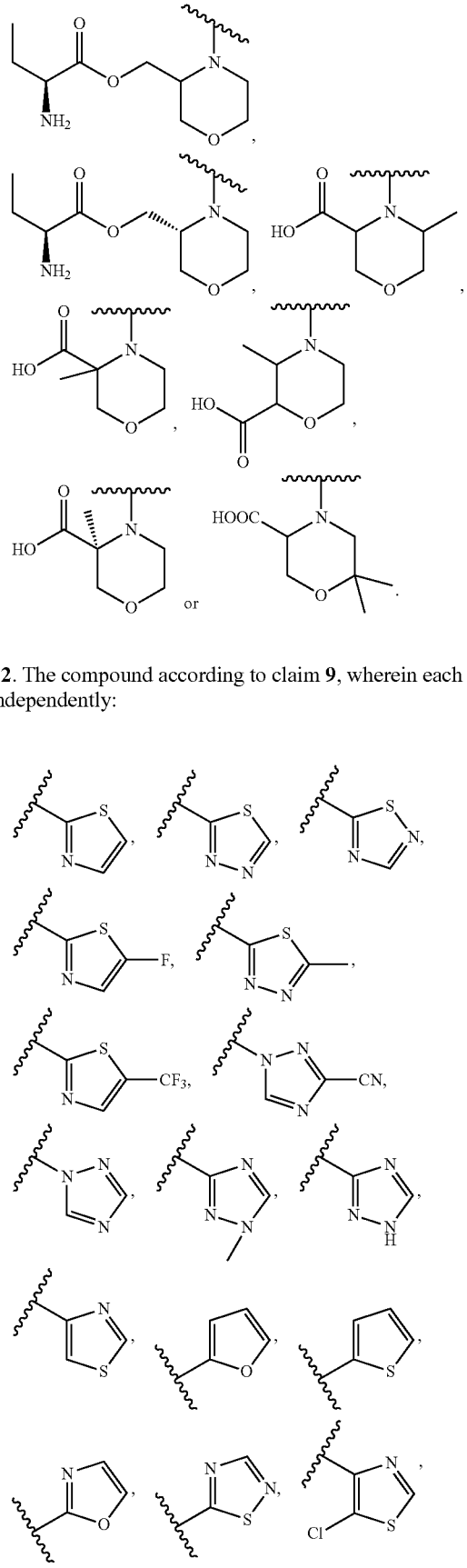
12. The compound according to claim 9, wherein each $R^3$ is independently:

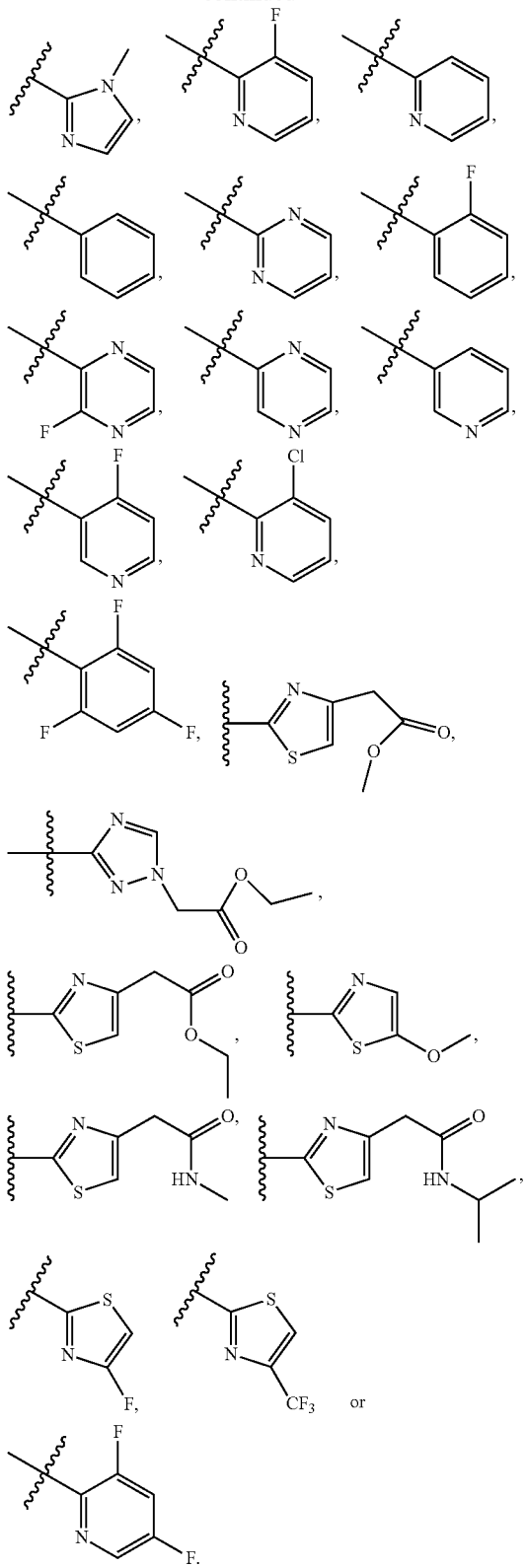
13. The compound according to claim 1 having one of the following structures:
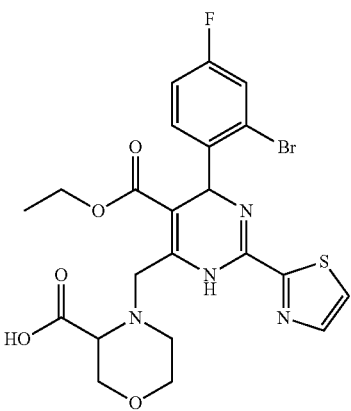
1
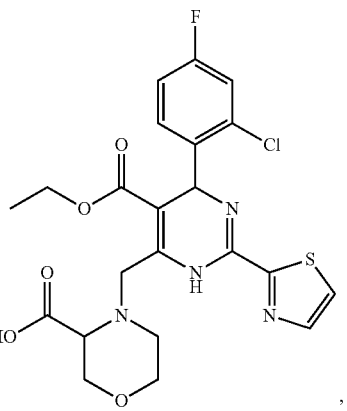
2
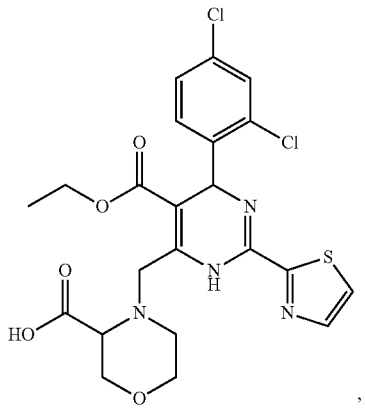
3
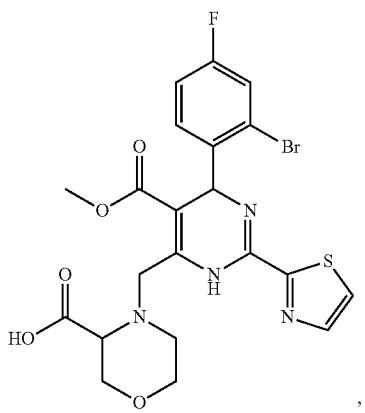
4

257
-continued
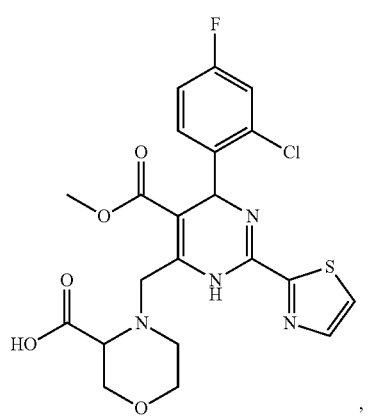
5
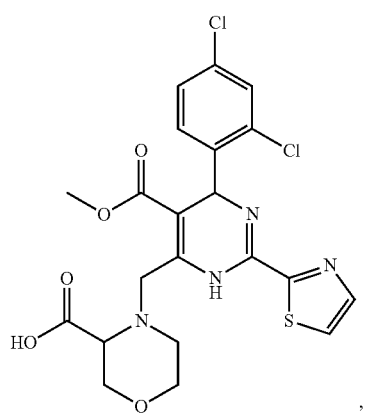
6
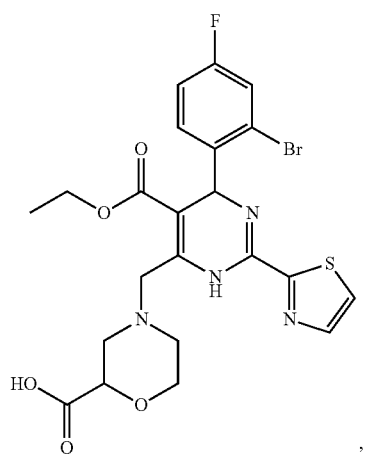
7
258
-continued
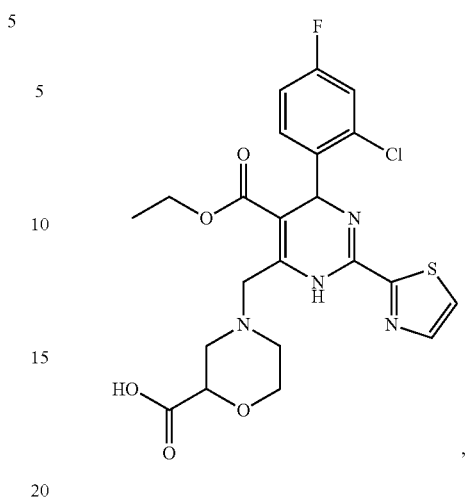
8
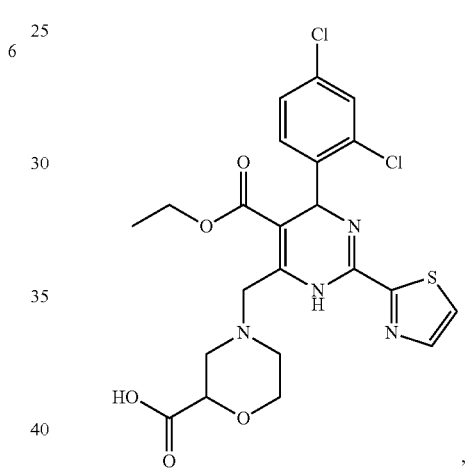
9
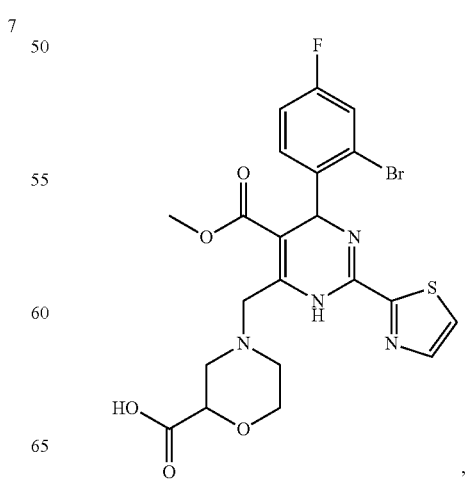
10

259
-continued
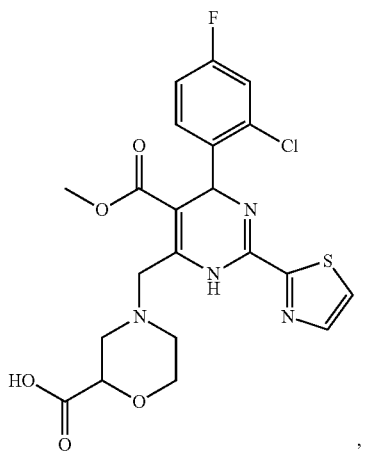
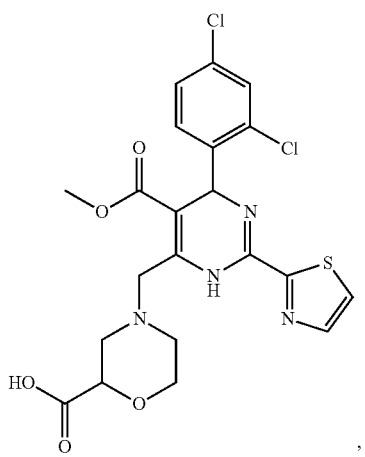
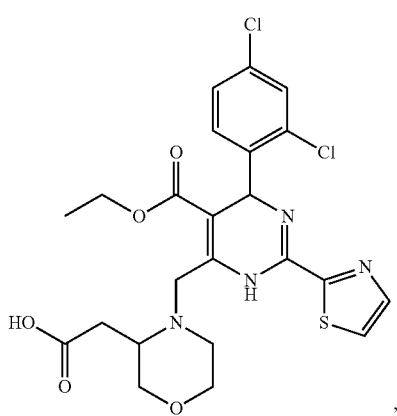
260
-continued
11
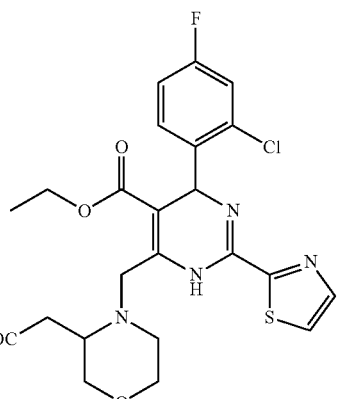
,
12
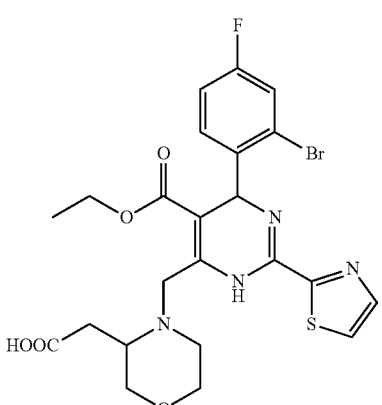
,
13
16
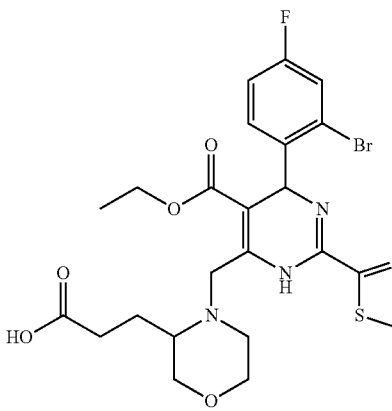
,
17
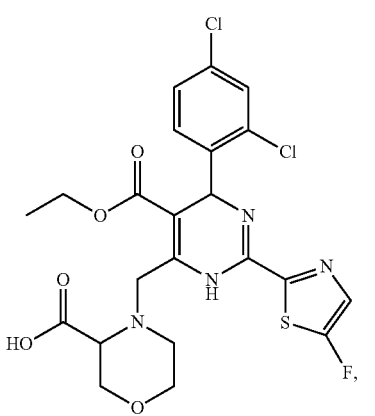

18
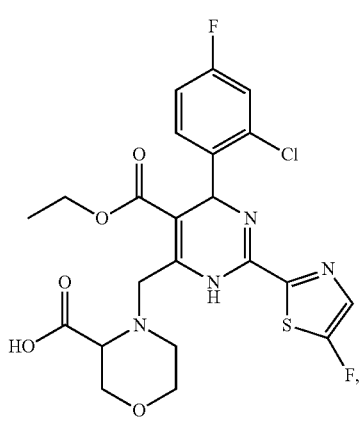
19
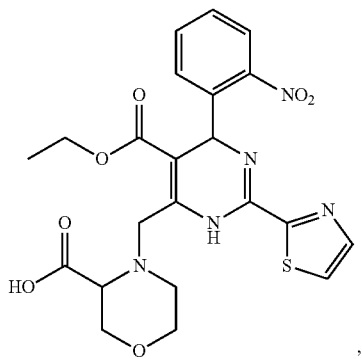
20
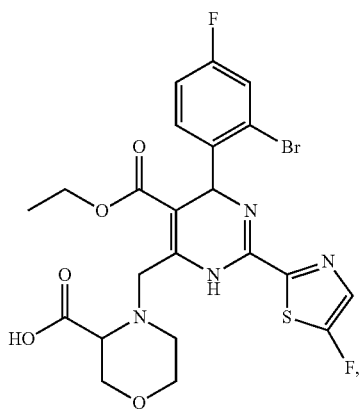
21
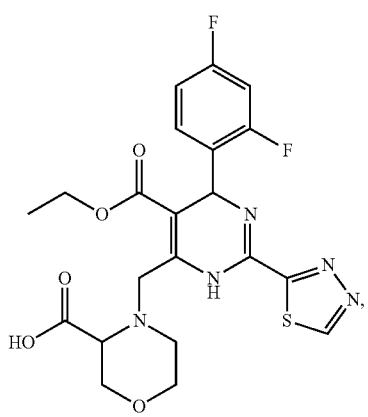
22
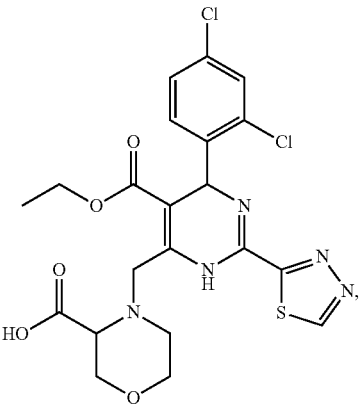
23
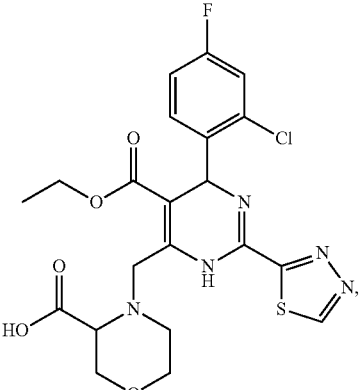
24
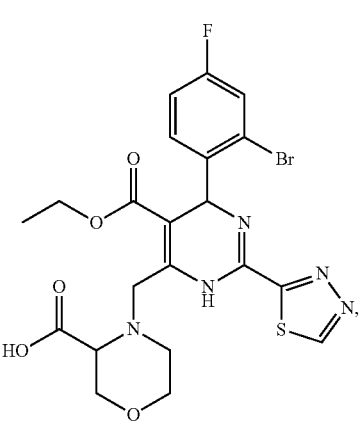
25
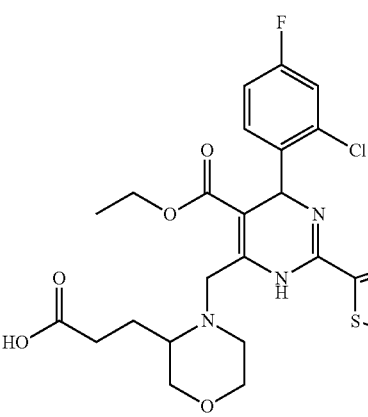

-continued
26
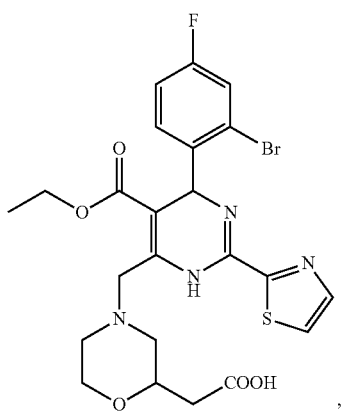
27
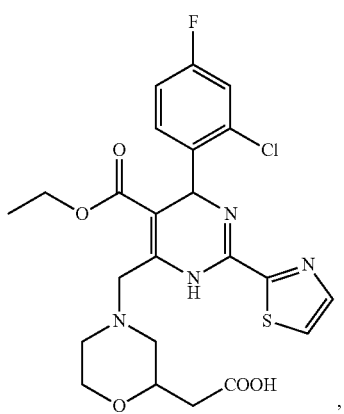
28
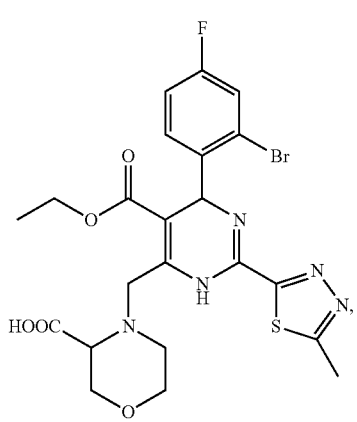
29
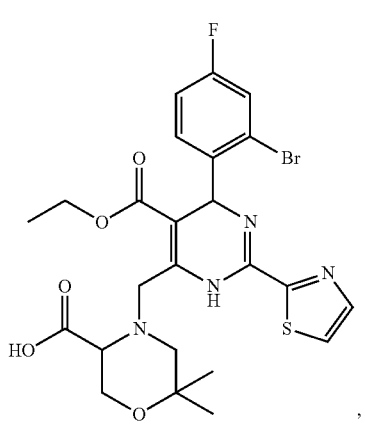
-continued
30
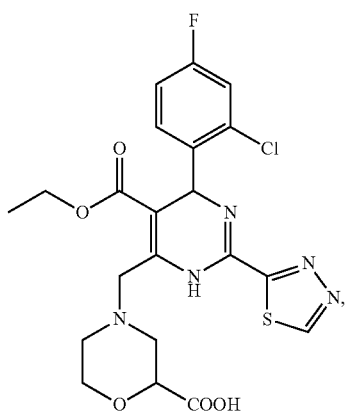
31
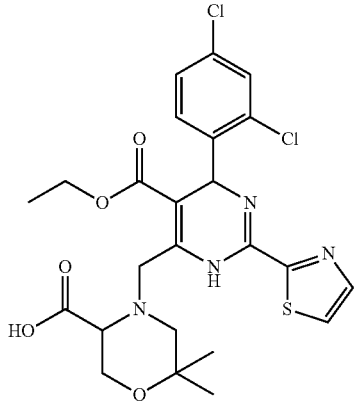
32
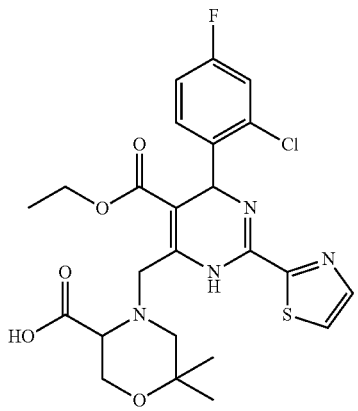
33
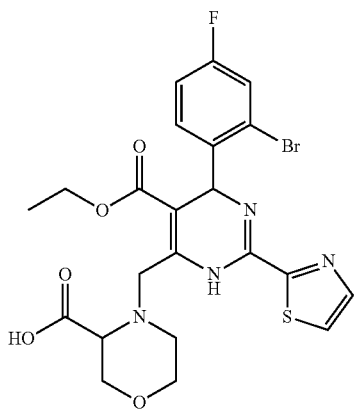

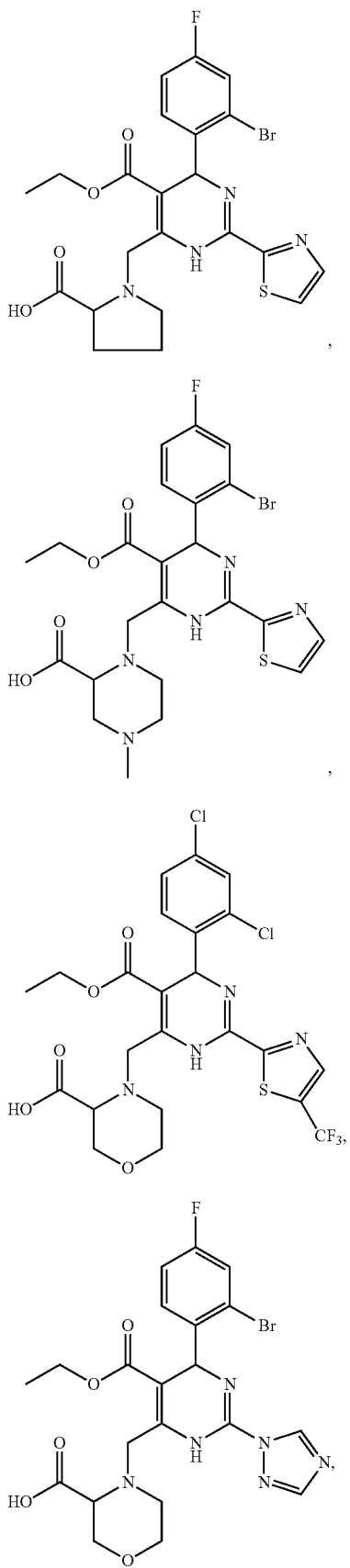
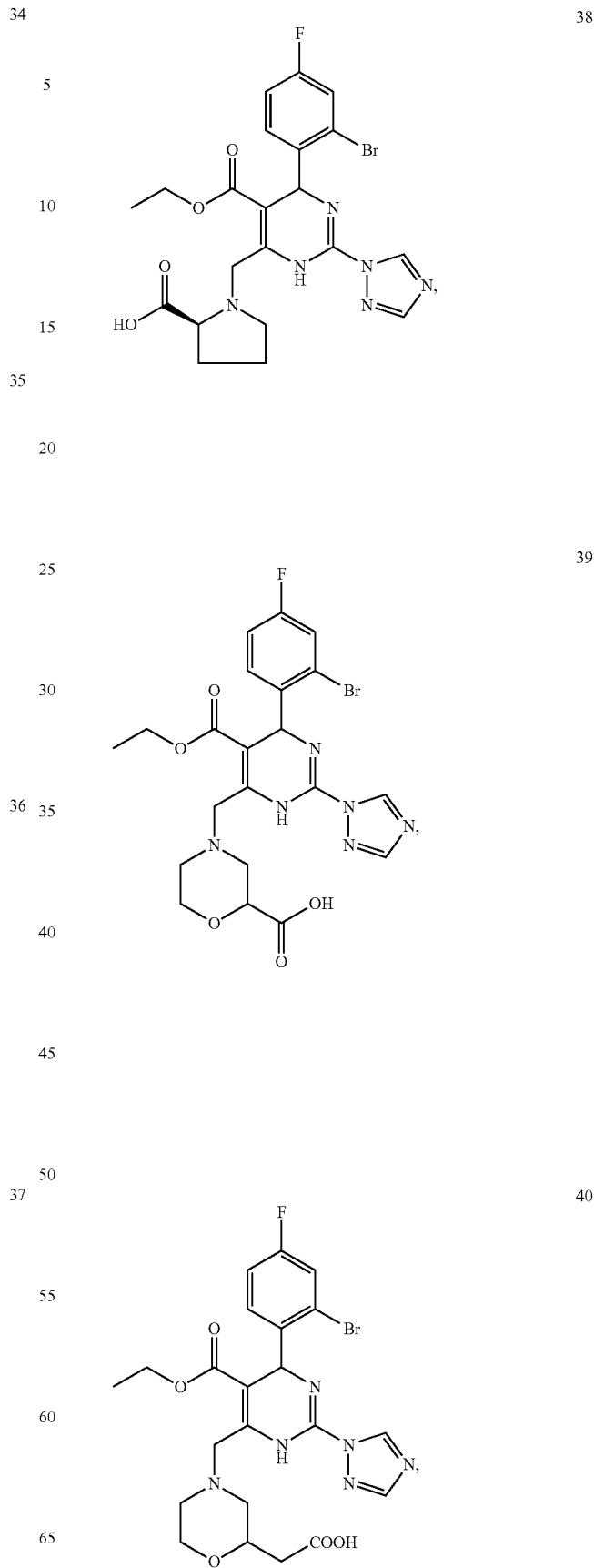

41
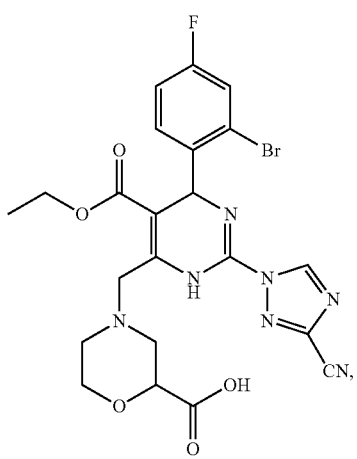
42
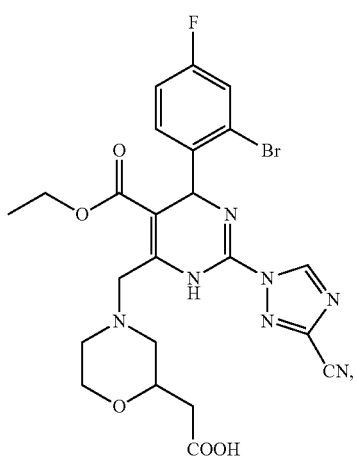
43
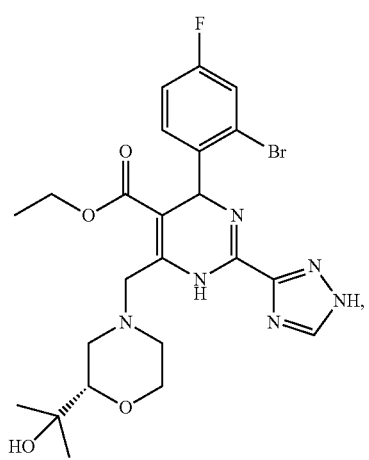
44
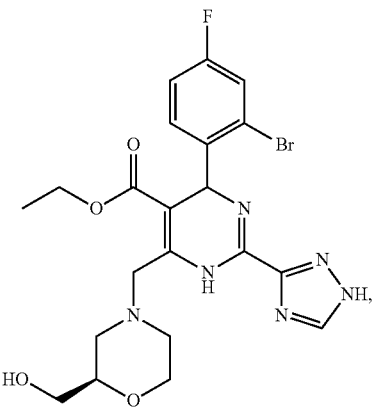
45
46
47

48 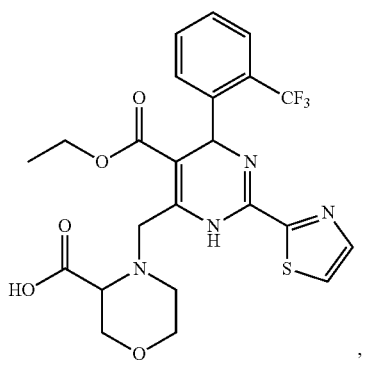
49 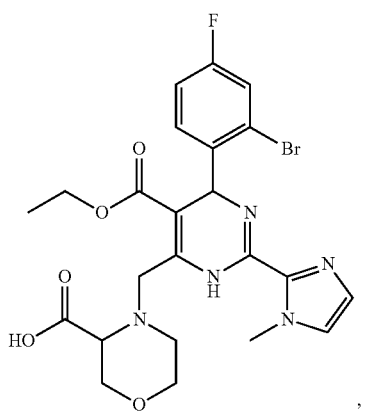
50 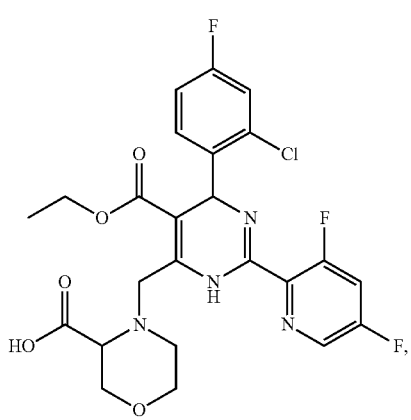
51 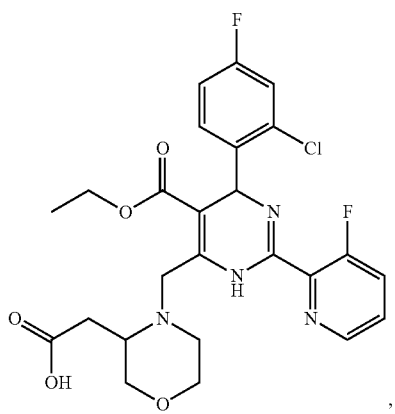
52 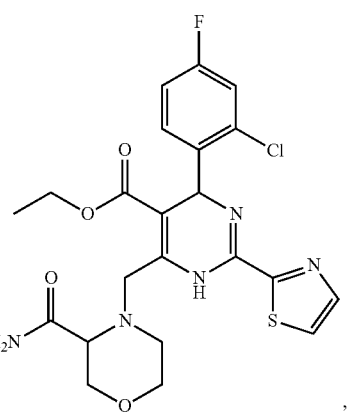
53 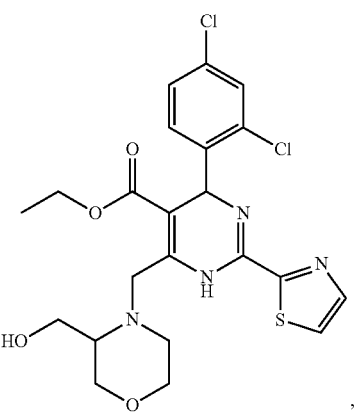
54 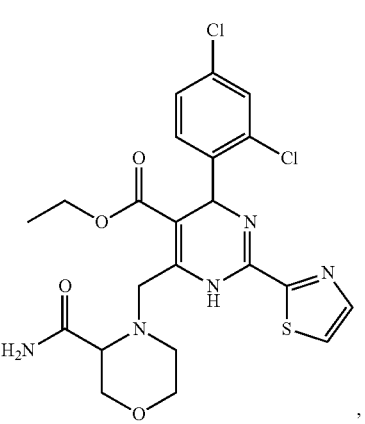
55 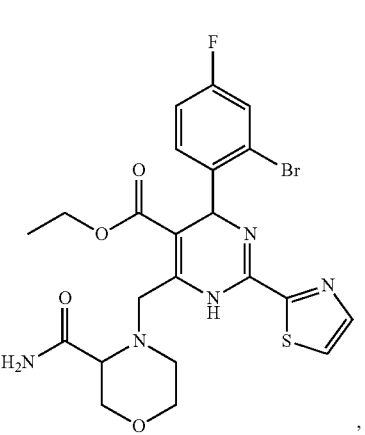

56
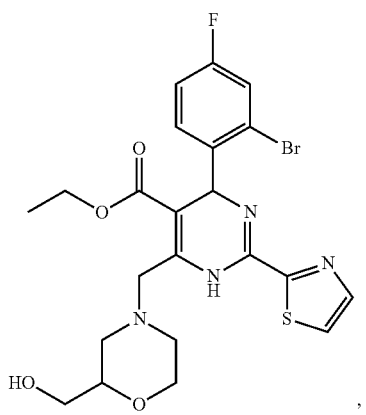
57
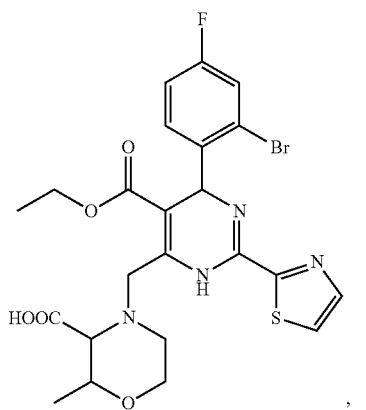
58
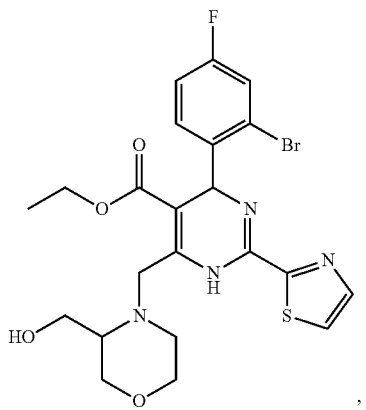
59
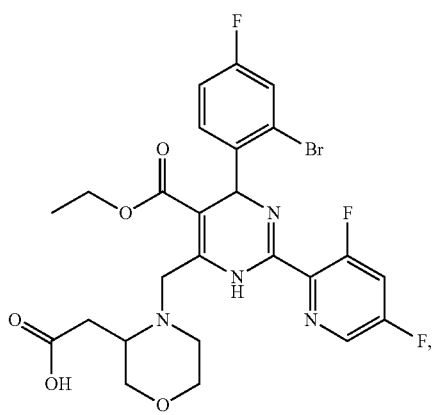
60
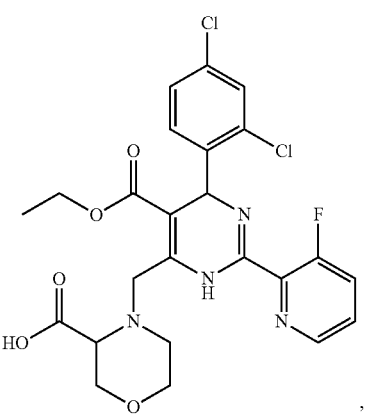
61
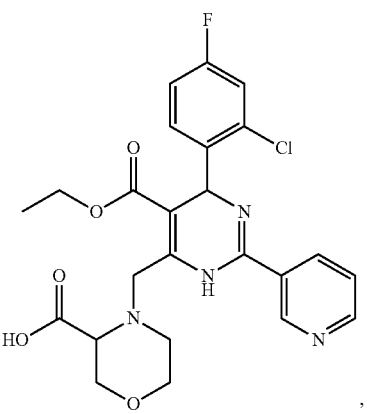
62
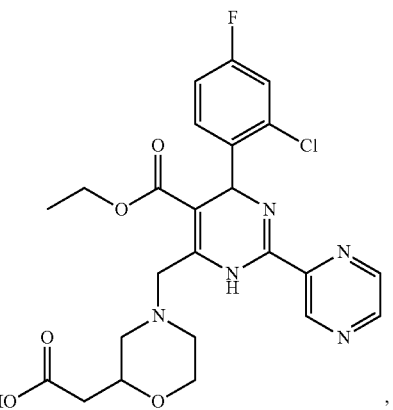
63
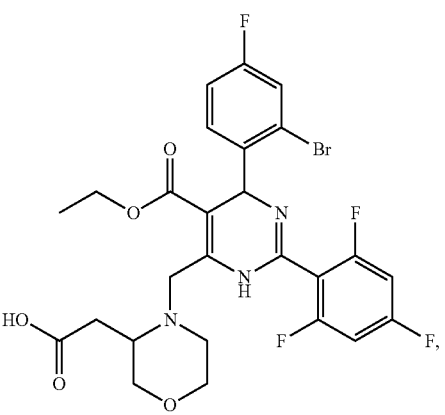

273
-continued
64
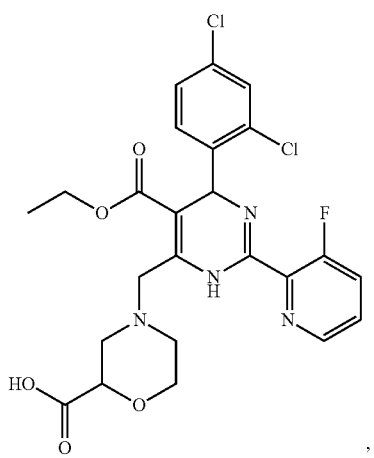
65
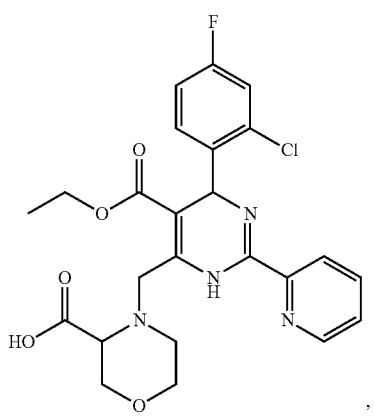
66
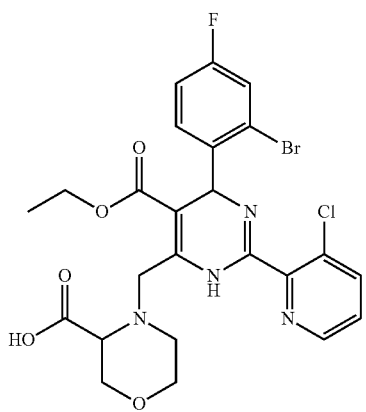
274
-continued
67
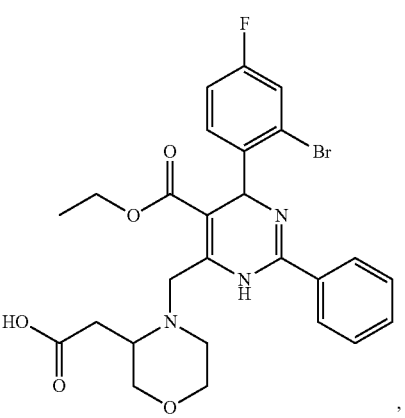
68
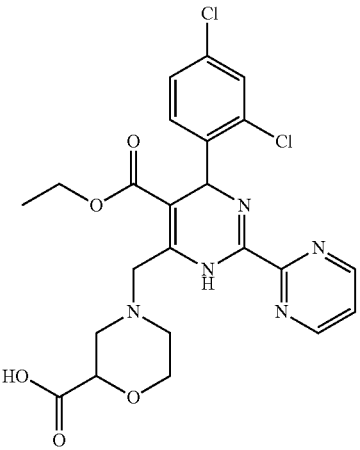
69
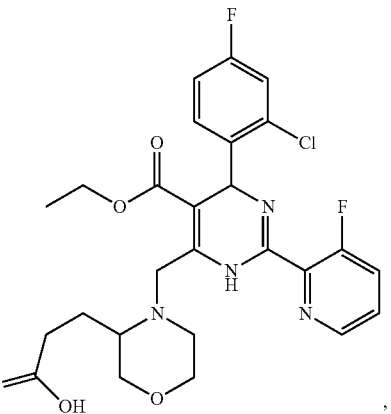

275
-continued
70 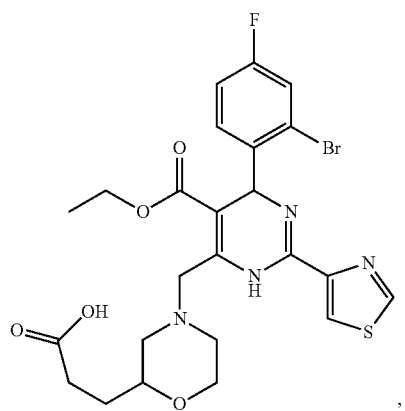
71 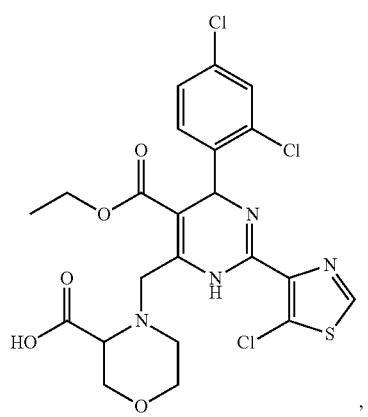
72 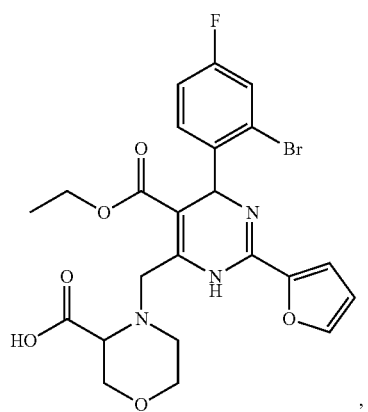
73 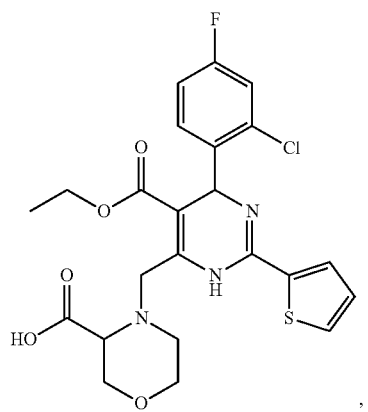
276
-continued
74 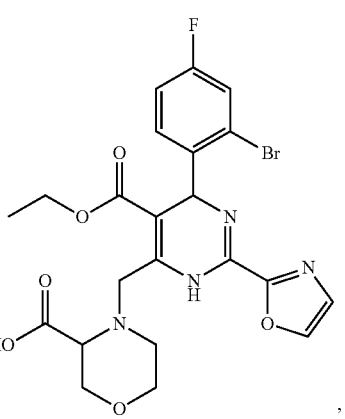
75 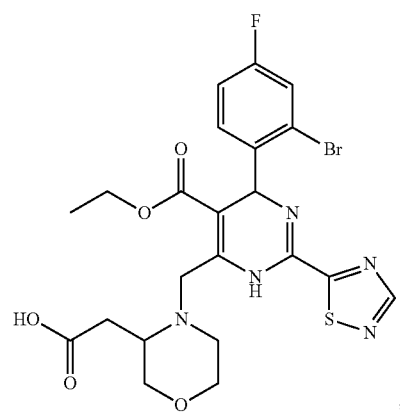
76 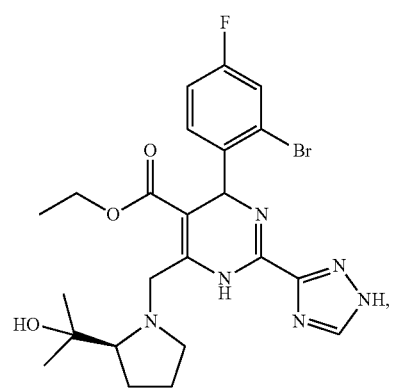
77 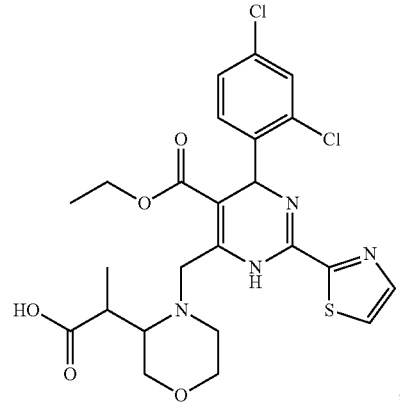

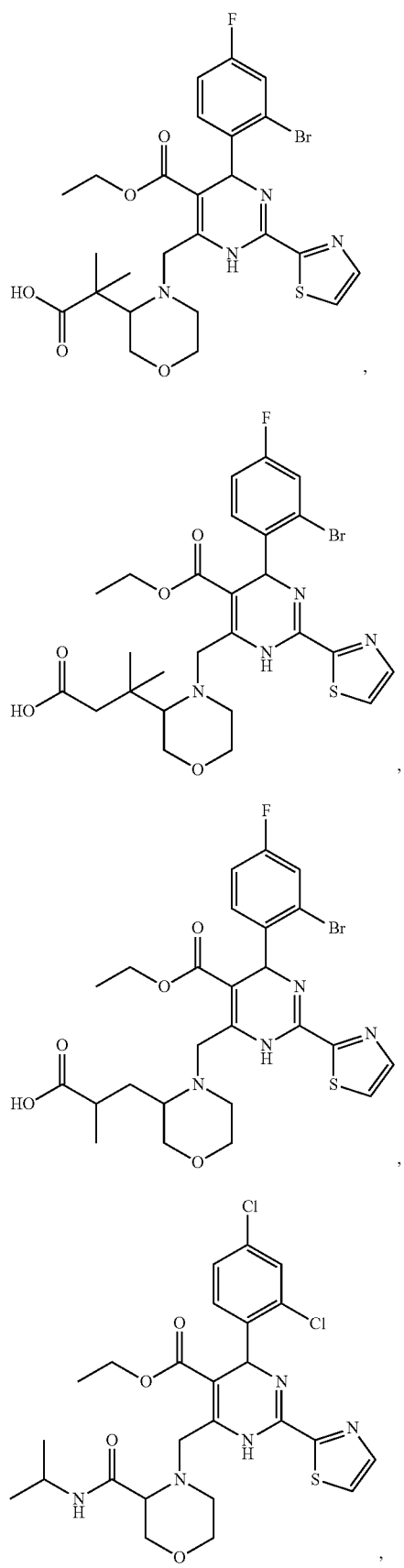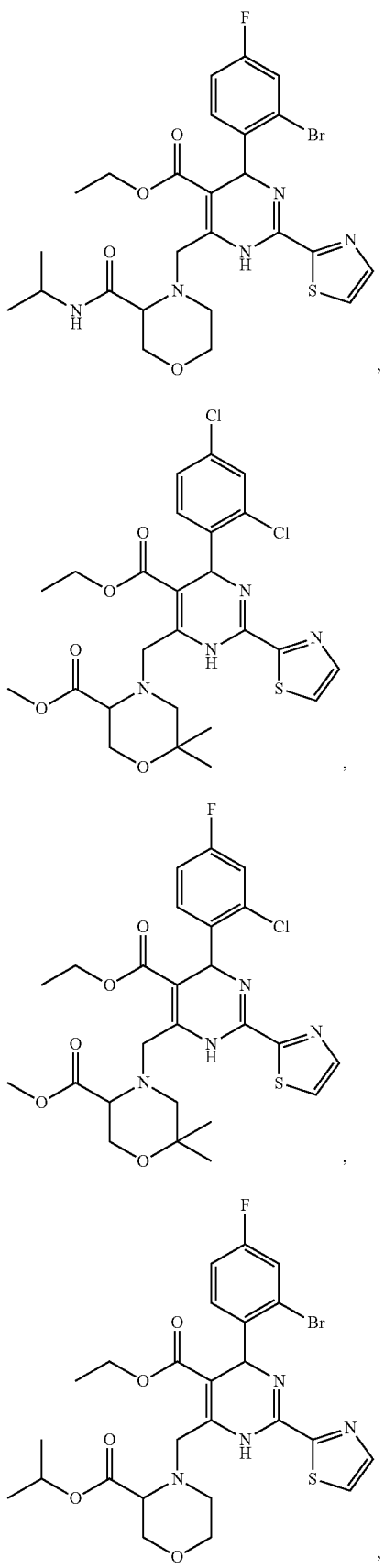

| 86 | 90 |
|---|---|
| 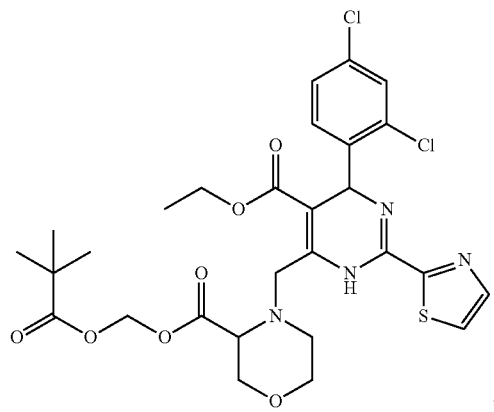 | 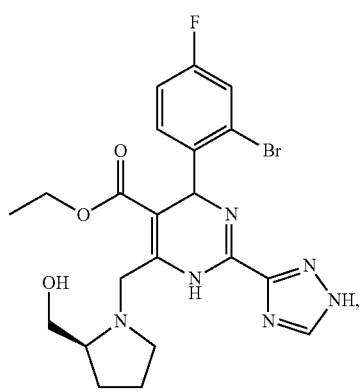 |
| 87 | |
| 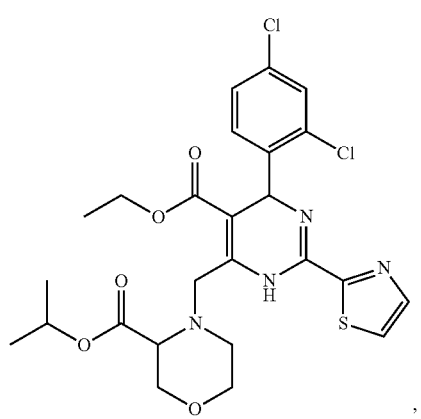 | 91 |
| | 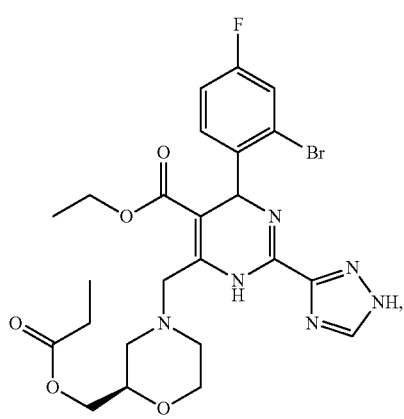 |
| 88 | |
| 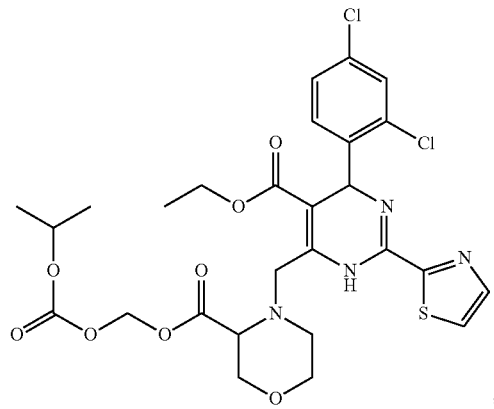 | 92 |
| 89 | 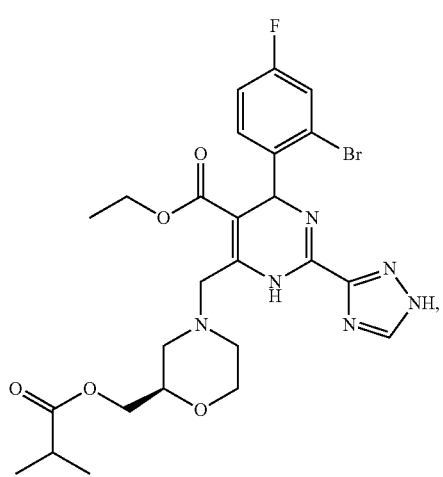 |
| 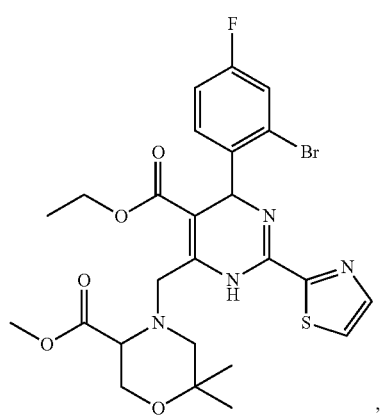 | |

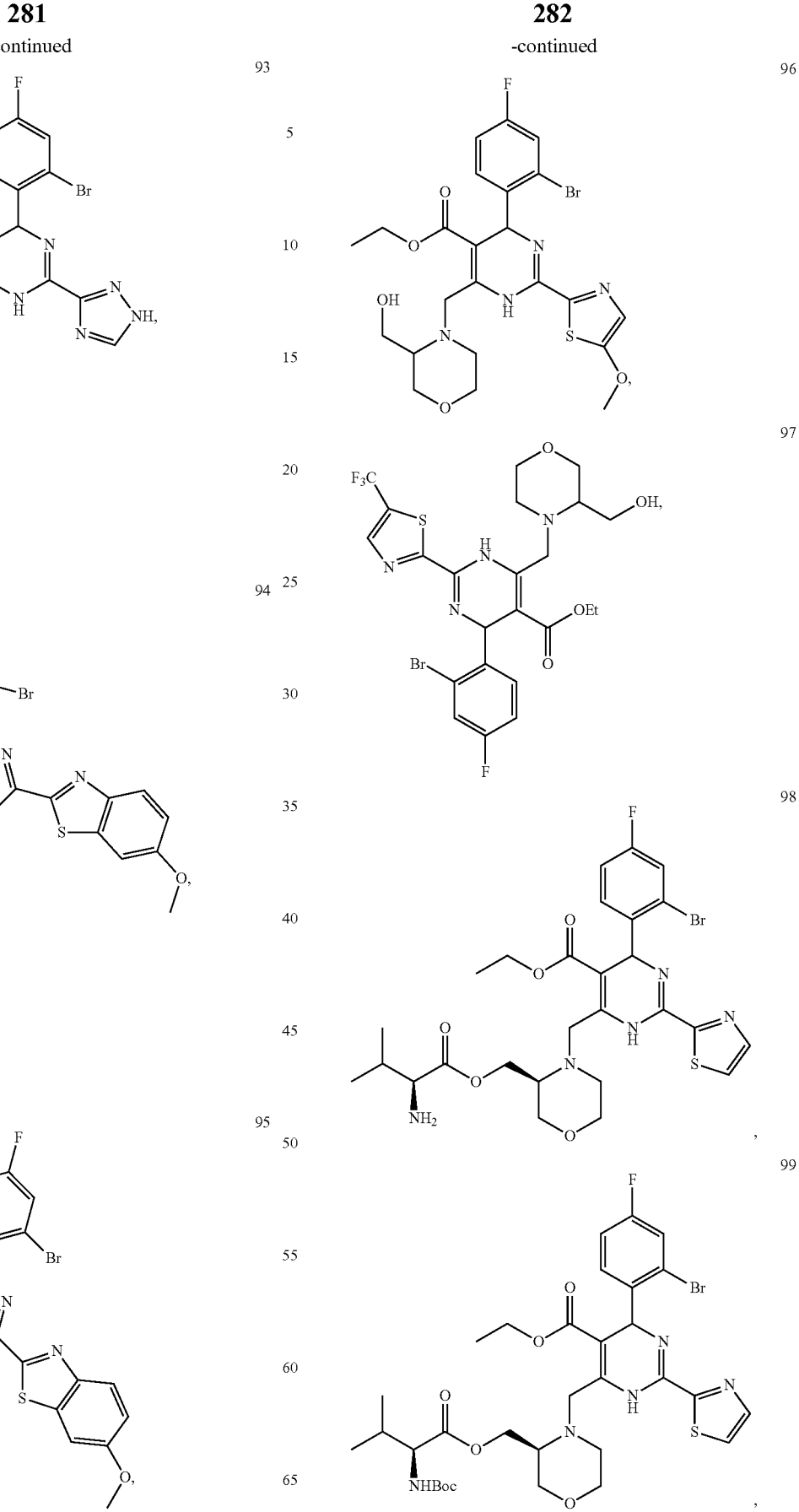

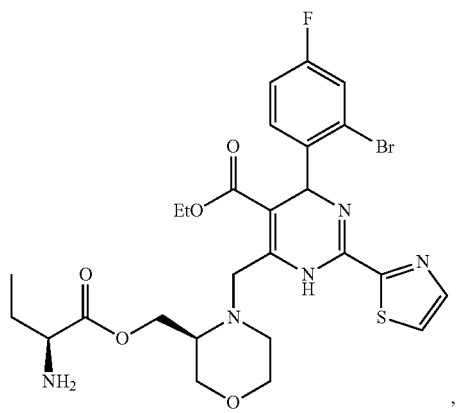
100
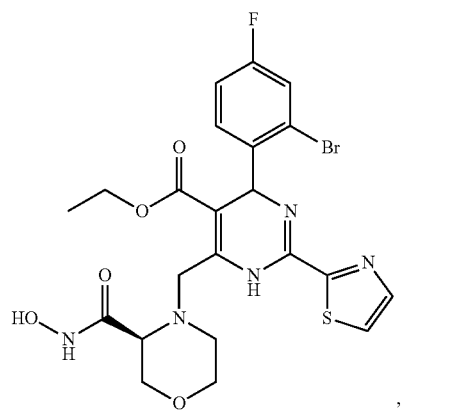
101
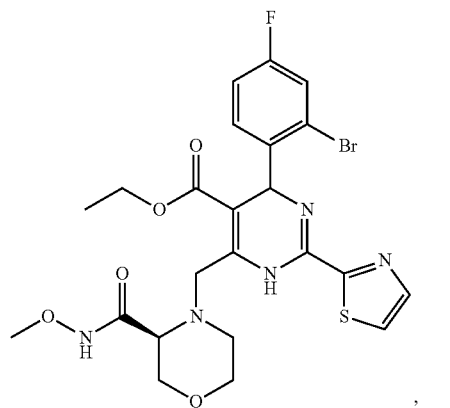
102
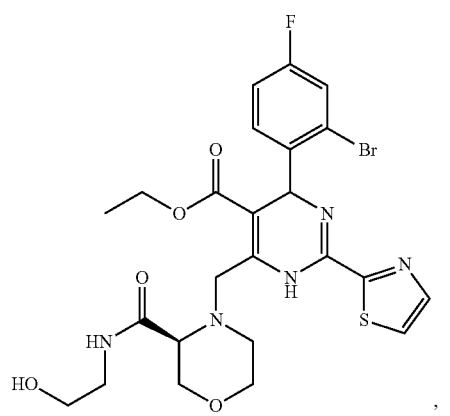
103
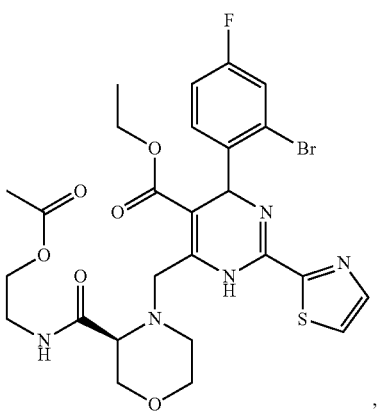
104
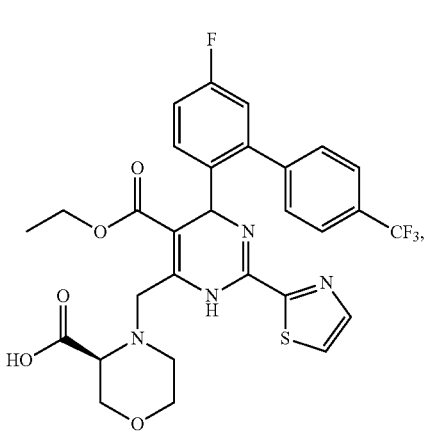
105
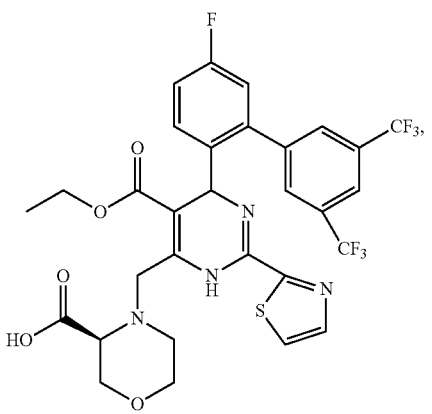
106
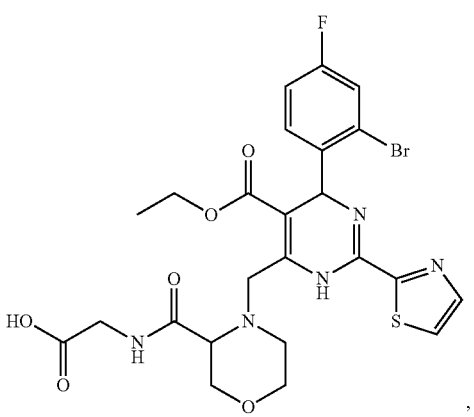
107

108 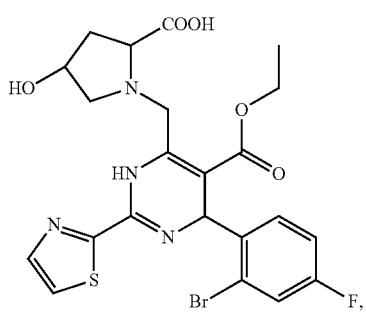
109 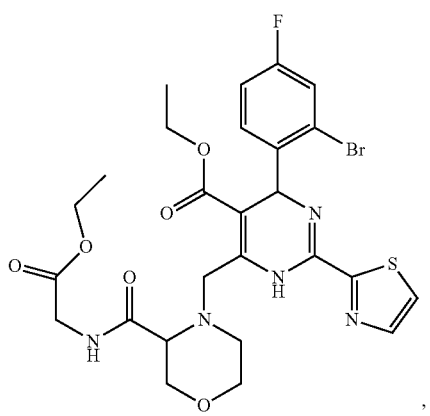
110 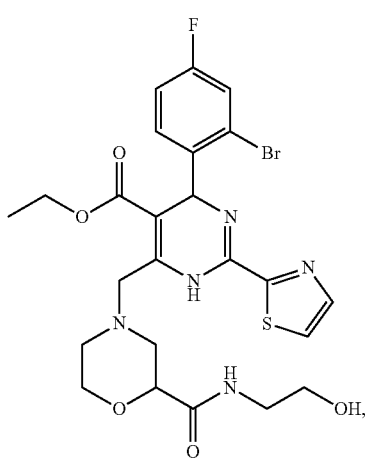
111 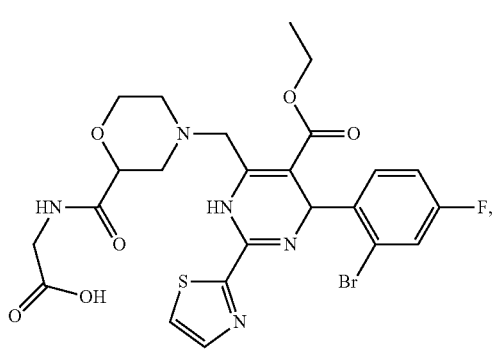
112 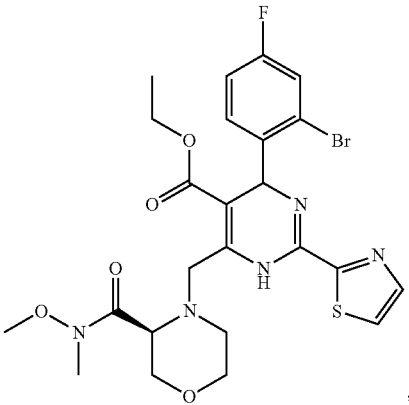
113 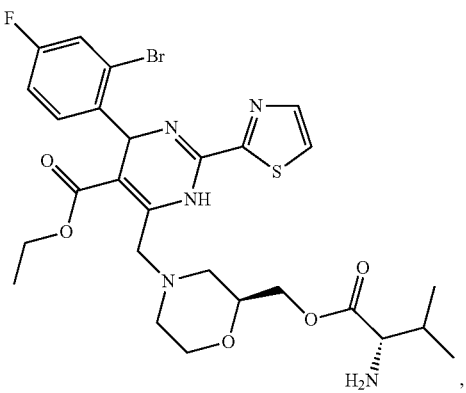
114 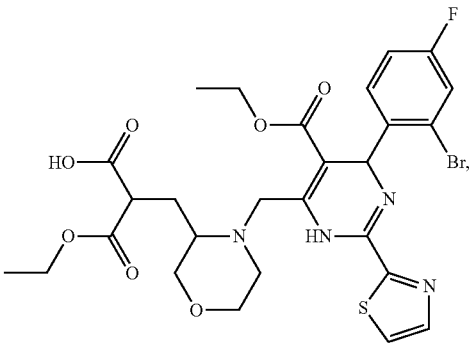
115 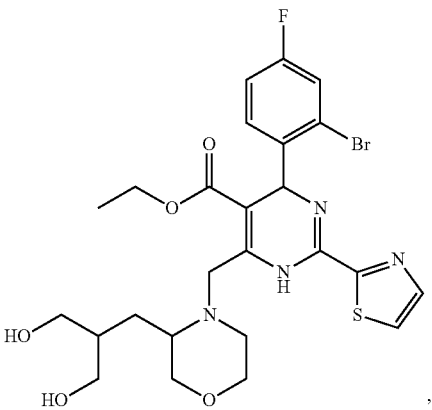

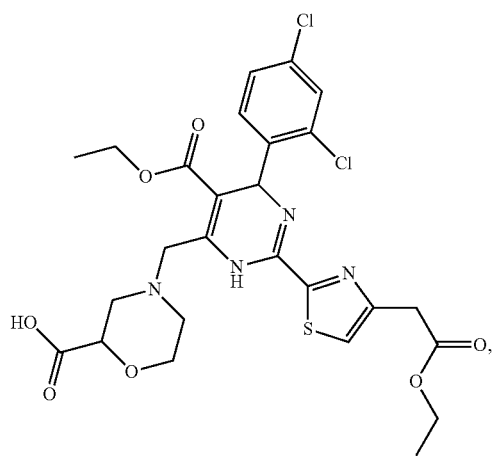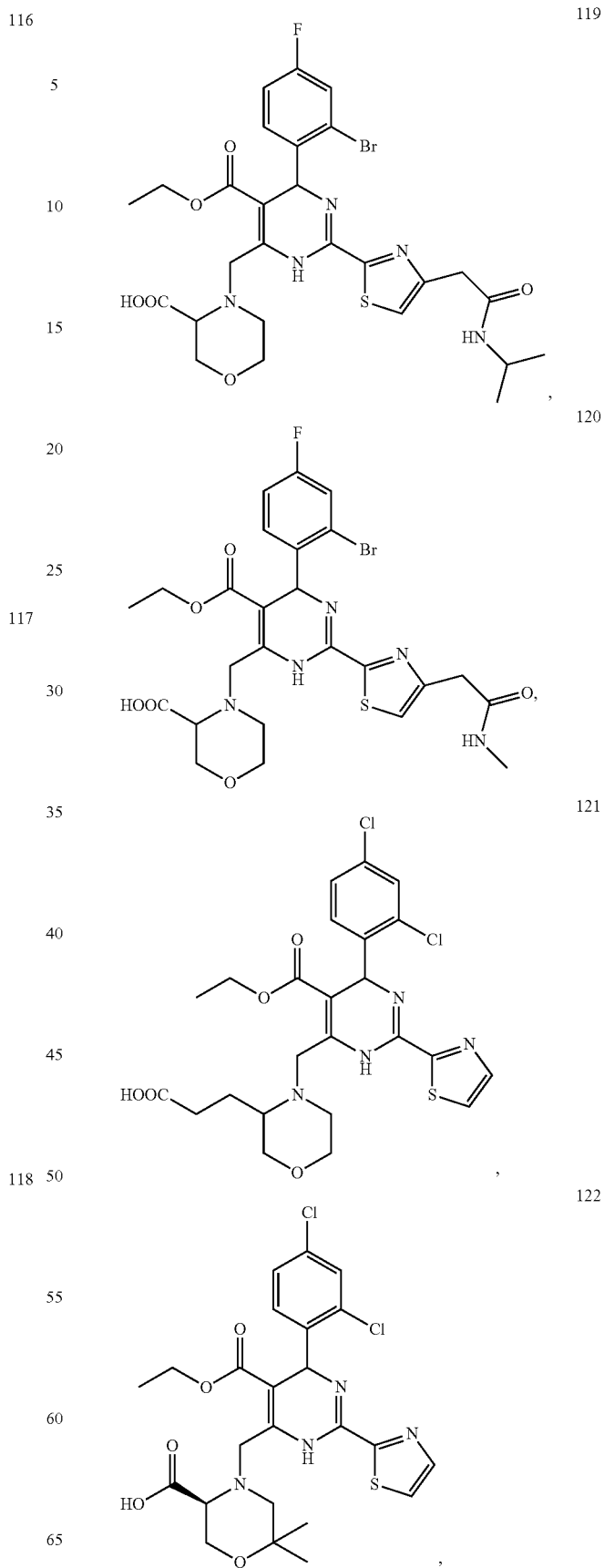

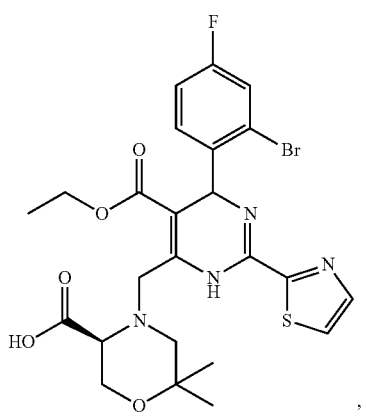
123
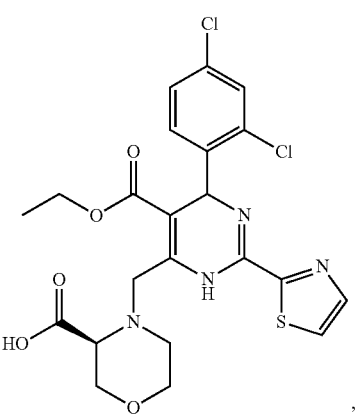
127
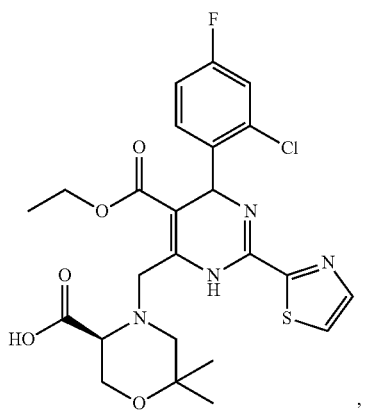
124
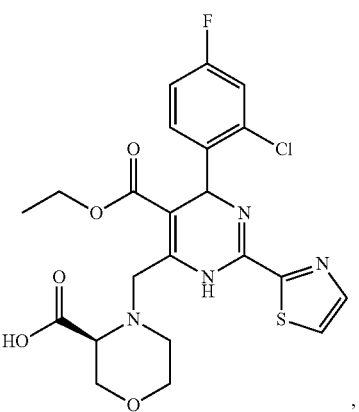
128
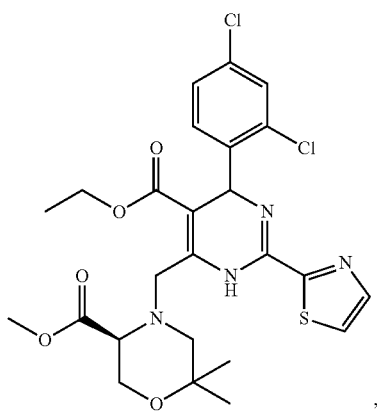
125
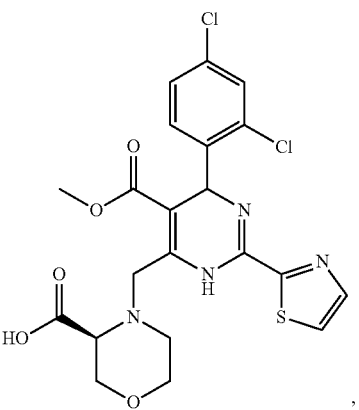
129
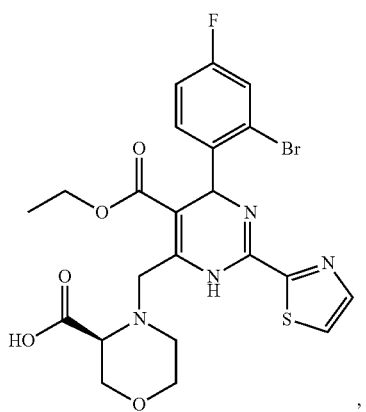
126
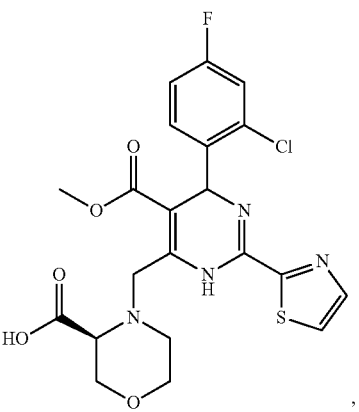
130

131 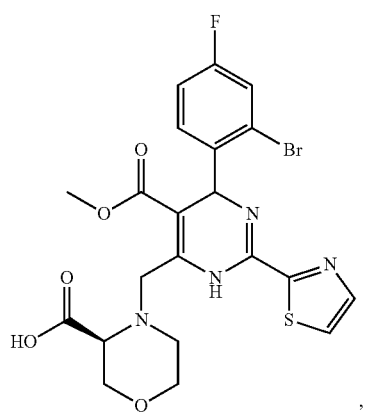
132 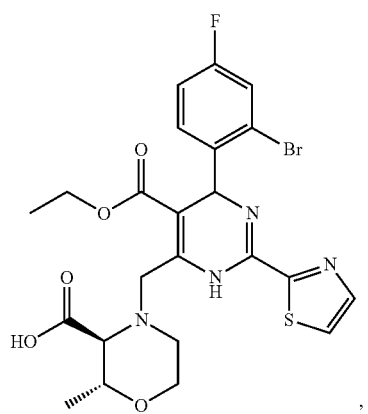
133 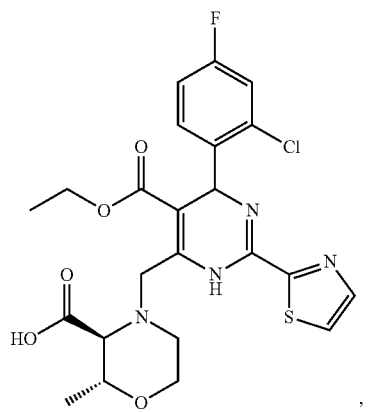
134 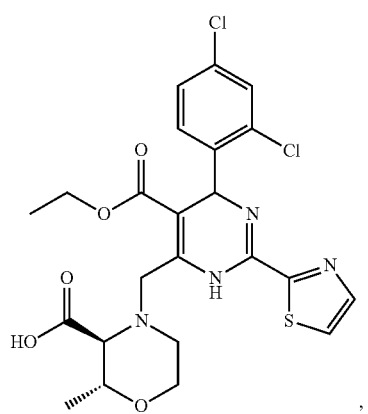
135 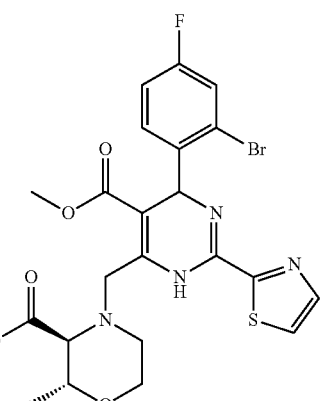
136 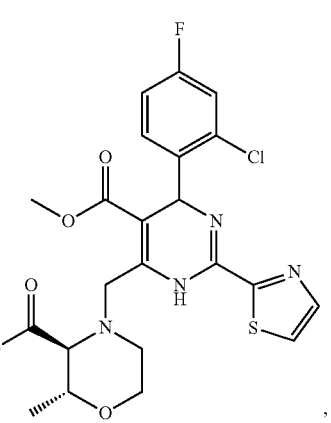
137 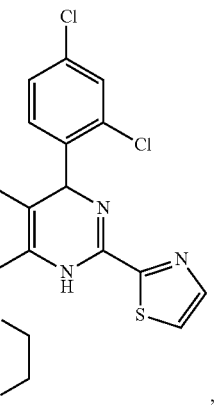
138 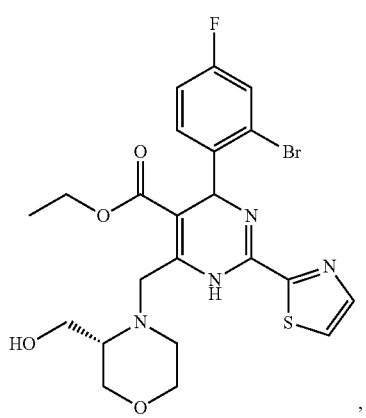

139
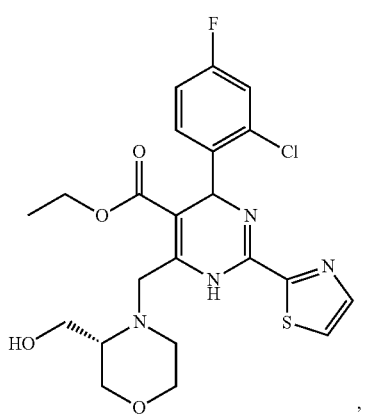
140
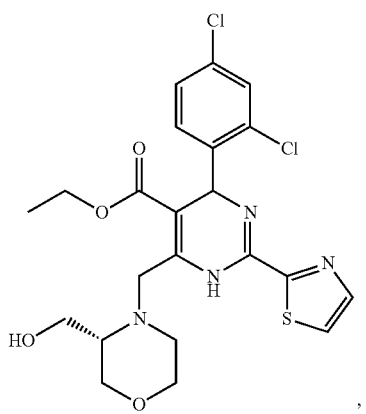
141
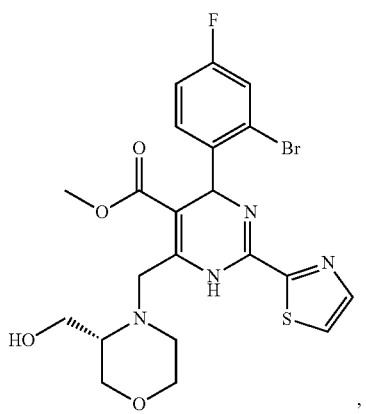
142
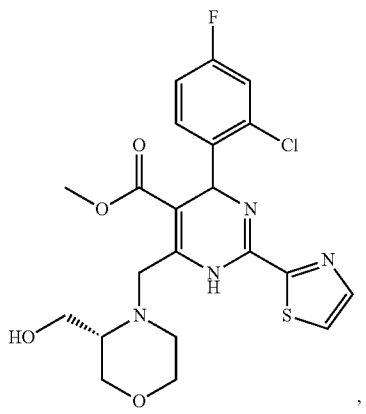
143
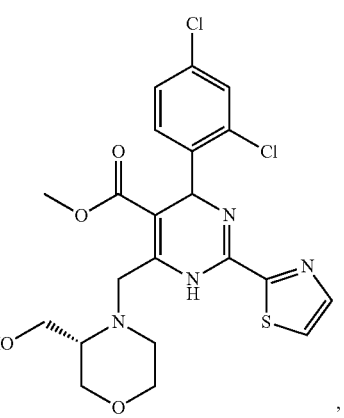
144
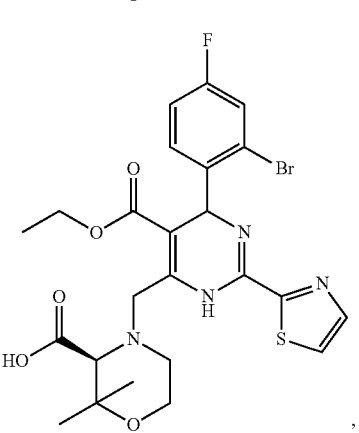
145
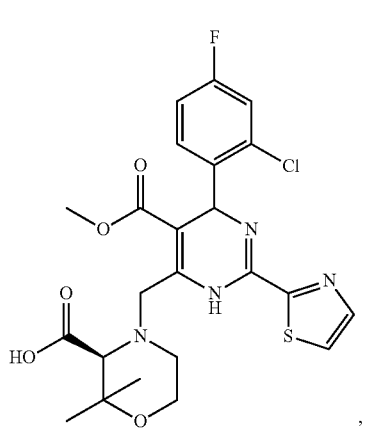
146
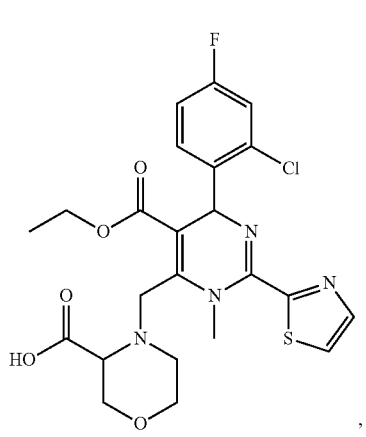

147
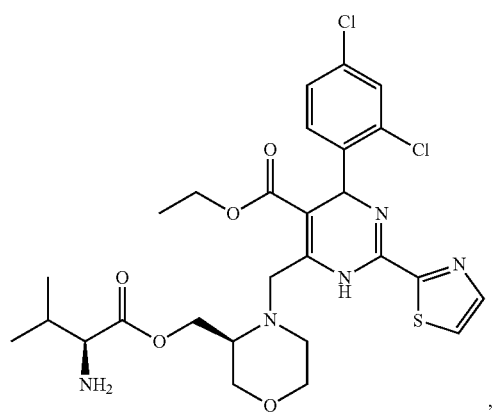
148
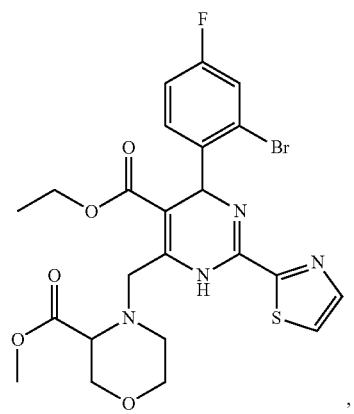
149
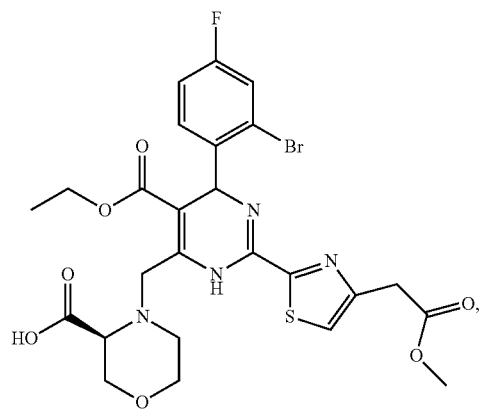
150
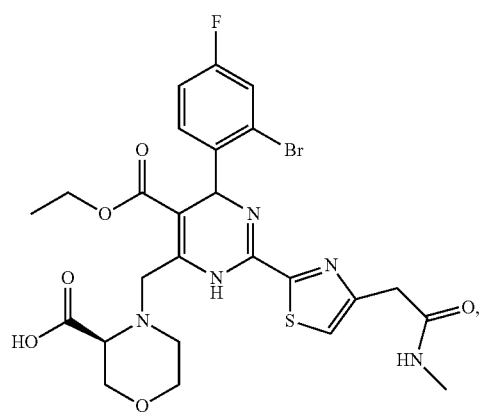
151
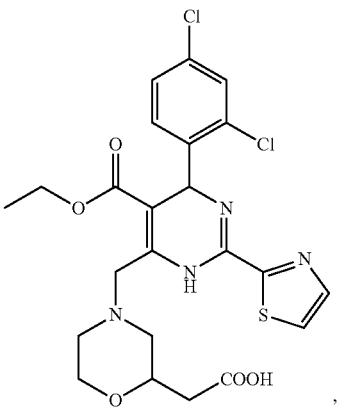
152
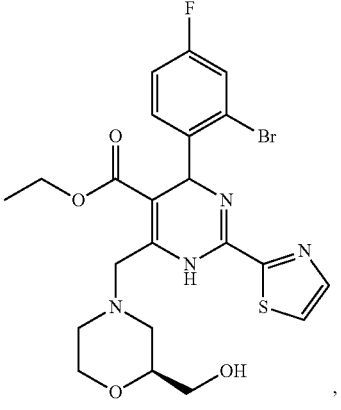
153
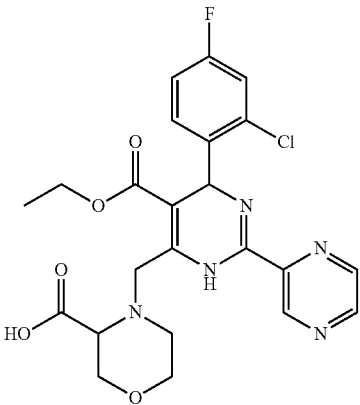
154
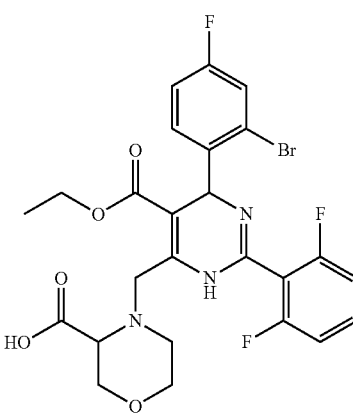

155 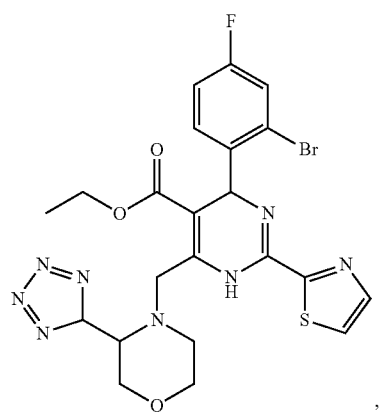,
156 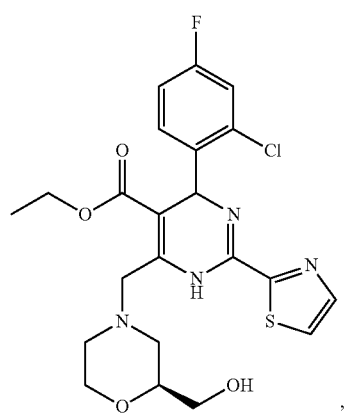,
157 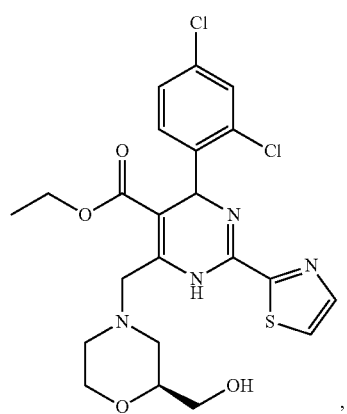,
158 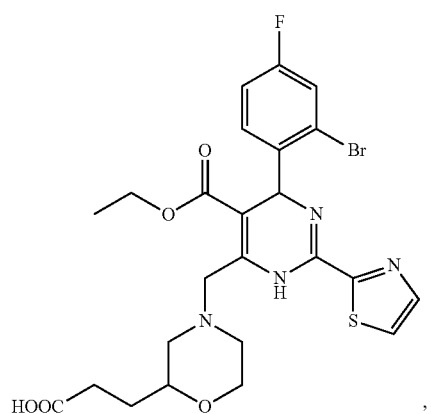,
159 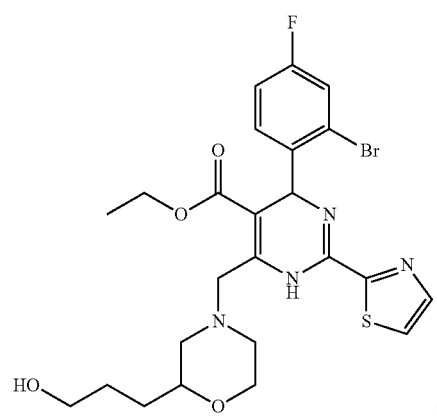,
160 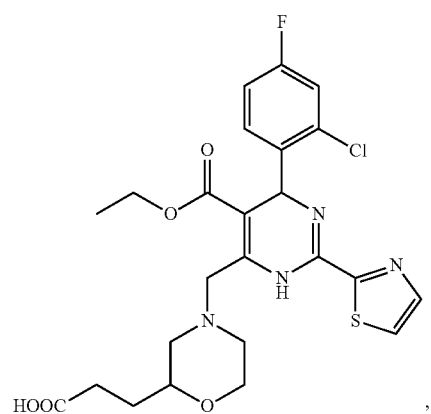,
161 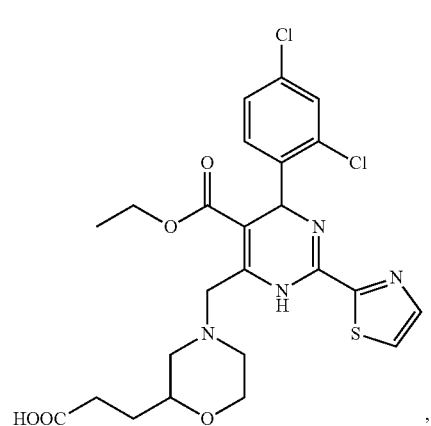,
162 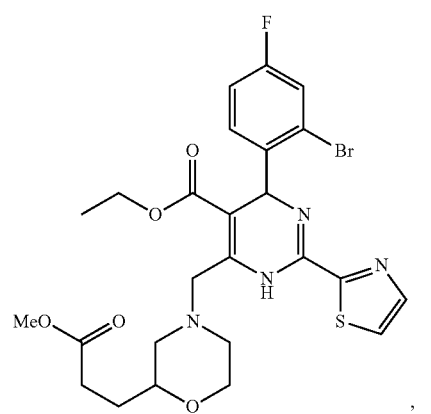, 163
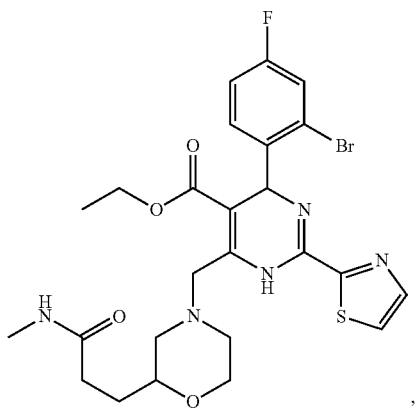
164
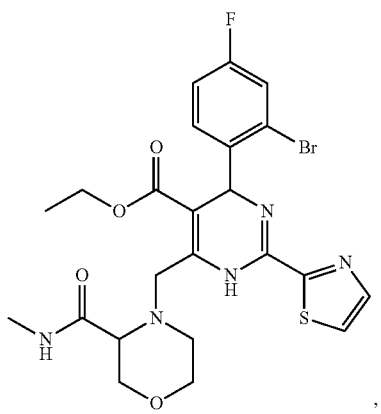
165
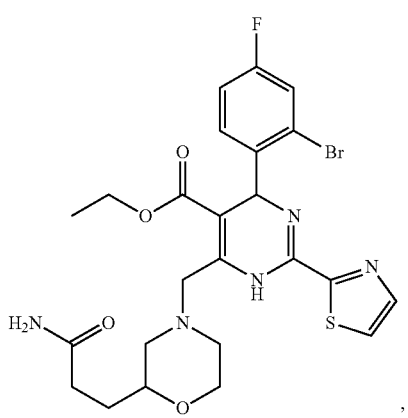
166
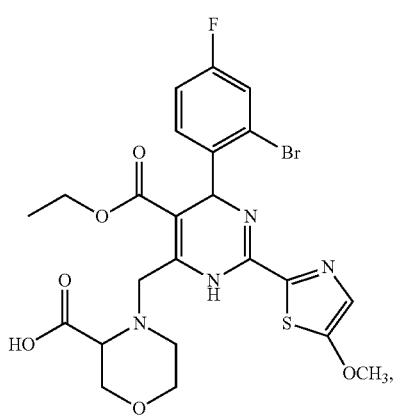
167
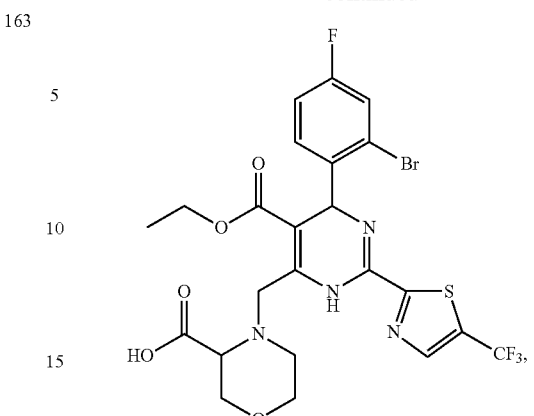
168
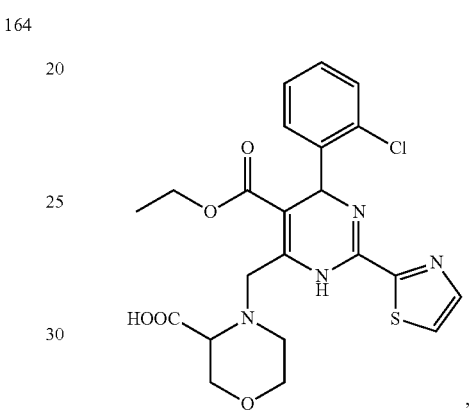
169
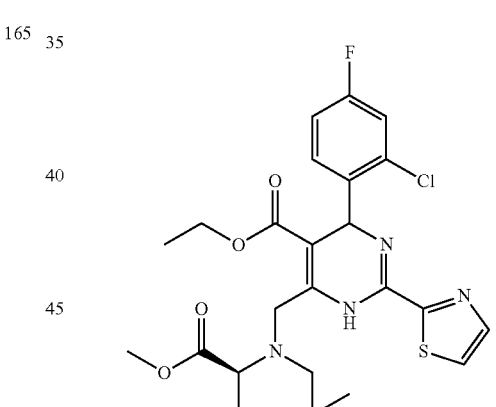
170
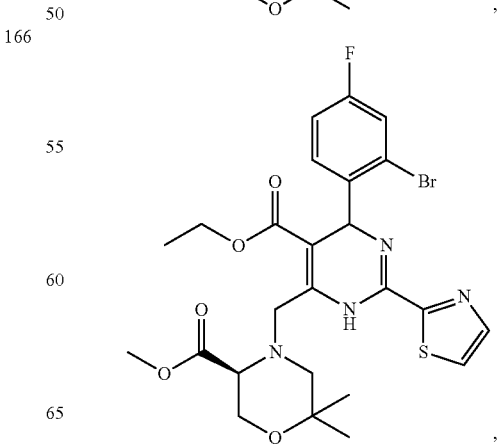

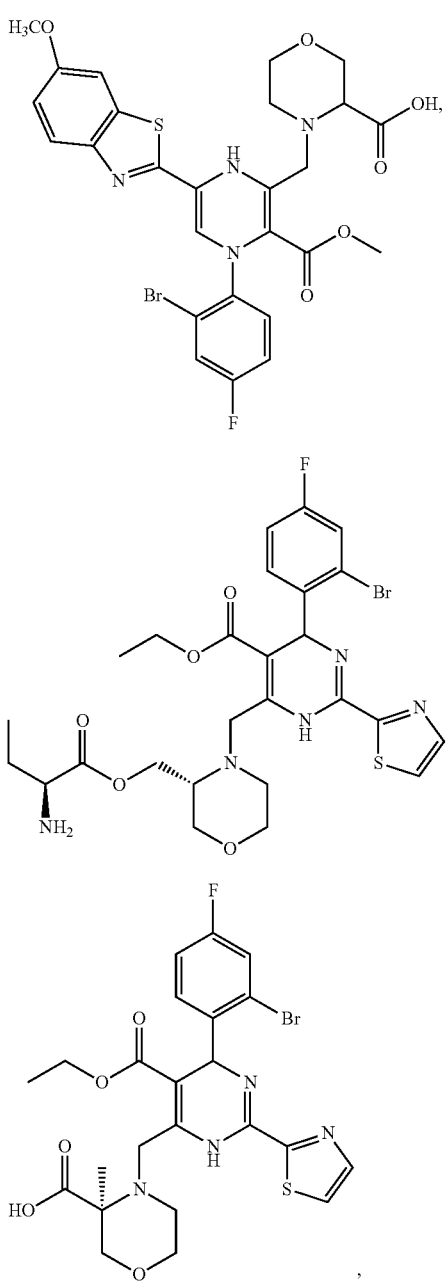

or an enantiomer, a diastereoisomer, a tautomer, a hydrate, a solvate, or a pharmaceutically acceptable salt thereof.

14. A pharmaceutical composition comprising the compound according to claim 1; and a pharmaceutically acceptable carrier, excipient, diluent, adjuvant, vehicle or a combination thereof.

15. The pharmaceutical composition according to claim 14 further comprises an anti-HBV agent.

16. The pharmaceutical composition according to claim 15, wherein the anti-HBV agent is a HBV polymerase inhibitor, immunomodulator or interferon.

17. The pharmaceutical composition according to claim 15, wherein the anti-HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole, or propagermanium.

18. A method for managing, treating or lessening a viral disease or a HBV disease in a patient, comprising administering to the patient with a therapeutically effective amount of the compound according to claim 1.

19. The method according to claim 18, wherein the viral disease or HBV disease is hepatitis B infection or a disease caused by hepatitis B infection.

20. The method according to claim 19, wherein the disease caused by hepatitis B infection is cirrhosis or hepatocellular carcinoma.

21. A method for managing, treating or lessening a viral disease or a HBV disease in a patient, comprising administering to the patient with a therapeutically effective amount of the pharmaceutical composition according to claim 14.

22. The method according to claim 21, wherein the viral disease or HBV disease is hepatitis B infection or a disease caused by hepatitis B infection.

23. The method according to claim 22, wherein the disease caused by hepatitis B infection is cirrhosis or hepatocellular carcinoma.

* * * * *